(12) United States Patent
Bridger et al.

(10) Patent No.: US 7,863,293 B2
(45) Date of Patent: *Jan. 4, 2011

(54) CXCR4 CHEMOKINE RECEPTOR BINDING COMPOUNDS

(75) Inventors: Gary J. Bridger, Bellingham, WA (US); Ernest J. McEachern, White Rock (CA); Renato Skerlj, Vancouver (CA); Dominique Schols, Herent (BE); Ian Baird, West Abbotsford (CA); Al Kaller, Vancouver (CA); Curtis Harwig, Vancouver (CA); Yongbao Zhu, Coquitlam (CA); Gang Chen, Langley (CA); Krystyna Skupinska, New Westminister (CA)

(73) Assignee: Genzyme Corporation, Cambridge, MA (US)

( * ) Notice: Subject to any disclaimer, the term of this patent is extended or adjusted under 35 U.S.C. 154(b) by 374 days.

This patent is subject to a terminal disclaimer.

(21) Appl. No.: 11/936,047

(22) Filed: Nov. 6, 2007

(65) Prior Publication Data
US 2008/0255197 A1 Oct. 16, 2008

Related U.S. Application Data

(62) Division of application No. 10/823,494, filed on Apr. 12, 2004, now Pat. No. 7,291,631.

(60) Provisional application No. 60/462,736, filed on Apr. 11, 2003, provisional application No. 60/505,688, filed on Sep. 23, 2003.

(51) Int. Cl.
*C07D 401/02* (2006.01)
*A61K 31/44* (2006.01)

(52) U.S. Cl. ............... 514/311; 514/314; 514/332; 514/336; 514/357; 546/171; 546/176; 546/255; 546/268.1; 546/329

(58) Field of Classification Search ............... None
See application file for complete search history.

(56) References Cited

U.S. PATENT DOCUMENTS

| 3,205,133 | A | * | 9/1965 | Biel et al. .................. 514/332 |
| 5,021,409 | A | | 6/1991 | Murrer et al. |
| 5,583,131 | A | | 12/1996 | Bridger et al. |
| 5,698,546 | A | | 12/1997 | Bridger et al. |
| 5,817,807 | A | | 10/1998 | Bridger et al. |
| 6,001,826 | A | | 12/1999 | Murrer et al. |
| 6,365,583 | B1 | | 4/2002 | MacFarland et al. |
| 2002/0147192 | A1 | | 10/2002 | Bridger et al. |
| 2003/0028022 | A1 | | 2/2003 | Bridger et al. |
| 2003/0220341 | A1 | | 11/2003 | Bridger et al. |

FOREIGN PATENT DOCUMENTS

| WO | WO-97/09976 | 3/1997 |
| WO | WO-00/02870 | 1/2000 |
| WO | WO-00/56729 | 9/2000 |
| WO | WO-02/22599 | 3/2002 |
| WO | WO-02/22600 | 3/2002 |
| WO | WO-02/34745 | 5/2002 |

OTHER PUBLICATIONS

Elderfield et al, Journal of Organic Chemistry (1960), vol. 25, pp. 1576-1583.*
Wu et al., Toxicology, 236, pp. 1-6, 2007.*
Abi-Younes et al., Circ. Res. (2000) 86:131-138.
Alkhatib et al., Science (1996) 272:1955-1958.
Arai et al., Eur. J. Haematol. (2000) 64:323-332.
Arenberg et al., J. Leukocyte Biol. (1997) 62:554-562.
Aiuti et al., J. Exp. Med. (1997) 185:111-120.
Blaak et al., Proc. Natl. Acad. Sci. (2000) 97:1269-1274.
Blanco et al., Antimicrobial Agents and Chemother. (2000) 44:51-56.
Bleul et al., J. Exp. Med. (1998) 187:753-762.
Bleul et al., Nature (1996) 382:829-833.
Bradstock et al., Leukemia (2000) 14:882-888.
Bridger et al., J. Med. Chem. (1999) 42:3971-3981.
Brinksma et al., Inorganica Chimica Acta (2002) 337:75-82.
Burger et al., Blood (1999) 94:3658-3667.
Carroll et al., Science (1997) 276:273-276.
Cocchi et al., Science (1995) 270:1811-1815.
Connor, J. Virol. (1994) 68:4400-4408.
Deng et al., Nature (1996) 381:661-666.
Donzella et al., Nature Medicine (1998) 4:72-77.
Dragic et al., Nature (1996) 381:667-673.
Egberink et al., J. Virol. (1999) 73:6346-6352.
Eitner et al., Transplantation (1998) 66:1551-1557.

(Continued)

*Primary Examiner* — Zinna N Davis
(74) *Attorney, Agent, or Firm* — Morrison & Foerster LLP

(57) ABSTRACT

The present invention relates to compounds that bind to chemokine receptors, and having the formula

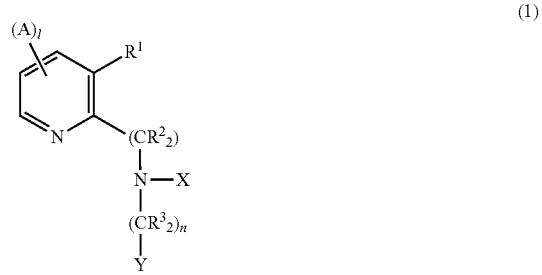

(1)

wherein each A, X, Y, $R^1$, $R^2$ and $R^3$ are substituents. The present invention also relates to methods of using such compounds, such as in treating HIV infection and inflammatory conditions such as rheumatoid arthritis. Furthermore, the present invention relates to methods to elevate progenitor and stem cell counts, as well as methods to elevate white blood cell counts, using such compounds.

18 Claims, 2 Drawing Sheets

OTHER PUBLICATIONS

Fedyk et al., J. Leukocyte Biol. (1999) 66:667-673.
Feng et al., Science (1996) 272:872-877.
Gonzalo et al., J. Immunol. (2000) 165:499-50.
Gupta et al., J. Biolog. Chem. (1998) 273(7):4282-4287.
International Search Report for PCT/US04/11328, mailed on Oct. 20, 2004, 2 pages.
Ishii et al., J. Immunol. (1999) 163:3612-3620.
Lataillade et al., Blood (2000) 95:756-768.
Liu et al., Cell (1996) 86:367-377.
Ma et al., Immunity (1999) 10:463-471.
Maekawa et al., Internal Medicine (2000) 39:90-100.
Michael et al., J. Virol. (1998) 72:6040-6047.
Michael et al., Nature Med. (1997) 3:338-340.
Miedema et al., Immune. Rev. (1994) 140:35-72.
Moore et al., J. Invest. Med. (1998) 46:113-120.
Moore et al., Trends Cardiovasc. Med. (1998) 8:51-58.
Murdoch et al., (2000) Blood 95:3032-3043.
Nagasawa et al., Nature (1996) 382:635-638.
Nagase, J. Immunol. (2000) 164:5935-5943.
Nanki et al., J. Immunol. (2000) 164:5010-5014.
Oberlin et al., Nature (1996) 382:833-835.
O'Brien et al., Lancet (1997) 349:1219.
Peled et al., Blood (2000) 95:3289-3296.
Peled et al., Science (1999) 283:845-848.
Ponath, Exp. Opin. Invest. Drugs (1998) 7:1-18.
Rana et al., J. Virol. (1997) 71:3219-3227.
Salcedo et al., Am. J. Pathol. (1999) 154:1125-1135.
Samson et al., Nature (1996) 382:722-725.
Schols et al., Antiviral Research (1997) 35:147-156.
Schols et al., J. Exp. Med. (1997) 186:1383-1388.
Schuitemaker et al., J. Virol. (1992) 66:1354-1360.
Seghal et al., J. Surg. Oncol. (1998) 69:99-104.
Simmons et al., J. Virol. (1996) 70:8355-8360.
Simmons et al., J. Virol. (1988) 72:8453-8457.
Tachibana et al., Nature (1998) 393:591-594.
Tersmette et al., J. Virol. (1988) 62:2026-2032.
Theodorou et al., Lancet (1997) 349:1219-1220.
Viardot et al., Ann. Hematol. (1998) 77:193-197.
Wyatt et al., Science (1998) 280:1884-1888.
Xia et al., J. Neurovirology (1999) 5:32-41.
Yssel et al., Clinical and Experimental Allergy (1998) 28:104-109.
Zhang et al., AIDS Res. Hum. Retroviruses (1997) 13:1357-1366.
Zhang et al., J. Virol. (1998) 72:9307-9312.
Zhang et al., J. Virol. (1999) 73:3443-3448.
Supplementary Partial European Search Report for EP 04759481.7, mailed Feb. 24, 2009, 4 pages.

* cited by examiner

CXCR4 CHEMOKINE RECEPTOR BINDING COMPOUNDS

CROSS-REFERENCE TO RELATED APPLICATIONS

This application is a divisional of U.S. application Ser. No. 10/823,494 filed Apr. 12, 2004, now U.S. Pat. No. 7,291,631, which claims the benefit of U.S. provisional application Ser. Nos. 60/462,736 filed Apr. 11, 2003, and 60/505,688 filed Sep. 23, 2003. The content of these applications are incorporated herein by reference.

TECHNICAL FIELD

This invention generally relates to novel compounds, pharmaceutical compositions and their use. This invention more specifically relates to novel heterocyclic compounds that bind to chemokine receptors, including CXCR4 and CCR5, and demonstrate protective effects against infection of target cells by a human immunodeficiency virus (HIV), as well as enhance the population of progenitor and/or stem cells, stimulate the production of white blood cells, and/or to effect regeneration of cardiac tissue.

BACKGROUND ART

Approximately 40 human chemokines have been described, that function, at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs*, 7:1-18, 1998). These chemotactic cytokines, or chemokines, constitute a family of proteins, approximately 8-10 kDa in size. Chemokines appear to share a common structural motif, that consists of 4 conserved cysteines involved in maintaining tertiary structure. There are two major subfamilies of chemokines: the "CC" or β-chemokines and the "CXC" or α-chemokines. The receptors of these chemokines are classified based upon the chemokine that constitutes the receptor's natural ligand. Receptors of the β-chemokines are designated "CCR"; while those of the α-chemokines are designated "CXCR."

Chemokines are considered to be principal mediators in the initiation and maintenance of inflammation (see *Chemokines in Disease* published by Humana Press (1999), Edited by C. Herbert; Murdoch, et al., *Blood* 95:3032-3043 (2000)). More specifically, chemokines have been found to play an important role in the regulation of endothelial cell function, including proliferation, migration and differentiation during angiogenesis and re-endothelialization after injury (Gupta, et al., *J. Biolog. Chem.*, 7:4282-4287, 1998). Two specific chemokines have been implicated in the etiology of infection by human immunodeficiency virus (HIV).

In most instances, HIV initially binds via its gp120 envelope protein to the CD4 receptor of the target cell. A conformational change appears to take place in the gp120 which results in its subsequent binding to a chemokine receptor, such as CCR5 (Wyatt et al., *Science*, 280:1884-1888 (1998)). HIV-1 isolates arising subsequently in the infection bind to the CXCR4 chemokine receptor. In view of the fact that the feline immunodeficiency virus, another related retrovirus, binds to a chemokine receptor without needing to bind first to the CD4 receptor, suggests that chemokine receptors may be the primordial obligate receptors for immunodeficiency retroviruses.

Following the initial binding by HIV to CD4, virus-cell fusion results, which is mediated by members of the chemokine receptor family, with different members serving as fusion cofactors for macrophage-tropic (M-tropic) and T cell line-tropic (T-tropic) isolates of HIV-1 (Carroll et al., *Science*, 276: 273-276 1997; Feng et al. *Science* 272, 872-877 (1996); Bleul et al. *Nature* 382, 829-833 (1996); Oberlin et al. *Nature* 382, 833-835 (1996); Cocchi et al. *Science* 270, 1811-1815 (1995); Dragic et al. *Nature* 381, 667-673 (1996); Deng et al. *Nature* 381, 661-666 (1996); Alkhatib et al. *Science* 272, 1955-1958, 1996). During the course of infection within a patient, it appears that a majority of HIV particles shift from the M-tropic to the more aggressive pathogenic T-tropic viral phenotype (Miedema et al., *Immune. Rev.*, 140:35 (1994); Blaak et al. *Proc. Natl. Acad. Sci.* 97, 1269-1274 (2000); Simmonds et al. *J. Virol.* 70, 8355-8360 (1996); Tersmette et al. *J. Virol.* 62, 2026-2032, 1988); Connor, R. I., Ho, D. D. *J. Virol.* 68, 4400-4408 (1994); Schuitemaker et al. *J. Virol.* 66, 1354-1360 (1992)). The M-tropic viral phenotype correlates with the virus's ability to enter the cell following binding of the CCR5 receptor, while the T-tropic viral phenotype correlates with viral entry into the cell following binding and membrane fusion with the CXCR4 receptor. Clinically observations suggest that patients who possess genetic mutations in the CCR5 or CXCR4 appear resistant or less susceptible to HIV infection (Liu et al. *Cell* 86, 367-377 (1996); Samson et al. *Nature* 382, 722-725 (1996); Michael et al. *Nature Med.* 3, 338-340 (1997); Michael et al. *J. Virol.* 72, 6040-6047 (1998); Obrien et al. *Lancet* 349, 1219 (1997); Zhang et al. *AIDS Res. Hum. Retroviruses* 13, 1357-1366 (1997); Rana et al. *J. Virol.* 71, 3219-3227 (1997); Theodorou et al. *Lancet* 349, 1219-1220 (1997). Despite the number of chemokine receptors which have been reported to HIV mediate entry into cells, CCR5 and CXCR4 appear to be the only physiologically relevant coreceptors used by a wide variety of primary clinical HIV-1 strains (Zhang et al. *J. Virol.* 72, 9307-9312 (1998); Zhang et al. *J. Virol.* 73, 3443-3448 (1999); Simmonds et al. *J. Virol.* 72, 8453-8457 (1988)). Fusion and entry of T-tropic viruses that use CXCR4 are inhibited by the natural CXC-chemokine stromal cell-derived factor-1, whereas fusion and entry of M-tropic viruses that use CCR5 are inhibited by the natural CC-chemokines namely, Regulated on Activation Normal T-cell Expressed and Secreted (RANTES) and Macrophage Inflammatory proteins (MIP-1 alpha and beta).

However, the binding of chemokine receptors to their natural ligands appears to serve a more evolutionary and central role than only as mediators of HIV infection. The binding of the natural ligand, pre-B-cell growth-stimulating factor/stromal cell derived factor (PBSF/SDF-1) to the CXCR4 chemokine receptor provides an important signaling mechanism: CXCR4 or SDF-1 knock-out mice exhibit cerebellar, cardiac and gastrointestinal tract abnormalities and die in utero (Zou et al., *Nature*, 393:591-594 (1998); Tachibana et al., *Nature*, 393:591-594 (1998); Nagasawa et al. *Nature* 382, 635-638 (1996)). CXCR4-deficient mice also display hematopoietic defects (Nagasawa et al. *Nature* 382, 635-638 (1996)); the migration of CXCR4 expressing leukocytes and hematopoietic progenitors to SDF-1 appears to be important for maintaining B-cell lineage and localization of CD34[+] progenitor cells in bone marrow (Bleul et al. *J. Exp. Med.* 187, 753-762 (1998); Viardot et al. *Ann. Hematol.* 77, 195-197 (1998); Auiti et al. *J. Exp. Med.* 185, 111-120 (1997); Peled et al. *Science* 283, 845-848 (1999); Qing et al. *Immunity* 10, 463-471 (1999); Lataillade et al. *Blood* 95, 756-768 (1999); Ishii et al. *J. Immunol.* 163, 3612-3620 (1999); Maekawa et al. *Internal Medicine* 39, 90-100 (2000); Fedyk et al. *J. Leukocyte Biol.* 66, 667-673 (1999); Peled et al. *Blood* 95, 3289-3296 (2000)).

The signal provided by SDF-1 on binding to CXCR4 may also play an important role in tumor cell proliferation and regulation of angiogenesis associated with tumor growth (See "*Chemokines and Cancer*" published by Humana Press (1999); Edited by B. J. Rollins; Arenburg et al. *J. Leukocyte Biol.* 62, 554-562 (1997); Moore et al. *J. Invest. Med.* 46, 113-120 (1998); Moore et al. *Trends cardiovasc. Med.* 8, 51-58 (1998); Seghal et al. *J. Surg. Oncol.* 69, 99-104 (1998)); the known angiogenic growth factors VEG-F and bFGF, upregulate levels of CXCR4 in endothelial cells, and SDF-1 can induce neovascularization in vivo (Salcedo et al. *Am. J. Pathol.* 154, 1125-1135 (1999)); Leukemia cells that express CXCR4 migrate and adhere to lymph nodes and bone marrow stromal cells that express SDF-1 (Burger et al. *Blood* 94, 3658-3667 (1999); Arai et al. *Eur. J. Haematol.* 64, 323-332 (2000); Bradstock et al. *Leukemia* 14, 882-888 (2000)).

The binding of SDF-1 to CXCR4 has also been implicated in the pathogenesis of atherosclerosis (Abi-Younes et al. *Circ. Res.* 86, 131-138 (2000)), renal allograft rejection (Eitner et al. *Transplantation* 66, 1551-1557 (1998)), asthma and allergic airway inflammation (Yssel et al. *Clinical and Experimental Allergy* 28, 104-109 (1998); *J. Immunol.* 164, 5935-5943 (2000); Gonzalo et al. *J. Immunol.* 165, 499-508 (2000)), Alzheimer's disease (Xia et al. *J. Neurovirology* 5, 32-41 (1999)) and Arthritis (Nanki et al. *J. Immunol.* 164, 5010-5014 (2000)).

In attempting to better understand the relationship between chemokines and their receptors, recent experiments to block the fusion, entry and replication of HIV via the CXCR4 chemokine receptor were carried out through the use of monoclonal antibodies or small molecules that appear to suggest a useful therapeutic strategy (Schols et al., *J. Exp. Med.* 186:1383-1388 (1997); Schols et al., *Antiviral Research* 35:147-156 (1997); Bridger et al. *J. Med. Chem.* 42, 3971-3981 (1999); Bridger et al. "Bicyclam Derivatives as HIV Inhibitors" in *Advances in Antiviral Drug Design* Volume 3, p 161-229; Published by JAI press (1999); Edited by E. De Clercq). Small molecules, such as bicyclams, appear to specifically bind to CXCR4 and not CCR5 (Donzella et al., *Nature Medicine*, 4:72-77 (1998)). These experiments demonstrated interference with HIV entry and membrane fusion into the target cell in vitro. More recently, bicyclams were also shown to inhibit fusion and replication of Feline Immunodeficiency Virus (FIV) that uses CXCR4 for entry (Egberink et al. *J. Virol.* 73, 6346-6352 (1999)).

Additional experiments have shown that the bicyclam dose-dependently inhibits binding of 125I-labeled SDF-1 to CXCR4 and the signal transduction (indicated by an increase in intracellular calcium) in response to SDF-1. Thus, the bicyclam also functioned as an antagonist to the signal transduction resulting from the binding of stromal derived factor or SDF-1α, the natural chemokine to CXCR4. Bicyclams also inhibited HIV gp120 (envelope)-induced apoptosis in non-HIV infected cells (Blanco et al. *Antimicrobial Agents and Chemother.* 44, 51-56 (2000)).

U.S. Pat. Nos. 5,583,131; 5,698,546; 5,817,807; 5,021,409; 6,001,826; and WO 00/02870, which are incorporated herein in their entirety by reference, disclose cyclic compounds that are active against HIV-1 and HIV-2 in in vitro tests. It was subsequently discovered and further disclosed in PCT WO 02/34745 that these compounds exhibit anti-HIV activity by binding to the chemokine receptor CXCR4 expressed on the surface of certain cells of the immune system. This competitive binding thereby protects these target cells from infection by HIV which utilize the CXCR4 receptor for entry. In addition, these compounds antagonize the binding, signaling and chemotactic effects of the natural ligand for CXCR4, the chemokine stromal cell-derived factor 1α (SDF-1). We further disclosed that these novel compounds demonstrate protective effects against HIV infection of target cells by binding in vitro to the CCR5 receptor.

Additionally we have disclosed in U.S. Pat. No. 6,365,583 that these cyclic polyamine antiviral agents described in the above-mentioned patents/patent applications have the effect of enhancing production of white blood cells as well as exhibiting antiviral properties. Thus, these agents are useful for controlling the side-effects of chemotherapy, enhancing the success of bone marrow transplantation, enhancing wound healing and burn treatment, as well as combating bacterial infections in leukemia.

More recently, we disclosed in PCT WO 00/56729, PCT WO 02/22600, PCT WO 02/22599, and PCT WO 02/34745 a series of heterocyclic compounds that exhibit anti-HIV activity by binding to the chemokine receptors CXCR4 and CCR5 expressed on the surface of certain cells of the immune system. This competitive binding thereby protects these target cells from infection by HIV which utilize the CXCR4 or CCR5 receptors for entry. In addition, these compounds antagonize the binding, signaling and chemotactic effects of the natural ligand for CXCR4, the chemokine stromal cell-derived factor 1α (SDF-1) and/or the natural ligand for CCR5, the chemokine RANTES.

The chemokine receptor, CXCR4 has been found to be essential for the vascularization of the gastrointestinal tract (Tachibana, et al., *Nature* (1998) 393:591-594) as well as haematopoiesis and cerebellar development (Zou, et al., *Nature* (1998) 393:591-594). Interference with any of these important functions served by the binding of pre-B-cell growth-stimulating factor/stromal derived factor (PBSF/SDF-1) to the CXCR4 chemokine receptor results in lethal deficiencies in vascular development, haematopoiesis and cardiogenesis. Similarly, fetal cerebellar development appears to rely upon the effective functioning of CXCR4 in neuronal cell migration and patterning in the central nervous system. This G-protein-coupled chemokine receptor appears to play a critical role in ensuring the necessary patterns of migration of granule cells in the cerebellar anlage.

Herein, we disclose compounds that have unique chemical attributes and that exhibit protective effects against HIV infection of target cells by binding to chemokine receptor CXCR4 or CCR5 in a similar manner to the previously disclosed macrocyclic compounds. In addition, these compounds antagonize the binding, signaling and chemotactic effects of the natural ligand for CXCR4, the chemokine stromal cell-derived factor 1α (SDF-1) and/or the natural ligand for CCR5 (the chemokine RANTES).

Further, the compounds of the invention have the effect of increasing progenitor cells and/or stem cells. Even further, the compounds have the effect of enhancing production of white blood cells as well as exhibiting antiviral properties. Thus, these agents are useful where treatment affects the activities within the bone marrow resulting in leukopenia, thus controlling the side-effects of chemotherapy, radiotherapy, enhancing the success of bone marrow transplantation, enhancing wound healing and burn treatment, as well as combating bacterial infections in leukemia. Further, the compounds of the invention effect regeneration of cardiac tissue.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are hereby incorporated in their entirety by reference herein.

DISCLOSURE OF THE INVENTION

The present invention provides novel compounds that bind CXCR4 chemokine receptors and interfere with the binding of the natural ligand thereto. The compounds of the present invention are useful as agents demonstrating protective effects on target cells from HIV infection, and which are useful to treat rheumatoid arthritis. Embodiments of the present invention are compounds that act as antagonists or agonists of chemokine receptors, which are useful as agents capable of reconstituting the immune system by increasing the level of $CD4^+$ cells; as antagonist agents of apoptosis in immune cells, such as $CD8^+$ cells, and neuronal cells; as antagonist agents of migration of human bone marrow B lineage cells to stromal-derived factor 1, as well as other biological activities related to the ability of these compounds to inhibit the binding of chemokines to their receptors.

The present invention relates to compounds having the formula

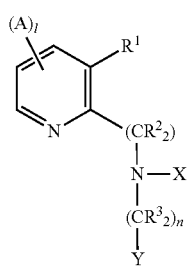

(1)

and the salts, prodrugs and stereoisomeric forms thereof, wherein X is $(CR^3{}_2)_o$—$(CR^3$=$CR^3)_p$—$(CR^3{}_2)_q$—$NR^5{}_2$; $(CR^3{}_2)_r$—$R^4$; a monocyclic or bicyclic ring optionally containing N, O or S; or a benzyl, each of which is optionally substituted; provided said benzyl is not substituted with a 5-6 membered aryl or heteroaryl via an L-NH-L linker, where each L is a bond, CO, $SO_2$ or $CH_2$;

Y is an optionally substituted nitrogen-containing monocyclic or bicyclic aromatic or partially aromatic moiety;

A and $R^1$ are each a non-interfering substituent, and provided that two As do not form an additional ring;

$R^2$ and $R^3$ are independently H or an optionally substituted alkyl;

$R^4$ is an optionally substituted heterocyclic ring; or a hetero compound containing at least one =O, SO, C=N, cyano, NROR, or halo, wherein said hetero compound is optionally substituted with a heterocyclic ring;

$R^5$ is H or alkyl;

wherein at least one of $R^1$ and $R^2$ is not H; and wherein $R^1$ and $R^2$ may be connected to form an additional ring if Y does not contain a 2-imidazoyl residue optionally connected to an additional ring;

l and n are independently 0-4;

p is 0-1;

o and q are independently 1-4;

r is 1-6;

provided that if X is $(CR^3{}_2)_r$—$R^4$, r is at least two if $R^4$ is 2-pyridinyl, quinolinyl, imidazolyl or furan; and further provided that said compound is not (1-pyridin-2-ethyl)-(2-pyridin-2-yl-ethyl)-pyridin-2-ylmethyl-amine.

In general, a "noninterfering substituent" is a substituent whose presence does not destroy the ability of the compound of Formula 1 to behave as a chemokine. Specifically, the presence of the substituent does not destroy the effectiveness of the compound. Because the compounds of the present invention have been shown to inhibit HIV replication, and specifically to interact with the CXCR4 receptor, the compounds of the invention are shown to be effective in treating conditions which require modulation of CXCR4 and CCR5 mediated activity.

Suitable noninterfering substituents include alkyl ($C_{1-10}$), alkenyl ($C_{2-10}$), alkynyl ($C_{2-10}$), aryl (5-12 members), arylalkyl, arylalkenyl, or arylalkynyl, each of which may optionally contain one or more heteroatoms selected from O, S, and N and each of which may further be substituted, for example, by =O; or optionally substituted forms of acyl, arylacyl, alkyl- alkenyl-, alkynyl- or arylsulfonyl and forms thereof which contain heteroatoms in the alkyl, alkenyl, alkynyl or aryl moieties. Other noninterfering substituents include halo, CN, $CF_3$, $NO_2$, OR, SR, $NR_2$, COOR, and $CONR_2$, where R is H or alkyl, alkenyl, alkynyl or aryl. Where the substituted atom is C, the substituents may include, in addition to the substituents listed above, halo, OOCR, NROCR, where an R is H or a substituent set forth above.

In the above formula 1, each optionally substituted moiety is substituted with one or more non-interfering substituents. For example, each optionally substituted moiety may be substituted with one or more inorganic substituents, halo; OR; $C_{1-6}$ alkyl or $C_{2-6}$ alkenyl optionally containing one or more N, O, or S, and optionally substituted with halo; cyano; optionally substituted carbonyl; $NR_2$; C=$NR_2$; an optionally substituted carbocyclic or heterocyclic ring; or an optionally substituted aryl or heteroaryl.

In other aspects, the invention is directed to pharmaceutical compositions containing at least one compound of Formula 1, and to methods of ameliorating conditions that are modulated by the CXCR4 receptor or the CCR5 receptor. Such conditions include HIV infection, diseases associated with inflammation, diseases that are associated with immunosuppression and certain tumors.

In addition, the invention is directed to methods of treating animal subjects, in particular, veterinary and human subjects, to enhance or elevate the number of progenitor cells and/or stem cells. The progenitor and/or stem cells may be harvested and used in cell transplantation. In one embodiment, bone marrow progenitor and/or stem cells are mobilized for myocardial repair. Further, the invention is directed to methods of treating animal subjects, in particular, veterinary and human patients, who are defective in white blood cell (WBC) count, or who would benefit from elevation of WBC levels using the compounds disclosed herein. Moreover, the invention is directed to methods of effecting regeneration of cardiac tissue in a subject in need of such regeneration using the disclosed compounds.

MODES OF CARRYING OUT THE INVENTION

Figure 1:
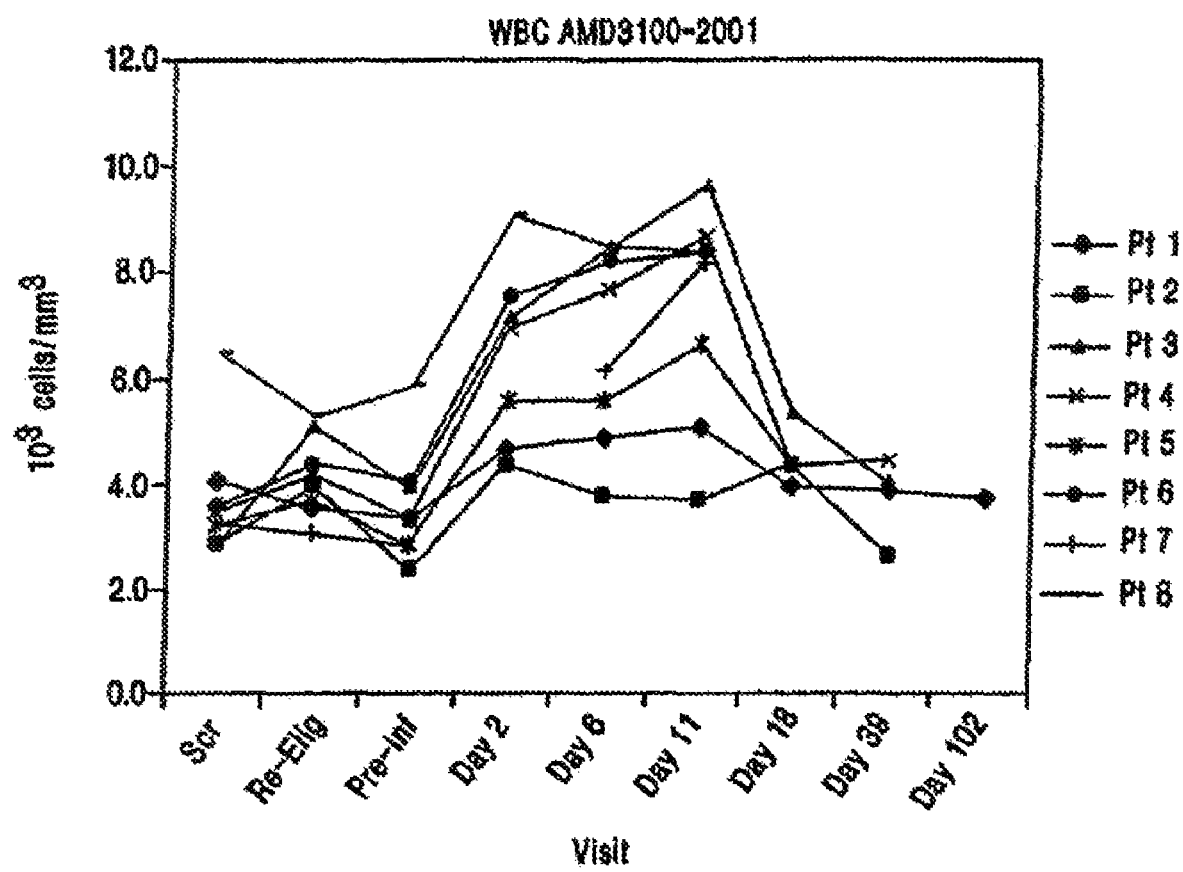
FIG. 1 is a graph showing the response of individual human patients to intravenous administration of AMD 3100.

The invention provides compounds described above of Formula 1 which are chemokines and thus modulators of chemokine receptors.

In more detail, the compounds bind chemokine receptors and interfere with the binding of the natural ligand thereto, and demonstrate protective effects on target cells from HIV infection. The compounds are also useful as antagonists or agonists of chemokine receptors, and are thus capable of reconstituting the immune system by increasing the level of CD4$^+$ cells; as antagonist agents of apoptosis in immune cells, such as CD8$^+$ cells, and neuronal cells; as antagonist agents of migration of human bone marrow B lineage cells to stromal-derived factor 1, as well as other biological activities related to the ability of these compounds to inhibit the binding of chemokines to their receptors.

The compounds also inhibit the binding and signaling induced by the natural ligand, the chemokine SDF-1. While not wishing to be bound by any theory, the compounds of Formula 1 which inhibit the binding of SDF-1 to CXCR4 effect an increase in stem and/or progenitor cells by virtue of such inhibition. Enhancing the stem and/or progenitor cells in blood is helpful in treatments to alleviate the effects of protocols that adversely affect the bone marrow, such as those that result in leukopenia. These are known side-effects of chemotherapy and radiotherapy. The compounds of Formula 1 also enhance the success of bone marrow transplantation, enhance wound healing and burn treatment, and aid in restoration of damaged organ tissue. They also combat bacterial infections that are prevalent in leukemia. The compounds of Formula 1 are used to mobilize and harvest CD34+ cells via apheresis with and without combinations with other mobilizing factors. The harvested cells are used in treatments requiring stem cell transplantations.

As used herein, the term "progenitor cells" refers to cells that, in response to certain stimuli, can form differentiated hematopoietic or myeloid cells. The presence of progenitor cells can be assessed by the ability of the cells in a sample to form colony-forming units of various types, including, for example, CFU-GM (colony-forming units, granulocyte-macrophage); CFU-GEMM (colony-forming units, multipotential); BFU-E (burst-forming units, erythroid); HPP-CFC (high proliferative potential colony-forming cells); or other types of differentiated colonies which can be obtained in culture using known protocols.

As used herein, "stem" cells are less differentiated forms of progenitor cells. Typically, such cells are often positive for CD34. Some stem cells do not contain this marker, however. These CD34+ cells can be assayed using fluorescence activated cell sorting (FACS) and thus their presence can be assessed in a sample using this technique.

In general, CD34+ cells are present only in low levels in the blood, but are present in large numbers in bone marrow. While other types of cells such as endothelial cells and mast cells also may exhibit this marker, CD34 is considered an index of stem cell presence.

Chemokine antagonists that interfere in the binding of a chemokine to its receptor are also useful to reconstitute the immune system by increasing the level of CD4$^+$ cells (Biard-Piechaczyk, et al., *Immunol. Lett.*, 70:1-3 1999); as antagonist agents of apoptosis in immune cells, such as CD8$^+$ cells (Herbin, et al., *Nature* 395: 189-193, 1998), and as antagonist agents of apoptosis in neuronal cells (Ohagen et al., *J. of Virol.*, 73: 897-906, 1999; and Hesselgesser, et al., *Curr. Biol.* 8: 595-598, 1998). Chemokine receptor antagonist agents also inhibit the migration of human bone marrow B lineage cells to stromal-derived factor 1 (See, for example: E. Fedyk, et al., *J of Leukocyte Biol.*, 66:667-783, 1999).

The invention includes pharmaceutical compositions comprising a therapeutically effective amount of a compound of Formula 1 along with at least one excipient, and methods of treating diseases of the human body or the bodies of other mammals with such compositions. The invention provides a method for blocking or interfering with the binding by a chemokine receptor with its natural ligand, comprising contacting of said chemokine receptor with an effective amount of the compound according to Formula 1. Also included is a method of protecting target cells possessing chemokine receptors, the binding to which by a pathogenic agent results in disease or pathology, comprising administering to a mammalian subject a pharmaceutical composition comprising a therapeutically effective amount of the compound according to Formula 1. The invention includes the use of a compound of Formula 1 in the manufacture of a medicament for the treatment of a disease in which blocking or interfering with binding of a chemokine receptor with its natural ligand is advantageous. The compound is formulated into a composition in amount corresponding to a therapeutically effective amount of a compound of Formula 1.

The Invention Compounds

The invention compounds are described generally by Formula 1 which is reproduced below for purposes of the present discussion.

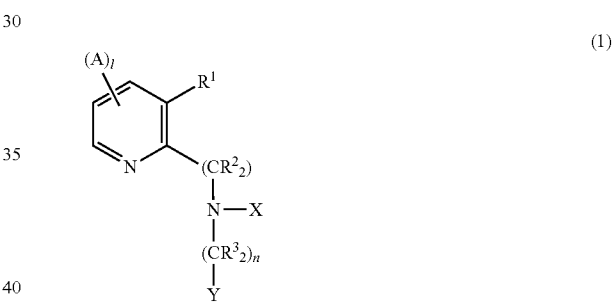

(1)

As set forth above, the substituent X can either be hydrogen or a substituent comprising at least one nitrogen atom and has in total 1-30 atoms that are other than hydrogen. Typically, embodiments of X include alkyl (1-10C), alkenyl (2-10C), or alkynyl (2-10C), aryl (5-12 ring members), arylalkyl, arylalkenyl, or arylalkynyl, each of which may optionally contain one or more heteroatom selected from O, S and N and each of which may further be substituted, including substitution by =O (such that the alkyl substituent become acyl, for instance) and wherein such further substituents may include, for example, OR, SR, NR$_2$ or halo, OOCR, NRCR, and the like, wherein R is H or a substituent such as those set forth above, but typically alkyl (1-6C). The alkyl, alkenyl, and alkynyl substituents may be straight or branched chain and may also be cyclic.

In the above Formula 1, X may be a disubstituted benzyl. In another example, X is a monocylic or bicyclic ring optionally containing N, O or S. Examples include but are not limited to cyclohexyl, piperidine, 8-aza-bicyclo[3.2.1]octane or 3-aza-bicyclo[3.2.1]octane.

In the above Formula 1, X may have the formula:

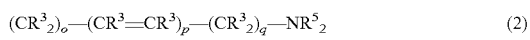

(2)

wherein each R$^3$ is H or an optionally substituted alkyl; and R$^5$ is H or alkyl.

In the above Formula 2, each of $R^3$ and $R^5$ may independently be H. In one example, p is 0. In another example, o and q together are 2-6.

In the above Formula 1, X may have the formula:

$$(CR^3{}_2)_r\text{—}R^4 \qquad (3)$$

wherein $R^4$ is an optionally substituted heterocyclic ring; or a hetero compound containing at least one =O, SO, C=N, cyano, NROR, or halo.

In the above Formula 3, $R^4$ may be an acyclic nitrogen-containing hetero compound. For example, $R^4$ may comprise a urea, hydroxyurea, sulfamide, acetamide, guanidine, cyanamide, hydroxylamine, cyanamide, imidazolidine-2-one, or a nicotinamide moiety. In another example, $R^4$ may be a nitrogen-containing heterocyclic ring or heteroaryl, such as azetidine, pyrrolidinyl, pyridinyl, thiophenyl, imidazolyl, or benzimidazolyl.

In the above Formula 1, Y may be a nitrogen-containing monocyclic or bicyclic aromatic or partially aromatic moiety. Particularly preferred embodiments of Y are those wherein Y is a monocyclic aromatic moiety containing a ring nitrogen at the position adjacent that attached to the remainder of the molecule. Such moieties include pyridine, pyrimidine, pyrazine, pyridazine, and the like. Y may also be a 5-membered ring containing nitrogen, preferably at the position adjacent the position attached to the remainder of the molecule and may further be fused to an additional ring; thus, Y also includes oxazole, thiazole, imidazole, pyrrole, and the like and may be fused to an additional ring, as an indole, benzimidazole, benzthiazole, and the like. Additional embodiments of Y include an isoquinoline or the tetrahydroquinoline system wherein the quinoline system is attached at position 8 to the remainder of the molecule.

In the above formula 1, A and $R^1$ substituents are generically defined as for X but preferred embodiments of $R^1$ include halo, optionally substituted aryl, arylalkyl, alkyl, alkoxy, $CF_3$, wherein preferred substituents on alkyl include OR, $NR_2$, SR, halo where R is H or alkyl (1-6C). Preferably, 1 is 0 or 2, more preferably 0 or 1.

Preferred embodiments of $R^2$ and $R^3$ include H, alkyl, and alkenyl especially H and methyl.

As used herein, the term "alkyl" encompasses a substituted or unsubstituted straight, branched or cycloalkyls. Examples of optionally substituted alkyl groups include methyl, ethyl, propyl, etc. and including cycloalkyls such as cyclopropyl, cyclobutyl, cyclopentyl, cyclohexyl, cycloheptyl, etc.; examples of optionally substituted alkenyl groups include allyl, crotyl, 2-pentenyl, 3-hexenyl, 2-cyclopentenyl, 2-cyclohexenyl, 2-cyclopentenylmethyl, 2-cyclohexenylmethyl, etc.; $C_{1-6}$ alkyl and alkenyl are preferred.

Examples of halogen include fluorine, chlorine, bromine, iodine, etc., with fluorine and chlorine preferred.

Examples of optionally substituted hydroxyl and thiol groups include optionally substituted alkyloxy or alkylthio (e.g., $C_{1-10}$ alkyl) such as methyl, ethyl, propyl, isopropyl, butyl, isobutyl, sec-butyl, tert-butyl, pentyl, cyclopropyl, cyclobutyl, cyclopentyl, cyclohexyl, cycloheptyl, etc.); an optionally substituted arylalkyloxy or arylalkylthio (e.g., phenyl-$C_{1-4}$ alkyl, e.g., benzyl, phenethyl, etc.). Where there are two adjacent hydroxyl or thiol substituents, the heteroatoms may be connected via an alkylene group such as $O(CH_2)_nO$ and $S(CH_2)_nS$ (where n=1-5). Examples include methylenedioxy, ethylenedioxy, etc. Oxides of thio-ether groups such as sulfoxides and sulfones are also envisioned.

Examples of optionally substituted hydroxyl groups also include optionally substituted $C_{2-4}$ alkanoyl (e.g., acetyl, propionyl, butyryl, isobutyryl, etc.), $C_{1-4}$ alkylsulfonyl (e.g., methanesulfonyl, ethanesulfonyl, etc.) and an optionally substituted aromatic and heterocyclic carbonyl group including benzoyl, pyridinecarbonyl etc.

Substituents on optionally substituted amino groups may bind to each other to form a cyclic amino group (e.g., 5- to 6-membered cyclic amino, etc. such as tetrahydropyrrole, piperazine, piperidine, pyrrolidine, morpholine, thiomorpholine, pyrrole, imidazole, etc.). Said cyclic amino group may have a substituent, and examples of the substituents include halogen (e.g., fluorine, chlorine, bromine, iodine, etc.), nitro, cyano, hydroxy group, thiol group, amino group, carboxyl group, an optionally halogenated $C_{1-4}$ alkyl (e.g., trifluoromethyl, methyl, ethyl, etc.), an optionally halogenated $C_{1-4}$ alkoxy (e.g., methoxy, ethoxy, trifluoromethoxy, trifluoroethoxy, etc.), $C_{2-4}$ alkanoyl (e.g., acetyl, propionyl, etc.), $C_{1-4}$ alkylsulfonyl (e.g., methanesulfonyl, ethanesulfonyl, etc.) the number of preferred substituents are 1 to 3.

An amino group may also be substituted once or twice (to form a secondary or tertiary amine) with a group such as an optionally substituted alkyl group including $C_{1-10}$ alkyl (e.g., methyl, ethyl propyl etc.); an optionally substituted alkenyl group such as allyl, crotyl, 2-pentenyl, 3-hexenyl, etc., or an optionally substituted cycloalkyl group such as cyclopropyl, cyclobutyl, cyclopentyl, cyclohexyl, cycloheptyl, etc. In these cases, $C_{1-6}$ alkyl, alkenyl and cycloalkyl are preferred. The amine group may also be optionally substituted with an aromatic or heterocyclic group, aralkyl (e.g., phenyl$C_{1-4}$alkyl) or heteroalkyl for example, phenyl, pyridine, phenylmethyl (benzyl), phenethyl, pyridinylmethyl, pyridinylethyl, etc. The heterocyclic group may be a 5 or 6 membered ring containing 1-4 heteroatoms.

An amino group may be substituted with an optionally substituted $C_{2-4}$ alkanoyl, e.g., acetyl, propionyl, butyryl, isobutyryl etc., or a $C_{1-4}$alkylsulfonyl (e.g., methanesulfonyl, ethanesulfonyl, etc.) or a carbonyl or sulfonyl substituted aromatic or heterocyclic ring, e.g., benzenesulfonyl, benzoyl, pyridinesulfonyl, pyridinecarbonyl etc. The heterocycles are as defined above.

Examples of optionally substituted carbonyl groups, or sulfonyl groups include optionally substituted forms of such groups formed from various hydrocarbyls such as alkyl, alkenyl and 5- to 6-membered monocyclic aromatic group (e.g., phenyl, pyridyl, etc.), as defined above.

The compounds may be supplied as "pro-drugs", that is, protected forms, which release the compound after administration to a subject. For example, the compound may carry a protective group which is split off by hydrolysis in body fluids, e.g., in the bloodstream, thus releasing active compound or is oxidized or reduced in body fluids to release the compound. A discussion of pro-drugs may be found in "Smith and Williams' Introduction to the Principles of Drug Design," H. J. Smith, Wright, Second Edition, London 1988.

The compounds may also be supplied as salts with organic or inorganic acids or bases that are nontoxic. Non-toxic in the present sense has to be considered with reference to the prognosis for the infected patient without treatment. Examples of inorganic bases with alkali metal hydroxides (e.g., sodium hydroxide, potassium hydroxide, etc.), alkaline earth metal hydroxides (e.g., of calcium, magnesium, etc.), and hydroxides of aluminum, ammonium, etc. Examples of organic bases include trimethylamine, triethylamine, pyridine, picoline, ethanolamine, diethanolamine, triethanolamine, dicyclohexylamine, N,N'-dibenzylethylenediamine, etc. Examples of inorganic acids include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

All of the compounds of the invention may contain a chiral center. If so, the invention includes mixtures of stereoisomers, individual stereoisomers, and enantiomeric mixtures, and mixtures of multiple stereoisomers. In short, the compound may be supplied in any desired degree of chiral purity.

Utility and Administration

The invention is directed to compounds of Formula 1 that modulate chemokine receptor activity. Chemokine receptors include but are not limited to CCR1, CCR2, CCR3, CCR4, CCR5, CXCR3, and CXCR4.

In one embodiment, the invention provides compounds of Formula 1 that demonstrate protective effects on target cells from HIV infection by binding specifically to the chemokine receptor thus affecting the binding of a natural ligand to the CCR5 and/or CXCR4 of a target cell.

In another embodiment, the compounds of the present invention are useful as agents which affect chemokine receptors, such as CCR1, CCR2, CCR3, CCR4, CCR5, CXCR3, CXCR4 where such chemokine receptors have been correlated as being important mediators of many inflammatory as well as immunoregulatory diseases.

Other diseases that are also implicated with chemokines as mediators include angiogenesis, and tumorigenesis such as brain, and breast tumors. Thus, a compound that modulates the activity of such chemokine receptors is useful for the treatment or prevention of such diseases.

The term "modulators" as used herein is intended to encompass antagonist, agonist, partial antagonist, and or partial agonist, i.e., inhibitors, and activators. In one embodiment of the present invention, compounds of Formula 1 demonstrate a protective effect against HIV infection by inhibiting the binding of HIV to a chemokine receptor such as CCR5 and/or CXCR4, of a target cell. Such modulation is obtained by a method which comprises contacting a target cell with an amount of the compound which is effective to inhibit the binding of the virus to the chemokine receptor.

Compounds that inhibit chemokine receptor activity and function may be used for the treatment of diseases that are associated with inflammation, including but are not limited to, inflammatory or allergic diseases such as asthma, allergic rhinitis, hypersensitivity lung diseases, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, systemic lupus erythematosus, myastenia gravis, juvenile onset diabetes; glomerulonephritis, autoimmune throiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinophilic myotis, eosiniphilic fasciitis; and cancers.

In addition compounds that activate or promote chemokine receptor function are used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round worms); Trichuriasis, Enterobiasis, Ascariasis, Hookworm, Strongyloidiasis, Trichinosis, filariasis; trematodes; visceral worms, visceral larva migtrans (e.g., Toxocara), eosinophilic gastroenteritis (e.g., *Anisaki* spp., *Phocanema* ssp.), cutaneous larva migrans (*Ancylostona braziliense, Ancylostoma caninum*); the malaria-causing protozoan *Plasmodium vivax*, Human cytomegalovirus, *Herpesvirus saimiri*, and Kaposi's sarcoma herpesvirus, also known as human herpesvirus 8, and poxvirus *Moluscum contagiosum*.

Typical conditions which may be ameliorated or otherwise benefited by the method of the invention include hematopoietic disorders, such as aplastic anemia, leukemias, drug-induced anemias, and hematopoietic deficits from chemotherapy or radiation therapy. The method of the invention is also useful in enhancing the success of transplantation during and following immunosuppressive treatments as well as in effecting more efficient wound healing and treatment of bacterial inflammation. The method of the present invention is further useful for treating subjects who are immunocompromised or whose immune system is otherwise impaired. Typical conditions which are ameliorated or otherwise benefited by the method of the present invention, include those subjects who are infected with a retrovirus and more specifically who are infected with human immunodeficiency virus (HIV). The method of the invention thus targets a broad spectrum of conditions for which elevation of progenitor cells and/or stem cells in a subject would be beneficial or, where harvesting of progenitor cells and/or stem cell for subsequent stem cell transplantation would be beneficial. In addition, the method of the invention targets a broad spectrum of conditions characterized by a deficiency in white blood cell count, or which would benefit from elevation of said WBC count.

The compounds of the invention, as they are polyamines, may be administered prepared in the forms of their acid addition salts or metal complexes thereof. Suitable acid addition salts include salts of inorganic acids that are biocompatible, including HCl, HBr, sulfuric, phosphoric and the like, as well as organic acids such as acetic, propionic, butyric and the like, as well as acids containing more than one carboxyl group, such as oxalic, glutaric, adipic and the like. Typically, at physiological pH, the compounds of the invention will be in the forms of the acid addition salts. Particularly preferred are the hydrochlorides. In addition, when prepared as purified forms, the compounds may also be crystallized as the hydrates.

The compounds of the invention may be prepared in the form of prodrugs, i.e., protected forms which release the compounds of the invention after administration to the subject. Typically, the protecting groups are hydrolyzed in body fluids such as in the bloodstream thus releasing the active compound or are oxidized or reduced in vivo to release the active compound. A discussion of prodrugs is found in *Smith and Williams Introduction to the Principles of Drug Design*, Smith, H. J.; Wright, 2$^{nd}$ ed., London (1988).

The compounds of the invention may be administered as sole active ingredients, as mixtures of various compounds of Formula 1, and/or in admixture with additional active ingredients that are therapeutically or nutritionally useful, such as antibiotics, vitamins, herbal extracts, anti-inflammatories, glucose, antipyretics, analgesics, granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin, growth related oncogene or chemotherapy and the like. In addition, the compounds of the invention may be administered in admixture with additional active ingredients that are therapeutically or nutritionally useful, such as antibiotics, vitamins, herbal extracts, anti-inflammatories, glucose, antipyretics, analgesics, and the like.

The compounds of the invention may be formulated for administration to animal subject using commonly understood formulation techniques well known in the art. Formulations which are suitable for particular modes of administration and for compounds of the type represented by those of Formula 1 may be found in *Remington's Pharmaceutical Sciences*, latest edition, Mack Publishing Company, Easton, Pa.

Preferably, the compounds are administered by injection, most preferably by intravenous injection, but also by subcutaneous or intraperitoneal injection, and the like. Additional parenteral routes of administration include intramuscular and intraarticular injection. For intravenous or parenteral administration, the compounds are formulated in suitable liquid form with excipients as required. The compositions may contain liposomes or other suitable carriers. For injection intravenously, the solution is made isotonic using standard preparations such as Hank's solution.

Besides injection, other routes of administration may also be used. The compounds may be formulated into tablets, capsules, syrups, powders, or other suitable forms for administration orally. By using suitable excipients, these compounds may also be administered through the mucosa using suppositories or intranasal sprays. Transdermal administration can also be effected by using suitable penetrants and controlling the rate of release.

The formulation and route of administration chosen will be tailored to the individual subject, the nature of the condition to be treated in the subject, and generally, the judgment of the attending practitioner.

Suitable dosage ranges for the compounds of Formula 1 vary according to these considerations, but in general, the compounds are administered in the range of about 0.1 µg/kg-5 mg/kg of body weight; preferably the range is about 1 µg/kg-300 µg/kg of body weight; more preferably about 10 µg/kg-100 µg/kg of body weight. For a typical 70-kg human subject, thus, the dosage range is from about 0.7 µg-350 mg; preferably about 700 µg-21 mg; most preferably about 700 µg-7 mg. Dosages may be higher when the compounds are administered orally or transdermally as compared to, for example, i.v. administration.

The compounds may be administered as a single bolus dose, a dose over time, as in i.v. or transdermal administration, or in multiple dosages.

In addition to direct administration to the subject, the compounds of Formula 1 can be used in ex vivo treatment protocols to prepare cell cultures which are then used to replenish the blood cells of the subject. Ex vivo treatment can be conducted on autologous cells harvested from the peripheral blood or bone marrow or from allografts from matched donors. The concentration of the compound or compounds of Formula 1 alone or in combination with other agents, such as macrophage inflammatory protein is a matter of routine optimization.

Compounds of the present invention further may be used in combination with any other active agents or pharmaceutical compositions where such combined therapy is useful to modulate chemokine receptor activity and thereby prevent and treat inflammatory and immunoregulatory diseases.

The compounds may further be used in combination with one or more agents useful in the prevention or treatment of HIV. Examples of such agents include:

(1) nucleotide reverse transcriptase inhibitor such as tenofovir disoproxil fumarate; lamivudine/zidovudine; abacavir/lamivudine/zidovudine; emtricitabine; amdoxovir; alovudine; DPC-817; SPD-756; SPD-754; GS7340; ACH-126,443 (beta)-L-F d4C; didanosine, zalcitabine, stavudine, adefovir, adefovir dipivoxil, fozivudine todoxil, etc.;

(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, TMC-125; DPC-083; capravarine; calanolide A; SJ-3366 series, etc.;

(3) protease inhibitors such as saquinavir, lopinavir/ritonavir, atazanavir, fosamprenavir, tipranavir, TMC-114, DPC-684, indinavir, nelfinavir, amprenavir, palinavir, lasinavir, etc.;

(4) entry inhibitors such as T-20; T-1249; PRO-542; PRO-140; TNX-355; BMS-806 series; and 5-Helix;

(5) CCR5-receptor inhibitors such as Sch-C (or SCH351125); Sch-D, and SCH350634; TAK779; UK 427, 857 and TAK 449;

(6) Integrase inhibitors such as L-870,810; GW-810781 (S-1360); and (7) Budding inhibitors such as PA-344; and PA-457.

Combinations of compounds of the present invention with HIV agents is not limited to (1), (2), and or (3), but includes combination with any agent useful for the treatment of HIV. Combinations the compounds of the invention and other HIV agents may be administered separately or in conjunction. The administration of one agent may be prior to, concurrent to, or subsequent to the administration of other agent(s).

Like the compounds of the present invention, AMD3100 is an antagonist with the CXCR4 chemokine receptor (Gerlach, et al., *J. Biol. Chem.* (2001) 276:14153-14160). These compounds interfere with the binding of bone marrow stromal cell derived SDF-1 with CXCR4 on stem cells which leads to the release of hematopoietic stem cells from bone marrow into the circulation (Broxmeyer, et al., *Blood* (2001) 98:811a (Abstract)). In a Phase 1 study at the University of Washington, Seattle, a single dose of 80 µg/kg of AMD-3100 resulted in a WBC count of 17,000/µl and a peak 6-fold increase in circulating CD34+ progenitor/stem cells at the 6 hour time point (Liles, et al., *Blood* (2001) 98:737a (Abstract)). In another recent study mice were injected with rhG-CSF and recombinant rat Stem Cell Factor (rrSCF) in order to mobilize large numbers of bone marrow stem cells into the circulation and then we induced a heart attack. The combination of rrSCF and rhG-CSF provides a peak number of circulating stem cells after 5 daily injections. At 27 days post surgery there was a 68% improvement in survival in the treated group versus the controls. At this time the dead tissue was replaced with regenerating myocardium and all functional parameters tested were improved compared with controls (Orlic, et al., *PNAS* (2001) 98:10344-10349).

Thus, the compounds of the invention are useful to stimulate the production and proliferation of stem cells and progenitor cells.

Subjects that will respond favorably to the method of the invention include medical and veterinary subjects generally, including human patients. Among other subjects for whom the methods of the invention is useful are cats, dogs, large animals, avians such as chickens, and the like. In general, any subject who would benefit from an elevation of progenitor cells and/or stem cells, or whose progenitor cells and/or stem cells are desirable for stem cell transplantation are appropriate for administration of the invention method.

Typical conditions which may be ameliorated or otherwise benefited by stimulation of hematopoiesis, include hematopoietic disorders, such as aplastic anemia, leukemias, drug-induced anemias, and hematopoietic deficits from chemotherapy or radiation therapy. The compounds of the invention are also useful in enhancing the success of transplantation during and following immunosuppressive treatments as well as in effecting more efficient wound healing and treatment of bacterial inflammation, and for treating subjects who are immuno-compromised or whose immune system is otherwise impaired. Typical conditions which are ameliorated or otherwise benefited by hematopoiesis stimulation include those subjects who are infected with a retrovirus and more specifically who are infected with human immunodeficiency virus (HIV). The compounds of the invention thus target a broad spectrum of conditions for which elevation of progenitor cells and/or stem cells in a subject would be beneficial or, where harvesting of progenitor cells and/or stem cell for subsequent stem cell transplantation or transfusion would be beneficial.

The invention compounds are also administered to regenerate myocardium by mobilizing bone marrow stem cells.

A broad range of routes of administration are contemplated. Thus, the compounds according to the present invention may be administered by oral, intramuscular, intraperitoneal, intravenous, intracisternal injection or infusion, subcutaneous injection, transdermal or transmucosal administration or by implant. They may also be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The compounds of the invention are used to treat animals, including mice, rats, horses, cattle, sheep, dogs, cats, and monkeys, and avians such as chickens and the like. The compounds of the invention are also effective for use in humans. In general, any subject who would benefit from an elevation of progenitor cells and/or stem cells, or whose progenitor cells and/or stem cells are desirable for stem cell transplantation are appropriate for administration of the invention method and/or any subject who has a WBC deficiency or, more generally, who would profit from the elevation of white blood cell count, or who would benefit from the regeneration of cardiac tissue is appropriate for administration of the invention method.

The invention also relates to a pharmaceutical composition comprising a pharmaceutically acceptable carrier or diluent and an effective amount of compound of Formula 1. The compounds may be administered alone or as an admixture with a pharmaceutically acceptable carrier (e.g., solid formulations such as tablets, capsules, granules, powders, etc.; liquid formulations such as syrups, injections, etc.) may be orally or non-orally administered. Examples of non-oral formulations include injections. drops, suppositories, pessaryies.

In the treatment or prevention of conditions which require chemokine receptor modulation an appropriate dosage level will generally be about 0.01 to 500 mg per kg subject body weight per day which can be administered in singe or multiple doses. Preferably, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

The following examples are offered to illustrate but not to limit the invention.

EXPERIMENTAL

The intermediate 8-amino-5,6,7,8-tetrahydroquinoline was prepared according to the procedures described in Bridger, et al. PCT/CA00/00321. The intermediates 1-(2-trimethylsilanyl-ethoxymethyl)-1H-benzimidazole-2-carbaldehyde; 6,7-dihydro-5H-quinolin-8-one, 4-(1,3-dioxo-1,3-dihydro-isoindol-2-yl)-butyraldehyde; 2-[4-(5,6,7,8-tetrahydro-quinolin-8-ylamino)-butyl]-isoindole-1,3-dione and N-(tert-butoxycarbonyl)-3-amino-propionaldehyde were prepared according to the procedures described in PCT/US02/41407. The intermediate 2-bromomethyl-5-cyanobenzoic acid methyl ester was prepared according to the procedures described in PCT/US01/29590. The intermediate 1-N-tert-butoxycarbonyl-2-chloromethylbenzimidazole was prepared as described by An et al., *Tetrahedron* 1998, 54, 3999-4012.

General Procedures

General Procedure A: N-Alkylation with Mesylates, Alkyl or Benzyl Halides

To a solution of amine (1-1.4 equivalents), DIPEA (or $K_2CO_3$) (1.5-2 equivalents) and KI (0.05-0.16 equivalent) in $CH_3CN$ or DMF (concentration ~0.1-0.2 M) was added the mesylate or alkyl or benzyl halide (such as 1-N-tert-butoxycarbonyl-2-chloromethylbenzimidazole) (1-1.4 equivalents) and the mixture stirred at 50-70° C. for 3-25 hours, as monitored by analytical thin layer chromatography. In a standard work-up, the reaction mixture was cooled, diluted with $CH_2Cl_2$ (10 mL/mmol amine) and poured into either saturated aqueous $NaHCO_3$ or brine (10 mL/mmol alcohol). The phases were separated and the aqueous phase extracted with $CH_2Cl_2$ (3×10 mL/mmol amine). The combined organic phases were dried ($Na_2SO_4$ or $MgSO_4$) and concentrated under reduced pressure. The crude material was purified by chromatography to afford the desired N-alkylated product.

General Procedure B: Direct Reductive Amination with $NaBH(OAc)_3$ or $NaBH_4$

To a stirred solution of the amine (1 equivalent) in $CH_2Cl_2$ (concentration ~0.2 M), at room temperature, was added the carbonyl compound (~1-2 equivalents), glacial HOAc (0-2 equivalents) and $NaBH(OAc)_3$ (~1.5-3 equivalents) and the resultant solution stirred at room temperature. In a standard work-up, the reaction mixture was poured into either saturated aqueous $NaHCO_3$ or 1.0 M aqueous NaOH (10 mL/mmol amine). The phases were separated and the aqueous phase extracted with $CH_2Cl_2$ (3×10 mL/mmol amine). The combined organic phases were dried ($Na_2SO_4$) and concentrated under reduced pressure. The crude material was purified by chromatography.

Similarly, to a stirred solution of the amine (1 equivalent) in anhydrous MeOH (concentration ~0.1 M), at room temperature, was added the carbonyl compound (1 equivalent). The resultant solution was stirred at room temperature or heated to reflux for 4-24 hours. $NaBH_4$ (1-2 equivalents) was added and the resultant mixture stirred at room temperature for ~20 minutes. In a standard work-up, the reaction mixture was concentrated, dissolved in $CH_2Cl_2$, washed consecutively with saturated aqueous $NaHCO_3$ and brine. The aqueous layers were extracted with $CH_2Cl_2$ (2×) and the combined organic extracts were dried ($MgSO_4$) and concentrated.

General Procedure C: Reaction of Alcohols with Methanesulfonyl Chloride

To a stirred solution of the alcohol (1 equivalent) and $Et_3N$ (1.5-2 equivalents) in $CH_2Cl_2$ (or THF) (concentration ~0.1 M) at room temperature (or 0° C.) was added methanesulfonyl chloride (MsCl) (~1.5 equivalents) and the reaction stirred at room temperature for 0.5-1 h. The reaction mixture was poured into either saturated aqueous $NaHCO_3$ or saturated $NH_4Cl$ (10 mL/mmol alcohol). The phases were separated and the aqueous phase extracted with $CH_2Cl_2$ (3×10 mL/mmol amine). The combined organic phases were dried ($Na_2SO_4$) and concentrated under reduced pressure. The crude material was either purified by chromatography or used without further purification in the N-alkylation step.

General Procedure D: Salt Formation Using Saturated HBr(g) or HCl(G) in Acetic Acid or MeOH To a solution of the free base in glacial HOAc or MeOH (2 mL) was added a saturated solution of HBr(g) or HCl(g) in HOAc or MeOH (2 mL). A large volume of $Et_2O$ (25 mL) was then added to precipitate a solid, which was allowed to settle to the bottom of the flask and the supernatant solution was decanted. The solid was washed by decantation with $Et_2O$ (3×25 mL) and the remaining traces of solvent were removed under vacuum. For additional purification, the solid was dissolved in MeOH and re-precipitated with a large volume of $Et_2O$. Washing the solid with $Et_2O$ by decantation, followed by drying of the solid in vacuo (0.1 Torr) gave the desired compound.

General Procedure E: Phthalimide Deprotection

To a solution of the phthalimide-protected amine in EtOH (0.2-0.4 M) was added $H_2NNH_2 \cdot H_2O$ (10 equiv). The resulting mixture was stirred at ambient temperature for 4-16 h, filtered, and concentrated. The crude product was purified by column chromatography on silica gel to afford the desired primary amine.

General Procedure F: Boc Deprotection with TFA

The Boc-protected amine was dissolved in $CH_2Cl_2$ (4 mL/mmol) and $CF_3COOH$ (TFA) (2 mL/mmol) was added. After stirring at room temperature for 2-16 h, the mixture was neutralized. In a standard work-up, the mixture was neutralized with saturated aqueous $NaHCO_3$ (20 mL) and extracted three times with $CH_2Cl_2$. The extracts were combined and dried over anhydrous $Na_2SO_4$. After filtration the solvent was removed, and the residue was purified by column chromatography (silica gel, $CH_2Cl_2/MeOH/NH_4OH$).

General Procedure G: EDCI Coupling

To a stirred solution of a 1° or 2° amine (0.1-0.3 mmol), 1-[3-(dimethylamino)propyl]-3-ethylcarbodiimide hydrochloride (EDCI) (1.5 equiv.), 1-hydroxy-benzotriazole hydrate (HOBT) (1.5 equiv.), and diisopropylethylamine (DIPEA) (2.0 equiv.) in $CH_2Cl_2$ or DMF (0.05 M), was added a carboxylic acid (1.0-2.0 equiv). The solution was stirred for 16 h at ambient temperature. The reaction was quenched with saturated $NaHCO_3$ solution and extracted three times with $CH_2Cl_2$. The combined organic layers were dried over $Na_2SO_4$, filtered, and concentrated. The resultant crude material was purified on a silica gel column (5% $MeOH/CH_2Cl_2$).

Intermediates

{4-[(1H-benzoimidazol-2-ylmethyl)-amino]-butyl}-carbamic acid tert-butyl ester

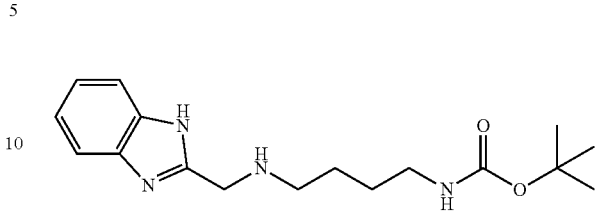

2-Chloromethylbenzimidazole (19.81 g, 118.9 mmol) was added as a solid to a mechanically stirred and cooled (1.2° C. internal temperature) solution of (4-amino-butyl)-carbamic acid tert-butyl ester (56.0 g, 297.3 mmol) and DIPEA (51.8 mL, 297.3 mmol) in $CH_3CN$ (3 L) under $N_2$. After 4.5 h at low temperature the cooling bath was removed and the mixture was concentrated in vacuo. The residue was taken up in $CH_2Cl_2$ (1.5 L) and washed with brine (1 L). The aqueous layer was extracted with $CH_2Cl_2$ (2×500 mL) and the combined organic layers were dried over $MgSO_4$ and concentrated in vacuo to afford a yellow foamy solid. Purification by column chromatography on silica gel ($CH_2Cl_2/MeOH/NH_4OH$ (98:1:1) to $CH_2Cl_2/MeOH/NH_4OH$ (80:10:10)) afforded product containing mixed fractions. Repurification of these fractions by column chromatography on silica gel ($CH_2Cl_2/MeOH/NH_4OH$ (98:3:3)) afforded the title compound as a yellow solid (16.5 g, 44%). $^1H$ NMR ($CDCl_3$) δ 1.50 (s, 9H), 1.60-1.64 (m, 4H), 2.70-2.74 (m, 2H), 3.10-3.18 (m, 2H), 4.13 (s, 2H), 4.86 (s, 1H), 7.19-7.25 (m, 2H), 7.50-7.95 (m, 2H), 10.4 (bs, 1H); $^{13}C$ NMR ($CDCl_3$) δ 26.1, 27.3, 28.1, 39.7, 41.2, 47.2, 47.7, 48.3, 49.4, 78.9, 121.7, 153.9, 155.9; ES-MS m/z 319 (M+H). Anal Calcd. For $C_{17}H_{26}N_4O_2 \cdot 0.2(H_2O)$: C, 63.41; H, 8.26; N, 17.40. Found: C, 63.51; H, 8.19; N, 17.33.

{4-[(3-methyl-pyridin-2-ylmethyl)-amino]-butyl}-carbamic acid tert-butyl ester

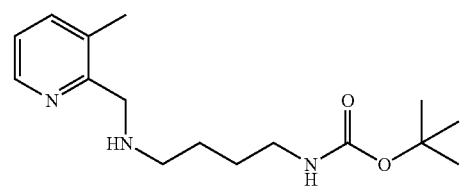

Using General Procedure B, 3-methyl-pyridine-2-carbaldehyde (2.87 g, 23.7 mmol) in dry MeOH (10 mL) was added to a solution (4-amino-butyl)-carbamic acid tert-butyl ester (4.47 g, 23.7 mmol) (Krapcho, A. et al. *Synth. Commun.* 1990, 20, 2559-2564) in dry MeOH (50 mL) and warmed to 50° C. under $N_2$ for 17 h. The mixture was cooled to ambient temperature and $NaBH_4$ (1.35 g, 35.7 mmol) was added, resulting in bubbling. The mixture was stirred for 90 min. under $N_2$ when the bubbling subsided. A solution of saturated $NaHCO_3$ (50 mL) and $CH_2Cl_2$ (150 mL) were added to the MeOH solution and the layers were separated. The aqueous layer was extracted with $CH_2Cl_2$ (3×100 mL), dried over $Na_2SO_4$ and concentrated in vacuo. Purification by column chromatography on silica gel (130 g) with $CH_2Cl_2/MeOH$ (96:4) to $CH_2Cl_2/MeOH/NH_4OH$ (88:8:4) afforded the title compound (6.05 g, 87%) as an orange oil which solidified on standing. ¹H NMR (CDCl₃) δ 1.35-1.50 (m, 4H), 1.43 (s, 9H), 2.05 (bs, 1H), 2.30 (s, 3H), 2.72 (t, 2H, J=6.5 Hz), 3.00-3.20 (m, 2H), 3.86 (s, 2H), 4.76 (bs, 1H), 7.07 (dd, 1H, 7.5, 4.5 Hz), 7.42 (d, 1H, J=7.5 Hz), 8.38 (d, 1H, J=4.5 Hz); ¹³C NMR (CDCl₃) δ 18.06, 27.45, 27.89, 28.43, 40.48, 49.54, 52.18, 78.89, 121.78, 130.84, 137.52, 146.41, 156.03, 157.25; ES-MS m/z 194 (M+H). Anal Calcd. For $C_{16}H_{27}N_3O_2 \cdot 0.2(H_2O)$: C, 64.70; H, 9.30; N, 14.15. Found: C, 65.07; H, 9.35; N, 14.29.

Following general procedure B described above, the following intermediates were prepared:

{4-[(3,5-dimethyl-pyridin-2-ylmethyl)-amino]-butyl}-carbamic acid tert-butyl ester

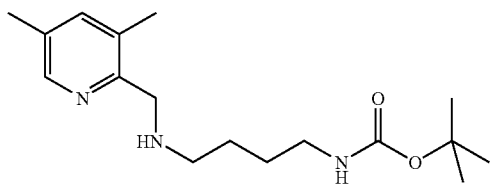

Colorless oil prepared from 3,5-dimethyl-pyridine-2-carbaldehyde and (4-amino-butyl)-carbamic acid tert-butyl ester ¹H NMR (CDCl₃) δ 1.43 (s, 9H), 1.53-1.60 (m, 4H), 2.27 (s, 6H), 2.65-2.75 (m, 2H), 3.10-3.16 (m, 2H), 3.83 (s, 2H), 4.76 (s, br, 1H), 7.24 (s, 1H), 8.21 (s, 1H).

{4-[(3-isopropyl-pyridin-2-ylmethyl)-amino]-butyl}-carbamic acid tert-butyl ester

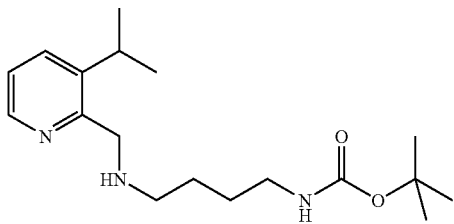

A pale yellow oil prepared from (4-amino-butyl)-carbamic acid tert-butyl ester and 3-isopropyl-pyridine-2-carbaldehyde. ¹H NMR (CDCl₃) δ 1.23 (d, 6H, J=6.6 Hz), 1.43 (s, 9H), 1.53-1.61 (m, 4H), 2.67-2.74 (m, 2H), 3.10-3.21 (m, 3H), 3.94 (s, 2H), 4.73 (s, br. 1H), 7.11-7.17 (m, 1H), 7.54-7.58 (m, 1H), 8.37-7.40 (m, 1H).

{4-[(3,5-Dimethyl-pyridin-2-ylmethyl)-amino]-butyl}-methyl-carbamic acid tert-butyl ester

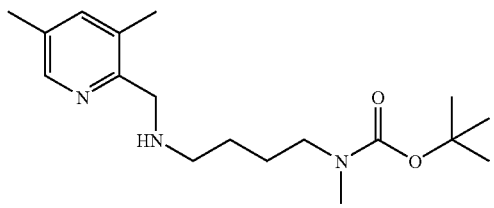

Yellow oil prepared from 3,5-dimethyl-pyridine-2-carbaldehyde and (4-amino-butyl)-methyl-carbamic acid tert-butyl ester. ¹H NMR (CDCl₃) δ 1.44 (s, 9H), 1.53-1.57 (m, 4H), 2.27 (s, 6H), 2.69-2.73 (m, 2H), 2.82 (s, 3H), 3.18-3.23 (m, 2H), 3.83 (s, 2H), 7.24 (s, 1H), 8.20 (s, 1H).

{4-[(5-Chloro-3-methyl-pyridin-2-ylmethyl)-amino]-butyl}-methyl-carbamic acid tert-butyl ester

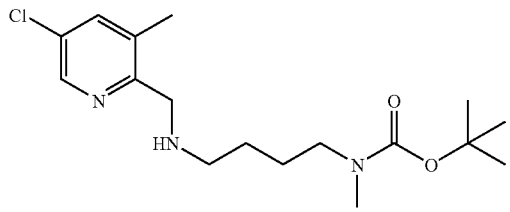

Yellow oil prepared from (4-amino-butyl)-methyl-carbamic acid tert-butyl ester and 5-chloro-3-methyl-pyridine-2-carbaldehyde. ¹H NMR (CDCl₃) δ 1.44 (s, 9H), 1.50-1.60 (m, 4H), 2.27 (s, 3H), 2.30-2.36 (m, 2H), 2.83 (s, 3H), 3.20-3.26 (m, 2H), 3.83 (s, 2H), 8.34 (d, 1H, J=1.5 Hz), 7.4 (d, 1H, J=1.9 Hz).

{trans-4-[(3-methyl-pyridin-2-ylmethyl)-amino]-cyclohexyl}-carbamic acid tert-butyl ester

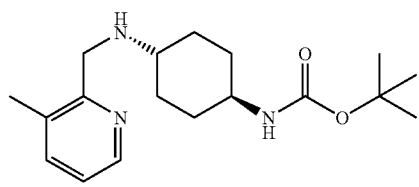

Obtained from 3-isopropyl-2-pyridine carboxaldehyde and N-tert-butoxycarbonyl-trans-1,4-cyclohexanediamine. ¹H NMR (CDCl₃) δ1.00-1.18 (m, 2H), 1.23 (d, 6H, J=7.0 Hz), 1.27-1.38 (m, 1H), 1.44 (s, 9H), 1.97-2.09 (m, 4H), 2.54 (t, 1H, J=11.0 Hz), 3.14 (septet, 1H, J=6.6 Hz), 3.42 (bs, 1H), 3.99 (s, 2H), 4.79 (bs, 1H), 7.15 (dd, 1H, J=7.9, 4.8 Hz), 7.56 (dd, 1H, J=7.9, 1.8 Hz), 8.37 (dd, 1H, J=4.8, 1.3 Hz).

2-[4-(1-pyridin-2-yl-ethylamino)-butyl]-isoindole-1,3-dione

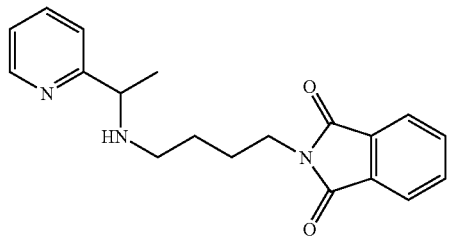

Mixture A: To a stirred solution of 1-pyridin-2-yl-ethylamine (5.26 g, 43.1 mmol) (Brunner H et al. *Monatsh. Chem.* 2002, 133, 115-126) and 4-(1,3-dioxo-1,3-dihydro-isoindol-2-yl)-butyraldehyde (9.352 g, 43.1 mmol) in THF (215 mL) at room temperature was added K₂CO₃ (5.987 g, 43.3 mmol) and the mixture stirred for 2 hours. The mixture was then filtered and chilled to −20° C.

Mixture B: To a stirred suspension of NaBH₄ (1.95 g, 51.6 mmol) in THF (215 mL) at −20° C. was added glacial HOAc (2.95 mL, 51.6 mmol) and the mixture stirred for 2 hours.

Mixture A was slowly added to Mixture B via cannula and the resulting mixture was stirred for 2 hours. NaBH$_4$ (313 mg, 8.27 mmol) was added to the mixture and stirring was continued for another 45 minutes. The ice bath was then removed and the reaction was quenched with saturated aqueous NaHCO$_3$. Once the mixture had warmed to room temperature the product was extracted with CH$_2$Cl$_2$ (4×150 mL). The organic phase was concentrated, and the residue was taken up in 5 v/v % AcOH (150 mL). The acidic phase was washed with MTBE (2×100 mL). Solid NaHCO$_3$ was added to the aqueous phase until pH=8.5. The product was extracted with CH$_2$Cl$_2$ (4×100 mL), dried (Na$_2$SO$_4$) filtered and concentrated under reduced pressure to give crude material as a yellow oil. Purification by flash chromatography (50:1:1 CH$_2$Cl$_2$:MeOH:NH$_4$OH) afforded pure 2-[4-(1-pyridin-2-yl-ethylamino)-butyl]-isoindole-1,3-dione as a white solid (5.60 g, 40%). $^1$H NMR (CDCl$_3$) δ 1.35 (d, 3H, J=7.0 Hz), 1.45-1.56 (m, 2H), 1.63-1.74 (m, 3H), 2.37-2.46 (m, 1H), 2.50-2.60 (m, 1H), 3.66 (t, 2H, J=7.2 Hz), 3.83 (q, 1H, J=6.7 Hz), 7.12 (ddd, 1H, J=7.6, 7.3, 1.3 Hz), 7.29 (d, 1H, J=8.0 Hz), 7.63 (td, 1H, J=7.7, 1.8 Hz), 7.68-7.72 (m, 2H), 7.79-7.84 (m, 2H), 8.53 (d, 1H, J=3.9 Hz).

TABLE 1

Preparation of Examples 1 and 2.

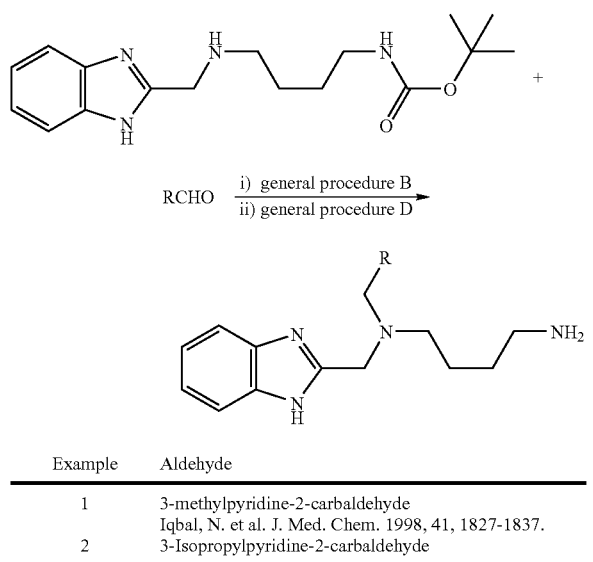

| Example | Aldehyde |
|---|---|
| 1 | 3-methylpyridine-2-carbaldehyde Iqbal, N. et al. J. Med. Chem. 1998, 41, 1827-1837. |
| 2 | 3-Isopropylpyridine-2-carbaldehyde |

Example 1

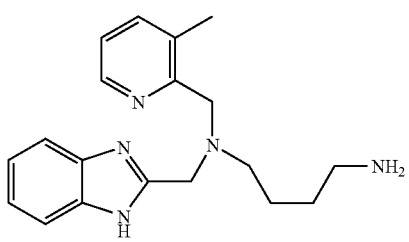

COMPOUND 1: N-(1H-benzimidazol-2-ylmethyl)-N-(3-methylpyridin-2-ylmethyl)-butane-1,4-diamine (HBr salt)

White solid. $^1$H NMR (D$_2$O) δ 1.59 (br, 4H), 2.47 (s, 3H), 2.81 (t, 2H, J=7.4 Hz), 2.92 (t, 2H, J=7.4 Hz), 4.34 (s, 2H), 4.47 (s, 2H), 7.59 (m, 2H), 7.77 (m, 2H), 7.81 (t, 1H, J=7.0 Hz), 8.31 (d, 1H, J=7.8 Hz), 8.57 (d, 1H, J=5.7 Hz). $^{13}$C NMR (D$_2$O) δ 17.03, 23.39, 24.94, 39.58, 50.78, 54.12, 55.26, 114.28 (2C), 125.95, 127.03 (2C), 130.93 (2C), 137.55, 138.40, 148.31, 150.42, 151.38. ES-MS m/z 324 (M+H). Anal. Calcd. for C$_{19}$H$_{25}$N$_5$·3.5HBr·1.4H$_2$O·0.4C$_4$H$_{10}$O: C, 37.40; H, 5.38; N, 10.59; Br, 42.28. Found: C, 37.46; H, 5.27; N, 10.57; Br, 42.16.

Example 2

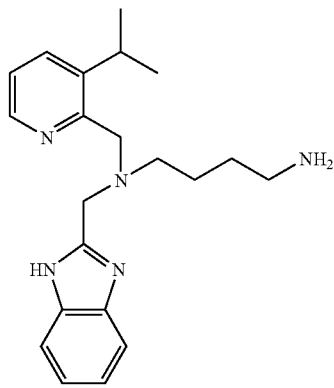

COMPOUND 2: N$^1$-(1H-benzoimidazol-2-ylmethyl)-N$^1$-(3-isopropylpyridin-2-ylmethyl)-butane-1,4-diamine (HBr salt)

A 50% solution of hydrogen peroxide (24.89 mL) was slowly added to a solution of 3-isopropyl-2-methyl-pyridine (24.5 g, 183 mmol) (Ishiguro et al. *Yakugaku Zasshi* 1958, 78, 220) in HOAc (280 mL). The mixture was warmed to 70° C. and stirred for 18 h, then cooled to room temperature and concentrated in vacuo to remove the majority of HOAc. The mixture was basified with a saturated solution of NaHCO$_3$ to pH 12 and extracted with CH$_2$Cl$_2$ (3×150 mL). The combined organic layers were dried over Na$_2$SO$_4$ and concentrated in vacuo to afford 3-isopropyl-2-methyl-pyridine 1-oxide (26.05 g, 94%) as a yellow oil. $^1$H NMR (CDCl$_3$) δ 1.24 (d, 6H, J=7.0 Hz), 2.56 (s, 3H), 3.13 (sep, 1H, J=7.0 Hz), 7.06-7.17 (m, 2H), 8.17 (d, 1H, J=6.6 Hz).

To a stirred solution of 3-isopropyl-2-methyl-pyridine 1-oxide (26.05 g, 173 mmol) in CH$_2$Cl$_2$ (690 mL) was added dropwise TFAA (51.83 mL) over 30 min. under N$_2$ then stirred for an additional 3 h. Caution: exothermic reaction on addition of TFAA. The mixture was concentrated in vacuo to a minimum volume. Brine (200 mL) was added, basified to pH 9 with solid K$_2$CO$_3$ slowly, then the aqueous mixture was extracted with CH$_2$Cl$_2$ (3×100 mL). The combined organic layers were dried over Na$_2$SO$_4$ and concentrated in vacuo to afford (3-isopropyl-pyridin-2-yl)-methanol (26 g, 99%) as an orange oil. $^1$H NMR (CDCl$_3$) δ 1.24 (d, 6H, 7.0 Hz), 2.92 (sep, 1H, J=6.6 Hz), 4.79 (s, 2H), 7.02-7.25 (m, 1H), 7.61 (d, 1H, J=7.9 Hz), 8.41 (d, 1H, J=4.8 Hz).

To a vigorously stirred solution of (3-isopropyl-pyridin-2-yl)-methanol (26 g, 170 mmol) in CH$_2$Cl$_2$ (575 mL) was added manganese(IV) oxide (105 g, 1.20 mol) under N$_2$. The mixture was stirred for 18 h then filtered through a celite pad and concentrated in vacuo. Purification by column chromatography on silica gel (EtOAc/hexanes, 1:3) afforded 3-isopropyl-pyridine-2-carbaldehyde (15.65 g, 61%) as an orange oil. $^1$H NMR (CDCl$_3$) δ 1.26 (d, 6H, J=7.0 Hz), 4.17 (sep, 1H, J=6.6 Hz) 7.45 (dd, 1H, J=7.9, 4.4 Hz), 7.84 (d, 1H, J=7.9 Hz), 8.56 (dd, 1H, J=4.4, 1.3 Hz), 10.2 (s, 1H).

COMPOUND 2 was isolated as a white solid. $^1$H NMR (D$_2$O): 1.09-1.11 (m, 6H), 1.57 (m, 4H), 2.74-2.87 (m, 2H), 2.87-3.00 (m, 2H), 3.12-3.27 (m, 1H), 4.41 (s, 2H), 4.45 (s, 2H), 7.50-7.62 (m, 2H), 7.62-7.77 (m, 2H), 7.87 (t, 1H, J=6.3 Hz), 8.47 (d, 1H, J=6.5 Hz), 8.58 (d, 1H, J=4.8 Hz). $^{13}$C NMR (D$_2$O): 14.54 (2 carbons), 22.04, 23.38, 24.93, 28.19, 39.57, 50.72, 53.54, 55.15, 114.28 (2 carbons), 126.55, 126.98 (2 carbons), 130.90 (2 carbons), 138.54, 144.73, 147.12, 150.00, 150.36. ES-MS m/z 352 (M+H); Anal. Calcd. for (C$_{21}$H$_{29}$N$_5$×3.3HBr×2.2 MeOH): C, 40.44; H, 6.01; N, 10.16; Br, 38.27. Found: C, 40.16; H, 5.63; N, 10.31; Br, 38.48.

TABLE 2

Preparation of Examples 3 to 38

| Example | Aldehyde |
|---|---|
| 3 | phenyl-1H-imidazole-2-carboxaldehyde |
| | Gebert, U et al. Justus Liebigs Ann. Chem. 1974, 644-654. |
| 4 | 2-phenyl-1H-imidazole-4-carboxaldehyde |
| 5 | 2-methyl-1H-imidazole-4-carboxaldehyde |
| 6 | 4-methyl-1H-imidazole-5-carboxaldehyde |
| 7 | 3-benzyloxy-pyrazine-2-carbaldehyde |
| | Breault, GA et al. PCT Int. Appl. (1996), WO 9603380 |
| 8 | 3-allyloxy-pyridine-2-carbaldehyde |
| 9 | 3-(2-methoxy-phenyl)-pyridine-2-carbaldehyde |
| 10 | 3-Thiophen-2-yl-pyridine-2-carbaldehyde |
| 11 | [2,3']Bipyridinyl-6'-carbaldehyde |
| 12 | pyridine-2-carboxaldehyde |
| 13 | 3-methyl-pyridine-2-carbaldehyde |
| 14 | 3-hydroxypyridine-2-carbaldehyde |
| | Wang, P-H. et al. J. Med. Chem. 1990, 33, 608-614. |
| 15 | 3-chloro-pyridine-2-carbaldehyde |
| | Iqbal, N. et al. J. Med. Chem. 1998, 41, 1827-1837 |
| 16 | 3-fluoro-pyridine-2-carbaldehyde |
| | Marsais, F. et al. Tetrahedron 1983, 39, 2009-2021. |
| 17 | 3-bromo-pyridine-2-carbaldehyde |
| | Bridger, G et al. PCT Int. Appl. (2002), WO 2002022600 |
| 18 | 3-(2,2,2-trifluoro-ethoxy)-pyridine-2-carbaldehyde |
| 19 | N-(2-formyl-pyridin-3-yl)-methanesulfonamide |
| | Bridger, G et al. PCT Int. Appl. (2002), WO 2002022600 |
| 20 | 3-benzyloxy-pyridine-2-carbaldehyde |
| | Desideri, N et al. Eur. J. Med. Chem. Chim. Ther. 1991, 26, 455-460. |

TABLE 2-continued

Preparation of Examples 3 to 38

| Example | Aldehyde |
|---|---|
| 21 | 3-methyl-5-trifluoromethyl-pyridine-2-carbaldehyde |
| 22 | 5-phenyl-pyridine-2-carbaldehyde |
| 23 | 1-allyl-1H-benzimidazol-2-carbaldehyde |
| | Bridger, G et al. PCT Int. Appl. (2003), WO 2003055876. |
| 24 | 1-allyl-1H-imidazole-2-carboxaldehyde |
| | Basso. D. at al. Tetrahedron 2002, 58, 4445-4450. |
| 25 | 4(5)-imidazole carboxaldehyde |
| 26 | 1-benzyl-1H-imidazole-5-carboxaldehyde |
| 27 | 2-ethyl-4-methyl-1H-imidazole-5-carboxaldehyde |
| 28 | 3-p-Tolyl-pyridine-2-carbaldehyde |
| 29 | 3-methoxypyridine-2-carboxaldehyde |
| | Comins, DL et al. J. Org. Chem. 1990, 55, 69-73. |
| 30 | 3-trifluoromethyl-pyridine-2-carbaldehyde |
| | Ashimori, A. et al. Chem. Pharm. Bull. 1990, 33, 2446-2458 |
| 31 | 3-isobutyl-pyridine-2-carbaldehyde |
| 32 | 1-phenyl-1H-benzimidazole-2-carboxaldehyde |
| | Chen, YL Eur. Pat. Appl. (1998), EP 276942. |
| 33 | 1-benzyl-1H-benzimidazole-2-carboxaldehyde |
| | Milgrom, LR et al. Tetrahedron 1996, 52, 9877-9890. |
| 34 | 3-(m-nitrophenyl)pyridine-2-carbaldehyde |
| 35 | isoquinoline-3-carbaldehyde |
| | Jones, D. et al. J. Med. Chem. 1965, 8, 676-680. |
| 36 | 3-(2-formyl-pyridin-3-yl)-benzoic acid methyl ester |
| 37 | 3,5-dimethyl-pyridine-2-carbaldehyde |
| 38 | 1-(2-pyridin-2-yl-ethyl)-1H-benzimidazole-2-carbaldehyde |

Example 3

COMPOUND 3: N[1]-(3-methyl-pyridin-2-ylmethyl)-N[1]-(1-phenyl-1H-imidazol-2-ylmethyl)-butane-1,4-diamine (HBr salt)

White solid. $^1$H NMR (D$_2$O) δ 1.37-1.51 (m, 4H), 2.32 (s, 3H), 2.60 (dd, 2H, J=6.9, 8.1 Hz), 2.86 (dd, 2H, J=6.9, 7.5 Hz), 4.05 (s, 2H), 4.23 (s, 2H), 7.47-7.51 (m, 2H), 7.56-7.67 (m, 5H), 7.83 (dd, 1H, J=6.0, 7.8 Hz), 8.30 (d, 1H, J=8.1 Hz), 8.46 (d, 1H, J=5.4 Hz); $^{13}$C NMR (D$_2$O) δ 16.98; 22.92, 24.87, 39.54, 48.47, 53.59, 54.42, 119.60, 124.83, 125.98 (3 carbons), 130.75 (2 carbons), 131.51, 134.35, 137.64, 138.39, 143.99, 148.43, 150.94; ES-MS m/z 350 (M+H). Anal. Calcd. for C$_{21}$H$_{27}$N$_5$.3.3HBr.2.5H$_2$O: C, 38.13; H, 5.38; N, 10.59; Br, 39.86. Found: C, 38.28; H, 5.67; N, 10.27; Br, 39.95.

Example 4

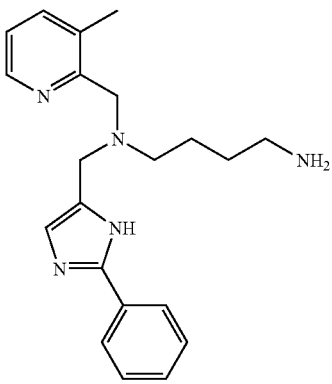

COMPOUND 4: N[1]-(3-methyl-pyridin-2-ylmethyl)-N[1]-(2-phenyl-3H-imidazol-4-ylmethyl)-butane-1,4-diamine Yellow oil. $^1$H NMR (CDCl$_3$) δ 1.49-1.68 (m, 4H), 2.47 (s, 3H), 2.51 (t, 2H, J=7.0 Hz), 2.76 (t, 2H, J=7.0 Hz), 3.51 (s, 2H), 3.74 (s, 2H), 6.94 (s, 1H), 7.23 (dd, 1H, J=7.9, 4.8 Hz), 7.29-7.34 (m, 1H), 7.44 (t, 2H, J=7.9 Hz), 7.57 (d, 1H, J=7.5 Hz), 7.96 (d, 2H, J=7.0 Hz), 8.51 (dd, 1H, J=4.4, 1.1 Hz); ES-MS m/z 350 (M+H).

Example 5

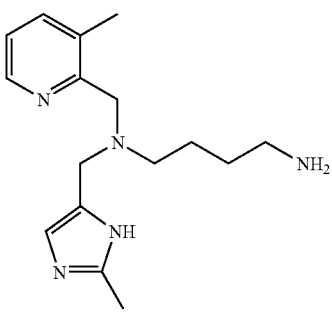

COMPOUND 5: N[1]-(2-methyl-3H-imidazol-4-ylmethyl)-N[1]-(3-methyl-pyridin-2-ylmethyl)-butane-1,4-diamine Colourless oil. $^1$H NMR (CDCl$_3$) δ 1.55-1.65 (m, 4H), 2.36 (s, 3H), 2.40 (s, 3H), 2.50 (t, 2H, J=6.1 Hz), 2.78 (t, 2H, J=6.1 Hz), 3.46 (s, 2H), 3.66 (s, 2H), 6.72 (s, 1H), 7.13 (dd, 1H, J=7.5, 4.8), 7.47 (d, 1H, J=7.5 Hz), 8.41 (d, 1H, J=4.8 Hz); ES-MS m/z 288 (M+H).

Example 6

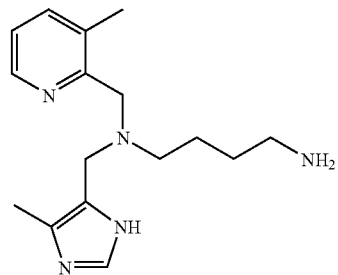

COMPOUND 6: N[1]-(5-methyl-3H-imidazol-4-ylmethyl)-N[1]-(3-methyl-pyridin-2-ylmethyl)-butane-1,4-diamine Colourless oil. $^1$H NMR (CDCl$_3$) δ 1.52-1.65 (m, 4H), 2.21 (s, 3H), 2.39 (s, 3H), 2.49 (t, 2H, J=6.1 Hz), 2.74 (t, 2H, J=6.1 Hz), 3.46 (s, 2H), 3.67 (s, 2H), 7.16 (dd, 1H, J=7.9, 4.4), 7.50 (d, 1H, J=7.9 Hz), 7.55 (s, 1H), 8.41 (d, 1H, J=4.8 Hz); ES-MS m/z 288 (M+H).

Example 7

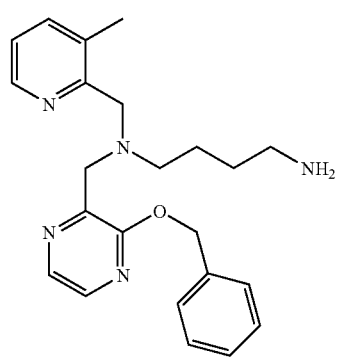

COMPOUND 7: N[1]-(3-Benzyloxy-pyrazin-2-ylmethyl)-N[1]-(3-methyl-pyridin-2-ylmethyl)-butane-1,4-diamine Colourless oil. $^1$H NMR (CDCl$_3$) δ 1.19 (m, 2H), 1.40 (m, 2H), 1.49 (br s, 2H), 2.07 (s, 3H), 2.40 (t, 2H, J=6.0 Hz), 2.50 (t, 2H, J=7.5 Hz), 3.79 (s, 2H), 3.83 (s, 2H), 5.33 (s, 2H), 7.01 (dd, 1H, J=9.0, 6.0 Hz), 7.26-7.35 (m, 6H), 7.97 (d, 1H, J=3.0 Hz), 8.05 (d, 1H, J=3.0), 8.30 (d, 1H, J=3.0). $^{13}$C NMR (CDCl$_3$) δ 18.39, 24.26, 31.79, 42.17, 53.99, 55.05, 60.06, 68.15, 122.60, 128.36, 128.41, 128.80, 133.87, 135.98, 138.19, 139.69, 145.13, 146.16. ES-MS m/z 392 [M+H]$^+$.

Example 8

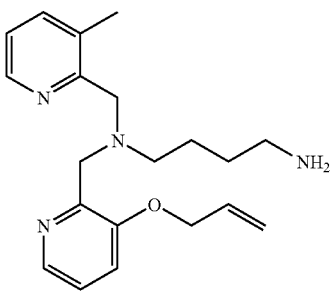

COMPOUND 8: N¹-(3-allyloxy-pyridin-2-ylmethyl)-N¹-(3-methyl-pyridin-2-ylmethyl)-butane-1,4-diamine (HBr salt)

To a solution of (3-allyloxy-pyridin-2-yl)-methanol (2.08 g, 12.6 mmol) (Chen, Y. L. Eur. Pat. Appl. (1985), EP 150984) in $CH_2Cl_2$ (60 mL) was added Dess-Martin Periodinane (5.82 g, 13.7 mmol), and stirred at room temperature for 24 hours. $CH_2Cl_2$ (40 mL), saturated $NaHCO_3$ (30 mL), and aqueous sodium thiosulfate (30 mL) were added and stirred for 40 minutes. The layers were separated and the aqueous phase was extracted with $CH_2Cl_2$ (2×50 mL). The combined organic extracts were washed with brine (1×75 mL), dried ($Na_2SO_4$), and concentrated to provide 2.02 g (98%) of 3-allyloxy-pyridine-2-carbaldehyde as a brown oil. ¹H NMR ($CDCl_3$) δ 4.71 (d, 2H, J=6.0 Hz), 5.37 (d, 1H, J=12.0 Hz), 5.50 (d, 1H, J=18.0 Hz), 5.99-6.12 (m, 1H), 7.38-7.48 (m, 2H), 8.40 (d, 1H, J=3.0 Hz), 10.41 (s, 1H).

COMPOUND 8 was isolated as a white solid. ¹H NMR ($D_2O$) δ 1.56-1.58 (m, 4H), 2.45 (s, 3H), 2.77-2.79 (m, 2H), 2.91-2.93 (m, 2H), 4.34 (s, 4H), 4.63-4.79 (m, 2H, overlaps with HOD), 5.29-5.42 (m, 2H), 5.93-6.04 (m, 1H), 7.81-7.90 (m, 2H), 8.07-8.10 (m, 1H), 8.29-8.31 (m, 2H), 8.52-8.53 (m, 1H). ¹³C NMR ($D_2O$) δ 17.11, 22.93, 24.97, 39.62, 52.03, 54.40, 54.98, 71.12, 119.86, 125.97, 127.70, 129.42, 131.48, 132.82, 137.49, 138.44, 142.78, 148.08, 151.39, 155.55. ES-MS m/z 341 (M+H). Anal. Calcd. for $C_{20}H_{28}N_4O$·3.4HBr·2.8$H_2O$: C, 36.07; H, 5.60; N, 8.41; Br, 40.79. Found: C, 36.08; H, 5.55; N, 8.24; Br, 40.90.

Example 9

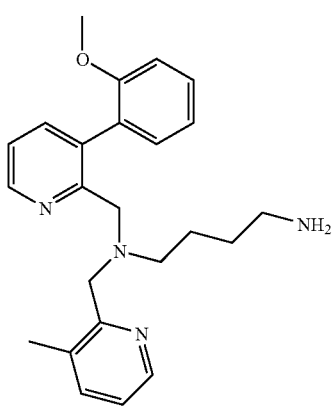

COMPOUND 9: N¹-[3-(2-methoxy-phenyl)-pyridin-2-ylmethyl]-N¹-(3-methyl-pyridin-2-ylmethyl)-butane-1,4-diamine (HBr salt)

A stirred solution of 3-bromo-pyridine-2-carbaldehyde (128 mg, 0.69 mmol) and 2-methoxybenzeneboronic acid (111 mg, 0.73 mmol) in a mixture of THF (0.75 mL), DME (2.0 mL) and 2M $Na_2CO_3$ (0.75 mL) was degassed with Ar for 15 minutes, after which $Pd(PPh_3)_4$ (41 mg, 0.034 mmol) was added and the heterogeneous mixture heated to 90° C. overnight. The reaction was quenched with brine (15 mL) and diluted with EtOAc (40 mL). The organic layer was separated, washed with brine (4×15 mL), dried ($Na_2SO_4$), filtered and concentrated in vacuo. Purification by flash chromatography on silica gel (EtOAc/Hexanes, 80:20, then 70:30) gave 3-(2-methoxy-phenyl)-pyridine-2-carbaldehyde (93 mg, 63%) as a yellow solid. ¹H NMR ($CDCl_3$) δ 3.74 (s, 3H), 6.99 (d, 1H, J=8.3 Hz), 7.10 (t, 1H, J=7.5 Hz), 7.25 (dd, 1H, J=7.4, 1.7 Hz), 7.40-7.49 (m, 1H), 7.55 (dd, 1H, J=7.9, 4.8 Hz), 7.74 (dd, 1H, J=7.9, 1.8 Hz), 8.80 (dd, 1H, J=4.6, 1.5 Hz), 9.95 (s, 1H).

COMPOUND 9 was isolated as a white solid. ¹H NMR ($D_2O$) δ 1.30-1.50 (m, 4H), 2.38 (s, 3H), 2.58 (t, 2H, J=7.8, 6.6 Hz), 2.78-2.88 (m, 2H), 3.78 (s, 3H), 4.03-4.22 (m, 4H), 7.12-7.23 (m, 2H), 7.29 (dd, 1H, J=7.5, 1.5 Hz), 7.54-7.63 (m, 1H), 7.83 (dd, 1H, J=7.8, 6.0 Hz), 8.02 (dd, 1H, J=7.8, 6.0 Hz), 8.31 (d, 1H, J=7.8 Hz), 8.43 (dd, 1H, J=7.8, 1.5 Hz), 8.55 (d, 1H, J=5.4 Hz), 8.78 (dd, 1H, J=6.0, 1.5 Hz); ¹³C NMR ($D_2O$) δ 17.16, 22.55, 24.94, 39.54, 54.07, 54.63, 56.00, 112.33, 121.92, 122.75, 126.02, 126.48, 131.22, 132.48, 137.63, 138.06, 138.68, 140.72, 148.37, 149.15, 150.93, 151.46, 156.22; ES-MS m/z 391 (M+H). Anal. Calcd. for $C_{24}H_{30}N_4$·3.5HBr·1.8$H_2O$·0.4$C_4H_{10}O$: C, 41.79; H, 5.63; N, 7.61; Br, 38.01. Found: C, 42.01; H, 5.58; N, 7.62; Br, 37.74.

Example 10

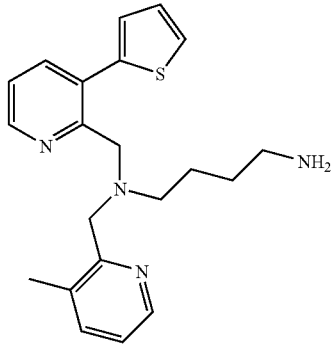

COMPOUND 10: N¹-(3-methyl-pyridin-2-ylmethyl)-N¹-(3-thiophen-2-yl-pyridin-2-ylmethyl)-butane-1,4-diamine (HBr salt)

A stirred solution of 3-bromo-pyridine-2-carbaldehyde (126 mg, 0.675 mmol) and 2-thiopheneboronic acid (91.6 mg, 0.716 mmol) in a mixture of THF (0.75 mL), DME (2.0 mL) and 2M $Na_2CO_3$ (0.75 mL) was degassed with Ar for 15 minutes, after which $Pd(PPh_3)_4$ (39 mg, 0.034 mmol) was added and the heterogeneous mixture heated to 90° C. for 4 h. The reaction was quenched with brine (15 mL) and diluted with EtOAc (40 mL). The organic layer was separated, washed with brine (2×15 mL), dried ($Na_2SO_4$), filtered and concentrated in vacuo. Purification by flash chromatography on silica gel (Hexanes/EtOAc, 80:20) gave 3-thiophen-2-yl-pyridine-2-carbaldehyde (81 mg, 63%) as a yellow oil. ¹H NMR ($CDCl_3$) δ 7.13-7.22 (m, 2H), 7.48-7.57 (m, 2H), 7.92 (dd, 1H, J=7.9, 1.9 Hz), 8.82 (dd, 1H, J=6.0, 1.5 Hz), 10.23 (s, 1H).

COMPOUND 10 was isolated as a white solid (182 mg, 72.3%). $^1$H NMR (D$_2$O) δ 1.45-1.59 (m, 4H), 2.43 (s, 3H), 2.66-2.76 (m, 2H), 2.84-2.95 (m, 2H), 4.28 (s, 2H), 4.52 (s, 2H), 7.27 (dd, 1H, J=5.1, 3.6 Hz), 7.37 (d, 1H, J=2.7 Hz), 7.74 (dd, 1H, J=5.1, 0.9 Hz), 7.84 (dd, 1H, J=7.8, 6.0 Hz), 8.00 (dd, 1H, J=8.1, 6.0 Hz), 8.33 (d, 1H, J=7.8 Hz), 8.56 (d, 2H, J=6.6 Hz), 8.78 (dd, 1H, J=7.8, 1.2 Hz); $^{13}$C NMR (D$_2$O) δ 17.28, 22.52, 24.95, 39.58, 54.29, 54.86, 126.08, 126.40, 128.92, 130.41, 131.14, 134.05, 134.46, 137.75, 138.82, 140.80, 148.20, 148.38, 150.54, 150.66; ES-MS m/z 367 (M+H). Anal. Calcd. for C$_{21}$H$_{26}$N$_4$S.3.4HBr.1.7H$_2$O.0.3C$_4$H$_{10}$O: C, 38.39; H, 5.20; N, 8.07; Br, 39.12. Found: C, 38.24; H, 5.18; N, 8.00; Br, 39.35.

Example 11

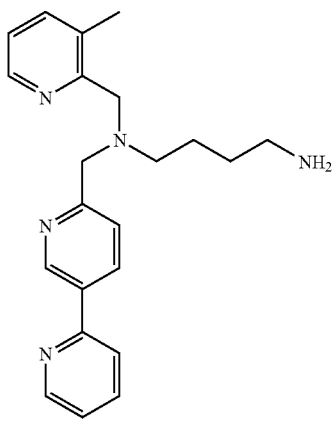

COMPOUND 11: N$^1$-[2,3']Bipyridinyl-6'-ylmethyl-N$^1$-(3-methyl-pyridin-2-ylmethyl)-butane-1,4-diamine (HBr salt)

To a stirred solution of 6'-methyl-[2,3']bipyridine (255 mg, 1.50 mmol) (Shindo, T. Japanese Pat. Appl. (2001) JP 2001139549) in 1,4-dioxane (3.5 mL) and water (0.5 mL) was added SeO$_2$ (222 mg, 2.00 mmol) and the resultant mixture was heated to reflux overnight. The reaction mixture was cooled to room temperature and concentrated under reduced pressure. The residue was purified by column chromatography on silica gel (2:1 hexanes/EtOAc) and provided the aldehyde (114 mg, 41%) as a yellow solid. $^1$H NMR (CDCl$_3$) δ 7.34-7.38 (m, 1H), 7.82-7.85 (m, 2H), 8.07 (dd, 1H, J=9, 1 Hz), 8.51 (ddd, 1H, J=9, 3, 1 Hz), 8.75-8.78 (m, 1H), 9.38 (dd, 1H, J=3, 1 Hz), 10.14 (s, 1H).

COMPOUND 11 was isolated as a white solid. $^1$H NMR (D$_2$O) δ 1.61-1.71 (m, 2H), 1.76-1.82 (m, 2H), 2.47 (s, 3H), 2.99 (t, 2H, J=7.5 Hz), 3.12 (t, 2H, J=7.5 Hz), 4.55 (s, 2H), 4.60 (s, 2H), 7.77 (br t, 1H, J=7.5 Hz), 8.07 (d, 1H, J=8.1 Hz), 8.12 (d, 1H, J=6.9 Hz), 8.23 (d, 1H, J=7.8 Hz), 8.35 (d, 1H, J=8.1 Hz), 8.59 (d, 1H, J=5.4 Hz), 8.65-8.71 (m, 2H), 8.89 (d, 1H, J=5.7 Hz), 9.19 (s, 1H); $^{13}$C NMR (D$_2$O) δ 17.41, 22.49, 24.76, 39.49, 53.95, 55.44, 57.45, 126.30, 126.92, 127.22, 127.46, 129.97, 137.59, 140.66, 142.19, 143.59, 145.39, 147.11, 147.46, 148.03, 148.70, 155.17. ES-MS m/z 362 (M+H). Anal. Calcd. for C$_{22}$H$_{27}$N$_5$.4.2HBr.2.6H$_2$O: C, 35.32; H, 4.90; N, 9.36; Br, 44.86. Found: C, 35.36; H, 5.09; N, 9.00; Br, 45.00.

Example 12

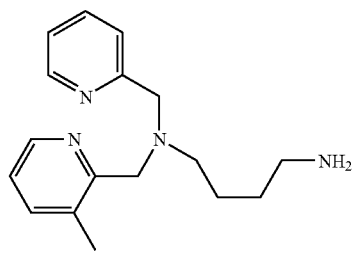

COMPOUND 12: N-(3-methylpyridin-2-ylmethyl)-N-pyridin-2-ylmethyl-butane-1,4-diamine (HBr salt)

Pale yellow solid. $^1$H NMR (D$_2$O) δ 1.55 (br, 4H), 2.47 (s, 3H), 2.75 (t, 2H, J=7.2 Hz), 2.92 (t, 2H, J=7.2 Hz), 4.29 (s, 2H), 4.35 (s, 2H), 7.34 (t, 1H, J=6.9 Hz), 7.97 (t, 1H, J=6.9 Hz), 8.06 (d, 1H, J=8.1 Hz), 8.33 (d, 1H, J=7.8 Hz), 8.57 (m, 2H), 8.74 (d, 1H, J=5.4 Hz). $^{13}$C NMR (D$_2$O) δ 17.04, 22.88, 24.96, 39.55, 53.83, 54.81, 56.31, 125.96, 126.80, 127.61, 137.57, 138.61, 141.96, 147.66, 148.20, 151.35, 152.85. ES-MS m/z 285 (M+H). Anal. Calcd. for C$_{17}$H$_{24}$N$_4$.3.6HBr.1.5H$_2$O: C, 33.88; H, 5.12; N, 9.30; Br, 47.73. Found: C, 34.00; H, 5.17; N, 9.11; Br, 47.54.

Example 13

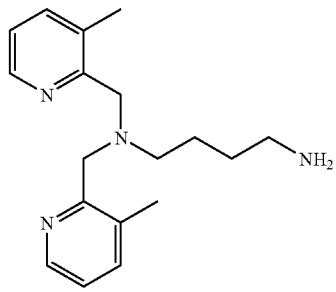

COMPOUND 13: N$^1$,N$^1$-bis-(3-methyl-pyridin-2-ylmethyl)-butane-1,4-diamine (HBr salt)

White solid. $^1$H NMR (CD$_3$OD) δ 1.67-1.78 (m, 2H), 1.83-1.94 (m, 2H), 2.27 (s, 6H), 3.00 (t, 2H, J=7.5 Hz), 3.32 (t, 2H, J=7.8 Hz), 4.46 (s, 4H), 7.29 (dd, 2H, J=5.1, 7.5 Hz), 7.66 (d, 2H, J=7.8 Hz), 8.32 (d, 2H, J=5.1 Hz); $^{13}$C NMR (D$_2$O) δ 17.27, 22.19, 24.58, 39.39, 55.83, 56.21, 124.71, 133.80, 140.96, 145.32, 149.55. ES-MS m/z 299 (M+H).

Anal. Calcd. for $C_{18}H_{26}N_4 \cdot 2.05HBr \cdot 0.8H_2O \cdot 0.1C_4H_{10}O$: C, 45.46; H, 6.35; N, 11.53; Br, 33.70. Found: C, 45.41; H, 6.43; N, 11.56; Br, 33.78.

Example 14

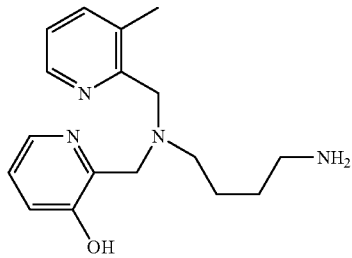

COMPOUND 14: 2-{[(4-aminobutyl)-(3-methyl-pyridin-2-ylmethyl)-amino]-methyl}-pyridin-3-ol (HBr salt)

White solid. $^1$H NMR (D$_2$O) δ 1.61 (br, 4H), 2.45 (s, 3H), 2.82 (t, 2H, J=7.4 Hz), 2.93 (t, 2H, J=6.9 Hz), 4.25 (s, 2H), 4.31 (s, 2H), 7.76 (m, 2H), 7.89 (dd, 1H, J=8.6, 1.2 Hz), 8.22 (dd, 1H, J=5.7, 0.9 Hz), 8.26 (d, 1H, J=7.8 Hz), 8.50 (d, 1H, J=5.7 Hz). $^{13}$C NMR (D$_2$O) δ 16.96, 22.99, 24.96, 39.60, 51.80, 54.05, 55.05, 125.91, 127.62, 132.33, 132.89, 137.42, 138.38, 140.39, 147.77, 151.45, 154.85. ES-MS m/z 301 (M+H). Anal. Calcd. for $C_{17}H_{24}N_5O \cdot 3.3HBr \cdot 1.8H_2O$: C, 34.04; H, 5.19; N, 9.34; Br, 43.96. Found: C, 34.40; H, 5.39; N, 8.98; Br, 43.70.

Example 15

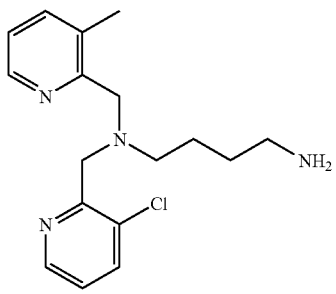

COMPOUND 15: $N^1$-(3-Chloro-pyridin-2-ylmethyl)-$N^1$-(3-methyl-pyridin-2-ylmethyl)-butane-1,4-diamine (HBr salt)

White solid. $^1$H NMR (D$_2$O) δ 1.64 (m, 2H), 1.76 (m, 2H), 2.44 (s, 3H), 2.97 (t, 2H, J=7.5 Hz), 3.07 (t, 2H, J=7.5 Hz), 4.51 (s, 2H), 4.57 (s, 2H), 7.71 (m, 2H), 8.16 (d, 1H, J=9.0 Hz), 8.26 (d, 1H, J=9.0 Hz), 8.51 (d, 1H, J=6.0 Hz), 8.61 (d, 1H, J=6.0 Hz). $^{13}$C NMR (D$_2$O) δ 17.22, 22.29, 24.74, 39.43, 54.62, 55.42, 125.96, 126.70, 133.27, 136.90, 140.84, 143.76, 146.39, 149.23, 149.95. ES-MS m/z 319 [M+H]$^+$.

Anal. Calcd. for $C_{17}H_{23}N_4Cl \cdot 3.3HBr \cdot 1.8H_2O$: C, 33.02; H, 4.87; N, 9.06; Cl, 5.73; Br, 42.65. Found: C, 32.79; H, 4.86; N, 8.88; Cl, 6.04; Br, 42.49.

Example 16

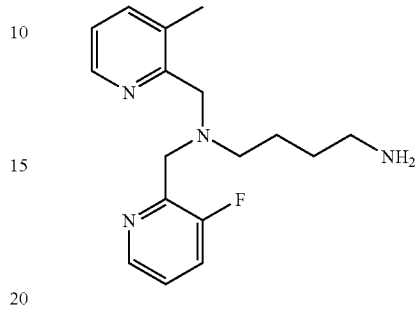

COMPOUND 16: $N^1$-(3-Fluoro-pyridin-2-ylmethyl)-$N^1$-(3-methyl-pyridin-2-ylmethyl)-butane-1,4-diamine (HBr salt)

White solid. $^1$H NMR (D$_2$O) δ 1.61-1.76 (m, 4H), 2.48 (s, 3H), 2.95 (m, 4H), 4.45 (s, 2H), 4.49 (s, 2H), 7.84 (m, 1H), 7.96 (m, 1H), 8.25 (m, 1H), 8.31 (d, 1H, J=6.0), 8.60 (d, 1H, J=6.0 Hz), 8.64 (d, 1H, J=6.0 Hz). $^{13}$C NMR (D$_2$O) δ 17.27, 22.61, 24.85, 39.54, 51.34, 53.82, 54.98, 126.31, 128.45, 132.54 (d, $J_{CF}$=18.0 Hz), 137.83, 139.44, 140.71, 148.03, 149.70, 157.26, 160.64. $^{19}$F NMR (D$_2$O) δ 42.26 (s). ES-MS m/z 303 [M+H]$^+$. Anal. Calcd. for $C_{17}H_{23}N_4F \cdot 3.7HBr \cdot 1.6H_2O$: C, 32.38; H, 4.78; N, 8.88; Br, 46.88. Found: C, 32.35; H, 4.83; N, 8.80; Br, 47.09.

Example 17

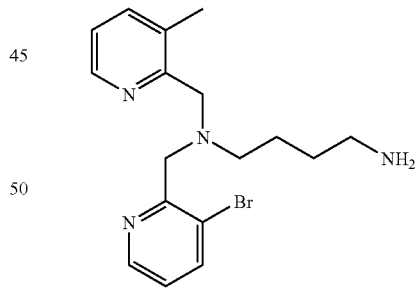

COMPOUND 17: $N^1$-(3-Bromo-pyridin-2-ylmethyl)-$N^1$-(3-methyl-pyridin-2-ylmethyl)-butane-1,4-diamine (HBr salt)

White solid. $^1$H NMR (D$_2$O) δ 1.66 (m, 2H), 1.78 (m, 2H), 2.46 (s, 3H), 2.99 (t, 2H, J=7.5 Hz), 3.10 (m, 2H), 4.54 (s, 2H), 4.59 (s, 2H), 7.64 (dd, 1H, J=7.5, 4.5 Hz), 7.72 (dd, 1H, J=7.5, 4.5 Hz), 8.17 (d, 1H, J=7.8 Hz), 8.43 (d, 1H, J=7.8), 8.53 (d, 1H, J=3.0 Hz), 8.66 (d, 1H, J=3.0). $^{13}$C NMR (D$_2$O) δ 17.27, 22.30, 24.76, 39.44, 54.73, 55.46, 57.46, 122.28, 125.94, 126.72, 136.85, 140.97, 144.21, 146.30, 147.00, 149.22, 151.03. ES-MS m/z 363/365 [M+H]⁺. Anal. Calcd. for C$_{17}$H$_{23}$N$_4$Br.3.1HBr.1.0H$_2$O: C, 32.30; H, 4.48; N, 8.86; Br, 51.82. Found: C, 32.43; H, 4.62; N, 8.75; Br, 51.58.

Example 18

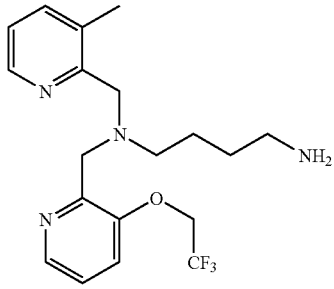

COMPOUND 18: N$^1$-(3-methyl-pyridin-2-ylmethyl)-N$^1$-[3-(2,2,2-trifluoro-ethoxy)-pyridin-2-ylmethyl]-butane-1,4-diamine 2-Chloro-3-(2,2,2-trifluoro-ethoxy)-pyridine (1.21 g, 5.73 mmol) (Hoglen, D. K. PCT Int. Appl. (2000), WO 2000005212) and 1,3-bis(diphenylphosphino)propane nickel (II) chloride (217 mg, 0.40 mmol) were taken up in Et$_2$O (40 mL) at room temperature. MeMgBr (3.0M in Et$_2$O, 2.25 ml, 5.73 mmol) was added dropwise via syringe over 3 minutes to give a tan slurry. The mixture was refluxed for 16 h, cooled to room temperature, quenched with water (60 mL) and extracted with CH$_2$Cl$_2$ (8×50 mL). The combined organic extracts were dried (Na$_2$SO$_4$), filtered, and concentrated in vacuo to afford 2-methyl-3-(2,2,2-trifluoro-ethoxy)-pyridine as an orange oil. Purification via column chromatography on silica gel (CH$_2$Cl$_2$) afforded 2-methyl-3-(2,2,2-trifluoro-ethoxy)-pyridine as a yellow solid (0.46 g, 42%). $^1$H NMR (CDCl$_3$) δ 2.52 (s, 3H), 4.36 (q, 2H, J=7.5 Hz), 7.06-7.14 (m, 2H), 8.19 (d, 1H, J=3.0 Hz). $^{19}$F NMR (CDCl$_3$) δ 2.03 (s).

Selenium dioxide (674 mg, 6.07 mmol) was added to a solution of 2-methyl-3-(2,2,2-trifluoro-ethoxy)-pyridine (464 mg, 6.21 mmol) dissolved in a mixture of water (2 mL) and 1,4-dioxane (15 mL). The resulting mixture was stirred at 100° C. for 48 hours. The reaction mixture was quenched with saturated NaHCO$_3$ (25 mL) and extracted with CH$_2$Cl$_2$ (5×50 mL). The combined organic extracts were dried (Na$_2$SO$_4$), filtered, concentrated in vacuo to afford an orange oil (443 mg). TLC analysis indicated a single species, however, $^1$H NMR analysis revealed a 3:1 mixture of 2-methyl-3-(2,2,2-trifluoro-ethoxy)-pyridine to 3-(2,2,2-trifluoro-ethoxy)-pyridine-2-carbaldehyde. The mixture was used without further purification in the reductive amination step. $^1$H NMR (CDCl$_3$) δ 4.52 (q, 2H, J=7.5 Hz), 7.47 (d, 1H, J=7.5 Hz), 7.51 (dd, 1H, J=6.0, 3.0 Hz), 8.55 (d, 1H, J=3.0 Hz), 10.36 (s, 1H).

COMPOUND 18 was isolated as a pale yellow oil. $^1$H NMR (CDCl$_3$) δ 1.24 (m, 2H), 1.44 (m, 2H), 2.08 (s, 3H), 2.14 (br s, 2H), 2.47 (m, 4H), 3.75 (s, 2H), 3.82 (s, 2H), 4.30 (q, 2H, J=7.5 Hz), 7.01 (m, 1H), 7.13 (m, 2H), 7.29 (d, 1H, J=7.8 Hz), 8.21 (d, 1H, J=3.0 Hz), 8.26 (d, 1H, J=3.0 Hz). $^{19}$F NMR (CDCl$_3$) δ 2.39 (s). $^{13}$C NMR (CDCl$_3$) δ 18.28, 24.25, 31.51, 41.98, 53.86, 55.20, 59.66, 66.24, 66.54 (q, J$_{CF}$=35.9), 119.86, 122.55, 123.46, 133.75, 138.25, 142.80, 146.19, 149.83, 153.53, 157.73. ES-MS m/z 383 [M+H]⁺. Anal. Calcd. for C$_{19}$H$_{25}$N$_4$O.0.1TFA.0.4H$_2$O: C, 57.50; H, 6.51; N, 13.97. Found: C, 57.63; H, 6.71; N, 13.70.

Example 19

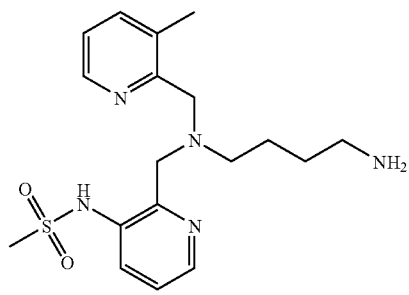

COMPOUND 19: N-(2-{[(4-amino-butyl)-(3-methyl-pyridin-2-ylmethyl)-amino]-methyl}-pyridin-3-yl)-methanesulfonamide (HBr salt)

White solid. $^1$H NMR (D$_2$O) δ 1.54-1.70 (m, 4H), 2.48 (s, 3H), 2.84-2.90 (m, 2H), 2.91-2.97 (m, 2H), 3.27 (s, 3H), 4.41 (s, 2H), 4.50 (s, 2H), 7.80 (dd, 1H, J=5.4, 7.8 Hz), 7.93 (dd, 1H, J=5.7, 8.4 Hz), 8.29 (d, 1H, J=7.8 Hz), 8.40 (dd, 1H, J=1.2, 8.4 Hz), 8.57 (d, 1H, J=5.4 Hz), 8.68 (dd, 1H, J=1.2, 5.7 Hz); $^{13}$C NMR (D$_2$O) δ 17.33, 22.42, 24.86, 39.50, 40.65, 53.87, 54.33, 55.18, 126.18, 127.25, 134.78, 137.66, 139.66, 141.35, 141.79, 147.84, 149.34, 149.76. ES-MS m/z 378 (M+H). Anal. Calcd. for C$_{18}$H$_{27}$N$_5$O$_2$S.4.0HBr.1.0H$_2$O.0.2C$_4$H$_{10}$O: C, 30.76; H, 4.81; N, 9.54; S, 4.37; Br, 43.54. Found: C, 30.75; H, 4.66; N, 9.39; S, 4.42; Br, 43.59.

Example 20

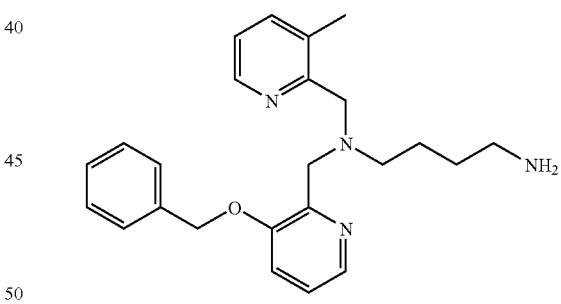

COMPOUND 20: N$^1$-(3-benzyloxy-pyridin-2-ylmethyl)-N$^1$-(3-methyl-pyridin-2-ylmethyl)-butane-1,4-diamine (HBr salt)

Pale yellow solid. $^1$H NMR (D$_2$O) δ 1.49 (s, br, 4H), 2.34 (s, 3H), 2.69 (s, br, 2H), 2.83 (s, br, 2H), 4.21 (s, 2H), 4.28 (s, 2H), 5.19 (s, 2H), 7.29 (s, 5H), 7.57 (t, 1H, J=6.9 Hz), 7.92 (dd, 1H, J=5.7, 8.7 Hz), 8.04 (d, 1H, J=7.8 Hz), 8.19-8.26 (m, 2H), 8.30 (d, 1H, J=5.7 Hz); $^{13}$C NMR (D$_2$O) δ 16.94, 23.04, 24.89, 39.62, 52.78, 54.48, 54.60, 68.29, 125.77, 128.07, 128.40, 129.33, 129.40, 129.79, 132.80, 134.87, 136.79, 137.73, 142.72, 147.72, 151.26, 156.12. ES-MS m/z 391 (M+H). Anal. Calcd. for C$_{24}$H$_{30}$N$_4$O.4.0HBr.3.0H$_2$O.0.3C$_4$H$_{10}$O: C, 38.29; H, 5.48; N, 7.09; Br, 40.43. Found: C, 38.21; H, 5.63; N, 7.12; Br, 40.67.

Example 21

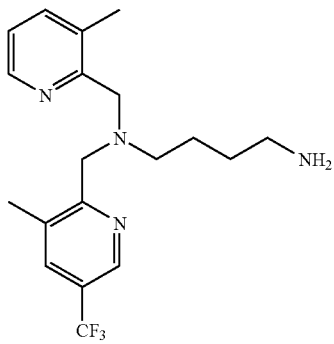

COMPOUND 21: N[1]-(3-methyl-5-trifluoromethyl-pyridin-2-ylmethyl)-N[1]-(3-methyl-pyridin-2-ylmethyl)-butane-1,4-diamine (HBr salt)

Under $N_2$, to a solution of 2,3-dichloro-5-trifluoromethyl-pyridine (2.16 g, 10.0 mmol) and 1,3-bis(diphenylphosphino) propane nickel(II) chloride (0.270 g, 0.500 mmol) in dry $Et_2O$ (50 mL) was added $CH_3MgBr$ (3.0 M in $Et_2O$, 8.33 mL, 25.0 mmol) at room temperature. After the addition the mixture was stirred at room temperature for 30 min, and then heated at reflux for 16 h. The solution was then cooled down, and $H_2O$ (50 mL) was added. The organic layer was collected, and the aqueous layer was extracted with $Et_2O$ (2×50 mL) and $CH_2Cl_2$ (50 mL). The organic layers were combined and dried over $MgSO_4$. After filtration the solvent was removed, and the residue was purified on silica gel column (4:1, $CH_2Cl_2/Et_2O$) to afford 2,3-dimethyl-5-trifluoromethyl-pyridine as a pale yellow liquid (0.725 g, 41%).

A mixture of 2,3-dimethyl-5-trifluoromethyl-pyridine (0.700 g, 4.00 mmol), 3-chloroperoxybenzoic acid (77%, 2.8 g, 12 mmol) in $CH_2Cl_2$ (20 mL) was stirred at room temperature for 20 h. After that period of time saturated aqueous $NaHCO_3$ (5 mL), and the mixture was extracted with $CH_2Cl_2$ (5×20 mL). The extracts were combined and dried over $Na_2SO_4$. After filtration the solvent was removed, and the residue was purified on silica gel column (EtOAc), affording 2,3-dimethyl-5-trifluoromethyl-pyridine 1-oxide as a pale yellow solid (0.620 g, 81%).

To a solution of 2,3-dimethyl-5-trifluoromethyl-pyridine 1-oxide (0.620 g, 3.24 mmol) in $CH_2Cl_2$ (20 mL) was added TFAA (1.36 g, 6.48 mmol) at room temperature. After the mixture was stirred at room temperature for 3 h, brine (5 mL) and $K_2CO_3$ (20 mL) were added. The mixture was stirred at room temperature for 1 h and then extracted with $CH_2Cl_2$ (3×20 mL). The extracts were combined and dried over $Na_2SO_4$. After filtration the solvent was removed, and the residue was purified on silica gel column (4:1, $CH_2Cl_2/Et_2O$), affording (2,3-dimethyl-5-trifluoromethyl-pyridin-2-yl)-methanol as a pale yellow oil (0.300 g, 48%).

A suspension of (2,3-dimethyl-5-trifluoromethyl-pyridin-2-yl)-methanol (0.300 g, 1.57 mmol)) and activated $MnO_2$ (1.36 g, 15.6 mmol) in $CH_2Cl_2$ (10 mL) was stirred at room temperature overnight. After that period of time the suspension was filtered through a celite cake. the solvent was removed from the filtrate, and the residue was purified on silica gel column ($CH_2Cl_2$) to afford 3-methyl-5-trifluoromethyl-pyridine-2-carbaldehyde as a pale yellow liquid (0.180 g, 61%). $^1$H NMR ($CD_3Cl$) δ 2.73 (s, 3H), 7.87 (s, 1H), 8.90 (s, 1H), 10.23 (s, 1H).

COMPOUND 21 was isolated as a white solid. $^1$H NMR ($D_2O$) δ 1.55-1.66 (m, 4H), 2.49 (s, 6H), 2.89-2.94 (m, 4H), 4.51 (s, 2H), 4.55 (s, 2H), 7.84 (dd, 1H, J=5.7, 8.1 Hz), 8.34 (d, 1H, J=8.1 Hz), 8.53 (s, 1H), 8.60 (d, 1H, J=5.7 Hz), 8.94 (s, 1H); $^{13}$C NMR ($D_2O$) δ 17.48, 17.65, 22.50, 24.82, 39.49, 54.45, 55.28, 55.42, 126.63, 137.69, 138.39, 138.48, 139.41, 143.21, 143.25 148.63, 148.74, 154.80; $^{19}$F NMR ($D_2O$) δ 13.32. ES-MS m/z 367 (M+H). Anal. Calcd. for $C_{19}H_{25}F_3N_4 \cdot 4.4HBr \cdot 3.5H_2O \cdot 0.9C_4H_{10}O$: C, 31.85; H, 5.37; N, 6.57; Br, 41.26. Found: C, 31.85; H, 5.13; N, 6.55; Br, 41.18.

Example 22

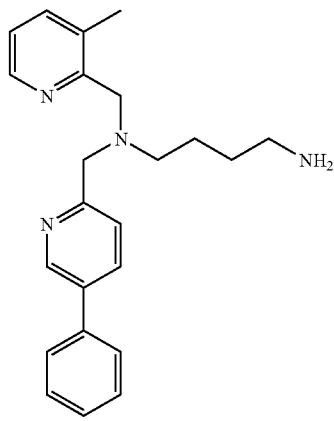

COMPOUND 22: N[1]-(3-methyl-pyridine-2-ylmethyl)-N[1]-(5-phenyl-pyridine-2-ylmethyl)-butane-1,4-diamine (HBr salt)

To a solution of 2-methyl-5-phenyl-pyridine (800 mg, 4.73 mmol) (Koyama, J. et al. *Heterocycles*, 1994, 38, 1595-1600) in mixture of dioxane/water (20 mL:2 mL) was added $SeO_2$ (577 mg, 5.20 mmol). The reaction mixture was heated to 110° C. overnight. Then the reaction mixture was cooled and concentrated in vacuo. Purification by flash column chromatography on silica gel using 1:4 hexanes/EtOAc afforded 5-phenyl-pyridine-2-carbaldehyde as a pale yellow solid (124 mg, 14%). $^1$H NMR ($CDCl_3$) δ 7.49-7.52 (m, 3H), 7.63-7.66 (m, 2H), 8.05 (s, 2H), 9.02 (d, 1H, J=3.0 Hz), 10.12 (s, 1H).

Using general procedure B with the above aldehyde gave 4-[(3-methyl-pyridine-2-ylmethyl)-(5-phenyl-pyridine-2-ylmethyl)-amino]-butyl}-carbamic acid tert-butyl ester as a pale yellow oil. Salt formation using general procedure D gave COMPOUND 22 as a pale yellow solid. $^1$H NMR ($D_2O$) δ 1.59-1.63 (br m, 4H), 2.48 (s, 3H), 2.82 (t, 2H, J=6.6 Hz), 2.95 (t, 2H, J=7.5 Hz), 4.33 (s, 2H), 4.39 (s, 2H), 7.60-7.62 (m, 3H), 7.75-7.77 (m, 2H), 7.83 (t, 1H, J=6.3 Hz), 8.11 (d, 1H, J=8.4 Hz), 8.32 (d, 1H, J=7.8 Hz), 8.58 (d, 1H, J=5.7 Hz), 8.75 (d, 1H, J=8.4 Hz), 9.00 (s, 1H). $^{13}$C NMR ($D_2O$) δ 17.09, 22.93, 24.99, 39.58, 53.89, 55.02, 56.18, 125.92, 127.73, 130.08, 130.63, 133.71, 137.54, 138.76, 139.87, 140.07, 144.98, 148.06, 150.88, 151.35. ES-MS m/z 361 [M+H]$^+$.

Anal. Calcd. for $C_{23}H_{28}N_4 \cdot 3.5HBr \cdot 1.7H_2O$: C, 40.97; H, 5.22; N, 8.31; Br, 41.47. Found: C, 40.87; H, 5.43; N, 7.99; Br, 41.81.

Example 23

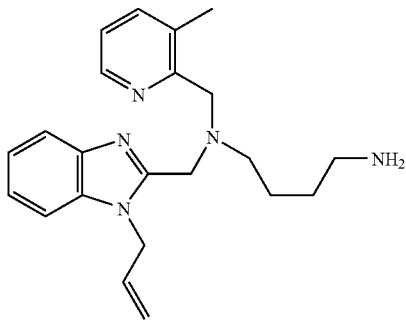

COMPOUND 23: N-(1-Allyl-1H-benzimidazol-2-ylmethyl)-N-(3-methyl-pyridin-2-yl-methyl)-butane-1,4-diamine (HBr salt)

White solid. $^1$H NMR (D$_2$O) δ 1.59 (br, 4H), 2.49 (s, 3H), 2.82 (br t, 2H, J=7.4 Hz), 2.92 (br t, 2H, J=6.9 Hz), 4.35 (s, 2H), 4.50 (s, 2H), 5.09 (m, 3H), 5.33 (d, 1H, J=10.8 Hz), 6.05 (m, 1H), 7.63 (m, 2H), 7.80 (m, 3H), 8.33 (d, 1H, J=7.5 Hz), 8.58 (d, 1H, J=5.4 Hz). $^{13}$C NMR (D$_2$O) δ 17.23, 23.04, 24.95, 39.61, 47.67, 50.21, 54.36, 55.30, 113.29, 114.56, 119.33, 126.05, 127.04, 127.45, 130.21, 130.26, 132.59, 137.65, 138.54, 148.51, 150.50, 151.12. ES-MS m/z 364 (M+H). Anal. Calcd. for $C_{22}H_{29}N_5 \cdot 3.1HBr \cdot 1.9H_2O$: C, 40.74; H, 5.58; N, 10.80; Br, 38.19. Found: C, 40.67; H, 5.49; N, 10.59; Br, 38.46.

Example 24

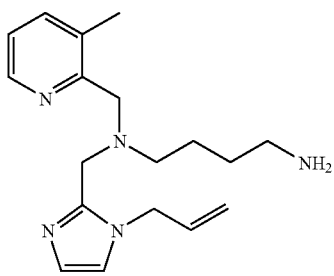

COMPOUND 24: Preparation of: $N^1$-(1-Allyl-1H-imidazol-2-ylmethyl)-$N^1$-(3-methyl-pyridin-2-ylmethyl)-butane-1,4-diamine (HBr salt)

White solid. $^1$H NMR (D$_2$O) δ 1.51-1.63 (m, 4H), 2.47 (s, 3H), 2.68-2.77 (m, 2H), 2.88-2.97 (m, 2H), 4.26 (s, 4H), 5.17 (d, 1H, J=17.5 Hz), 5.37 (d, 1H, J=10.5 Hz), 5.93-6.06 (m, 1H), 7.45 (d, 2H, J=5.7 Hz), 7.86 (t, 1H, J=6.8 Hz), 8.37 (d, 1H, J=7.5 Hz), 8.59 (d, 1H, J=5.7 Hz); $^{13}$C NMR (D$_2$O) δ 17.2, 23.0, 25.0, 39.6, 49.1, 50.4, 53.9, 55.0, 119.4, 120.1, 123.6, 126.1, 130.8, 137.7, 138.5, 143.9, 148.5, 151.2; ES-MS m/z 314 (M+H). Anal Calcd. For $C_{18}H_{27}N_5 \cdot 4.6(HBr) \cdot 3.0(H_2O)$: C, 29.15; H, 5.11; N, 9.44; Br, 49.82. Found: C, 29.29; H, 5.38; N, 9.05; Br, 49.85.

Example 25

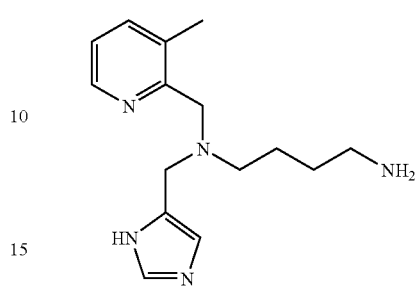

COMPOUND 25: Preparation of: $N^1$-(3H-Imidazol-4-ylmethyl)-$N^1$-(3-methyl-pyridin-2-ylmethyl)-butane-1,4-diamine Yellow oil. $^1$H NMR (CDCl$_3$) δ 1.47-1.66 (m, 4H), 2.43 (s, 3H), 2.49 (t, 1H, J=6.6 Hz), 2.74 (t, 1H, J=6.6 Hz), 3.48 (s, 2H), 3.66 (s, 2H), 6.89 (s, 1H), 7.19 (dd, 1H, J=7.5, 4.8 Hz), 7.53 (d, 1H, J=7.0 Hz), 7.67 (s, 1H), 8.43 (d, 1H, J=4.8); ES-MS m/z 274 (M+H).

Example 26

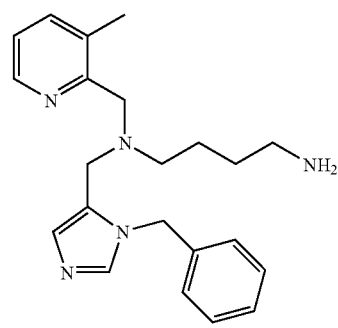

COMPOUND 26: $N^1$-(3-Benzyl-3H-imidazol-4-ylmethyl)-$N^1$-(3-methyl-pyridin-2-ylmethyl)-butane-1,4-diamine Yellow oil. $^1$H NMR (CDCl$_3$) 1.27-1.35 (m, 2H), 1.39-1.49 (m, 2H), 2.23 (s, 3H), 2.47 (t, 2H, J=7.0 Hz), 2.57 (t, 2H, J=7.0 Hz), 3.46 (s, 2H), 3.74 (s, 2H), 5.05 (s, 2H), 6.78-6.81 (m, 2H), 6.97 (s, 1H), 7.07 (dd, 1H, J=7.9, 4.8 Hz), 7.21-7.25 (m, 3H), 7.39 (d, 1H, J=7.9 Hz), 7.43 (s, 1H), 8.30 (dd, 1H, J=4.8, 1.5 Hz); ES-MS m/z 364 (M+H).

Example 27

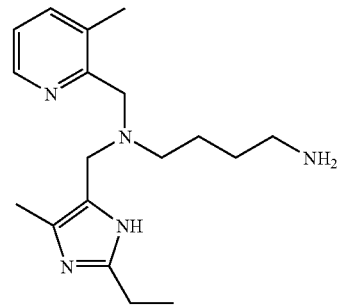

COMPOUND 27: $N^1$-(2-Ethyl-5-methyl-3H-imidazol-4-ylmethyl)-$N^1$-(3-methyl-pyridin-2-ylmethyl)-butane-1,4-diamine Yellow oil. $^1$H NMR (CDCl$_3$) δ 1.34 (t, 3H, J=7.5 Hz), 1.47-1.67 (m, 4H), 2.13 (s, 3H), 2.37 (s, 3H), 2.47 (t, 2H, J=7.0 Hz), 2.72-2.80 (m, 4H), 3.40 (s, 2H), 3.68 (s, 2H), 7.17 (dd, 1H, J=7.5, 4.8), 7.51 (d, 1H, J=7.0 Hz), 8.41 (d, 1H, J=4.8 Hz); ES-MS m/z 316 (M+H).

Example 28

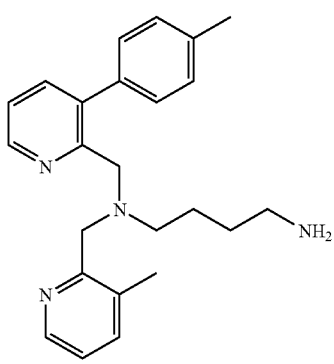

COMPOUND 28: $N^1$-(3-methyl-pyridin-2-ylmethyl)-$N^1$-(3-p-tolyl-pyridin-2-ylmethyl)-butane-1,4-diamine (HBr salt)

To a stirred degassed solution of 3-bromo-2-pyridinecarboxaldehyde (198 mg, 1.06 mmol) and 4-methylbenzene boronic acid (152 mg, 1.12 mmol) in DME/THF (3.5 mL, 2.5:1) were added a 2 M Na$_2$CO$_3$ solution (0.9 mL) and Pd(PPh$_3$)$_4$ (63 mg, 0.055 mmol). The reaction mixture was flushed with Ar and maintained under Ar while being heated at 90° C. overnight. The mixture was then cooled and diluted with EtOAc (40 mL) and brine (30 mL). The organic layer was washed with brine (1×30 mL), dried (Na$_2$SO$_4$), filtered and concentrated. Purification of the resultant oil by column chromatography with silica gel (Hexanes/EtOAc, 2:1) afforded 3-p-tolyl-pyridine-2-carbaldehyde (161 mg, 77%) as a yellow oil. $^1$H NMR (CDCl$_3$) δ 2.43 (s, 3H), 7.25-7.28 (m, 4H), 7.53 (dd, 1H, J=9, 6 Hz), 7.79 (dd, 1H, J=9, 1 Hz), 8.80 (dd, J=3, 1 Hz), 10.09 (s, 1H).

COMPOUND 28 was isolated as a white solid. $^1$H NMR (D$_2$O) δ 1.44-1.48 (m, 4H), 2.38 (s, 3H), 2.40 (s, 3H), 2.63 (t, 2H, J=7.2 Hz), 2.85 (t, 2H, J=6.9 Hz), 4.15 (s, 2H), 4.38 (s, 2H), 7.34 (d, 2H, J=8.1 Hz), 7.40 (d, 2H, J=8.1 Hz), 7.85 (dd, 1H, J=7.8, 6.3 Hz), 8.04 (dd, 1H, J=8.1, 6.0 Hz), 8.32 (d, 1H, J=7.8 Hz), 8.47 (dd, 1H, J=8.1, 1.2 Hz), 8.53 (d, 1H, J=5.7 Hz), 8.79 (dd, 1H, J=5.4, 1.2 Hz); $^{13}$C NMR (D$_2$O) δ 17.14, 20.84, 22.44, 24.93, 39.56, 54.11, 54.54, 125.97, 126.59, 129.55, 130.22, 131.24, 137.65, 138.58, 140.51, 140.83, 141.31, 148.34, 150.24, 150.88. ES-MS m/z 375 (M+H).

Anal. Calcd. for C$_{24}$H$_{30}$N$_4$.3.5HBr.1.8H$_2$O.0.5C$_4$H$_{10}$O: C, 42.94; H, 5.84; N, 7.70; Br, 38.46. Found: C, 42.99; H, 5.88; N, 7.73; Br, 38.28

Example 29

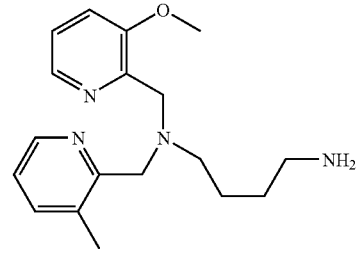

COMPOUND 29: N-(3-methoxypyridin-2-ylmethyl)-N-(3-methylpyridin-2-ylmethyl)-butane-1,4-diamine (HBr salt)

White solid. $^1$H NMR (D$_2$O) δ 1.63 (br, 4H), 2.42 (s, 3H), 2.88 (t, 2H, J=7.7 Hz), 2.94 (t, 2H, J=7.1 Hz), 3.98 (s, 3H), 4.33 (s, 2H), 4.35 (s, 2H), 7.75 (t, 1H, J=6.9 Hz), 7.83 (t, 1H, J=7.4 Hz), 7.99 (d, 1H, J=8.7 Hz), 8.22 (d, 1H, J=7.8 Hz), 8.26 (d, 1H, J=5.4 Hz), 8.51 (d, 1H, J=5.4 Hz). $^{13}$C NMR (D$_2$O) δ 17.00, 22.80, 24.92, 39.55, 51.92, 54.29, 55.12, 57.34, 125.94, 127.69, 127.74, 132.96, 137.36, 138.71, 142.41, 147.68, 151.14, 156.40. ES-MS m/z 315 (M+H). Anal. Calcd. for C$_{18}$H$_{26}$N$_4$O.4.1HBr.1.2H$_2$O.0.3C$_4$H$_{10}$O: C, 33.42; H, 5.19; N, 8.12; Br, 47.48. Found: C, 33.39; H, 5.30; N, 8.11; Br, 47.46.

Example 30

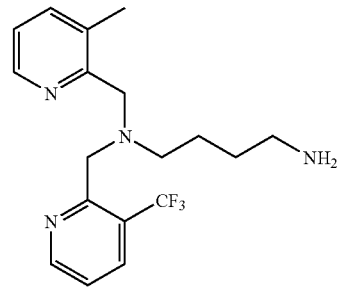

COMPOUND 30: $N^1$-(3-methyl-pyridin-2-ylmethyl)-$N^1$-(3-trifluoromethyl-pyridin-2-ylmethyl)-butane-1,4-diamine (HBr salt)

White solid. $^1$H NMR (CDCl$_3$) δ 1.68 (m, 2H), 1.83 (m, 2H), 2.37 (s, 3H), 2.96 (t, 2H, J=7.5 Hz), 3.28 (t, 2H, J=8.1 Hz), 4.60 (s, 2H), 4.72 (s, 2H), 7.53 (m, 1H), 7.68 (m, 1H), 7.95 (d, 1H, J=7.8 Hz), 8.30 (d, 1H, J=8.1 Hz), 8.46 (m, 1H), 8.81 (m, 1H). $^{19}$F NMR (CDCl$_3$) δ 15.09 (s). $^{13}$C NMR (D$_2$O) δ 17.05, 22.11, 24.51, 39.30, 55.45, 55.55, 55.85, 124.80, 125.18, 125.36, 135.20, 137.80, 137.86, 143.32, 143.42, 148.78, 150.26, 151.06. ES-MS m/z 353 [M+H]$^+$. Anal.

Calcd. for $C_{18}H_{23}N_4F_3 \cdot 2.4HBr \cdot 1.6H_2O$: C, 37.57; H, 5.01; N, 9.74; Br, 33.33. Found: C, 37.84; H, 4.98; N, 9.69; Br, 32.95.

Example 31

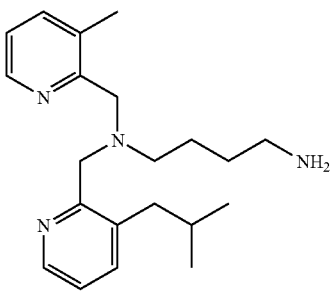

COMPOUND 31: $N^1$-(3-isobutyl-pyridin-2-ylmethyl)-$N^1$-(3-methyl-pyridin-2-ylmethyl)-butane-1,4-diamine (HBr salt)

3-Isobutyl-2-methyl-pyridine (Ishiguro et al. *Yakugaku Zasshi* 1958, 78, 220) (970 mg, 6.51 mmol) was suspended in a mixture of hydrogen peroxide (5 mL) and HOAc (45 mL) and the resulting mixture was stirred at 100° C. for 2.5 hours. The solvent was removed under reduced pressure and the resulting oily mixture was quenched with saturated $NaHCO_3$ (60 mL) and extracted with $CH_2Cl_2$ (10×100 mL). The combined organic extracts were dried ($MgSO_4$), filtered, and concentrated in vacuo to yield 3-isobutyl-2-methyl-pyridine-1-oxide as a colorless oil (821 mg, 76%). $^1$H NMR (CDCl$_3$) δ 0.93 (d, 6H, J=6.0 Hz), 1.84 (m, 1H), 2.51 (d, 2H, J=6.0 Hz), 2.52 (s, 3H), 7.03 (m, 2H), 8.18 (d, 1H, J=6.0 Hz).

3-Isobutyl-2-methyl-pyridine-1-oxide (821 mg, 4.97 mmol) was dissolved in $Ac_2O$ (10 mL) and stirred at 100° C. for 16 hours. The $Ac_2O$ was removed under reduced pressure and the resulting brown oil was quenched with saturated $NaHCO_3$ (30 mL) and extracted with $CH_2Cl_2$ (6×50 mL). The combined organic extracts were dried ($Na_2SO_4$), filtered, and concentrated in vacuo to yield a brown oil. Purification was avoided at this step due to the identical $R_f$ values of the two products formed. The brown oil was dissolved in MeOH (20 mL) and powdered $K_2CO_3$ (2.05 g) was added. The mixture was stirred at room temperature for 2.5 hours. The solid was removed via suction filtration and the filtrate was concentrated in vacuo to give a brown oil. Purification via column chromatography on silica gel ($CH_2Cl_2$:MeOH, 95:5, v/v) afforded (3-isobutyl-pyridin-2-yl)-methanol as a yellow oil (383 mg, 78%, 2-steps). $^1$H NMR (CDCl$_3$) δ 0.93 (d, 6H, J=6.0 Hz), 1.86 (m, 1H), 2.38 (d, 2H, J=6.0 Hz), 4.73 (s, 2H), 4.90 (br s, 1H), 7.18 (dd, 1H, J=9.0, 3.0 Hz), 7.45 (d, 1H, J=9.0), 8.41 (d, 1H, J=6.0 Hz).

$MnO_2$ (2.01 g, 23.2 mmol) was added to a flask containing a solution of (3-isobutyl-pyridin-2-yl)-methanol (383 mg, 2.32 mmol) in $CH_2Cl_2$ (15 mL). The black mixture was stirred at room temperature for 22 hours and then filtered through celite. The filtrate was concentrated in vacuo to give a yellow oil. Purification via column chromatography on silica gel ($CH_2Cl_2$:MeOH, 97.5:2.5, v/v) afforded 3-isobutyl-pyridine-2-carbaldehyde as an orange oil (344 mg, 91%). $^1$H NMR (CDCl$_3$) δ 0.93 (d, 6H, J=6.0 Hz), 1.87 (m, 1H), 2.94 (d, 2H, J=6.0 Hz), 7.39 (dd, 1H, J=9.0, 3.0 Hz), 7.60 (d, 1H, J=9.0), 8.67 (d, 1H, J=6.0 Hz), 10.18 (s, 1H).

COMPOUND 31 was isolated as a white solid. $^1$H NMR ($D_2O$) δ 0.91 (d, 6H, J=7.5 Hz), 1.56 (m, 4H), 1.89 (m, 1H), 2.48 (s, 3H), 2.72 (m, 4H), 2.91 (br t, 2H), 4.33 (s, 2H), 4.38 (s, 2H), 7.84 (m, 2H), 7.86 (m, 2H), 8.60 (m, 2H). $^{13}$C NMR ($D_2O$) δ 17.28, 21.71, 22.94, 24.98, 29.34, 39.54, 39.59, 54.21, 54.41, 55.02, 125.98, 137.53, 139.01, 139.52, 140.71, 148.13, 148.49, 150.58, 150.95. ES-MS m/z 341 [M+H]$^+$. Anal. Calcd. for $C_{21}H_{32}N_4 \cdot 3.0HBr \cdot 1.1H_2O$: C, 41.82; H, 6.22; N, 9.29; Br, 39.75. Found: C, 41.65; H, 6.18; N, 9.22; Br, 39.88.

Example 32

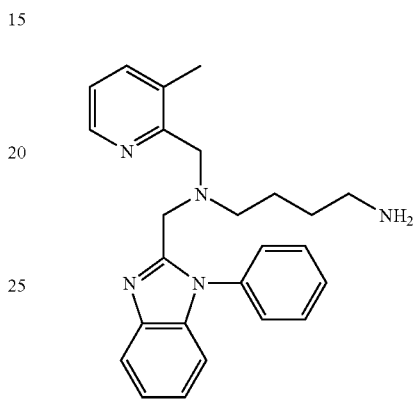

COMPOUND 32: $N^1$-(3-methyl-pyridin-2-ylmethyl)-$N^1$-(1-phenyl-1H-benzoimidazol-2-ylmethyl)-butane-1,4-diamine (HBr salt)

$^1$H NMR ($D_2O$) δ 1.49 (br s, 4H), 2.39 (s, 3H), 2.66 (br s, 2H), 2.88 (br s, 2H), 4.19 (s, 2H), 4.41 (s, 2H), 7.49 (d, 1H, J=8.1 Hz), 7.59-7.77 (m, 7H), 7.84-7.92 (m, 2H), 8.34 (d, 1H, J=8.1 Hz), 8.55 (d, 1H, J=5.7 Hz); $^{13}$C NMR ($D_2O$) δ 17.12, 23.02, 24.89, 39.57, 49.83, 54.05, 54.76, 113.44, 114.60, 126.06, 127.23, 127.54, 127.79, 130.17, 131.17, 131.96, 133.98, 137.68, 138.48, 148.51, 152.29, 150.98; ES-MS m/z 400 (M+H). Anal. Calcd. For $C_{25}H_{29}N_5 \cdot 3.4HBr \cdot 2.8H_2O \cdot 0.5C_4H_{10}O$: C, 42.55; H, 5.69; N, 9.19; Br, 35.65. Found: C, 42.52; H, 5.68; N, 9.23; Br, 35.65.

Example 33

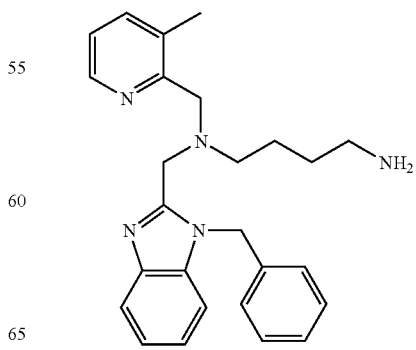

COMPOUND 33: N[1]-(1-Benzyl-1H-benzoimidazol-2-ylmethyl)-N[1]-(3-methyl-pyridin-2-ylmethyl)-butane-1,4-diamine (HBr salt)

$^1$H NMR (D$_2$O) δ 1.48 (br s, 4H), 2.41 (s, 3H), 2.72 (br s, 2H), 2.85 (br s, 2H), 4.22 (s, 2H), 4.46 (s, 2H), 5.74 (s, 2H), 7.19-7.22 (m, 2H), 7.37-7.39 (m, 3H), 7.58-7.67 (m, 2H), 7.75-7.86 (m, 3H), 8.29 (d, 1H, J=7.8 Hz), 8.49 (d, 1H, J=5.7 Hz); $^{13}$C NMR (D$_2$O) δ 17.12, 22.61, 24.89, 39.53, 48.69, 50.09, 54.00, 55.05, 113.28, 114.77, 126.02, 127.28, 127.54, 129.31, 129.77, 130.65, 132.98, 133.96, 137.61, 138.52, 148.43, 150.63, 150.90; ES-MS m/z 414 (M+H). Anal. Calcd. For C$_{26}$H$_{31}$N$_5$.3.1HBr.1.0H$_2$O: C, 45.76; H, 5.33; N, 10.26; Br, 36.30. Found: C, 45.70; H, 5.22; N, 10.09; Br, 36.29.

Example 34

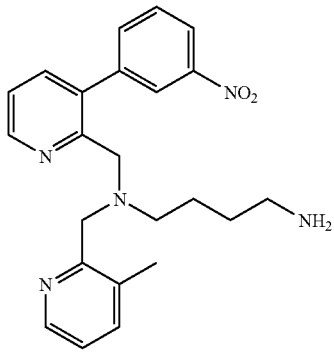

COMPOUND 34: N[1]-(3-methyl-pyridin-2-ylmethyl)-N[1]-[3-(3-nitro-phenyl)-pyridin-2-ylmethyl]-butane-1,4-diamine (HBr salt)

To a stirred solution of [3-(3-nitrophenyl)-pyridin-2-yl]-methanol (69 mg, 0.30 mmol) (Agrawal, K. C. et al. *J. Med. Chem.* 1974, 17, 631-5) in dry CH$_2$Cl$_2$ (5 mL) was added activated MnO$_2$ (90% purity, <10 micron, 251 mg, 2.89 mmol). The resulting heterogeneous mixture was stirred 2 d, at which point the black slurry was filtered through a cake of celite and washed with CH$_2$Cl$_2$ (3×15 mL). The combined washings were concentrated to afford 66 mg (96%) of 3-(3-nitrophenyl)-pyridine-2-carbaldehyde as a pale white solid, which was used in subsequent reactions without further purification. $^1$H NMR (CDCl$_3$) δ 7.60-7.69 (m, 3H), 7.77 (dd, 1H, J=7.8, 1.5 Hz), 8.21-8.23 (m, 1H), 8.30-8.35 (m, 1H), 8.91 (dd, 1H, J=4.5, 1.5 Hz), 10.12 (s, 1H).

COMPOUND 34 was isolated as a white solid. $^1$H NMR (D$_2$O) δ 1.48-1.53 (br m, 4H), 2.38 (s, 3H), 2.71-2.75 (m, 2H), 2.87-2.89 (m, 2H), 4.23 (s, 2H), 4.38 (s, 2H), 7.78-7.86 (m, 3H), 8.06 (dd, 1H, J=7.8, 5.7 Hz), 8.27 (d, 1H, J=8.1 Hz), 8.34 (br s, 1H), 8.42-8.48 (m, 1H), 8.49 (dd, 1H, J=7.8, 1.2 Hz), 8.55 (d, 1H, J=5.4 Hz), 8.88 (dd, 1H, J=5.7, 1.2 Hz). $^{13}$C NMR (D$_2$O) δ 17.14, 22.40, 24.82, 39.45, 54.27, 54.62, 54.72, 124.25, 125.04, 125.95, 126.54, 131.03, 135.80, 136.09, 137.31, 138.58, 139.51, 142.72, 147.41, 147.56, 148.54, 150.36. ES-MS m/z 406 (M+H). Anal. Calcd. for C$_{23}$H$_{27}$N$_5$O$_2$.3.2HBr.1.7H$_2$O: C, 39.75; H, 4.87; N, 10.08; Br, 36.79. Found: C, 40.07; H, 5.02; N, 9.72; Br, 36.39.

Example 35

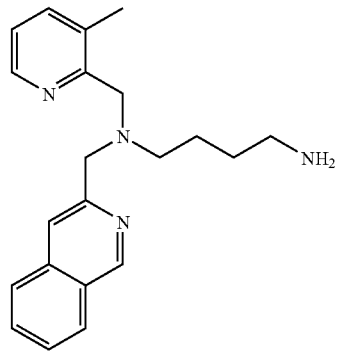

COMPOUND 35: N[1]-Isoquinolin-3-ylmethyl-N[1]-(3-methyl-pyridin-2-ylmethyl)-butane-1,4-diamine $^1$H NMR (D$_2$O) δ 7.71-7.74 (m, 1H), 7.99-8.03 (m, 1H), 8.20-8.24 (m, 3H), 8.39-8.44 (m, 2H), 8.52 (d, 1H, J=5.7 Hz), 9.62 (s, 1H). $^{13}$C NMR (D$_2$O) δ 17.0, 22.8, 25.1, 39.6, 53.6, 54.9, 56.2, 125.6, 125.8, 127.0, 127.7, 130.8, 131.6, 137.4, 138.0, 138.5, 139.4, 140.9, 147.9, 148.0, 151.7. ES-MS m/z 335 [M+H]$^+$. Anal. Calcd. for C$_{21}$H$_{26}$N$_4$.3.2HBr.3.5H$_2$O: C, 38.42; H, 5.56; N, 8.54; Br, 38.95. Found: C, 38.28; H, 5.28; N, 8.30; Br, 39.18.

Example 36

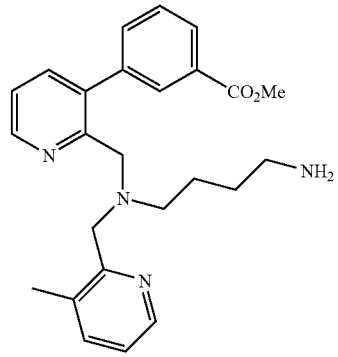

COMPOUND 36: 3-(2-{[(4-Amino-butyl)-(3-methyl-pyridin-2-ylmethyl)-amino]-methyl}-pyridin-3-yl)-benzoic acid methyl ester (HBr salt)

A stirred solution of 3-Tributylstannanyl-pyridine-2-carbaldehyde (256 mg, 0.65 mmol) and methyl 3-bromobenzoate (128 mg, 0.59 mmol) in DMF (2.1 mL) was degassed with Ar for 5 minutes, after which PdCl$_2$(PPh$_3$)$_2$ (25 mg, 0.036 mmol) and CuO (34 mg, 0.43 mmol) was added and the mixture heated to 110° C. overnight. The reaction was cooled to room temperature, and diluted with saturated aqueous NaHCO$_3$ (15 mL) and EtOAc (40 mL). The organic phase was separated, washed with brine (3×15 mL), dried (MgSO$_4$), filtered, and concentrated under reduced pressure. Purification by flash chromatography on silica gel (Hexanes/EtOAc, 60:40) gave 3-(2-Formyl-pyridin-3-yl)-benzoic acid methyl ester (25 mg, 17%) as a white solid. $^1$H NMR (CDCl$_3$) δ 3.92 (s, 3H), 7.47-7.56 (m, 2H), 7.58 (d, 1H, J=4.9 Hz), 8.03 (s, 1H), 8.07-8.20 (m, 1H), 8.86 (dd, 1H, J=4.9, 1.8 Hz), 10.08 (s, 1H).

COMPOUND 36 was isolated as a white solid. $^1$H NMR (D$_2$O) δ 1.49 (br t, 4H), 2.31 (s, 3H), 2.47 (s, 3H), 2.63-2.69 (m, 2H), 2.85-2.92 (m, 2H), 3.97 (s, 3H), 4.09 (s, 2H), 4.32 (s, 2H), 7.71 (d, 2H, J=4.8 Hz), 8.01 (s, 1H), 8.07 (dd, 1H, J=7.8, 6.0 Hz), 8.13 (s, 1H), 8.14-8.21 (m, 1H), 8.33 (s, 1H), 8.49 (d, 1H, J=7.2 Hz), 8.84 (d, 1H, J=5.1 Hz); $^{13}$C NMR (D$_2$O) δ 17.04, 17.54, 22.56, 24.92, 39.54, 53.43, 53.79, 54.46, 54.71, 126.67, 130.14, 130.24, 130.98, 130.96, 134.46, 134.70, 136.99, 137.56, 138.28, 140.02, 141.52, 147.43, 148.13, 149.00, 150.47, 168.82; ES-MS m/z 433 (M+H). Anal. Calcd. for C$_{264}$H$_{32}$N$_4$O$_2$.3.2HBr.3.4H$_2$O: C, 41.49; H, 5.62; N, 7.441; Br, 33.97. Found: C, 41.50; H, 5.70; N, 7.34; Br, 34.00.

Example 37

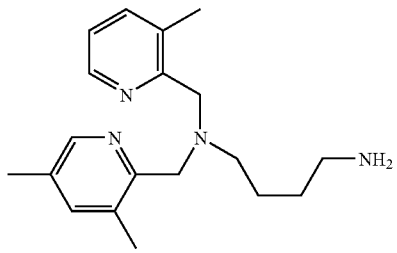

COMPOUND 37: N-(3,5-Dimethyl-pyridin-2-ylmethyl)-N-(3-methyl-pyridin-2-ylmethyl)-butane-1,4-diamine (HBr salt)

To a solution of (3,5-dimethyl-pyridin-2-yl)-methanol (2.12 g, 15.45 mmol) (Weidmann, K. et al. *J. Med. Chem.* 1992, 35, 438-450) in CH$_2$Cl$_2$ (50 mL) was added MnO$_2$ (9.41 g, 108.18 mmol) and the reaction mixture was refluxed overnight. Then it was cooled and the mixture was filtered through a layer of celite. The filtrate was concentrated to afford a brown/yellow oil. Purification by flash column chromatography on silica gel using 30% EtOAc/hexane afforded 3,5-dimethyl-pyridine-2-carbaldehyde as a yellow oil (960 mg, 31% over 3 steps). $^1$H NMR (CDCl$_3$) δ 2.39 (s, 3H), 2.62 (s, 3H), 7.41 (s, 1H), 8.47 (s, 1H), 10.15 (s, 1H).

COMPOUND 37 was isolated as a white solid. $^1$H NMR (D$_2$O) δ 1.55 (br, 4H), 2.44 (s, 3H), 2.45 (s, 3H), 2.48 (s, 3H), 2.70 (t, 2H, J=7.7 Hz), 2.90 (t, 2H, J=6.9 Hz), 4.26 (s, 2H), 4.30 (s, 2H), 7.84 (t, 1H, J=6.9 Hz), 8.18 (s, 1H), 8.34 (d, 1H, J=8.1 Hz), 8.41 (s, 1H), 8.57 (d, 1H, J=5.1 Hz). $^{13}$C NMR (D$_2$O) δ 17.17, 17.28, 17.57, 22.97, 25.04, 39.59, 54.16, 54.43, 55.11, 125.99, 136.96, 137.55, 137.71, 138.06, 138.61, 147.96, 148.46, 149.28, 151.20. ES-MS m/z 313 (M+H). Anal. Calcd. for C$_{19}$H$_{28}$N$_4$.3.6HBr.1.7H$_2$O.0.2C$_4$H$_{10}$O: C, 36.63; H, 5.74; N, 8.63; Br, 44.31. Found: C, 36.77; H, 5.53; N, 8.64; Br, 44.18.

Example 38

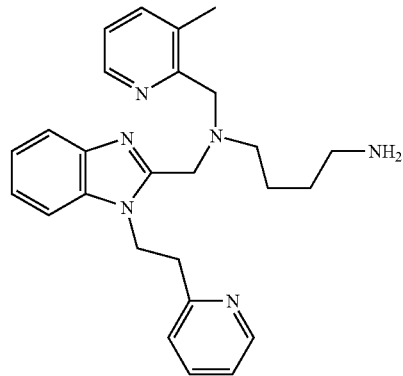

COMPOUND 38: N-(3-methyl-pyridin-2-ylmethyl)-N-[1-(2-pyridin-2-ylethyl)-1H-benzimidazol-2-ylmethyl]-butane-1,4-diamine (HBr salt)

Under an atmosphere of Ar, 1-(2-pyridin-2-yl-ethyl)-1H-benzimidazole (0.46 g, 2.1 mmol) (Ichikawa, M. et al. *Chem. Pharm. Bull.* 1981, 29, 3042-7) was dissolved in anhydrous THF (10 mL), cooled to −40° C., and treated with tert-BuLi (1.5 mL, 1.7M, 2.5 mmol) for 30 minutes. DMF (0.80 mL, 10.3 mmol) was then added and the solution slowly warmed to room temperature. After 1 hour, water (10 mL) and saturated aqueous NaHCO$_3$ solution (10 mL) were added and the medium was extracted with EtOAc (3×25 mL). The combined organic phases were then dried (MgSO$_4$), filtered, and concentrated under reduced pressure. The crude product was then purified by column chromatography with silica gel (50:1:0.1 MeOH:NH$_4$OH:CH$_2$Cl$_2$) to afford 1-(2-pyridin-2-yl-ethyl)-1H-benzimidazole-2-carbaldehyde as a brown liquid that was used immediately in the next reaction (147 mg, 28%).

COMPOUND 38 was isolated as a pale peach-colored solid. $^1$H NMR (D$_2$O) δ 1.62 (br, 4H), 2.49 (s, 3H), 2.84 (br t, 2H, J=7.8 Hz), 2.95 (br t, 2H, J=6.9 Hz), 3.66 (t, 2H, J=7.1 Hz), 4.38 (s, 2H), 4.53 (s, 2H), 4.96 (t, 2H, J=7.1 Hz), 7.40 (d, 1H, J=8.4 Hz), 7.49 (t, 1H, J=7.2 Hz), 7.59 (t, 1H, J=8.1 Hz), 7.80 (m, 2H), 7.88 (t, 1H, J=6.6 Hz), 7.92 (d, 1H, J=8.1 Hz), 8.30 (d, 1H, J=7.8 Hz), 8.45 (dt, 1H, J=8.0, 1.5 Hz), 8.56 (t, 2H, J=4.7 Hz). $^{13}$C NMR (D$_2$O) δ 17.17, 23.29, 24.93, 33.17, 39.54, 44.17, 50.68, 54.47, 55.54, 112.05, 114.96, 125.99, 126.63, 127.27, 127.51, 128.58, 130.50, 132.31, 137.54, 138.49, 142.20, 147.83, 148.43, 151.04, 151.11, 151.78. ES-MS m/z 429 (M+H). Anal. Calcd. for C$_{26}$H$_{32}$N$_6$.4.3HBr.1.5H$_2$O.C$_4$H$_{10}$O: C, 39.79; H, 5.24; N, 10.09; Br, 41.24. Found: C, 39.88; H, 5.13; N, 10.11; Br, 41.14.

TABLE 3

Preparation of Examples 39 to 78

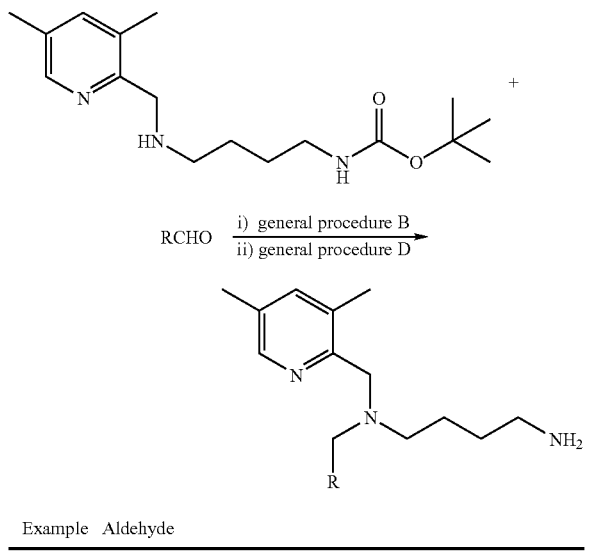

| Example | Aldehyde |
|---------|----------|
| 39 | 3-Isopropylpyridine-2-carbaldehyde |
| 40 | acetic acid 1-(2-formyl-pyridin-3-yl)-1-methyl-ethyl ester |
| 41 | 3-cyclopentyloxy-pyridine-2-carbaldehyde |
| 42 | 1-(3-methyl-but-2-enyl)-1H-benzoimiazole-2-carbaldehyde |
| 43 | 3-[1-(4-Chloro-phenyl)-1-methyl-ethyl]-pyridine-2-carbaldehyde |
| 44 | 3-[1-(4-fluoro-phenyl)-cyclopentyl]-pyridine-2-carbaldehyde |
| 45 | 3-(1-methoxy-cyclobutyl)-pyridine-2-carbaldehyde |
| 46 | 3-[1-(4-fluoro-phenyl)-1-methyl-ethyl]-pyridin-2-carbaldehyde |
| 47 | 3-(1-methoxy-cyclohexyl)-pyridine-2-carbaldehyde |
| 48 | 4-methyl-pyridine-2-carbaldehyde |
| 49 | 4-tert-Butyl-pyridine-2-carbaldehyde |
|    | Nugent, R. A. et al. PCT Int. Appl. (1996) WO 9635678 |
| 50 | 3-methyl-pyrazine-2-carbaldehyde |
|    | Mertes, MP et al. J. Med. Chem. 1970, 13, 77-82 |
| 51 | 3-(1-Phenyl-cyclopentyl)-pyridine-2-carbaldehyde |
| 52 | ethyl 2-formyl nicotinate |
|    | Graf, E. et al., Synthesis 1999, 8, 1216-1222 |
| 53 | 3-vinyl-pyridine-2-carbaldehyde |
| 54 | 3-(4-methanesulfonyl-phenyl)-pyridine-2-carbaldehyde |
| 55 | 3-thiazol-2-yl-pyridine-2-carbaldehyde |
| 56 | 3,4-dimethyl-pyridine-2-carbaldehyde |
| 57 | 5,6,7,8-Tetrahydro-isoquinoline-1-carbaldehyde |
|    | Nugent, R. A. et al. PCT Int. Appl. (1996) WO 9635678 |
| 58 | 3-phenoxy-pyridine-2-carbaldehyde |
| 59 | isoquinoline-1-carbaldehyde |
|    | Barrows et al. J. Am. Chem. Soc. 1942, 64, 2430 |
| 60 | 5,6-Dihydro-4H-imidazo[4,5,1-ij]quinoline-2-carbaldehyde |
|    | Chen, YL Eur. Pat. Appl. (1998), EP 276942 |
| 61 | 3-Benzenesulfinyl-pyridine-2-carbaldehyde |
| 62 | 3-Phenylsulfanyl-pyridine-2-carbaldehyde |
| 63 | [3,3']bipyridinyl-2-carbaldehyde |
| 64 | 3-(2,2-dimethyl-propyl)-pyridine-2-carbaldehyde |
| 65 | 3-cyclohexyl-pyridine-2-carbaldehyde |
| 66 | 4-phenyl-pyridine-2-carbaldehyde |
|    | Agrawal, K.C. et al. J. Med. Chem. 1975, 18, 368 |
| 67 | 3-(3,5-difluoro-phenyl)-pyridine-2-carbaldehyde |
| 68 | 3-(1-methyl-1-phenyl-ethyl)-pyridine-2-carbaldehyde |
| 69 | N-(2-formyl-pyridin-3-yl)-benzamide |
| 70 | pyridine-2-carboxaldehyde |
| 71 | 5-methyl-pyridine-2-carbaldehyde |
| 72 | 6-methyl-pyridine-2-carbaldehyde |
| 73 | 4-Nitro-2-pyridine carboxaldehyde |
|    | Odashima, T. et al. Bull. Chem. Soc. Jpn. 1993, 66, 797-803. |
| 74 | 4-Chloro-2-pyridine carboxaldehyde |
|    | Shigeto, N. et al. Synthesis 1996, 8, 991-996. |

TABLE 3-continued

Preparation of Examples 39 to 78

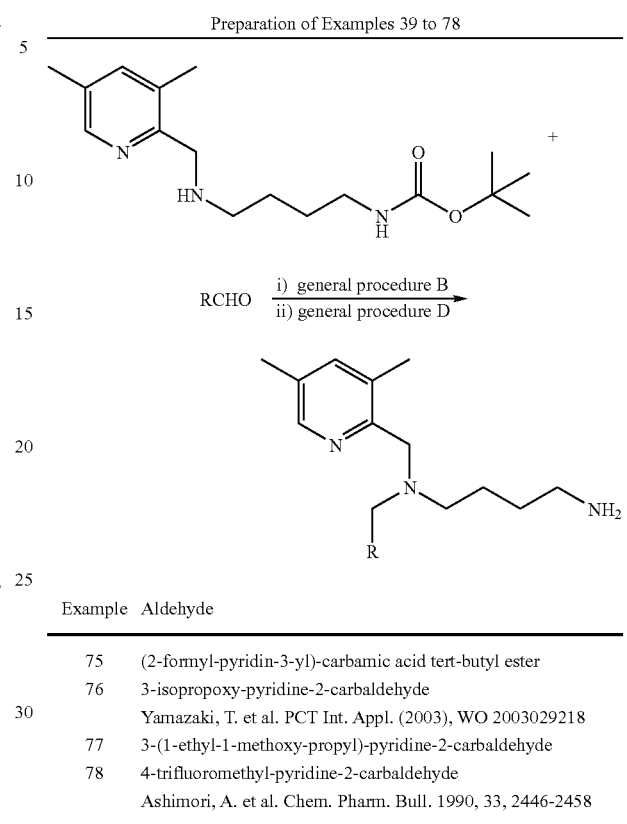

| Example | Aldehyde |
|---------|----------|
| 75 | (2-formyl-pyridin-3-yl)-carbamic acid tert-butyl ester |
| 76 | 3-isopropoxy-pyridine-2-carbaldehyde |
|    | Yamazaki, T. et al. PCT Int. Appl. (2003), WO 2003029218 |
| 77 | 3-(1-ethyl-1-methoxy-propyl)-pyridine-2-carbaldehyde |
| 78 | 4-trifluoromethyl-pyridine-2-carbaldehyde |
|    | Ashimori, A. et al. Chem. Pharm. Bull. 1990, 33, 2446-2458 |

Example 39

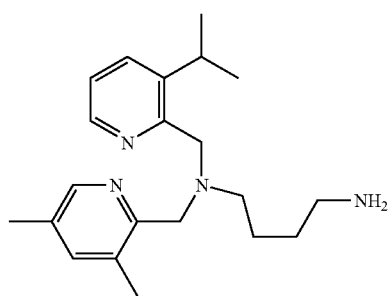

COMPOUND 39: N-(3,5-Dimethylpyridin-2-ylmethyl)-N-(3-isopropylpyridin-2-ylmethyl)-butane-1,4-diamine (HBr salt)

White solid. $^1$H NMR (D$_2$O) δ 1.26 (d, 6H, J=6.9 Hz), 1.54 (br, 4H), 2.45 (s, 6H), 2.70 (t, 2H, J=6.9 Hz), 2.90 (t, 2H, J=6.9 Hz), 3.29 (sep, 1H, J=6.9 Hz), 4.26 (s, 2H), 4.38 (s, 2H), 7.92 (t, 1H, J=6.9 Hz), 8.20 (s, 1H), 8.42 (s, 1H), 8.52 (d, 1H, J=8.1 Hz), 8.58 (d, 1H, J=5.4 Hz). $^{13}$C NMR (D$_2$O) δ 17.20, 17.56, 22.12 (2C), 23.01, 25.02, 28.29, 39.57, 53.74, 54.04, 54.99, 126.58, 136.99, 137.55, 138.07, 138.69, 144.86, 147.30, 147.86, 149.29, 149.86. ES-MS m/z 341 (M+H). Anal. Calcd.

for $C_{21}H_{32}N_4 \cdot 3.3HBr \cdot 2.3H_2O$: C, 38.87; H, 6.20; N, 8.63; Br, 40.63. Found: C, 39.04; H, 6.37; N, 8.45; Br, 40.53.

Example 40

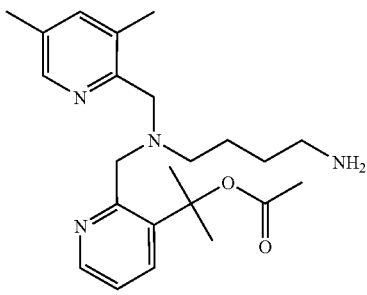

COMPOUND 40: Acetic acid 1-(2-{[(4-amino-butyl)-(3,5-dimethyl-pyridin-2-ylmethyl)-amino]-methyl}-pyridin-3-yl)-1-methyl-ethyl ester MeMgBr (3.0 M in $Et_2O$, 4.63 ml, 13.9 mmol) was added dropwise via syringe to a solution of 1-(2-methyl-pyridin-3-yl)-ethanone (1.88 g, 13.9 mmol) (Sanders et al. *J. Org. Chem.* 1978, 43, 324) in $Et_2O$ (60 mL) to give a white slurry. The mixture was refluxed for 16 h, cooled to room temperature, quenched with water (50 mL) and extracted with $CH_2Cl_2$ (7×60 mL). The combined organic extracts were dried ($Na_2SO_4$), filtered, and concentrated in vacuo to afford a yellow oil. Purification via column chromatography on silica gel ($CH_2Cl_2$:MeOH, 95:5, v/v) afforded 2-(2-methyl-pyridin-3-yl)-propan-2-ol as a white crystalline solid (1.30 g, 62%). $^1H$ NMR ($CDCl_3$) δ 1.67 (s, 6H), 2.79 (s, 3H), 7.08 (m, 1H), 7.75 (d, 1H, J=7.5 Hz), 8.36 (d, 1H, J=3.0 Hz).

2-(2-methyl-pyridin-3-yl)-propan-2-ol (1.30 g, 8.61 mmol) and DMAP (30 mg) were combined in $Ac_2O$ (8 mL) and stirred at 100° C. for 16 hours. Following removal of the solvent under reduced pressure, the brown residue was quenched with saturated $NaHCO_3$ (50 mL) and extracted with $CH_2Cl_2$ (5×60 mL). The combined organic extracts were dried ($Na_2SO_4$), filtered, and concentrated in vacuo to afford a yellow oil. Purification via column chromatography on silica gel ($CH_2Cl_2$:MeOH, 95:5, v/v) afforded acetic acid 1-methyl-1-(2-methyl-pyridin-3-yl)-ethyl ester as a white crystalline solid (1.25 g, 75%). $^1H$ NMR ($CDCl_3$) δ 1.80 (s, 3H), 2.05 (s, 3H), 2.66 (s, 3H), 7.12 (dd, 1H, J=9.0, 6.0 Hz), 7.62 (dd, 1H, J=9.0, 3.0 Hz), 8.39 (dd, 1H, J=6.0, 3.0 Hz).

Selenium dioxide (1.44 g, 13.0 mmol) was added to a solution of acetic acid 1-methyl-1-(2-methyl-pyridin-3-yl)-ethyl ester (1.25 g, 6.48 mmol) dissolved in a mixture of water (2.5 mL) and 1,4-dioxane (25 mL). The resulting mixture was stirred at 100° C. for 60 hours. The solvent was removed under reduced pressure and the brown oil was quenched with saturated $NaHCO_3$ (30 mL) and extracted with $CH_2Cl_2$ (5×50 mL). The combined organic extracts were dried ($Na_2SO_4$), filtered, and concentrated in vacuo to afford a brown oil. Purification via column chromatography on silica gel (hexanes:EtOAc, 1:1, v/v) afforded acetic acid 1-(2-formyl-pyridin-3-yl)-1-methyl-ethyl ester as a yellow oil (0.62 g, 46%). $^1H$ NMR ($CDCl_3$) δ 1.91 (s, 6H), 2.03 (s, 3H), 7.48 (dd, 1H, J=9.0, 6.0 Hz), 7.83 (dd, 1H, J=9.0, 3.0 Hz), 8.69 (dd, 1H, J=6.0, 3.0 Hz), 10.49 (s, 1H).

Using general procedure B with acetic acid 1-(2-formyl-pyridin-3-yl)-1-methyl-ethyl ester and {4-[(3,5-dimethyl-pyridin-2-ylmethyl)-amino]-butyl}-carbamic acid tert-butyl ester gave acetic acid 1-(2-{[(4-tert-butoxycarbonylamino-butyl)-(3,5-dimethyl-pyridin-2-ylmethyl)-amino]-methyl}-pyridin-3-yl)-1-methyl-ethyl ester was obtained as a colorless oil. $^1H$ NMR ($CDCl_3$) δ 1.35 (m, 2H), 1.43 (s, 9H), 1.55 (m, 2H), 1.76 (s, 6H), 1.95 (s, 3H), 2.13 (s, 3H), 2.26 (s, 3H), 2.60 (t, 2H, J=6.0 Hz), 2.98 (m, 2H), 3.79 (s, 2H), 3.96 (s, 2H), 5.29 (br s, 1H), 7.16 (dd, 1H, J=6.0, 3.0 Hz), 7.20 (s, 1H), 7.65 (d, 1H, J=9.0 Hz), 8.17 (s, 1H), 8.50 (d, 1H, J=3.0 Hz).

COMPOUND 40 was isolated as a pale yellow oil. $^1H$ NMR ($CDCl_3$) δ 1.29 (m, 2H), 1.49 (m, 2H), 1.70 (s, 6H), 1.89 (s, 3H), 2.13 (s, 3H), 2.20 (s, 3H), 2.32 (br s, 2H), 2.53 (m, 4H), 3.77 (s, 2H), 3.91 (s, 2H), 7.10 (dd, 1H, J=6.0, 3.0 Hz), 7.16 (s, 1H), 7.59 (d, 1H, J=7.8 Hz), 8.12 (s, 1H), 8.44 (d, 1H, J=3.0 Hz). $^{13}C$ NMR ($CDCl_3$) δ 18.27, 18.60, 22.33, 23.59, 28.81, 31.71, 42.03, 54.45, 58.65, 58.76, 81.39, 122.10, 131.95, 133.02, 134.12, 139.10, 139.85, 146.66, 147.48, 154.52, 155.98, 169.81. ES-MS m/z 399 [M+H]$^+$. Anal. Calcd. for $C_{23}H_{34}N_4O_2 \cdot 0.25TFA$: C, 66.09; H, 8.08; N, 13.12. Found: C, 65.98; H, 8.13; N, 13.22.

Example 41

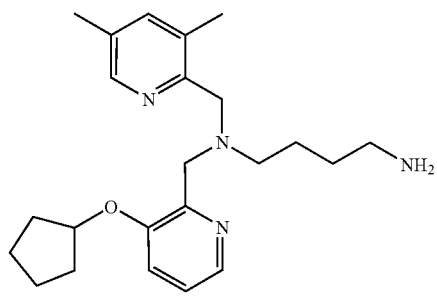

COMPOUND 41: $N^1$-(3-cyclopentyloxy-pyridin-2-ylmethyl)-$N^1$-(3,5-dimethyl-pyridin-2-ylmethyl)-butane-1,4-diamine (HBr salt)

To a cold (−78° C.), stirred solution of 2-bromo-3-cyclopentyloxy-pyridine (0.860 g, 3.82 mmol) (Kawasaki, M. et al. PCT Int. Appl. (2000) WO 2000020391) in dry THF (20 mL) under $N_2$ was added slowly n-BuLi (2.5 M in hexanes, 1.83 mL, 4.58 mmol). Following the addition the mixture was stirred at −78° C. for 10 min, and brought to room temperature. After being stirred at room temperature for 30 min the solution was cooled to −78° C., and then dry DMF (3.0 mL) was added. The solution was warmed to room temperature and stirred for 1 h. $H_2O$ (30 mL) was then added. The residue was extracted with EtOAc (3×30 mL), and the extracts were combined and dried over $MgSO_4$. After filtration the solvent was removed, and the residue was purified on a silica gel column (3:2, $CH_2Cl_2$/EtOAc) to afford a liquid (0.350 g) containing ~60% 3-cyclopentyloxy-pyridine-2-carbaldehyde (0.21 g, 30%) and ~40% 3-cyclopentyloxy-pyridine. The product was used in subsequent steps without further purification.

White solid. $^1H$ NMR ($D_2O$) δ 1.56-1.79 (m, 10H), 1.92-1.98 (m, 2H), 2.41 (s, 3H), 2.42 (s, 3H), 2.73-2.78 (m, 2H), 2.91-2.94 (m, 2H), 4.26 (s, 4H), 5.0-5.05 (m, 1H), 7.84 (dd, 1H, J=6.0, 8.4 Hz), 8.07 (d, 1H, J=8.4 Hz), 8.14 (s, 1H), 8.25 (d, 1H, J=6.0 Hz), 8.37 (s, 1H); $^{13}C$ NMR ($D_2O$) δ 17.13, 17.61, 23.03, 23.96, 24.00, 32.45, 39.65, 51.70, 54.10, 55.24, 83.53, 127.46, 129.90, 132.22, 136.92, 137.57, 137.91, 143.08, 147.98, 149.02, 155.08. ES-MS m/z 383 (M+H). Anal. Calcd. for $C_{23}H_{34}N_4 \cdot 4.4HBr \cdot 3.7H_2O \cdot 0.2C_4H_{10}O$: C, 34.86; H, 5.88; N, 6.83; Br, 42.87. Found: C, 34.75; H, 5.81; N, 6.86; Br, 43.02.

Example 42

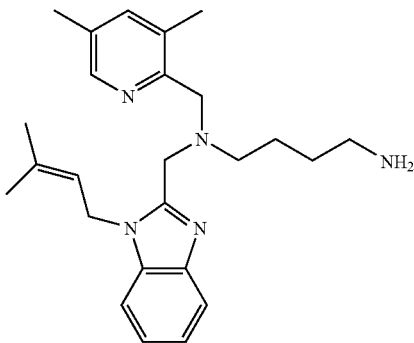

COMPOUND 42: $N^1$-(3,5-dimethyl-pyridin-2-ylmethyl)-$N^1$-[1-(3-methyl-but-2-enyl)-1H-benzoimidazol-2-ylmethyl]-butane-1,4-diamine To a solution of (1H-benzoimidazol-2-yl)-methanol (457 mg, 3.09 mmol) and 4-bromo-2-methyl-2-butene (0.36 mL, 3.09 mmol) in DMF (10 mL) was added DIPEA (0.69 mL, 3.70 mmol) at 60° C. overnight and in the morning, the mixture was cooled and concentrated. The residue was dissolved in saturated $NaHCO_3$ (20 mL) and extracted with $CH_2Cl_2$ (3×30 mL). The combined organic layers were dried ($MgSO_4$), filtered, and concentrated to afford a brown oil. Purification by flash column chromatography on silica gel using 2% MeOH/$CH_2Cl_2$ afforded [1-(3-methyl-but-2-enyl)-1H-benzoimidazol-2-yl]-methanol as a pale yellow solid (241 mg, 36%). $^1$H NMR ($CDCl_3$) δ 1.72 (s, 3H), 1.87 (s, 3H), 4.80 (d, 2H, J=6.6 Hz), 4.86 (s, 2H), 5.21 (td, 1H, J=6.0, 1.2 Hz), 7.19-7.23 (m, 3H), 7.65-7.68 (m, 1H).

To a solution of the above alcohol (241 mg, 1.11 mmol) in $CH_2Cl_2$ (10 mL) was added $MnO_2$ (678 mg, 7.80 mmol). The dark suspension was stirred overnight. The mixture was filtered through a layer of celite and the filtrate was concentrated to afford 1-(3-methyl-but-2-enyl)-1H-benzoimiazole-2-carbaldehyde as a yellow oil (218 mg, 91%). $^1$H NMR ($CDCl_3$) δ 1.68 (s, 3H), 1.86 (s, 3H), 5.22 (br s, 3H), 7.34 (s, 1H), 7.89 (s, 1H), 10.08 (s, 1H).

COMPOUND 42 was isolated as a yellow oil. $^1$H NMR ($CDCl_3$) δ 1.23-1.33 (m, 4H), 1.49-1.61 (m, 2H), 1.64 (s, 3H), 1.71 (s, 3H), 2.23 (s, 3H), 2.25 (s, 3H), 2.55 (q, 2H, J=8.7 Hz), 3.77 (s, 2H), 3.88 (s, 2H), 4.59 (d, 2H, J=6.3 Hz), 4.95 (br t, 1H, J=6.3 Hz), 7.17-7.21 (m, 4H), 7.67-7.72 (m, 1H), 8.19 (s, 1H). $^{13}$C NMR ($CDCl_3$) δ 18.31, 18.49, 23.81, 25.83, 31.95, 42.16, 42.28, 51.77, 55.00, 59.06, 110.09, 119.94, 120.35, 122.04, 122.64, 122.93, 132.77, 135.22, 135.86, 139.17, 142.80, 146.97, 152.10, 154.03. ES-MS m/z 406 [M+H]$^+$.

Anal Calcd. for $C_{25}H_{36}N_5 \cdot 0.1CH_2Cl_2$: C, 72.63; H, 8.79; N, 16.87. Found: C, 72.98; H, 8.80; N, 17.18.

Example 43

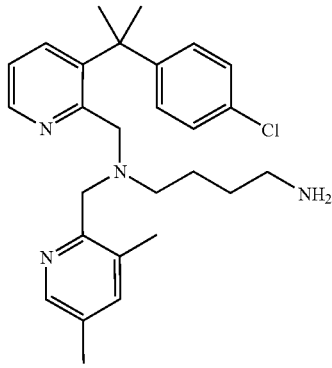

COMPOUND 43: $N^1$-{3-[1-(4-chloro-phenyl)-1-methyl-ethyl]-pyridin-2-ylmethyl}-$N^1$-(3,5-dimethyl-pyridin-2-ylmethyl)-butane-1,4-diamine (HBr salt)

To a suspension of $AlCl_3$ (6.14 g, 46.03 mmol) in chlorobenzene (10 mL) was added a solution of 2-(2-methyl-pyridin-3-yl)-propano-2-ol (1.00 g, 6.61 mmol) in chlorobenzene (15 mL) and the resulting suspension was stirred overnight. Then the mixture was poured into ice (100 mL), basified with NaOH (10 N) to pH14, and extracted with EtOAc (3×40 mL). The combined organic extracts were washed with brine (2×50 mL), dried ($MgSO_4$), filtered, and concentrated to afford 3-[1-(4-chloro-phenyl)-1-methyl-ethyl]-2-methyl-pyridine as a yellow liquid. Purification by flash column chromatography on silica gel using hexanes/EtOAc (2:1) afforded the product as a yellow oil (1.10 g, 68%).

To a solution of the above chloride (1.10 g, 4.48 mmol) in $CH_2Cl_2$ (10 mL) was added 3-chloroperoxybenzoic acid (1.30 g, 5.82 mmol, 1.3 mmol) and the reaction mixture was stirred overnight. The mixture was washed with NaOH (1N, 20 mL) and extracted with $CH_2Cl_2$ (2×30 mL). The combined organic extracts were dried ($MgSO_4$), filtered, and A solution of the above N-oxide (1.03 g, 3.94 mmol) in $Ac_2O$ (5 mL) was stirred at 80° C. for 2 h. The reaction mixture was cooled and concentrated. Then the residue was dissolved in $CH_2Cl_2$ (20 mL) and washed with saturated $NaHCO_3$ (3×20 mL). The organic layer was dried ($MgSO_4$), filtered, and concentrated to afford a brown oil. Purification by flash column chromatography on silica gel using hexanes/EtOAc (3:1) afforded acetic acid 3-[1-(4-chloro-phenyl)-1-methyl-ethyl]-pyridin-2-ylmethyl ester as a light brown oil (340 mg, 28%).

To a solution of the above acetate (340 mg, 1.12 mmol) in MeOH (10 mL) was added $K_2CO_3$ (309 mg, 2.24 mmol). After 1.5 h, the solvent was removed under reduced pressure. The residue was dissolved in $CH_2Cl_2$ (20 mL) and washed with water (3×20 mL). The organic layer was dried ($MgSO_4$), filtered, and concentrated to afford {3-[1-(4-chloro-phenyl)-1-methyl-ethyl]-pyridin-2-yl}-methanol as a pale yellow solid (288 mg, 98%). $^1$H NMR ($CDCl_3$) δ 1.65 (s, 6H), 3.93 (s, 2H), 4.93 (br s, 1H), 7.06 (dd, 2H, J=6.0, 3.0 Hz), 7.25 (dd, 2H, J=6.0, 3.0 Hz), 7.33 (dd, 1H, J=6.0, 3.0 Hz), 7.90 (dd, 1H, J=7.5, 3.0 Hz), 8.47 (dd, 1H, J=6.0, 3.0 Hz).

To a solution of the above alcohol (288 mg, 1.10 mmol) in CH$_2$Cl$_2$ (10 mL) was added MnO$_2$ (670 mg, 7.70 mmol) and the dark suspension was stirred for 3 d. The mixture was filtered through a layer of celite and the filtrate was concentrated to afford a pale yellow oil. Purification by flash column chromatography on silica gel using hexanes/EtOAc (2:1) afforded the aldehyde slightly impure as a pale yellow oil (173 mg). No further purification was performed.

COMPOUND 43 was isolated as a pale yellow solid. $^1$H NMR (D$_2$O) δ 1.14-1.24 (m, 2H), 1.37-1.39 (m, 2H), 1.75 (s, 6H), 2.28-2.32 (m, 5H), 2.45 (s, 3H), 2.85 (t, 2H, J=7.2 Hz), 3.71 (s, 2H), 3.74 (s, 2H), 7.25 (d, 2H, J=8.4 Hz), 7.40 (d, 2H, J=8.1 Hz), 8.04 (t, 1H, J=7.5 Hz), 8.17 (s, 1H), 8.39 (s, 1H), 8.70 (d, 1H, J=5.4 Hz), 8.86 (d, 1H, J=7.8 Hz). $^{13}$C NMR (D$_2$O) δ 17.21, 17.53, 22.15, 24.91, 29.45, 39.48, 42.88, 52.60, 53.96, 54.52, 126.48, 128.57, 129.45, 132.67, 136.80, 137.48, 138.56, 139.61, 145.04, 146.27, 147.22, 147.65, 149.03, 151.76. ES-MS m/z 451 [M+H]$^+$. Anal. Calcd. for C$_{27}$H$_{35}$N$_4$Cl.3.0HBr.1.8H$_2$O: C, 44.66; H, 5.77; N, 7.71; Br, 33.01. Found: C, 44.81; 5.76; N, 7.55; Br, 32.88.

Example 44

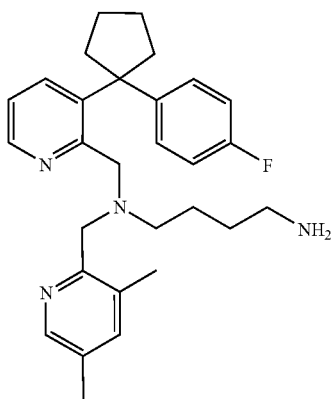

COMPOUND 44: N$^1$-(3,5-dimethyl-pyridin-2-ylmethyl)-N$^1$-{3-[1-(4-fluoro-phenyl)-cyclopentyl]-pyridin-2-ylmethyl}-butane-1,4-diamine (HBr salt)

To a suspension of AlCl$_3$ (4.05 g, 30.36 mmol) in fluorobenzene (10 mL) was added a solution of the 1-(2-bromopyridin-3-yl)-cyclopentanol (1.05 g, 4.33 mmol) in fluorobenzene (15 mL) and the resulting mixture was stirred overnight. The mixture was poured into ice (100 ml), basified with NaOH (10 N) to pH14, and extracted with EtOAc (4×40 mL). The combined organic extracts were washed with brine (2×50 mL), dried (MgSO$_4$), filtered, and concentrated to afford a brown oil. Purification by flash column chromatography on silica gel using hexanes/EtOAc (2:1) afforded 2-bromo-3-[1-(4-fluoro-phenyl)-cyclopentyl]-pyridine as a yellow oil (956 mg, 69%).

To a solution of the above bromide (1.03 g, 3.82 mmol) in THF (15 mL) at −78° C. was added n-BuLi (3.6 mL, 8.03 mmol). After 1 h at −78° C., N-formylpiperidine (0.51 mL, 0.46 mmol) was added and the reaction mixture was warmed to 0° C. After 1 h, the mixture was quenched with HCl (1N, 5 mL), basified with Na$_2$CO$_3$ (s) to pH10, and extracted with Et$_2$O (3×20 mL). The combined organic layers were dried (MgSO$_4$), filtered, and concentrated to afford an orange oil. Purification by flash column chromatography on silica gel using hexanes/EtOAc (2:1) afforded 3-[1-(4-fluoro-phenyl)-cyclopentyl]-pyridine-2-carbaldehyde as a yellow oil (180 mg, 17%).

COMPOUND 44 was isolated as a pale yellow solid. $^1$H NMR (D$_2$O) (a mixture of rotamers) δ 1.54-1.56 (m, 4H), 1.76-1.96 (m, 2H), 2.16-2.22 (m, 2H), 2.23-2.39 (m, 2H), 2.44 (s, 3H), 2.46 (s, 3H), 2.68-2.73 (m, 2H), 2.89-2.90 (m, 2H), 3.51-3.70 (m, 2H), 4.26 and 4.27 (s, total 2H), 4.37 and 4.39 (s, total 2H), 7.08-7.23 (m, 2H), 7.28-7.31 (m, 1H), 7.35-7.47 (m, 1H), 7.91-7.97 (m, 1H), 8.19 (d, 1H, J=8.4 Hz), 8.41 (d, 1H, J=9.9 Hz), 8.59-8.64 (m, 2H). $^{13}$C NMR (D$_2$O) (a mixture of rotamers) δ 17.10, 17.49, 22.88, 25.02, 32.03, 32.54, 33.32, 34.11, 38.56, 38.81, 39.09, 39.53, 39.77, 41.02, 54.05, 55.04, 115.49, 115.75, 116.04, 124.92, 126.63, 128.57, 129.02, 137.06, 137.69, 138.13, 138.75, 145.25, 145.59, 147.82, 149.24. ES-MS m/z 461 [M+H]$^+$. Anal. Calcd. for C$_{29}$H$_{37}$N$_4$F.3.7HBr.2.8CH$_3$OH: C, 43.45; H, 6.11; N, 6.88; Br, 35.78. Found: C, 43.50; H, 5.77; N, 6.88; Br, 35.78.

Example 45

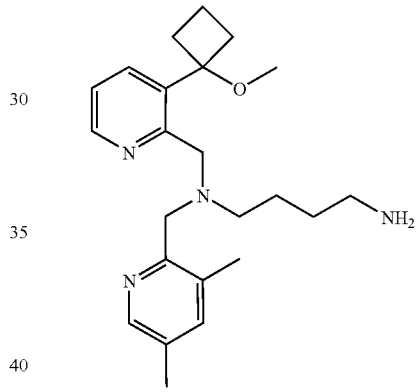

COMPOUND 45: N$^1$-(3,5-dimethyl-pyridin-2-ylmethyl)-N$^1$-[3-(1-methoxy-cyclobutyl)-pyridin-2-ylmethyl]-butane-1,4-diamine (HBr salt)

To a solution of diisopropylamine (3.0 mL, 21.40 mmol) in THF (10 mL) at −78° C. was added n-BuLi (7.6 mL, 17.84 mmol). After 30 min, a solution of 2-bromopyridine (1.1 mL, 11.89 mmol) in THF (30 mL) was added and stirring was continued at −78° C. After 45 min, cyclobutanone (1.0 g, 14.27 mmol) was added and the mixture was stirred at −78° C. for 1.5 h. After warming to room temperature, the mixture was quenched with water (20 mL), diluted with saturated NH$_4$Cl (15 mL), and extracted with Et$_2$O (3×30 mL). The combined organic layer was dried (MgSO$_4$), filtered, and concentrated to afford an orange oil. Purification by flash column chromatography on silica gel using hexanes/EtOAc (2:1) afforded 1-(2-bromo-pyridin-3-yl)-cyclobutanol as an orange oil (1.0 g, 37%). $^1$H NMR (CDCl$_3$) δ 1.69-1.73 (m, 1H), 2.19-2.22 (m, 1H), 2.49-2.55 (m, 2H), 2.61-2.68 (m, 2H), 3.01 (s, 1H), 7.29 (dd, 1H, J=5.1, 4.8 Hz), 7.68 (dd, 1H, J=7.7, 2.1 Hz), 8.28 (dd, 1H, J=4.7, 1.8 Hz).

To a solution of the above alcohol (410 mg, 1.80 mmol) in DMF (5 mL) was added NaH (60%, 108 mg, 2.70 mmol). After 1 h, MeI (0.23 mL, 3.60 mmol) was added. After 1.5 h, the reaction mixture was filtered and the filtrate was concentrated to afford an orange oil. Purification by flash column chromatography using hexanes/EtOAc (2:1) afforded 2-bromo-3-(1-methoxy-cyclobutyl)-pyridine as a pale yellow solid (308 mg, 71%). $^1$H NMR (CDCl$_3$) δ 1.61-1.71 (m, 1H), 2.04-2.14 (m, 1H), 2.56 (t, 4H, J=7.5 Hz), 2.96 (s, 3H), 7.25-7.30 (m, 1H), 7.64 (dd, 1H, J=7.5, 2.1 Hz), 8.31 (dd, 1H, J=4.7, 1.8 Hz).

The aldehyde was prepared from the above bromide by nucleophilic substitution with a formyl group, as exemplified in Example 41. COMPOUND 45 was isolated as a pale yellow solid. $^1$H NMR (D$_2$O) δ 1.49 (br s, 4H), 1.71 (br s, 1H), 2.03 (br s, 1H), 2.40 (s, 3H), 2.42 (s, 3H), 2.53 (br s, 4H), 2.65 (br s, 2H), 2.85 (br s, 2H), 2.94 (s, 3H), 4.24 (s, 2H), 4.32 (s, 2H), 7.95 (t, 1H, J=6.3 Hz), 8.15 (s, 1H), 8.41 (s, 1H), 8.56 (d, 1H, J=7.2 Hz), 8.69 (d, 1H, J=5.1 Hz). $^{13}$C NMR (D$_2$O) δ 13.63, 17.06, 17.49, 22.64, 24.92, 31.62, 39.45, 51.07, 53.88, 54.51, 54.95, 81.68, 125.99, 136.62, 137.42, 138.55, 139.76, 140.76, 145.21, 147.58, 148.81, 152.98. ES-MS m/z 383 [M+H]$^+$. Anal. Calcd. for C$_{23}$H$_{34}$N$_4$O.3.1HBr.2.4H$_2$O: C, 40.83; H, 6.24; N, 8.28; Br, 36.61. Found: C, 40.87; H, 6.05; N, 8.11; Br, 36.61.

Example 46

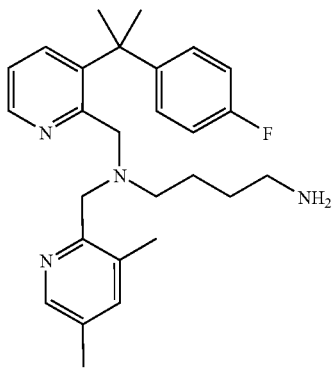

COMPOUND 46: N$^1$-(3,5-dimethyl-pyridin-2-ylmethyl)-N$^1$-{3-[1-(2-fluoro-phenyl)-1-methyl-ethyl]-pyridin-2-ylmethyl}-butane-1,4-diamine (HBr salt)

3-[1-(4-fluoro-phenyl)-1-methyl-ethyl]-pyridin-2-carbaldehyde as a yellow oil was prepared similarly using the method for making compound 43. 1H NMR (CDCl$_3$) δ 1.76 (s, 6H), 6.93 (t, 2H, J=9.0 Hz), 7.05-7.10 (m, 2H), 7.51 (dd, 1H, J=6.0, 3.0 Hz), 8.07 (dd, 1H, J=9.0, 3.0 Hz), 8.71 (dd, 1H, J=6.0, 3.0 Hz), 9.74 (s, 1H).

COMPOUND 46 was isolated as a pale yellow solid. $^1$H NMR (D$_2$O) δ 1.18-1.21 (m, 2H), 1.32-1.42 (m, 2H), 1.75 (s, 6H), 2.27-2.30 (m, 2H), 2.30 (s, 3H), 2.44 (s, 3H), 2.82 (t, 2H, J=7.5 Hz), 3.72 (s, 2H), 3.74 (s, 2H), 7.10-7.15 (m, 2H), 7.28 (dd, 2H, J=8.6, 5.4 Hz), 8.03 (dd, 1H, J=8.0, 6.0 Hz), 8.14 (s, 1H), 8.38 (s, 1H), 8.68 (d, 1H, J=5.4 Hz), 8.85 (d, 1H, J=8.1 Hz). $^{13}$C NMR (D$_2$O) δ 17.13, 17.49, 22.21, 24.87, 29.64, 39.39, 42.73, 52.79, 54.06, 54.69, 115.98, 116.26, 126.40, 128.65, 128.76, 136.66, 137.44, 138.69, 139.63, 143.50, 144.81, 147.23, 147.85, 148.85, 151.77, 160.19, 163.42. ES-MS m/z 435 [M+H]$^+$. Anal. Calcd. for C$_{27}$H$_{35}$N$_4$F.2.9HBr.2.5H$_2$O.0.3C$_4$H$_{10}$O: C, 45.99; H, 6.28; N, 7.61; Br, 31.46. Found: C, 45.81; H, 6.03; N, 7.47; Br, 31.74.

Example 47

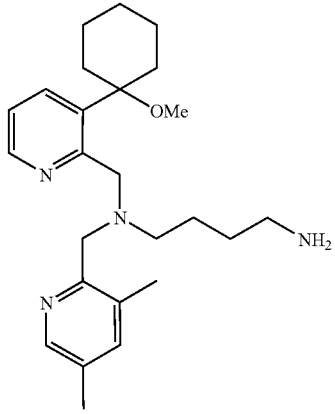

COMPOUND 47: N$^1$-(3,5-dimethyl-pyridin-2-ylmethyl)-N$^1$-[3-(1-methoxy-cyclohexyl)-pyridin-2-ylmethyl]-butane-1,4-diamine (HBr salt)

To a solution of diisopropylamine (2.6 mL, 18.88 mmol) in THF (8 mL) at −78° C. was added n-BuLi (7.4 mL, 15.73 mmol) to generate LDA. After 30 min, a solution of 2-bromopyridine (1.0 mL, 10.49 mmol) in THF (30 mL) was added to the LDA in situ. After 1 h at −78° C., cyclohexanone (1.3 mL, 12.59 mmol) was added dropwise. After 1.5 h the mixture was warmed to room temperature and quenched with water (10 mL). The mixture was diluted with saturated NH$_4$Cl (10 mL) and extracted with Et$_2$O (4×20 mL). The combined organic layer was dried (MgSO$_4$), filtered, and concentrated to afford a brown oil. Purification by flash column chromatography on silica gel using hexanes/EtOAc (2:1) afforded the impure product as an orange solid (0.96 g, 36%).

To a solution of the above alcohol (960 mg, 3.73 mmol) in DMF (5 mL) was added NaH (60%, 220 mg, 5.60 mmol) and after 1 h, MeI (0.47 mL, 7.46 mmol) was added. After 1.5 h, the mixture was filtered and the filtrate was concentrated. Purification by flash column chromatography on silica gel using hexanes/EtOAc (2:1) afforded 2-bromo-3-(1-methoxy-cyclohexyl)-pyridine as a bright yellow oil (686 mg, 68%). $^1$H NMR (CDCl$_3$) δ 1.62-1.83 (m, 8H), 2.34-2.37 (m, 2H), 3.02 (s, 3H), 7.23-7.27 (m, 1H), 7.70 (dd, 1H, J=6.0, 3.0 Hz), 8.28 (dd, 1H, J=6.0, 3.0 Hz).

3-(1-methoxy-cyclohexyl)-pyridine-2-carbaldehyde as a yellow oil was prepared from the above bromide by nucleophilic substitution with a formyl group, as exemplified in Example 44. $^1$H NMR (CDCl$_3$) δ 1.63-1.82 (m, 8H), 2.18 (d, 2H, J=10.1 Hz), 2.96 (s, 3H), 7.40 (dd, 1H, J=8.5, 5.1 Hz), 7.72 (d, 1H, J=8.1 Hz), 8.69 (d, 1H, J=5.3 Hz), 10.79 (s, 1H).

COMPOUND 47 was isolated as a yellow solid. $^1$H NMR (D$_2$O) δ 1.52-1.83 (m, 12H), 2.21 (d, 2H, J=12.9 Hz), 2.45 (s, 6H), 2.69 (br t, 2H, J=7.8 Hz), 2.90 (br t, 2H, J=6.9 Hz), 3.01 (s, 3H), 4.28 (s, 2H), 4.58 (s, 2H), 7.96 (dd, 1H, J=8.0 Hz), 8.20 (s, 1H), 8.45 (s, 1H), 8.56 (d, 1H, J=8.1 Hz), 8.71 (d, 1H, J=5.4 Hz). $^{13}$C NMR (D$_2$O) δ 14.52, 17.22, 17.54, 21.41, 23.10, 24.78, 24.98, 33.93, 39.49, 50.29, 53.87, 54.84, 55.69, 66.47, 79.46, 126.43, 136.83, 137.53, 138.45, 140.17,

Example 48

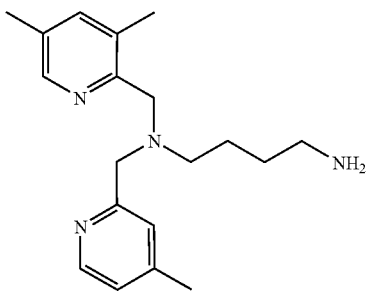

COMPOUND 48: N'-(3,5-Dimethyl-pyridin-2-ylmethyl)-N'-(4-methyl-pyridin-2-ylmethyl)-butane-1,4-diamine (HBr salt)

$^1$H NMR (D$_2$O) δ 1.52-1.60 (m, 4H), 2.25 (s, 3H), 2.42 (s, 3H), 2.65 (s, 3H), 2.70-2.75 (m, 2H), 2.90-2.95 (m, 2H), 4.20 (s, 2H), 4.23 (s, 2H), 7.76 (d, 1H, J=5.9 Hz), 7.84 (s, 1H), 8.16 (s, 1H), 8.37 (s, 1H), 8.52 (d, 1H, J=6.1 Hz); $^{13}$C NMR (D$_2$O) δ 16.96, 17.51, 22.10, 23.03, 25.03, 39.62, 53.64, 55.10, 56.20, 127.32, 127.95, 136.93, 137.52, 137.81, 140.60, 148.43, 149.11, 151.79, 162.35; ES-MS m/z 313 (M+H). Anal Calcd. For C$_{19}$H$_{28}$N$_4$.3.5(HBr).2.8(H$_2$O).0.5(CH$_2$Cl$_2$): C, 34.02; H, 5.58; N, 8.14; Br, 40.62. Found: C, 33.72; H, 5.56; N, 7.99; Br, 40.70.

Example 49

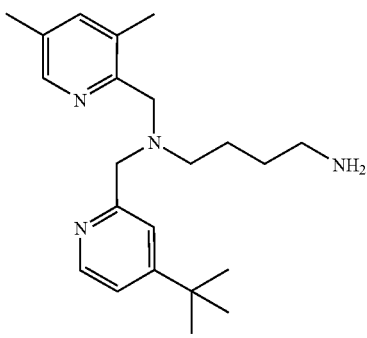

COMPOUND 49: N'-(4-tert-Butyl-pyridin-2-ylmethyl)-N'-(3,5-dimethyl-pyridin-2-ylmethyl)-butane-1,4-diamine (HBr salt)

$^1$H NMR (D$_2$O) 1.34 (s, 9H), 1.52-1.62 (m, 4H), 2.43 (s, 3H), 2.76-2.81 (m, 2H), 2.92-2.97 (m, 2H), 4.20 (s, 2H), 4.26 (s, 2H), 7.94-7.97 (m, 2H), 8.15 (s, 1H), 8.36 (s, 1H), 8.56 (d, 1H, J=6.3 Hz); $^{13}$C NMR (D$_2$O) δ 16.95, 17.47, 22.96, 25.03, 29.54, 39.61, 53.68, 55.57, 56.53, 124.10, 124.43, 136.90, 137.54, 137.77, 140.93, 148.45, 149.13, 152.09, 173.93; ES-MS m/z 355 (M+H). Anal Calcd. For C$_{22}$H$_{34}$N$_4$.4.1(HBr).2.7(H$_2$O).0.3(C$_4$H$_{10}$O): C, 36.80; H, 6.19; N, 7.40; Br, 43.27. Found: C, 36.95; H, 6.08; N, 7.34; Br, 43.10.

Example 50

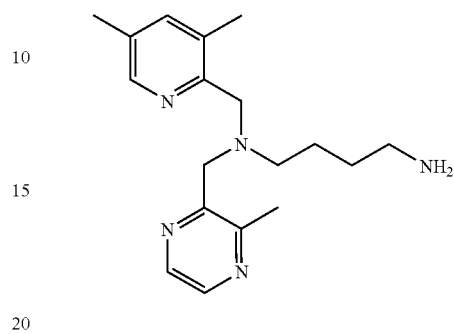

COMPOUND 50: N'-(3,5-Dimethyl-pyridin-2-ylmethyl)-N'-(3-methyl-pyrazin-2-ylmethyl)-butane-1,4-diamine HBr salt $^1$H NMR (D$_2$O) δ 1.66-1.76 (m, 2H), 1.82-1.92 (m, 2H), 2.36 (s, 3H), 2.37 (s, 3H), 2.54 (s, 3H), 3.01 (t, 2H, J=7.6 Hz), 3.30 (t, 2H, J=8.1 Hz), 4.53 (s, 2H), 4.55 (s, 2H), 7.92 (s, 1H), 8.32 (s, 1H), 8.40 (d, 1H, J=2.7 Hz), 8.47 (d, 1H, J=2.6 Hz); $^{13}$C NMR (D$_2$O) δ 17.17, 17.50, 19.30, 22.28, 24.65, 39.39, 54.43, 56.25, 136.20, 137.35, 141.67, 141.93, 142.07, 145.07, 146.10, 148.64, 152.60; ES-MS m/z 314 (M+H). Anal Calcd. For C$_{18}$H$_{27}$N$_5$.2.6(HBr).2.0(H$_2$O): C, 38.62; H, 6.05; N, 12.51; Br, 37.11. Found: C, 38.87; H, 5.94; N, 12.13; Br, 36.95.

Example 51

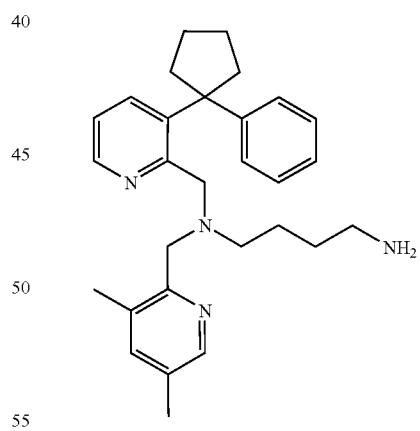

COMPOUND 51: N$^1$-(3,5-Dimethyl-pyridin-2-ylmethyl)-N$^1$-[3-(1-phenyl-cyclopentyl)-pyridin-2-ylmethyl]-butane-1,4-diamine (HBr salt)

To a cold (−78° C.) solution of LDA (24.5 mmol) in dry THF (100 mL) was added 2-bromopyridine (2.0 mL, 20.9 mmol) and the resultant solution was stirred for 90 minutes. Cyclopentanone (4.0 mL, 45.2 mmol) was added and the mixture was stirred for and additional 80 minutes. The mixture was treated with saturated aqueous NaHCO$_3$ (20 mL) and warmed to room temperature. The mixture was diluted with EtOAc (300 mL) and the phases were separated. The organic phase was washed with saturated aqueous NaHCO₃ (3×25 mL) and brine (3×25 mL), dried (MgSO₄), and concentrated. Purification of the crude material by column chromatography on silica gel (3:1 hexanes-EtOAc) provided 2.00 g (40%) of 1-(2-Bromo-pyridin-3-yl)-cyclopentanol as a yellow oil.

3-(1-Phenyl-cyclopentyl)-pyridine-2-carbaldehyde as a yellow oil was prepared from 2-Bromo-3-(1-phenyl-cyclopentyl)-pyridine, following similar procedures as described in Example 44. ES-MS m/z 252 (M+H).

COMPOUND 51 was isolated as a white solid. NMR and HPLC analysis indicated that COMPOUND 51 existed as a mixture of rotamers. $^1$H NMR (D₂O) δ 1.50-1.60 (m, 4H), 1.76-1.98 (m, 2H), 2.01-2.48 (m, 10H), 2.70-2.92 (m, 4H), 3.31-3.72 (m, 2H), 4.28 (d, 2H, J=5.4 Hz), 4.40 (d, 2H, J=8.4 Hz), 7.15-7.43 (m, 5H), 7.92-7.98 (m, 1H0, 8.19-8.22 (m, 1H), 8.38-8.44 (m, 1H), 8.55-8.64 (m, 2H); $^{13}$C NMR (D₂O) δ 17.17, 17.52, 22.99, 25.04, 32.69, 33.61, 34.22, 34.93, 38.79, 39.57, 41.19, 42.63, 45.02, 45.83, 54.08, 55.11, 126.62, 126.96, 127.61, 129.28, 137.13, 137.70, 138.16, 138.77, 145.26, 145.62, 146.16, 147.84, 149.28, 150.23, 150.37; ES-MS m/z 443 (M+H). Anal. Calcd. For C₂₉H₃₈N₄·3.0HBr·3.0H₂O·0.3C₄H₁₀O: C, 47.62; H, 6.62; N, 7.36; Br, 31.47. Found: C, 47.96; H, 6.34; N, 7.27; Br, 31.14.

Example 52

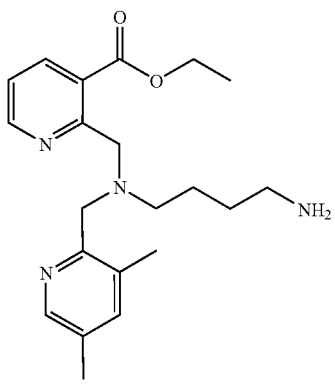

COMPOUND 52: 2-{[(4-Amino-butyl)-(3,5-dimethyl-pyridin-2-ylmethyl)-amino]-methyl}-nicotinic acid ethyl ester (HBr salt)

$^1$H NMR (D₂O) δ 1.40 (t, 3H, J=7.2 Hz), 1.68-1.73 (m, 2H), 1.81-1.85 (m, 2H), 2.38 (s, 3H), 2.42 (s, 3H), 2.97-3.03 (m, 2H), 3.21-3.26 (m, 2H), 4.44 (q, 2H, J=7.2 Hz), 4.58 (s, 2H), 4.88 (s, 2H), 7.76 (dd, 1H, J=7.5, 5.4 Hz), 7.99 (s, 1H), 8.34 (s, 1H), 8.66 (d, 1H, J=7.8 Hz), 8.77 (d, 1H, J=4.8 Hz). $^{13}$C NMR (D₂O) δ 13.76, 17.43, 17.55, 22.10, 24.66, 39.37, 54.27, 55.99, 56.96, 63.97, 125.78, 127.48, 137.24, 138.12, 140.98, 144.02, 144.29, 147.55, 148.66, 152.44, 165.70. ES-MS m/z 371 (M+H). Anal. Calcd. for C₂₁H₃₀N₄O₂·3.4HBr·3.2H₂O: C, 35.87; H, 5.70; N, 7.97; Br, 38.63. Found: C, 35.95; H, 5.89; N, 7.86; Br, 38.58.

Example 53

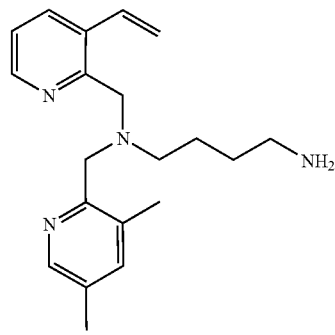

COMPOUND 53: N$^1$-(3,5-Dimethyl-pyridin-2-ylmethyl)-N$^1$-(3-vinyl-pyridin-2-ylmethyl)-butane-1,4-diamine (HBr salt)

To a solution of 2-methyl-3-pyridinyl trifluoromethanesulfonate (1.067 g, 4.43 mmol) in CH₂Cl₂ (25 mL) was added 3-chloroperoxybenzoic acid (77%, 1.48 g, 6.60 mmol) and the reaction mixture stirred at rt for 5 h. The mixture was then diluted with CH₂Cl₂ (35 mL) and saturated aqueous NaHCO₃ (25 mL). The aqueous layer was extracted with CH₂Cl₂ (2×10 mL) and the combined organic layers dried (Na₂SO₄) and concentrated to afford a clear oil (1.40 g). Purification of the crude material by column chromatography on silica gel (40% EtOAc/Hexanes then 100% EtOAc then 4% MeOH/EtOAc) afforded the desired N-oxide (1.01 g, 89%) as a clear oil To an Ar-purged solution of the triflate from above (470 mg, 1.83 mmol) in dioxane (5 mL) was added tributyl(vinyl)tin (621 mg, 1.96 mmol), LiCl (262 mg, 6.18 mmol) and Pd(PPh₃)₄ (81 mg, 0.070 mmol) and the suspension heated to 100° C. overnight. The mixture was concentrated and purified by column chromatography on silica gel (6% MeOH/CH₂Cl₂) to afford the vinyl-coupled product as a clear oil (176 mg, 71%).

A solution of the above N-oxide (170 mg, 1.26 mmol) in Ac₂O (2.5 mL) was heated to 80° C. for 4.5 h then cooled to rt and diluted with CH₂Cl₂ (30 mL) and saturated aqueous NaHCO₃ (30 mL). The aqueous layer was extracted with CH₂Cl₂ (1×15 mL) and the combined organic layers were dried (Na₂SO₄), filtered, and concentrated to afford a brown oil (225 mg). Purification of the crude oil by column chromatography on silica gel (Et₂O/hexanes, 1:1) afforded the desired acetate (137 mg, 61%) as a clear oil To a solution of the acetate (137 mg, 0.77 mmol) in MeOH (5 mL) was added K₂CO₃ (215 mg, 1.56 mmol) and the mixture stirred at rt for 2.5 h. The reaction was concentrated, diluted with CH₂Cl₂ (30 mL) and H₂O (25 mL) and the aqueous phase extracted with CH₂Cl₂ (2×15 mL). The combined organic layers were dried (Na₂SO₄) and concentrated to afford the alcohol (100 mg) as a clear oil.

To a solution of the above alcohol (100 mg) in CH₂Cl₂ (5 mL) was added MnO₂ (548 mg, 6.30 mmol) and the reaction stirred at rt overnight. The mixture was filtered through a layer of celite, washing with MeOH/CH₂Cl₂. The filtrate was concentrated to afford a yellow oil. Purification by flash column chromatography on silica gel using 1:2 EtOAc/hexanes afforded the title product as a yellow oil (42 mg, 41% over 2 steps). $^1$H NMR (CDCl$_3$) δ 5.55 (dd, 1H, J=11.1, 0.9 Hz), 5.81 (dd, 1H, J=17.7, 0.9 Hz), 7.47 (dd, 1H, J=8.1, 4.8 Hz), 7.73 (dd, 1H, J=17.7, 11.1 Hz), 7.98 (br d, 1H, J=8.1 Hz), 8.71 (br d, 1H, J=4.8 Hz), 10.20 (s, 1H).

COMPOUND 53 was isolated as a white solid. $^1$H NMR (D$_2$O) δ 1.55-1.62 (m, 4H), 2.42 (s, 3H), 2.44 (s, 3H), 2.74-2.79 (m, 2H), 2.91-2.96 (m, 2H), 4.25 (s, 2H), 4.39 (s, 2H), 5.80 (d, 1H, J=11.1 Hz), 6.03 (d, 1H, J=17.4 Hz), 6.98 (dd, 1H, J=17.4, 11.1 Hz), 7.93 (dd, 1H, J=7.8, 6 Hz), 8.15 (s, 1H), 8.38 (s, 1H), 8.61-8.66 (m, 2H). $^{13}$C NMR (D$_2$O) δ 17.11, 17.51, 22.79, 25.03, 39.60, 53.90, 54.20, 55.35, 124.36, 126.53, 128.49, 136.97, 137.62, 138.11, 140.12, 143.99, 147.87, 149.17, 149.53. ES-MS m/z 325 (M+H). Anal. Calcd. for C$_{20}$H$_{28}$N$_4$.3.4HBr.2.4H$_2$O: C, 37.37; H, 5.68; N, 8.72; Br, 42.26. Found: C, 39.29; H, 5.91; N, 8.32; Br, 42.65.

Example 54

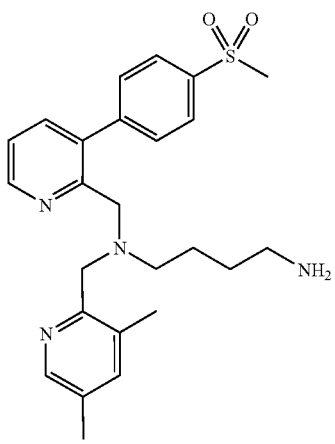

COMPOUND 54: N$^1$-(3,5-Dimethyl-pyridin-2-ylmethyl)-N$^1$-[3-(4-methanesulfonyl-phenyl)-pyridin-2-ylmethyl]-butane-1,4-diamine (HBr salt)

To a stirred degassed solution of 2-methyl-3-pyridinyl trifluoromethanesulfonate (741 mg, 3.07 mmol) and 4-(methylthio)phenyl boronic acid (578 mg, 3.44 mmol) in DME/THF (5 mL, 4:1) were added a 2 M Na$_2$CO$_3$ solution (1.0 mL) and Pd(PPh$_3$)$_4$ (147 mg, 0.127 mmol). The reaction mixture was flushed and stirred under Ar while being heated at 100° C. overnight. The mixture was then cooled and concentrated in vacuo. Purification of the resultant oil by column chromatography with silica gel (Hexanes/EtOAc, 4:1 then 1:1) afforded the coupled product (560 mg, 85%) as a yellow oil.

To a solution of the biaryl compound from above (555 mg, 2.58 mmol) in CH$_2$Cl$_2$ (20 mL) was added 3-chloroperoxybenzoic acid (1.955 g, 8.72 mmol) and the mixture stirred for 1.5 h. The reaction was diluted with CH$_2$Cl$_2$ (25 mL) and saturated aqueous NaHCO$_3$ (30 mL) and the organic layer washed with saturated aqueous NaHCO$_3$ (2×25 mL), dried (Na$_2$SO$_4$) and concentrated. The crude solid was purified by column chromatography on silica gel (CH$_2$Cl$_2$/MeOH, 96:4 then 92:8) to afford the desired sulfone N-oxide (575 mg, 85%) as a white solid. A solution of the resultant N-oxide (575 mg, 2.19 mmol) in Ac$_2$O (3 mL) was stirred at 85° C. for 3 h then diluted with CH$_2$Cl$_2$ (25 mL) and MeOH (10 mL) and concentrated. The residue was diluted with CH$_2$Cl$_2$ (25 mL) and saturated aqueous NaHCO$_3$ (25 mL) and the organic phase was washed with saturated aqueous NaHCO$_3$ (20 mL). The combined organic extracts were dried (Na$_2$SO$_4$), concentrated and purified by column chromatography on silica gel (CH$_2$Cl$_2$/MeOH, 96:4) to give the desired acetate (0.59 g) as an orange oil.

To a solution of the impure acetate from above (0.59 g) in MeOH (10 mL) was added K$_2$CO$_3$ (545 mg, 3.95 mmol) and the mixture stirred overnight. The reaction was concentrated, diluted with CH$_2$Cl$_2$ (30 mL) and saturated aqueous NaHCO$_3$ (25 mL) and the aqueous phase extracted with CH$_2$Cl$_2$ (1×10 mL). The combined organic extracts were dried (Na$_2$SO$_4$) and concentrated to give the desired alcohol (333 mg, 58% 2 steps) as a beige solid.

To a stirred solution of the alcohol from above (333 mg, 1.27 mmol) in dry CH$_2$Cl$_2$ (10 mL) was added activated MnO$_2$ (90% purity, <10 micron, 1.16 g, 13.3 mmol). The resulting heterogeneous mixture was stirred overnight, at which point the black slurry was filtered through a cake of celite and washed with CH$_2$Cl$_2$ and MeOH (3×15 mL). The combined washings were concentrated and purified by column chromatography on silica gel (CH$_2$Cl$_2$/MeOH, 98:2) to afford 327 mg (approx 55%) 3-(4-methanesulfonyl-phenyl)-pyridine-2-carbaldehyde as an impure mixture, which was used in subsequent reactions without further purification.

COMPOUND 54 was isolated as a beige solid. $^1$H NMR (D$_2$O) δ 1.47-1.51 (m, 4H), 2.33 (s, 3H), 2.47 (s, 3H), 2.64-2.68 (m, 2H), 2.87-2.91 (m, 2H), 3.35 (s, 3H), 4.13 (s, 2H), 4.33 (s, 2H), 7.74 (d, 2H, J=8.4 Hz), 8.07-8.15 (m, 4H), 8.39 (s, 1H), 8.53 (dd, 1H, J=7.8, 1.2 Hz), 8.88 (dd, 1H, J=6.0, 1.2 Hz). $^{13}$C NMR (D$_2$O) δ 17.06, 17.57, 22.58, 24.91, 39.53, 43.75, 53.81, 54.63, 54.68, 126.75, 128.38, 130.90, 136.97, 137.68, 138.26, 139.23, 140.18, 140.40, 142.03, 147.38, 148.03, 149.13, 150.51. ES-MS m/z 453 (M+H). Anal. Calcd. for C$_{25}$H$_{32}$N$_4$O$_2$S.3.3HBr.2.3H$_2$O.0.4C$_4$H$_{10}$O: C, 40.41; H, 5.60; N, 7.09; Br, 33.35. Found: C, 40.33; H, 5.56; N, 7.07; Br, 33.47.

Example 55

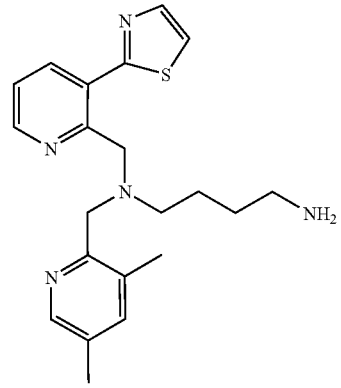

COMPOUND 55: N$^1$-(3,5-Dimethyl-pyridin-2-ylmethyl)-N$^1$-(3-thiazol-2-yl-pyridin-2-ylmethyl)-butane-1,4-diamine (HBr salt)

To a stirred degassed solution of 3-tri-n-butylstannanyl-pyridine-2-carbaldehyde (WO 02142273; PCT/US01/46884) (576 mg, 1.47 mmol) and 2-bromothiazole (0.15 mL, 1.66 mmol) in DMF (3.5 mL) were added copper(II) oxide (1.73 mmol), PdCl$_2$(PPh$_3$)$_4$ (66 mg, 0.094 mmol) and Pd(PPh$_3$)$_4$ (38 mg, 0.033 mmol). The reaction mixture was flushed and stirred under Ar while being heated at 90° C. overnight. The mixture was then cooled, diluted with EtOAc (40 mL) and brine (30 mL). The organic layer was washed with brine (1×20 mL), dried (Na$_2$SO$_4$) and concentrated in vacuo. Purification of the resultant oil by column chromatography with silica gel (Hexanes/EtOAc, 2:1 then 1:2) afforded the coupled product as a white solid (33 mg, 9%).

COMPOUND 55 was isolated as a brown solid: $^1$H NMR (D$_2$O) δ 1.61-1.68 (m, 2H), 1.75-1.79 (m, 2H), 2.34 (s, 3H), 2.37 (s, 3H), 2.93-2.98 (m, 2H), 3.10-3.15 (m, 2H), 4.49 (s, 2H), 4.73 (s, 2H), 7.83 (dd, 1H, J=8.1, 5.7 Hz), 7.87 (d, 1H, J=3.0 Hz), 8.00 (s, 1H), 8.03 (d, 1H, J=3.0 Hz), 8.27 (s, 1H), 8.48 (d, 1H, J=7.5 Hz), 8.73 (d, 1H, J=4.5 Hz). $^{13}$C NMR (D$_2$O) δ 17.34, 17.48, 22.06, 24.68, 39.34, 53.72, 55.62, 56.87, 124.29, 126.43, 130.87, 137.16, 138.06, 140.42, 143.93, 144.05, 144.34, 146.10, 149.00, 147.91. ES-MS m/z 382 (M+H). Anal. Calcd. for C$_{21}$H$_{27}$N$_5$S.3.8HBr.2.0H$_2$O: C, 34.79; H, 4.84; N, 9.66; Br, 41.88. Found: C, 34.79; H, 4.84; N, 9.28; Br, 41.98.

Example 56

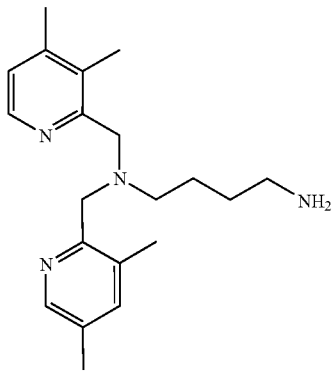

COMPOUND 56: N$^1$-(3,5-Dimethyl-pyridin-2-ylmethyl)-N$^1$-(3,4-dimethyl-pyridin-2-ylmethyl)-butane-1,4-diamine (HBr salt)

A CH$_2$Cl$_2$ solution (10 mL) of (3,4-dimethyl-pyridin-2-yl)-methanol (271 mg, 1.98 mmol) (Katz, R. B. et al. *Synth. Commun.* 1989, 19, 317-25) was treated with MnO$_2$ (2.10 g, 21.8 mmol), and the resultant black suspension was stirred at room temperature overnight. The black suspension was filtered through a celite pad and the filtrate was concentrated in vacuo to afford 3,4-Dimethyl-pyridine-2-carbaldehyde (215 mg, 80%), without further purification, as a red oil. $^1$H NMR (CDCl$_3$) δ 2.37 (s, 3H), 2.60 (s, 3H), 7.22-7.29 (m, 1H), 8.52 (d, 1H, J=4.3 Hz), 10.20 (s, 1H).

COMPOUND 56 was isolated as a white solid: $^1$H NMR (D$_2$O) δ 1.54-1.59 (m, 4H), 2.35 (s, 3H), 2.44 (s, 6H), 2.53 (s, 3H), 2.70-2.75 (m, 2H), 2.90-2.94 (m, 2H), 4.24 (s, 2H), 4.29 (s, 2H), 7.72 (d, 1H, J=6.0 Hz), 8.17 (s, 1H), 8.39-8.41 (m, 2H). $^{13}$C NMR (D$_2$O) δ 13.69, 17.10, 17.48, 20.92, 22.96, 25.05, 39.58, 54.08, 54.65, 55.37, 127.18, 136.25, 136.98, 137.28, 137.56, 138.01, 148.04, 149.21, 160.57. ES-MS m/z 327 (M+H). Anal. Calcd. for C$_{20}$H$_{30}$N$_4$.3.6HBr.1.6H$_2$O.0.3C$_4$H$_{10}$O: C, 38.07; H, 6.00; N, 8.38; Br, 43.01. Found: C, 38.19; H, 5.86; N, 8.28; Br, 42.81.

Example 57

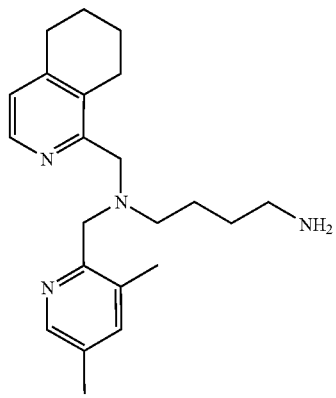

COMPOUND 57: N$^1$-(3,5-Dimethyl-pyridin-2-ylmethyl)-N$^1$-(5,6,7,8-tetrahydro-isoquinolin-1-ylmethyl)-butane-1,4-diamine (HBr salt)

$^1$H NMR (D$_2$O) δ 1.53-1.59 (m, 4H), 1.80-1.85 (m, 4H), 2.44 (s, 6H), 2.69-2.78 (m, 4H), 2.92-3.01 (m, 4H), 4.21 (s, 2H), 4.24 (s, 2H), 7.62 (d, 1H, J=6.0 Hz), 8.18 (s, 1H), 8.33 (d, 1H, J=6.0 Hz), 8.41 (s, 1H). $^{13}$C NMR (D$_2$O) δ 17.09, 17.46, 20.65, 21.15, 22.98, 24.47, 25.02, 30.50, 39.54, 53.96, 54.20, 55.37, 126.67, 136.10, 136.28, 136.95, 137.50, 137.96, 148.03, 149.17, 150.15, 160.63. ES-MS m/z 353 (M+H). Anal. Calcd. for C$_{22}$H$_{32}$N$_4$.3.2HBr.2.0H$_2$O.0.3C$_4$H$_{10}$O: C, 41.61; H, 6.35; N, 8.37; Br, 38.18. Found: C, 41.38; H, 6.12; N, 8.23; Br, 38.42.

Example 58

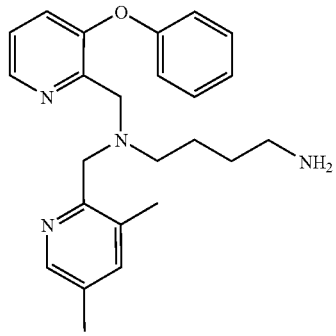

COMPOUND 58: N$^1$-(3,5-Dimethyl-pyridin-2-ylmethyl)-N$^1$-(3-phenoxy-pyridin-2-ylmethyl)-butane-1,4-diamine To a solution of 2-methyl-3-phenoxy-pyridine (0.501 g, 2.70 mmol) (Butler, D E et al. *J. Med. Chem* 1981, 24, 346-350) in CH$_2$Cl$_2$ (2.7 mL) was added 3-chloroperoxybenzoic acid (0.698 g, 4.05 mmol) and the solution stirred at room temperature for 24 h. Reaction mixture was diluted with CH₂Cl₂ (30 mL) and the organic layer was washed with saturated aqueous NaHCO₃ (2×30 mL), dried (MgSO₄), and concentrated to give 2-methyl-3-phenoxy-pyridine 1-oxide as a brown oil, which was used without further purification. ¹H NMR (CDCl₃) δ 2.54 (s, 3H), 6.77 (d, 1H), 6.97-7.06 (m, 3H), 7.16-7.21 (m, 1H), 7.34-7.41 (m, 2H), 8.11 (m, 1H).

A solution of 2-methyl-3-phenoxy-pyridine 1-oxide (0.690 g, 3.40 mmol) in Ac₂O (3.4 mL) stirred at 80° C. for 3 h. The solution was concentrated and the resulting residue was diluted with CH₂Cl₂ (30 mL). The organic layer was washed with saturated aqueous NaHCO₃ (2×30 mL), dried (MgSO₄), and concentrated. Purification by column chromatography on silica gel with hexanes/Et₂O (1:1) afforded acetic acid 3-phenoxy-pyridin-2-ylmethyl ester as a clear oil (0.234 g, 28%). ¹H NMR (CDCl₃) δ 2.07 (s, 3H), 5.34 (s, 2H), 7.00 (d, 2H, J=8.0 Hz), 7.13-7.23 (m, 2H), 7.36 (m, 2H), 8.39 (dd, 1H, J=3.4, 2.1 Hz).

To a solution of acetic acid 3-phenoxy-pyridin-2-ylmethyl ester (0.234 g, 0.96 mmol) in MeOH (10 mL) was added K₂CO₃ (0.264 g, 1.92 mmol) and the mixture stirred at room temperature for 2 h. The mixture was concentrated and the resultant residue was diluted with CH₂Cl₂ (30 mL). The organic layer was washed with saturated aqueous NaHCO₃ (2×30 mL), dried (MgSO₄), and concentrated to give (3-phenoxy-pyridin-2-yl)-methanol as a clear oil (0.130 g, 68%), which was used without further purification. ¹H NMR (CDCl₃) δ 4.26 (t, 1H, J=4.8 Hz), 4.84 (d, 2H, J=4.3 Hz), 6.97 (m, 2H), 7.18 (m, 3H), 7.37 (m, 2H), 8.32 (dd, 1H, J=2.9, 1.4 Hz).

To a solution of (3-phenoxy-pyridin-2-yl)-methanol (0.130 g, 0.646 mmol) in CH₂Cl₂ (7 mL) was added MnO₂ (10 microns, 90+%) (0.645 g, 7.42 mmol) and the resulting black mixture stirred for 24 h. The mixture was filtered through celite and washed with CH₂Cl₂. The solution was concentrated to give 3-phenoxy-pyridine-2-carbaldehyde as a yellow oil (0.085 g, 67%). ¹H NMR (CDCl₃) δ 6.97-7.43 (m, 7H), 8.50 (dd, 1H, J=2.8, 1.2 Hz), 10.42 (s, 1H).

COMPOUND 58 was isolated as a white solid. ¹H NMR (D₂O) δ 1.59-1.68 (m, 4H), 2.37-2.52 (m, 6H), 2.85-2.96 (m, 4H), 4.32 (s, 2H), 4.40 (s, 2H), 7.13 (d, 2H, J=8.0 Hz), 7.36-7.38 (m, 1H), 7.49-7.54 (t, 2H, J=7.9 Hz,), 7.81-7.88 (m, 2H), 8.10 (s, 1H), 8.30 (s, 1H), 8.45 (d, 1H, J=5.6 Hz). ¹³C NMR (D₂O) δ 17.0, 17.5, 22.7, 25.0, 39.6, 51.9, 53.7, 55.0, 120.3, 126.7, 127.7, 131.2, 132.7, 136.4, 137.5, 137.6, 138.3, 143.7, 147.6, 148.8, 154.1, 155.3. ES-MS m/z 391 [M+H]⁺. Anal. Calcd. for C₂₄H₃₀N₄O.3.8HBr.1.9H₂O.0.5C₄H₁₀O: C, 40.59; H, 5.58; N, 7.28; Br, 39.47. Found: C, 40.52; H, 5.53; N, 7.28; Br, 39.57.

Example 59

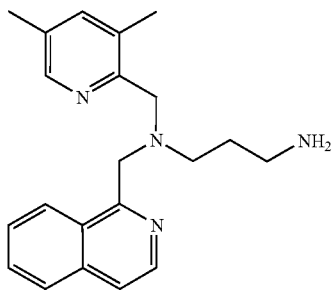

COMPOUND 59: N¹-(3,5-Dimethyl-pyridin-2-ylmethyl)-N¹-isoquinolin-1-ylmethyl-butane-1,4-diamine (HBr salt)

¹H NMR (D₂O) δ 1.58-1.75 (m, 4H), 2.27 (s, 3H), 2.36 (s, 3H), 2.92-2.97 (m, 4H), 4.23 (s, 2H), 4.84 (s, 2H), 7.97-8.04 (m, 3H), 8.16-8.18 (m, 2H), 8.25 (d, 1H, J=6.6 Hz), 8.38 (d, 1H, J=6.6 Hz), 8.54 (d, 1H, J=8.7 Hz) ppm. ¹³C NMR (D₂O) δ 17.1, 17.3, 23.0, 25.0, 39.6, 54.1, 54.8, 56.5, 66.5, 125.8, 127.1, 128.8, 130.3, 131.8, 136.8, 137.3, 138.0, 138.9, 147.5, 148.7, 156.4 ppm. ES-MS m/z 349 (M+H). Anal. Calcd. for C₂₂H₂₈N₄.3.1HBr.1.9H₂O: C, 41.71; H, 5.55; N, 8.84; Br, 39.10. Found: C, 41.97; H, 5.66; N, 8.46; Br, 38.97.

Example 60

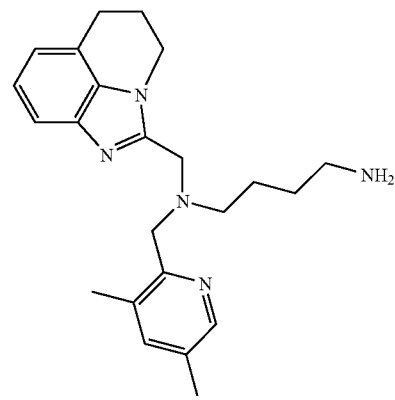

COMPOUND 60: N¹-(5,6-Dihydro-4H-imidazo[4,5,1-ij]quinolin-2-ylmethyl)-N¹-(3,5-dimethyl-pyridin-2-ylmethyl)-butane-1,4-diamine (HBr salt)

¹H NMR (D₂O) δ 1.50-1.74 (m, 4H), 2.23-2.32 (m, 2H), 2.36 (s, 3H), 2.45 (s, 3H), 2.84 (t, 2H, J=6.3 Hz), 2.95 (t, 2H, J=6.3 Hz), 3.04 (t, 2H, J=5.7 Hz), 4.27 (s, 2H), 4.39 (t, 2H, J=5.7 Hz), 4.43 (s, 2H), 7.36 (d, 1H, J=6.6 Hz), 7.45-7.58 (m, 2H), 8.12 (s, 1H), 8.36 (s, 1H); ¹³C NMR (D₂O) δ 17.02, 17.44, 22.14, 22.99, 23.36, 25.00, 39.63, 44.05, 49.35, 54.04, 55.86, 111.34, 124.00, 126.17, 127.59, 128.86, 130.13, 136.94, 137.63, 137.85, 148.17, 148.31, 149.15; ES-MS m/z 378 (M+H). Anal. Calcd. For C₂₃H₃₁N₅.3.3HBr.2.0H₂O: C, 40.59; H, 5.67; N, 10.29; Br, 38.74. Found: C, 40.65; H, 5.70; N, 10.08; Br, 38.71.

Example 61

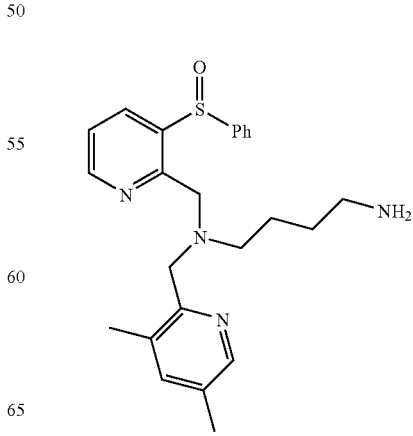

COMPOUND 61: N$^1$-(3-Benzenesulfinyl-pyridin-2-ylmethyl)-N$^1$-(3,5-dimethyl-pyridin-2-ylmethyl)-butane-1,4-diamine To a stirred solution of 3-Bromo-2-methyl-pyridine (1.96 g, 11.4 mmol) in glacial HOAc (20 mL) at room temperature was added 50% H$_2$O$_2$ (0.77 mL) and the solution was heated to 70° C. After 2 h, the reaction mixture was cooled to room temperature, additional H$_2$O$_2$ (0.80 mL) was added, and the solution was heated at 70° C. overnight. The reaction mixture was cooled to room temperature and concentrated under reduced pressure. The residue was dissolved in CH$_2$Cl$_2$ (80 mL) and treated with saturated aqueous NaHCO$_3$ (20 mL). The aqueous phase was separated and extracted with CH$_2$Cl$_2$ (4×20 mL). The combined organic extracts were dried (Na$_2$SO$_4$), filtered, and concentrated to provide 3-Bromo-2-methyl-pyridine 1-oxide (1.79 g, 84%) as a white solid. $^1$H NMR (CDCl$_3$) δ 2.70 (s, 3H), 7.00 (t, 1H, J=7.0 Hz), 7.44 (d, 1H, J=7.9 Hz), 8.23 (d, 1H, J=6.5 Hz). 3-Bromo-2-methyl-pyridine 1-oxide was used without further purification.

To a suspension of 60% NaH (577 mg, 14.4 mmol) in DMF (15 mL) at 0° C. was added thiophenol (1.47 mL, 14.4 mmol) and the resultant mixture was warmed to room temperature and stirred for 1.5 h. To this mixture was added the 3-Bromo-2-methyl-pyridine 1-oxide (900 mg, 4.79 mmol) and the resultant yellow solution was heated to 80° C. for 96 h. The reaction mixture was cooled to room temperature and concentrated under reduced pressure. The residue was treated with EtOAc (100 mL), washed with brine (4×50 mL), dried (Na$_2$SO$_4$), filtered, and concentrated under reduced pressure. Purification by flash chromatography on silica gel (EtOAc/MeOH, 100:0 then 95:5) gave a mixture of 2-methyl-3-phenylsulfanyl-pyridine 1-oxide and a di-substituted thiophenol by-product. The mixture was treated with Ac$_2$O (3 mL) and heated at 80° C. overnight. The mixture was cooled to room temperature, diluted with CH$_2$Cl$_2$ (40 mL), H$_2$O (10 mL) and saturated aqueous NaHCO$_3$ (40 mL). The aqueous phase was separated and extracted with CH$_2$Cl$_2$ (2×20 mL). The combined organic extracts were dried (Na$_2$SO$_4$), filtered, and concentrated. Purification by flash chromatography on silica gel (Hexanes/EtOAc, 70:30) gave Acetic acid 3-phenylsulfanyl-pyridin-2-ylmethyl ester (259 mg, 25% over 2 steps) as a yellow oil. $^1$H NMR (CDCl$_3$) δ 2.11 (s, 3H), 5.37 (s, 2H), 7.18 (dd, 1H, J=7.9, 4.9 Hz), 7.27-7.38 (m, 5H), 7.53 (dd, 1H, J=7.9, 1.7 Hz), 8.50 (dd, 1H, J=4.7, 1.8 Hz).

To a solution of Acetic acid 3-phenylsulfanyl-pyridin-2-ylmethyl ester (259 mg, 1.00 mmol) in MeOH (6 mL) at −20° C. was added a solution of oxone monopersulfate compound (735 mg, 1.20 mmol) in H$_2$O (6 mL), and the mixture was stirred for 15 minutes, and diluted with H$_2$O (30 mL) and CH$_2$Cl$_2$ (40 mL). The aqueous phase was separated and extracted with CH$_2$Cl$_2$ (2×15 mL). The combined organic extracts were dried (Na$_2$SO$_4$), filtered, and concentrated under reduced pressure. Acetic acid 3-benzenesulfinyl-pyridin-2-ylmethyl ester was used without further purification.

To a solution of the crude Acetic acid 3-benzenesulfinyl-pyridin-2-ylmethyl ester (268 mg) in anhydrous MeOH (4 mL) was added powdered K$_2$CO$_3$ (254 mg, 1.84 mmol) and the mixture was stirred at room temperature for 3 h. The reaction mixture was diluted with CH$_2$Cl$_2$ (30 mL), filtered by vacuum filtration, and the filtrate was concentrated. Purification by flash chromatography on silica gel (Hexanes/EtOAc, 20:80 then 0:100) provided (3-Benzenesulfinyl-pyridin-2-yl)-methanol (128 mg, 42% over 2 steps) as a colorless oil. $^1$H NMR (CDCl$_3$) δ 4.18 (t, 1H, J=5.7 Hz), 4.58 (dd, 1H, J=14.8, 4.3 Hz), 4.88 (dd, 1H, J=14.9, 5.3 Hz), 7.45-7.53 (m, 4H), 7.59-7.66 (m, 2H), 8.33 (dd, 1H, J=7.9, 1.4 Hz), 8.66 (dd, 1H, J=5.3, 1.8 Hz).

To a stirred solution of the alcohol from above (128 mg, 0.513 mmol) in CH$_2$Cl$_2$ (3.5 mL) was added MnO$_2$ (450 mg, 5.13 mmol) and the reaction mixture was allowed to stir overnight at room temperature. The mixture was filtered through celite, and concentrated to give a 3:1 mixture of 3-Benzenesulfinyl-pyridine-2-carbaldehyde and (3-Benzenesulfinyl-pyridin-2-yl)-methanol (115 mg), which was used without further purification in subsequent steps.

COMPOUND 61 was isolated as a colorless oil. $^1$H NMR (CDCl$_3$) δ 1.18-1.38 (m, 2H), 1.39-1.67 (m, 4H), 2.21 (s, 3H), 2.24 (s, 3H), 2.48-2.61 (m, 4H), 3.74 (d, 1H, J=12.6 Hz), 3.84 (d, 1H, J=12.6 Hz), 3.94 (s, 2H), 7.21 (s, 1H), 7.29-7.50 (m, 6H), 8.16 (dd, 1H, J=7.8, 1.5 Hz), 8.19 (s, 1H), 8.57 (dd, 1H, J=4.8, 1.5 Hz); $^{13}$C NMR (CDCl$_3$) δ 18.30, 18.73, 23.92, 42.19, 54.25, 58.37, 58.47, 124.11, 125.58, 129.57, 131.37, 132.39, 133.26, 134.14, 139.22, 142.60, 145.28, 146.80, 151.16, 153.80, 156.97; ES-MS m/z 423 (M+H). Anal. Calcd. for C$_{24}$H$_{30}$N$_4$OS·0.3 CH$_2$Cl$_2$: C, 65.14; H, 6.88; N, 12.50. Found: C, 65.17; H, 7.21; N, 12.42.

Example 62

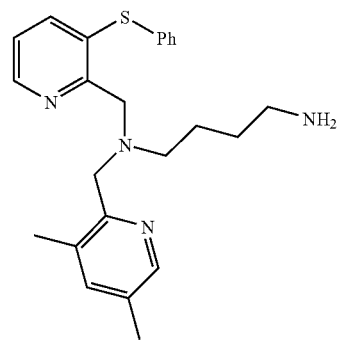

COMPOUND 62: N$^1$-(3,5-Dimethyl-pyridin-2-ylmethyl)-N$^1$-(3-phenylsulfanyl-pyridin-2-ylmethyl)-butane-1,4-diamine (HBr salt)

To a stirred solution of N,N-diisopropylamine (0.91 mL, 6.5 mmol) in dry THF (15 mL) at −78° C. was added n-BuLi (2.1 M in hexanes, 2.6 mL, 5.5 mmol) and the resultant solution was stirred for 20 minutes. To the solution of LDA was added 2-bromopyridine (0.48 mL, 5.0 mmol) and the resultant orange solution was stirred for 2 h at −78° C., after which a dry THF solution (10 mL) of phenyl disulfide (1.31 g, 6.0 mmol) was added. The resultant yellow solution was stirred at this temperature for 1 h and then stirred an additional 2 h at room temperature. The reaction mixture was diluted with brine (30 mL) and H$_2$O (5 mL), and extracted with Et$_2$O (3×30 mL). The combined organic extracts were dried (MgSO$_4$), filtered, and concentrated under reduced pressure. Purification by flash chromatography on silica gel (Hexanes/EtOAc, 90:10) gave impure 2-Bromo-3-phenylsulfanyl-pyridine (570 mg).

3-Phenylsulfanyl-pyridine-2-carbaldehyde was prepared from 2-Bromo-3-phenylsulfanyl-pyridine as an orange solid by nucleophilic substitution with a formyl group, as exemplified in Example 44. $^1$H NMR (CDCl$_3$) δ 7.12 (d, 1H, J=7.9

Hz), 7.21 (dd, 1H, J=8.3, 4.4 Hz), 7.44-7.54 (m, 3H), 7.55-7.63 (m, 2H), 8.49 (dd, 1H, J=4.3, 1.7 Hz), 10.22 (s, 1H); ES-MS m/z 216 (M+H).

COMPOUND 62 was isolated as a white solid. $^1$H NMR (D$_2$O) δ 1.57-1.69 (m, 4H), 2.43 (s, 6H), 2.80-2.89 (m, 2H), 2.90-3.00 (m, 2H), 4.29 (s, 2H), 4.35 (s, 2H), 7.51 (s, 5H), 7.63-7.71 (m, 1H), 7.97 (d, 1H, J=8.4 Hz), 8.11 (s, 1H), 8.40 (s, 1H), 8.52 (d, 1H, J=5.1 Hz); $^{13}$C NMR (D$_2$O) δ 17.18, 17.50, 22.60, 24.98, 39.57, 53.88, 55.05, 55.36, 126.25, 129.54, 130.48, 130.93, 134.09, 136.99, 137.65, 138.77, 139.24, 139.82, 145.63, 147.20, 148.63, 150.17; ES-MS m/z 407 (M+H). Anal. Calcd. for C$_{24}$H$_{30}$N$_4$S.3.3HBr.1.4H$_2$O: C, 41.25; H, 5.21; N, 8.02; Br, 37.73. Found: C, 41.35; H, 5.38; N, 7.86; Br, 37.57.

Example 63

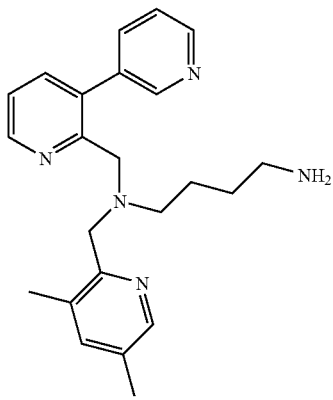

COMPOUND 63: N$^1$-[3,3']Bipyridinyl-2-ylmethyl-N$^1$-(3,5-dimethyl-pyridin-2-ylmethyl)-butane-1,4-diamine (HBr salt)

A mixture of 3-tributylstannanyl-pyridine (255 mg, 0.693 mmol), 3-Bromo-pyridine-2-carbaldehyde (123 mg, 0.660 mmol), and Pd(PPh$_3$)$_4$ (53.1 mg, 0.046 mmol) in toluene (4 mL) was heated to 90° C. for 23 h and cooled to room temperature. The reaction mixture was diluted with EtOAc (50 mL), washed with brine (3×20 mL), dried (Na$_2$SO$_4$), filtered, and concentrated under reduced pressure. Purification by flash chromatography on silica gel (Hexanes/EtOAc, 70:30, then 0:100) afforded [3,3']Bipyridinyl-2-carbaldehyde (35 mg, 29%) as a yellow oil.

COMPOUND 63 was isolated as a white solid. $^1$H NMR (D$_2$O) δ 1.54 (br s, 4H), 2.37 (s, 3H), 2.46 (s, 3H), 2.77 (br s, 2H), 2.90 (br s, 2H), 4.26 (s, 2H), 4.40 (s, 2H), 8.06 (t, 1H, J=6.6 Hz), 8.12 (s, 1H), 8.27 (t, 1H, J=6.6 Hz), 8.42 (s, 1H), 8.48 (d, 1H, J=7.5 Hz), 8.72 (d, 1H, J=7.2 Hz), 8.95 (d, 1H, J=4.8 Hz), 8.97-9.05 (m, 2H); $^{13}$C NMR (D$_2$O) δ 17.16, 17.56, 22.83, 24.83, 39.46, 54.13, 54.99, 55.36, 126.58, 128.32, 133.13, 134.52, 136.59, 137.48, 139.20, 142.09, 143.02, 144.80, 146.84, 147.01, 147.48, 148.30, 151.17; ES-MS m/z 376 (M+H). Anal. Calcd. for C$_{23}$H$_{29}$N$_5$.4.1HBr.2.9H$_2$O: C, 36.37; H, 5.16; N, 9.22; Br, 43.13. Found: C, 36.34; H, 5.29; N, 8.97; Br, 43.35.

Example 64

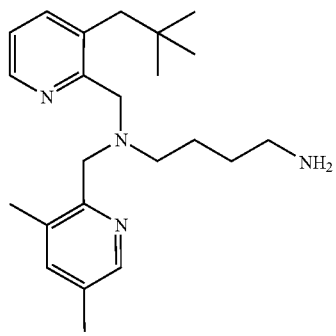

COMPOUND 64: N$^1$-[3-(2,2-Dimethyl-propyl)-pyridin-2-ylmethyl]-N$^1$-(3,5-dimethyl-pyridin-2-ylmethyl)-butane-1,4-diamine (HCl salt)

To a cold solution (−40° C.) of 1-(2-bromo-pyridin-3-yl)-2,2-dimethyl-propan-1-ol (8.18 g, 33.5 mmol) (Romero, D. L. et al. J. Med. Chem. 1994, 37, 999-1014) in dry THF (310 mL) was added dropwise a solution of 1.6 M MeLi in Et$_2$O (23.1 mL, 36.9 mmol). The solution was warmed to room temperature and stirred 15 min before the addition of carbon disulfide (2.22 mL, 36.9 mmol). The solution was stirred 50 min and then MeI (2.50 mL, 40.2 mmol) was added. The mixture was stirred 1.5 h and was quenched with a saturated solution of NaHCO$_3$ (100 mL). The solution was extracted with Et$_2$O (3×120 mL). The combined organic portions were dried with Na$_2$SO$_4$, filtered, and concentrated under reduced pressure. The residue was purified by flash chromatography (5% EtOAc/hexanes) to afford 8.58 g (81%) of Dithiocarbonic acid [1-(2-bromo-pyridin-3-yl)-2,2-dimethyl-propyl] ester methyl ester as a yellow oil. $^1$H NMR (CDCl$_3$) δ 1.09 (s, 9H), 2.55 (s, 3H), 6.50 (s, 1H), 7.26 (dd, 1H, J=4.7, 7.7 Hz), 7.60 (dd, 1H, J=2.0, 7.7 Hz), 8.30 (dd, 1H, J=1.9, 4.7 Hz).

The xanthate (8.47 g, 26.7 mmol) was dissolved in toluene (450 mL). Tributyltin hydride (14.4 mL, 53.4 mmol) was added and the mixture was immediately warmed in a preheated bath at 70° C. 1,1'-Azobis(cyclohexanecarbonitrile) (652 mg, 2.67 mmol) was added after 8 min. The solution was stirred 2.5 h in which a second portion of 1,1'-azobis(cyclohexanecarbonitrile) (326 mg, 1.34 mmol) was added after 2 h. The mixture was cooled to room temperature and a saturated solution of NaHCO$_3$ (200 mL) was added. The solution was extracted with Et$_2$O (3×200 mL) and the combined organic portions were washed with brine (50 mL), dried with Na$_2$SO$_4$, filtered, and concentrated under reduced pressure. The residue was purified by flash chromatography (5% Et$_2$O/hexanes) to afford 4.71 g (77%) of 2-Bromo-3-(2,2-dimethyl-propyl)-pyridine. $^1$H NMR (CDCl$_3$) δ 0.99 (s, 9H), 2.74 (s, 2H), 7.19 (dd, 1H, J=4.7, 7.5 Hz), 7.49 (dd, 1H, J=1.6, 7.5 Hz), 8.23 (dd, 1H, J=1.6, 4.7 Hz).

3-(2,2-Dimethyl-propyl)-pyridine-2-carbaldehyde as a yellow oil was prepared from 2-Bromo-3-(2,2-dimethyl-propyl)-pyridine by nucleophilic displacement with a formyl group, as exemplified in Example 41. $^1$H NMR (CDCl$_3$) δ 0.88 (s, 9H), 3.10 (s, 2H), 7.37 (dd, 1H, J=4.5, 7.8 Hz), 7.56 (dd, 1H, J=1.3, 7.8 Hz), 8.67 (dd, 1H, J=1.3, 4.5 Hz), 10.17 (s, 1H).

Obtained COMPOUND 64 as a white solid. $^1$H NMR (D$_2$O) δ 0.91 (s, 9H), 1.70-1.40 (m, 4H), 2.42 (s, 3H), 2.44 (s, 3H), 2.65-2.80 (m, 4H), 2.80-2.95 (m, 2H), 4.23 (s, 2H), 4.35 (s, 2H), 7.80-7.90 (m, 1H), 8.12 (s, 1H), 8.34 (d, 1H, J=7.8 Hz), 8.39 (s, 1H), 8.63 (d, 1H, J=5.8 Hz); $^{13}$C NMR (D$_2$O) δ 17.04, 17.45, 22.93, 25.00, 28.70, 33.19, 39.53, 43.39, 53.85, 54.44, 55.23, 125.48, 136.99, 137.65, 138.18, 139.16, 139.72, 147.82, 149.11, 150.04, 151.17; ES-MS m/z 370 (M+H). Anal. Calcd. For C$_{23}$H$_{36}$N$_4$·3.3HCl·2.3H$_2$O: C, 52.09; H, 8.34; N, 10.56; Cl, 22.06. Found: C, 52.24; H, 8.30; N, 10.20; Cl, 21.87.

Example 65

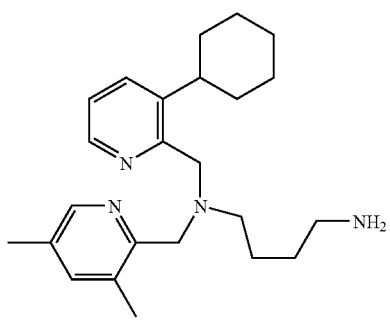

COMPOUND 65: N-(3-Cyclohexyl-pyridin-2-ylmethyl)-N-(3,5-dimethyl-pyridin-2-ylmethyl)-butane-1,4-diamine (HBr salt)

A 50 mL round bottom containing 2-methyl-3-phenylpyridine (0.43 g, 2.5 mmol) in TFA (12 mL) was purged with Ar. PtO$_2$ (125 mg, 5.1 mmol) was then added and hydrogen gas bubbled through the suspension continuously for 5 hours. The reaction was then stirred under a static atmosphere of hydrogen for an additional 64 hours. The mixture was then treated with 15% aqueous NaOH solution (10 mL) and extracted with CH$_2$Cl$_2$ (3×20 mL). The combined organics were then dried (Na$_2$SO$_4$), filtered, and concentrated under reduced pressure to yield, after column chromatography with silica gel (100:1 CH$_2$Cl$_2$/MeOH), 3-cyclohexyl-2-methylpyridine (173 mg, 39%). $^1$H NMR (CDCl$_3$) δ 1.25-1.45 (m, 5H), 1.78-1.89 (m, 5H), 2.57 (s, 3H), 2.68 (m, 1H), 7.09 (m, 1H), 7.48 (d, 1H, J=6.0 Hz), 8.31 (d, 1H, J=2.8 Hz).

A solution of 3-cyclohexyl-2-methylpyridine (170 mg, 1.0 mmol), in CH$_2$Cl$_2$ (5 mL) was treated with MCPBA (0.33 g, 1.9 mmol) for 18 hours. The solution was then washed with saturated NaHCO$_3$ solution (5 mL), the phases separated, and the aqueous extracted with CH$_2$Cl$_2$ (2×10 mL). The combined organic phases were then dried (Na$_2$SO$_4$), filtered, and concentrated to afford crude 3-cyclohexyl-2-methylpyridine N-oxide as a white solid (0.215 g) which was used immediately in the next reaction.

The N-oxide from above (0.215 g) was dissolved in Ac$_2$O (2.5 mL) and heated to 90° C. for 24 h followed by removal of the solvent under reduced pressure. The crude material was purified by column chromatography (50:1 CH$_2$Cl$_2$/MeOH) to give the rearranged acetic acid 3-cyclohexyl-pyridin-2-ylmethyl ester as a light brown solid (0.23 g, 99%, 2 steps). $^1$H NMR (CDCl$_3$) δ 1.25-1.45 (m, 5H), 1.78-1.86 (m, 5H), 2.13 (s, 3H), 2.70 (m, 1H), 7.24 (m, 1H), 7.62 (d, 1H, J=6.0 Hz), 8.46 (d, 1H, J=2.8 Hz).

A solution of the above ester (0.23 g, 1.0 mmol) in anhydrous MeOH (5 mL) was treated with K$_2$CO$_3$ (0.27 g, 2.0 mmol) and stirred at room temperature for 3.5 h. The mixture was concentrated under reduced pressure and water (5 ml) was added. The aqueous solution was then extracted with CH$_2$Cl$_2$ (3×10 mL) and the combined organic phases dried (Na$_2$SO$_4$), filtered, and concentrated under reduced pressure. This gave the desired (3-cyclohexyl-pyridin-2-yl)-methanol as a brown liquid (0.15 g, 79%) that was used immediately in the next reaction.

(3-cyclohexyl-pyridin-2-yl)-methanol (0.15 g, 0.80 mmol) was then dissolved in anhydrous CH$_2$Cl$_2$ (5 mL) and treated with MnO$_2$ (0.68 g, 8.0 mmol) for 16 h at room temperature. The black mixture was then filtered through a celite pad (rinsing through with CH$_2$Cl$_2$) and the filtrate concentrated under reduced pressure. This gave, after column chromatography with silica gel (50:1 CH$_2$Cl$_2$/MeOH), the desired 3-cyclohexyl-pyridine-2-carbaldehyde (54 mg, 36%) as a pale residue. $^1$H NMR (CDCl$_3$) δ 1.23-1.50 (m, 5H), 1.78-1.86 (m, 5H), 3.78 (m, 1H), 7.42 (m, 1H), 7.81 (d, 1H, J=7.0 Hz), 8.65 (d, 1H, J=3.0 Hz), 10.20 (s, 1H, (CHO)).

COMPOUND 65 was isolated as a white solid. $^1$H NMR (D$_2$O) δ 1.27-1.62 (m, 9H), 1.77 (m, 3H), 1.86 (m, 2H), 2.47 (s, 6H), 2.70 (m, 2H), 2.90 (m, 3H), 4.26 (s, 2H), 4.37 (s, 2H), 7.91 (t, 1H, J=6.8 Hz), 8.21 (s, 1H), 8.42 (s, 1H), 8.49 (d, 1H, J=8.1 Hz), 8.57 (d, 1H, J=5.7 Hz). $^{13}$C NMR (D$_2$O) δ 17.21, 17.55, 23.11, 25.05, 25.62, 26.40 (2C), 32.88 (2C), 38.49, 39.58, 53.78, 54.13, 55.12, 126.55, 137.11, 137.68, 138.12, 138.58, 145.28, 146.31, 147.86, 149.33, 150.00. ES-MS m/z 381 (M+H). Anal. Calcd. for C$_{24}$H$_{36}$N$_4$·3.5HBr·1.5H$_2$O·C$_4$H$_{10}$O: C, 42.68; H, 6.51; N, 7.78; Br, 38.82. Found: C, 42.74; H, 6.56; N, 7.79; Br, 38.62.

Example 66

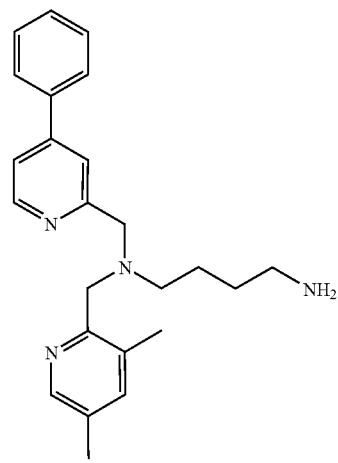

COMPOUND 66: N-(3,5-dimethyl-pyridin-2-ylmethyl)-N-(4-phenyl-pyridin-2-ylmethyl)-butane-1,4-diamine $^1$H NMR (CDCl$_3$) δ 1.45 (p, 2H, J=6.0 Hz), 1.61 (p, 2H, J=6.0 Hz), 2.24 (s, 3H), 2.32 (s, 3H), 2.56 (t, 2H, J=6.0 Hz), 2.73 (t, 2H, J=6.0 Hz), 3.78 (s, 2H), 3.81 (s, 2H), 7.21 (s, 1H), 7.35 (d, 1H, J=6.0 Hz), 7.45-7.52 (m, 3H), 7.56 (s, 1H), 7.61 (d, 1H, J=6.0 Hz), 8.21 (s, 1H), 8.59 (d, 1H, J=6.0 Hz). HPLC: 96%.

Example 67

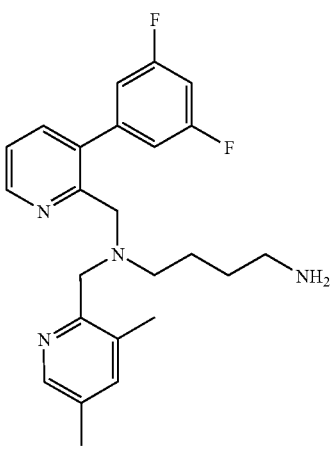

COMPOUND 67: $N^1$-[3-(3,5-Difluoro-phenyl)-pyridin-2-ylmethyl]-$N^1$-(3,5-dimethyl-pyridin-2-ylmethyl)-butane-1,4-diamine HCl salt To a solution of 3-bromo-pyridine-2-carbaldehyde (1.2 g, 6.45 mmol) dissolved in ethylene glycol dimethyl ether (25 mL), THF (10 mL) and saturated solution of $Na_2CO_3$ (9 mL) was added 3,5 difluorophenyl boronic acid (1.12 g, 7.10 mmol). Purge the mixture with Ar gas (10 min). To this mixture was added $Pd(PPh_3)_4$ (373 mg, 0.33 mmol) and stir under a positive pressure of Ar at 90° C. for 16 hours. The reaction mixture was quenched with a solution of saturated $NaHCO_3$ (50 mL). Extract with $CH_2Cl_2$ (2×50 mL). The combined organic extracts were dried ($Na_2SO_4$), filtered, and concentrated in vacuo to afford a light yellow oil. Purification via column chromatography on silica gel ($CH_2Cl_2$:MeOH: 80:20, v/v/v) afforded 3-(3,5-difluoro-phenyl)-pyridine-2-carbaldehyde as a white solid (0.86 g, 61%). $^1$H NMR ($CDCl_3$) δ 6.59 (m, 1H), 6.92 (m, 2H), 7.60 (m, 1H), 7.76 (d, 1H, J=7.5 Hz), 8.88 (d, 1H, J=3.5 Hz), 10.11 (s, 1H).

COMPOUND 67 was isolated as a white solid. $^1$H NMR ($D_2O$) δ 1.54 (s, 4H), 2.28 (s, 3H), 2.40 (s, 3H), 2.81 (m, 4H), 4.16 (s, 2H), 4.33 (s, 2H), 6.99 (d, 2H, J=6.1 Hz), 7.13 (m, 1H), 7.87 (dd, 1H, J=5.3, 8.3 Hz), 7.99 (s, 1H), 8.29 (m, 2H), 8.75 (d, 1H, J=6.1 Hz); $^{13}$C NMR ($D_2O$) δ 16.97, 17.47, 22.49, 24.85, 39.45, 53.92, 54.61, 54.77, 105.10, 105.44, 105.77, 112.77, 112.89, 113.12, 126.39, 136.74, 137.52, 138.91, 142.58, 147.02, 147.16, 148.42, 150.33. ES-MS m/z 411 (M+H). Anal. Calcd. For ($C_{24}H_{28}N_4F_2$) 3.3 (HCl): C, 54.29; H, 5.94; N, 10.55. Found: C, 54.27; H, 6.28; N, 10.55.

Example 68

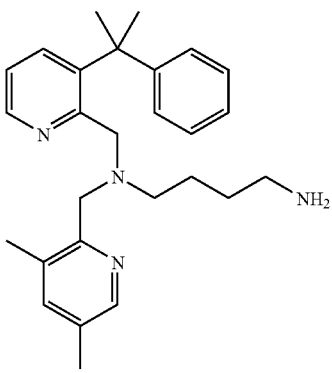

COMPOUND 68: $N^1$-(3,5-Dimethyl-pyridin-2-ylmethyl)-$N^1$-[3-(1-methyl-1-phenyl-ethyl)-pyridin-2-ylmethyl]-butane-1,4-diamine HCl salt To a mixture of $AlCl_3$ (2.173 g, 16.3 mmol) in benzene (20 mL) was added a solution of 2-(2-methyl-pyridin-3-yl)-propan-2-ol (0.455 g, 3.00 mmol) in benzene (10 mL) and the resultant mixture was stirred at room temperature overnight. The mixture was poured onto ice (~200 mL), diluted with EtOAc (200 mL), and neutralized with 10 N NaOH (4 mL). The phases were separated and the organic phase was washed with brine (3×25 mL), dried ($MgSO_4$), and concentrated. Purification of the crude material by column chromatography on silica gel (20:1 $CH_2Cl_2$-MeOH) provided 0.479 g (75%) of 2-methyl-3-(1-methyl-1-phenyl-ethyl)-pyridine as a colorless oil. $^1$H NMR ($CDCl_3$) δ 1.68 (s, 6H), 2.01 (s, 3H), 7.11-7.20 (m, 4H), 7.24-7.30 (m, 2H), 7.86 (dd, 1H, J=8.1, 1.5 Hz), 8.39 (dd, 1H, J=4.8, 1.5 Hz).

To a solution of 2-methyl-3-(1-methyl-1-phenyl-ethyl)-pyridine (0.582 g, 2.75 mmol) in $CH_2Cl_2$ (14 mL) was added 3-chloroperoxybenzoic acid (1.468 g, 8.51 mmol) and the resultant mixture was stirred at room temperature for 3 hours. The mixture was diluted with $CH_2Cl_2$ (50 mL), washed with saturated aqueous $NaHCO_3$ (3×15 mL), dried ($Na_2SO_4$), and concentrated. Purification of the crude material by column chromatography on silica gel (25:1 $CH_2Cl_2$-MeOH) provided 0.663 g of the N-oxide as a colorless oil. The oil (0.663 g) was dissolved in $Ac_2O$ (14 mL) and heated at 80° C. overnight. The mixture was cooled to room temperature and concentrated. Purification of the crude material by column chromatography on silica gel (40:1 $CH_2Cl_2$-MeOH) followed by column chromatography on silica gel (2:1 hexanes-EtOAc) provided 0.335 g (45% over 2 steps) of Acetic acid 3-(1-methyl-1-phenyl-ethyl)-pyridin-2-ylmethyl ester as a colorless oil.

The oil (0.335 g) was dissolved in MeOH (12 mL), treated with $K_2CO_3$ (0.251 g, 1.82 mmol) and the resultant mixture was stirred at room temperature for 90 minutes. The mixture was concentrated and the residue was partitioned between $CH_2Cl_2$ (25 mL) and saturated aqueous $NaHCO_3$ (10 mL). The phases were separated and the aqueous phase was extracted with $CH_2Cl_2$ (3×10 mL). The combined organic extracts were dried ($Na_2SO_4$), and concentrated and provided 0.265 g (94%) of [3-(1-methyl-1-phenyl-ethyl)-pyridin-2-yl]-methanol as a yellow oil. $^1$H NMR ($CDCl_3$) δ 1.67 (s, 6H), 3.90 (s, 2H), 4.92 (br s, 1H), 7.11-7.30 (m, 6H), 7.92 (dd, 1H, J=1.5, 8.1 Hz), 8.45 (dd, 1H, J=1.5, 4.8 Hz). The yellow oil (0.261 g, 1.15 mmol) was dissolved in $CH_2Cl_2$ (11 mL), treated with $MnO_2$ (1.04 g, 12.0 mmol), and stirred at room temperature overnight. The mixture was filtered through celite and the cake was washed with $CH_2Cl_2$. The solvent was removed from the filtrate under reduced pressure and provided 0.19 g (73%) of 3-(1-methyl-1-phenyl-ethyl)-pyridine-2-carbaldehyde as a colorless oil. $^1$H NMR ($CDCl_3$) δ 1.79 (s, 6H), 7.06-7.28 (m, 5H), 7.51 (dd, 1H, J=8, 6 Hz), 8.08 (d, 1H, J=8 Hz), 8.71 (d, 1H, J=6 Hz), 9.74 (s, 1H).

COMPOUND 68 was isolated as a white solid. $^1$H NMR ($D_2O$) δ 1.10-1.21 (m, 2H), 1.27-1.38 (m, 2H), 1.72 (s, 6H), 2.18 (t, 2H, J=7.5 Hz), 2.25 (s, 3H), 2.41 (s, 3H), 2.78 (t, 2H, J=7.5 Hz), 3.55 (s, 2H), 3.72 (s, 2H), 7.25 (d, 2H, J=7.0 Hz), 7.32-7.39 (m, 3H), 8.02 (t, 1H, J=7.0 Hz), 8.12 (s, 1H), 8.36 (s, 1H), 8.66 (d, 1H, J=5.0 Hz), 8.85 (d, 1H, J=8.0 Hz); $^{13}$C NMR ($D_2O$) δ 17.26, 17.52, 21.70, 22.37, 24.88, 29.56, 39.42, 43.16, 52.66, 54.18, 54.54, 126.42, 126.85(2), 127.62, 129.61(2), 136.79, 137.43, 138.13, 139.17, 145.23, 147.41, 147.53, 148.24, 149.23, 152.08; ES-MS m/z 417 (M+H). Anal. Calcd. For $C_{27}H_{36}N_4$.3.2HCl.1.4$H_2O$: C, 58.07; H, 7.58; N, 10.03; Cl, 20.31. Found: C, 57.96; H, 7.48; N, 10.31; Cl, 20.15.

Example 69

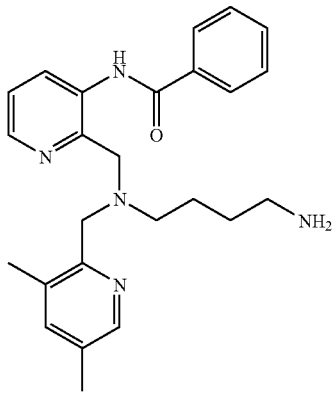

COMPOUND 69: N-(2-{[(4-amino-butyl)-(3,5-dimethyl-pyridin-2-ylmethyl)-amino]-methyl}-pyridin-3-yl)-benzamide To a solution of (2-formyl-pyridin-3-yl)-carbamic acid tert-butyl ester (0.581 g, 2.66 mmol) in dry MeOH (10 mL) was slowly added $NaBH_4$ (0.200 g, 5.32 mmol). The mixture was stirred for 40 min, and saturated aqueous $NaHCO_3$ (10 mL) was added. The MeOH was removed, and the aqueous residue was extracted with $CH_2Cl_2$ (5×25 mL). The organic extracts were combined, and dried over anhydrous $Na_2SO_4$. After filtration the solvent was removed by evaporation under vacuum, affording (2-hydroxymethyl-pyridin-3-yl)-carbamic acid tert-butyl ester as a white solid.

Using General Procedure F, the white solid was treated with TFA (1 mL) in $CH_2Cl_2$ (4 mL) to remove the Boc protecting group. (3-Amino-pyridin-2-yl)-methanol was obtained as a pale yellow oil (0.214 g, 67% two steps) after purification by flash chromatography on a silica gel column (100:5:1 $CH_2Cl_2$/MeOH/$NH_4OH$). $^1H$ NMR ($CDCl_3$) δ 3.76 (s, br. 2H), 4.08 (s, br. 1H), 4.67 (s, 2H), 6.97 (d, 1H, J=7.8 Hz), 7.04-7.09 (m, 2H), 7.99 (d, 1H, J=4.5 Hz).

To a solution of (3-amino-pyridin-2-yl)-methanol (0.310 g, 2.54 mmol) and $Et_3N$ (0.570 g, 5.33 mmol) in dry $CH_2Cl_2$ (20 mL) was added benzoyl chloride (0.700 g, 5.08 mmol) dropwise. After the mixture was stirred for 18 h $CH_2Cl_2$ was removed, and then MeOH (5 mL) and saturated aqueous $K_2CO_3$ (25 mL) were added. The mixture was stirred for 2 h, and then extracted with $CH_2Cl_2$ (5×50 mL). The combined extracts were dried over anhydrous $Na_2SO_4$. After filtration the solvent was removed by evaporation under vacuum, and the residue was purified by flash chromatography on a silica gel column (2:1 $CH_2Cl_2$/$Et_2O$), affording N-(2-hydroxymethyl-pyridin-3-yl)-benzamide as a white solid. The white solid was dissolved in $CH_2Cl_2$ (15 mL), and activated $MnO_2$ (0.660 g, 7.68 mmol) was added. The suspension was stirred for 64 h, and then filtered through a celite cake. The filtrate was concentrated by evaporation under vacuum, and a brown residue was purified by flash chromatography on a silica gel column (4:1 $CH_2Cl_2$/$Et_2O$), affording N-(2-formyl-pyridin-3-yl)-benzamide as a pale yellow solid (0.139 g, 24% two steps). $^1H$ NMR ($CDCl_3$) δ 7.54-7.62 (m, 4H), 8.07 (d, 2H, J=7.2 Hz), 8.54 (d, 1H, J=4.2 Hz), 9.32 (d, 1H, J=8.7 Hz), 10.19 (s, 1H).

COMPOUND 69 was obtained as a colorless oil. $^1H$ NMR ($CDCl_3$) δ 1.27-1.36 (m, 2H), 1.51-1.58 (m, 2H), 2.12 (s, 3H), 2.16 (s, 3H), 2.52 (t, 2H, J=6.9 Hz), 2.57-2.62 (m, 2H), 3.73 (s, 2H), 4.00 (s, 2H), 7.10 (s, 1H), 7.21-7.26 (m, 1H), 7.40 (t, 2H, J=7.5 Hz), 7.48-7.53 (m, 1H), 7.62 (s, 1H), 8.13 (d, 2H, J=7.8 Hz), 8.22 (d, 1H, J=4.5 Hz), 8.67 (d, 1H, J=8.4 Hz); $^{13}C$ NMR ($CDCl_3$) δ 18.16, 18.67, 24.08, 31.95, 42.21, 55.11, 56.83, 61.71, 123.22, 128.55, 128.63, 129.00, 131.00, 131.54, 131.93, 135.56, 136.11, 138.70, 143.84, 147.21, 147.76, 152.87, 167.26. ES-MS m/z 418 (M+H). Anal. Calcd. for $C_{25}H_{31}N_5O.0.1CH_2Cl_2$: C, 70.76; H, 7.38; N, 16.44. Found: C, 70.75; H, 7.67; N, 16.39.

Example 70

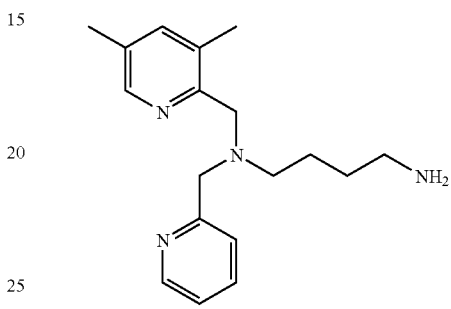

COMPOUND 70: $N^1$-(3,5-dimethyl-pyridin-2-ylmethyl)-$N^1$-pyridin-2-ylmethyl-butane-1,4-diamine (HBr salt)

$^1H$ NMR ($D_2O$) δ 1.57-1.58 (m, 4H), 2.43 (s, 3H), 2.45 (s, 3H), 2.72 (t, 2H, J=7.8 Hz), 2.94 (t, 2H, J=6.9 Hz), 4.23 (s, 2H), 4.33 (s, 2H), 7.93-7.99 (m, 1H), 8.06 (d, 1H, J=8.1 Hz), 8.17 (s, 1H), 8.40 (s, 1H), 8.50-8.57 (m, 1H), 8.74 (d, 1H, J=5.4 Hz); $^{13}C$ NMR ($D_2O$) δ 16.98, 17.53, 23.00, 25.01, 39.61, 53.61, 54.96, 56.29, 126.77, 127.62, 136.92, 137.54, 137.90, 141.81, 147.79, 148.27, 149.16, 153.04. ES-MS m/z 299 (M+H). Anal. Calcd. for $C_{18}H_{26}N_4.3.6HBr.1.4H_2O.0.5CH_2Cl_2$: C, 33.80; H, 5.12; N, 8.52; Br, 43.76. Found: C, 33.66; H, 5.14; N, 8.38; Br, 43.88.

Example 71

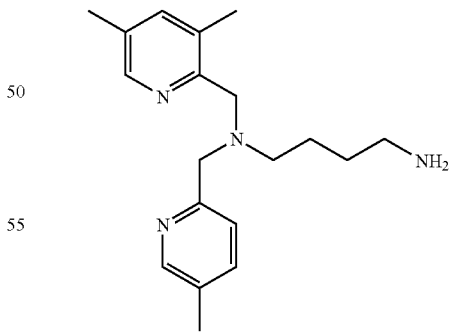

COMPOUND 71: $N^1$-(3,5-dimethyl-pyridin-2-ylmethyl)-$N^1$-(5-methyl-pyridin-2-ylmethyl)-butane-1,4-diamine (HBr salt)

$^1H$ NMR ($D_2O$) δ 1.63-1.69 (m, 2H), 1.79-1.84 (m, 2H), 2.16 (s, 3H), 2.25 (s, 3H), 2.26 (s, 3H), 2.94-2.99 (m, 2H), 3.15-3.20 (m, 2H), 4.28 (s, 2H), 4.30 (s, 2H), 7.32 (d, 1H, J=8.1 Hz), 7.58 (s, 1H), 7.62 (d, 1H, J=8.1 Hz), 8.15 (s, 1H), 8.26 (s, 1H); $^{13}$C NMR (D$_2$O) δ 18.32, 18.80, 19.03, 23.60, 25.96, 40.76, 55.97, 56.94, 60.29, 126.75, 134.93, 136.77, 136.88, 141.39, 144.36, 144.70, 148.14, 149.84, 150.01. ES-MS m/z 313 (M+H). Anal. Calcd. for C$_{19}$H$_{28}$N$_4$.1.9HBr.1.4H$_2$O: C, 46.44; H, 6.71; N, 11.40; Br, 30.89. Found: C, 46.52; H, 6.51; N, 11.09; Br, 30.99.

Example 72

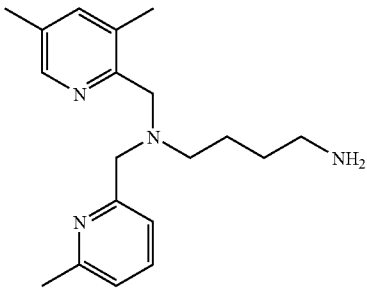

COMPOUND 72: N$^1$-(3,5-dimethyl-pyridin-2-ylmethyl)-N$^1$-(6-methyl-pyridin-2-ylmethyl)-butane-1,4-diamine (HBr salt)

$^1$H NMR (D$_2$O) δ 1.58-1.60 (m, 4H), 2.41 (s, 3H), 2.45 (s, 3H), 2.72-2.77 (m, 5H), 2.92-2.96 (m, 2H), 4.19 (s, 2H), 4.22 (s, 2H), 7.74 (d, 1H, J=7.8 Hz), 7.86 (d, 1H, J=7.8 Hz), 8.16 (s, 1H), 8.31-8.36 (m, 2H); $^{13}$C NMR (D$_2$O) δ 16.91, 17.51, 19.50, 22.87, 25.02, 39.64, 53.27, 54.93, 56.12, 124.91, 127.51, 136.77, 137.43, 137.69, 147.11, 148.61, 149.01, 152.12, 155.08. ES-MS m/z 313 (M+H). Anal. Calcd. for C$_{19}$H$_{28}$N$_4$.4.1HBr.1.7H$_2$O.0.7CH$_2$Cl$_2$: C, 32.22; H, 5.07; N, 7.63; Br, 44.62. Found: C, 32.58; H, 5.12; N, 7.49; Br, 44.48.

Example 73

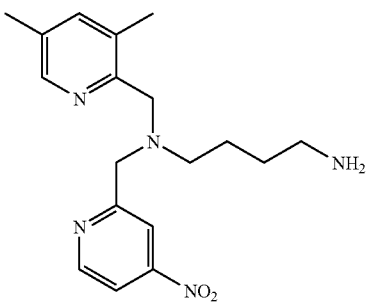

COMPOUND 73: N$^1$-(3,5-dimethyl-pyridin-2-ylmethyl)-N$^1$-(4-nitro-pyridin-2-ylmethyl)-butane-1,4-diamine (HBr salt)

$^1$H NMR (D$_2$O) δ 1.64-1.75 (m, 2H), 1.82-1.93 (m, 2H), 2.42 (s, 3H), 2.44 (s, 3H), 3.02 (t, 2H, J=7.5 Hz), 3.22-3.28 (m, 2H), 4.61 (s, 2H), 4.62 (s, 2H), 8.11 (s, 1H), 8.19 (dd, 1H, J=2.1 Hz, 5.7 Hz), 8.31 (d, 1H, J=2.1 Hz), 8.45 (s, 1H), 8.91 (d, 1H, J=5.7 Hz); $^{13}$C NMR (D$_2$O) δ 17.47, 17.67, 22.27, 24.65, 39.41, 53.23, 55.78, 58.10, 117.88, 118.11, 138.00, 138.65, 140.61, 143.41, 148.43, 151.61, 155.42, 155.64. ES-MS m/z 344 (M+H). Anal. Calcd. for C$_{18}$H$_{25}$N$_5$O$_2$.3.3HBr.1.2H$_2$O.0.2C$_4$H$_{10}$O: C, 34.91; H, 5.09; N, 10.83; O, 8.41; Br, 40.76. Found: C, 35.10; H, 5.07; N, 10.75; O, 8.37; Br, 40.37.

Example 74

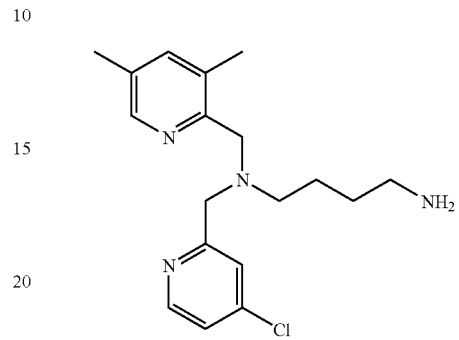

COMPOUND 74: N$^1$-(4-chloro-pyridin-2-ylmethyl)-N$^1$-(3,5-dimethyl-pyridin-2-ylmethyl)-butane-1,4-diamine (HBr salt)

$^1$H NMR (D$_2$O) δ 1.69-1.85 (m, 4H), 2.27 (s, 3H), 2.34 (s, 3H), 3.00 (t, 2H, J=7.5 Hz), 3.11 (t, 2H, J=7.2 Hz), 4.21 (s, 2H), 4.29 (s, 2H), 7.38 (dd, 1H, J=1.2, 5.1 Hz), 7.49 (d, 1H, J=1.2 Hz), 7.77 (s, 1H), 8.23 (s, 1H), 8.36 (d, 1H, J=5.1 Hz); $^{13}$C NMR (D$_2$O) δ 16.93, 17.49, 22.71, 24.78, 39.54, 54.37, 55.94, 59.46, 124.65, 125.47, 134.73, 136.18, 141.38, 144.99, 146.14, 147.56, 150.03, 155.52. ES-MS m/z 333 (M+H). Anal. Calcd. for C$_{18}$H$_{25}$N$_4$Cl.1.7HBr.1.9H$_2$O.0.2C$_4$H$_{10}$O: C, 43.47; H, 6.31; N, 10.79; Cl, 6.83; Br, 26.14. Found: C, 43.78; H, 5.92; N, 10.35; Cl, 7.06; Br, 25.88.

Example 75

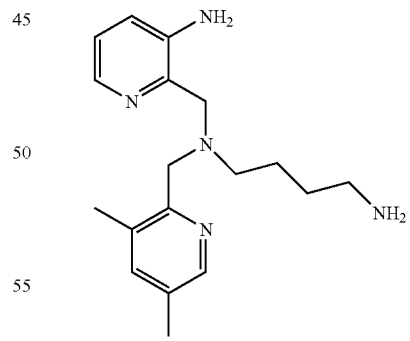

COMPOUND 75: (N$^1$-(3-amino-pyridin-2-ylmethyl)-N$^1$-(3-isopropyl-pyridin-2-ylmethyl)-butane-1,4-diamine (HBr salt)

$^1$H NMR (D$_2$O) δ 1.57-1.70 (m, 4H), 2.37 (s, 3H), 2.38 (s, 3H), 2.80-2.86 (m, 2H), 2.96 (t, 2H, J=7.2 Hz), 4.10 (s, 2H), 4.16 (s, 2H), 7.52 (dd, 1H, J=5.2, 8.7 Hz), 7.59 (dd, 1H, J=1.5, 8.7 Hz), 7.93 (dd, 1H, J=1.5, 5.2 Hz), 8.04 (s, 1H), 8.32 (s,

1H); $^{13}$C NMR (D$_2$O) δ 17.21, 17.52, 22.91, 25.10, 39.70, 53.52, 53.75, 56.10, 126.76, 129.88, 130.72, 135.08, 136.66, 137.49, 138.08, 145.71, 147.88, 148.81. ES-MS m/z 314 (M+H). Anal. Calcd. for C$_{18}$H$_{27}$N$_5$.5.3HBr.1.2H$_2$O.0.5C$_4$H$_{10}$O: C, 29.99; H, 5.00; N, 8.74; Br, 52.87. Found: C, 30.02; H, 5.16; N, 8.75; Br, 52.80.

Example 76

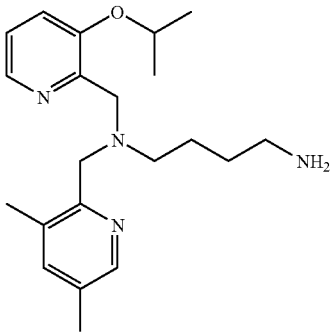

COMPOUND 76: N$^1$-(3,5-dimethyl-pyridin-2-ylmethyl)-N$^1$-(3-isopropoxy-pyridin-2-ylmethyl)-butane-1,4-diamine (HBr salt)

$^1$H NMR (D$_2$O) δ 1.29 (d, 6H, J=6.0 Hz), 1.56-1.58 (m, 4H), 2.40 (s, 6H), 2.74-2.79 (m, 2H), 2.91 (t, 2H, J=6.6 Hz), 4.28 (s, 4H), 4.85 (septet, 1H, J=6.0 Hz), 7.84 (dd, 1H, J=5.7, 8.7 Hz), 8.08 (d, 1H, J=8.7 Hz), 8.—(s, 1H), 8.25 (d, 1H, J=5.7 Hz), 8.37 (s, 1H); $^{13}$C NMR (D$_2$O) δ 17.30, 17.72, 21.40, 23.00, 24.99, 39.68, 51.76, 54.13, 55.23, 74.59, 127.63, 130.14, 132.50, 137.00, 137.58, 138.07, 142.91, 147.72, 149.10, 155.02. ES-MS m/z 357 (M+H). Anal. Calcd. for C$_{21}$H$_{32}$N$_4$O.3.8HBr.4.8H$_2$O.0.1C$_4$H$_{10}$O: C, 33.92; H, 6.17; N, 7.39; Br, 40.06. Found: C, 33.88; H, 6.22; N, 7.34; Br, 40.21.

Example 77

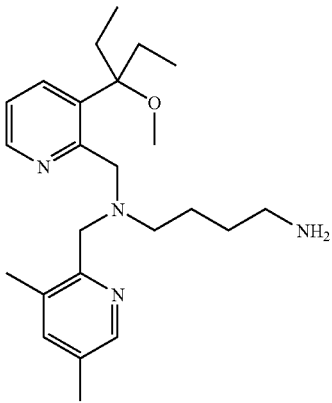

COMPOUND 77: N$^1$-(3,5-dimethyl-pyridin-2-ylmethyl)-N$^1$-[3-(1-ethyl-1-methoxy-propyl)-pyridin-2-ylmethyl]-butane-1,4-diamine To a stirred solution of ethyl 2-methyl nicotinate (1.04 g, 6.30 mmol) in dry THF (30 mL) was slowly added EtMgBr (3.0 M in Et$_2$O, 5.2 mL, 16 mmol). The mixture was warmed to reflux and stirred for 60 h under N$_2$. The suspension was cooled, poured into ice (50 mL) and stirred for 3 h. The layers were separated, and the aqueous layer was extracted with Et$_2$O (5×100 mL). The combined organic layers were dried over anhydrous Na$_2$SO$_4$. After filtration the solvent was removed by evaporation under vacuum, and the residue was purified by flash chromatography on a silica gel column (1:1 Et$_2$O/CH$_2$Cl$_2$), affording 3-(2-methyl-pyridin-3-yl)-pentan-3-ol as a yellow solid (0.447 g, 40%). $^1$H NMR (CDCl$_3$) δ 0.77 (t, 6H, J=7.5 Hz), 1.80-2.12 (m, 4H), 2.70 (s, 3H), 7.12 (dd, 1H, J=4.8, 7.8 Hz), 7.87 (dd, 1H, J=7.8, 1.5 Hz), 8.39 (dd, 1H, J=4.8, 1.5 Hz).

A solution of 3-(2-methyl-pyridin-3-yl)-pentan-3-ol (0.444 g, 2.48 mmol) and NaOH (0.125 g, 5.2 mmol) in DMF (—mL) was stirred for 16 h. MeI (0.55 g, 3.9 mmol) was added. The mixture was stirred for 6 h, and the solvent was removed by evaporation under vacuum. Brine (25 mL) was added, and the aqueous mixture was extracted with CH$_2$Cl$_2$ (4×25 mL). The combined organic layers were dried over anhydrous Na$_2$SO$_4$. After filtration the solvent was removed by evaporation under vacuum, and the residue was purified by flash chromatography on a silica gel column (1:1 Et$_2$O/CH$_2$Cl$_2$), affording 3-(1-ethyl-1-methoxy-propyl)-2-methyl-pyridine (0.176 g, 37%). $^1$H NMR (CDCl$_3$) δ 0.73 (t, 6H, J=7.5 Hz), 1.87-2.04 (m, 4H), 2.77 (s, 3H), 3.01 (s, 3H), 7.09 (dd, 1H, J=8.1, 4.8 Hz), 7.56 (dd, 1H, J=8.1, 1.5 Hz), 8.40 (dd, 1H, J=4.8, 1.5 Hz).

To a solution of 3-(1-ethyl-1-methoxy-propyl)-2-methyl-pyridine (0.176 g, 0.911 mmol) in CH$_2$Cl$_2$ (10 mL) was added 3-chloroperoxybenzoic acid (0.473 g, 2.75 mmol). The mixture was stirred for 16 h and concentrated by evaporation under vacuum. The residue was purified by flash chromatography on a silica gel column (6:1 EtOAc/MeOH), affording 3-(1-ethyl-1-methoxy-propyl)-2-methyl-pyridine 1-oxide as a white solid (0.188 g, 98%). $^1$H NMR (CDCl$_3$) δ 0.74 (t, 6H, J=7.5 Hz), 1.94 (q, 4H, J=7.5 Hz), 2.80 (s, 3H), 3.01 (s, 3H), 7.07-7.10 (m, 1H), 7.21 (d, 1H, J=8.1 Hz), 8.27 (d, 1H, J=6.3 Hz).

To a solution of 3-(1-ethyl-1-methoxy-propyl)-2-methyl-pyridine (0.185 g, 0.884 mmol) in CH$_2$Cl$_2$ (3 mL) was added TFAA (1 mL). The mixture was stirred for 24 h. K$_2$CO$_3$ (0.60 g, 4.3 mmol) in water (10 mL) was added. The aqueous mixture was extracted with CH$_2$Cl$_2$ (4×25 mL), and the combined organic layers were dried over anhydrous Na$_2$SO$_4$. After filtration the solvent was removed by evaporation under vacuum, and the residue was purified by flash chromatography on a silica gel column (3:1 Et$_2$O/CH$_2$Cl$_2$), affording [3-(1-ethyl-1-methoxy-propyl)-pyridin-2-yl]-methanol as a yellow oil (0.111 g, 60%). $^1$H NMR (CDCl$_3$) δ 0.70 (t, 6H, J=7.5 Hz), 1.76-1.88 (m, 2H), 1.89-2.01 (m, 2H), 3.06 (s, 3H), 4.93 (s, 2H), 7.21 (dd, 1H, J=7.8, 4.8 Hz), 7.56 (dd, 1H, J=7.8, 1.5 Hz), 8.47 (dd, 1H, J=4.8, 1.5 Hz).

Activated MnO$_2$ (0.458 g, 5.26 mmol) was added to a stirred solution of [3-(1-ethyl-1-methoxy-propyl)-pyridin-2-yl]-methanol (0.110 g, 0.526 mmol) in CH$_2$Cl$_2$ (3 mL). The mixture was stirred for 16 h, and then filtered through a celite cake. The filtrate was concentrated by evaporation under vacuum, and the residue was purified by flash chromatography on a silica gel column (CH$_2$Cl$_2$), affording 3-(1-ethyl-1-methoxy-propyl)-pyridine-2-carbaldehyde as yellow oil (0.086 g, 46%). $^1$H NMR (CDCl$_3$) δ 0.71 (t, 6H, J=7.5 Hz), 1.83-2.09 (m, 4H) 3.16 (s, 3H), 7.37 (dd, 1H, J=7.7, 4.8 Hz), 7.62 (dd, 1H, J=7.8, 1.5 Hz), 8.65 (dd, 1H, J=4.8, 1.5 Hz), 10.57 (s, 1H).

COMPOUND 77 was obtained as a colorless oil $^1$H NMR (CDCl$_3$) δ 0.67 (t, 6H, J=7.5 Hz), 1.45-1.51 (m, 2H), 1.55-1.64 (m, 2H), 1.78-2.00 (m, 4H), 2.19 (s, 3H), 2.25 (s, 3H), 2.51-2.56 (m, 2H), 2.76-2.80 (m, 2H), 2.96 (s, 3H), 3.77 (s, 2H), 4.11 (s, 2H), 7.15 (dd, 1H, J=4.5, 8.1 Hz), 7.21 (s, 1H), 7.60 (dd, 1H, J=1.5, 8.1 Hz), 8.21 (s, 1H), 8.56 (dd, 1H, J=1.5, 4.5 Hz); $^{13}$C NMR (CDCl$_3$) δ 7.92, 18.05, 18.49, 24.86, 26.66, 30.37, 41.12, 49.54, 58.08, 58.51, 77.42, 82.27, 121.61, 131.90, 132.42, 137.12, 138.05, 139.12, 146.61, 147.19, 154.02, 157.62. ES-MS m/z 399 (M+H). Anal. Calcd. for C$_{24}$H$_{38}$N$_4$O.0.55CH$_2$Cl$_2$: C, 66.22; H, 8.85; N, 12.58. Found: C, 66.35; H, 8.79; N, 12.30.

Example 78

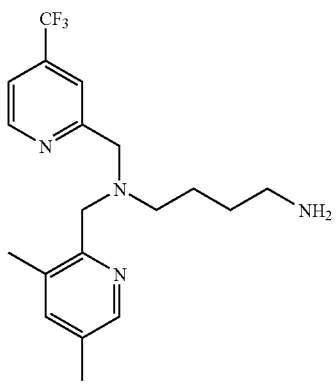

COMPOUND 78: $N^1$-(3,5-dimethyl-pyridin-2-ylmethyl)-$N^1$-(4-trifluoromethyl-pyridin-2-ylmethyl)-butane-1,4-diamine (HBr salt)

$^1$H NMR (D$_2$O) δ 1.61-1.69 (m, 2H), 1.72-1.81 (m, 2H), 2.43 (s, 3H), 2.45 (s, 3H), 2.98 (t, 2H, J=7.5 Hz), 3.04-3.10 (m, 2H), 4.51 (s, 2H), 4.57 (s, 2H), 8.06 (d, 1H, J=5.7 Hz), 8.16 (s, 1H), 8.18 (s, 1H), 8.45 (s, 1H), 8.92 (d, 1H, J=5.7 Hz); $^{13}$C NMR (D$_2$O) δ 17.50, 17.70, 22.40, 24.75, 39.49, 53.17, 55.63, 56.96, 121.99 (q, J=274 Hz), 122.62, 122.92, 138.19, 138.72, 139.40, 143.83 (q, J=35 Hz), 144.32, 147.22, 149.38, 153.97. ES-MS m/z 367 (M+H). Anal. Calcd. for C$_{19}$H$_{25}$F$_3$N$_4$.3.7HBr.3.4H$_2$O.0.2C$_4$H$_{10}$O: C, 32.06; H, 5.09; N, 7.55; Br, 39.85. Found: C, 32.10; H, 4.96; N, 7.51; Br, 39.80.

TABLE 4

Preparation of Examples 79 to 83

| Example | Aldehyde |
|---------|----------|
| 79 | 3,5-dichloro-pyridine-2-carbaldehyde Bonjouklian, R. et al. PCT Int. Appl. (2002), WO 2002081482 |
| 80 | 5-chloro-3-methyl-pyridine-2-carbaldehyde |
| 81 | 3-chloro-5-methyl-pyridine-2-carbaldehyde |
| 82 | 5-fluoro-3-methyl-pyridine-2-carbaldehyde |
| 83 | 3,5-difluoro-pyridine-2-carbaldehyde |

Example 79

COMPOUND 79: $N^1$-(3,5-dichloro-pyridin-2-ylmethyl)-$N^1$-(3-isopropyl-pyridin-2-ylmethyl)-butane-1,4-diamine (HBr salt)

$^1$H NMR (D$_2$O) δ 1.21 (d, 6H, J=6.6 Hz), 1.65-1.76 (m, 2H), 1.85-1.95 (m, 2H), 3.00 (t, 2H, J=7.5 Hz), 3.18 (septet, 1H, J=6.6 Hz), 3.34-3.40 (m, 2H), 4.63 (s, 2H), 4.73 (s, 2H), 7.73 (dd, 1H, J=5.7, 8.4 Hz), 7.98 (d, 1H, J=2.1 Hz), 8.24 (dd, 1H, J=1.2, 8.4 Hz), 8.41 (d, 1H, J=2.1 Hz), 8.51 (dd, 1H, J=1.2, 5.7 Hz); $^{13}$C NMR (D$_2$O) δ 22.09, 22.37, 24.54, 28.55, 39.34, 53.87, 55.88, 56.31, 126.95, 131.91, 132.86, 138.66, 142.01, 142.26, 145.38, 146.29, 146.81, 147.33. ES-MS m/z 382 (M+H). Anal. Calcd. for C$_{19}$H$_{26}$Cl$_2$N$_4$.3.6HBr.1.1H$_2$O.0.5C$_4$H$_{10}$O: C, 34.58; H, 5.08; N, 7.68; Cl, 9.72; Br, 39.43. Found: C, 34.40; H, 5.16; N, 7.76; Cl, 9.60; Br, 39.54.

Example 80

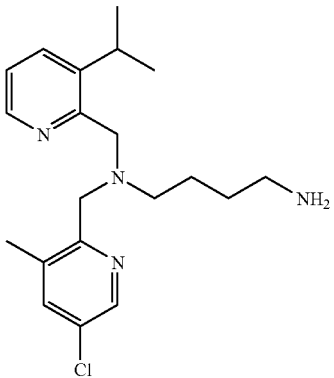

COMPOUND 80: $N^1$-(5-chloro-3-methyl-pyridin-2-ylmethyl)-$N^1$-(3-isopropyl-pyridin-2-ylmethyl)-butane-1,4-diamine (HBr salt)

5-chloro-3-methylpyridine-2-carbaldehyde as yellow fine needles was obtained from 2-Bromo-5-chloro-3-methylpyridine by nucleophilic substitution with a formyl group, as exemplified in Example 41. $^1$H NMR (δ, CDCl$_3$): 10.14 (s, 1H), 8.59 (s, 1H), 7.63 (s, 1H), 2.66 (s, 3H).

COMPOUND 80 was isolated as a white solid. $^1$H NMR (D$_2$O) δ 1.27 (d, 6H, J=6.9 Hz), 1.50-1.70 (m, 4H), 2.47 (s, 3H), 2.80-2.88 (m, 2H), 2.90-2.95 (m, 2H), 3.31 (septet, 1H, J=6.9 Hz), 4.40 (s, 2H), 4.52 (s, 2H), 7.93 (t, 1H, J=6.9 Hz), 8.33 (s, 1H), 8.51 (d, 1H, J=6.9 Hz), 8.61 (d, 1H, J=6.9 Hz), 8.70 (s, 1H); $^{13}$C NMR (D$_2$O) δ 17.45, 22.28, 22.77, 24.94, 28.45, 39.56, 53.85, 54.60, 55.15, 126.89, 133.38, 138.30, 139.0.7, 139.36, 144.77, 146.75, 147.52, 148.53, 149.82. ES-MS m/z 361 (M+H). Anal. Calcd. for C$_{20}$H$_{29}$ClN$_4$.3.3HBr.1.3H$_2$O.0.2C$_4$H$_{10}$O: C, 37.50; H, 5.58; N, 8.41; Cl, 5.32; Br, 39.58. Found: C, 37.43; H, 5.62; N, 8.23; Cl, 5.40; Br, 39.62.

Example 81

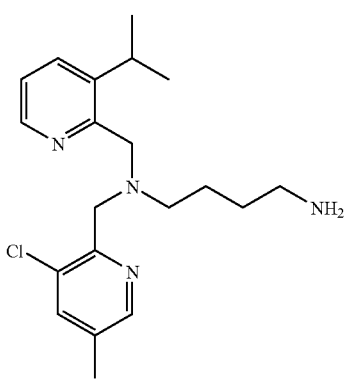

COMPOUND 81: $N^1$-(3-chloro-5-methyl-pyridin-2-ylmethyl)-$N^1$-(3-isopropyl-pyridin-2-ylmethyl)-butane-1,4-diamine (HBr salt)

At −78° C., under N$_2$, BuLi (2.5 M in hexanes, 0.80 mL, 2.0 mmol) was added to a solution of TMEDA (0.30 mL, 2.0 mmol) in dry Et$_2$O (20 mL). After addition the mixture was warmed to room temperature. After stirred at room temperature for 30 min the mixture was cooled to −78° C., and added to a solution of 3-chloro-5-methyl-pyridine (0.255 g, 2.00 mmol) (Bushby et al. *J. Chem. Soc. Perkin Trans. I* 1978, 1578) in dry Et$_2$O (10 mL) pre-cooled at −78° C. The mixture was stirred at −78° C. for 30 min and then warmed to room temperature for 1 h. Water (15 mL) was added, and the mixture was extracted with Et$_2$O (3×40 mL). The organic extracts were combined and dried over anhydrous Na$_2$SO$_4$. After filtration the solvent was removed by evaporation under vacuum, and the residue was purified by flash chromatography on a silica gel column (CH$_2$Cl$_2$) to afford 3-chloro-5-methyl-pyridine-2-carbaldehyde (0.096 g, 31%). $^1$H NMR (CDCl$_3$) δ 2.44 (s, 3H), 7.65 (s, 1H), 8.54 (s, 1H), 10.28 (s, 1H).

COMPOUND 81 was isolated as a colorless oil. $^1$H NMR (D$_2$O) δ 1.27 (d, 6H, J=6.9 Hz), 1.55-1.69 (m, 4H), 2.48 (s, 3H), 2.82-2.88 (m, 2H), 2.92-2.97 (m, 2H), 3.29 (septet, 1H, J=6.9 Hz), 4.46 (s, 2H), 4.50 (s, 2H), 7.91 (dd, 1H, J=5.7, 8.1 Hz), 8.37 (s, 1H), 8.49 (dd, 1H, J=1.2, 8.1 Hz), 8.52-8.60 (m, 2H); $^{13}$C NMR (D$_2$O) δ 17.80, 22.29, 22.73, 24.97, 28.38, 39.62, 53.67, 54.42, 54.96, 126.85, 133.75, 138.97, 139.28, 140.84, 144.96, 147.43, 147.50, 147.71, 148.97. ES-MS m/z 361 (M+H). Anal. Calcd. for C$_{20}$H$_{29}$ClN$_4$.3.7HBr.2.0H$_2$O.0.2C$_4$H$_{10}$O: C, 34.01; H, 5.24; N, 7.85; Cl, 6.96; Br, 41.45. Found: C, 33.92; H, 5.51; N, 7.50; Cl, 7.01; Br, 41.75.

Example 82

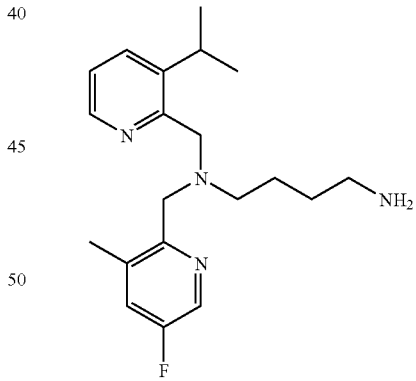

COMPOUND 82: $N^1$-(5-fluoro-3-methyl-pyridin-2-ylmethyl)-$N^1$-(3-isopropyl-pyridin-2-ylmethyl)-butane-1,4-diamine (HBr salt)

A mixture of 3-fluoro-5,6-dimethyl-pyridine (0.230 g, 1.84 mmol) (Ife, R. J. Eur. Pat. Appl. (1987), EP 246774), 3-chloroperoxybenzoic acid (77%, 1.24 g, 5.5 mmol) in CH$_2$Cl$_2$ (25 mL) was stirred for 16 h. The solution was concentrated, and the residue was purified by flash chromatography on a silica gel column (8:1 EtOAc/MeOH), affording 3-fluoro-5,6-dimethyl-pyridine-1-oxide as a white solid (0.225 g 87%).

To a solution of the oxide (0.225 g, 1.59 mmol) in dry $CH_2Cl_2$ (10 mL) was added TFAA (1.00 g, 4.78 mmol), and the mixture was stirred for 6 h. Saturated aqueous $K_2CO_3$ (5 mL) and brine (5 mL) were added, and the mixture was stirred for 10 min. The reaction mixture was extracted with $CH_2Cl_2$ (3×30 mL). The extracts were combined and dried over anhydrous $Na_2SO_4$. After filtration the solvent was removed by evaporation under vacuum, and the residue was purified by flash chromatography on a silica gel column (4:1 $CH_2Cl_2$/$Et_2O$), affording a colorless liquid. $MnO_2$ (0.500 g, 5.81 mmol) was activated at 60° C. under vacuum for 15 min, and a solution of the liquid in $CH_2Cl_2$ (15 mL) was added. After the suspension was stirred for 2 h. it was filtered through a celite cake. The filtrate was concentrated under vacuum to afford the 5-fluoro-3-methyl-pyridine-2-carbaldehyde as colorless liquid (0.0620 g, 28% two steps). $^1H$ NMR ($CDCl_3$) δ 2.67 (s, 3H), 7.11 (dd, 1H, J=2.4, 9.0 Hz), 8.46 (d, 1H, J=2.4 Hz), 10.11 (s, 1H).

COMPOUND 82 was isolated as a white solid. $^1H$ NMR ($CD_3OD$) δ 1.30 (d, 6H, J=6.6 Hz), 1.71-1.80 (m, 2H), 1.90-1.98 (m, 2H), 2.44 (s, 3H), 2.97 (t, 2H, J=7.5 Hz), 3.19 (septet, 1H, J=6.6 Hz), 3.31-3.34 (m, 2H), 4.67 (s, 2H), 4.80 (s, 2H), 7.56-7.62 (m, 1H), 7.73-7.78 (m, 1H), 8.07-8.12 (m, 1H), 8.46 (s, 1H), 8.55-8.58 (m, 1H); $^{13}C$ NMR ($D_2O$) δ 17.61, 22.27, 22.65, 24.88, 28.42, 39.52, 53.92, 54.70, 55.14, 126.71, 129.76 (d, J=33 Hz), 133.69 (d, J=18 Hz), 139.11 (d, J=6.9 Hz), 140.01, 143.91, 147.10, 147.73, 148.38, 159.65 (d, J=153 Hz). ES-MS m/z 345 (M+H). Anal. Calcd. for $C_{20}H_{29}FN_4\cdot3.2HBr\cdot1.0H_2O\cdot0.4C_4H_{10}O$: C, 39.85; H, 5.91; N, 8.61; Br, 39.27. Found: C, 39.56; H, 6.05; N, 8.57; Br, 39.09.

Example 83

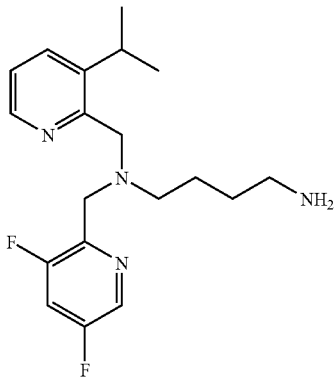

COMPOUND 83: $N^1$-(3,5-difluoro-pyridin-2-ylmethyl)-$N^1$-(3-isopropyl-pyridin-2-ylmethyl)-butane-1,4-diamine (HBr salt)

To a solution of 3,5-difluoro-pyridine-2-carbonitrile (0.440 g, 3.14 mmol) (Niewoehner, U. et al. PCT Int. Appl. (2001), WO 2001068647) in dry $CH_2Cl_2$ (20 mL) cooled at −78° C., was added DIBAL-H (1.0 M in $CH_2Cl_2$, 3.2 mL, 3.2 mmol). After the mixture was stirred at −78° C. for 1 h, aqueous HCl (3 N, 10 mL) was added, and the mixture was warmed to room temperature. Saturated aqueous $NaHCO_3$ (20 mL) was added, and the mixture was extracted with $CH_2Cl_2$ (3×20 mL). The extracts were combined and dried over anhydrous $Na_2SO_4$. After filtration the solvent was removed by evaporation under vacuum, and the residue was purified by flash chromatography on a silica gel column ($CH_2Cl_2$), affording afford 3,5-difluoro-pyridine-2-carbaldehyde as a colorless crystalline solid (0.0880 g, 20%). $^1H$ NMR ($CDCl_3$) δ 7.32-7.39 (m, 1H), 8.53 (d, 1H, J=2.4 Hz), 10.16 (s, 1H).

COMPOUND 83 was isolated as a white solid. $^1H$ NMR ($D_2O$) δ 1.23 (d, 6H, J=6.6 Hz), 1.66-1.76 (m, 2H), 1.80-1.98 (m, 2H), 3.02 (t, 2H, J=7.5 Hz), 3.18 (septet, 1H, J=6.6 Hz), 3.30-3.35 (m, 2H), 4.55 (s, 2H), 4.72 (s, 2H), 7.56-7.64 (m, 1H), 7.79-7.84 (m, 1H), 8.30-8.40 (m, 2H), 8.56-8.59 (m, 1H); $^{13}C$ NMR ($D_2O$) δ 22.12, 22.44, 24.56, 28.64, 39.40, 52.54, 53.00, 55.61, 114.18 (t, J=53 Hz), 127.30, 134.59 (dd, J=4.2, 25 Hz), 136.04 (d, J=15 Hz), 142.04, 142.86, 144.90, 147.36, 158.42 (dd, J=6.5, 142 Hz), 160.95 (dd, J=6.5, 142 Hz). ES-MS m/z 349 (M+H). Anal. Calcd. for $C_{19}H_{26}F_2N_4\cdot3.0HBr\cdot1.4H_2O\cdot0.4C_4H_{10}O$: C, 38.30; H, 5.59; N, 8.67; Br, 37.10. Found: C, 38.34; H, 5.39; N, 8.51; Br, 36.98.

TABLE 5

Preparation of Examples 84 to 88

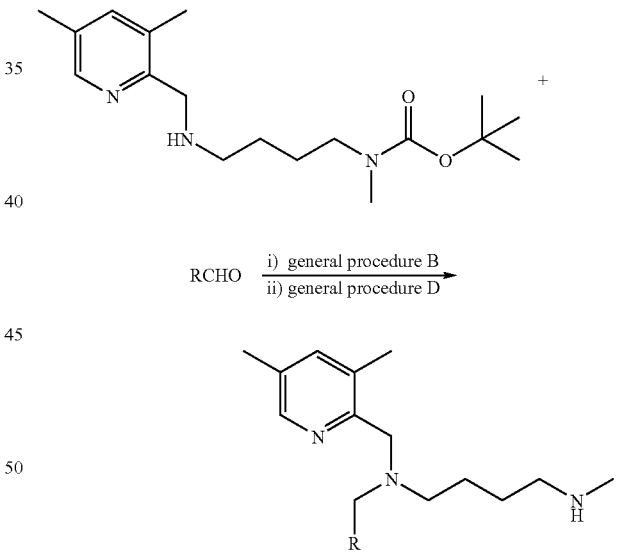

| Example | Aldehyde |
|---|---|
| 84 | isoquinoline-1-carbaldehyde |
| 85 | 3-Isopropylpyridine-2-carbaldehyde |
| 86 | 3-[1-(4-Chloro-phenyl)-1-methyl-ethyl]-pyridine-2-carbaldehyde |
| 87 | 3-[1-(4-Fluoro-phenyl)-1-methyl-ethyl]-pyridine-2-carbaldehyde |
| 88 | 3-(1-methyl-1-phenyl-ethyl)-pyridine-2-carbaldehyde |

Example 84

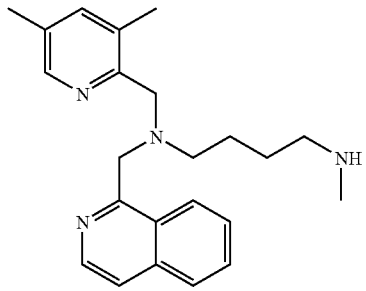

COMPOUND 84: N-(3,5-Dimethyl-pyridin-2-ylmethyl)-N-isoquinolin-1-ylmethyl-N'-methyl-butane-1,4-diamine HBr salt $^1$H NMR (D$_2$O) δ 1.60-1.70 (m, 4H), 2.27 (s, 3H), 2.36 (s, 3H), 2.64 (s, 3H), 2.90-3.00 (m, 4H), 4.27 (s, 2H), 4.83 (s, 2H), 7.96-8.10 (m, 3H), 8.20-8.23 (m, 2H), 8.25 (d, 1H, J=6.5 Hz), 8.37 (d, 1H, J=6.5 Hz), 8.53 (d, 1H, J=8.6 Hz); $^{13}$C NMR (D$_2$O) δ 17.11, 17.29, 23.01, 23.70, 33.08, 49.09, 54.11, 54.72, 56.45, 125.76, 127.06, 128.77, 130.19, 131.82, 136.79, 137.31, 137.98, 138.85, 147.42, 148.76, 156.34; ES-MS m/z 363 (M+H). Anal Calcd. For C$_{23}$H$_{30}$N$_4$.3.9(HBr).0.3 (H$_2$O).0.4 (C$_4$H$_{10}$O): C, 41.43; H, 5.44; N, 7.87; Br, 43.70. Found: C, 41.35; H, 5.53; N, 7.87; Br, 43.91.

Example 85

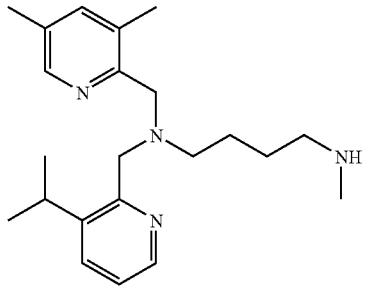

COMPOUND 85: N-(3,5-Dimethyl-pyridin-2-ylmethyl)-N-(3-isopropyl-pyridin-2-ylmethyl)-N'-methyl-butane-1,4-diamine HBr salt $^1$H NMR (D$_2$O) δ 1.24 (d, 1H, J=6.8 Hz), 1.50-1.55 (m, 2H), 2.42 (s, 6H), 2.60 (s, 3H), 2.63-2.68 (m, 2H), 2.89-2.94 (m, 2H), 3.26 (sep., 1H, J=6.7 Hz), 4.23 (s, 2H), 4.36 (s, 2H), 7.89 (dd, 1H, J=7.7, 6.2 Hz), 8.17 (s, 1H), 8.40 (s, 1H), 8.49 (d, 1H, J=8.1 Hz), 8.56 (d, 1H, J=5.7 Hz); $^{13}$C NMR (D$_2$O) δ 17.10, 17.48, 22.03, 22.92, 23.65, 28.25, 29.98, 33.03, 48.99, 53.65, 53.96, 54.91, 126.54, 136.96, 137.56, 138.02, 138.63, 144.81, 147.28, 147.82, 149.24, 149.82; ES-MS m/z 354 (M+H). Anal Calcd. For C$_{22}$H$_{34}$N$_4$.3.98(HBr).0.36(H$_2$O): C, 40.02; H, 5.96; N, 7.97; Br, 45.24. Found: C, 40.36; H, 6.00; N, 8.06; Br, 45.64.

Example 86

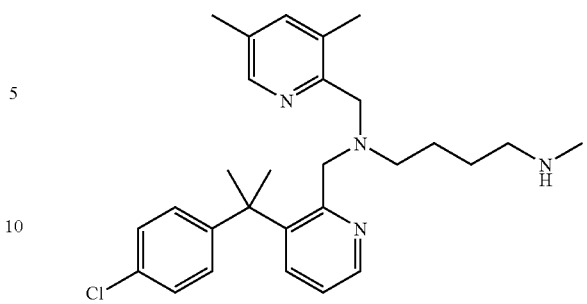

COMPOUND 86: N-{3-[1-(4-Chloro-phenyl)-1-methyl-ethyl]-pyridin-2-ylmethyl}-N-(3,5-dimethyl-pyridin-2-ylmethyl)-N'-methyl-butane-1,4-diamine HBr salt $^1$H NMR (D$_2$O) δ 1.14-1.24 (m, 2H), 1.32-1.42 (s, 2H), 1.73 (s, 6H), 2.23-2.28 (m, 2H), 2.31 (s, 3H), 2.43 (s, 3H), 2.63 (s, 3H), 2.86 (t, 2H, J=7.7 Hz), 3.69 (s, 2H), 3.73 (s, 2H), 7.24 (d, 2H, J=8.5 Hz), 7.39 (d, 2H, J=8.4 Hz), 8.04 (dd, 1H, J=7.9, 6.1 Hz), 8.17 (s, 1H), 8.38 (s, 1H), 8.68 (d, 1H, J=5.5 Hz), 8.86 (d, 1H, J=8.3 Hz). $^{13}$C NMR (D$_2$O) δ 17.19, 17.50, 22.03, 23.52, 29.42, 33.04, 42.88, 48.91, 52.52, 53.82, 54.43, 126.51, 128.57, 129.43, 132.65, 136.88, 137.53, 138.29, 139.37, 145.27, 146.21, 147.26, 147.73, 149.24, 151.83; ES-MS m/z 465 (M+H). Anal Calcd. For C$_{27}$H$_{37}$N$_4$Cl.3.3 (HBr).0.8(H$_2$O).0.7 (C$_4$H$_{10}$O): C, 45.52; H, 6.27; N, 7.12; Br, 33.53; Cl, 4.51. Found: C, 45.65; H, 6.02; N, 7.30; Br, 33.27; Cl, 4.17.

Example 87

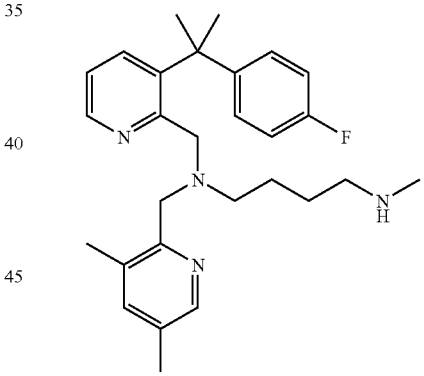

COMPOUND 87: N-(3,5-Dimethyl-pyridin-2-ylmethyl)-N-{3-[1-(4-fluoro-phenyl)-1-methyl-ethyl]-pyridin-2-ylmethyl}-N$^1$-methyl-butane-1,4-diamine HBr salt $^1$H NMR (D$_2$O) δ 1.12-1.23 (m, 2H), 1.31-1.42 (m, 2H), 1.74 (s, 6H), 2.26 (t, 2H, J=7.5 Hz), 2.30 (s, 3H), 2.44 (s, 3H), 2.62 (s, 3H), 2.84 (t, 2H, J=7.5 Hz), 3.70 (s, 2H), 3.74 (s, 2H), 7.12 (t, 2H, J=8.0 Hz), 7.24-7.29 (m, 2H), 8.03 (t, 1H, J=7.0 Hz), 8.15 (s, 1H), 8.38 (s, 1H), 8.67 (d, 1H, J=5.0 Hz), 8.86 (d, 1H, J=8.0 Hz); $^{13}$C NMR (D$_2$O) δ 17.15, 17.50, 22.15, 23.51, 29.65(2), 33.04, 42.76, 48.88, 52.71, 53.95, 54.60, 115.98, 116.27, 126.47, 128.68, 128.79, 136.78, 137.51, 138.34, 139.36, 143.49, 145.14, 147.30, 147.97, 149.18, 151.88, 160.17, 163.40; ES-MS m/z 449 (M+H). Anal. Calcd. For C$_{28}$H$_{37}$N$_4$F.3.2HBr.2.8CH$_4$O: C, 46.40; H, 6.50; N, 7.03; Br, 32.07. Found: C, 46.46; H, 6.50; N, 6.96; Br, 32.00.

Example 88

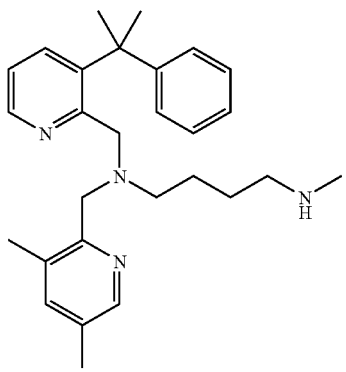

COMPOUND 88: N-(3,5-dimethyl-pyridin-2-ylmethyl)-N'-methyl-N-[3-(1-methyl-1-phenyl-ethyl)-pyridin-2-ylmethyl]-butane-1,4-diamine (HBr salt)

$^1$H NMR (D$_2$O) δ 1.15-1.21 (m, 2H), 1.35-1.41 (m, 2H), 1.75 (s, 6H), 2.20-2.26 (m, 2H), 2.28 (s, 3H), 2.44 (s, 3H), 2.64 (s, 3H), 2.83-2.89 (m, 2H), 3.59 (s, 2H), 3.76 (s, 2H), 7.28-7.31 (m, 2H), 7.33-7.43 (m, 3H), 8.05 (dd, 1H, J=6.0, 8.1 Hz), 8.14 (s, 1H), 8.39 (s, 1H), 8.70 (d, 1H, J=6.0 Hz), 8.88 (d, 1H, J=8.1 Hz); $^{13}$C NMR (D$_2$O) δ 17.42, 17.63, 22.35, 23.58, 29.69, 33.17, 43.21, 48.97, 52.76, 54.17, 54.60, 126.50, 126.94, 127.64, 129.66, 136.83, 137.44, 138.22, 139.27, 145.27, 147.42, 147.55, 148.23, 149.29, 152.05. ES-MS m/z 431 (M+H). Anal. Calcd. for C$_{28}$H$_{38}$N$_4$·3.3HBr·2.0H$_2$O·0.6C$_4$H$_{10}$O: C, 46.92; H, 6.64; N, 7.20; Br, 33.89. Found: C, 46.99; H, 6.49; N, 7.17; Br, 33.77.

TABLE 6

Preparation of Examples 89 to 90

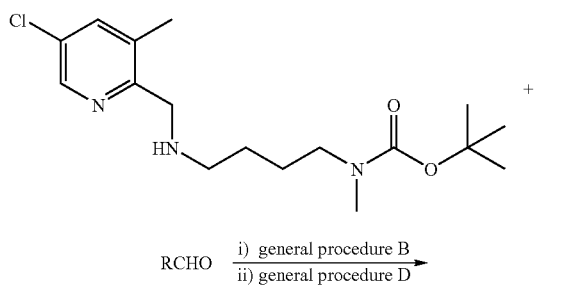

| Example | Aldehyde |
|---|---|
| 89 | 3-Isopropylpyridine-2-carbaldehyde |
| 90 | 3-[1-(4-Fluoro-phenyl)-1-methyl-ethyl]-pyridine-2-carbaldehyde |

Example 89

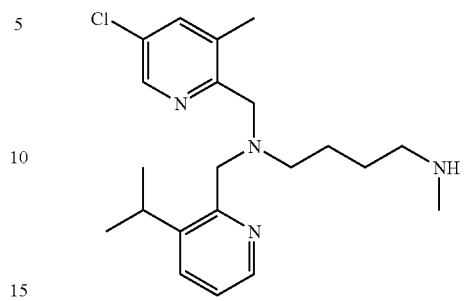

COMPOUND 89: N-(5-Chloro-3-methyl-pyridin-2-ylmethyl)-N-(3-isopropyl-pyridin-2-ylmethyl)-N'-methyl-butane-1,4-diamine HBr salt $^1$H NMR (D$_2$O) δ 1.26 (d, 1H, J=6.8 Hz), 1.56-1.65 (m, 4H), 2.43 (s, 3H), 2.64 (s, 3H), 2.87-2.99 (m, 4H), 3.26 (sep., 1H, J=6.7 Hz), 4.39 (s, 2H), 4.51 (s, 2H), 7.87 (dd, 1H, J=8.0, 5.8 Hz), 8.24-8.25 (m, 2H), 8.44 (d, 1H, J=8.2 Hz)), 8.57 (d, 1H, J=4.9 Hz), 8.64 (d, 1H, J=1.6 Hz); $^{13}$C NMR (D$_2$O) δ 17.21, 22.12, 22.56, 23.49, 28.34, 33.04, 48.89, 53.87, 54.69, 55.10, 126.59, 133.24, 137.86, 139.72, 139.88, 143.79, 145.78, 146.99, 148.46, 149.58; ES-MS m/z 375 (M+H). Anal Calcd. For C$_{21}$H$_{31}$N$_4$Cl·4.1(HBr)·2.3(H$_2$O)·0.4(C$_4$H$_{10}$O): C, 34.90; H, 5.66; N, 7.20; Br, 42.12; Cl, 4.56. Found: C, 34.88; H, 5.59; N, 7.21; Br, 42.04; Cl, 4.49

Example 90

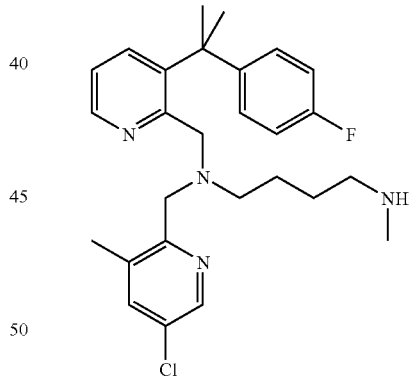

COMPOUND 90: N-(5-Chloro-3-methyl-pyridin-2-ylmethyl)-N-{3-[1-(4-fluoro-phenyl)-1-methyl-ethyl]-pyridin-2-ylmethyl}-N'-methyl-butane-1,4-diamine HBr salt $^1$H NMR (D$_2$O) δ 1.40-1.54 (m, 4H), 1.70 (s, 6H), 2.26 (s, 3H), 2.66 (s, 3H), 2.68-2.72 (m, 2H), 2.89-2.93 (m, 2H), 3.81 (s, 2H), 3.98 (s, 2H), 7.07 (t, 2H, J=8.8 Hz), 7.21-7.26 (m, 2H), 7.80 (dd, 1H, J=7.9, 5.6 Hz), 8.05 (s, 1H), 8.50 (s, 1H), 8.55 (d, 1H, J=8.0 Hz), 8.60 (d, 1H, J=5.2 Hz); $^{13}$C NMR (D$_2$O) δ 17.24, 21.94, 23.24, 29.75, 33.18, 42.30, 48.78, 54.23, 54.69, 55.89, 115.91, 116.19, 125.63, 128.64, 128.75, 132.86, 136.52, 140.70, 142.56, 143.27, 144.17, 15.91, 148.18, 149.71; ES-MS m/z 469 (M+H). Anal Calcd. For C$_{27}$H$_{34}$N$_{4}$ClF.3.3(HBr).1.4(H$_{2}$O): C, 42.60; H, 5.31; N, 7.36; Br, 34.64; Cl, 4.66; F, 2.50. Found: C, 42.94; H, 5.57; N, 7.06; Br, 34.35; Cl, 4.56; F, 2.33.

TABLE 7

Preparation of Examples 91 to 99

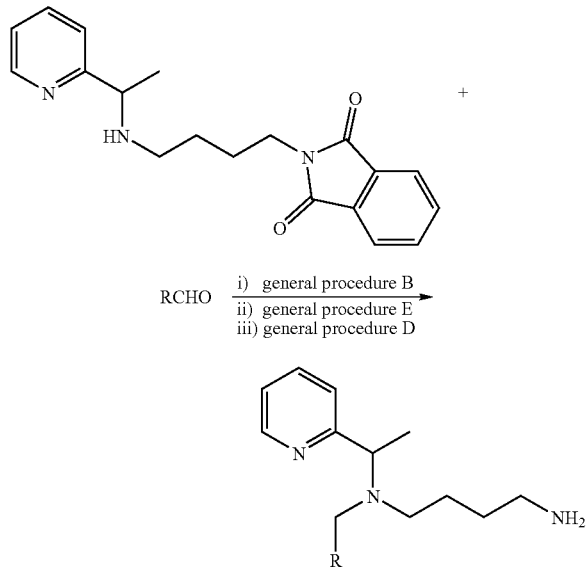

| Example | Aldehyde |
|---|---|
| 91 | 1-methyl-2-formylbenzimidazole |
| 92 | 1-allyl-1H-imidazole-2-carboxaldehyde |
| 93 | 3-isobutyl-pyridine-2-carbaldehyde |
| 94 | 3-trifluoromethyl-pyridine-2-carbaldehyde |
| 95 | (2-formyl-pyridin-3-yl)-carbamic acid tert-butyl ester Venuti, MC J. Med. Chem. 1998, 31, 2136-2145 |
| 96 | 3,5-dimethyl-pyridine-2-carbaldehyde |
| 97 | 6-methyl-pyridine-2-carbaldehyde |
| 98 | 5-methyl-pyridine-2-carbaldehyde Jones et al. J. Chem. Soc. C 1969, 2249 |
| 99 | 3-methyl-pyridine-2-carbaldehyde |

Example 91

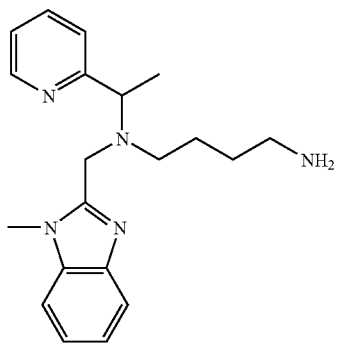

COMPOUND 91: N$^1$-(1-methyl-1H-benzoimidazol-2-ylmethyl)-N$^1$-(5,6,7,8-tetrahydro-quinolin-8-yl)-butane-1,4-diamine (HBr salt)

Off-white solid. $^1$H NMR (D$_2$O) δ 1.55-1.60 (m, 4H), 1.65 (d, 3H, J=6.9 Hz), 2.63-2.70 (m, 1H), 2.79-2.91 (m, 3H), 3.97 (s, 3H), 4.46 (d, 2H, J=1.8 Hz), 4.59 (q, 1H, J=6.6 Hz), 7.61-7.64 (m, 2H), 7.76-7.79 (m, 2H), 7.92 (t, 1H, J=6.6 Hz), 8.11 (d, 1H, J=8.1 Hz), 8.52 (t, 1H, J=7.8 Hz), 8.52 (t, 1H, J=7.8 Hz), 8.74 (d, 1H, J=5.7 Hz). $^{13}$C NMR (D$_2$O) δ 13.54, 24.31, 24.98, 31.57, 39.56, 46.79, 52.73, 59.49, 112.79, 114.29, 126.55, 126.73, 126.83, 127.20, 129.96, 133.45, 141.94, 148.01, 151.67, 156.38. MS-ES m/z 338 [M+H]$^+$. Anal. Calcd. for C$_{20}$H$_{27}$N$_{5}$.3.0HBr.1.9H$_{2}$O: C, 39.10; H, 5.54; N, 11.40; Br, 39.01. Found: C, 39.11; H, 5.44; N, 11.15; Br, 39.04.

Example 92

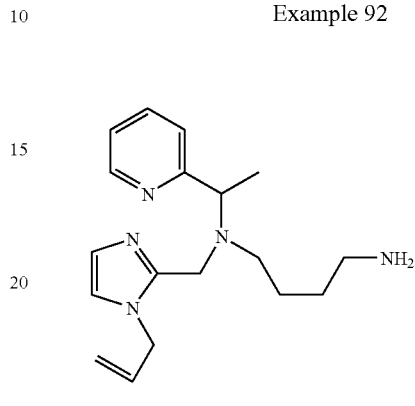

COMPOUND 92: N-(1-Allyl-1H-imidazol-2-ylmethyl)-N-(1-pyridin-2-yl-ethyl)-butane-1,4-diamine (HBr salt)

White solid. $^1$H NMR (D$_2$O) δ 1.51 (br, 4H), 1.59 (d, 3H, J=6.9 Hz), 2.55 (br m, 1H), 2.72 (br m, 1H), 4.16 (s, 2H), 4.48 (q, 1H, J=6.8 Hz), 5.14 (d, 1H, J=17.1 Hz), 5.35 (d, 1H, J=10.2 Hz), 5.96 (m, 1H), 7.42 (br, 2H), 7.99 (t, 1H, J=6.9 Hz), 8.09 (d, 1H, J=8.4 Hz), 8.59 (d, 1H, J=8.1 Hz), 8.75 (d, 1H, J=5.1 Hz). $^{13}$C NMR (D$_2$O) δ 13.77, 25.03, 25.78, 40.37, 46.72, 51.01, 52.75, 59.77, 119.88, 120.85, 124.46, 127.37, 127.60, 131.52, 142.69, 145.71, 148.95, 157.25. ES-MS m/z 314 (M+H). Anal. Calcd. for C$_{18}$H$_{27}$N$_{5}$.3.0HBr.2.1H$_2$O.0.2C$_4$H$_{10}$O: C, 37.09; H, 5.99; N, 11.50; Br, 39.37. Found: C, 37.04; H, 5.76; H, 11.42; Br, 39.51.

Example 93

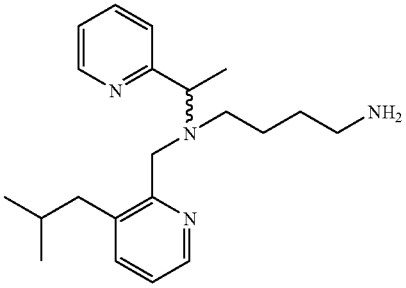

COMPOUND 93: N$^1$-(3-Isobutyl-pyridin-2-ylmethyl)-N$^1$-(1-pyridin-2-yl-ethyl)-butane-1,4-diamine (HBr salt)

White solid. $^1$H NMR (D$_2$O) δ 0.91 (d, 6H, J=6.0 Hz), 1.59 (m, 4H), 1.60 (d, 3H, J=6.0 Hz), 2.61 (m, 1H), 2.67 (d, 3H, J=6.0 Hz), 2.87 (m, 2H), 4.34 (s, 2H), 4.59 (q, 1H, J=7.5 Hz), 7.89 (t, 1H, J=7.5 Hz), 8.00 (t, 1H, J=7.5 Hz), 8.14 (d, 1H, J=8.1 Hz), 8.37 (d, 1H, J=8.1 Hz), 8.62 (m, 2H), 8.64 (d, 1H, J=6.0 Hz). $^{13}$C NMR (D$_2$O) δ 14.94, 21.72, 23.84, 24.96, 28.98, 39.23, 39.47, 50.83, 52.48, 59.82, 125.86, 126.77, 126.86, 138.85, 140.17, 142.16, 148.09, 148.49, 151.74, 156.07. ES-MS m/z 341 [M+H]$^+$. Anal. Calcd. for C$_{21}$H$_{32}$N$_4$·3.3HBr·1.5H$_2$O: C, 39.75; H, 6.08; N, 8.83; Br, 41.55. Found: C, 39.93; H, 6.14; N, 9.09; Br, 41.39.

Example 94

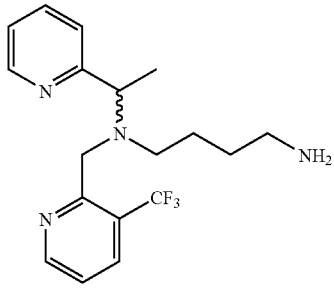

COMPOUND 94: N$^1$-(1-pyridin-2-yl-ethyl)-N$^1$-(3-trifluoromethyl-pyridin-2-ylmethyl)-butane-1,4-diamine (HBr salt)

Yellow solid. $^1$H NMR (D$_2$O) δ 1.62-1.80 (m+d, 7H), 2.93 (m, 2H), 3.19-3.32 (m, 2H), 4.73 (s, 2H), 4.96 (m, 1H), 7.66 (m, 1H), 7.75 (m, 1H), 7.85 (d, 1H, J=7.5 Hz), 8.16 (t, 1H, J=6.0 Hz), 8.34 (d, 1H, J=7.8 Hz), 8.64 (d, 1H, J=4.5 Hz), 8.85 (d, 1H, J=4.5 Hz). $^{19}$F NMR (CDCl$_3$) δ 14.65 (s). $^{13}$C NMR (D$_2$O) δ 13.79, 15.57, 22.30, 24.44, 26.54, 39.21, 39.51, 49.19, 52.18, 53.32, 54.90, 63.26, 124.82, 125.64, 126.40, 138.65, 142.71, 147.11, 149.20, 150.36, 152.72. ES-MS m/z 353 [M+H]$^+$. Anal. Calcd. for C$_{18}$H$_{23}$N$_4$F$_3$·3.2HBr·1.8H$_2$O: C, 33.58; H, 4.67; N, 8.70; Br, 39.72. Found: C, 33.78; H, 4.72; N, 8.77; Br, 39.43.

Example 95

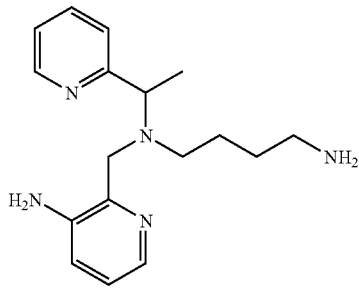

COMPOUND 95: N$^1$-(3-amino-pyridin-2-ylmethyl)-N$^1$-(1-pyridin-2-yl-ethyl)-butane-1,4-diamine (HBr salt)

White solid. $^1$H NMR (D$_2$O) δ 1.55-1.61 (m, 8H), 2.63-2.70 (m, 1H), 2.77-2.84 (m, 1H), 2.90-2.92 (m, 3H), 4.09 (s, 2H), 4.49-4.55 (m, 1H), 7.55-7.65 (m, 2H), 7.92 (t, 1H, J=6.9 Hz), 7.97-8.01 (m, 2H), 8.46-8.51 (m, 1H), 8.71 (d, 1H, J=5.7 Hz). $^{13}$C NMR (D$_2$O) δ 13.77, 23.94, 25.04, 39.57, 49.76, 52.87, 59.46, 126.40, 126.61, 126.73, 129.63, 130.67, 136.27, 142.03, 145.24, 147.70, 156.06. ES-MS m/z 300 (M+H). Anal. Calcd. for C$_{17}$H$_{25}$N$_5$·3.4HBr·H$_2$O: C, 34.15; H, 5.23; N, 11.71; Br, 45.44. Found: C, 34.22; H, 5.12; N, 11.31; Br, 45.74.

Example 96

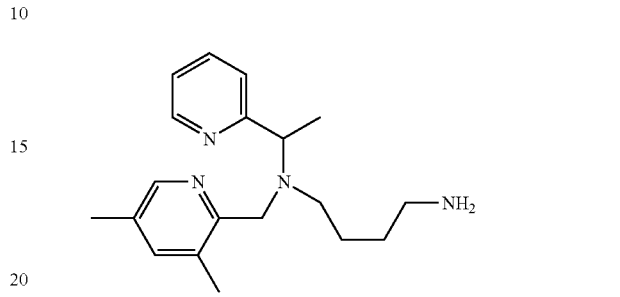

COMPOUND 96: N-(3,5-dimethylpyridin-2-ylmethyl)-N-(1-pyridin-2-yl-ethyl)-butane-1,4-diamine (HBr salt)

White solid. $^1$H NMR (D$_2$O) δ 1.48 (br, 4H), 1.58 (d, 3H, J=6.6 Hz), 2.40 (s, 3H), 2.46 (s, 3H), 2.60 (m, 1H), 2.73 (m, 1H), 2.86 (br, 2H), 4.23 (s, 2H), 4.56 (q, 1H, J=6.6 Hz), 7.99 (t, 1H, J=6.7 Hz), 8.14 (m, 2H), 8.40 (s, 1H), 8.58 (t, 1H, J=7.8 Hz), 8.76 (d, 1H, J=5.1 Hz). $^{13}$C NMR (D$_2$O) δ 14.82, 16.85, 17.53, 24.02, 25.02, 39.53, 50.76, 52.68, 59.84, 126.77, 126.82, 136.27, 137.33, 137.59, 142.07, 148.13, 149.10, 149.21, 156.23. ES-MS m/z 3—(M+H). Anal. Calcd. for C$_{19}$H$_{28}$N$_4$·3.2HBr·2.3H$_2$O: C, 37.24; H, 5.89; N, 9.14; Br, 41.72. Found: C, 37.41; H, 5.97; N, 8.80; Br, 41.62.

Example 97

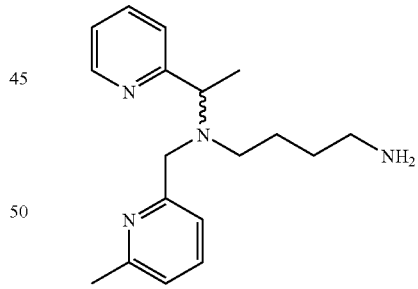

COMPOUND 97: N$^1$-(6-methyl-pyridin-2-ylmethyl)-N$^1$-(1-pyridin-2-yl-ethyl)-butane-1,4-diamine (HBr salt)

White solid. $^1$H NMR (CD$_3$OD) δ 1.62-1.82 (m, 7H), 2.72 (s, 3H), 2.90-3.00 (m, 3H), 3.11 (septa, 1H, J=6.3 Hz), 4.45 (s, 2H), 4.74 (q, 1H, J=6.9 Hz), 7.54 (d, 1H, J=7.5), 7.67-7.72 (m, 2H), 7.86 (d, 1H, J=7.8 Hz), 8.09 (t, 1H, J=7.8 Hz), 8.23 (t, 1H, J=7.2 Hz), 8.78 (d, 1H, J=4.5 Hz). $^{13}$C NMR (D$_2$O) δ 13.31, 21.40, 23.15, 24.81, 39.51, 51.92, 53.83, 61.11, 123.31, 125.42, 125.95, 126.18, 143.69, 145.68, 151.67, 155.75, 156.64. ES-MS m/z 299 [M+H]$^+$. Anal. Calcd. for $C_{18}H_{26}N_4 \cdot 4.3HBr \cdot 0.9CH_4O \cdot 0.7H_2O$: C, 33.00; H, 5.17; N, 8.15; Br, 49.95. Found: C, 32.80; H, 4.97; N, 8.07; Br, 50.32.

Example 98

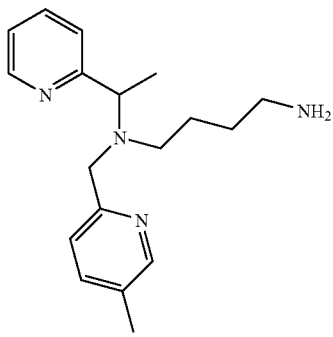

COMPOUND 98: $N^1$-(5-methyl-pyridin-2-ylmethyl)-$N^1$-(1-pyridin-2-yl-ethyl)-butane-1,4-diamine (HBr salt)

White solid (143 mg, 90%). $^1$H NMR ($D_2O$) δ 1.42-1.54 (m, 4H), 1.60 (d, 3H, J=6.6 Hz), 2.50 (s, 3H), 2.50-2.61 (m, 1H), 2.65-2.81 (m, 1H), 2.82-2.96 (m, 2H), 4.25 (s, 2H), 4.54 (dd, 1H, J=13.5, 6.6 Hz), 7.91 (d, 1H, J=8.1 Hz), 7.98 (t, 1H, J=6.6 Hz), 8.11 (d, 1H, J=7.8 Hz), 8.35 (d, 1H, J=8.1 Hz), 8.50-8.62 (m, 2H), 8.76 (d, 1H, J=5.4 Hz); $^{13}$C NMR ($D_2O$) δ 13.51, 17.74, 24.13, 25.02, 39.57, 51.83, 52.42, 59.10, 126.50, 126.66, 126.71, 138.23, 140.83, 142.01, 147.97, 148.37, 151.05, 156.58; ES-MS m/z 299 (M+H). Anal. Calcd. for $C_{18}H_{26}N_4 \cdot 3.5$ $HBr \cdot 1.1H_2O \cdot 0.5C_4H_{10}O$: C, 36.14; H, 5.38; N, 8.87; Br, 44.29. Found: C, 36.08; H, 5.59; N, 8.79; Br, 44.35.

Example 99

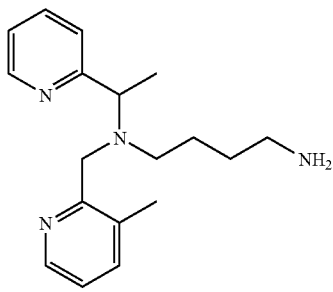

COMPOUND 99: $N^1$-(3-methyl-pyridin-2-ylmethyl)-$N^1$-(1-pyridin-2-yl-ethyl)-butane-1,4-diamine HCl salt $^1$H NMR ($D_2O$) δ 1.50 (m, 4H), 1.61 (d, 3H, J=7.5 Hz), 2.44 (s, 3H), 2.78 (m, 4H), 4.30 (s, 2H), 4.59 (dd, 1H, J=7.5, 13.6 Hz), 7.82 (m, 1H), 8.03 (m, 1H), 8.—(d, 1H, J=8.3 Hz), 8.32 (d, 1H, J=7.5 Hz), 8.59 (m, 2H), 8.77 (d, 1H, J=7.0 Hz); $^{13}$C NMR ($D_2O$) δ 14.55, 16.89, 23.83, 24.95, 39.47, 51.08, 52.72, 60.11, 66.47, 125.78, 126.63, 126.77, 136.85, 138.62, 142.49, 147.66, 147.83, 152.10, 156.03. ES-MS m/z 299 (M+H). Anal. Calcd. For ($C_{18}H_{26}N_4$) 2.88 (HCl) 3.57 ($H_2O$): C, 46.21; H, 7.76; N, 11.97; Cl, 21.84. Found: C, 46.19; H, 7.37; N, 12.00; Cl, 21.81.

TABLE 8

Preparation of Examples 100 to 116

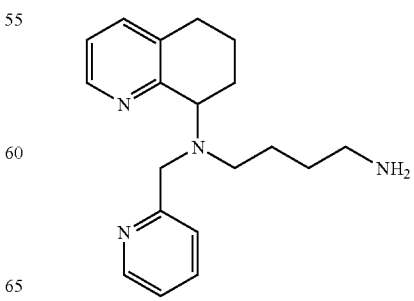

| Example | Aldehyde |
|---|---|
| 100 | pyridine-2-carbaldehyde |
| 101 | 3-chloro-pyridine-2-carbaldehyde |
| 102 | 3,5-dimethyl-pyridine-2-carbaldehyde |
| 103 | 2-(4,6-dimethylpyridinyl)-carboxaldehyde |
| | Bridger, G et al. PCT Int. Appl. (2002), WO 2002022600 |
| 104 | 6-methyl-pyridine-2-carbaldehyde |
| 105 | 3-methyl-pyridine-2-carbaldehyde |
| 106 | 3-hydroxypyridine-2-carbaldehyde |
| 107 | 3-Isopropylpyridine-2-carbaldehyde |
| 108 | (2-formyl-pyridin-3-yl)-carbamic acid tert-butyl ester |
| 109 | 4-methyl-pyridine-2-carbaldehyde |
| | Goodson, PA et al. J. Am. Chem. Soc. 1990, 112, 6248-6254. |
| 110 | 5-methyl-pyridine-2-carbaldehyde |
| 111 | N-(2-formyl-pyridin-3-yl)-methanesulfonamide |
| 112 | 2-quinoline-carboxaldehyde |
| 113 | pyridazine-3-carbaldehyde |
| | Maury, G. et al. Bull. Soc. Chim. Belg. 1982, 91, 153-162 |
| 114 | 2-thiazol-carboxaldehyde |
| 115 | 1,3-benzothiazole-2-carbaldehyde |
| 116 | pyrazine-2-carbaldehyde |
| | Tagawa, Y. et al. Heterocycles 2003, 60, 953-958 |

Example 100

COMPOUND 100: N[1]-pyridine-2-ylmethyl-N[1]-(5,6,7,8-tetrahydro-quinolin-8-yl)-butane-1,4-diamine (HBr salt)

Yellow oil. $^1$H NMR (D$_2$O) δ 1.53 (m, 5H), 1.73-1.87 (m, 1H), 2.04 (br q, 1H, J=12.6 Hz), 2.16-2.21 (m, 1H), 2.39-2.43 (m, 1H), 2.52-2.59 (m, 1H), 2.79-2.88 (m, 3H), 3.01 (dd, 2H, J=21.6, 3.6 Hz), 4.36 (q, 2H, J=15.5 Hz), 4.45-4.49 (m, 1H), 7.82 (dd, 1H, J=7.8, 6.0 Hz), 7.95 (t, 1H, J=6.6 Hz), 8.05 (d, 1H, J=8.1 Hz), 8.29 (d, 1H, J=8.1 Hz), 8.51 (br t, 1H, J=8.1 Hz), 8.59 (d, 1H, J$_1$=5.4 Hz), 8.75 (d, 1H, J=6.0 Hz). $^{13}$C NMR (D$_2$O) δ 20.37, 20.44, 25.07, 25.30, 27.71, 39.50, 51.41, 53.65, 60.40, 125.85, 126.69, 127.32, 139.62, 140.52, 141.81, 147.60, 147.80, 151.33, 153.77. ES-MS m/z 311 [M+H]$^+$. Anal. Calcd. for C$_{19}$H$_{26}$N$_4$.3.1HBr.2.5H$_2$O: C, 37.64; H, 5.67; N, 9.24; Br, 40.85. Found: C, 37.90; H, 5.74; N, 9.17; Br, 40.56.

Example 101

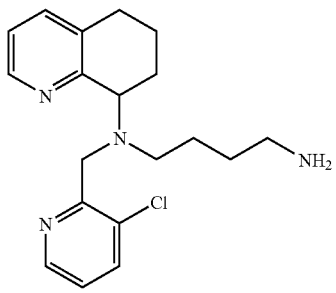

COMPOUND 101: N[1]-(3-chloro-pyridin-2-ylmethyl)-N[1]-(5,6,7,8-tetrahydro-quinolin-8-yl)-butane-1,4-diamine (HBr salt)

White solid. $^1$H NMR (D$_2$O) δ 1.60-1.95 (br m, 5H), 2.18 (m, 2H), 2.55 (m, 1H), 2.90 (m, 4H), 3.16 (m, 1H), 3.45 (m, 1H), 4.43 (m, 1H), 7.37 (dd, 1H, J=7.5, 3.0 Hz), 7.45 (dd, 1H, J=7.5, 3.0 Hz), 7.75 (d, 1H, J=7.5 Hz), 7.91 (d, 1H, J=7.5 Hz), 8.37 (m, 1H), 8.56 (d, 1H, J=4.8 Hz). $^{13}$C NMR (D$_2$O) δ 20.34, 21.57, 22.86, 24.35, 27.41, 39.18, 51.55, 52.78, 63.49, 124.90, 125.82, 136.30, 139.15, 140.38, 146.29, 147.27. ES-MS m/z 345 [M+H]$^+$. Anal. Calcd. for C$_{19}$H$_{25}$N$_4$Cl.1.9HBr.1.4H$_2$O: C, 43.56; H, 5.71; N, 10.70; Cl, 6.77; Br, 28.98. Found: C, 43.68; H, 5.55; N, 10.58; Cl, 6.75; Br, 28.76.

Example 102

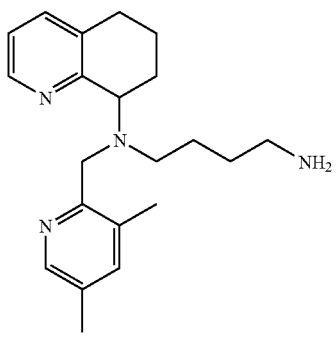

COMPOUND 102: N[1]-(3,5-Dimethyl-pyridin-2-ylmethyl)-N[1]-(5,6,7,8-tetrahydro-quinolin-8-yl)-butane-1,4-diamine (HBr salt)

Yellow solid. $^1$H NMR (D$_2$O) δ 1.39-1.46 (m, 4H), 1.74-1.88 (m, 1H), 2.03-2.21 (m, 2H), 2.43 (s, 3H), 2.47 (s, 3H), 2.52 (m, 2H), 2.72-2.86 (m, 3H), 2.99-3.01 (m, 2H), 4.26 (ABq, 2H, J=69.6, 17.7 Hz), 4.47 (dd, 1H, J=10.8, 5.4 Hz), 7.85 (dd, 1H, J=7.8, 6.0 Hz), 8.20 (s, 1H), 8.34 (d, 1H, J=8.1 Hz), 8.45 (s, 1H), 8.60 (d, 1H, J=5.4 Hz). $^{13}$C NMR (D$_2$O) δ 17.02, 17.54, 20.50, 20.68, 25.14, 25.37, 27.84, 39.47, 51.89, 61.14, 125.85, 136.47, 137.32, 137.80, 139.50, 140.67, 147.99, 148.80, 149.09, 151.14. ES-MS m/z 339 [M+H]$^+$. Anal. Calcd. for C$_{21}$H$_{30}$N$_4$.3.0HBr.1.8H$_2$O: C, 41.10; H, 6.01; N, 9.13; Br, 39.06. Found: C, 41.08; H, 5.88; N, 9.11; Br, 38.98.

Example 103

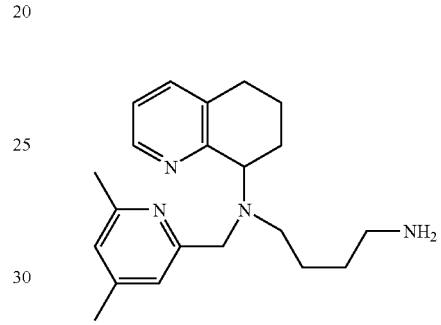

COMPOUND 103: N-(4,6-dimethylpyridin-2-ylmethyl)-N-(5,6,7,8-tetrahydroquinolin-8-yl)-butane-1,4-diamine (HBr salt)

White solid. $^1$H NMR (D$_2$O) δ 1.53 (br, 4H), 1.79 (br m, 1H), 1.96 (m, 1H), 2.14 (br m, 1H), 2.35 (br m, 1H), 2.50 (br m, 1H), 2.56 (s, 3H), 2.72 (s, 3H), 2.74 (br m, 1H), 2.90 (br, 2H), 2.98 (br, 2H), 4.14 (br s, 2H), 4.37 (m, 1H), 7.57 (s, 1H), 7.78 (s, 1H), 7.83 (t, 1H, J=6.9 Hz), 8.31 (d, 1H, J=8.1 Hz), 8.55 (d, 1H, J=5.7 Hz). $^{13}$C NMR (D$_2$O) δ 19.27, 20.06, 20.45, 21.87, 25.14, 25.25, 27.65, 39.59, 51.22, 52.89, 59.57, 125.37, 125.78, 127.87, 139.25, 140.52, 147.85, 151.67, 151.79, 153.62, 161.59. ES-MS m/z 340 (M+H). Anal. Calcd. for C$_{21}$H$_{30}$N$_4$.3.6HBr.2.2H$_2$O: C, 37.68; H, 5.72; N, 8.37; Br, 42.97. Found: C, 37.59; H, 5.70; N, 7.98; Br, 43.09.

Example 104

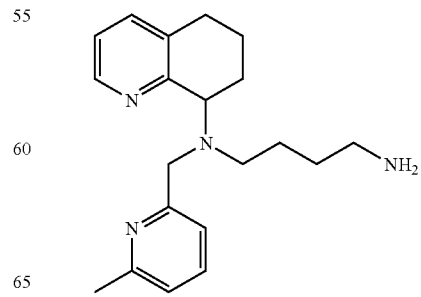

COMPOUND 104: N$^1$-(6-methyl-pyridin-2-ylmethyl)-N$^1$-(5,6,7,8-tetrahydro-quinolin-8-yl)-butane-1,4-diamine Yellow oil. $^1$H NMR (CDCl$_3$) δ 1.35-1.52 (m, 6H), 1.60-1.74 (m, 1H), 1.79-2.0 (m, 2H), 2.12-2.17 (m, 1H), 2.48 (s, 3H), 2.57-2.87 (m, 6H), 3.65-3.85 (m, 2H), 4.12-4.17 (m, 1H), 6.74 (d, 1H, J=7.2 Hz), 6.99-7.02 (m, 1H), 7.30 (d, 1H, J=7.5 Hz), 7.52 (t, 1H, J=7.8 Hz), 7.60 (d, 1H, J=7.8 Hz), 8.47 (d, 1H, J=4.2 Hz); $^{13}$C NMR (D$_2$O) δ 21.86, 24.69, 26.50, 26.56, 29.70, 31.74, 42.27, 53.16, 58.30, 61.22, 119.96, 121.36, 121.75, 134.55, 136.75, 136.95, 147.50, 157.33, 158.56, 161.77. ES-MS m/z 325.4 (M+H). Anal. Calcd. for C$_{20}$H$_{28}$N$_4$.0.1H$_2$O.0.1CH$_2$Cl$_2$: C, 72.12; H, 8.55; N, 16.74. Found: C, 72.18; H, 8.67; N, 16.31.

Example 105

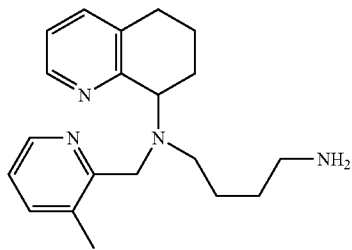

COMPOUND 105: N-(3-methylpyridin-2-ylmethyl)-N-(5,6,7,8-tetrahydroquinolin-8-yl)-butane-1,4-diamine (HBr salt)

White solid. $^1$H NMR (D$_2$O) δ 1.47 (br, 4H), 1.78 (br m, 1H), 2.17 (br m, 2H), 2.48 (s, 3H), 2.52 (br m, 2H), 2.77 (br m, 1H), 2.81 (m, 2H), 3.01 (m, 2H), 4.22 (d, 1H, J=18.0 Hz), 4.46 (d, 1H, J=18.0 Hz), 4.50 (m, 1H), 7.86 (m, 2H), 8.35 (m, 2H), 8.62 (m, 2H). $^{13}$C NMR (D$_2$O) δ 17.19, 20.51, 20.75, 25.13, 25.38, 27.86, 39.47, 51.94, 52.28, 61.22, 125.89 (2C), 137.35, 138.41, 139.50, 140.73, 148.09, 148.33, 151.05, 151.91. ES-MS m/z 325 (M+H). Anal. Calcd. for C$_{20}$H$_{28}$N$_4$.3.1HBr.1.1H$_2$O.0.3C$_4$H$_{10}$O: C, 41.25; H, 5.93; N, 9.08; Br, 40.12. Found: C, 41.08; H, 5.84; N, 9.09; Br, 40.44.

Example 106

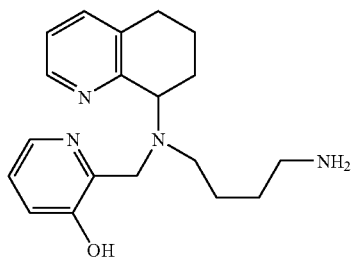

COMPOUND 106: 2-{[(4-aminobutyl)-(5,6,7,8-tetrahydroquinolin-8-yl)-amino]-methyl}-pyridin-3-ol (HBr salt)

White solid. $^1$H NMR (D$_2$O) δ 1.52 (br, 4H), 1.80 (m, 1H), 2.04 (m, 1H), 2.16 (m, 1H), 2.41 (br, 1H), 2.56 (br, 1H), 2.80 (br, 1H), 2.88 (br, 2H), 2.99 (br, 2H), 4.15 (d, 1H, J=16.8 Hz), 4.30 (d, 1H, J=16.5 Hz), 4.56 (m, 1H), 7.79 (t, 1H, J=7.2 Hz), 7.81 (t, 1H, J=7.2 Hz), 7.93 (d, 1H, J=8.4 Hz), 8.26 (d, 1H, J=6.9 Hz), 8.28 (d, 1H, J=6.9 Hz), 8.55 (d, 1H, J=5.4 Hz). $^{13}$C NMR (D$_2$O) δ 20.51 (2C), 25.09, 25.20, 27.68, 39.55, 49.13, 51.69, 60.55, 125.80, 127.33, 132.21, 132.45, 139.28, 140.41, 141.58, 147.64, 151.43, 154.69. ES-MS m/z 325 (M+H). Anal. Calcd. for C$_{19}$H$_{26}$N$_4$O.3.5HBr.1.8H$_2$O.0.4C$_4$H$_{10}$O: C, 36.84; H, 5.57; N, 8.34; Br, 41.63. Found: C, 36.91; H, 5.44; N, 8.33; Br, 41.62.

Example 107

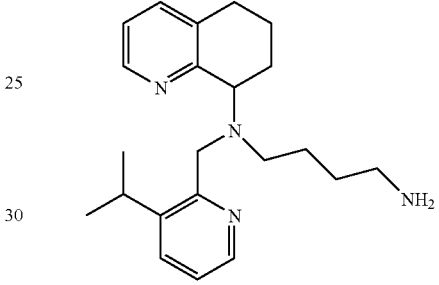

COMPOUND 107: The (N$^1$-(3-isopropyl-pyridin-2-ylmethyl)-N$^1$-(5,6,7,8-tetrahydro-quinolin-8-yl)-butane-1,4-diamine (HBr salt)

White solid. $^1$H NMR (D$_2$O) δ 1.23 (d, 3H, J=6.6 Hz), 1.29 (d, 3H, J=6.6 Hz), 1.58-1.66 (m, 4H), 1.80-1.89 (m, 1H), 2.09-2.23 (m, 2H), 2.48-2.54 (m, 1H), 2.74-2.80 (m, 1H), 2.85-3.14 (m, 5H), 3.23 (septet, 1H, J=6.6 Hz), 4.37 (d, 1H, J=16.8 Hz), 4.62-4.68 (m, 2H), 7.65-7.70 (m, 1H), 7.77-7.81 (m, 1H), 8.11 (d, 1H, J=7.8 Hz), 8.32 (d, 1H, J=7.8 Hz), 8.55 (d, 1H, J=5.1 Hz), 8.61-8.63 (m, 1H); $^{13}$C NMR (D$_2$O) δ 20.50, 21.24, 22.30, 22.38, 24.45, 24.87, 27.79, 28.13, 39.42, 51.92, 51.98, 62.05, 125.51, 126.01, 138.92, 141.39, 141.50, 142.46, 144.90, 145.54, 149.02, 150.25. ES-MS m/z 353 (M+H). Anal. Calcd. for C$_{22}$H$_{32}$N$_4$.2.6HBr.1.2H$_2$O.0.1C$_4$H$_{10}$O: C, 45.45; H, 6.47; N, 9.47; Br, 35.10. Found: C, 45.59; H, 6.48; N, 9.42; Br, 34.89.

Example 108

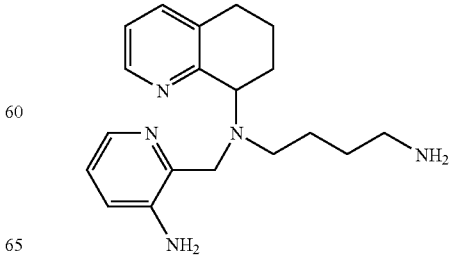

COMPOUND 108: $N^1$-(3-Amino-pyridin-2-ylm-ethyl)-$N^1$-(5,6,7,8-tetrahydro-quinolin-8-yl)-butane-1,4-diamine (HBr salt)

Off-white solid. $^1$H NMR (D$_2$O) δ 1.51-1.60 (m, 4H), 1.74-1.89 (m, 1H), 2.02-2.25 (m, 2H), 2.37-2.47 (m, 1H), 2.48-2.60 (m, 1H), 2.70-2.84 (m, 1H), 2.85-2.92 (m, 2H), 2.93-3.03 (m, 2H), 4.07 (d, 1H, J=17.1 Hz), 4.23 (d, 1H, J=17.1 Hz), 4.46 (dd, 1H, J=10.7, 5.9 Hz), 7.65 (dd, 1H, J=8.4, 5.7 Hz), 7.75 (d, 1H, J=8.7 Hz), 7.84 (dd, 1H, J=7.8, 6.0 Hz), 8.07 (d, 1H, J=5.4 Hz), 8.32 (d, 1H, J=7.8 Hz), 8.59 (d, 1H, J=5.7 Hz); $^{13}$C NMR (D$_2$O) δ 20.51, 20.57, 25.16, 25.30, 27.81, 39.52, 50.33, 52.15, 60.69, 125.83, 126.54, 129.76, 130.98, 136.47, 139.40, 140.58, 145.28, 147.97, 151.22; ES-MS m/z 326 (M+H). Anal. Calcd. for C$_{19}$H$_{27}$N$_5$.3.1HBr.0.9H$_2$O: C, 38.52; H, 5.43; N, 11.82; Br, 41.81. Found: C, 38.87; H, 5.27; N, 11.44; Br, 41.43.

Example 109

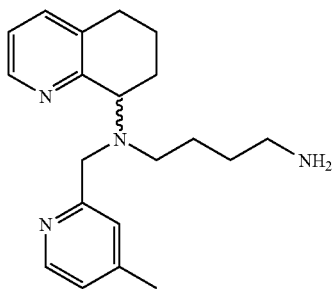

COMPOUND 109: $N^1$-(4-methyl-pyridin-2-ylm-ethyl)-$N^1$-(5,6,7,8-tetrahydro-quinolin-8-yl)-butane-1,4-diamine (HBr salt)

White powder. $^1$H NMR (CD$_3$OD) δ 1.66-1.99 (m, 6H), 2.10-2.15 (m, 1H), 2.19-2.26 (m, 1H), 2.54-2.58 (m, 1H), 2.88-3.04 (m, 5H), 3.30-3.32 (m, 2H), 4.41 (A part of AB, 1H, 15.9 Hz), 4.54 (B part of AB, J=15.9 Hz), 4.71 (dd, 1H, J=10.8, 5.4 Hz), 7.41-7.46 (m, 3H), 7.80-7.82 (br, 1H), 8.55-8.60 (m, 2H). $^{13}$C NMR (D$_2$O) δ 21.84, 22.15, 23.21, 24.95, 26.11, 28.96, 40.61, 53.06, 55.83, 64.36, 125.99, 126.32, 127.04, 137.52, 141.86, 147.10, 148.54, 151.72, 153.11, 154.05. ES-MS m/z 325 [M+H]$^+$. Anal. Calcd. for C$_{20}$H$_{28}$N$_4$.2.0HBr.0.7H$_2$O0.8C$_2$H$_4$O$_2$: C, 47.74; H, 6.41; N, 10.31; Br, 28.77. Found: C, 47.77; H, 6.39; N, 10.33; Br, 28.81.

Example 110

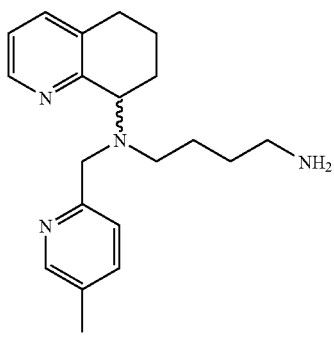

COMPOUND 110: $N^1$-(5-methyl-pyridin-2-ylm-ethyl)-$N^1$-(5,6,7,8-tetrahydro-quinolin-8-yl)-butane-1,4-diamine (HBr salt)

White powder. $^1$H NMR (CD$_3$OD) δ 1.69-1.77 (m, 2H), 1.81-1.91 (m, 4H), 2.10-2.15 (m, 1H), 2.19-2.25 (m, 1H), 2.43 (s, 3H), 2.54-2.58 (m, 1H), 2.89-3.00 (m, 5H), 3.30-3.32 (m, 2H), 4.41 (A part of AB, 1H, J=15.6 Hz), 4.56 (B part of AB, J=15.6 Hz), 4.72 (dd, 1H, J=11.1, 5.1 Hz), 7.47-7.56 (m, 2H), 7.80-7.87 (m, 2H), 8.56-8.60 (m, 2H). $^{13}$C NMR (D$_2$O) δ 14.55, 17.75, 20.41, 20.87, 23.88, 24.68, 27.54, 39.33, 51.71, 54.49, 61.86, 66.48, 125.15, 125.31, 136.62, 137.80, 143.13, 143.73, 146.29, 148.78, 150.05. ES-MS m/z 325 [M+H]$^+$. Anal. Calcd. for C$_{20}$H$_{28}$N$_4$.2.3HBr.1.0H$_2$O.0.7C$_2$H$_4$O$_2$: C, 45.05; H, 6.20; N, 9.82; Br, 32.21. Found: C, 45.24; H, 6.33; N, 9.84; Br, 31.91.

Example 111

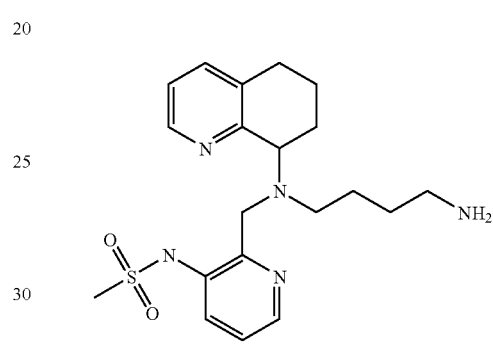

COMPOUND 111: The N-(2-{[(4-amino-butyl)-(5,6,7,8-tetrahydro-quinolin-8-yl)-amino]-methyl}-pyridin-3-yl)-methanesulfonamide (HBr salt)

White solid. $^1$H NMR (D$_2$O) δ 1.42-1.54 (m, 4H), 1.75-1.90 (m, 1H), 2.05-2.21 (m, 2H), 2.43-2.47 (m, 1H), 2.54-2.64 (m, 1H), 2.81-2.87 (m, 3H), 2.98-3.06 (m, 2H), 3.30 (s, 3H), 4.37 (d, 1H, J=17.7 Hz), 4.52-4.63 (m, 2H), 7.82 (dd, 1H, J=5.7, 7.8 Hz), 8.02 (dd, 1H, J=5.4, 8.4 Hz), 8.28 (d, 1H, J=7.8 Hz), 8.52 (d, 1H, J=8.4 Hz), 8.61 (d, 1H, J=5.7 Hz), 8.78 (d, 1H, J=5.4 Hz); $^{13}$C NMR (D$_2$O) δ 20.46, 20.88, 25.05, 25.09, 27.81, 39.49, 40.94, 51.54, 51.99, 61.43, 125.91, 127.27, 134.65, 140.28, 140.71, 142.89, 147.38, 150.50. ES-MS m/z 404 (M+H). Anal. Calcd. for C$_{20}$H$_{29}$N$_5$O$_2$S.3.5HBr.0.6H$_2$O.0.3C$_4$H$_{10}$O: C, 35.38; H, 5.14; N, 9.73; Br, 38.85; S, 4.45. Found: C, 35.28; H, 5.17; N, 9.83; Br, 39.01: S, 4.46.

Example 112

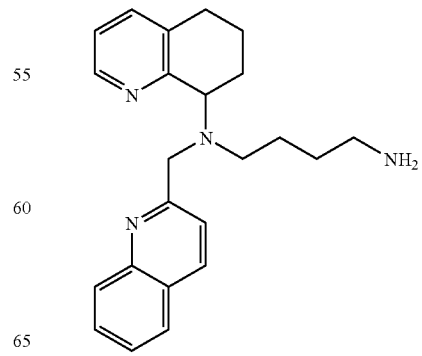

COMPOUND 112: The $N^1$-quinolin-2-ylmethyl-$N^1$-(5,6,7,8-tetrahydro-quinolin-8-yl)-butane-1,4-diamine (HBr salt)

$^1$H NMR (D$_2$O) δ 1.58-1.70 (m, 4H), 1.78-1.83 (m, 1H), 2.02-2.18 (m, 2H), 2.40-2.45 (m, 1H), 2.54-2.66 (m, 1H), 2.85-3.00 (m, 5H), 4.40-4.58 (m, 3H), 7.78-7.83 (m, 1H), 7.92-7.97 (m, 1H), 8.11-8.17 (m, 2H), 8.26-8.34 (m, 3H), 8.55-7.59 (m, 1H), 9.00-9.07 (m, 1H). $^{13}$C NMR (D$_2$O) δ 20.40, 20.49, 25.13, 25.36, 27.74, 39.59, 51.75, 54.21, 60.05, 120.39, 122.17, 125.86, 128.81, 129.71, 130.39, 135.76, 138.25, 139.53, 140.65, 147.90, 148.12, 151.46, 157.39. ES-MS m/z 361 (M+H). Anal. Calcd. for C$_{23}$H$_{28}$N$_4$.3.0HBr.2.8H$_2$O: C, 42.26; H, 5.64; N, 8.57; Br, 36.67. Found: C, 42.36; H, 5.36; N, 8.33; Br, 36.51.

Example 113

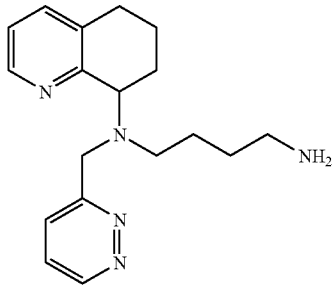

COMPOUND 113: The $N^1$-pyridazin-3-ylmethyl-$N^1$-(5,6,7,8-tetrahydro-quinolin-8-yl)-butane-1,4-diamine (HBr salt)

$^1$H NMR (D$_2$O) δ 1.51-1.72 (m, 4H), 1.75-1.88 (m, 1H), 1.96-2.09 (m, 1H), 2.10-2.19 (m, 1H), 2.37-2.41 (m, 1H), 2.58-2.66 (m, 1H), 2.84-2.99 (m, 5H), 4.40-4.90 (m, 3H), 7.80 (dd, 1H, J=6.3, 7.5 Hz), 8.27 (d, 1H, J=7.5 Hz), 8.46 (dd, 1H, J=5.1, 8.4 Hz), 8.58-8.63 (m, 2H), 9.48 (d, 1H, J=5.1 Hz); $^{13}$C NMR (D$_2$O) δ 20.52, 20.66, 25.02, 25.13, 27.58, 39.63, 51.33, 53.81, 59.92, 125.75, 135.29, 137.19, 139.79, 140.19, 147.25, 149.19, 151.70, 163.52. ES-MS m/z 312 (M+H). Anal. Calcd. for C$_{18}$H$_{25}$N$_5$.4.0HBr.1.1H$_2$O.0.1C$_4$H$_{10}$O: C, 33.37; H, 4.90; N, 10.57; Br, 48.62. Found: C, 33.49; H, 4.90; N, 10.55; Br, 48.04.

Example 114

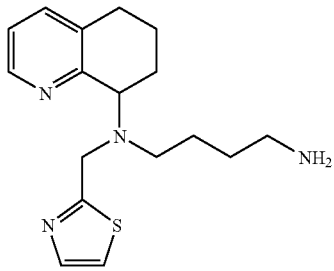

COMPOUND 114: $N^1$-(5,6,7,8-tetrahydro-quinolin-8-yl)-$N^1$-thiazol-2-ylmethyl-butane-1,4-diamine (HBr salt)

$^1$H NMR (D$_2$O) δ 1.60-1.73 (m, 4H), 1.77-1.87 (m, 1H), 1.92-2.04 (m, 1H), 2.10-2.18 (m, 1H), 2.32-2.36 (m, 1H), 2.61-2.69 (m, 1H), 2.84-3.00 (m, 5H), 4.32-4.53 (m, 3H), 7.79-7.83 (m, 1H), 7.91 (d, 2H, J=3.6 Hz), 8.04 (d, 1H, J=3.6 Hz), 8.27 (d, 1H, J=7.8 Hz), 8.56 (d, 1H, J=5.7 Hz); $^{13}$C NMR (D$_2$O) δ 20.41, 20.65, 25.03, 25.19, 27.67, 39.64, 50.76, 51.48, 59.64, 124.06, 125.88, 135.94, 139.94, 140.47, 147.60, 151.27, 174.20; ES-MS m/z 317 (M+H). Anal. Calcd. for C$_{17}$H$_{24}$N$_4$S.3.1HBr.0.9H$_2$O.0.4CH$_2$Cl$_2$: C, 33.85; H, 4.85; N, 9.07; Br, 40.12; S, 5.19. Found: C, 33.66; H, 4.81; N, 9.10; Br, 40.05; S, 5.11.

Example 115

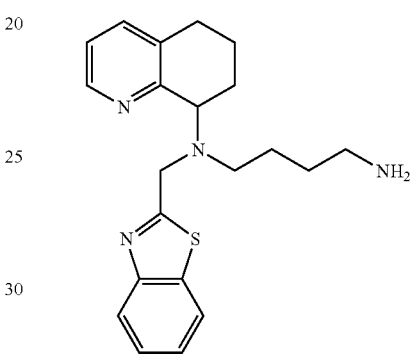

COMPOUND 115: The $N^1$-benzothiazol-2-ylmethyl-$N^1$-(5,6,7,8-tetrahydro-quinolin-8-yl)-butane-1,4-diamine (HBr salt)

$^1$H NMR (D$_2$O) δ 1.61-1.73 (m, 5H), 1.95-1.99 (m, 1H), 2.10-2.14 (m, 1H), 2.27-2.30 (m, 1H), 2.64-2.71 (m, 1H), 2.84-2.94 (m, 5H), 4.17-4.32 (m, 2H), 4.37-4.40 (m, 1H), 7.45 (t, 1H, J=7.5 Hz), 7.53 (t, 1H, J=7.5 Hz), 7.69 (dd, 1H, J=5.4, 7.8 Hz), 7.89 (d, 1H, J=7.5 Hz), 7.96 (d, 1H, J=7.5 Hz), 8.17 (d, 1H, J=7.8 Hz), 8.50 (d, 1H, J=5.4 Hz); $^{13}$C NMR (D$_2$O) δ20.45, 20.54, 25.06, 25.09, 27.56, 39.68, 51.67, 52.41, 59.50, 121.46, 123.05, 125.61, 126.75, 127.73, 134.11, 139.72, 140.01, 147.05, 149.66, 151.59, 173.42. ES-MS m/z 367 (M+H). Anal. Calcd. for C$_{21}$H$_{26}$N$_4$S.2.0HBr.1.1H$_2$O.0.3C$_4$H$_{10}$O: C, 46.75; H, 5.87; N, 9.82; Br, 28.02; S, 5.62. Found: C, 46.62; H, 5.69; N, 9.74; Br, 28.21; S, 5.64.

Example 116

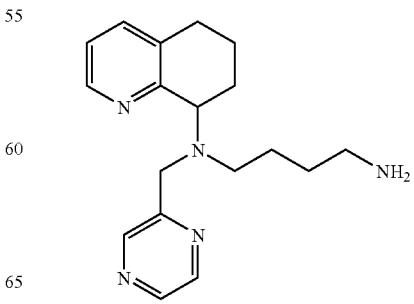

COMPOUND 116: The N¹-pyrazin-2-ylmethyl-N¹-(5,6,7,8-tetrahydro-quinolin-8-yl)-butane-1,4-diamine ¹H NMR (CDCl₃) δ 1.30-1.45 (m, 4H), 1.68-1.85 (m, 2H), 1.90-2.05 (m, 1H), 2.08-2.15 (m, 1H), 2.55-2.59 (m, 2H), 2.62-2.83 (m, 4H), 3.77 (d, 1H, J=15.6 Hz), 3.99 (d, 1H, J=15.6 Hz), 4.10 (dd, 1H, J=6.0, 9.0 Hz), 7.01 (dd, 1H, J=4.5, 7.5 Hz), 7.31 (d, 1H, J=7.5 Hz), 8.35-8.38 (m, 2H), 8.45 (d, 1H, J=3.3 Hz), 8.97 (s, 1H); ¹³C NMR (CDCl₃) δ 21.54, 26.34, 26.98, 29.37, 31.68, 42.22, 53.04, 56.46, 61.42, 121.77, 134.34, 136.67, 142.62, 143.30, 145.93, 147.32, 157.78, 158.08. ES-MS m/z 312 (M+H). Anal. Calcd. for C₁₈H₂₅N₅.0.2CH₂Cl₂: C, 66.56; H, 7.80; N, 21.32. Found: C, 66.68; H, 7.99; N, 21.40.

TABLE 9

Preparation of Examples 117 to 119

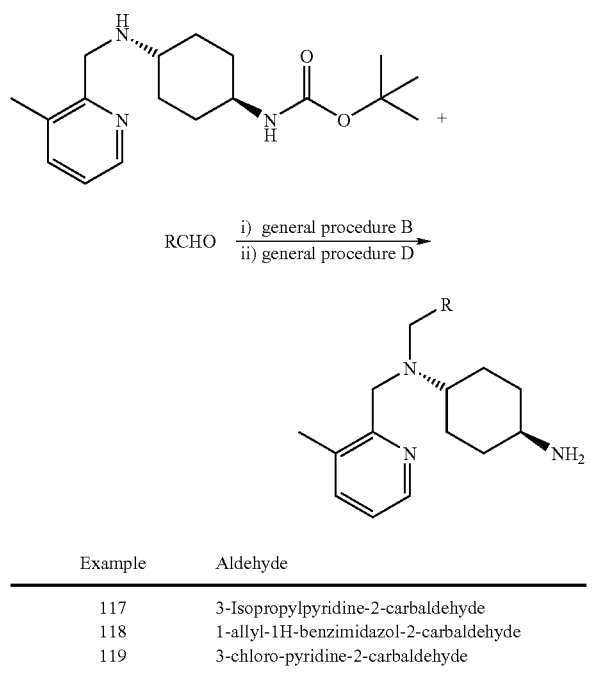

| Example | Aldehyde |
|---------|----------|
| 117 | 3-Isopropylpyridine-2-carbaldehyde |
| 118 | 1-allyl-1H-benzimidazol-2-carbaldehyde |
| 119 | 3-chloro-pyridine-2-carbaldehyde |

Example 117

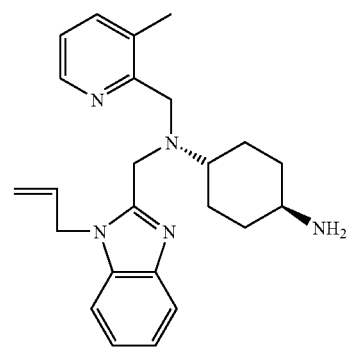

COMPOUND 117: N-(3-Isopropyl-pyridin-2-ylmethyl)-N-(3-methyl-pyridin-2-ylmethyl)-cyclohexane-1,4-diamine HBr salt White solid. ¹H NMR (D₂O) δ 1.28 (d, 6H, J=7.0 Hz), 1.36-1.48 (m, 2H), 1.53-1.66 (m, 2H), 2.09-2.20 (m, 4H), 2.52 (s, 3H), 2.75 (t, 1H, J=11.7 Hz), 3.18 (t, 1H, 11.9 Hz), 3.34 (septet, 1H, J=6.6 Hz), 4.34 (s, 2H), 4.42 (s, 2H), 7.84 (dd, 1H, J=7.9, 6.7 Hz), 7.91 (dd, 1H, J=7.8, 6.4 Hz), 8.35 (d, 1H, J=8.3 Hz), 8.52 (d, 1H, J=8.3 Hz), 8.58 (d, 2H, J=6.14 Hz); ¹³C NMR (D2O) δ 17.2, 22.2 (2C), 25.9 (2C), 28.3, 29.5 (2C), 49.7, 50.4, 51.1, 60.44, 126.1, 126.7, 137.9, 139.0, 144.8, 148.4, 149.9, 151.2; ES-MS m/z 353 (M+H). Anal Calcd. For C₂₂H₃₂N₄.(HBr).(CH₃CO₂H): C, 43.52; H, 5.93; N, 8.60; Br, 38.03. Found: C, 43.37; H, 6.15; N, 8.70; Br, 37.93.

Example 118

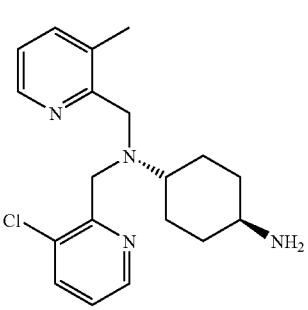

COMPOUND 118: N-(1-allyl-1H-benzimidazol-2-ylmethyl)-N-(3-methyl-pyridin-2-ylmethyl)-cyclohexane-1,4-diamine HBr salt White solid. ¹H NMR (D₂O) δ 1.52 (m, 4H), 2.06 (m, 4H), 2.48 (s, 3H), 2.81 (m, 1H), 3.14 (m, 1H), 4.36 (s, 2H), 4.50 (s, 2H), 5.12 (m, 3H), 5.34 (d, 1H, J=10.5 Hz), 6.05 (m, 1H), 7.60 (m, 2H), 7.78 (m, 3H), 8.27 (d, 1H, J=7.9 Hz), 8.54 (d, 1H, J=5.7 Hz); ¹³C NMR (D₂O) δ 17.19, 25.91, 29.45, 47.07, 47.54, 49.67, 51.02, 60.63, 113.21, 114.48, 119.04, 125.97, 127.15, 127.56, 130.25, 132.48, 137.66, 138.50, 148.50, 150.55, 151.40. ES-MS m/z 390 (M+H). Anal. Calcd. for C₂₄H₃₁N₅ 3.32HBr 2.39H₂O 0.19C₄H₁₀O: C, 41.60; H, 5.78; N, 9.79; Br, 37.06. Found: C, 41.61; H, 5.47; N, 9.69; Br, 37.03.

Example 119

COMPOUND 119: N-(3-Chloropyridin-2-ylmethyl)-N-(3-methylpyridin-2-ylmethyl)-cyclohexane-1,4-diamine (HBr salt)

White solid. $^1$H NMR (D$_2$O): 1.47 (m, 2H), 1.70 (m, 2H), 2.20 (m, 4H), 2.38 (s, 3H), 3.16 (m, 2H), 4.43 (s, 2H), 4.47 (s, 2H), 7.49 (dd, 1H, J=5.4, 7.8 Hz), 7.57 (dd, 1H, J=6.9, 13.2 Hz), 8.04 (d, 2H, J=7.8 Hz), 8.40 (d, 1H, J=5.4 Hz), 8.46 (d, 1H, J=4.8 Hz). $^{13}$C NMR (D$_2$O): 21.98, 24.69, 39.42, 53.17, 54.49, 56.21, 126.50, 128.01, 129.08, 131.58 (2 carbons), 132.15, 142.44, 144.65, 146.92, 149.84. ES-MS 320.4 m/z [M+H]$^+$; Anal. Calcd. for (C$_{19}$H$_{25}$N$_4$Cl×3.1 HBr×2.5H$_2$O): C, 35.62; H, 5.21; N, 8.74; Br, 38.66. Found: C, 35.72; H, 5.16; N, 8.64; Br, 38.28.

TABLE 10

Preparation of Examples 120 to 143

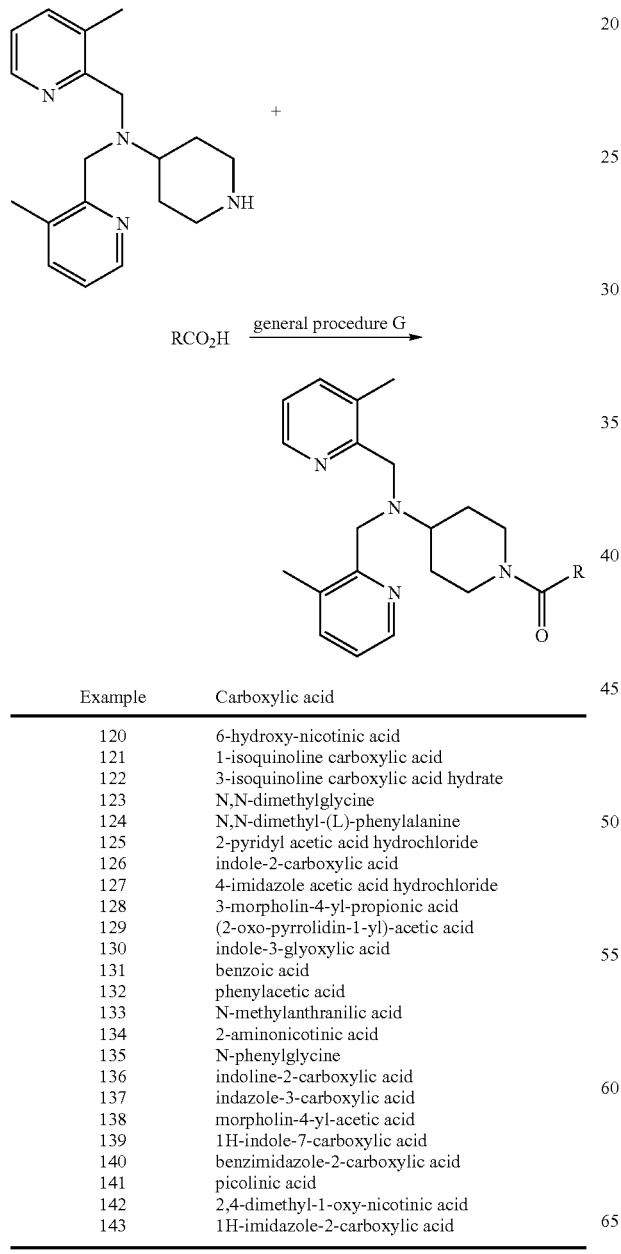

| Example | Carboxylic acid |
|---|---|
| 120 | 6-hydroxy-nicotinic acid |
| 121 | 1-isoquinoline carboxylic acid |
| 122 | 3-isoquinoline carboxylic acid hydrate |
| 123 | N,N-dimethylglycine |
| 124 | N,N-dimethyl-(L)-phenylalanine |
| 125 | 2-pyridyl acetic acid hydrochloride |
| 126 | indole-2-carboxylic acid |
| 127 | 4-imidazole acetic acid hydrochloride |
| 128 | 3-morpholin-4-yl-propionic acid |
| 129 | (2-oxo-pyrrolidin-1-yl)-acetic acid |
| 130 | indole-3-glyoxylic acid |
| 131 | benzoic acid |
| 132 | phenylacetic acid |
| 133 | N-methylanthranilic acid |
| 134 | 2-aminonicotinic acid |
| 135 | N-phenylglycine |
| 136 | indoline-2-carboxylic acid |
| 137 | indazole-3-carboxylic acid |
| 138 | morpholin-4-yl-acetic acid |
| 139 | 1H-indole-7-carboxylic acid |
| 140 | benzimidazole-2-carboxylic acid |
| 141 | picolinic acid |
| 142 | 2,4-dimethyl-1-oxy-nicotinic acid |
| 143 | 1H-imidazole-2-carboxylic acid |

Example 120

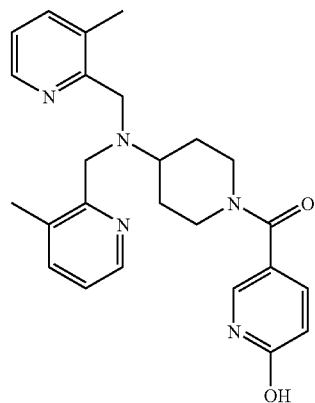

COMPOUND 120: {4-[bis-(3-methyl-pyridin-2-ylmethyl)-amino]-piperidin-1-yl}-(6-hydroxy-pyridin-3-yl)-methanone $^1$H NMR (CDCl$_3$) δ 1.46-1.69 (m, 4H), 1.98-2.02 (m, 2H), 2.11 (s, 6H), 2.80-2.81 (m, 3H), 3.85 (s, 4H), 4.29 (s, 1H), 6.60 (d, 1H, J=9.3 Hz), 7.09-7.—(m, 2H), 7.39 (d, 2H, J=7.5 Hz), 7.54-7.63 (m, 2H), 8.36 (d, 2H, J=8.4 Hz). $^{13}$C NMR (CDCl$_3$) δ 18.39, 27.87, 45.97, 55.04, 57.92, 115.85, 120.20, 122.90, 133.80, 136.42, 138.50, 141.34, 146.32, 157.39, 165.13, 167.01. ES-MS m/z 466.10 (M+H). Anal. Calcd. for C$_{25}$H$_{29}$N$_5$O$_2$.1.92H$_2$O: C, 64.42; H, 7.10; N, 15.03. Found: C, 64.46; H, 6.93; N, 14.82.

Example 121

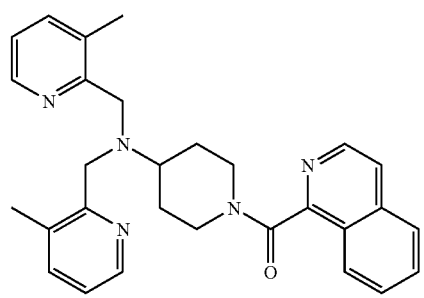

COMPOUND 121: {4-[Bis-(3-methyl-pyridin-2-ylmethyl)-amino]-piperidin-1-yl}-isoquinolin-1-yl-methanone $^1$H NMR (CDCl$_3$) δ 1.60-1.70 (m, 2H), 1.82-1.95 (m, 2H), 2.08 (s, 6H), 2.68-2.95 (m, 3H), 3.40 (br d, 1H, J=13.8 Hz), 3.77 (d, 2H, J=12.3 Hz), 3.90 (d, 2H, J=12.3 Hz), 5.01 (br d, 1H, J=13.8 Hz), 7.09 (dd, 2H, J=7.5, 4.8 Hz), 7.36 (d, 2H, J=7.5 Hz), 7.59-7.74 (m, 3H), 7.87 (d, 1H, J=8.1 Hz), 8.01 (d, 1H, J=8.1 Hz), 8.34 (d, 2H, J=3.6 Hz), 8.52 (d, 1H, J=5.7 Hz); ES-MS m/z 466 (M+H).

Example 122

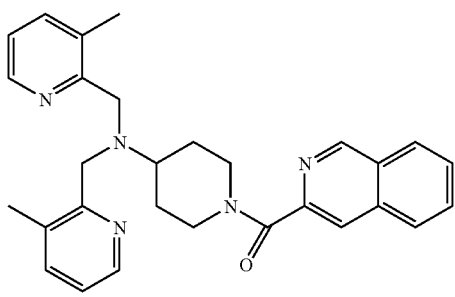

COMPOUND 122: {4-[Bis-(3-methyl-pyridin-2-ylmethyl)-amino]-piperidin-1-yl}-isoquinolin-3-yl-methanone ¹H NMR (CDCl₃) δ 1.70-1.98 (m, 4H), 2.09 (s, 6H), 2.64-2.85 (m, 2H), 2.94-3.03 (m, 1H), 3.78 (d, 2H, J=12.6 Hz), 3.91 (d, 2H, J=12.6 Hz), 4.07 (br d, 1H, J=12.6 Hz), 4.87 (br d, 1H, J=12.6 Hz), 7.09 (dd, 2H, J=7.8, 4.8 Hz), 7.37 (d, 2H, J=7.8 Hz), 7.65-7.77 (m, 2H), 7.90 (d, 1H, J=7.8 Hz), 8.02 (d, 1H, J=7.8 Hz), 8.03 (s, 1H), 8.35 (d, 2H, J=3.6 Hz), 9.23 (s, 1H); ES-MS m/z 466 (M+H).

Example 123

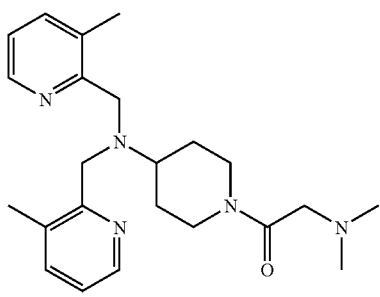

COMPOUND 123: 1-{4-[Bis-(3-methyl-pyridin-2-ylmethyl)-amino]-piperidin-1-yl}-2-dimethylamino-ethanone ¹H NMR (CDCl₃) δ 1.55-1.67 (m, 2H), 1.84-1.87 (m, 1H), 2.01-2.09 (m, 7H), 2.28-2.41 (m, 7H), 2.68-2.88 (m, 2H), 3.07 (d, 1H, J=13.2 Hz), 3.14 (d, 1H, J=13.2 Hz), 3.76 (d, 2H, J=12.3 Hz), 3.87 (d, 2H, J=12.3 Hz), 4.14 (br d, 1H, J=12.9 Hz), 4.66 (br d, 1H, J=12.9 Hz), 7.08 (dd, 2H, J=7.5, 4.8 Hz), 7.36 (d, 2H, J=7.5 Hz), 8.35 (d, 2H, J=3.3 Hz); ES-MS m/z 396 (M+H).

Example 124

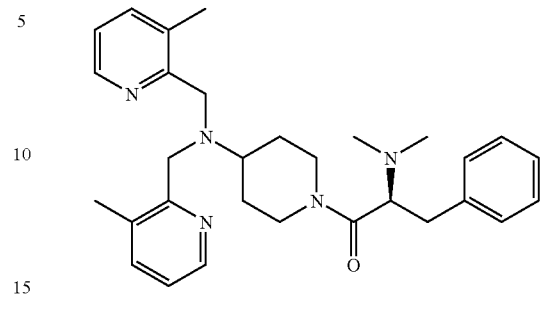

COMPOUND 124: 1-{4-[Bis-(3-methyl-pyridin-2-ylmethyl)-amino]-piperidin-1-yl}-2-dimethylamino-3-phenyl-propan-1-one ¹H NMR (CDCl₃) δ 1.13-1.26 (m, 2H), 1.54-2.89 (m, 20H), 3.18-3.27 (m, 1H), 3.27-3.86 (m, 4H), 4.67-4.70 (m, 1H), 7.07 (dd, 2H, J=6.9, 4.8 Hz), 7.20-7.27 (m, 5H), 7.35 (d, 2H, J=6.9 Hz), 8.32 (d, 2H, J=3.6 Hz); ES-MS m/z 486 (M+H).

Example 125

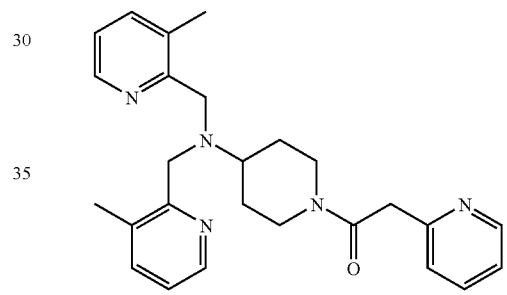

COMPOUND 125: 1-{4-[Bis-(3-methyl-pyridin-2-ylmethyl)-amino]-piperidin-1-yl}-2-pyridin-2-yl-ethanone ¹H NMR (CDCl₃) δ 1.28-1.42 (m, 1H), 1.53-1.65 (m, 1H), 1.84-1.93 (m, 2H), 2.05 (s, 6H), 2.35-2.43 (m, 1H), 2.65-2.73 (m, 1H), 2.79-2.87 (m, 1H), 3.69 (d, 2H, J=12.3 Hz), 3.80 (d, 2H, J=12.3 Hz), 3.94 (s, 2H), 4.14 (br d, 1H, J=12.6 Hz), 4.70 (br d, 1H, J=12.6 Hz), 7.07 (dd, 2H, J=7.5, 5.1 Hz), 7.13-7.17 (m, 1H), 7.34-7.37 (m, 3H), 7.63 (t, 1H, J=7.5 Hz), 8.33 (d, 2H, J=4.5 Hz), 8.52 (d, 1H, J=4.8 Hz); ES-MS m/z 430 (M+H).

Example 126

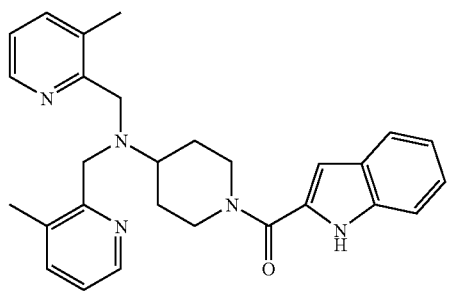

COMPOUND 126: {4-[Bis-(3-methyl-pyridin-2-ylmethyl)-amino]-piperidin-1-yl}-(1H-indol-2-yl)-methanone ¹H NMR (CDCl₃) δ 1.70-1.83 (m, 2H), 2.04-2.10 (m, 8H), 2.82-2.90 (m, 3H), 3.85 (s, 4H), 4.80 (br d, 2H, J=13.2 Hz), 6.78 (d, 1H, J=1.5 Hz), 7.08-7.17 (m, 3H), 7.25-7.30 (m, 1H), 7.37-7.43 (m, 3H), 7.66 (d, 1H, J=4.8 Hz), 8.36 (dd, 2H, J=4.5, 1.2 Hz), 9.—(br s, 1H); ES-MS m/z 454 (M+H).

Example 127

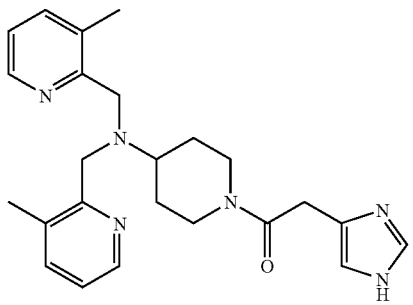

COMPOUND 127: 1-{4-[Bis-(3-methyl-pyridin-2-ylmethyl)-amino]-piperidin-1-yl}-2-(1H-imidazol-4-yl)-ethanone ¹H NMR (CDCl₃) δ 1.44-1.64 (m, 2H), 1.85-2.00 (m, 2H), 2.07 (s, 6H), 2.40-2.44 (m, 1H), 2.69-2.77 (m, 1H), 2.86-2.94 (m, 1H), 3.72-3.85 (m, 6H), 4.09 (br d, 1H, J=12.6 Hz), 4.69 (br d, 1H, J=12.6 Hz), 6.91 (s, 1H), 7.08 (dd, 2H, J=7.5, 4.8 Hz), 7.36 (d, 2H, J=7.5 Hz), 7.55 (s, 1H), 8.33 (d, 2H, J=3.6 Hz); ES-MS m/z 419 (M+H).

Example 128

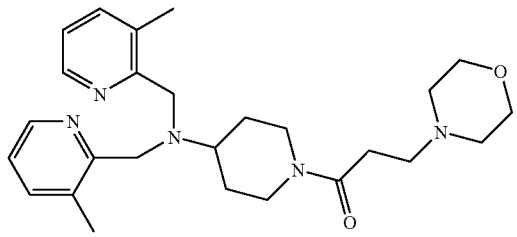

COMPOUND 128: 1-{4-[Bis-(3-methyl-pyridin-2-ylmethyl)-amino]-piperidin-1-yl}-3-morpholin-4-yl-propan-1-one ¹H NMR (CDCl₃) δ 1.58 (m, 2H), 1.84 (d, 1H, J=12.6 Hz), 2.05 (br, 1H), 2.36 (t, 1H, J=12.3 Hz), 2.49 (m, 4H), 2.55 (d, 2H, J=8.1 Hz), 2.73 (m, 3H), 2.88 (t, 1H, J=12.3 Hz), 3.71 (m, 6H), 3.89 (m, 3H), 4.69 (d, 1H, J=12.6 Hz), 7.09 (m, 2H), 7.37 (d, 2H, J=8.1 Hz), 8.34 (d, 2H, J=3.9 Hz). ES-MS m/z 452 (M+H).

Example 129

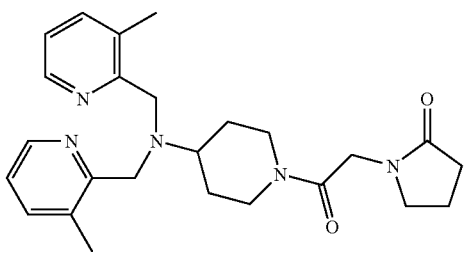

COMPOUND 129: 1-(2-{4-[Bis-(3-methyl-pyridin-2-ylmethyl)-amino]-piperidin-1-yl}-2-oxo-ethyl)-pyrrolidin-2-one ¹H NMR (CDCl₃) δ 1.59 (m, 2H), 1.89 (d, 1H, J=13.8 Hz), 2.07 (m, 3H), 2.08 (s, 6H), 2.43 (m, 3H), 2.74 (m, 1H), 2.88 (t, 1H, J=10.8 Hz), 3.50 (m, 2H), 3.82 (m, 5H), 4.06 (d, 1H, J=15.9 Hz), 4.15 (d, 1H, J=15.6 Hz), 4.62 (d, 1H, J=12.0 Hz), 7.09 (m, 2H), 7.37 (d, 2H, J=7.5 Hz), 8.34 (d, 2H, J=3.6 Hz). ES-MS m/z 436 (M+H).

Example 130

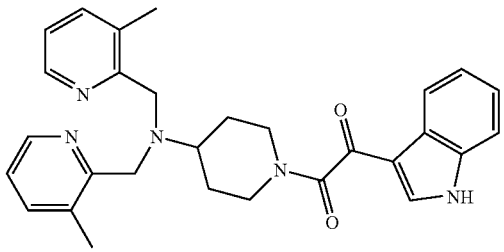

COMPOUND 130: 1-{4-[Bis-(3-methyl-pyridin-2-ylmethyl)-amino]-piperidin-1-yl}-2-(1H-indol-3-yl)-ethane-1,2-dione ¹H NMR (CDCl₃) δ 1.69 (m, 2H), 1.85 (br, 1H), 2.00 (br, 1H), 2.06 (s, 6H), 2.57 (t, 1H, J=12.3 Hz), 2.85 (q, 2H, J=12.9 Hz), 3.82 (m, 5H), 4.72 (d, 1H, J=12.0 Hz), 7.09 (m, 2H), 7.28 (br, 2H), 7.37 (m, 3H), 7.86 (s, 1H), 8.32 (m, 3H), 10.35 (br, 1H(NH)). ES-MS m/z 482 (M+H).

Example 131

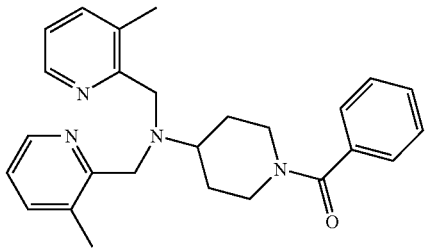

COMPOUND 131: {4-[Bis-(3-methyl-pyridin-2-ylmethyl)-amino]-piperidin-1-yl}-phenyl-methanone ¹H NMR (CDCl₃) δ 1.58 (m, 1H), 1.93 (br, 2H), 2.08 (s, 6H), 2.60 (br, 1H), 2.74-2.95 (m, 3H), 3.83 (m, 5H), 4.80 (br, 1H), 7.09 (m, 2H), 7.39 (m, 7H), 8.35 (d, 2H, J=3.9 Hz). ES-MS m/z 415 (M+H).

Example 132

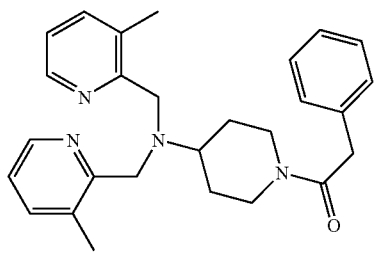

COMPOUND 132: 1-{4-[Bis-(3-methyl-pyridin-2-ylmethyl)-amino]-piperidin-1-yl}-2-phenyl-ethanone ¹H NMR (CDCl₃) δ 1.23 (dq, 1H, J=12.3, 3.9 Hz), 1.60 (dq, 1H, J=12.6, 3.9 Hz), 1.84 (d, 2H, J=11.7 Hz), 2.04 (s, 6H), 2.36 (t, 1H, J=11.4 Hz), 2.65 (m, 1H), 3.80 (t, 1H, J=11.4 Hz), 3.65 (d, 2H, J=12.6 Hz), 3.74 (s, 2H), 3.79 (d, 2H, J=12.3 Hz), 3.91 (d, 1H, J=13.2 Hz), 4.71 (d, 1H, J=12.3 Hz), 7.07 (m, 2H), 7.20-7.39 (m, 7H), 8.32 (d, 2H, J=3.9 Hz). ES-MS m/z 429 (M+H).

Example 133

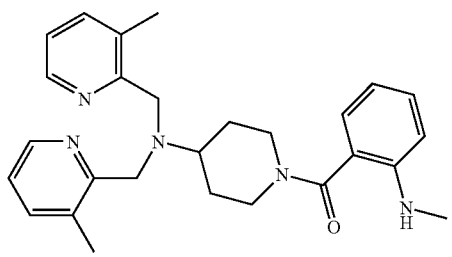

COMPOUND 133: {4-[Bis-(3-methyl-pyridin-2-ylmethyl)-amino]-piperidin-1-yl}-(2-methylamino-phenyl)-methanone ¹H NMR (CDCl₃) δ 1.67 (m, 2H), 1.94 (br, 2H), 2.09 (s, 6H), 2.74 (br, 1H), 2.80 (d, 3H, J=5.1 Hz), 3.83 (m, 4H), 5.07 (q, 1H, J=5.1 Hz), 6.66 (m, 2H), 7.08 (m, 3H), 7.26 (m, 1H), 7.37 (d, 2H, J=7.2 Hz), 8.35 (d, 2H, J=3.9 Hz). ES-MS m/z 444 (M+H).

Example 134

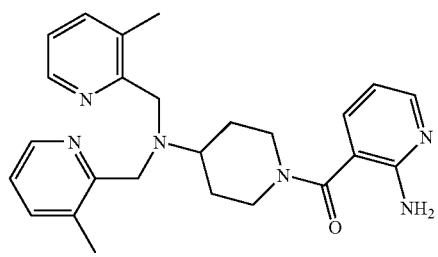

COMPOUND 134: (2-Amino-pyridin-3-yl)-{4-[Bis-(3-methyl-pyridin-2-ylmethyl)-amino]-piperidin-1-yl}-methanone ¹H NMR (CDCl₃) δ 1.65 (m, 2H), 1.97 (d, 2H, J=12.6 Hz), 2.09 (s, 6H), 2.80 (br, 3H), 3.83 (s, 4H), 5.12 (s 2H), 6.66 (m, 1H), 7.09 (m, 2H), 7.36 (m, 3H), 8.11 (dd, 1H, J=4.8, 1.5 Hz), 8.35 (d, 2H, J=4.2 Hz). ES-MS m/z 431 (M+H).

Example 135

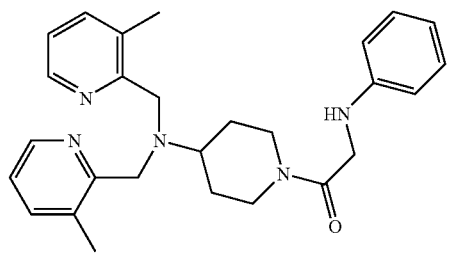

COMPOUND 135: 1-{4-[Bis-(3-methyl-pyridin-2-ylmethyl)-amino]-piperidin-1-yl}-2-phenylamino-ethanone ¹H NMR (CDCl₃) δ 1.64 (dq, 2H, J=12.3, 3.6 Hz), 1.90 (d, 2H, J=12.3 Hz), 2.08 (s, 6H), 2.10 (br, 1H), 2.48 (t, 1H, J=12.6 Hz), 2.78 (m, 1H), 2.93 (m, 1H), 3.74-3.94 (m, 7H), 4.72 (d, 2H, J=12.9 Hz), 4.92 (m, 1H(NH)), 6.63 (d, 2H, J=7.8 Hz), 6.72 (t, 1H, J=7.5 Hz), 7.09 (m, 2H), 7.20 (t, 2H, J=7.5 Hz), 7.38 (d, 2H, J=7.5 Hz), 8.35 (d, 2H, J=3.9 Hz). ES-MS m/z 444 (M+H).

Example 136

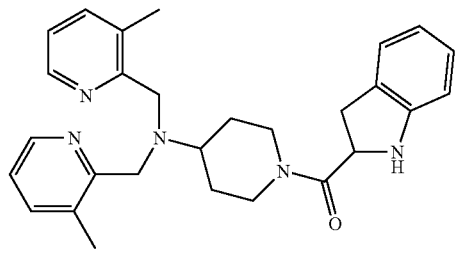

COMPOUND 136: {4-[Bis-(3-methyl-pyridin-2-ylmethyl)-amino]-piperidin-1-yl}-(2,3-dihydro-1H-indol-2-yl)-methanone $^1$H NMR (CDCl$_3$) δ 1.63 (br, 2H), 1.88 (br, 1H), 2.09 (s, 6H), 2.44 (t, 1H, J=16.5 Hz), 2.78 (t, 1H, J=11.4 Hz), 2.95 (q, 1H, J=11.4 Hz), 3.—(m, 1H), 3.49 (q, 1H, J=12.9 Hz), 3.77 (d, 2H, J=12.3 Hz), 3.90 (m, 3H), 4.56 (m, 1H), 4.65 (br, 2H), 6.75 (m, 2H), 7.04 (m, 2H), 7.09 (m, 2H), 7.37 (d, 2H, J=7.2 Hz), 8.36 (d, 2H, J=3.9 Hz). ES-MS m/z 456 (M+H).

Example 137

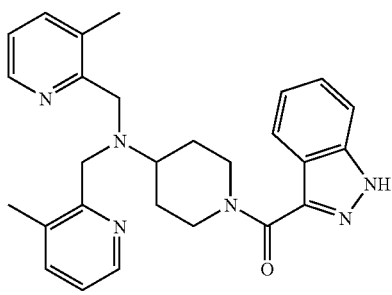

COMPOUND 137: {4-[Bis-(3-methyl-pyridin-2-ylmethyl)-amino]-piperidin-1-yl}-(1H-indazol-3-yl)-methanone $^1$H NMR (CDCl$_3$) δ 1.72 (q, 1H, J=12.3 Hz), 1.92 (br, 2H), 2.11 (s, 6H), 2.15 (br, 1H), 2.63 (m, 1H), 2.95 (br, 2H), 3.80 (d, 2H, J=12.0 Hz), 3.98 (d, 2H, J=12.9 Hz), 4.91 (d, 1H, J=12.0 Hz), 7.11 (m, 2H), 7.22 (d, 1H, J=7.8 Hz), 7.39 (m, 4H), 8.09 (d, 1H, J=8.4 Hz), 8.36 (d, 2H, J=3.6 Hz). ES-MS m/z 455 (M+H).

Example 138

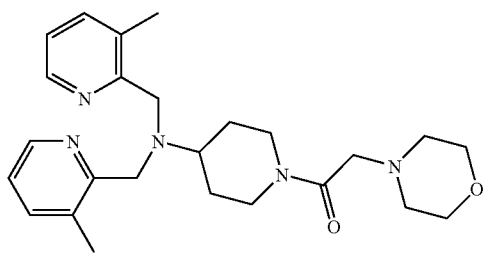

COMPOUND 138: 1-{4-[Bis-(3-methyl-pyridin-2-ylmethyl)-amino]-piperidin-1-yl}-2-morpholin-4-yl-ethanone $^1$H NMR (CDCl$_3$) δ 1.60 (m, 2H), 1.85 (d, 1H, J=11.1 Hz), 2.05 (br, 1H), 2.09 (s, 6H), 2.36 (t, 1H, J=12.3 Hz), 2.51 (m, 4H), 2.74 (m, 1H), 2.86 (m, 1H), 3.12 (d, 1H, J=13.5 Hz), 3.22 (d, 1H, J=13.5 Hz), 3.72 (m, 4H), 3.75 (d, 2H, J=12.6 Hz), 3.86 (d, 1H, J=12.6 Hz), 4.11 (d, 1H, J=13.2 Hz), 4.65 (d, 1H, J=12.6 Hz), 7.09 (m, 2H), 7.37 (d, 2H, J=7.2 Hz), 8.34 (d, 2H, J=3.9 Hz). ES-MS m/z 438 (M+H).

Example 139

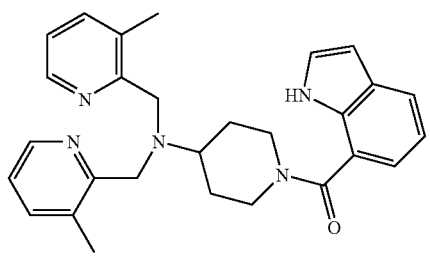

COMPOUND 139: {4-[Bis-(3-methyl-pyridin-2-ylmethyl)-amino]-piperidin-1-yl}-(1H-indol-7-yl)-methanone $^1$H NMR (CDCl$_3$) δ 1.72 (dq, 1H, J=12.3, 4.2 Hz), 1.98 (br, 2H), 2.10 (s, 6H), 2.85 (m, 3H), 3.85 (s, 2H), 4.52 (br, 2H), 6.57 (m, 1H), 7.10 (m, 3H), 7.21 (d, 1H, J=6.9 Hz), 7.37 (d, 2H, J=7.2 Hz), 7.71 (d, 1H, J=7.8 Hz), 8.36 (d, 2H, J=3.6 Hz), 9.15 (br, 1H(NH)). ES-MS m/z 454 (M+H).

Example 140

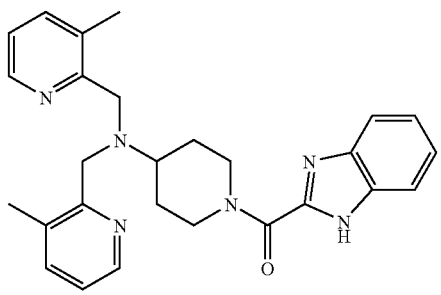

COMPOUND 140: (1H-benzoimidazol-2-yl)-{4-[bis-(3-methyl-pyridin-2-ylmethyl)-amino]-piperidin-1-yl}-methanone $^1$H NMR (CHCl$_3$) δ 1.71-1.92 (m, 2H), 2.00-2.22 (m, 9H), 2.72 (t, 1H, J=12.6 Hz), 2.84-2.92 (m, 1H), 3.08 (t, 1H, J=12.6 Hz), 3.84 (s, 4H), 4.93 (d, 1H, J=12.9 Hz), 6.16 (d, 1H, J=12.9 Hz), 7.08 (dd, 2H, J=4.8, 7.2 Hz), 7.26-7.38 (m, 4H), 7.51 (br s, 1H), 7.81 (br s, 1H), 8.35 (d, 2H, J=4.8 Hz); $^{13}$C NMR (CHCl$_3$) δ 18.4, 27.4, 28.7, 44.2, 47.1, 55.0, 57.8, 112.2, 121.3, 122.8, 123.3, 125.3, 133.8, 138.5, 146.3, 157.5, 159.0; ES-MS m/z 477 (M+Na). Anal. Calcd. for C$_{27}$H$_{30}$N$_6$O.0.3CH$_2$Cl$_2$: C, 68.30; H, 6.42; N, 17.51. Found: C, 68.09; H, 6.38; N, 17.51.

Example 141

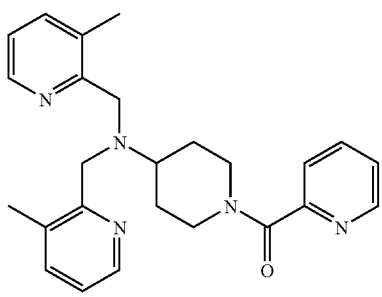

COMPOUND 141: {4-[bis-(3-methyl-pyridin-2-ylmethyl)-amino]-piperidin-1-yl}-pyridin-2-yl-methanone $^1$H NMR (CDCl$_3$) δ 1.70-1.80 (m, 2H), 1.94-1.96 (m, 2H), 2.08 (s, 6H), 2.63 (t, 1H, J=11.4 Hz), 2.74-2.82 (m, 1H), 2.94 (t, 1H, J=11.7 Hz), 3.75-3.99 (m, 5H), 4.82 (d, 1H, J=12.0 Hz), 7.07-7.10 (m, 2H), 7.35-7.38 (m, 3H), 7.58 (d, 1H, J=7.8 Hz), 7.79 (t, 1H, J=7.5 Hz), 8.33-8.34 (m, 2H), 8.58-8.59 (m, 1H). $^{13}$C NMR (CDCl$_3$) δ 18.37, 27.41, 28.11, 42.97, 47.60, 55.02, 57.84, 122.80, 123.81, 124.68, 133.78, 137.40, 138.42, 146.30, 148.85, 154.86, 157.54, 168.00. ES-MS m/z 416.2 (M+H). Anal. Calcd. for C$_{25}$H$_{29}$N$_5$O.0.2CH$_2$Cl$_2$.0.3H$_2$O: C, 69.12; H, 6.90; N, 15.99. Found: C, 69.39; H, 6.85; N, 16.22.

Example 142

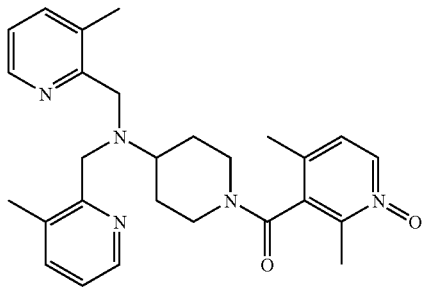

COMPOUND 142: {4-[bis-(3-methyl-pyridin-2-ylmethyl)-amino]-piperidin-1-yl}-(2,4-dimethyl-1-oxy-pyridin-3-yl)-methanone $^1$H NMR (CDCl$_3$) 1.45-1.73 (m, 1H), 1.83 (s, 3H), 2.09 (d, 6H, J=3.9 Hz), 2.16 (s, 2H), 2.34 (d, 3H, J=14.4 Hz), 2.50 (s, 1H), 2.64 (t, 1H, J=12.9 Hz), 2.76-2.91 (m, 2H), 3.36 (d, 1H, J=12.6 Hz), 3.75-3.88 (m, 4H), 4.88 (d, 1H, J=12.9 Hz), 6.97-7.04 (m, 1H), 7.10 (t, 2H, J=5.4 Hz), 7.38 (d, 2H, J=7.2 Hz), 8.16 (d, 1H, J=6.3 Hz), 8.33-8.34 (m, 2H). $^{13}$C NMR (CDCl$_3$) 15.90, 18.61, 28.10, 41.98, 46.73, 55.28, 57.88, 122.96, 125.25, 125.47, 133.21, 133.74, 138.53, 138.80, 145.50, 146.36, 157.23, 165.09. ES-MS m/z 461.1 (M+H).

Anal. Calcd. for C$_{27}$H$_{35}$N$_5$O$_2$.0.5CH$_2$Cl$_2$.0.5H$_2$O: C, 64.38; H, 7.27; N, 13.65. Found: C, 64.72; H, 7.31; N, 13.68.

Example 143

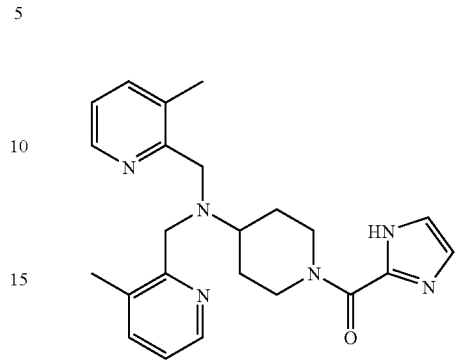

COMPOUND 143: {4-[(3,5-dimethyl-pyridin-2-ylmethyl)-(3-methyl-pyridin-2-ylmethyl)-amino]-piperidin-1-yl}-(1H-imidazol-2-yl)-methanone $^1$H NMR (CDCl$_3$) δ 1.50-1.72 (m, 2H), 2.08 (m, 8H), 2.61 (t, 1H, J=6.0 Hz), 2.84 (t, 1H, J=6.0 Hz), 2.98 (t, 1H, J=6.0 Hz), 3.83 (s, 4H), 4.80 (br d, 1H, J=15.0 Hz), 6.—(br d, 1H, J=15.0 Hz), 7.06-7.11 (m, 2H), 7.20 (s, 1H), 7.37 (d, 2H, J=9.0 Hz), 8.36 (d, 2H, J=3.0 Hz), 10.62 (br s, 1H). ES-MS m/z 405 [M+H]$^+$.

Example 144

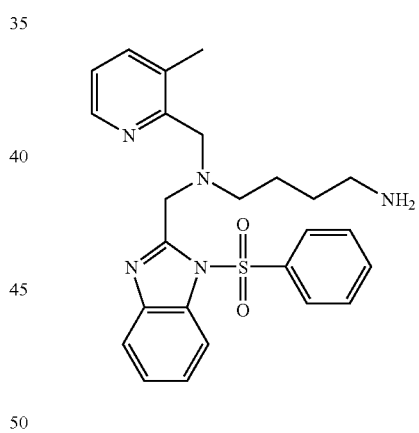

COMPOUND 144: N$^1$-(1-Benzenesulfonyl-1H-benzoimidazol-2-ylmethyl)-N$^1$-(3-methyl-pyridin-2-ylmethyl)-butane-1,4-diamine Using General Procedure A: A solution of {4-[(3-methyl-pyridin-2-ylmethyl)-amino]-butyl}-carbamic acid tert-butyl ester (0.605 g, 2.06 mmol), 1-(tert-butoxycarbonyl)-2-(chloromethyl)-benzimidazole (0.804 g, 3.01 mmol), KI (72 mg, 0.43 mmol) and DIPEA (0.70 mL, 4.02 mmol) in CH$_3$CN (10 mL) was heated at 80° C. for 6 hours. Purification of the crude material by column chromatography on silica gel (15:1 CH$_2$Cl$_2$-MeOH) followed by column chromatography on silica gel (NH$_4$OH saturated Et$_2$O) provided 0.82 g (76%) of 2-{[(4-tert-Butoxycarbonylamino-butyl)-(3-methyl-pyridin-2-ylmethyl)-amino]-methyl}-benzoimidazole-1-carboxylic acid tert-butyl ester as a white foam.

To a solution of 2-{[(4-tert-Butoxycarbonylamino-butyl)-(3-methyl-pyridin-2-ylmethyl)-amino]-methyl}-benzoimidazole-1-carboxylic acid tert-butyl ester (0.82 g, 1.57 mmol) in EtOH (8 mL) was added anhydrous hydrazine (0.50 mL, 15.9 mmol) and the resultant mixture was stirred at room temperature overnight. The mixture was filtered through filter paper and concentrated. Purification of the crude material by column chromatography on silica gel (20:1:1 $CH_2Cl_2$-MeOH—$NH_4OH$) provided 0.42 g (62%) of {4-[(1H-benzoimidazol-2-ylmethyl)-(3-methyl-pyridin-2-ylmethyl)-amino]-butyl}-carbamic acid tert-butyl ester as white solid.

To a solution of {4-[(1H-benzoimidazol-2-ylmethyl)-(3-methyl-pyridin-2-ylmethyl)-amino]-butyl}-carbamic acid tert-butyl ester (0.215 g, 0.51 mmol) in $CH_2Cl_2$ (10 mL) was added $Et_3N$ (0.30 mL, 2.15 mmol) followed by benzenesulfonyl chloride (0.—ml, 1.02 mmol) and the resultant solution was stirred at room temperature overnight. The mixture was diluted with $CH_2Cl_2$ (40 mL), washed with brine (3×10 mL), dried ($Na_2SO_4$), and concentrated. Purification of the crude material by column chromatography on silica gel (15:1 $CH_2Cl_2$-MeOH) provided 0.202 g (70%) of {4-[(1-Benzenesulfonyl-1H-benzoimidazol-2-ylmethyl)-(3-methyl-pyridin-2-ylmethyl)-amino]-butyl}-carbamic acid tert-butyl ester as an orange-brown oil.

To a solution of {4-[(1-Benzenesulfonyl-1H-benzoimidazol-2-ylmethyl)-(3-methyl-pyridin-2-ylmethyl)-amino]-butyl}-carbamic acid tert-butyl ester (0.202 g, 0.36 mmol) in $CH_2Cl_2$ (3 mL) was added TFA (2 mL) and the resultant solution was stirred at room temperature for 1 hour. The mixture was concentrated and the residue was portioned between $CH_2Cl_2$ (10 mL) and saturated $Na_2CO_3$ (5 mL). Solid $Na_2CO_3$ was added until the aqueous phase was basic (pH~9) to litmus paper. The phases were separated and the aqueous phase was extracted with $CH_2Cl_2$ (3×10 mL). The combined organic extracts were dried ($Na_2SO_4$) and concentrated. Purification of the crude material by radial chromatography on silica gel (1 mm plate, 50:1:1 $CH_2Cl_2$-MeOH—$NH_4OH$) provided 72 mg (42%) of COMPOUND 144 as a pale yellow oil. $^1H$ NMR ($CDCl_3$) δ 1.25-1.37 (m, 2H), 1.47-1.57 (m, 4H), 2.16 (s, 3H), 2.58 (t, 2H, J=7.2 Hz), 2.78 (t, 2H, J=7.5 Hz), 4.03 (s, 2H), 4.33 (s, 2H), 7.07 (dd, 1H, J=4.8, 7.5 Hz), 7.30-7.44 (m, 5H), 7.55-7.60 (m, 1H), 7.68-7.72 (m, 1H), 7.93-8.03 (m, 3H), 8.35 (d, 1H, J=4.2 Hz); $^{13}C$ NMR ($CDCl_3$) δ 18.78, 23.49, 31.79, 42.22, 52.27, 53.79, 57.83, 113.92, 120.73. 122.61, 125.01, 125.47, 127.66, 129.70, 133.28, 133.45, 134.77, 138.31, 138.69, 142.14, 146.48, 152.39, 157.18; ES-MS m/z 464 (M+H). Anal. Calcd. For $C_{25}H_{29}N_5O_2S$.0.7$H_2O$: C, 63.06; H, 6.43; N, 14.71; S, 6.73. Found: C, 63.10; H, 6.48; N, 14.42; S, 6.52.

Example 145

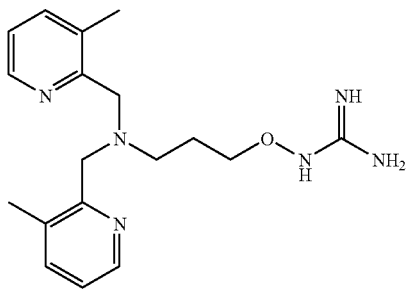

COMPOUND 145: N-{3-[Bis-(3-methyl-pyridin-2-ylmethyl)-amino]-1-propoxy}-guanidine (HBr salt)

Using General Procedure B: Reaction of [N,N'-di-(tert-butoxycarbonyl)]-3-amino-1-propoxyguanidine (0.363 g, 1.09 mmol) (Lu, T. et al. PCT Int. Appl. (1999), WO 9955355) and 3-methyl-pyridine-2-carboxaldehyde (0.398 g, 3.28 mmol) with $NaBH(OAc)_3$ (1.11 g, 5.22 mmol) in $CH_2Cl_2$ (10 mL) for 16 hours followed by purification of the crude material by column chromatography on silica gel ($NH_4OH$ saturated $Et_2O$) provided 0.341 g (58%) of a white solid. General Procedure D: Conversion to the HBr salt with simultaneous deprotection gave COMPOUND 145 as a white solid. $^1H$ NMR ($D_2O$) δ 1.85-1.94 (m, 2H), 2.52 (s, 6H), 2.77-2.82 (m, 2H), 3.85-3.89 (m, 2H), 4.36 (s, 4H), 7.89 (dd, 2H, J=5.7, 7.8 Hz), 8.39 (d, 2H, J=7.8 Hz), 8.62 (d, 2H, J=5.7 Hz); $^{13}C$ NMR ($D_2O$) δ 17.25, 24.21, 51.88, 54.30, 75.08, 126.12, 137.82, 138.74, 148.57, 150.94; ES-MS m/z 343 (M+H). Anal. Calcd. For $C_{18}H_{26}N_6O$.4.1HBr.0.7$H_2O$.0.1$CH_3OH$: C, 31.77; H, 5.01; N, 11.64; Br, 45.37. Found: C, 31.99; H, 4.85; N, 11.67; Br, 45.11.

Example 146

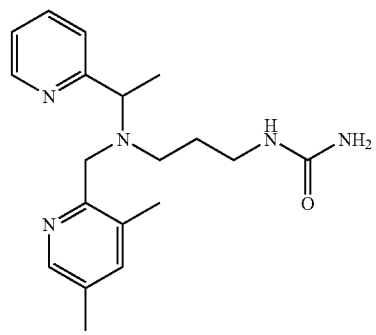

COMPOUND 146: {3-[(3,5-Dimethyl-pyridin-2-ylmethyl)-(1-pyridin-2-yl-ethyl)-amino]-propyl}-urea (HBr salt)

Using General Procedure B: Reaction of (3-Amino-propyl)-carbamic acid tert-butyl ester and 2-acetylpyridine with $NaBH(OAc)_3$ in $CH_2Cl_2$ gave [3-(1-pyridin-2-yl-ethylamino)-propyl]-carbamic acid tert-butyl ester as a colorless oil.

Using General Procedure B: Reaction of [3-(1-pyridin-2-yl-ethylamino)-propyl]-carbamic acid tert-butyl ester and 3,5-dimethyl-pyridine-2-carboxaldehyde with $NaBH(OAc)_3$ in $CH_2Cl_2$ gave $N^1$-(3,5-Dimethyl-pyridin-2-ylmethyl)-$N^1$-(1-pyridin-2-yl-ethyl)-propane-1,3-diamine as a colorless oil. $^1H$ NMR ($CDCl_3$) δ 1.45-1.66 (m, 7H), 2.25 (s, 3H), 2.26 (s, 3H), 2.42-2.65 (m, 4H), 3.75 (d, 1H, J=12.6 Hz), 3.81 (d, 1H, J=12.6 Hz), 4.01 (q, 1H, J=6.6 Hz), 7.11-7.16 (m, 1H), 7.22 (br s, 1H), 7.38 (d, 1H, J=7.8 Hz), 7.62 (dt, 1H, J=7.8, 1.8 Hz), 8.18 (br s, 1H), 8.55 (d, 1H, J=4.5 Hz).

To a solution of $N^1$-(3,5-Dimethyl-pyridin-2-ylmethyl)-$N^1$-(1-pyridin-2-yl-ethyl)-propane-1,3-diamine (60 mg, 0.20 mmol) in 2-propanol (2 mL) was added trimethylsilyl-isocyanate (40 μL, 0.30 mmol). The resultant solution was stirred at room temperature for 24 hours then concentrated. Purification of the crude material by radial chromatography on silica gel (1 mm plate, 20:1:1 $CH_2Cl_2$-MeOH—$NH_4OH$)

provided 58 mg (85%) of the free base as a white foam. Conversion to the HBr salt using General Procedure D gave COMPOUND 146 (79 mg, 72%) as a white solid. $^1$H NMR (D$_2$O) δ 1.45-1.55 (m, 5H), 2.38 (s, 3H), 2.43 (s, 3H), 2.46-2.69 (m, 2H), 2.89 (dd, 2H, J=6.3, 6.3 Hz), 4.18 (s, 2H), 4.52 (q, 1H, J=6.6 Hz), 7.97 (dd, 1H, J=6.6, 6.9 Hz), 8.10 (d, 1H, J=8.1 Hz), 8.15 (s, 1H), 8.38 (s, 1H), 8.57 (t, 1H, J=8.1 Hz), 8.74 (d, 1H, J=5.4 Hz); $^{13}$C NMR (D$_2$O) δ 14.64, 16.81, 17.46, 27.15, 37.62, 50.15, 50.69, 59.79, 126.76, 136.36, 137.34, 137.65, 142.02, 148.06, 149.07, 156.24; ES-MS m/z 342 (M+H). Anal. Calcd. For C$_{19}$H$_{27}$N$_5$O.3.2HBr.2H$_2$O: C, 35.66; H, 5.45; N, 10.94; Br, 39.95. Found: C, 35.89; H, 5.64; N, 10.57; Br, 40.29.

Example 147

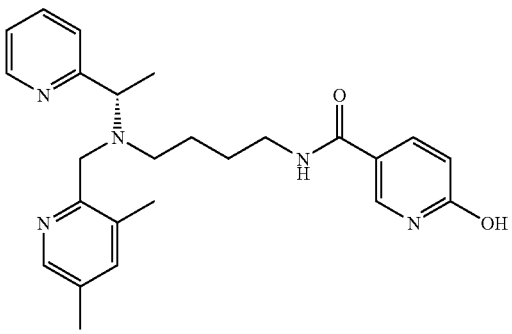

COMPOUND 147: (S)-N-{4-[(3,5-Dimethyl-pyridin-2-ylmethyl)-(1-pyridin-2-yl-ethyl)-amino]-butyl}-6-hydroxy-nicotinamide (HBr salt)

To a solution of (S)-N-(3,5-dimethylpyridin-2-ylmethyl)-N-(1-pyridin-2-yl-ethyl)-butane-1,4-diamine (HCl salt) (405 mg, 0.803 mmol) in water (2 mL) was added 1.0 N NaOH (5 mL). The mixture was extracted with CH$_2$Cl$_2$ (5×10 mL). The combined organic extracts were dried (Na$_2$SO$_4$) and concentrated and provided 0.22 g (88%) of (S)-N$^1$-(3,5-Dimethyl-pyridin-2-ylmethyl)-N$^1$-(1-pyridin-2-yl-ethyl)-butane-1,4-diamine.

Using General Procedure G: To a solution of (S)-N$^1$-(3,5-Dimethyl-pyridin-2-ylmethyl)-N$^1$-(1-pyridin-2-yl-ethyl)-butane-1,4-diamine (0.11 g, 0.35 mmol) in dry DMF (7 mL) was added 6-hydroxy-nicotinic acid (79 mg, 0.57 mmol) followed by EDCI (115 mg, 0.59 mmol), HOBT (86 mg, 0.63 mmol), and DIPEA (0.20 mL, 1.15 mmol). Purification of the crude material by radial chromatography on silica gel (1 mm plate, 10:1:1 CH$_2$Cl$_2$-MeOH—NH$_4$OH) provided 45 mg (29%) of the free base of the title compound as a colorless oil. Using General Procedure D: Conversion to the HBr salt gave COMPOUND 147 (49 mg, 62%) as a white solid. $^1$H NMR (D$_2$O) δ 1.19-1.57 (m, 4H), 1.58 (d, 3H, J=6.9 Hz), 2.35 (s, 3H), 2.39 (s, 3H), 2.51-2.71 (m, 2H), 3.20 (t, 2H, J=6.3 Hz), 4.22 (s, 2H), 4.55 (q, 1H, J=6.9 Hz), 6.64 (d, 1H, J=9.6 Hz), 7.82 (dd, 1H, J=2.7, 9.6 Hz), 7.94-7.99 (m, 2H), 8.05-8.12 (m, 2H), 8.35 (s, 1H), 8.55 (dt, 1H, J=1.5, 8.1 Hz), 8.75 (dd, 1H, J=1.2, 5.7 Hz); $^{13}$C NMR (D$_2$O) δ 14.53, 16.73, 17.45, 24.48, 26.53, 39.24, 51.26, 53.06, 60.39, 115.68, 119.28, 126.70, 135.93, 137.14, 137.29, 137.42, 140.95, 141.95, 148.01, 148.77, 149.56, 156.29, 165.39, 166.54; ES-MS m/z 434 (M+H). Anal. Calcd. For C$_{25}$H$_{31}$N$_5$O$_2$.3.5HBr.3.0H$_2$O: C, 38.96; H, 5.30; N, 9.09; Br, 36.28. Found: C, 38.99; H, 5.29; N, 8.95; Br, 36.24.

Example 148

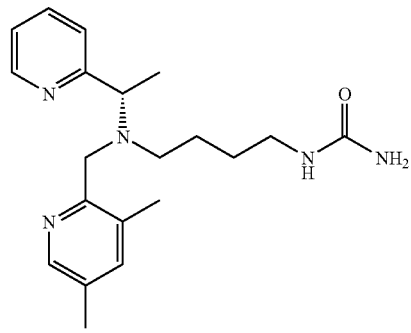

COMPOUND 148: (S)-{4-[(3,5-Dimethyl-pyridin-2-ylmethyl)-(1-pyridin-2-yl-ethyl)-amino]-butyl}-urea (HBr salt)

To a solution of (S)-N$^1$-(3,5-Dimethyl-pyridin-2-ylmethyl)-N$^1$-(1-pyridin-2-yl-ethyl)-butane-1,4-diamine (63 mg, 0.21 mmol) in 2-propanol (1 mL) was added trimethylsilyl-isocyanate (40 μL, 0.30 mmol). The resultant solution was stirred at room temperature for 6 hours then concentrated. Purification of the crude material by radial chromatography on silica gel (1 mm plate, 50:1:1 CH$_2$Cl$_2$-MeOH—NH$_4$OH) provided 31 mg (41%) of the free base of the title compound as a white foam. Using General Procedure D: Conversion to the HBr salt gave COMPOUND 148 (43 mg, 72%) as a white solid. $^1$H NMR (D$_2$O) δ 1.29 (br s, 4H), 1.59 (d, 3H, J=6.6 Hz), 2.42 (s, 3H), 2.47 (s, 3H), 2.51-2.68 (m, 2H), 2.92 (br s, 2H), 4.24 (s, 2H), 4.57 (q, 1H, J=6.6 Hz), 7.97-8.02 (m, 1H), 8.11-8.18 (m, 2H), 8.41 (s, 1H), 8.56-8.62 (m, 1H), 8.77 (d, 1H, J=5.4 Hz); $^{13}$C NMR (D$_2$O) δ 14.63, 16.78, 17.50, 24.06, 27.15, 39.52, 51.05, 52.94, 60.19, 126.67, 126.74, 136.16, 137.31, 137.65, 142.10, 147.93, 148.95, 149.33, 156.40, 161.76; ES-MS m/z 356 (M+H). Anal. Calcd. For C$_{20}$H$_{29}$N$_5$O.3.3HBr.2.5H$_2$O: C, 35.99; H, 5.63; N, 10.49; Br, 39.50. Found: C, 36.26; H, 5.38; N, 10.10; Br, 39.78.

Example 149

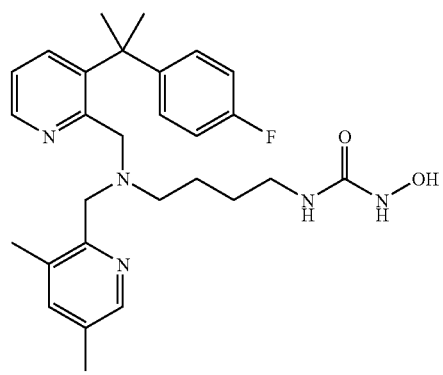

COMPOUND 149: 1-{4-[(3,5-Dimethyl-pyridin-2-ylmethyl)-[3-(1-methyl-1-(4-fluoro-phenyl)-ethyl)-pyridin-2-ylmethyl]-amino]-butyl}-3-(hydroxy)-urea To a solution of $N^1$-(3,5-Dimethyl-pyridin-2-ylmethyl)-$N^1$-{3-[1-(4-fluoro-phenyl)-1-methyl-ethyl]-pyridin-2-ylmethyl}-butane-1,4-diamine (0.210 g, 0.48 mmol) in dry THF (4 mL) was added 1,1'-carbonyldiimidazole (79 mg, 0.49 mmol), and the resultant solution was stirred room temperature for 30 minutes. The mixture was concentrated and the resultant oil was dissolved in DMF (2 mL), treated with DIPEA (0.50 mL, 2.87 mmol) and $NH_2OH \cdot HCl$ (134 mg, 1.93 mmol), and heated at 60° C. overnight. The mixture was cooled to room temperature, diluted with $CH_2Cl_2$ (50 mL), washed with brine (3×10 mL), dried ($Na_2SO_4$) and concentrated. Purification of the crude material by column chromatography on silica gel (20:21:1 $CH_2Cl_2$-MeOH—$NH_4OH$) provided 143 mg (59%) of COMPOUND 149 as a white solid. $^1H$ NMR ($CDCl_3$) δ 1.34 (br s, 4H), 1.65 (s, 6H), 1.93-2.25 (m, 8H), 3.09 (d, 2H, J=5.1 Hz), 3.32 (s, 2H), 3.45 (s, 2H), 6.87-7.09 (m, 5H), 7.21-7.38 (m, 3H), 7.89 (d, 1H, J=7.2 Hz), 8.14 (s, 1H), 8.53 (d, 1H, J=3.3 Hz), 10.27 (br s, 1H); $^{13}C$ NMR ($CDCl_3$) δ 18.26, 18.75, 23.87, 28.13, 31.51, 39.41, 42.50, 53.98, 57.19, 58.03, 115.56 (d, $J_{C-F}$=21 Hz), 122.18, 127.72 (d, $J_{C-F}$=7.5 Hz), 132.12, 132.87, 134.56, 139.50, 143.67, 145.71, 146.71, 146.97, 153.38, 157.78, 161.31 (d, $J_{C-F}$=243 Hz), 162.84; ES-MS m/z 494 (M+H). Anal. Calcd. For $C_{28}H_{36}N_5O_2F \cdot 0.7H_2O$: C, 66.43; H, 7.45; N, 13.83; F, 3.75. Found: C, 66.04; H, 7.29; N, 14.22; F, 3.85.

Example 150

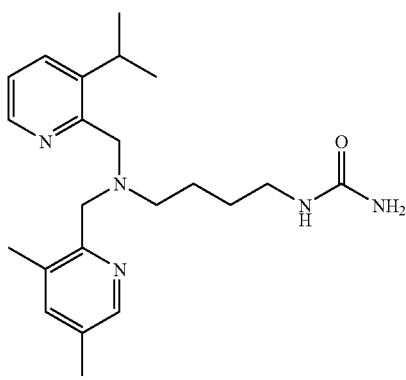

COMPOUND 150: {4-[(3,5-Dimethyl-pyridin-2-ylmethyl)-(3-isopropyl-pyridin-2-ylmethyl)-amino]-butyl}-urea (HBr salt)

To a solution of $N^1$-(3,5-Dimethyl-pyridin-2-ylmethyl)-$N^1$-{3-isopropyl-pyridin-2-ylmethyl}-butane-1,4-diamine (78 mg, 0.23 mmol) in 2-propanol (2 mL) was added trimethylsilyl-isocyanate (32 μL, 0.24 mmol). The resultant solution was stirred at room temperature overnight then concentrated. Purification of the crude material by radial chromatography on silica gel (1 mm plate, 20:1:1 $CH_2Cl_2$-MeOH—$NH_4OH$) provided 57 mg (64%) of the free base of the title compound as a white solid.

Using General Procedure D: Conversion to the HBr salt gave COMPOUND 150 as a white solid. $^1H$ NMR ($D_2O$) δ 1.20-1.48 (m, 10H), 2.46 (s, 3H), 2.47 (s, 3H), 2.60-2.66 (m, 2H), 2.95 (t, 2H, J=6.0 Hz), 3.32 (septet, 1H, J=6.6 Hz), 4.27 (s, 2H), 4.39 (s, 2H), 7.93 (dd, 1H, J=7.8, 6.0 Hz), 8.22 (s, 1H), 8.44 (s, 1H), 8.54 (d, 1H, J=7.8 Hz), 8.59 (d, 1H, J=6.0 Hz); $^{13}C$ NMR ($D_2O$) δ 17.17, 17.57, 22.09, 23.21, 27.12, 28.30, 38.97, 39.71, 54.03, 54.34, 55.37, 126.56, 136.92, 137.54, 138.05, 138.65, 144.82, 147.22, 148.02, 149.27, 150.03, 161.62; ES-MS m/z 384 (M+H). Anal. Calcd. For $C_{22}H_{33}N_5O \cdot 3.7HBr \cdot 3.5H_2O$: C, 35.42; H, 5.90; N, 9.39; Br, 39.63. Found: C, 35.47; H, 5.85; N, 9.02; Br, 39.70.

Example 151

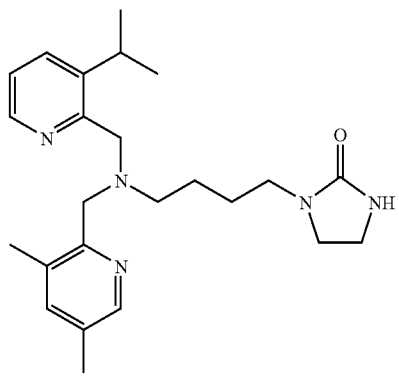

COMPOUND 151: 1-{4-[(3,5-Dimethyl-pyridin-2-ylmethyl)-(3-isopropyl-pyridin-2-ylmethyl)-amino]-butyl}-imidazolidin-2-one To a cold (0° C.) solution of $N^1$-(3,5-Dimethyl-pyridin-2-ylmethyl)-$N^1$-{3-isopropyl-pyridin-2-ylmethyl}-butane-1,4-diamine (163 mg, 0.48 mmol) in $CH_2Cl_2$ (5 mL) was added 2-chloroethylisocyanate (50 μL, 0.59 mmol) and the resultant mixture was stirred for 80 minutes then concentrated to provide a yellow oil. To a cold (0° C.) solution of the yellow oil in THF (5 mL) was added NaH (95% dry, 39 mg, 0.98 mmol). The cooling bath was removed and the resultant mixture was stirred at room temperature overnight. The mixture was treated with brine (10 mL) and extracted with $CH_2Cl_2$ (5×20 mL). The combined organic extracts were dried ($Na_2SO_4$) and concentrated. Purification of the crude material by column chromatography on silica gel (10:1:1 $CH_2Cl_2$-MeOH—$NH_4OH$) followed by radial chromatography on silica gel (1 mm plate, 50:1:1 $CH_2Cl_2$-MeOH—$NH_4OH$) provided 82 mg (41%) of COMPOUND 151 as a colorless oil. $^1H$ NMR ($CDCl_3$) δ 0.98 (d, 6H, J=6.9 Hz), 1.26-1.36 (m, 2H), 1.42-1.52 (m, 2H), 2.19 (s, 3H), 2.28 (s, 3H), 2.53 (dd, 2H, J=7.2, 7.2 Hz), 2.90-3.06 (m, 3H), 3.27-3.39 (m, 4H), 3.72 (s, 4H), 4.21 (br s, 1H), 7.—(dd, 1H, J=7.2, 4.8 Hz), 7.25 (s, 1H), 7.51 (dd, 1H, J=7.8, 1.5 Hz), 8.19 (s, 1H), 8.33 (dd, 1H, J=4.8, 1.5 Hz); $^{13}C$ NMR ($CDCl_3$) δ 18.27, 18.30, 23.51 (2 carbons), 24.36, 25.98, 27.46, 38.56, 43.75, 45.40, 54.47, 58.99, 59.59, 123.06, 132.12, 133.16, 133.61, 138.92, 144.24, 145.99, 146.57, 154.48, 156.29, 163.37; ES-MS m/z 410 (M+H). Anal. Calcd. For $C_{24}H_{35}N_5O \cdot 0.7H_2O$: C, 68.28; H, 8.69; N, 16.59. Found: C, 68.24; H, 8.52; N, 16.36.

Example 152

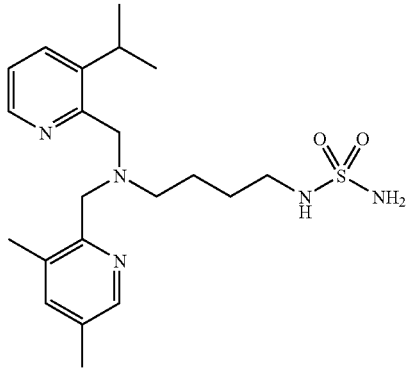

COMPOUND 152: {4-[(3,5-Dimethyl-pyridin-2-ylmethyl)-(3-isopropyl-pyridin-2-ylmethyl)-amino]-butyl}-sulfamide A solution of $N^1$-(3,5-Dimethyl-pyridin-2-ylmethyl)-$N^1$-{3-isopropyl-pyridin-2-ylmethyl}-butane-1,4-diamine (110 mg, 0.328 mmol) and sulfamide (94 mg, 0.98 mmol) in 1,4-dioxane (6 mL) was refluxed for 25 hours then cooled to room temperature and concentrated. Purification of the crude material by radial chromatography on silica gel (1 mm plate, 50:1:1 $CH_2Cl_2$-MeOH—$NH_4OH$) provided 51 mg (35%) of COMPOUND 152 as a white foam. $^1H$ NMR ($CDCl_3$) δ 1.03 (d, 6H, J=6.6 Hz), 1.42-1.50 (m, 2H), 1.59-1.66 (m, 2H), 2.15 (s, 3H), 2.28 (s, 3H), 2.58 (t, 2H, J=6.6 Hz), 2.93-3.03 (m, 3H), 3.70 (s, 2H), 3.73 (s, 2H), 5.15 (br s, 2H), 6.04 (br s, 1H), 7.16 (dd, 1H, J=7.8, 4.8 Hz), 7.25 (s, 1H), 7.54 (dd, 1H, J=7.8, 1.0 Hz), 8.25 (s, 1H), 8.41 (dd, 1H, J=4.8, 1.0 Hz); $^{13}C$ NMR ($CDCl_3$) δ 18.29, 18.37, 21.98, 23.60 (2 carbons), 27.53, 27.73, 42.81, 53.61, 57.69, 58.48, 123.28, 132.37, 133.15, 133.93, 139.23, 144.17, 146.13, 146.64, 154.10, 155.82; ES-MS m/z 420 (M+H). Anal. Calcd. For $C_{21}H_{33}N_5O_2S \cdot 0.3CH_2Cl_2 \cdot 0.5H_2O$: C, 56.34; H, 7.68; N, 15.42; S, 7.06. Found: C, 56.69; H, 7.45; N, 15.05; S, 6.76.

Example 153

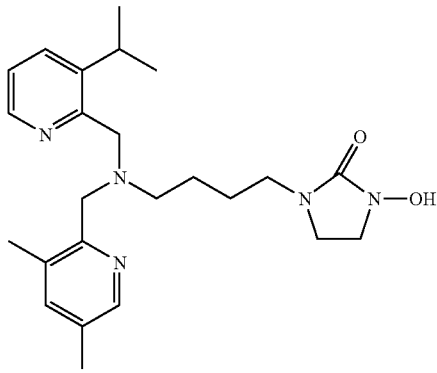

COMPOUND 153: 1-{4-[(3,5-Dimethyl-pyridin-2-ylmethyl)-(3-isopropyl-pyridin-2-ylmethyl)-amino]-butyl}-3-hydroxy-imidazolidin-2-one To a solution of 4-aminobutyraldehyde dimethyl acetal (2.73 g, 20.5 mmol) in THF (50 mL) was added 1,1'-carbonyldiimidazole (3.39 g, 20.9 mmol) and the resultant mixture was stirred at room temperature for 45 minutes. The mixture was concentrated under reduced pressure and the residue was dissolved in DMF (50 mL) and treated with DIPEA (18 mL, 103 mmol) and benzyloxyamine hydrochloride (10.2 g, 64.0 mmol). The mixture was heated at 60° C. overnight then concentrated under reduced pressure. The residue was dissolved in EtOAc (200 mL) and the solution was washed with brine (5×25 mL), dried ($MgSO_4$), and concentrated. Purification of the crude material by column chromatography on silica gel (4:1 hexanes-EtOAc followed by 100% EtOAc) provided 4.29 g (73%) of 3-(4,4-dimethoxy-butyl)-1-(benzyloxy)-urea as a yellow oil.

To a solution of 3-(4,4-dimethoxy-butyl)-1-(benzyloxy)-urea (4.14 g, 14.7 mmol) in DMF (40 mL) was added NaH (60 wt % in mineral oil, 0.659 g, 16.5 mmol). After 30 minutes, 1,2-dibromoethane (1.30 mL, 15.1 mmol) was added and the mixture was stirred for an additional 40 minutes. An additional amount of NaH (60 wt % in mineral oil, 0.636 g, 15.9 mmol) was added and the mixture was stirred at room temperature for 3 hours. The mixture was diluted with EtOAc (150 mL), washed with brine (5×25 mL), dried ($MgSO_4$), and concentrated. Purification of the crude material by column chromatography on silica gel (1:1 hexanes-EtOAc) provided 1.61 g (36%) of 1-Benzyloxy-3-(4,4-dimethoxy-butyl)-imidazolidin-2-one as a colorless oil.

To a solution of 1-Benzyloxy-3-(4,4-dimethoxy-butyl)-imidazolidin-2-one (1.61 g, 5.22 mmol) in EtOH (50 mL) was added ammonium formate (3.34 g, 52.9 mmol) and 10 wt % Pd/C (50% wet with water, 800 mg) and the mixture was stirred at room temperature for 2 hours. The mixture was vacuum filtered through celite and the cake was washed with EtOH. The solvent was removed from the filtrate under reduced pressure and the thus obtained solid was partitioned between water (10 mL) and $CH_2Cl_2$ (50 mL). The phases were separated and the aqueous phase was extracted with $CH_2Cl_2$ (3×10 mL). The combined organic extracts were dried ($Na_2SO_4$) and concentrated. Purification of the crude material by column chromatography on silica gel (100% EtOAc) provided 0.75 g (66%) of 1-(4,4-Dimethoxy-butyl)-3-hydroxy-imidazolidin-2-one as a colorless oil. ES-MS m/z 241 (M+Na).

To a solution of 1-(4,4-Dimethoxy-butyl)-3-hydroxy-imidazolidin-2-one (0.753 g, 3.45 mmol) in THF (3 mL) was added 1.0 N HCl (18 mL) and the mixture was stirred at room temperature overnight. The mixture was saturated with solid $Na_2CO_3$ (~2 g) and extracted with $CH_2Cl_2$ (5×10 mL). The combined organic extracts were dried ($Na_2SO_4$) and concentrated and provided 0.30 g (51%) of 4-(3-Hydroxy-2-oxo-imidazolidin-1-yl)-butyraldehyde as a yellow oil. $^1H$ NMR ($CDCl_3$) δ 1.83-1.91 (m, 2H), 2.53 (t, 2H, J=6.9 Hz), 3.25 (t, 2H, J=6.9 Hz), 3.30 (t, 2H, J=6.9 Hz), 3.48 (t, 2H, J=6.9 Hz), 7.75 (br s, 1H), 9.70 (s, 1H).

To a solution of 3,5-dimethyl-pyridine-2-carbaldehyde (0.566 g, 4.18 mmol) in MeOH (20 mL) was added $NH_4OAc$ (4.30 g, 55.7 mmol) and $NaBH_3CN$ (0.399 g, 6.35 mmol) and the resultant mixture was heated to reflux for 18 hours then cooled to room temperature. The mixture was treated 1.0 N NaOH (20 mL) and the resultant mixture was extracted with $CH_2Cl_2$ (5×20 mL). The combined organic extracts were dried ($Na_2SO_4$) and concentrated and provided 0.60 g of an orange slushy solid. Using General Procedure B: Reaction of the orange slushy solid above and 3-isopropyl-pyridine-2-carbaldehyde with NaBH(OAc)₃ in CH₂Cl₂ gave a yellow oil. The oil (0.426 g) was dissolved in THF (10 mL), treated with Boc₂O (226 mg, 1.04 mmol), and stirred at room temperature for 2 hours. The mixture was concentrated. Purification of the crude material by column chromatography on silica gel (1:1 hexanes-EtOAc) provided 0.163 g (43%) of (3,5-Dimethyl-pyridin-2-ylmethyl)-(3-isopropyl-pyridin-2-ylmethyl)-carbamic acid tert-butyl ester as a yellow oil. Deprotection with TFA following General Procedure F gave (3,5-Dimethyl-pyridin-2-ylmethyl)-(3-isopropyl-pyridin-2-ylmethyl)-amine as a yellow oil. $^1$H NMR (CDCl₃) δ 1.23 (d, 6H, J=6.9 Hz), 2.27 (s, 3H), 2.30 (s, 3H), 3.22 (septet, 1H, J=6.9 Hz), 3.96 (s, 2H), 4.05 (s, 2H), 7.14 (dd, 1H, J=7.8, 4.8 Hz), 7.23 (s, 1H), 7.55 (d, 1H, J=7.8 Hz), 8.22 (s, 1H), 8.39 (dd, 1H, J=4.8 Hz);

Using General Procedure B: Reaction of (3,5-Dimethyl-pyridin-2-ylmethyl)-(3-isopropyl-pyridin-2-ylmethyl)-amine and 4-(3-Hydroxy-2-oxo-imidazolidin-1-yl)-butyraldehyde with NaBH(OAc)₃ in CH₂Cl₂ gave COMPOUND 153 as a colorless oil. $^1$H NMR (CDCl₃) δ 0.98 (d, 6H, J=6.9 Hz), 1.28-1.46 (m, 4H), 2.19 (s, 3H), 2.28 (s, 3H), 2.53 (dd, 2H, J=7.2, 7.2 Hz), 2.93 (septet, 1H, J=6.9 Hz), 3.05 (t, 2H, J=7.2 Hz), 3.14 (t, 2H, J=7.2 Hz), 3.41 (t, 2H, J=7.2 Hz), 3.72 (s, 4H), 7.14 (dd, 1H, J=7.5, 4.8 Hz), 7.25 (s, 1H), 7.51 (dd, 1H, J=7.5, 1.2 Hz), 8.10 (br s, 1H), 8.19 (s, 1H), 8.33 (dd, 1H, J=4.8, 1.2 Hz); $^{13}$C NMR (CDCl₃) δ 18.29 (2 carbons), 23.52 (2 carbons), 24.17, 25.51, 27.48, 41.29, 44.36, 48.91, 54.31, 58.75, 59.38, 123.20, 132.28, 133.29, 133.85, 139.13, 144.34, 145.95, 146.48, 154.29, 156.08, 165.16; ES-MS m/z 426 (M+H). Anal. Calcd. For C₂₄H₃₅N₅O₂.1.2H₂O: C, 64.46; H, 8.43; N, 15.66. Found: C, 64.57; H, 8.03; N, 15.28.

Example 154

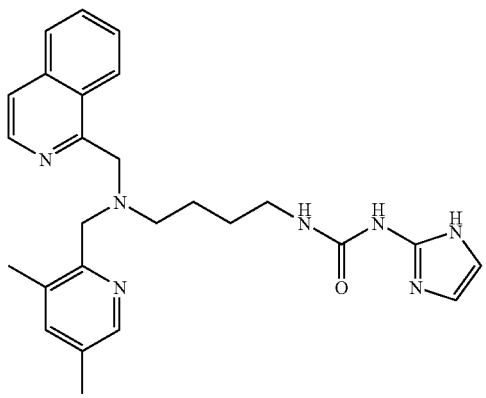

COMPOUND 154: 1-{4-[(3,5-Dimethyl-pyridin-2-ylmethyl)-isoquinolin-1-ylmethyl-amino]-butyl}-3-(1H-imidazol-2-yl)-urea To a warm (70° C.), stirred, solution of N-(3,5-Dimethyl-pyridin-2-ylmethyl)-N¹-isoquinolin-1-ylmethyl-butane-1,4-diamine (0.130 g, 0.37 mmol) and DIPEA (0.39 mL, 2.24 mmol) in DMF (4 mL) was added freshly prepared imidazole-1-carboxylic acid (1H-imidazol-2-yl)-amide (2 equiv). After 1 hour, the mixture was cooled to room temperature, diluted with brine (5 mL) and extracted with CH₂Cl₂ (4×10 mL). The combined organic extracts were washed with water (5×10 mL), dried (Na₂SO₄) and concentrated. Purification of the crude material by column chromatography on silica gel (20:1:1 CH₂Cl₂-MeOH—NH₄OH) provided 75 mg (42%) of COMPOUND 154 as a white solid. $^1$H NMR (CDCl₃) δ 1.32-1.36 (m, 2H), 1.56-1.72 (m, 2H), 2.18 (s, 3H), 2.29 (s, 3H), 2.68-2.77 (m, 4H), 3.80 (s, 2H), 4.—(s, 2H), 6.72 (s, 2H), 7.24-7.26 (m, 1H), 7.39-7.44 (m, 1H), 7.57-7.63 (m, 2H), 7.74-7.78 (m, 2H), 7.86 (d, 1H, J=8.4 Hz), 8.46 (s, 1H), 8.50 (d, 1H, J=5.7 Hz); $^{13}$C NMR (CDCl₃) δ 18.33, 18.72, 23.45, 27.95, 38.86, 55.10, 58.91, 59.22, 121.06, 126.47, 127.09, 127.31, 128.06, 130.36, 132.61, 133.16, 136.57, 139.42, 141.66, 144.62, 147.15, 153.65, 156.21, 158.75; ES-MS m/z 480 (M+23). Anal. Calcd. For C₂₆H₃₁N₇O.0.8CH₃OH: C, 66.62; H, 7.13; N, 20.29. Found: C, 66.84; H, 6.93; N, 20.23.

Example 155

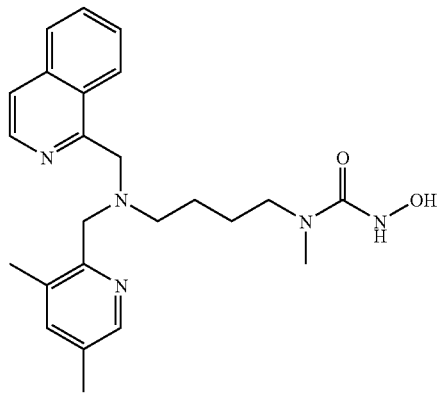

COMPOUND 155: 1-{4-[(3,5-Dimethyl-pyridin-2-ylmethyl)-isoquinolin-1-ylmethyl-amino]-butyl}-3-hydroxy-1-methyl-urea Using General Procedure B: Reaction of (4-Amino-butyl)-methyl-carbamic acid tert-butyl ester and 3,5-dimethyl-pyridine-2-carbaldehyde with NaBH(OAc)₃ in CH₂Cl₂ gave {4-[(3,5-Dimethyl-pyridin-2-ylmethyl)-amino]-butyl}-methyl-carbamic acid tert-butyl ester as a colorless oil.

Using General Procedure B: Reaction of {4-[(3,5-Dimethyl-pyridin-2-ylmethyl)-amino]-butyl}-methyl-carbamic acid tert-butyl ester and 1-isoquinoline-carbaldehyde with NaBH(OAc)₃ in CH₂Cl₂ gave {4-[(3,5-Dimethyl-pyridin-2-ylmethyl)-isoquinolin-1-ylmethyl-amino]-butyl}-methyl-carbamic acid tert-butyl ester as a yellow oil.

Deprotection with TFA following General Procedure F gave N-(3,5-Dimethyl-pyridin-2-ylmethyl)-N-isoquinolin-1-ylmethyl-N'-methyl-butane-1,4-diamine as a yellow oil.

To a solution of N-(3,5-Dimethyl-pyridin-2-ylmethyl)-N-isoquinolin-1-ylmethyl-N'-methyl-butane-1,4-diamine (0.196 g, 0.54 mmol) in dry THF (5.5 mL) was added N-(phenoxycarbonyl)hydroxylamine (0.168 g, 1.09 mmol) and the resultant solution was stirred at 60° C. overnight. The mixture was cooled to room temperature and concentrated. Purification of the crude material by column chromatography on silica gel (8:1:1 CH₂Cl₂-MeOH—NH₄OH) provided 126 mg (54%) of COMPOUND 155 as a white solid. $^1$H NMR (CDCl₃) δ 1.25-1.37 (m, 2H), 1.42-1.52 (m, 2H), 2.11 (s, 3H), 2.28 (s, 3H), 2.59 (t, 2H, J=6.9 Hz), 2.72 (s, 2H), 3.07 (t, 2H, J=6.9 Hz), 3.80 (s, 2H), 4.18 (s, 2H), 6.91 (br s, 1H), 7.25-7.31

(m, 2H), 7.44 (t, 1H, J=7.5 Hz), 7.55 (d, 1H, J=5.7 Hz), 7.62 (t, 1H, J=7.5 Hz), 7.77 (d, 1H, J=8.1 Hz), 8.03 (d, 1H, J=8.4 Hz), 8.25 (s, 1H), 8.43 (d, 1H, J=5.7 Hz); $^{13}$C NMR (CDCl$_3$) δ 18.33, 18.47, 23.20, 25.62, 33.88, 48.61, 54.33, 59.22, 59.48, 120.92, 126.87, 126.93, 127.22, 128.10, 130.30, 132.34, 133.19, 136.62, 139.25, 141.63, 146.86, 154.12, 159.23, 162.01; ES-MS m/z 444 (M+23). Anal. Calcd. For C$_{24}$H$_{31}$N$_5$O$_2$.0.5H$_2$O: C, 66.95; H, 7.49; N, 16.27. Found: C, 67.04; H, 7.46; N, 16.23.

Example 156

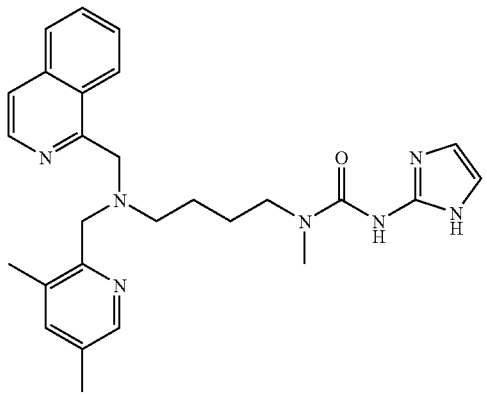

COMPOUND 156: 1-{4-[(3,5-Dimethyl-pyridin-2-ylmethyl)-isoquinolin-1-ylmethyl-amino]-butyl}-3-(1H-imidazol-2-yl)-1-methyl-urea To a warm (70° C.), stirred, solution of N-(3,5-Dimethyl-pyridin-2-ylmethyl)-N-isoquinolin-1-ylmethyl-N'-methyl-butane-1,4-diamine (0.204 g, 0.56 mmol) and DIPEA (0.59 mL, 3.39 mmol) in DMF (5 mL) was added freshly prepared imidazole-1-carboxylic acid (1H-imidazol-2-yl)-amide (2 equivs). After 1.5 hours, the mixture was cooled to room temperature and concentrated under reduced pressure. The residue was dissolved in CH$_2$Cl$_2$ (50 mL) and washed with water (5×10 mL). The organic phase was dried (Na$_2$SO$_4$) and concentrated. Purification of the crude material by column chromatography on silica gel (20:1:1 CH$_2$Cl$_2$-MeOH—NH$_4$OH) provided 234 mg (86%) of COMPOUND 156 as a white solid. $^1$H NMR (CDCl$_3$) δ 1.26-1.34 (m, 2H), 1.42-1.48 (m, 2H), 2.09 (s, 3H), 2.28 (s, 3H), 2.58 (t, 2H, J=7.5 Hz), 2.74 (s, 3H), 3.10 (t, 2H, J=7.5 Hz), 3.80 (s, 2H), 4.17 (s, 2H), 6.68 (s, 2H), 7.24-7.26 (m, 1H), 7.35-7.40 (m, 1H), 7.52-7.60 (m, 2H), 7.73 (d, 1H, J=8.1 Hz), 7.97 (d, 1H, J=8.7 Hz), 8.22 (s, 1H), 8.41 (d, 1H, J=5.7 Hz); $^{13}$C NMR (CDCl$_3$) δ 18.33, 18.40, 23.93, 25.82, 34.90, 48.89, 54.57, 59.86, 59.96, 120.82, 126.71, 126.92, 127.20, 128.12, 130.13, 132.27, 133.15, 136.62, 139.08, 141.76, 145.16, 146.87, 154.33, 156.14, 159.39; ES-MS m/z 472 (M+1). Anal. Calcd. For C$_{27}$H$_{33}$N$_7$O.0.5H$_2$O: C, 67.48; H, 7.13; N, 20.40. Found: C, 67.57; H, 7.08; N, 20.52.

Example 157

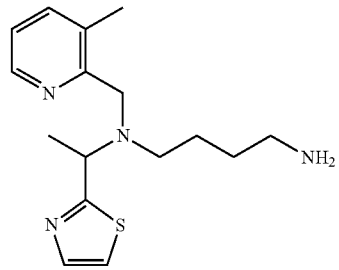

COMPOUND 157: N'-(3-methyl-pyridin-2-ylmethyl)-N''-(1-thiazol-2-yl-ethyl)-butane-1,4-diamine HBr salt Using General Procedure B: Reaction of (4-amino-butyl)-carbamic acid tert-butyl ester and 2-acetyl thiazole in MeOH with NaBH$_4$ gave [4-(1-thiazol-2-yl-ethylamino)-butyl]-carbamic acid tert-butyl ester as a colorless oil. $^1$H NMR (CDCl$_3$) δ 1.44 (s, 9H), 1.50-1.57 (m, 4H), 1.66 (d, 3H, J=6.5 Hz), 2.58-2.69 (m, 2H), 3.08-3.14 (m, 2H), 4.15 (q, 1H, J=6.7 Hz), 7.24 (d, 1H, J=3.3 Hz), 7.70 (d, 1H, J=3.3 Hz).

Using General Procedure B: Reaction of [4-(1-thiazol-2-yl-ethylamino)-butyl]-carbamic acid tert-butyl ester and 3-methyl-2-pyridine carbaldehyde in CH$_2$Cl$_2$ with NaBH(OAc)$_3$ gave {4-[(3-methyl-pyridin-2-ylmethyl)-(1-thiazol-2-yl-ethyl)-amino]-butyl}-carbamic acid tert-butyl ester as an oil. $^1$H NMR (CDCl$_3$) δ 1.25-1.41 (m, 2H), 1.43 (s, 9H), 1.45-1.53 (m, 2H), 1.55 (d, 3H, J=Hz), 2.47-2.52 (m, 5H), 2.98-3.04 (m, 2H), 3.83 (d, 1H, J=Hz), 4.00 (d, 1H, J=Hz), 4.11 (q, 1H, J=Hz), 4.53 (bs, 1H), 7.10 (dd, 1H, J=7.6, 4.8 Hz), 7.23 (d, 1H, J=3.3 Hz), 7.44 (d, 1H, J=6.8 Hz), 7.66 (d, 1H, J=3.3 Hz), 8.36 (dd, 1H, J=4.8, 1.1 Hz).

Deprotection with TFA using General Procedure F and salt formation using General Procedure D gave COMPOUND 157 as a white solid. $^1$H NMR (D$_2$O) δ 1.54-1.63 (m, 4H), 1.72 (d, 3H, J=7.0 Hz), 2.45 (s, 3H), 2.70-2.80 (m, 1H), 2.86-2.95 (m, 3H), 4.23 (d, 1H, J=18.4 Hz), 4.35 (d, 1H, J=18.0 Hz), 4.82 (q, 1H, J=7.0 Hz), 7.83 (dd, 1H, J=7.4, 6.1 Hz), 7.94 (d, 1H, J=3.7 Hz), 8.07 (d, 1H, J=3.7 Hz), 8.31 (d, 1H, J=5.7 Hz), 8.57 (d, 1H, J=7.9 Hz); $^{13}$C NMR (D$_2$O) δ 14.87, 17.03, 24.47, 24.97, 39.55, 50.63, 52.50, 58.23, 123.87, 125.93, 136.71, 137.21, 138.84, 147.83, 151.55, 175.84; ES-MS m/z 305 (M+H). Anal Calcd. For C$_{16}$H$_{24}$N$_4$S.4.0(HBr).0.2(C$_4$H$_{10}$O): C, 29.41; H, 5.11; N, 8.17; Br, 46.58; S, 4.67. Found C, 29.66; H, 5.35; N, 8.21; Br, 46.29; S, 4.70.

Example 158

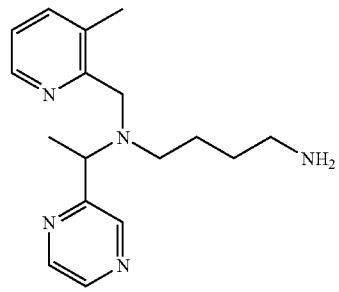

COMPOUND 158: N$^1$-(3-methyl-pyridin-2-ylmethyl)-N$^1$-(1-pyrazin-2-yl-ethyl)-butane-1,4-diamine HBr salt Using General Procedure B: Reaction of (4-amino-butyl)-carbamic acid tert-butyl ester and 2-acetyl pyrazine in MeOH with NaBH$_4$ gave [4-(1-pyrazin-2-yl-ethylamino)-butyl]-carbamic acid tert-butyl ester (294 mg, 91%) as a colorless oil. $^1$H NMR (CDCl$_3$) δ 1.44 (s, 9H), 1.50-1.57 (m, 4H), 1.59 (d, 3H, J=6.6 Hz), 2.38-2.43 (m, 1H), 2.51-2.59 (m, 1H), 3.08-3.14 (m, 2H), 3.08 (m, 2H), 3.91 (d, 1H, J=6.7 Hz), 4.72 (bs, 1H), 8.45 (d, 1H, J=2.5 Hz), 8.53 (d, 1H, J=2.6 Hz), 8.60 (s, 1H).

Using General Procedure B: Reaction of [4-(1-pyrazin-2-yl-ethylamino)-butyl]-carbamic acid tert-butyl ester and 3-methyl-pyridine-2-carbaldehyde in CH$_2$Cl$_2$ with NaBH(OAc)$_3$ gave {4-[(3-methyl-pyridin-2-ylmethyl)-(1-pyrazin-2-yl-ethyl)-amino]-butyl}-carbamic acid tert-butyl ester (229 m, 63%) as an oil. $^1$H NMR (CDCl$_3$) δ 1.26-1.39 (m, 6H), 1.43 (s, 9H), 1.50 (d, 1H, J=7.0 Hz), 2.30 (s, 3H), 2.90-2.96 (m, 2H), 4.05 (s, 2H), 4.08 (d, 1H, J=7.0 Hz) 7.10 (dd, 1H, J=7.5, 4.8 Hz), 7.41 (d, 1H, J=7.5 Hz), 8.37 (dd, 1H, J=5.1, 1.2 Hz), 8.39 (s, 1H), 8.48-8.50 (m, 1H), 8.63 (d, 1H, J=1.5 Hz).

Deprotection with TFA using General Procedure F and salt formation using General Procedure D gave COMPOUND 158 as a white solid. $^1$H NMR (D$_2$O) δ 1.57-1.75 (m, 6H), 2.32 (s, 3H), 2.92 (t, 2H, J=7.2 Hz), 3.04-3.24 (m, 2H), 4.44 (d, 1H, J=17.4 Hz), 4.54 (d, 1H, J=17.3 Hz), 7.57 (dd, 1H, J=7.8, 5.5 Hz), 7.99 (d, 1H, J=7.8 Hz), 8.46 (d, 1H, J=4.7 Hz), 8.58 (d, 1H, J=2.7 Hz), 8.7 (dd, 1H, J=2.6, 1.5 Hz), 8.75 (d, 1H, J=1.4 Hz); $^{13}$C NMR (D$_2$O) 614.12, 22.87, 24.63, 39.35, 51.36, 53.03, 61.36, 125.30, 134.96, 142.07, 143.85, 144.13, 144.33, 145.19, 149.81, 153.38; ES-MS m/z 300 (M+H). Anal Calcd. For C$_{17}$H$_{25}$N$_5$.3.7(HBr).1.6(H$_2$O): C, 32.53; H, 5.12; N, 11.16; Br, 47.11. Found C, 32.48; H, 5.25; N, 10.95; Br, 47.34.

Example 159

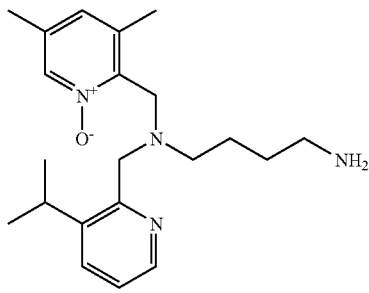

COMPOUND 159: N'-(3,5-Dimethyl-1-oxy-pyridin-2-ylmethyl)-N'-(3-isopropyl-pyridin-2-ylmethyl)-butane-1,4-diamine (HBr salt)

Hydroxylamine hydrochloride (3.00 g, 43.2 mmol) was added to a stirred solution of 3,5-dimethyl-pyridine-2-carbaldehyde (2.94 g, 21.6 mmol) in MeOH (36 mL) at ambient temperature under N$_2$. A suspension formed immediately. The mixture was concentrated after stirring for 16 h to remove the methanol. The slurry was dissolved in saturated NaHCO$_3$ solution (50 mL) and extracted with EtOAc (5×40 mL). The combine organic layers were dried over Na$_2$SO$_4$ and concentrated in vacuo to afford 3,5-methyl-pyridine-2-carbaldehyde oxime as a white solid (3.15 g, 97%). $^1$H NMR (CDCl$_3$) δ 2.32 (s, 3H), 2.45 (s, 3H), 7.34 (s, 1H), 8.34 (s, 1H), 8.42 (s, 1H).

3,5-Dimethyl-pyridine-2-carbaldehyde oxime (3.15 g, 21.0 mmol), NH$_4$OH (105 mL), ammonium acetate (3.24 g, 42.0 mmol), zinc dust (8.24 g, 126 mol) and EtOH (35 mL) were combined and warmed to 55° C. The mixture was stirred for 20 h, then cooled to ambient temperature and filtered through a celite pad to remove the zinc. The celite pad was thoroughly washed with methanol. The filtrate was concentrated in vacuo and the resulting aqueous mixture was extracted with CH$_2$Cl$_2$ (8×250 mL). The aqueous layer was basified to pH 14 with 10 N NaOH and extracted further with CH$_2$Cl$_2$/i-PrOH, 95:5 (5×250 mL). The combined organic layers were dried over Na$_2$SO$_4$ and concentrate in vacuo. Purification by flash chromatography on silica gel (CH$_2$Cl$_2$/MeOH/NH$_4$OH, 95:4:1) afforded C-(3,5-dimethyl-pyridin-2-yl)-methylamine as an orange oil. $^1$H NMR (CDCl$_3$) δ 2.26 (s, 3H), 2.28 (s, 3H), 3.91 (s, 2H), 7.24 (s, 1H), 8.23 (s, 1H).

A solution C-(3,5-dimethyl-pyridin-2-yl)-methylamine (354 mg, 2.60 mmol), Boc$_2$O (567 mg, 2.6 mmol) and DIPEA (453 μL, 5.2 mmoL) in THF was stirred at ambient temperature for 18 h. After the solvent was removed in vacuo, the residue was taken up in a saturated solution of NaHCO$_3$ (25 mL) and extracted with CH$_2$Cl$_2$ (3×50 mL). The combined organic layers were dried over Na$_2$SO$_4$ and concentrated in vacuo to afford (3,5-dimethyl-pyridin-2-ylmethyl)-carbamic acid tert-butyl ester (657 mg, >99%). $^1$H NMR (CDCl$_3$) δ 1.48 (s, 9H), 2.41 (s, 3H), 2.29 (s, 3H), 4.37 (d, 2H, J=6.0 Hz), 6.15 (bs, 1H), 7.26 (s, 1H), 8.19 (s, 1H).

A solution of (3,5-dimethyl-pyridin-2-ylmethyl)-carbamic acid tert-butyl ester (657 mg, 2.60 mmol) and 3-chloroperoxybenzoic acid (1.35 g, 7.8 mmol) in CH$_2$Cl$_2$ (26 mL) was stirred at ambient temperature for 3 h, then concentrated to dryness in vacuo. The solid was taken up in MeOH and silica gel (20 g) and concentrated to dryness. The silica mixture was then purified by flash chromatography on silica gel using EtOAc/MeOH (1:0 to 6:1) to afford (3,5-dimethyl-1-oxy-pyridin-2-ylmethyl)-carbamic acid tert-butyl ester as a white solid (454 mg, 69%). $^1$H NMR (CDCl$_3$) δ 1.40 (s, 9H), 2.25 (s, 3H), 2.49 (s, 3H), 4.49 (d, 2H, J=6.0 Hz), 6.16 (bs, 1H), 6.95 (s, 1H), 7.97 (s, 1H).

To a solution of (3,5-dimethyl-1-oxy-pyridin-2-ylmethyl)-carbamic acid tert-butyl ester (454 mg, 1.80 mmol) in CH$_2$Cl$_2$ (12 mL) was added TFA (3 mL) and stirred for 3 h. A 10 N NaOH solution (7 mL) was added, then diluted with water (15 mL) and extracted with 95:5 CH$_2$Cl$_2$/i-PrOH (10×70 mL). The combined organic layers were dried over Na$_2$SO$_4$ and concentrated in vacuo to afford C-(3,5-dimethyl-1-oxy-pyridin-2-yl)-methylamine (266 mg, 97%) as an oil. $^1$H NMR (CDCl$_3$) δ 2.24 (s, 3H), 2.36 (s, 3H), 4.03 (s, 2H), 6.92 (s, 1H), 7.98 (s, 1H).

Using General Procedure B: Reaction of C-(3,5-dimethyl-1-oxy-pyridin-2-yl)-methylamine, 3-isopropyl-pyridine-2-carbaldehyde and NaBH(OAc)$_3$ gave (3,5-dimethyl-1-oxy-pyridin-2-ylmethyl)-(3-isopropyl-pyridin-2-ylmethyl)-amine (68.1 mg, 38%) as an oily residue. $^1$H NMR (CDCl$_3$) δ 1.24 (s, 9H), 2.23 (s, 3H), 2.35 (s, 3H), 4.01 (s, 2H), 4.08 (s, 2H), 6.89 (s, 1H), 7.14 (dd, 1H, J=7.79, 4.74 Hz), 7.56 (dd, 1H, J=7.9, 1.6 Hz), 7.98 (s, 1H), 8.37 (dd, 1H, J=4.7, 1.6 Hz).

Using General Procedure B: Reaction of the amine above and 4-(1,3-Dioxo-1,3-dihydro-isoindol-2-yl)-butyraldehyde with NaBH(OAc)$_3$ in CH$_2$Cl$_2$ gave a crude product mixture which was dissolved in EtOH and reacted with H$_2$NNH$_2$.H$_2$O. Aqueous work-up and purification by flash chromatography on silica gel using CH$_2$Cl$_2$/MeOH/NH$_4$OH (84:15:1) afforded N'-(3,5-dimethyl-1-oxy-pyridin-2-ylmethyl)-N'-(3-isopropyl-pyridin-2-ylmethyl)-butane-1,4-diamine (63.3 mg, 79%) as an oily residue. ¹H NMR (CDCl₃) δ 1.08 (d, 6H, J=6.9 Hz), 1.25-1.35 (m, 2H), 1.49-1.58 (m, 2H), 2.15 (s, 3H), 2.23 (s, 3H), 2.54-2.59 (m, 4H), 3.15 (sep, 1H, J=6.9 Hz), 3.79 (s, 2H), 4.04 (s, 2H), 6.49 (s, 1H), 7.16 (dd, 1H, J=7.9, 4.8 Hz), 7.53 (dd, 1H, J=7.8, 1.6 Hz), 8.00 (s, 1H), 8.36 (dd, 1H, J=4.7, 1.7 Hz).

Conversion to the HBr salt using General Procedure D gave COMPOUND 159 as a white solid. ¹H NMR (D₂O) δ 1.21 (d, 6H, J=6.8 Hz), 1.61-1.75 (m, 2H), 1.81-1.89 (m, 2H), 2.27 (s, 3H), 2.40 (s, 3H), 2.93-2.99 (m, 2H), 3.05 (sep, 1H, J=6.8 Hz), 3.27-3.32 (m, 2H), 4.57 (s, 2H), 4.60 (s, 2H), 7.42 (s, 1H), 7.52 (dd, 1H, J=8.0, 5.1 Hz), 8.02 (d, 1H, J=8.0 Hz), 8.11 (s, 1H), 8.36 (d, 1H, J=5.0 Hz); ¹³C NMR (D2O) δ 17.50, 18.39, 22.25, 22.61, 24.42, 28.22, 39.21, 51.61, 55.07, 55.52, 125.52, 135.76, 137.71, 138.28, 138.47, 138.73, 143.68, 144.14, 147.26; ES-MS m/z 357 (M+H). Anal Calcd. For C₂₁H₃₂N₄O.3.9(HBr).3.6(H₂O).0.3(C₄H₁₀O): C, 35.12; H, 6.12; N, 7.38; Br, 41.05. Found: C, 34.93; H, 5.83; N, 7.30; Br, 41.25.

Example 160

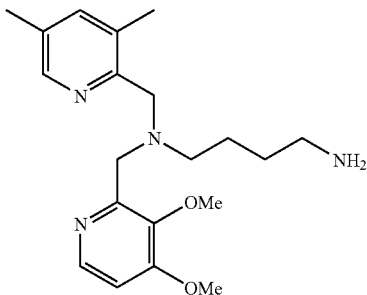

COMPOUND 160: N'-(3,4-Dimethoxy-pyridin-2-ylmethyl)-N'-(3,5-dimethyl-pyridin-2-ylmethyl)-butane-1,4-diamine Using General Procedure A: Reaction of {4-[(3-methyl-pyridin-2-ylmethyl)-amino]-butyl}-carbamic acid tert-butyl ester, 3,4-dimethoxy-2-chloromethyl pyridinium hydrochloride, DIPEA and KI in CH₃CN gave {4-[(3,4-dimethoxy-pyridin-2-ylmethyl)-(3,5-dimethyl-pyridin-2-ylmethyl)-amino]-butyl}-carbamic acid tert-butyl ester as an oily residue. ¹H NMR (CDCl₃) δ 1.30-1.35 (m, 2H), 1.43 (s, 9H), 1.48-1.55 (m, 2H), 2.14 (s, 3H), 2.27 (s, 3H), 2.95-3.00 (m, 2H), 3.76 (s, 6H), 3.91 (s, 3H), 5.14 (bs, 1H), 6.79 (d, 1H, J=6.9 Hz), 7.22 (s, 1H), 8.19 (s, 1H), 8.25 (d, 1H, J=6.9 Hz).

Deprotection with TFA using General Procedure F gave N'-(3,4-dimethoxy-pyridin-2-ylmethyl)-N'-(3,5-dimethyl-pyridin-2-ylmethyl)-butane-1,4-diamine as a colorless oil. ¹H NMR (CDCl₃) δ 1.30-1.35 (m, 2H), 1.48-1.53 (m, 2H), 2.16 (s, 3H), 2.25 (s, 3H), 2.49-2.60 (m, 4H), 3.72 (s, 3H), 3.77 (s, 4H), 3.90 (s, 3H), 6.77 (d, 1H, J=6.9 Hz), 7.20 (s, 1H), 8.17 (s, 1H), 8.24 (d, 1H, J=6.9 Hz).

Conversion to the HBr salt using General Procedure D gave COMPOUND 160 as a white solid (105 mg, 67%). ¹H NMR (D₂O) δ 1.56-1.60 (m, 4H), 2.40 (s, 3H), 2.43 (s, 3H), 2.70-2.76 (m, 2H), 2.90-2.97 (m, 2 h), 3.89 (s, 3H), 4.—(s, 3H), 4.18 (s, 2H), 4.20 (s, 2H), 7.49 (d, 1H, J=6.9 Hz), 8.—(s, 1H), 8.35 (s, 1H), 8.41 (d, 1H, J=6.90 Hz); ¹³C NMR (D₂O) δ 16.89, 17.44, 22.96, 24.98, 39.59, 51.07, 53.70, 55.25, 58.42, 62.23, 110.29, 136.88, 137.38, 137.68, 139.61, 144.98, 145.69, 148.35, 148.80, 166.53; ES-MS m/z 359 (M+H). Anal Calcd. For C₂₀H₃₀N₄O₂.4.3(HBr).1.8(H₂O).0.5 (C₄H₁₀O): C, 34.06; H, 5.57; N, 7.22; Br, 44.28. Found: C, 34.14; H, 5.37; N, 7.22; Br, 44.23.

Example 161

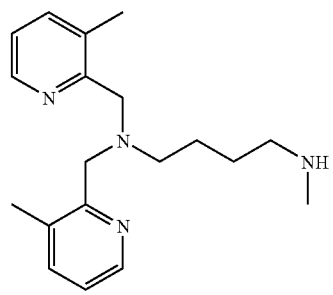

COMPOUND 161: N'-methyl-N,N-bis-(3-methyl-pyridin-2-ylmethyl)-butane-1,4-diamine (HBr salt)

Using General Procedure B: Reaction of (4-amino-butyl)-methyl-carbamic acid tert-butyl ester, 3-methyl-pyridine-2-carbaldehyde and NaBH(OAc)₃ in CH₂Cl₂ gave {4-[bis-(3-methyl-pyridin-2-ylmethyl)-amino]-butyl}-methyl-carbamic acid tert-butyl ester as yellow solid. ¹H NMR (CDCl₃) δ 1.23-1.33 (m, 2H), 1.39-1.42 (m, 11H), 2.14 (s, 6H), 2.52 (t, 2H, J=7.0 Hz), 2.72 (s, 3H), 3.00-3.06 (m, 2H), 3.73 (s, 4H), 7.09 (dd, 2H, J=7.5, 4.9 Hz), 7.39 (d, 2H, J=7.4 Hz), 8.36 (d, 2H, J=4.1 Hz).

Conversion to the HBr salt using General Procedure D gave COMPOUND 161 as an orange solid. ¹H NMR (D₂O) δ 1.50-1.55 (m, 4H), 2.46 (s, 6H), 2.60 (s, 3H), 2.89-2.93 (m, 2H), 2.66-2.69 (m, 2H), 4.31 (s, 4H), 7.83 (dd, 2H, J=7.6, 6.2 Hz), 8.33 (d, 2H, J=7.8 Hz), 8.56 (d, 2H, J=5.8 Hz); ¹³C NMR (D₂O) δ 17.20, 22.81, 23.63, 33.04, 48.99, 54.40, 54.94, 126.00, 137.70, 138.59, 148.47, 151.04; ES-MS m/z 3—(M+H). Anal Calcd. For C₁₉H₂₈N₄.4.7(HBr).2.8(H₂O).0.3 (C₄H₁₀O): C, 31.70; H, 5.44; N, 7.32; Br, 49.06. Found: C, 31.64; H, 5.31; N, 7.36; Br, 49.08.

Example 162

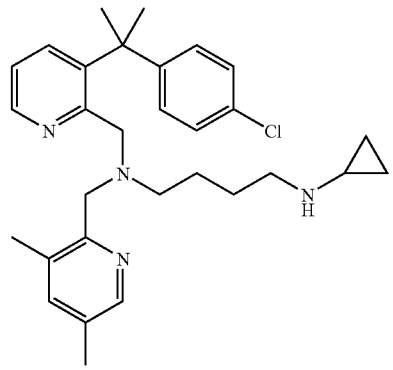

135

COMPOUND 162: N-{3-[1-(4-Chloro-phenyl)-1-methyl-ethyl]-pyridin-2-ylmethyl}-N'-cyclopropyl-N-(3,5-dimethyl-pyridin-2-ylmethyl)-butane-1,4-diamine (HBr salt)

To a solution cooled (0° C.) solution of {3-[1-(4-chloro-phenyl)-1-methyl-ethyl]-pyridin-2-yl}-methanol (206 mg, 0.768 mmol) and Et₃N (165 µL, 1.15 mmol) in CH₂Cl₂ (4 mL) was added MsCl (67 µL, 0.845 mmol). The mixture was warmed to ambient temperature and stirred for 1 h. Water (10 mL) was added and the mixture was extracted with CH₂Cl₂ (3×30 mL). The combined organic layers were dried over Na₂SO₄ and concentrated in vacuo to afford methanesulfonic acid 3-[1-(4-chloro-phenyl)-1-methyl-ethyl]-pyridin-2-ylmethyl ester (269 mg, 99%) as a yellow solid. ¹H NMR (CDCl₃) δ 1.70 (s, 6H), 3.01 (s, 3H), 4.78 (s, 2H), 7.05 (d, 2H, J=6.0 Hz), 7.29 (d 2H, J=6.0 Hz), 7.37 (dd, 1H, J=6.0, 3.0 Hz), 7.96 (dd, 1H, J=7.5, 3.0 Hz), 8.59 (dd, 1H, J=6.0, 3.0 Hz).

Using General Procedure A: Reaction of cyclopropyl-{4-[(3,5-dimethyl-pyridin-2-ylmethyl)-amino]-butyl}-carbamic acid tert-butyl ester and DIPEA in CH₃CN with methanesulfonic acid 3-[1-(4-chloro-phenyl)-1-methyl-ethyl]-pyridin-2-ylmethyl ester gave {4-[{3-[1-(4-chloro-phenyl)-1-methyl-ethyl]-pyridin-2-ylmethyl}-(3,5-dimethyl-pyridin-2-ylmethyl)-amino]-butyl}-cyclopropyl-carbamic acid tert-butyl ester as an oil. ¹H NMR (CDCl₃) δ 0.51-0.54 (m, 2H), 0.64-0.70 (m, 2H), 1.21-1.28 (m, 4H), 1.42 (s, 9H), 1.63 (s, 6H), 2.14 (s, 3H), 2.28 (s, 3H), 2.33-2.40 (m, 3H), 3.00-3.04 (m, 2H), 3.27 (s, 2H), 2.62 (s, 2H), 6.90 (d, 2H, J=8.6 Hz), 7.14 (d, 2H, J=8.5 Hz), 7.20-7.22 (m, 2H), 7.84 (d, 1H, J=7.4 Hz), 8.12 (s, 1H), 8.53 (d, 1H, J=3.3 Hz).

Conversion to the HBr salt using General Procedure D gave COMPOUND 162 as a beige solid. ¹H NMR (D₂O) δ 0.80-0.90 (m, 4H), 1.14-1.22 (m, 4H), 1.38-1.43 (m, 2H), 1.74 (s, 6H), 2.25-2.33 (m, 5H), 2.45 (s, 3H), 2.65 (s, 1H), 2.96-3.01 (m, 2H), 3.54 (dd, 1H, J=13.7, 6.7 Hz), 3.73-3.74 (m, 4H), 7.25 (d, 2H, J=8.1 Hz), 7.40 (d, 2H, J=8.1 Hz), 8.02-8.07 (m, 1H), 8.18 (s, 1H), 8.39 (s, 1H), 8.68 (d, 1H, J=5.3 Hz), 8.67 (d, 1H, J=8.8 Hz); ¹³C NMR (D₂O) δ 17.19, 17.50, 22.01, 23.52, 29.42, 30.28, 42.88, 48.02, 52.52, 53.74, 54.41, 126.51, 128.57, 129.43, 132.66, 136.87, 137.53, 138.29, 139.36, 145.27, 146.20, 147.26, 147.71, 149.25, 151.81; ES-MS m/z 492 (M+H). Anal Calcd. For C₃₀H₃₉N₄Cl.3.7(HBr).2.5 (H₂O).0.5(C₄H₁₀O): C, 44.05; H, 6.09; N, 6.42; Br, 33.88; Cl, 4.06. Found: C, 43.96; H, 6.09; N, 6.55; Br, 33.96; Cl, 3.88.

Example 163

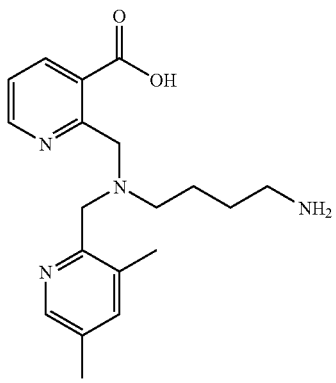

136

COMPOUND 163: 2-{[(4-Amino-butyl)-(3,5-dimethyl-pyridin-2-ylmethyl)-amino]-methyl}-nicotinic acid (HBr)

To a solution of Boc-protected 2-{[(4-Amino-butyl)-(3,5-dimethyl-pyridin-2-ylmethyl)-amino]-methyl}-nicotinic acid ethyl ester (96 mg, 0.20 mmol) in THF/H₂O (3 mL, 1:1) was added LiOH (52 mg, 2.17 mmol) and the reaction stirred at 50° C. overnight. The mixture was cooled, neutralized to pH 4-5 with 6 N HCl and 10% aqueous citric acid and extracted with CH₂Cl₂ (2×20 mL). The pH of the aqueous phase was adjusted to 7 with saturated aqueous NaHCO₃ and the aqueous layer extracted again with CH₂Cl₂ (2×10 mL). The combined organic extracts were dried (Na₂SO₄) and concentrated to afford a clear oil (110 mg). Purification of this material by radial chromatography on silica gel (1 mm plate, CH₂Cl₂/MeOH/NH₄OH, 50:1:1 then 25:1:1 then 10:1:1) gave the acid (47 mg, 53%) as a clear oil. Simultaneous deprotection and salt conversion gave COMPOUND 163 as a white solid: ¹H NMR (D₂O) δ 1.63-1.70 (m, 2H), 1.72-1.81 (m, 2H), 2.41 (s, 3H), 2.43 (s, 3H), 2.96 (br t, 2H, J=7.8 Hz), 3.05 (br t, 2H, J=7.8 Hz), 4.48 (s, 2H), 4.75 (s, 2H), 7.85 (dd, 1H, J=7.8, 5.4 Hz), 8.08 (s, 1H), 8.38 (s, 1H), 8.64 (dd, 1H, J=7.8, 1.2 Hz), 8.76 (dd, 1H, J=5.4, 1.2 Hz). ¹³C NMR (D₂O) δ 17.33, 17.54, 22.29, 24.73, 39.42, 53.92, 55.69, 55.61, 126.27, 131.26, 137.39, 138.13, 139.91, 144.98, 146.46, 148.34, 151.81, 168.56. ES-MS m/z 343 (M+H). Anal. Calcd. for C₁₉H₂₆N₄O₂.3.3HBr.2.6H₂O: C, 34.77; H, 5.30; N, 8.54; Br, 40.18. Found: C, 34.93; H, 5.52; N, 8.23; Br, 39.96.

Example 164

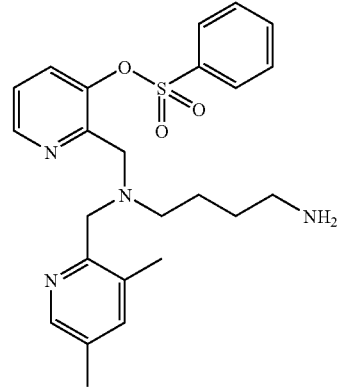

COMPOUND 164: benzenesulfonic acid 2-{[(4-amino-butyl)-(3,5-dimethyl-pyridin-2-ylmethyl)-amino]-methyl}-pyridin-3-yl ester (HBr salt)

Using General Procedure B: Reaction of {4-[(3,5-dimethyl-pyridin-2-ylmethyl)-amino]-butyl}-carbamic acid tert-butyl ester and 3-hydroxy-2-pyridine carboxaldehyde in dry CH₂Cl₂ with NaBH(OAc)₃ gave the 3-hydroxypyridine derivative.

To a solution of the 3-hydroxypyridine derivative from above (143 mg, 0.345 mmol), Et₃N (0.14 mL, 1.0 mmol) and catalytic DMAP (5 mg) in CH₂Cl₂ (5 mL) was added benzene sulfonyl chloride (0.09 mL, 0.71 mmol) and the reaction stirred at rt over 2 d. The mixture was then diluted with CH₂Cl₂ (25 mL) and saturated aqueous NaHCO₃ (25 mL). The aqueous layer was extracted with CH₂Cl₂ (2×10 mL) and the combined organic layers dried ($Na_2SO_4$) and concentrated to afford a yellow oil (191 mg). Purification of the crude by radial chromatography on silica gel (1 mm plate, $CH_2Cl_2$/MeOH/$NH_4OH$, 100:1:1 then 50:1:1) afforded sulfonylated derivative (147 mg, 77%).

Conversion to the HBr salt with simultaneous removal of the Boc protecting group gave COMPOUND 164 as a beige solid (168 mg, 80%): $^1H$ NMR ($D_2O$) δ 1.61-1.65 (m, 4H), 2.38 (s, 3H), 2.41 (s, 3H), 2.89-2.97 (m, 4H), 4.05 (s, 2H), 4.33 (s, 2H), 7.62-7.67 (m, 2H), 7.72 (dd, 1H, J=8.4, 5.4 Hz), 7.80-7.86 (m, 3H), 7.93 (d, 1H, J=8.4 Hz), 8.08 (s, 1H), 8.35 (s, 1H), 8.63 (d, 1H, J=4.8 Hz). $^{13}C$ NMR ($D_2O$) δ 17.26, 17.62, 22.43, 24.71, 39.45, 51.67, 52.75, 55.40, 127.27, 128.93, 130.67, 132.98, 136.82, 136.92, 137.31, 138.14, 139.65, 144.98, 145.12, 145.50, 146.71, 148.51. ES-MS m/z 455 (M+H). Anal. Calcd. for $C_{24}H_{30}N_4O_3S.3.5HBr.1.2H_2O.0.5C_4H_{10}O$: C, 39.21; H, 5.18; N, 7.03; Br, 35.11. Found: C, 39.29; H, 5.14; N, 7.07; Br, 35.00.

Example 165

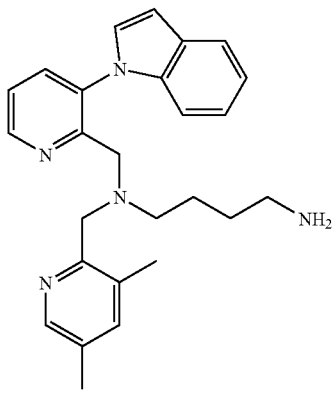

COMPOUND 165: $N^1$-(3,5-Dimethyl-pyridin-2-ylmethyl)-$N^1$-(3-indol-1-yl-pyridin-2-ylmethyl)-butane-1,4-diamine To a solution of 3-bromo-2-cyanopyridine (Sakamoto, T. et al., *Chem. Pharm. Bull.* 1985, 33(2), 565-571) (340 mg, 1.86 mmol) and indole (436 mg, 3.72 mmol) in toluene (15 mL) was added $Cs_2CO_3$ (737 mg, 2.26 mmol), 4,5-bis(diphenylphosphino)-9,9-dimethylxanthene (83 mg, 0.143 mmol) and $Pd_2(dba)_3$ (42 mg, 0.046 mmol) and the reaction stirred at 110° C. for 2.5 d. The mixture was concentrated and purified by column chromatography on silica gel (EtOAc/Hexanes, 2:1) to give 3-indol-1-yl-pyridine-2-carbonitrile (362 mg, 89%) as a beige solid.

A mixture of 3-indol-1-yl-pyridine-2-carbonitrile (164 mg, 0.75 mmol) in $NH_3$ saturated MeOH (6 mL) was treated with Raney nickel (0.25 g), and placed under 40 psi $H_2$ on a Parr shaker, for 4 h. The mixture was filtered through celite and the cake was washed with methanol. The eluant was concentrated under reduced pressure. Purification of the crude material by column chromatography on silica gel ($CH_2Cl_2$-MeOH, 96:4 then 9:1) provided 96 mg (57%) of C-(3-Indol-1-yl-pyridin-2-yl)-methylamine as a clear oil. $^1H$ NMR ($CDCl_3$) δ 1.65 (br s, 2H), 3.72 (s, 2H), 6.73 (d, 1H, J=3.3 Hz), 6.95-7.03 (m, 1H), 7.16-7.21 (m, 3H), 7.38 (dd, 1H, J=9, 6 Hz), 7.66-7.71 (m, 2H), 8.71 (d, 1H, J=4.5 Hz).

Using General Procedure B: Reaction of C-(3-Indol-1-yl-pyridin-2-yl)-methylamine and 4-(1,3-dioxo-1,3-dihydro-isoindol-2-yl)-butyraldehyde in $CH_2Cl_2$ with $NaBH(OAc)_3$ gave the desired secondary amine as a pale brown oil.

Using General Procedure B: Reaction of the secondary amine from above and 3,5-dimethyl-2-pyridinecarboxaldehyde in $CH_2Cl_2$ (5 mL) with $NaBH(OAc)_3$ gave the desired tertiary amine as a clear oil. To a solution of the phthalimide from above (98 mg, 0.18 mmol) in EtOH (3 mL) was added $H_2NNH_2.H_2O$ (0.10 mL, 3.21 mmol) and the resultant mixture was stirred at room temperature for 3.5 h. The mixture was concentrated and purified by radial chromatography on silica gel (1 mm plate, $CH_2Cl_2$/MeOH/$NH_4OH$, 50:1:1 then 25:1:1) to give COMPOUND 165 (49 mg, 66%) as a clear oil: $^1H$ NMR ($CDCl_3$) δ 1.00-1.03 (m, 4H), 1.37 (br s, 2H), 1.90 (s, 3H), 2.21 (s, 3H), 2.30-2.37 (m, 4H), 3.66 (s, 2H), 3.70 (s, 2H), 6.54 (d, 1H, J=3.0 Hz), 7.00 (dd, 1H, J=6.0, 3.3 Hz), 7.05 (s, 1H), 7.11-7.16 (m, 2H), 7.21 (d, 1H, J=3.3 Hz), 7.35 (dd, 1H, J=7.8, 4.8 Hz), 7.61-7.66 (m, 2H), 8.02 (s, 1H), 8.68 (dd, 1H, J=4.8, 1.8 Hz). $^{13}C$ NMR ($CDCl_3$) δ 18.21, 18.32, 23.65, 31.75, 42.15, 53.82, 56.31, 59.14, 103.79, 110.37, 120.66, 121.35, 122.75, 123.28, 129.02, 129.39, 131.79, 132.84, 135.91, 136.50, 137.43, 139.06, 146.40, 148.60, 154.27, 156.86. ES-MS m/z 414 (M+H). Anal. Calcd. for $C_{26}H_{31}N_5.0.7H_2O$: C, 73.28; H, 7.66; N, 16.43. Found: C, 73.37; H, 7.57; N, 16.43.

Example 166

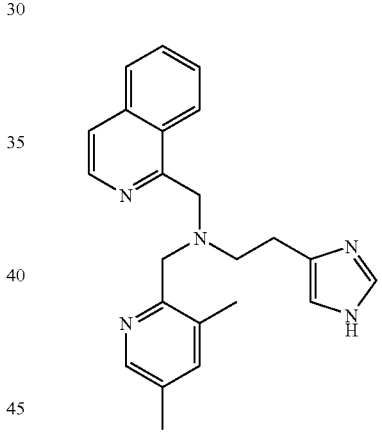

COMPOUND 166: (3,5-Dimethyl-pyridin-2-ylmethyl)-[2-(1H-imidazol-4-yl)-ethyl]-isoquinolin-1-ylmethyl-amine To a solution of [2-(1H-imidazol-4-yl)-ethyl]-carbamic acid tert-butyl ester (1.66 g, 7.87 mmol) (Nigam, S. C. et al. *Synth. Commun.* 1989, 19, 3139-42) and $Et_3N$ (1.8 mL, 12.9 mmol) in $CH_2Cl_2$ (25 mL) at 0° C. was added p-toluene sulfonyl chloride (1.83 g, 9.62 mmol) and the reaction stirred at room temperature for 2 d. The mixture was diluted with $CH_2Cl_2$ (30 mL) and saturated aqueous $NaHCO_3$ (40 mL) and the aqueous layer extracted with $CH_2Cl_2$ (2×10 mL). The combined organic extracts were dried ($Na_2SO_4$), concentrated and purified by column chromatography on silica gel ($CH_2Cl_2$/MeOH, 98:2) to give the tosyl-protected imidazole (2.14 g, 74%) as a beige solid.

Deprotection with TFA using General Procedure F gave 2-[1-(toluene-4-sulfonyl)-1H-imidazol-4-yl]-ethylamine (1.—g, 73%) as a brown oil. $^1H$ NMR ($CDCl_3$) δ 1.29 (br s, 2H), 2.44 (s, 3H), 2.64 (t, 2H, J=6 Hz), 2.96 (t, 2H, J=6 Hz), 7.05 (s, 1H), 7.36 (d, 2H, J=9 Hz), 7.82 (d, 2H, J=9 Hz), 7.94 (s, 1H).

Using General Procedure B: Reaction of 2-[1-(Toluene-4-sulfonyl)-1H-imidazol-4-yl]-ethylamine and isoquinoline-1-carbaldehyde in CH$_2$Cl$_2$ (8.5 mL) with NaBH(OAc)$_3$ gave the desired amine as a yellow oil.

Using General Procedure B: Reaction of the amine from above and 3,5-dimethyl-2-pyridinecarboxaldehyde in CH$_2$Cl$_2$ (10 mL) with NaBH(OAc)$_3$ gave the desired tertiary amine as a yellow oil.

To a solution of the tosyl-protected imidazole from above (169 mg, 0.32 mmol) in MeOH (5 mL) was added HOBT (172 mg, 1.28 mmol) and the reaction stirred 4 h then concentrated and purified by radial chromatography on silica gel (1 mm plate, CH$_2$Cl$_2$/MeOH/NH$_4$OH, 25:1:1 then 10:1:1) to afford COMPOUND 166 (76 mg, 64%) as a clear oil: $^1$H NMR (CDCl$_3$) δ 2.07 (s, 3H), 2.09 (s, 3H), 2.28 (br s, 1H), 2.90-2.93 (m, 2H), 2.97-3.02 (m, 2H), 3.84 (s, 2H), 4.26 (s, 2H), 6.77 (s, 1H), 6.94 (s, 1H), 7.38-7.44 (m, 2H), 7.54-7.64 (m, 3H), 7.78 (s, 1H), 7.99 (d, 1H, J=8.7 Hz), 8.29 (d, 1H, J=6.0 Hz). $^{13}$C NMR (CDCl$_3$) δ 18.06, 18.59, 23.22, 55.90, 56.88, 60.51, 120.92, 124.31, 126.73, 126.96, 127.03, 127.59, 130.25, 130.46, 131.49, 131.85, 135.00, 136.12, 138.74, 141.11, 146.09, 153.58, 158.42. ES-MS m/z 372 (M+H). Anal. Calcd. for C$_{23}$H$_{25}$N$_5$.0.5CH$_2$Cl$_2$.0.7H$_2$O: C, 66.17; H, 6.47; N, 16.42. Found: C, 66.50; H, 6.56; N, 16.35.

Example 167

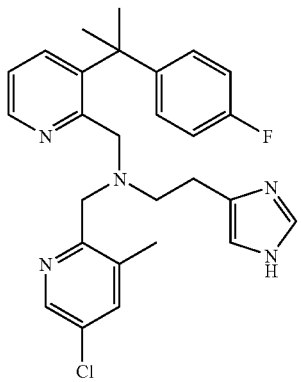

COMPOUND 167: (5-Chloro-3-methyl-pyridin-2-ylmethyl)-{3-[1-(4-fluoro-phenyl)-1-methyl-ethyl]-pyridin-2-ylmethyl}-[2-(1H-imidazol-4-yl)-ethyl]-amine Using General Procedure B: Reaction of 2-[1-(Toluene-4-sulfonyl)-1H-imidazol-4-yl]-ethylamine and 3-[1-(4-Fluoro-phenyl)-1-methyl-ethyl]-pyridine-2-carbaldehyde in CH$_2$Cl$_2$ with NaBH(OAc)$_3$ gave the desired amine as a clear oil.

Using General Procedure B: Reaction of the amine from above and 3-methyl-5-chloro-2-pyridinecarboxaldehyde in CH$_2$Cl$_2$ with NaBH(OAc)$_3$ gave the desired tertiary amine as a white foam.

To a solution of the tosyl-protected imidazole from above (112 mg, 0.18 mmol) in MeOH (5 mL) was added HOBT (107 mg, 0.79 mmol) and the reaction stirred 2 d then concentrated and purified by radial chromatography on silica gel (1 mm plate, CH$_2$Cl$_2$/MeOH/NH$_4$OH, 25:1:1) to afford COMPOUND 167 (51 mg, 59%) as a clear oil: $^1$H NMR (CDCl$_3$) δ 1.66 (s, 6H), 1.98 (br s, 1H), 2.00 (s, 3H), 2.53-2.57 (m, 4H), 3.30 (s, 2H), 3.41 (s, 2H), 6.64 (s, 1H), 6.86-6.92 (m, 2H), 7.01-7.06 (m, 2H), 7.26-7.32 (m, 2H), 7.56 (s, 1H), 7.94 (dd, 1H, J=8.1, 1.2 Hz), 8.18 (d, 1H, J=1.8 Hz), 8.55 (d, 1H, J=3.0 Hz). $^{13}$C NMR (CDCl$_3$) δ 18.12, 22.79, 31.42, 42.46, 53.58, 57.64, 58.33, 115.67 (d, J=20.9 Hz), 122.49, 124.64, 127.53 (d, J=7.7 Hz), 129.99, 130.75, 134.62, 134.79, 137.78, 143.93, 144.84, 145.37, 146.43, 154.74, 158.32, 161.46 (d, J=244.0 Hz). ES-MS m/z 478 (M+H). Anal. Calcd. for C$_{27}$H$_{29}$N$_5$FCl.0.7H$_2$O: C, 66.10; H, 6.25; N, 14.27. Found: C, 66.17; H, 6.20; N, 13.89.

Example 168

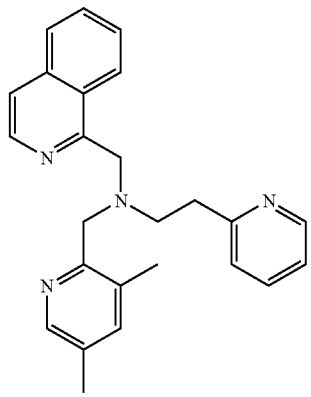

COMPOUND 168: (3,5-Dimethyl-pyridin-2-ylmethyl)-isoquinolin-1-ylmethyl-(2-pyridin-2-yl-ethyl)-amine Using General Procedure B: Reaction of 2-(2-aminoethyl) pyridine and 3,5-dimethyl-2-pyridinecarboxaldehyde in CH$_2$Cl$_2$ (10 mL) with NaBH(OAc)$_3$ gave the desired amine.

Using General Procedure B: Reaction of the amine from above and isoquinoline-1-carbaldehyde in CH$_2$Cl$_2$ with NaBH(OAc)$_3$ gave COMPOUND 168 as a clear oil: $^1$H NMR (CDCl$_3$) δ 1.89 (s, 3H), 2.26 (s, 3H), 3.00-3.03 (br s, 4H), 3.87 (s, 2H), 4.26 (s, 2H), 6.80 (d, 1H, J=7.8 Hz), 6.97 (dd, 1H, J=6.9, 5.1 Hz), 7.16 (s, 1H), 7.28-7.37 (m, 2H), 7.53 (d, 1H, J=5.7 Hz), 7.58 (d, 1H, J=7.2 Hz), 7.73 (d, 1H, J=8.1 Hz), 7.90 (d, 1H, J=8.4 Hz), 8.20 (s, 1H), 8.38 (d, 1H, J=5 Hz), 8.42 (d, 1H, J=6 Hz). $^{13}$C NMR (CDCl$_3$) δ 18.29, 18.32, 34.81, 55.13, 59.54, 59.58, 120.92, 121.24, 123.38, 126.72, 127.06, 127.10, 128.15, 130.14, 132.29, 133.40, 136.39, 136.61, 139.09, 141.68, 146.72, 149.20, 154.18, 159.17, 160.94. ES-MS m/z 383 (M+H). Anal. Calcd. for C$_{25}$H$_{26}$N$_4$.1.0H$_2$O.0.5CH$_2$Cl$_2$: C, 69.14; H, 6.60; N, 12.65. Found: C, 69.35; H, 6.69; N, 12.58.

Example 169

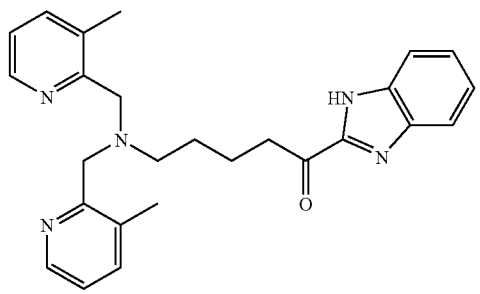

141

COMPOUND 169: 1-(1H-Benzimidazol-2-yl)-5-[bis-(3-methyl-pyridin-2-ylmethyl)-amino]-pentan-1-one Using General Procedure B: Reaction of 3-methyl-2-aminomethylpyridine and 3-methyl-2-pyridinecarboxaldehyde in $CH_2Cl_2$ with $NaBH(OAc)_3$ gave bis-(3-methyl-pyridin-2-ylmethyl)-amine as a yellow oil. $^1H$ NMR ($CDCl_3$) δ 2.33 s, 6H), 4.06 (s, 4H), 7.08 (dd, 2H, J=9, 6 Hz), 7.42 (dd, 2H, J=9, 3 Hz), 8.41 (d, 2H, J=3 Hz).

To a solution of Bis-(3-methyl-pyridin-2-ylmethyl)-amine (481 mg, 2.12 mmol) and methyl 5-bromovalerate (0.40 mL, 2.80 mmol) in DMF (5 mL) was added $K_2CO_3$ (600 mg, 4.35 mmol) and KI (20 mg) and the reaction stirred at 70° C. overnight. The reaction was diluted with $H_2O$ (20 mL) and $CH_2Cl_2$ (25 mL) and the aqueous layer was extracted with $CH_2Cl_2$ (2×20 mL). The combined organic extracts were washed with brine (3×20 mL), dried ($Na_2SO_4$), concentrated and purified by column chromatography on silica gel ($CH_2Cl_2$/MeOH, 96:4 then 92:8) to give the N-alkylated product (542 mg, 75%) as a brown oil.

To a solution of the methyl ester from above (281 mg, 0.82 mmol) in THF/$H_2O$ (6 mL, 1:1) was added LiOH—$H_2O$ (354 mg, 8.44 mmol) and the reaction stirred at 50° C. overnight. The reaction was neutralized to pH 5-6 with 6 N HCl and extracted with $CH_2Cl_2$ (3×20 mL) and $CHCl_3$ (2×20 mL). The combined organic layers were dried ($Na_2SO_4$) and concentrated to afford the desired acid, used without further purification in the next reaction.

Using General Procedure G: To a solution of the acid from above (approx 0.82 mmol) in $CH_2Cl_2$ (10 mL) was added N,O-dimethylhydroxylamine-HCl (100 mg, 1.03 mmol), EDCI (191 mg, 1.00 mmol), HOBT (141 mg, 1.04 mmol), and DIPEA (0.50 mL, 2.88 mmol).

The crude material was purified by column chromatography on silica gel ($CH_2Cl_2$-MeOH, 96:4 then 92:8) to provide 233 mg (77%, 2 steps) of the Weinreb amide as a pale yellow oil.

To a solution of SEM-protected benzimidazole (171 mg, 0.69 mmol) in THF (10 mL) at −78° C. was added t-BuLi (0.70 mL, 1.11 mmol, 1.7 M in pentane) and the solution stirred at −78° C. for 25 min. A solution of the Weinreb amide from above (188 mg, 0.51 mmol) in THF (3 mL) was then added an the reaction stirred from −78° C. to room temperature overnight. The mixture was diluted with saturated aqueous $NH_4Cl$ (5 mL), saturated aqueous $NaHCO_3$ (25 mL) and $CH_2Cl_2$ (40 mL) and the layers separated. The aqueous layer was extracted with $CH_2Cl_2$ (1×15 mL), dried ($Na_2SO_4$), concentrated and purified by column chromatography on silica gel ($CH_2Cl_2$-MeOH—$NH_4OH$, 96:4:0 then 90:8:2) to provide 220 mg (77%) of the SEM-protected benzimidazole adduct as a brown oil.

A solution of the adduct from above (246 mg, 0.44 mmol) in 6 N HCl/THF (6 mL, 2:1) was stirred at 60° C. for 3 h. The reaction was cooled and neutralized to pH 9-10 with 10 N NaOH. The aqueous phase was extracted with $CH_2Cl_2$ (3×15 mL) and the combined organic layers dried ($Na_2SO_4$), concentrated and purified by column chromatography on silica gel ($CH_2Cl_2$-MeOH—$NH_4OH$, 96:4:0 then 92:6:2) to provide COMPOUND 169 (166 mg, 88%) as a yellow foam: $^1H$ NMR ($CDCl_3$) δ 1.56-1.61 (m, 4H), 2.07 (br s, 1H), 2.—(s, 6H), 2.55-2.58 (m, 2H), 3.09-3.14 (m, 2H), 3.75 (s, 4H), 7.05 (dd, 2H, J=7.5, 4.8 Hz), 7.34-7.40 (m, 4H), 7.51 (d, 1H, J=7.2 Hz), 7.89 (d, 1H, J=7.5 Hz), 8.33 (d, 2H, J=6 Hz). $^{13}C$ NMR ($CDCl_3$) δ 17.85, 21.59, 26.12, 38.03, 54.18, 59.06, 121.45, 122.35, 123.36, 133.40, 138.01, 145.58, 147.82, 156.82, 194.12. ES-MS m/z 428 (M+H). Anal. Calcd. for $C_{26}H_{29}N_5O.0.1H_2O$: C, 72.73; H, 6.85; N, 16.31. Found: C, 72.68; H, 6.92; N, 15.94.

142

Example 170

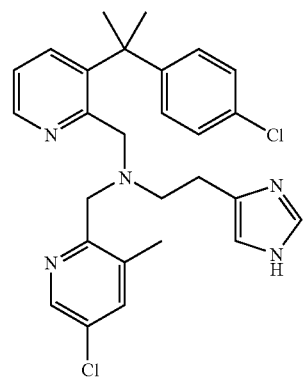

COMPOUND 170: (5-Chloro-3-methyl-pyridin-2-ylmethyl)-{3-[1-(4-chloro-phenyl)-1-methyl-ethyl]-pyridin-2-ylmethyl}-[2-(1H-imidazol-4-yl)-ethyl]-amine Using General Procedure B: Reaction of 2-[1-(Toluene-4-sulfonyl)-1H-imidazol-4-yl]-ethylamine and 3-methyl-5-chloro-2-pyridinecarboxaldehyde in $CH_2Cl_2$ with $NaBH(OAc)_3$ gave the desired amine as a yellow oil.

Using General Procedure B: Reaction of the amine from above and 3-[1-(4-chloro-phenyl)-1-methyl-ethyl]-pyridine-2-carbaldehyde in $CH_2Cl_2$ with $NaBH(OAc)_3$ gave the tosyl-protected imidazole.

To a solution of the tosyl-protected imidazole from above (approx 0.24 mmol) in MeOH (5 mL) was added HOBT (134 mg, 0.99 mmol) and the reaction stirred overnight then concentrated and purified by radial chromatography on silica gel (1 mm plate, $CH_2Cl_2$/MeOH/$NH_4OH$, 50:1:1 then 25:1:1) to afford COMPOUND 170 (100 mg, 83% over 2 steps) as a clear oil: $^1H$ NMR ($CDCl_3$) δ 1.65 (s, 6H), 2.00 (s, 3H), 2.02 (br s, 1H), 2.57-2.59 (br s, 4H), 3.33 (s, 2H), 3.42 (s, 2H), 6.65 (s, 1H), 7.00 (d, 2H, J=8.7 Hz), 7.16 (d, 2H, J=8.7 Hz), 7.27-7.32 (m, 2H), 7.56 (s, 1H), 7.92 (d, 1H, J=8.1 Hz), 8.19 (d, 1H, J=2.1 Hz), 8.55 (d, 1H, J=3 Hz). $^{13}C$ NMR ($CDCl_3$) δ 18.12, 22.82, 31.24, 42.60, 53.59, 57.68, 57.99, 122.53, 124.29, 127.41, 128.96, 130.16, 130.67, 132.26, 134.56, 134.87, 137.79, 143.59, 144.83, 146.54, 148.24, 154.73, 158.28. ES-MS m/z 494 (M+H). Anal. Calcd. for $C_{27}H_{29}N_5Cl_2.0.4H_2O.0.8CH_2Cl_2$: C, 58.62; H, 5.56; N, 12.29. Found: C, 58.57; H, 5.52; N, 12.44.

Example 171

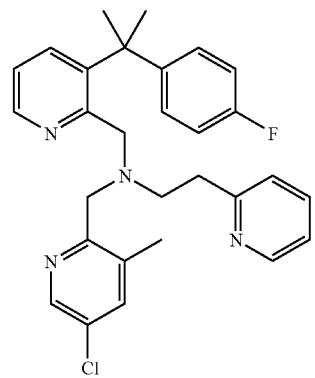

143

COMPOUND 171: (5-Chloro-3-methyl-pyridin-2-ylmethyl)-{3-[1-(4-fluoro-phenyl)-1-methyl-ethyl]-pyridin-2-ylmethyl}-(2-pyridin-2-yl-ethyl)-amine Using General Procedure B: Reaction of 2-(2-aminoethyl)pyridine and 3-[1-(4-fluoro-phenyl)-1-methyl-ethyl]-pyridine-2-carbaldehyde in $CH_2Cl_2$ with $NaBH(OAc)_3$ gave the desired amine as a yellow oil.

Using General Procedure B: Reaction of the amine from above and 3-methyl-5-chloro-2-pyridinecarboxaldehyde in $CH_2Cl_2$ with $NaBH(OAc)_3$ gave COMPOUND 171 as a clear oil: $^1H$ NMR ($CDCl_3$) δ 1.61 (s, 6H), 2.10 (s, 3H), 2.75-2.84 (m, 4H), 3.40 (s, 2H), 3.66 (s, 2H), 6.83-6.96 (m, 5H), 7.03 (dd, 1H, J=6.6, 5.1 Hz), 7.22 (dd, 1H, J=7.8, 4.8 Hz), 7.33 (d, 1H, J=1.8 Hz), 7.48 (dt, 1H, J=7.5, 1.5 Hz), 7.85 (d, 1H, J=7.8 Hz), 8.25 (d, 1H, J=2.1 Hz), 8.40 (d, 1H, J=4.8 Hz), 8.54 (d, 1H, J=3 Hz). $^{13}C$ NMR ($CDCl_3$) δ 17.98, 31.13, 34.55, 42.10, 53.97, 57.43, 57.56, 115.03 (d, J=20.8 Hz), 120.66, 121.50, 123.02, 127.05 (d, J=7.6 Hz), 129.97, 133.83, 134.72, 135.90, 137.09, 143.20, 144.44, 145.44, 146.48, 148.83, 155.50, 157.58, 160.81, 160.87 (d, J=245.3 Hz). ES-MS m/z 490 (M+H). Anal. Calcd. for $C_{29}H_{30}N_4FCl.0.4H_2O$: C, 70.19; H, 6.26; N, 11.29; F, 3.83. Found: C, 70.14; H, 6.19; N, 11.35; F, 3.67.

Example 172

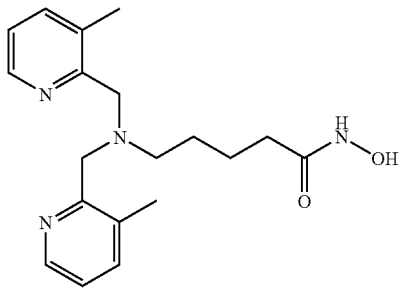

COMPOUND 172: 5-[Bis-(3-methyl-pyridin-2-ylmethyl)-amino]-pentanoic acid hydroxyamide To a mixture of Na metal (1—mg, 4.91 mmol) in MeOH (5 mL) was added $NH_2OH$—HCl (204 mg, 2.94 mmol) followed by a solution of 5-[Bis-(3-methyl-pyridin-2-ylmethyl)-amino]-pentanoic acid methyl ester (126 mg, 0.37 mmol) in MeOH (7 mL) and the reaction stirred 1.5 h. An additional amount of Na (134 mg, 5.83 mmol) and $NH_2OH$—HCl (208 mg, 2.99 mmol) was then added and the mixture stirred another 40 min then quenched with water (2-3 mL). The mixture was concentrated and diluted with $H_2O$ (10 mL), saturated aqueous $NaHCO_3$ (to pH 10) and $CHCl_3$ (25 mL) and stirred vigorously overnight. The layers were separated and the aqueous was extracted with $CHCl_3$ (2×15 mL). The combined organic extracts were dried ($Na_2SO_4$), concentrated and purified by radial chromatography on silica gel (1 mm plate, $CH_2Cl_2$/MeOH/$NH_4OH$, 50:1:1 then 25:1:1 then 10:1:1) to give COMPOUND 172 (47 mg, 37%) as a white solid: $^1H$ NMR ($CDCl_3$) δ 1.54-1.58 (m, 4H), 2.11 (s, 6H), 2.12-2.15 (m, 2H), 2.52-2.55 (m, 2H), 3.71 (s, 4H), 7.12 (dd, 2H, J=9, 6 Hz), 7.42 (d, 2H, J=9 Hz), 8.36 (d, 2H, J=6 Hz). $^{13}C$ NMR ($CDCl_3$) δ 17.91, 21.92, 23.16, 31.68, 52.73, 57.23, 122.58, 133.61, 138.43, 145.52, 156.61, 170.55. ES-MS m/z 343 (M+H). Anal. Calcd. for $C_{19}H_{26}N_4O_2.1.3CH_3OH$: C, 63.48; H, 8.19; N, 14.59. Found: C, 63.66; H, 8.03; N, 14.33.

Example 173

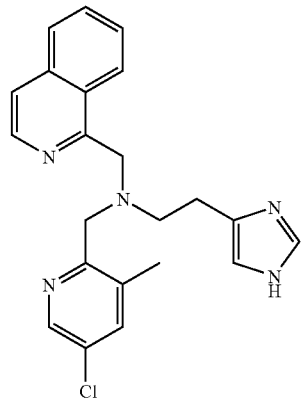

COMPOUND 173: (5-Chloro-3-methyl-pyridin-2-ylmethyl)-[2-(1H-imidazol-4-yl)-ethyl]-isoquinolin-1-ylmethyl-amine Using General Procedure B: Reaction of 2-[1-(Toluene-4-sulfonyl)-1H-imidazol-4-yl]-ethylamine and 3-methyl-5-chloro-2-pyridinecarboxaldehyde in $CH_2Cl_2$ with NaBH$(OAc)_3$ gave the desired amine as a yellow oil.

Using General Procedure B: Reaction of the amine from above and isoquinoline-1-carboxaldehyde in $CH_2Cl_2$ with $NaBH(OAc)_3$ gave the tosyl-protected imidazole, to which was added HOBT. Purification by radial chromatography on silica gel (1 mm plate, $CH_2Cl_2$/MeOH/$NH_4OH$, 50:1:1 then 25:1:1) gave COMPOUND 173 as a clear oil: $^1H$ NMR ($CDCl_3$) δ 2.08 (s, 3H), 2.92-2.95 (m, 2H), 3.02-3.06 (m, 2H), 3.84 (s, 2H), 4.30 (s, 2H), 6.81 (s, 1H), 7.06 (d, 1H, J=1.5 Hz), 7.42 (d, 1H, J=5.7 Hz), 7.47 (dt, 1H, J=8.1, 1.2 Hz), 7.57-7.69 (m, 3H), 7.77 (s, 1H), 8.01 (d, 1H, J=8.4 Hz), 8.29 (d, 1H, J=5.7 Hz). $^{13}C$ NMR ($CDCl_3$) δ 18.56, 23.25, 56.40, 57.17, 60.09, 121.07, 124.06, 126.33, 127.30, 127.44, 129.98, 130.50, 133.98, 134.88, 136.09, 137.30, 141.00, 144.39, 154.81, 158.23. ES-MS m/z 392 (M+H). Anal. Calcd. for $C_{22}H_{22}N_5Cl.0.5CH_2Cl_2.1.0H_2O$: C, 59.74; H, 5.57; N, 15.48; Cl, 15.67. Found: C, 59.60; H, 5.42; N, 15.35; Cl, 16.02.

Example 174

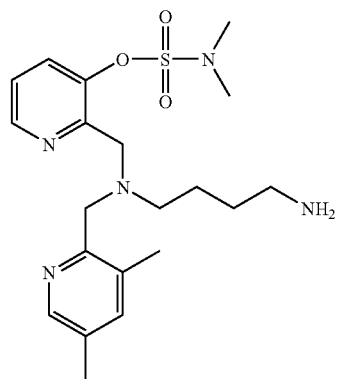

COMPOUND 174: Dimethyl-sulfamic acid 2-{[(4-amino-butyl)-(3,5-dimethyl-pyridin-2-ylmethyl)-amino]-methyl}-pyridin-3-yl ester Using General Procedure B: Reaction of 3-hydroxypyridine-2-carbaldehyde and [4-(3,5-dimethyl-pyridin-2-ylamino)-butyl]-carbamic acid tert-butyl ester in $CH_2Cl_2$ with $NaBH(OAc)_3$ gave {4-[(3,5-dimethyl-pyridin-2-ylmethyl)-(3-hydroxy-pyridin-2-ylmethyl)-amino]-butyl}-carbamic acid tert-butyl ester as a brown oil (0.640 g, 55%). $^1$H NMR ($CDCl_3$) δ 1.34-1.52 (m, 13H), 2.29 (m, 6H), 2.60 (m, 2H), 2.95 (m, 2H), 3.79 (s, 2H), 3.87 (s, 2H), 4.53 (br s, 1H), 7.08-7.16 (m, 1H), 7.32 (s, 1H), 8.00 (dd, 1H, J=2.8, 1.3 Hz), 8.29 (s, 1H).

To a solution of {4-[(3,5-dimethyl-pyridin-2-ylmethyl)-(3-hydroxy-pyridin-2-ylmethyl)-amino]-butyl}-carbamic acid tert-butyl ester (0.190 g, 0.46 mmol) in $CH_2Cl_2$ (4 mL) was added dimethylsulfamoylchloride (0.160 mL, 1.49 mmol), $NEt_3$ (0.300 g, 2.16 mmol) and DMAP (catalytic) and the reaction mixture stirred for 48 h. The mixture was diluted with $CH_2Cl_2$ (30 mL) and the organic layer was washed with saturated aqueous $NaHCO_3$ (2×30 mL), dried ($MgSO_4$), and concentrated. Purification by column chromatography on silica gel with saturated $NH_4OH$ in $Et_2O$ afforded {4-[(3,5-dimethyl-pyridin-2-ylmethyl)-(3-dimethylsulfamoyloxy-pyridin-2-ylmethyl)-amino]-butyl}-carbamic acid tert-butyl ester (0.054 g, 23%) $^1$H NMR ($CDCl_3$) δ 1.30-1.53 (m, 13H), 2.11 (s, 3H), 2.25 (s, 3H), 2.50-2.54 (m, 2H), 2.94-3.00 (m, 8H), 3.74 (s, 2H), 3.91 (s, 2H), 5.11 (br s, 1H), 7.16 (s, 1H), 7.23 (dd, 1H, J=6.6, 4.8 Hz), 7.72 (d, 1H, J=8.3 Hz), 8.—(s, 1H), 8.51 (d, 1H, J=4.1 Hz).

Conversion to the HBr salt using General Procedure D gave COMPOUND 174 as a white solid. $^1$H NMR ($D_2O$) δ 1.64-1.75 (m, 4H), 2.40 (s, 6H), 2.94-2.98 (m, 2H), 3.06 (s, 6H), 4.45 (s, 2H), 4.49 (s, 2H), 7.73-7.78 (m, 1H), 8.05 (s, 1H), 8.15 (d, 1H, J=8.8 Hz), 8.37 (s, 1H), 8.61 (d, 1H, J=5.0 Hz). $^{13}$C NMR ($D_2O$) δ 14.5, 17.2, 17.5, 22.5, 24.7, 38.8, 39.4, 53.1, 54.0, 55.8, 127.1, 136.1, 136.9, 137.8, 140.0, 144.7, 145.6, 146.1, 146.9, 147.8. ES-MS m/z 422 [M+H]$^+$. Anal. Calcd. for $C_{20}H_{31}N_5O_3S\cdot3.4HBr\cdot2.0H_2O\cdot0.3C_4H_{10}O$: C, 33.73; H, 5.53; N, 9.28; Br, 35.99. Found: C, 33.66; H, 5.51; N, 9.33; Br, 36.09.

Example 175

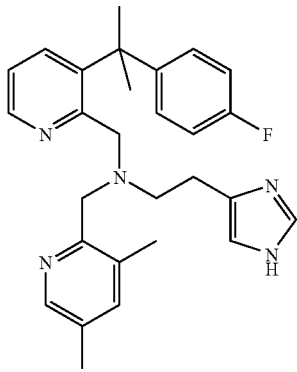

COMPOUND 175: (3,5-dimethyl-pyridin-2-ylmethyl)-{3-[1-(4-fluoro-phenyl)-1-methyl-ethyl]-pyridin-2-ylmethyl}-[2-(1H-imidazol-4-yl)-ethyl]-amine Using General Procedure B: Reaction of 2-[1-(toluene-4-sulfonyl)-1H-imidazol-4-yl]-ethylamine and 3,5-dimethyl-pyridine-2-carbaldehyde in $CH_2Cl_2$ with $NaBH(OAc)_3$ gave (3,5-dimethyl-pyridin-2-ylmethyl)-{2-[1-(toluene-4-sulfonyl)-1H-imidazol-4-yl]-ethyl}-amine. $^1$H NMR ($CDCl_3$) δ 2.26 (d, 6H, J=8.65 Hz), 2.44 (s, 3H), 2.78 (t, 2H, J=7.06 Hz), 2.97 (t, 2H, J=7.02 Hz), 3.85 (s, 2H), 7.09 (s, 1H), 7.23 (s, 1H), 7.34 (d, 2H, J=7.84 Hz), 7.81 (d, 2H, J=8.34 Hz), 7.92 (s, 1H), 8.18 (s, 1H).

Using General Procedure B: Reaction of (3,5-dimethyl-pyridin-2-ylmethyl)-{2-[1-(toluene-4-sulfonyl)-1H-imidazol-4-yl]-ethyl}-amine and 3-[1-(4-fluoro-phenyl)-1-methyl-ethyl]pyridine-2-carbaldehyde in $CH_2Cl_2$ with $NaBH(OAc)_3$ gave (3,5-dimethyl-pyridin-2-ylmethyl)-{3-[1-(4-fluoro-phenyl)-1-methyl-ethyl]-pyridin-2-ylmethyl}-{2-[1-{toluene-4-sulfonyl)-1H-imidazol-4-yl]-ethyl}-amine (87.3 mg, 39%).

To a solution of (3,5-dimethyl-pyridin-2-ylmethyl)-{3-[1-(4-fluoro-phenyl)-1-methyl-ethyl]-pyridin-2-ylmethyl}-{2-[1-{toluene-4-sulfonyl)-1H-imidazol-4-yl]-ethyl}-amine (87.3 mg, 0.143 mmol) in anhydrous MeOH (1.5 mL) was added HOBT (77.1 mg, 0.57 mmol). After stirring overnight the reaction mixture was concentrated. Purification by radial chromatography on silica gel using 5% $MeOH/CH_2Cl_2$ afforded COMPOUND 175 (36 mg, 55%) as a clear oil. $^1$H NMR ($CDCl_3$) δ 1.65 (s, 6H), 1.97 (s, 3H), 2.20 (s, 3H), 2.53 (s, 4H), 3.30 (s, 2H), 3.37 (s, 2H), 6.63 (s, 1H), 6.88 (t, 2H, J=8.52 Hz), 7.04 (m, 3H), 7.30 (m, 1H), 7.61 (s, 1H), 7.93 (d, 1H, J=7.91 Hz), 8.05 (s, 1H), 8.55 (d, 1H, J=3.58 Hz). $^{13}$C NMR ($CDCl_3$) δ 18.1, 18.2, 22.8, 31.4, 42.4, 53.3, 57.8, 58.8, 115.5, 115.8, 122.4, 124.1, 127.5, 127.6, 130.2, 132.1, 132.6, 134.5, 134.7, 139.2, 144.0, 145.4, 146.4, 146.5, 153.4, 158.5, 159.8. ES-MS m/z 458 [M+H]$^+$. Anal. Calcd. for $C_{28}H_{32}FN_5\cdot1.1H_2O\cdot0.3CH_2Cl_2$: C, 73.49; H, 7.05; N, 15.30. Found: C, 70.02; H, 7.02; N, 14.87.

Example 176

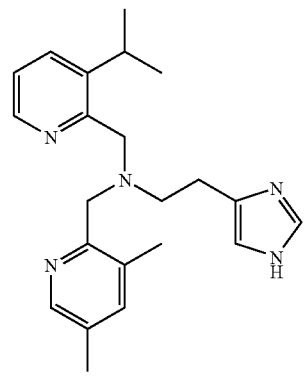

COMPOUND 176: (3,5-dimethyl-pyridin-2-ylmethyl)-[2-(1H-imidazol-4-yl)-ethyl]-(3-isopropyl-pyridin-2-ylmethyl)-amine Using General Procedure B: Reaction of (3,5-dimethyl-pyridin-2-ylmethyl)-{2-[1-(toluene-4-sulfonyl)-1H-imidazol-4-yl]-ethyl}-amine and 3-isopropyl-pyridine-2-carbaldehyde in $CH_2Cl_2$ (5 mL) with $NaBH(OAc)_3$ gave (3,5-dimethyl-pyridin-2-ylmethyl)-(3-isopropyl-pyridin-2-ylmethyl)-{2-[1-(toluene-4-sulfonyl)-1H-imidazol-4-yl]-ethyl}-amine. $^1$H NMR ($CDCl_3$) δ 0.91 (d, 6H, J=6.51 Hz), 2.04 (s, 3H), 2.24 (s, 1H), 2.26 (s, 3H), 2.41 (s, 3H), 2.71 (m, 2H), 2.82 (m, 2H), 3.75 (d, 4H, J=4.50 Hz), 6.63 (s, 1H), 7.14

(q, 1H, J=4.25 Hz), 7.22 (s, 1H), 7.30 (d, 2H, 7.86 Hz), 7.49 (d, 1H, J=7.0 Hz), 7.70 (d, 2H, J=8.40 Hz), 7.80 (s, 1H), 8.19 (s, 1H), 8.32 (d, 1H, J=4.19 Hz).

To a solution of (3,5-dimethyl-pyridin-2-ylmethyl)-(3-isopropyl-pyridin-2-ylmethyl)-{2-[1-(toluene-4-sulfonyl)-1H-imidazol-4-yl]-ethyl}-amine (99.1 mg, 0.19 mmol) in anhydrous MeOH (1.5 mL) was added HOBT (108.5 mg, 0.803 mmol) and the resulting mixture was stirred overnight. The mixture was concentrated and purified by radial chromatography on silica gel (1 mm plate; using 6% MeOH/$CH_2Cl_2$, followed by $CH_2Cl_2$/MeOH/$NH_4OH$; 17:1:1) to afford COMPOUND 176 as a light brown oil (43.4 mg, 62%). $^1$H NMR ($CDCl_3$) δ 1.00 (d, 6H, J=9.0 Hz), 2.07 (s, 3H), 2.21 (s, 3H), 2.86 (s, 4H), 3.09 (qnt, 1H, J=6.0 Hz), 3.77 (s, 2H), 3.84 (s, 2H), 6.70 (s, 1H), 7.11 (m, 2H), 7.43 (d, 1H, J=7.8 Hz), 7.57 (s, 1H), 8.14 (s, 1H), 8.32 (d, 1H, J=4.7 Hz). $^{13}$C NMR ($CDCl_3$) δ 18.2, 18.3, 23.0, 23.5, 27.8, 54.8, 57.6, 58.2, 123.0, 124.4, 130.4, 132.0, 132.6, 133.6, 134.9, 139.1, 143.6, 145.8 146.3, 153.9, 155.7. ES-MS m/z 364 [M+H]$^+$. Anal. Calcd. for $C_{22}H_{29}N_5$·0.6$H_2O$·0.1 $CH_2Cl_2$: C, 72.69; H, 8.04; N, 19.27. Found: C, 69.46; H, 8.11; N, 18.24.

Example 177

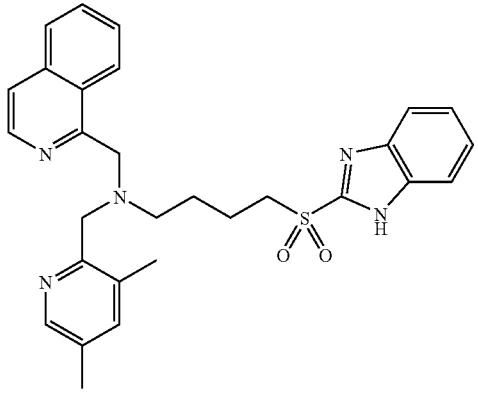

COMPOUND 177: [4-(1H-benzoimidazole-2-sulfonyl)-butyl]-(3,5-dimethyl-pyridin-2-ylmethyl)-isoquinolin-1-ylmethyl-amine To a stirred solution of 2-mercaptobenzimidazole (2.0 g, —mmol) and N-(4-bromobutyl)phthalimide (3.8 g, —mmol) in EtOH (50 mL) was added solid $K_2CO_3$ (2.2 g, 16 mmol). The resulting mixture was heated to reflux for 18 h, then cooled to room temperature and saturated aqueous $NaHCO_3$ (50 mL) was added. The phases were separated, and the aqueous layer was extracted with $CH_2Cl_2$ (3×50 mL) then the combined organic fractions were dried ($MgSO_4$), and concentrated. Purification of the crude material thus obtained by flash chromatography (silica gel, hexane/EtOAc; 4:1) afforded 4.2 g of 2-[4-(1H-benzoimidazol-2-ylsulfanyl)-butyl]-isoindole-1,3-dione (90% yield).

To a stirred solution of the above sulfide (4.2 g, 12 mmol) in $CH_2Cl_2$ (100 mL) was slowly added solid 3-chloroperoxybenzoic acid (77% purity, 8.0 g, 46 mmol). The solution was stirred for 18 h, then saturated aqueous $NaHCO_3$ (100 mL) was added. The biphasic mixture was extracted with $CH_2Cl_2$ (3×100 mL), then the combined organic fractions were dried ($MgSO_4$), and concentrated. The crude sulfone thus obtained (4.5 g, 98% yield) was used directly in the next step.

Deprotection with $H_2NNH_2$·$H_2O$ following General Procedure E gave 4-(1H-benzoimidazole-2-sulfonyl)-butylamine.

A solution of 4-(1H-benzoimidazole-2-sulfonyl)-butylamine (350 mg, 1.4 mmol) and 3,5-dimethylpyridine-2-carbaldehyde (187 mg, 1.4 mmol) in dry MeOH (10 mL) was stirred for 3 h. At this time, solid $NaBH_4$ (116 mg, 4.2 mmol) was added in one portion. Stirring was continued for 1 h, then saturated aqueous $NaHCO_3$ (10 mL) and $CH_2Cl_2$ (20 mL) was added. The biphasic mixture was extracted with $CH_2Cl_2$ (3×20 mL), then the combined organic fractions were dried ($MgSO_4$), and concentrated. Purification of the crude material by flash chromatography (silica gel, $CH_2Cl_2$/MeOH/$NH_4OH$; 20:2:1) afforded 70 mg of [4-(1H-benzoimidazole-2-sulfonyl)-butyl]-(3,5-dimethyl-pyridin-2-ylmethyl)-amine (14% yield). $^1$H NMR ($CDCl_3$) δ 184-1.86 (m, 4H), 2.26 (s, 3H), 2.29 (s, 3H), 2.95-3.00 (m, 2H), 3.34-3.56 (m, 2H), 4.12 (s, 2H), 7.34-7.37 (m, 2H), 7.44 (s, 1H), 7.67-7.71 (m, 2H), 8.19 (s, 1H).

Using General Procedure B: Reaction of [4-(1H-benzoimidazole-2-sulfonyl)-butyl]-(3,5-dimethyl-pyridin-2-ylmethyl)-amine and isoquinoline-1-carbaldehyde in $CH_2Cl_2$ with $NaBH(OAc)_3$ gave COMPOUND 177 as a white foam (50% yield). $^1$H NMR ($CDCl_3$) δ 1.51-1.63 (m, 4H), 2.10 (s, 3H), 2.27 (s, 3H), 2.42-2.45 (m, 2H), 3.26-3.30 (m, 2H), 3.81 (s, 2H), 4.17 (s, 2H), 7.12 (t, 1H, J=8 Hz), 7.27 (s, 1H), 7.37-7.42 (m, 2H), 7.50-7.55 (m, 2H), 7.69-7.74 (m, 3H), 8.05 (d, 1H, J=8 Hz), 8.28 (br s, 1H), 8.40 (d, 1H, J=6 Hz); $^{13}$C NMR ($CDCl_3$) δ 17.9, 18.3, 21.4, 23.7, 53.1, 54.4, 57.7, 58.7, 117.2, 120.8, 124.8, 125.9, 126.9, 127.6, 130.2, 132.4, 133.1, 136.3, 139.5, 140.9, 146.2, 148.0, 153.1, 158.2; ES-MS m/z 514 [M+H]$^+$. Anal. Calcd. for $C_{29}H_{31}N_5O_2S$·1.3$CH_3OH$: C, 65.54; H, 6.57; N, 12.61; S, 5.77. Found: C, 65.67; H, 6.41; N, 12.23; S, 5.43.

Example 178

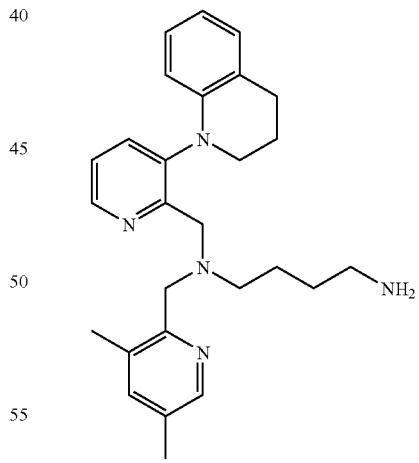

COMPOUND 178: $N^1$-[3-(3,4-Dihydro-2H-quinolin-1-yl)-pyridin-2-ylmethyl]-$N^1$-(3,5-dimethyl-pyridin-2-ylmethyl)-butane-1,4-diamine (HCl salt)

A 250 mL round bottom flask was fitted with a magnetic stirrer and a reflux condenser (with a septum and $N_2$ inlet on top). $Cs_2CO_3$ (13.04 g, 40 mmol), 3-bromopyridine-2-carbonitrile (2.66 g, 20 mmol), toluene (100 mL), 1,2,3,4-tetrahydroquinoline (2.76 mL, 22 mmol), and 4,5-bis-(diphenylphosphanyl)-9,9-dimethyl-9H-xanthene (174 mg, 1.5% mol) were added in sequence. The mixture was degassed at room temperature by bubbling $N_2$ through the suspension with stirring for 5 minutes. $Pd_2(dba)_3$ (90 mg, 0.5% mol) was added and the mixture was degassed again for 1 h at room temperature. The mixture was heated to 120° C. (bath) and refluxed under $N_2$ in the dark. After two days, the mixture was cooled to room temperature. Another batch of 1,2,3,4-tetrahydroquinoline (2 mL), and $Pd_2(dba)_3$ (90 mg) were added. The system was degassed again for 1 h, and the heating was resumed. After another two days, the reaction mixture was cooled to room temperature and was concentrated by rotary evaporation under high vacuum. The residue was absorbed onto silica gel (50 mL) and loaded to a dry-packed silica gel column (200 mL silica). The column was eluted with 20% AcOEt/hexanes to afford a mixture of product and 3-bromo-2-cyanopyridine. The mixture was recrystallized from hexanes-AcOEt to give the product, 3-(3,4-dihydro-2H-quinoline-1-yl)pyridine-2-carbonitrile, as yellow crystals, 2.90 g (61.4%). $^1$H NMR ($CDCl_3$) δ 2.06 (tt, 2H, J=5.7, 6.6 Hz), 2.91 (t, 2H, J=6.6 Hz), 3.76 (t, 2H, J=5.7 Hz), 6.56 (d, 1H, J=8.1 Hz), 6.85 (dd, 1H, J=0.9, 7.5 Hz), 6.98 (br, t, 1H, J=7.5 Hz), 7.10 (br, d, 1H, J=7.5 Hz), 7.42 (dd, 1H, J=4.5, 8.4 Hz), 7.72 (dd, 1H, J=1.2, 8.4 Hz), 8.42 (dd, 1H, J=1.5, 4.5 Hz).

Raney-Ni slurry (6 g) was placed in a 1 L heavy-duty hydrogenation flask under a $N_2$ blanket. The catalyst was allowed to settle and the supernatant was removed by suction. The catalyst was washed with anhydrous MeOH (100 mL×3) by settlement and suction. Then 3-(3,4-dihydro-2H-quinoline-1-yl)pyridine-2-carbonitrile (2.35 g, 10 mmol) was added as a MeOH solution (170 mL) and the mixture was saturated with $NH_3$ by bubbling anhydrous $NH_3$ through the mixture for 10 minutes at room temperature. The mixture was hydrogenated at 40 psi for 4 h at room temperature on a Parr hydrogenation apparatus. The mixture was filtered through a celite pad (60 mL sintered glass funnel, 1 cm thickness) and the filter cake was washed with MeOH (total filtrate ~200 mL). The filtrate was concentrated to dryness by rotary evaporation, and the residue was purified by silica gel column chromatography (200 mL silica, 10% $MeOH/CH_2Cl_2$ containing 1% $NH_4OH$) to give C-[3-(3,4-dihydro-2H-quinoline-1-yl)pyridine-2-yl]methylamine as a yellow oil, 2.19 g (92%).

Using General Procedure B: Reaction of C-[3-(3,4-dihydro-2H-quinoline-1-yl)pyridine-2-yl]methylamine in $CH_2Cl_2$ and 3,5-Dimethyl-pyridine-2-carbaldehyde with $NaBH(OAc)_3$ gave [3-(3,4-Dihydro-2H-quinolin-1-yl)-pyridin-2-ylmethyl]-(3,5-dimethyl-pyridin-2-ylmethyl)-amine.

Using General Procedure B: Reaction of [3-(3,4-Dihydro-2H-quinolin-1-yl)-pyridin-2-ylmethyl]-(3,5-dimethyl-pyridin-2-ylmethyl)-amine in $CH_2Cl_2$ and 4-(1,3-Dioxo-1,3-dihydro-isoindol-2-yl)-butyraldehyde (1.36 g, 6.28 mmol) with $NaBH(OAc)_3$ gave 2-{4-[[3-(3,4-Dihydro-2H-quinolin-1-yl)-pyridin-2-ylmethyl]-(3,5-dimethyl-pyridin-2-ylmethyl)-amino]-butyl}-isoindole-1,3-dione as a yellow fluffy solid. $^1$H NMR ($CDCl_3$) δ 1.35-1.50 (m, 4H), 1.95-1.80 (m, 2H), 2.03 (s, 3H), 2.22 (s, 3H), 2.50-2.65 (m, 2H), 2.65-2.95 (m, 2H), 3.27-3.40 (m, 2H), 3.45-3.55 (m, 2H), 3.65-3.80 (m, 4H), 5.99 (d, 1H, J=7.7 Hz), 6.59 (t, 1H, J=7.7 Hz), 6.81 (t, 1H, J=1.3, 7.7 Hz), 6.95 (d, 1H, J=7.7 Hz), 7.07 (s, 1H), 7.21 (dd, 1H, J=4.6, 7.9 Hz), 7.50 (dd, 1H, J=1.0, 7.9 Hz), 7.65-7.75 (m, 2H), 7.75-7.85 (m, 2H), 8.9 (s, 1H), 8.53 (dd, 1H, J=1.0, 4.6 Hz). Deprotection with $H_2NNH_2 \cdot H_2O$ following General Procedure E gave $N^1$-[3-(3,4-Dihydro-2H-quinolin-1-yl)-pyridin-2-ylmethyl]-$N^1$-(3,5-dimethyl-pyridin-2-ylmethyl)-butane-1,4-diamine as a free base.

Using General Procedure D: Conversion to the HCl salt gave COMPOUND 178 as a yellow solid. $^1$H NMR ($D_2O$) δ 1.40-1.60 (m, 4H), 1.95-2.15 (m, 4H), 2.35 (s, 3H), 2.45 (s, 3H), 2.60-2.75 (m, 2H), 2.75-3.00 (m, 4H), 3.45-3.60 (m, 2H), 4.07 (s, 2H), 4.17 (s, 2H), 6.23 (d, 1H, J=8.3 Hz), 6.85-7.05 (m, 2H), 7.24 (d, 1H, J=7.2 Hz), 7.97 (dd, 1H, J=5.5, 8.2 Hz), 8.15 (s, 1H), 8.32 (s, 1H), 8.45 (d, 1H, J=8.2 Hz), 8.62 (d, 1H, J=5.5 Hz); $^{13}$C NMR ($D_2O$) δ 16.94, 17.51, 20.83, 22.30, 24.90, 26.93, 39.49, 51.07, 53.07, 53.65, 54.50, 115.28, 121.04, 126.38, 127.37, 127.78, 130.60, 136.76, 137.48, 138.42, 138.70, 143.40, 145.65, 146.30, 147.58, 148.82, 150.26; ES-MS m/z 431 (M+H). Anal. Calcd. For $C_{27}H_{37}N_5 \cdot 3.2HCl \cdot 1.7H_2O \cdot 0.3CH_3COOH$: C, 55.53; H, 7.56; N, 11.73; Cl, 19.01. Found: C, 55.62; H, 7.23; N, 11.91; Cl, 18.91.

Example 179

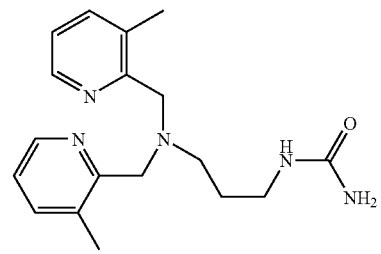

COMPOUND 179: {3-[Bis-(3-methyl-pyridin-2-ylmethyl)-amino]-propyl}-urea (HBr salt)

Using General Procedure B: Reaction of (3-aminopropyl)-carbamic acid tert-butyl ester (Houssin, R. et al. *Synthesis* 1988, 3, 259-261), 3-methylpyridine-2-carboxaldehyde and $NaBH(OAc)_3$ gave {3-[Bis-(3-methyl-pyridin-2-ylmethyl)-amino]-propyl}-carbamic acid tert-butyl ester as a light brown solid (0.17 g, 55%). $^1$H NMR ($CDCl_3$) δ 1.43 (s, 9H), 1.70 (m, 2H), 2.16 (s, 6H), 2.64 (t, 2H, J=7.5 Hz), 3.02 (m, 2H), 3.74 (s, 4H), 6.02 (br, 1H(NH)), 7.07 (m, 2H), 7.38 (d, 2H, J=6.0 Hz), 8.40 (d, 2H, J=2.8 Hz). Deprotection with TFA following General Procedure F gave N,N-Bis-(3-methyl-pyridin-2-ylmethyl)-propane-1,3-diamine (0.14 g, excess) was isolated, which was used immediately in the next reaction.

The amine from above was dissolved in i-PrOH (3 mL) and treated with trimethylsilylisocyanate (93 μL, 0.69 mmol) at room temperature for 16 hours. The solution was then concentrated under reduced pressure and dried in vacuo. The crude material was then purified by column chromatography with silica gel (20:1:0.1 $CH_2Cl_2/MeOH/NH_4OH$) to give {3-[Bis-(3-methyl-pyridin-2-ylmethyl)-amino]-propyl}-urea as a colorless oil (82 mg, 51% 2 steps). $^1$H NMR ($CDCl_3$) δ 1.67 (m, 2H), 2.22 (s, 6H), 2.67 (t, 2H, J=7.5 Hz), 3.10 (m, 2H), 3.69 (s, 4H), 4.78 (br, 2H($NH_2$)), 7.10 (m, 2H), 7.42 (d, 2H, J=6.0 Hz), 8.36 (d, 2H, J=2.8 Hz). Conversion to the HBr salt gave COMPOUND 179 as a white solid. $^1$H NMR ($D_2O$) δ 1.66 (m, 2H), 2.51 (s, 6H), 2.68 (m, 2H), 2.99 (t, 2H, J=6.5 Hz), 4.32 (s, 4H), 7.87 (t, 2H, J=6.9 Hz), 8.38 (d, 2H, J=7.8 Hz), 8.61 (d, 1H, J=5.4 Hz). $^{13}$C NMR ($D_2O$) δ 17.25 (2C), 26.16, 37.79, 52.47, 54.30 (2C), 126.06 (2C), 137.83 (2C), 138.72 (2C), 148.54 (2C), 150.98 (2C), 161.74. ES-MS m/z 328 (M+H). Anal. Calcd. for $C_{18}H_{25}N_5O.3.0HBr.2.7H_2O$: C, 34.94; H, 5.44; N, 11.32; Br, 38.74. Found: C, 34.99; H, 5.34; N, 10.92; Br, 38.86.

Example 180

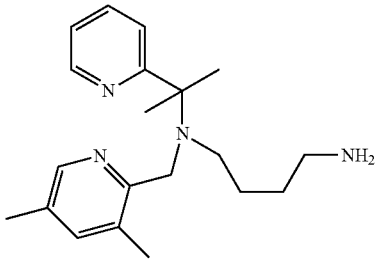

COMPOUND 180: $N^1$-(3,5-Dimethyl-pyridin-2-ylmethyl)-$N^1$-(1-methyl-1-pyridin-2-yl-ethyl)-butane-1,4-diamine (HBr salt)

Using General Procedure B: Reaction of 1-methyl-1-pyridin-2-yl-ethylamine, 3,5-dimethylpyridine-2-carbaldehyde and NaBH(OAc)$_3$ in CH$_2$Cl$_2$ gave (3,5-dimethyl-pyridin-2-ylmethyl)-(1-methyl-1-pyridin-2-yl-ethyl)-amine as a light brown oil (94 mg, 36%).

Using General Procedure B: Reaction of the secondary amine from above, 4-(1,3-dioxo-1,3-dihydro-isoindol-2-yl)-butyraldehyde and NaBH(OAc)$_3$ in CH$_2$Cl$_2$ gave 2-{4-[(3,5-dimethyl-pyridin-2-ylmethyl)-(1-methyl-1-pyridin-2-yl-ethyl)-amino]-butyl}-isoindole-1,3-dione as a light brown oil (115 mg, 71%). $^1$H NMR (CDCl$_3$): δ 0.66 (m, 2H), 1.17 (m, 2H), 1.52 (s, 6H), 2.18 (s, 3H), 2.36 (s, 3H), 2.45 (t, 2H, J=7.5 Hz), 3.24 (t, 2H, J=7.5 Hz), 7.05 (m, 2H), 7.58 (dt, 1H, J=7.5, 1.5 Hz), 7.70 (m, 2H), 7.75 (m, 1H), 7.80 (m, 2H), 8.11 (s, 1H), 8.50 (d, 1H, J=4.8 Hz). Deprotection with H$_2$NNH$_2$.H$_2$O following General Procedure E gave $N^1$-(3,5-Dimethyl-pyridin-2-ylmethyl)-$N^1$-(1-methyl-1-pyridin-2-yl-ethyl)-butane-1,4-diamine as a pale colored residue.

Using General Procedure D: Conversion to the HBr salt gave COMPOUND 180 as a white solid. $^1$H NMR (D$_2$O) δ 1.29-1.45 (br, 4H), 1.61 (s, 6H), 2.45 (s, 3H), 2.47 (s, 3H), 2.55 (t, 2H, J=7.5 Hz), 2.75 (t, 2H, J=7.5 Hz), 4.36 (s, 2H), 7.99 (t, 1H, J=6.8 Hz), 8.17 (t, 2H, J=4.5 Hz), 8.45 (s, 1H), 8.58 (dt, 1H, J=8.0, 1.5 Hz), 8.82 (d, 1H, J=5.4 Hz). $^{13}$C NMR (D$_2$O) δ 16.93, 17.56, 23.28 (2C), 24.96, 25.88, 39.40, 49.68, 54.02, 63.96, 125.96, 126.70, 135.65, 137.20, 137.31, 142.30, 148.69, 149.21, 150.43, 159.84. ES-MS m/z 327 (M+H). Anal. Calcd. for $C_{20}H_{30}N_4.3.2HBr.1.8H_2O.0.3C_4H_{10}O$: C, 39.78; H, 6.27; N, 8.75; Br, 39.95. Found: C, 39.67; H, 5.99; N, 8.66; Br, 39.99.

Example 181

COMPOUND 181: N-(4-{(3,5-Dimethyl-pyridin-2-ylmethyl)-[3-(1-hydroxy-1-methyl-ethyl)-pyridin-2-ylmethyl]-amino}-butyl)-6-hydroxy-nicotinamide Using General Procedure B: Reaction of acetic acid 1-(2-formyl-pyridin-3-yl)-1-methyl-ethyl ester, {4-[(3,5-dimethyl-pyridin-2-ylmethyl)-amino]-butyl}-carbamic acid tert-butyl ester and NaBH(OAc)$_3$ in CH$_2$Cl$_2$CH$_2$Cl$_2$ gave acetic acid 1-(2-{[(4-tert-butoxycarbonylamino-butyl)-(3,5-dimethyl-pyridin-2-ylmethyl)-amino]-methyl}-pyridin-3-yl)-1-methyl-ethyl ester (0.83 g, 75%). Deprotection with TFA using General Procedure F gave acetic acid 1-(2-{[(4-amino-butyl)-(3,5-dimethyl-pyridin-2-ylmethyl)-amino]-methyl}-pyridin-3-yl)-1-methyl-ethyl ester. $^1$H NMR (CDCl$_3$) δ 1.30 (m, 2H), 1.53 (m, 2H), 1.76 (s, 6H), 1.94 (s, 3H), 2.18 (s, 3H), 2.26 (s, 3H), 2.60 (m, 4H), 3.84 (s, 2H), 3.97 (s, 2H), 7.15 (m, 1H), 7.21 (s, 1H), 7.64 (d, 1H, J=7.0 Hz), 8.18 (s, 1H), 8.50 (d, 1H, J=3.0 Hz).

Using General Procedure G: A solution of acetic acid 1-(2-{[(4-amino-butyl)-(3,5-dimethyl-pyridin-2-ylmethyl)-amino]-methyl}-pyridin-3-yl)-1-methyl-ethyl ester (0.22 g, 0.55 mmol) in DMF (5.5 mL) was treated with 2-hydroxynicotinic acid (100 mg, 0.72 mmol), EDCI (137 mg, 0.72 mmol), HOBT (97 mg, 0.72 mmol), DMAP (—mg, 0.11 mmol), and DIPEA (0.19 mL, 1.1 mmol) at room temperature for 5 hours. Radial chromatography on a silica gel plate (20:1:1 CH$_2$Cl$_2$:MeOH:NH$_4$OH) afforded acetic acid 1-{2-[((3,5-dimethyl-pyridin-2-ylmethyl)-{4-[(6-hydroxy-pyridine-3-carbonyl)-amino]-butyl}-amino)-methyl]-pyridin-3-yl}-1-methyl-ethyl ester (54.4 mg, 19%).

A solution of the above compound (52 mg, 0.10 mmol) in anhydrous MeOH (1.0 mL) was treated with K$_2$CO$_3$ (28 mg, 0.20 mmol) and stirred at room temperature for 2 h. The mixture was then concentrated under reduced pressure and water (5 ml) was added. Aqueous work-up and purification with radial chromatography on a silica gel plate (20:1:1 CH$_2$Cl$_2$:MeOH:NH$_4$OH) gave COMPOUND 181 as a pale brown residue. $^1$H NMR (CDCl$_3$) δ 1.45 (s, 6H), 1.48 (m, 2H), 1.74 (m, 2H), 2.18 (s, 3H), 2.26 (s, 3H), 2.57 (br t, 2H, J=7.5 Hz), 3.22 (q, 2H, J=6.1 Hz), 3.79 (s, 2H), 4.24 (s, 2H), 6.52 (d, 1H, J=9.6 Hz), 7.22 (m, 1H), 7.28 (s, 1H), 7.66 (dd, 1H, J=8.1, 1.4 Hz), 7.88 (br t, 1H, J=5.4 Hz), 8.03 (dd, 1H, J=9.6, 2.4 Hz), 8.17 (m, 2H), 8.39 (dd, 1H, J=1.5, 4.8 Hz). $^{13}$C NMR (CDCl$_3$) δ 17.94, 18.43, 19.87, 25.90, 31.28 (2C), 37.70, 51.00, 55.63, 61.67, 71.79, 114.76, 119.41, 123.02, 132.54, 132.74, 134.68, 137.14, 139.38, 139.52, 144.33, 146.40, 146.62, 151.92, 154.68, 164.09, 164.76. ES-MS m/z 478 (M+H). Anal. Calcd. for $C_{27}H_{35}N_5O_3.0.6CH_2Cl_2.0.3C_6H_{12}$: C, 63.76; H, 7.24; N, 12.65. Found: C, 63.39; H, 7.24; N, 12.63.

Example 182

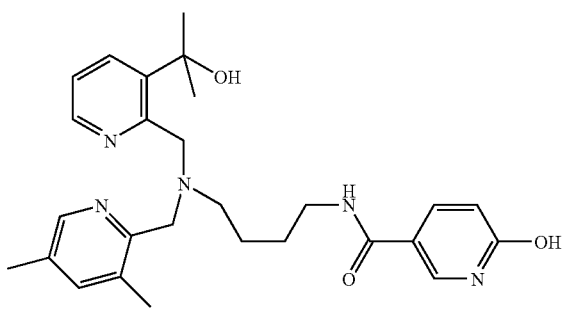

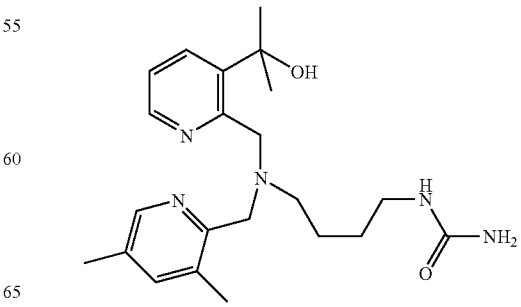

COMPOUND 182: (4-{(3,5-Dimethyl-pyridin-2-ylmethyl)-[3-(1-hydroxy-1-methyl-ethyl)-pyridin-2-ylmethyl]-amino}-butyl)-urea A solution of acetic acid 1-(2-{[(4-amino-butyl)-(3,5-dimethyl-pyridin-2-ylmethyl)-amino]-methyl}-pyridin-3-yl)-1-methyl-ethyl ester (223 mg, 0.56 mmol) in i-PrOH (3.7 mL) and treated with trimethylsilylisocyanate (110 µL, 0.78 mmol) at room temperature for 16 hours. The solution was then concentrated under reduced pressure and dried in vacuo. The crude material was then purified by column chromatography with silica gel (20:1:1 $CH_2Cl_2$/MeOH/$NH_4OH$) to give almost pure acetic acid 1-(2-{[(3,5-dimethyl-pyridin-2-ylmethyl)-(4-ureido-butyl)-amino]-methyl}-pyridin-3-yl)-1-methyl-ethyl ester as a colorless oil (227 mg, 92%).

A solution of the above compound (225 mg, 0.52 mmol) in anhydrous MeOH (2.5 mL) was treated with $K_2CO_3$ (140 mg, 1.0 mmol) and stirred at room temperature for 2 h. The mixture was concentrated under reduced pressure and water (10 ml) was added. Aqueous work-up and purification using radial chromatography on a silica gel plate (20:1:1 $CH_2Cl_2$:MeOH:$NH_4OH$), gave COMPOUND 182 as a pale brown residue. $^1$H NMR (CDCl$_3$) δ 1.38 (m, 2H), 1.46 (s, 6H), 1.66 (m, 2H), 2.19 (s, 3H), 2.27 (s, 3H), 2.59 (br t, 2H, J=7.5 Hz), 3.05 (q, 2H, J=6.1 Hz), 3.78 (s, 2H), 4.26 (s, 2H), 4.55 (br, 2H, (NH$_2$)), 5.85 (br, 1H, (NH)), 7.20 (m, 1H), 7.26 (s, 1H), 7.64 (dd, 1H, J=8.0, 1.6 Hz), 8.20 (s, 1H), 8.41 (dd, 1H, J=4.5, 1.5 Hz). $^{13}$C NMR (CDCl$_3$) δ 17.93, 18.40, 21.69, 26.96, 31.31 (2C), 39.09, 52.86, 56.11, 62.04, 71.70, 122.91, 132.33, 132.38, 134.55, 139.14, 144.22, 146.61, 146.69, 151.62, 154.32, 159.31. ES-MS m/z 400 (M+H). Anal. Calcd. for $C_{22}H_{33}N_5O_2 \cdot 0.5CH_2Cl_2 \cdot 0.1C_6H_{12}$: C, 61.60; H, 7.88; N, 15.55. Found: C, 61.83; H, 8.19; N, 15.55.

Example 183

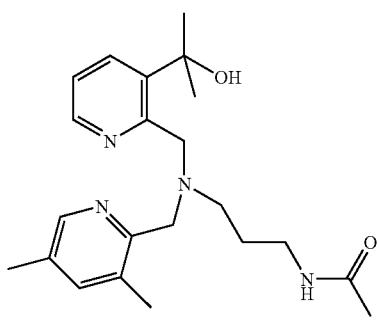

COMPOUND 183: N-(3-{(3,5-dimethyl-pyridin-2-ylmethyl)-[3-(1-hydroxy-1-methyl-ethyl)-pyridin-2-ylmethyl]-amino}-propyl)-acetamide Using General Procedure B: Reaction of (3-aminopropyl)-carbamic acid tert-butyl ester and 3,5-dimethylpyridine-2-carboxaldehyde in anhydrous MeOH with NaBH$_4$ gave {3-[(3,5-dimethyl-pyridin-2-ylmethyl)-amino]-propyl}-carbamic acid tert-butyl ester as a brown oil.

Using General Procedure B: Reaction of {3-[(3,5-dimethyl-pyridin-2-ylmethyl)-amino]-propyl}-carbamic acid tert-butyl ester, acetic acid 1-(2-formyl-pyridin-3-yl)-1-methyl-ethyl ester and NaBH(OAc)$_3$ gave 1-(2-{[(3-tert-butoxycarbonylamino-propyl)-(3,5-dimethyl-pyridin-2-ylmethyl)-amino]-methyl}-pyridin-3-yl)-1-methyl-ethyl ester (0.68 g, 74%). $^1$H NMR (CDCl$_3$) δ 1.47 (s, 9H), 1.70 (m, 2H), 1.77 (s, 6H), 1.98 (s, 3H), 2.23 (s, 3H), 2.25 (s, 3H), 2.64 (br t, 2H, J=7.5 Hz), 3.08 (br q, 2H, J=6.1 Hz), 3.69 (s, 2H), 3.89 (s, 2H), 7.16 (m, 1H), 7.21 (s, 1H), 7.53 (br, 1H, (NH)), 7.66 (d, 1H, J=7.0 Hz), 8.18 (s, 1H), 8.61 (d, 1H, J=3.0 Hz). Deprotection of the above compound with TFA using General Procedure F gave acetic acid 1-(2-{[(3-amino-propyl)-(3,5-dimethyl-pyridin-2-ylmethyl)-amino]-methyl}-pyridin-3-yl)-1-methyl-ethyl ester (0.43 g, 80%).

A portion of the amine from above (69 mg, 0.18 mmol) was dissolved in $CH_2Cl_2$ (1.0 mL) and treated with Et$_3$N (50 µL, 0.36 mmol) and Ac$_2$O (26 µL, 0.27 mmol) for 1 hour. Brine solution (3 mL) was added and the aqueous phase was extracted with $CH_2Cl_2$ (3×5 mL). The combined organic phases were then dried (Na$_2$SO$_4$), decanted, and concentrated under reduced pressure to give acetic acid 1-(2-{[(3-acetylamino-propyl)-(3,5-dimethyl-pyridin-2-ylmethyl)-amino]-methyl}-pyridin-3-yl)-1-methyl-ethyl ester as a light brown liquid (78 mg, 100%).

A solution of the above compound (78 mg, 0.18 mmol) in anhydrous MeOH (1.0 mL) was treated with K$_2$CO$_3$ (76 mg, 0.55 mmol) and stirred at room temperature for 3.5 h. The mixture was concentrated under reduced pressure and water (5 ml) was added. The aqueous solution was then extracted with CH$_2$Cl$_2$ (3×10 mL) and the combined organic phases dried (Na$_2$SO$_4$), decanted, and concentrated under reduced pressure. This gave pure COMPOUND 183 as a pale brown residue (60 mg, 86%, 2 steps). $^1$H NMR (CDCl$_3$) δ 1.48 (s, 6H), 1.81 (m, 2H), 1.88 (s, 3H), 2.23 (s, 3H), 2.25 (s, 3H), 2.62 (t, 2H, J=7.5 Hz), 3.22 (t, 2H, J=7.0 Hz), 3.76 (s, 2H), 4.21 (s, 2H), 7.15 (m, 1H), 7.22 (s, 1H), 7.61 (d, 1H, J=7.2 Hz), 8.16 (s, 1H), 8.37 (d, 1H, J=4.5 Hz). $^{13}$C NMR (CDCl$_3$) δ 18.25, 18.75, 23.46, 25.18, 31.73 (2C), 37.72, 52.10, 53.82, 57.00, 62.52, 71.88, 122.96, 132.38, 132.66, 134.63, 139.37, 144.38, 146.79, 147.05, 152.75, 155.48, 170.40. ES-MS m/z 385 (M+H). Anal. Calcd. for $C_{22}H_{32}N_4O_2 \cdot 1.0CH_2Cl_2$: C, 58.85; H, 7.30; N, 11.93. Found: C, 59.11; H, 7.33; N, 11.92.

Example 184

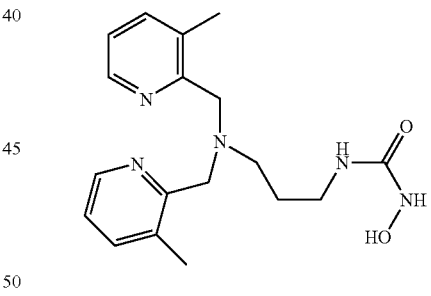

COMPOUND 184: {3-[Bis-(3-methyl-pyridin-2-ylmethyl)-amino]-propyl}-hydroxyurea A solution of Bis-(3-methyl-pyridin-2-ylmethyl)-propane-1,3-diamine (145 mg, 0.51 mmol) and 1,1-carbonyldiimidazole (82 mg, 0.51 mmol) in THF (5 mL) was stirred for 30 minutes at room temperature. The solvent was then removed under reduced pressure and the residue dissolved in DMF (3 mL). The solution was then treated with NH$_2$OH.HCl (142 mg, 2.0 mmol) and DIPEA (0.44 mL, 2.5 mmol) and stirred at room temperature for 18 hours. The reaction was then partitioned between CH$_2$Cl$_2$ (15 mL) and brine (10 mL) and separated. The organic phase was then washed several times with brine (4×10 mL) and the organic phase dried (Na$_2$SO$_4$) and concentrated under reduced pressure to afford, after column chromatography with silica gel (20:1:0.1 CH$_2$Cl$_2$:MeOH:NH$_4$OH), COMPOUND 184 as a white solid (99 mg, 57%).

$^1$H NMR (CDCl$_3$) δ 1.67 (q, 2H), 2.29 (s, 6H), 2.75 (t, 2H, J=5.4 Hz), 3.23 (q, 2H, J=5.4 Hz), 3.71 (s, 4H), 6.52 (s, 1H), 7.15 (m, 2H), 7.48 (d, 2H, J=7.5 Hz), 7.92 (br, 1H), 8.37 (d, 2H, J=4.5 Hz), 10.50 (br, 1H). $^{13}$C NMR (CDCl$_3$) δ 18.65 (2C), 25.93, 39.87, 55.28, 58.14 (2C), 122.66 (2C), 133.52 (2C), 138.71 (2C), 146.15 (2C), 155.97 (2C), 162.36. ES-MS m/z 366 (M+H). Anal. Calcd. for C$_{18}$H$_{25}$N$_5$O$_2$.0.2CH$_2$Cl$_2$: C, 60.65; H, 7.10; N, 19.43. Found: C, 60.80; H, 7.26; N, 19.72.

Example 185

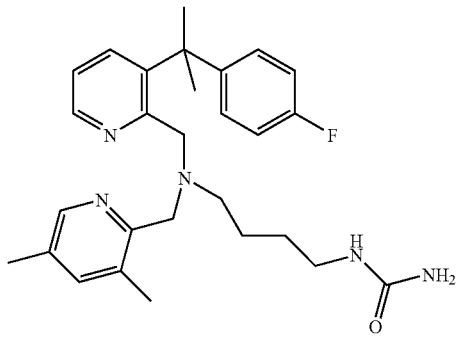

COMPOUND 185: [4-((3,5-Dimethyl-pyridin-2-ylmethyl)-{3-[1-(4-fluoro-phenyl)-1-methyl-ethyl]-pyridin-2-ylmethyl}-amino)-butyl]-urea The amine N$^1$-(3,5-dimethyl-pyridin-2-ylmethyl)-N$^1$-{3-[1-(2-fluoro-phenyl)-1-methyl-ethyl]-pyridin-2-ylmethyl}-butane-1,4-diamine (0.23 g, 0.53 mmol) was dissolved in i-PrOH (4.6 mL) and treated with trimethylsilylisocyanate (87 μL, 0.64 mmol) at room temperature for 16 hours. The solution was concentrated under reduced pressure and dried in vacuo. The crude material was then purified by column chromatography with silica gel (50:1 CH$_3$CN/NH$_4$OH) to give COMPOUND 185 as a white solid (65 mg, 30% 2 steps). $^1$H NMR (CDCl$_3$): δ 1.43 (br, 2H), 1.60 (br, 2H), 1.68 (s, 6H), 2.12 (s, 3H), 2.30 (s, 3H), 3.09 (br, 2H), 3.30 (br, 4H), 3.75 (br, 2H), 6.93 (m, 2H), 7.07 (m, 2H), 7.32 (s, 1H), 7.40 (m, 1H), 8.01 (d, 1H, J=7.8 Hz), 8.16 (s, 1H), 8.52 (d, 1H, J=3.6 Hz). $^{13}$C NMR (CDCl$_3$) δ 17.32, 17.88, 22.50, 26.71, 30.35 (2C), 38.38, 41.76, 54.63, 55.15, 57.00, 115.22, 115.55 (d, 2C, $^2$J=84 Hz), 119.13, 123.52, 127.72 (d, 2C, $^3$J=31 Hz), 131.41, 135.03, 139.74, 143.68, 146.60, 147.07, 150.79, 161.17 (d, 1C, $^1$J=979 Hz), 160.31, 161.31, 161.75, 173.28. ES-MS m/z 478 (M+H). Anal. Calcd. for C$_{28}$H$_{36}$N$_5$OF.1.5CH$_2$Cl$_2$: C, 58.56; H, 6.50; N, 11.58. Found: C, 58.43; H, 6.53; N, 11.86.

Example 186

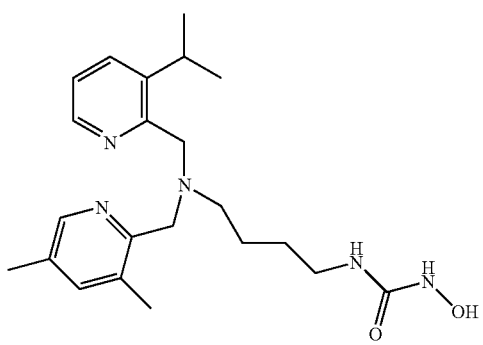

COMPOUND 186: {4-[(3,5-Dimethyl-pyridin-2-ylmethyl)-(3-isopropyl-pyridin-2-ylmethyl)-amino]-butyl}-hydroxyurea A solution of N$^1$-(3,5-dimethyl-pyridin-2-ylmethyl)-N$^1$-(3-isopropyl-pyridin-2-ylmethyl)-butane-1,4-diamine (111 mg, 0.33 mmol) and 1,1-carbonyldiimidazole (53 mg, 0.33 mmol) in THF (3.5 mL) was stirred for 30 minutes at room temperature. The solvent was then removed under reduced pressure and the residue dissolved in DMF (2 mL). The solution was then treated with NH$_2$OH.HCl (91 mg, 1.3 mmol) and DIPEA (0.28 mL, 1.6 mmol) and stirred at room temperature for 18 hours. The reaction was then partitioned between CH$_2$Cl$_2$ (15 mL) and brine (10 mL) and separated. The organic phase was then washed several times with brine (4×10 mL) and the organic phase dried (Na$_2$SO$_4$) and concentrated under reduced pressure to afford, after column chromatography with silica gel (20:1:0.2 CH$_2$Cl$_2$:MeOH:NH$_4$OH), COMPOUND 186 as a white solid (91 mg, 70%). $^1$H NMR (CDCl$_3$): δ 1.03 (d, 6H, J=6.6 Hz), 1.37 (qt, 2H, J=6.6 Hz), 1.57 (qt, 2H, J=6.6 Hz), 2.20 (s, 3H), 2.28 (s, 3H), 2.54 (t, 2H, J=6.9 Hz), 3.03 (s, 1H, J=7.0 Hz), 3.14 (q, 2H, J=6.0 Hz), 3.75 (s, 2H), 3.78 (s, 2H), 6.70 (br t, 1H(NH)), 6.78 (s, 1H(NH)), 7.17 (m, 1H), 7.26 (s, 1H), 7.55 (d, 1H, J=7.2 Hz), 8.18 (s, 1H), 8.32 (dd, 1H, J=4.8, 1.5 Hz). $^{13}$C NMR (CDCl$_3$) δ 17.91, 18.00, 22.79, 23.18 (2C), 27.27, 27.78, 39.06, 53.76, 57.70, 58.38, 122.97, 132.08, 133.09, 133.77, 139.05, 144.12, 145.46, 145.97, 153.63, 155.36, 162.46. ES-MS m/z 422 (M+H). Anal. Calcd. for C$_{22}$H$_{33}$N$_5$O$_2$.0.2CH$_2$Cl$_2$: C, 64.02; H, 8.08; N, 16.81. Found: C, 63.95; H, 8.30; N, 17.03.

Example 187

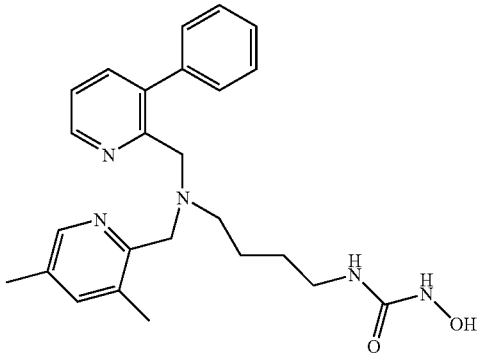

COMPOUND 187: {4-[(3,5-Dimethyl-pyridin-2-ylmethyl)-(3-phenyl-pyridin-2-ylmethyl)-amino]-butyl}-hydroxyurea A solution of N$^1$-(3,5-dimethyl-pyridin-2-ylmethyl)-N$^1$-(3-phenyl-pyridin-2-ylmethyl)-butane-1,4-diamine (170 mg, 0.46 mmol) and 1,1-carbonyldiimidazole (74 mg, 0.45 mmol) in THF (4.5 mL) was stirred for 30 minutes at room temperature. The solvent was then removed under reduced pressure and the residue dissolved in DMF (2 mL). The solution was then treated with NH$_2$OH.HCl (126 mg, 1.8 mmol) and DIPEA (0.40 mL, 2.3 mmol) and stirred at room temperature for 18 hours. The reaction was then partitioned between CH$_2$Cl$_2$ (15 mL) and brine (10 mL) and separated. The organic phase was then washed several times with brine (4×10 mL) and the organic phase dried (Na₂SO₄) and concentrated under reduced pressure to afford, after column chromatography with silica gel (14:1:0.2 CH₂Cl₂:MeOH:NH₄OH), COMPOUND 187 as a white solid (132 mg, 67%). ¹H NMR (CDCl₃): δ 1.24 (br, 4H), 2.02 (s, 3H), 2.24 (s, 3H), 2.33 (br t, 2H), 2.99 (br q, 2H), 3.68 (s, 2H), 3.87 (s, 2H), 6.78 (br, 1H, (NH)), 7.05 (br, 1H, (NH)), 7.17 (s, 1H), 7.28 (m, 3H), 7.36 (br, 3H), 7.56 (d, 1H, J=7.5 Hz), 8.09 (s, 1H), 8.59 (d, 1H, J=3.6 Hz). ¹³C NMR (CDCl₃) δ 17.88, 17.94, 23.03, 27.69, 39.06, 53.18, 57.17, 57.68, 122.23, 127.50, 128.30 (2C), 129.15 (2C), 131.78, 132.89, 138.26, 138.65, 139.27 (2C), 145.83, 147.47, 153.49, 155.65, 162.41. ES-MS m/z 456 (M+H). Anal. Calcd. for C₂₅H₃₁N₅O₂.0.9H₂O: C, 66.76; H, 7.35; N, 15.57. Found: C, 66.65; H, 7.18; N, 15.75.

Example 188

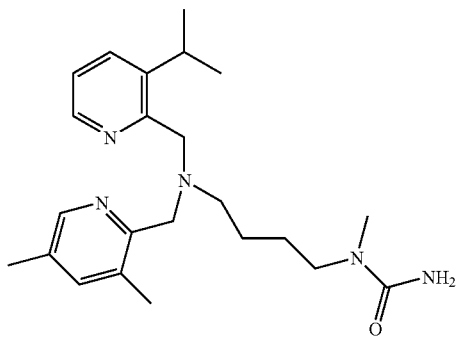

COMPOUND 188: 1-{4-[(3,5-Dimethyl-pyridin-2-ylmethyl)-(3-isopropyl-pyridin-2-ylmethyl)-amino]-butyl}-1-methyl-urea (HBr salt)

A solution of N-(3,5-dimethyl-pyridin-2-ylmethyl)-N-(3-isopropyl-pyridin-2-ylmethyl)-N'-methyl-butane-1,4-diamine (134 mg, 0.38 mmol) in i-PrOH (2 mL) was treated with trimethylsilylisocyanate (72 µL, 0.53 mmol) at room temperature for 16 hours. The solution was concentrated under reduced pressure and dried in vacuo. The crude material was then purified by column chromatography with silica gel (20:1:0.1 CH₂Cl₂/MeOH/NH₄OH) to give 1-{4-[(3,5-Dimethyl-pyridin-2-ylmethyl)-(3-isopropyl-pyridin-2-ylmethyl)-amino]-butyl}-1-methyl-urea as a colorless oil (52 mg, 42%, 2 steps). Conversion to the HBr salt gave COMPOUND 188 as a white solid. ¹H NMR (D₂O) δ 1.28 (d, 6H, J=6.6 Hz), 1.36 (br m, 4H), 2.47 (s, 6H), 2.63 (br t, 1H, J=6.7 Hz), 2.73 (s, 3H), 3.—(t, 2H, J=6.0 Hz), 3.30 (br sept, 1H), 4.24 (s, 2H), 4.39 (s, 2H), 7.93 (m, 1H), 8.22 (s, 1H), 8.44 (s, 1H), 8.53 (d, 1H, J=8.1 Hz), 8.60 (d, 1H, J=5.4 Hz). ¹³C NMR (D₂O) δ 17.17, 17.57, 22.10 (2C), 23.36, 24.98, 28.30, 34.47, 48.11, 54.20, 54.53, 55.68, 126.59, 136.90, 137.56, 138.05, 138.64, 144.85, 147.19, 148.07, 149.29, 150.09, 161.12. ES-MS m/z 398 (M+H). Anal. Calcd. for C₂₃H₃₅N₅O.3.5HBr.4.0H₂O: C, 36.70; H, 6.23; N, 9.30; Br, 37.15. Found: C, 36.87; H, 6.04; N, 9.10; Br, 36.88.

Example 189

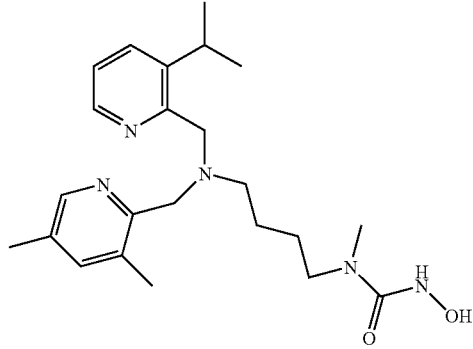

COMPOUND 189: 1-{4-[(3,5-Dimethyl-pyridin-2-ylmethyl)-(3-isopropyl-pyridin-2-ylmethyl)-amino]-butyl}-1-methyl-hydroxyurea A solution of N-(3,5-dimethyl-pyridin-2-ylmethyl)-N-(3-isopropyl-pyridin-2-ylmethyl)-N¹-methyl-butane-1,4-diamine (150 mg, 0.42 mmol) and N-(phenoxycarbonyl)hydroxylamine (84 mg, 0.55 mmol) in anhydrous THF (4 mL) was stirred for 16 hours at 70° C. The solution was then cooled and concentrated under reduced pressure and dried in vacuo. The crude material was purified by column chromatography with silica gel (14:1:0.1 CH₂Cl₂/MeOH/NH₄OH) to give COMPOUND 189 as a white solid (25 mg, 15%). ¹H NMR (CDCl₃): δ 1.00 (d, 6H, J=6.6 Hz), 1.40 (m, 4H), 2.17 (s, 3H), 2.27 (s, 3H), 2.54 (t, 2H, J=6.7 Hz), 2.79 (s, 3H), 2.96 (sep, 1H, J=6.9 Hz), 3.—(t, 2H, J=6.9 Hz), 3.72 (s, 2H), 3.74 (s, 2H), 7.16 (m, 1H), 7.25 (s, 1H), 7.45 (br, 1H, (NH)), 7.53 (dd, 1H, J=7.8, 1.5 Hz), 8.20 (s, 1H), 8.36 (dd, 1H, J=4.8, 1.5 Hz). ¹³C NMR (CDCl₃) δ 18.40 (2C), 23.23, 23.59 (2C), 25.58, 27.68, 33.96, 48.64, 54.05, 58.33, 59.04, 123.20, 132.30, 133.20, 133.84, 139.14, 144.27, 146.18, 146.73, 154.32, 156.11, 162.07. ES-MS m/z 414 (M+H). Anal. Calcd. for C₂₃H₃₅N₅O₂.0.2H₂O: C, 64.72; H, 8.29; N, 16.27. Found: C, 64.75; H, 8.50; N, 16.15.

Example 190

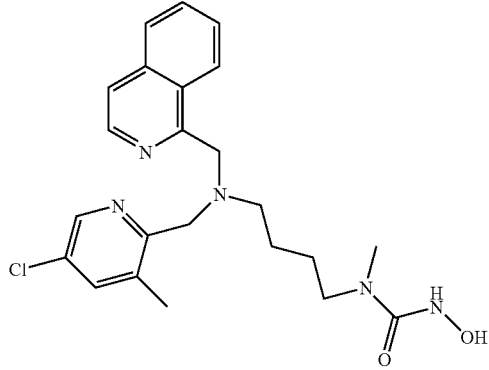

COMPOUND 190: 1-{4-[(5-Chloro-3-methyl-pyridin-2-ylmethyl)-isoquinolin-1-ylmethyl-amino]-butyl}-1-methyl-hydroxyurea Using General Procedure B: Reaction of {4-[(5-chloro-3-methyl-pyridin-2-ylmethyl)-amino]-butyl}-methyl-carbamic acid tert-butyl ester, isoquinoline-1-carbaldehyde and NaBH(OAc)$_3$ in CH$_2$Cl$_2$ gave {4-[(5-chloro-3-methyl-pyridin-2-ylmethyl)-isoquinolin-1-ylmethyl-amino]-butyl}-methyl-carbamic acid tert-butyl ester as a light brown solid. $^1$H NMR (CDCl$_3$): δ 1.29 (br, 2H), 1.41 (s, 9H), 1.50 (br, 2H), 2.01 (s, 3H), 2.59 (t, 2H, J=7.0 Hz), 2.68 (s, 3H), 3.02 (br, 2H), 3.78 (s, 2H), 4.19 (s, 2H), 7.35 (s, 1H), 7.45 (t, 1H, J=7.0 Hz), 7.55 (d, 1H, J=7.0 Hz), 7.62 (t, 1H, J=7.0 Hz), 7.78 (d, 1H, J=7.0 Hz), 8.05 (d, 1H, J=7.0 Hz), 8.29 (s, 1H), 8.42 (d, 1H, J=5.8 Hz). Deprotection with TFA using General Procedure F gave N-(5-chloro-3-methyl-pyridin-2-ylmethyl)-N$^1$-isoquinolin-1-ylmethyl-N-methyl-butane-1,4-diamine.

A solution of the above amine (217 mg, 0.57 mmol) and N-(phenoxycarbonyl)-hydroxylamine (176 mg, 1.15 mmol) in anhydrous THF (6 mL) was stirred for 16 hours at 75° C. The solution was then cooled and concentrated under reduced pressure and dried in vacuo. The crude material was purified by column chromatography with silica gel (20:1 CH$_3$CN/NH$_4$OH) to give COMPOUND 190 as a white solid (153 mg, 61%). $^1$H NMR (CDCl$_3$): δ 1.36 (m, 2H), 1.51 (m, 2H), 2.07 (s, 3H), 2.61 (t, 2H, J=7.0 Hz), 2.75 (s, 3H), 3.11 (t, 2H, J=7.2 Hz), 3.80 (s, 2H), 4.20 (s, 2H), 7.14 (br, 1H, (NH)), 7.38 (s, 1H), 7.48 (t, 1H, J=7.4 Hz), 7.56 (d, 1H, J=5.7 Hz), 7.64 (t, 1H, J=7.2 Hz), 7.78 (d, 1H, J=8.1 Hz), 8.05 (d, 1H, J=7.0 Hz), 8.33 (s, 1H), 8.44 (d, 1H, J=5.8 Hz). $^{13}$C NMR (CDCl$_3$) δ 18.06, 22.85, 25.22, 33.47, 48.24, 54.15, 58.54, 59.06, 120.64, 126.18, 126.75, 126.98, 127.65, 130.02, 130.52, 134.78, 136.25, 137.43, 141.28, 144.81, 155.09, 158.43, 161.60. ES-MS m/z 443 (M+H). Anal. Calcd. for C$_{23}$H$_{28}$N$_5$O$_2$Cl.0.4H$_2$O.0.1CH$_2$Cl$_2$: C, 60.62; H, 6.39; N, 15.30; Cl, 9.30. Found: C, 68.86; H, 6.44; N, 15.34; Cl, 8.91.

Example 191

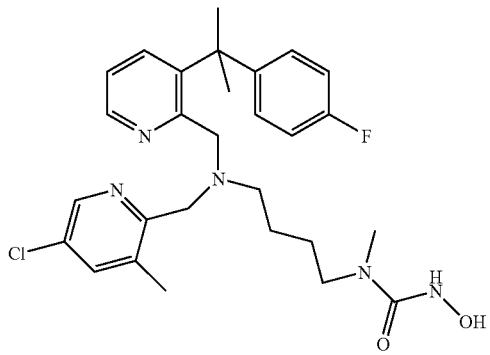

COMPOUND 191: 1-{4-[(5-Chloro-3-methyl-pyridin-2-ylmethyl)-{3-[1-(4-fluoro-phenyl)-1-methyl-ethyl]-pyridin-2-ylmethyl}-amino]-butyl}-1-methyl-hydroxyurea Using General Procedure B: Reaction of {4-[(5-chloro-3-methyl-pyridin-2-ylmethyl)-amino]-butyl}-methyl-carbamic acid tert-butyl ester, 3-[1-(4-fluoro-phenyl)-1-methyl-ethyl]-pyridine-2-carbaldehyde and NaBH(OAc)$_3$ gave [4-((5-chloro-3-methyl-pyridin-2-ylmethyl)-{3-[1-(4-fluoro-phenyl)-1-methyl-ethyl]-pyridin-2-ylmethyl}-amino]-butyl]-methyl-carbamic acid tert-butyl ester as a light brown solid. Deprotection with TFA using General Procedure F gave N-(5-Chloro-3-methyl-pyridin-2-ylmethyl)-N-{3-[1-(4-fluoro-phenyl)-1-methyl-ethyl]-pyridin-2-ylmethyl}-N$^1$-methyl-butane-1,4-diamine (326 mg, excess) which was used immediately in the next reaction.

A solution of the above amine (321 mg, 0.61 mmol) and N-(phenoxycarbonyl)-hydroxylamine (187 mg, 1.22 mmol) in anhydrous THF (6 mL) was stirred for 16 hours at 75° C. The solution was then cooled and concentrated under reduced pressure and dried in vacuo. The crude material was purified by column chromatography with silica gel (20:1 CH$_3$CN/NH$_4$OH) to give COMPOUND 191 as a white solid (121 mg, 38%, 2 steps). $^1$H NMR (CDCl$_3$): δ 1.30 (m, 2H), 1.47 (m, 2H), 1.63 (s, 6H), 2.18 (s, 3H), 2.28 (br, 2H), 2.86 (s, 3H), 3.—(t, 2H, J=7.5 Hz), 3.26 (br, 2H), 3.55 (br, 2H), 6.89 (m, 2H), 6.99 (m, 2H), 7.22 (m, 1H), 7.37 (s, 1H), 7.89 (d, 1H, J=7.8 Hz), 8.04 (br, 1H, (NH)), 8.27 (s, 1H), 8.59 (d, 1H, J=3.6 Hz). $^{13}$C NMR (CDCl$_3$) δ 18.69, 23.12, 25.11, 31.48 (2C), 34.15, 42.50, 48.27, 53.14, 57.23, 58.05, 115.55 (d, 2C, J=84 Hz), 122.16, 127.63 (d, 2C, J=31 Hz), 130.56, 134.52, 134.82, 137.82, 143.68, 145.15, 145.70, 147.31, 155.21, 157.68, 161.23 (d, 1C, 974 Hz), 162.37. ES-MS m/z 528 (M+H). Anal. Calcd. for C$_{28}$H$_{35}$N$_5$O$_2$ClF.0.7H$_2$O.0.1CH$_2$Cl$_2$: C, 61.46; H, 6.72; N, 12.75; Cl, 7.75. Found: C, 61.62; H, 6.58; N, 12.88; Cl, 7.51.

Example 192

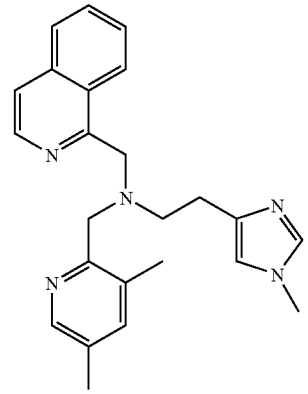

COMPOUND 192: (3,5-dimethyl-pyridin-2-ylmethyl)-isoquinolin-1-ylmethyl-[2-(1-methyl-1H-imidazol-4-yl)-ethyl]-amine To a solution of [2-(1H-imidazol-4-yl)-ethyl]-carbamic acid tert-butyl ester (512 mg, 2.42 mmol) in THF (20 mL) at −10° C. was added NaH (60%, 97 mg, 2.42 mmol). After stirring at −10° C. for 30 min, MeI (0.14 mL, 2.17 mmol) was added. After stirring at −10° C. for 2.5 h, the reaction mixture was concentrated to afford a yellow oil. Purification by flash column chromatography on silica gel using 2% MeOH/CH$_2$Cl$_2$ afforded [2-(1-methyl-1H-imidazol-4-yl)-ethyl]-carbamic acid tert-butyl ester as a yellow oil (144 mg, 34%). Deprotection with TFA using General Procedure F gave [2-(1methyl-1H-imidazol-4-yl)-ethyl]-amine as a yellow oil (51 mg, 25%).

Using General Procedure B: Reaction of the above amine and 2-isoquinoline carbaldehyde with NaBH(OAc)$_3$ gave (3,5-dimethyl-pyridin-2-ylmethyl)-isoquinolin-1-ylmethyl-[2-(1-methyl-1H-imidazol-4-yl)-ethyl]-amine as a yellow oil (18 mg, 33%).

Using General Procedure B: Reaction of the above amine and 3,5-dimethyl-pyridin-3-2-carbaldehyde in CH$_2$Cl$_2$, with NaBH(OAc)$_3$ gave COMPOUND 192 as a yellow oil (7 mg, 27%). $^1$H NMR (CDCl$_3$) δ 2.00 (s, 3H), 2.26 (s, 3H), 2.80-2.84 (m, 2H), 2.89-2.93 (m, 2H), 3.47 (s, 3H), 3.87 (s, 2H), 4.25 (s, 2H), 6.25 (s, 1H), 7.21 (d, 2H, J=6.0 Hz), 7.35 (t, 1H, J=6.0 Hz), 7.53 (d, 1H, J=6.0 Hz), 7.59 (t, 1H, J=6.0 Hz), 7.75 (d, 1H, J=9.0 Hz), 7.96 (d, 1H, J=9.0 Hz), 8.19 (s, 1H), 8.41 (d, 1H, J=6.0 Hz). $^{13}$C NMR (CDCl$_3$) δ 18.32, 25.48, 31.02, 33.72, 54.79, 59.18, 59.80, 116.98, 120.86, 126.81, 127.07, 130.22, 137.07, 139.16, 141.68, 146.67. ES-MS m/z 386 [M+H]$^+$.

Example 193

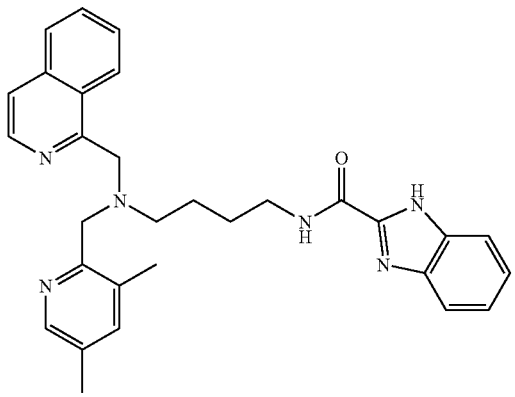

COMPOUND 193: 1H-benzoimidazole-2-carboxylic acid-{4-[(3,5-dimethyl-pyridin-2-ylmethyl)-isoquinolin-1-ylmethyl-amino]-butyl}-amide Using General Procedure G: A mixture of N$^1$-(3,5-dimethyl-pyridin-2-ylmethyl)-N$^1$-isoquinolin-1-ylmethyl-butane-1,4-diamine (121 mg, 0.35 mmol), 1H-benzimidazole-2-carboxylic acid (70%, 97 mg, 0.42 mmol) (*Eur. J. Med. Chem.* 1993, 28, 71), HOBT (61 mg, 0.46 mmol), EDCI (91 mg, 0.46 mmol), and DIPEA (90 μL, 0.53 mmol) in DMF (5 mL) was stirred at room temperature overnight. Workup and purification gave the product as a pale yellow oil. (71 mg, 41%). $^1$H NMR (CDCl$_3$) δ 1.40-1.47 (m, 2H), 1.56-1.63 (m, 2H), 2.06 (s, 3H), 2.25 (s, 3H), 2.62 (t, 2H, J=7.5 Hz), 3.30 (q, 2H, J=6.0 Hz), 3.81 (s, 2H), 4.18 (s, 2H), 7.21 (s, 1H), 7.30-7.33 (m, 2H), 7.49-7.55 (m, 3H), 7.70-7.75 (m, 3H), 7.99 (d, 1H, J=6.0 Hz), 8.21 (s, 1H), 8.40 (d, 1H, J=6.0 Hz). $^{13}$C NMR (CDCl$_3$) δ 18.32, 23.96, 27.56, 39.69, 53.84, 54.24, 59.72, 59.87, 112.7, 120.80, 120.88, 123.66, 125.22, 126.83, 127.24, 128.12, 130.18, 132.31, 133.15, 134.62, 136.64, 139.13, 141.77, 143.22, 145.43, 146.90, 154.28, 159.30, 159.68. ES-MS m/z 515 [M+H]$^+$. Anal. Calcd. for C$_{30}$H$_{32}$N$_6$O.1.6CH$_2$Cl$_2$: C, 60.39; H, 5.64; N, 13.37. Found: C, 60.20; H, 5.52; N, 13.54.

Example 194

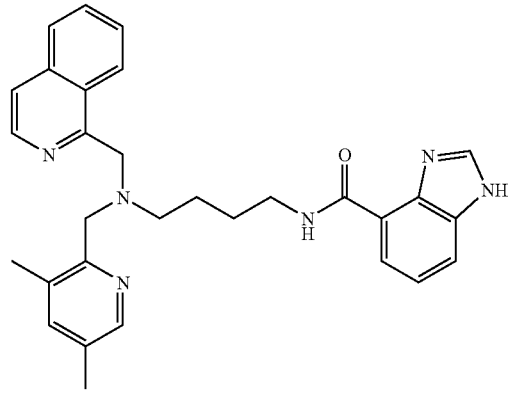

COMPOUND 194: 1H-benzimidazole-4-carboxylic acid-{4-[(3,5-dimethyl-pyridin-2-ylmethyl)-isoquinolin-1-ylmethyl-amino]-butyl}-amide To a solution of N$^1$-(3,5-dimethyl-pyridin-2-ylmethyl)-N$^1$-isoquinolin-1-ylmethyl-butane-1,4-diamine (83 mg, 0.24 mmol) in CH$_2$Cl$_2$ (5 mL) was added Et$_3$N (0.13 mL, 0.96 mmol) and 1H-benzoimidazole-4-carbonyl chloride (86 mg, 0.48 mmol) and the mixture was stirred for 2 d. Then it was diluted with CH$_2$Cl$_2$ (20 mL) and washed with saturated NaHCO$_3$ (3×15 mL). The organic layer was dried (MgSO$_4$), filtered, and concentrated to afford a yellow oil. Purification by radial chromatography on silica gel (1 mm plate; using CH$_2$Cl$_2$/MeOH/NH$_4$OH; 50:1:1) afforded the product as a yellow oil (34 mg, 29%). $^1$H NMR (CDCl$_3$) δ 1.48-1.53 (m, 2H), 1.66 (s, 6H), 1.72 (br m, 2H), 2.03 and 2.07 (s, total 3H), 2.25 and 2.27 (s, total 3H), 2.64 (t, 2H, J=7.5 Hz), 3.30 (br m, 1H), 3.40 (br m, 1H), 3.81 and 3.87 (s, total 2H), 4.21 and 4.25 (s, total 2H), 7.37-7.42 (m, 2H), 7.55-7.57 (m, 2H), 8.04-8.07 (m, 2H), 8.13-8.17 (m, 2H), 8.38 and 8.40 (s, total 1H), 9.79 (br s, 1H). $^{13}$C NMR (CDCl$_3$) δ 18.32, 18.43, 24.42, 26.61, 27.88, 30.10, 39.57, 53.83, 54.90, 58.23, 59.54, 115.20, 121.06, 123.26, 123.88, 126.80, 127.01, 127.27, 128.13, 130.33, 132.48, 133.33, 136.67, 139.37, 141.47, 146.47, 146.58, 154.16, 159.19. ES-MS m/z 493 [M+H]$^+$. Anal. Calcd. for C$_{30}$H$_{32}$N$_6$O.1.4.CH$_2$Cl$_2$: C, 61.67; H, 5.74; N, 13.74. Found: C, 62.01; H, 5.79; N, 13.67.

Example 195

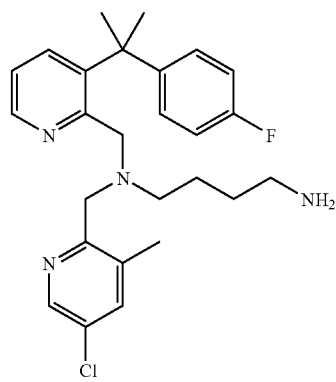

COMPOUND 195: N-(5-chloro-3-methyl-pyridin-2-ylmethyl)-N-{3-[1-(4-fluoro-phenyl)-1-methyl-ethyl]-pyridin-2-ylmethyl}-butane-1,4-diamine HBr salt Using General Procedure B: Reaction of (4-amino-butyl)-carbamic acid tert-butyl ester in $CH_2Cl_2$ and 5-chloro-3-methyl-pyridine-2-carbaldehyde with $NaBH(OAc)_3$ gave {4-[(5-chloro-3-methyl-pyridin-2-ylmethyl)-amino]-butyl}-carbamic acid tert-butyl ester as a colorless oil. $^1$H NMR ($CDCl_3$) δ 1.41 (s, 9H), 1.54 (m, 4H), 2.13 (s, 1H), 2.28 (s, 3H), 2.68 (t, 2H, J=6.0 Hz), 3.11 (d, 2H, J=6.0 Hz), 3.81 (s, 2H), 4.77 (br s, 1H), 7.41 (s, 1H), 8.31 (s, 1H).

Using General Procedure B: Reaction of {4-[(5-chloro-3-methyl-pyridin-2-ylmethyl)-amino]-butyl}-carbamic acid tert-butyl ester in $CH_2Cl_2$ and 3-[1-(4-fluoro-phenyl)-1-methyl-ethyl]-pyridine-2-carbaldehyde with $NaBH(OAc)_3$ gave [4-((5-chloro-3-methyl-pyridin-2-ylmethyl)-{3-[1-(4-fluoro-phenyl)-1-methyl-ethyl]-pyridin-2-ylmethyl}-amino)-butyl]-carbamic acid tert-butyl ester as a colorless oil. $^1$H NMR ($CDCl_3$) δ 1.26 (m, 4H), 1.44 (s, 9H), 1.64 (s, 6H), 2.13 (s, 3H), 2.31 (t, 2H, J=7.5 Hz), 2.94 (d, 2H, J=6.0 Hz), 3.28 (s, 2H), 3.51 (s, 2H), 5.12 (br s, 1H), 6.90-6.98 (m, 4H), 7.23 (dd, 1H, J=7.5, 3.0 Hz), 7.36 (s, 1H), 7.86 (d, 1H, J=9.0 Hz), 8.25 (d, 1H, J=3.0 Hz), 8.53 (d, 1H, J=3.0 Hz).

Using General Procedure D: Conversion to the HBr salt gave COMPOUND 195 as a pale yellow crystalline solid. $^1$H NMR ($D_2O$) δ 1.35 (m, 2H), 1.45 (m, 1H), 1.71 (s, 6H), 2.29 (s, 3H), 2.56 (t, 1H, J=6.0 Hz), 2.87 (t, 1H, J=6.5 Hz), 3.82 (s, 2H), 3.90 (s, 2H), 7.08 (t, 2H, J=7.5 Hz), 7.25 (t, 2H, J=7.5 Hz), 7.91 (t, 1H, J=6.0 Hz), 8.17 (s, 1H), 8.58 (s, 1H), 8.64 (m, 2H). $^{13}$C NMR ($D_2O$) δ 17.3, 22.0, 24.7, 29.7, 39.3, 42.5, 53.7, 54.4, 55.4, 115.9, 116.2, 125.9, 128.6, 128.7, 133.1, 137.3, 140.7, 141.7, 142.5, 143.8, 144.9, 146.7, 148.8, 150.5, 160.0, 163.3. HPLC: 99%. ES-MS m/z 455 [M+H]$^+$. Anal. Calcd. for $C_{26}H_{32}N_4ClF.1.4H_2O.2.8HBr$: C, 44.00; H, 5.34; N, 7.88; Cl, 5.48; Br, 31.47. Found: C, 44.15; H, 5.32; N, 7.75; Cl, 5.47; Br, 31.24.

Example 196

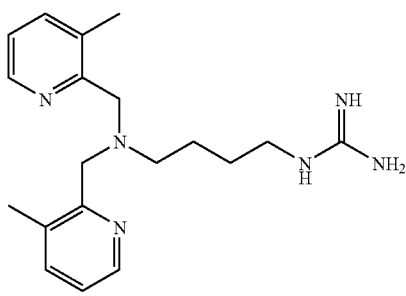

COMPOUND 196: N-{4-[bis-(3-methyl-pyridin-2-ylmethyl)-amino]-butyl}-guanidine

To a solution of $N^1,N^1$-bis-(3-methyl-pyridin-2-ylmethyl)-butane-1,4-diamine (0.1970 g, 0.46 mmol) in DMF (5 mL) was added 1H-pyrazole-carboxamidine hydrochloride (0.0681 g, 0.46 mmol) and DIPEA (0.48 mL, 2.76 mmol) and stirred at room temperature for 16 hours. The reaction mixture was concentrated, and purification of the crude material by column chromatography on silica gel (20:1:1, then 10:1:1, then 1:1:1 $CH_2Cl_2$-MeOH—$NH_4OH$) followed by radial chromatography on silica gel (20:4:1 $CH_2Cl_2$-MeOH—$NH_4OH$) provided 0.1380 g (64%) of COMPOUND 196 as a white solid. $^1$H NMR ($CDCl_3$) δ 1.49-1.53 (m, 2H), 1.65-1.69 (m, 2H), 2.17 (s, 6H), 2.70-2.75 (m, 4H), 3.12-3.14 (m, 2H), 3.87 (s, 4H), 7.10-7.14 (m, 2H), 7.41-7.44 (m, 2H), 8.34-8.39 (m, 2H). $^{13}$C NMR ($CDCl_3$) δ 18.53, 23.14, 26.99, 41.30, 54.57, 58.09, 123.15, 133.48, 138.87, 146.21, 155.66, 158.02. ES-MS m/z 341.3 (M+H). Anal. Calcd. for $C_{19}H_{28}N_6.1.1CH_2Cl_2.1.8H_2O$: C, 51.77; H, 7.31; N, 18.02. Found: C, 51.50; H, 7.04; N, 18.31.

Example 197

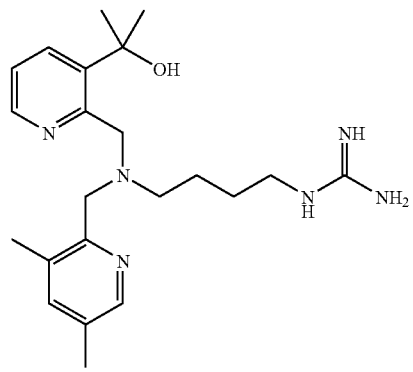

COMPOUND 197: N-(4-{(3,5-dimethyl-pyridin-2-ylmethyl)-[3-(1-hydroxy-1-methyl-ethyl)-pyridin-2-ylmethyl]-amino}-butyl)-guanidine To a solution of 2-(2-{[(4-Amino-butyl)-(3,5-dimethyl-pyridin-2-ylmethyl)-amino]-methyl}-pyridin-3-yl)-propan-2-ol (0.1423 g, 0.28 mmol) in DMF (3 mL) was added 1H-pyrazole-carboxamidine hydrochloride (0.0440 g, 0.28 mmol) and DIPEA (0.29 mL, 1.68 mmol) and stirred at room temperature for 20 hours. The reaction mixture was concentrated, and purification of the crude material by column chromatography on silica gel (5:1:1 $CH_2Cl_2$-MeOH—$NH_4OH$) followed by radial chromatography on silica gel (10:2:1 $CH_2Cl_2$-MeOH—$NH_4OH$) provided 0.1367 g (41%) of COMPOUND 197 as a white solid. $^1$H NMR ($CDCl_3$) δ 1.43-1.48 (m, 8H), 1.68-1.70 (m, 2H), 2.21 (s, 3H), 2.25 (s, 3H), 2.71-2.73 (m, 4H), 3.15-3.17 (m, 3H), 3.47 (s, 2H), 3.91 (s, 2H), 4.32 (s, 2H), 7.18-7.21 (m, 1H), 7.59-7.63 (m, 1H), 7.92-7.93 (m, 1H), 8.17 (s, 1H), 8.37-8.39 (m, 1H). $^{13}$C NMR ($CDCl_3$) δ 18.31, 18.65, 22.77, 26.67, 31.59, 41.57, 54.09, 56.32, 61.95, 72.43, 123.57, 132.52, 132.92, 135.02, 139.67, 144.31, 146.94, 147.10, 150.68, 153.40, 158.00. ES-MS m/z 400 (M+H). Anal. Calcd. for $C_{22}H_{34}N_6O.1.9CH_2Cl_2.1.5H_2O$: C, 48.91; H, 7.01; N, 14.32. Found: C, 48.68; H, 6.83; N, 14.68.

Example 198

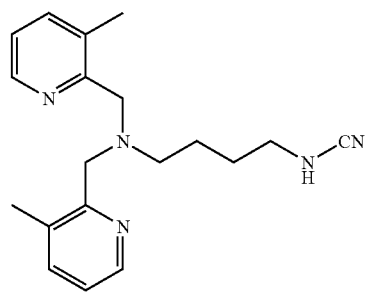

COMPOUND 198: 4-[Bis-(3-methyl-pyridin-2-ylmethyl)-amino-]butyl-cyanamide

To a 0° C. solution of $N^1,N^1$-bis-(3-methyl-pyridin-2-ylmethyl)-butane-1,4-diamine (237 mg, 0.80 mmol) in MeOH (10 mL) was added NaOAc (200 mg, 2.39 mmol) and cyanogen bromide (94 mg, 1.03 mmol) and stirred at room temperature for 17 hours. Water (10 mL) was added and the reaction mixture was extracted with $CH_2Cl_2$ (4×40 mL). The extracts were washed with brine (20 mL), dried ($Na_2SO_4$), filtered and concentrated to provide pure COMPOUND 198 as a beige solid (190 mg, 74%). $^1H$ NMR ($CDCl_3$) δ 1.45-1.51 (m, 2H), 1.65-1.63 (m, 2H), 2.12 (s, 6H), 2.61-2.65 (m, 2H), 2.83-2.89 (m, 2H), 3.68 (s, 4H), 7.08 (dd, 2H, J=4.2, 7.8 Hz), 7.38 (d, 2H, J=7.8 Hz), 7.57 (br s, 1H), 8.37 (d, 2H, J=4.2 Hz). $^{13}C$ NMR ($CDCl_3$) δ 18.5, 21.1, 28.3, 44.4, 53.6, 58.2, 118.9, 122.9, 133.4, 138.6, 146.6, 156.7. ES-MS m/z 324 (M+H). Anal. Calcd. for $C_{19}H_{25}N_5 \cdot 0.4\ CH_2Cl_2 \cdot 0.1CH4O$: C, 64.95; H, 7.32; N, 19.42. Found: C, 64.65; H, 7.22; N, 19.27.

Example 199

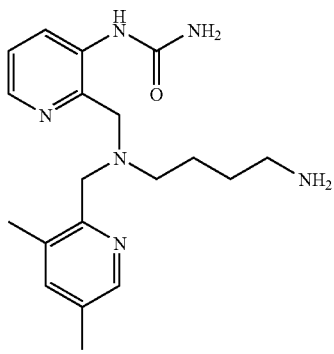

COMPOUND 199: (2-{[(4-amino-butyl)-(3,5-dimethyl-pyridin-2-ylmethyl)-amino]-methyl}-pyridin-3-yl)-urea Using General Procedure B: Reaction of 2-(aminomethyl)-3,5-dimethylpyridine, (2-formyl-pyridin-3-yl)-carbamic acid tert-butyl ester and $NaBH(OAc)_3$ gave an impure oil, which was further reacted with 4-(1,3-dioxo-1,3-dihydro-isoindol-2-yl)-butyraldehyde and $NaBH(OAc)_3$ to give the desired intermediate as an oil. Deprotection with TFA using General Procedure F gave 2-{4-[(3-Amino-pyridin-2-ylmethyl)-(3,5-dimethyl-pyridin-2-ylmethyl)-amino]-butyl}-isoindole-1,3-dione as a colorless oil. $^1H$ NMR ($CDCl_3$) δ 1.43-1.44 (m, 4H), 2.26 (s, 6H), 2.52-2.56 (m, 2H), 3.51-3.57 (m, 2H), 3.71 (s, 2H), 3.76 (s, 2H), 4.98 (s, 2H), 6.82-6.85 (m, 1H), 6.92-6.96 (m, 1H), 7.22 (s, 1H), 7.69-7.72 (m, 2H), 7.80-7.85 (m, 3H), 8.21 (s, 1H).

A solution of 2-{4-[(3-amino-pyridin-2-ylmethyl)-(3,5-dimethyl-pyridin-2-ylmethyl)-amino]-butyl}-isoindole-1,3-dione (0.246 g, 0.555 mmol) and trimethylsilyl isocyanate (0.094 g, 0.82 mmol) in dry i-PrOH (6 mL) was stirred for 20 h. The i-PrOH was then removed in vacuo, and the residue was purified by flash chromatography on a silica gel column (40:2:1 $CH_2Cl_2/MeOH/NH_4OH$) to afford an impure oil. Deprotection with $NH_2NH_2 \cdot H_2O$ using General Procedure E gave COMPOUND 199 as a colorless oil. $^1H$ NMR ($CDCl_3$) δ 1.24-1.37 (m, 2H), 1.39-1.52 (m, 2H), 2.29 (s, 3H), 2.32 (s, 3H), 2.45 (t, 2H, J=6.9 Hz), 2.54 (t, 2H, J=6.9 Hz), 3.79 (s, 2H), 3.80 (s, 2H), 5.57 (s, 2H), 7.12 (dd, 1H, J=4.8, 8.1 Hz), 7.30 (s, 1H), 8.05 (d, 1H, J=4.8 Hz), 8.26 (s, 1H), 8.52 (d, 1H, J=8.1 Hz); $^{13}C$ NMR ($CDCl_3$) δ 18.29, 19.08, 24.11, 31.17, 41.98, 53.96, 56.45, 61.36, 123.38, 126.07, 131.94, 132.28, 137.29, 139.69, 141.72, 145.54, 147.49, 153.56, 157.27; ES-MS m/z 379 (M+Na). Anal Calcd. For $C_{19}H_{28}N_6O \cdot 1.4CH_3OH$: C, 61.05; H, 8.44; N, 20.94; Found: C, 61.51; H, 8.06; N, 20.69.

Example 200

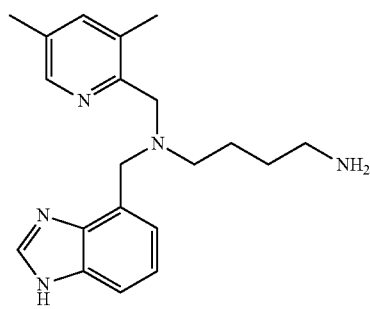

COMPOUND 200: $N^1$-(1H-benzoimidazol-4-ylmethyl)-$N^1$-(3,5-dimethyl-pyridin-2-ylmethyl)-butane-1,4-diamine (HBr salt)

Using General Procedure A reaction of 4-[(3,5-dimethyl-pyridin-2-ylmethyl)-amino]-butyl}-carbamic acid tert-butyl ester, 4-bromomethyl-benzoimidazole-1-carboxylic acid tert-butyl ester (Moon, M. W. et al. J. Med. Chem. 1992, 35, 1076-1092), KI and DIPEA in $CH_3CN$ gave a pale yellow foam. Deprotection with TFA using General Procedure F gave a colorless oil. Conversion to the HBr salt gave COMPOUND 200 as a white solid. $^1H$ NMR ($D_2O$) δ 1.70-1.81 (m, 2H), 1.87-1.98 (m, 2H), 2.13 (s, 3H), 2.19 (s, 3H), 3.05 (t, 2H, J=7.5 Hz), 3.31 (t, 2H, J=7.8 Hz), 4.28 (s, 2H), 4.56 (s, 2H), 7.48-7.54 (m, 2H), 7.66-7.71 (m, 2H), 7.89 (s, 1H), 9.21 (s, 1H); $^{13}C$ NMR ($D_2O$) δ 16.84, 17.13, 22.27, 24.85, 39.53, 53.32, 55.97, 56.74, 115.59, 121.06, 127.35, 129.24, 129.96, 130.71, 134.19, 135.61, 139.68, 140.79, 144.52, 147.08. ES-MS m/z 338 (M+H). Anal. Calcd. for $C_{20}H_{27}N_5 \cdot 4.2HBr \cdot 1.5H_2O \cdot 0.3C_4H_{10}O$: C, 35.05; H, 5.16; N, 9.64; Br, 46.19. Found: C, 34.99; H, 4.99; N, 9.67; Br, 46.19.

Example 201

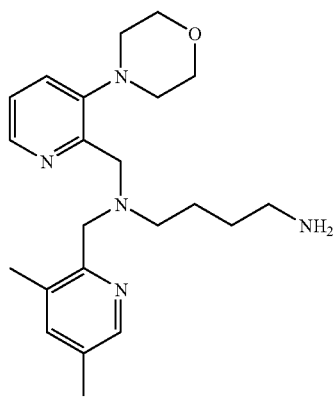

COMPOUND 201: N¹-(3,5-dimethyl-pyridin-2-ylmethyl)-N¹-(3-morpholin-4-yl-pyridin-2-ylmethyl)-butane-1,4-diamine (HBr salt)

A mixture of 3-chloro-pyridine (1.14 g, 10.0 mmol) and 3-chloroperoxybenzoic acid (77%, 4.5 g, 20 mmol) in $CH_2Cl_2$ (30 mL) was stirred at room temperature for 16 h. Saturated aqueous $NaHCO_3$ (10 mL) was added, and the mixture was extracted with $CH_2Cl_2$ (5×30 mL). The extracts were combined and dried over anhydrous $Na_2SO_4$. After filtration the solvent was removed by evaporation under vacuum, and the residue was purified by flash chromatography on a silica gel column (EtOAc), affording 3-chloro-pyridine-1-oxide as a pale yellow solid (1.03 g, 80%).

A solution of 3-chloro-pyridine 1-oxide (4.00 g, 31.0 mmol) in morpholine (15 mL) was heated at reflux for 4 days. After the reaction mixture was cooled to room temperature excess morpholine was removed under reduced pressure, and the residue was purified by flash chromatography on a silica gel column (6:1 EtOAc/MeOH) followed by recrystallization from $CH_2Cl_2/Et_2O$, affording 4-(1-oxy-pyridin-3-yl)-morpholine as a pale brown solid (3.59 g, 64%). $^1H$ NMR ($CDCl_3$) δ 3.15-3.19 (m, 4H), 3.83-3.87 (m, 4H), 6.81 (dd, 1H, J=2.1, 8.7 Hz), 7.12 (dd, 1H, J=6.3, 8.7 Hz), 7.76-7.78 (m, 1H), 7.88-7.90 (m, 1H).

A mixture of 4-(1-oxy-pyridin-3-yl)-morpholine (1.00 g, 5.55 mmol), trimethylsilyl cyanide (1.65 g, 16.7 mmol) and triethyl amine (1.37 g, 13.9 mmol) in dry $CH_3CN$ (20 mL) was heated at reflux for 16 h, yielding a red solution. The reaction mixture was then cooled to room temperature, and saturated aqueous $NaHCO_3$ (20 mL) was added. After concentrated under reduced pressure the mixture was extracted with $CH_2Cl_2$ (4×30 mL). The extracts were combined and dried over anhydrous $Na_2SO_4$. After filtration the solvent was removed by evaporation under vacuum, and the residue was purified by flash chromatography on a silica gel column (EtOAc) to afford 3-morpholin-4-yl-pyridine-2-carbonitrile as an orange solid (1.01 g, 96%). $^1H$ NMR ($CDCl_3$) δ 3.22-3.25 (m, 4H), 3.85-3.92 (m, 4H), 7.35-7.45 (m, 2H), 8.28-8.29 (m, 1H).

A solution of 3-morpholin-4-yl-pyridine-2-carbonitrile (0.500 g, 2.64 mmol) in MeOH (10 mL) was added to a flask charged with Raney Ni (pre-washed with methanol) (~0.5 g) in MeOH (10 mL). After saturated with $NH_3$ gas the mixture was shaken under $H_2$ (40 psi) for 3 h. The reaction mixture was then filtered through a celite cake, and the filtrate was concentrated under reduced pressure. The residue was purified by flash chromatography on a silica gel column (500:25:6 $CH_2Cl_2$/MeOH/$NH_4OH$), affording C-(3-morpholin-4-yl-pyridin-2-yl)-methylamine as a pale yellow oil (0.480 g, 94%). $^1H$ NMR ($CDCl_3$) δ 2.90-2.93 (m, 4H), 3.85-3.90 (m, 4H), 4.02 (s, 2H), 7.16 (dd, 1H, J=4.5, 8.1 Hz), 7.35 (dd, 1H, J=1.2, 8.1 Hz), 8.33 (dd, 1H, J=1.2, 4.5 Hz).

Using General Procedure B: Reaction of C-(3-morpholin-4-yl-pyridin-2-yl)-methylamine, 3.5-dimethyl-pyridine-2-carbaldehyde and $NaBH(OAc)_3$ gave (3,5-dimethyl-pyridin-2-ylmethyl)-(3-morpholin-4-yl-pyridin-2-ylmethyl)-amine as a colorless oil. $^1H$ NMR ($CDCl_3$) δ 2.27 (s, 3H), 2.30 (s, 3H), 2.92-2.95 (m, 4H), 3.79-3.82 (m, 4H), 3.95 (s, 2H), 4.03 (s, 2H), 7.14 (dd, 1H, J=4.5, 8.1 Hz), 7.23 (s, 1H), 7.33 (dd, 1H, J=1.2, 8.1 Hz), 8.22 (s, 1H), 8.31 (dd, 1H, J=1.2, 4.5 Hz). Further reaction of (3,5-dimethyl-pyridin-2-ylmethyl)-(3-morpholin-4-yl-pyridin-2-ylmethyl)-amine, 4-(1,3-dioxo-1,3-dihydro-isoindol-2-yl)-butyraldehyde and $NaBH(OAc)_3$ following General Procedure B gave a colorless oil. Deprotection with $NH_2NH_2.H_2O$, following General Procedure E, gave a colorless oil. Subsequent conversion to the HBr salt gave COMPOUND 201 as a pale yellow solid. $^1H$ NMR ($D_2O$) δ 1.58-1.70 (m, 4H), 2.42 (s, 3H), 2.44 (s, 3H), 2.78-2.84 (m, 2H), 2.94-3.02 (m, 2H), 3.04 (s, br., 4H), 3.96 (s, br., 4H), 4.24 (s, 2H), 4.28 (s, 2H), 7.80-7.88 (m, 1H), 8.07-8.15 (m, 2H), 8.8.36-8.42 (m, 2H); $^{13}C$ NMR ($D_2O$) δ 17.21, 17.49, 23.06, 25.05, 39.66, 51.91, 52.65, 54.34, 55.96, 66.81, 126.80, 135.15, 136.40, 137.34, 137.78, 137.91, 147.61, 148.92, 149.75. ES-MS m/z 384 (M+H). Anal. Calcd. for $C_{22}H_{33}N_5O.3.3HBr.1.5H_2O.0.3C_4H_{10}O$: C, 39.82; H, 6.09; N, 10.01; Br, 37.68. Found: C, 39.83; H, 6.20; N, 10.08; Br, 37.59.

Example 202

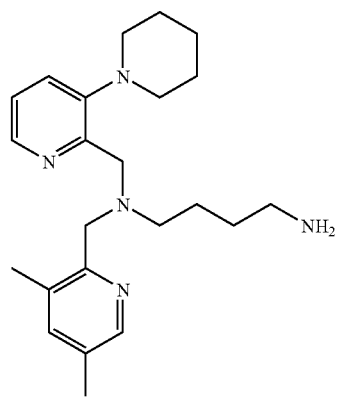

COMPOUND 202: N¹-(3,5-dimethyl-pyridin-2-ylmethyl)-N¹-(3,4,5,6-tetrahydro-2H-[1,3']bipyridinyl-2'-ylmethyl)-butane-1,4-diamine (HBr salt)

A solution of 3-chloro-pyridine 1-oxide (2.40 g, 18.5 mmol) in piperidine (6 mL) was heated at 140° C. for 2 days. After the reaction mixture was cooled to room temperature the amine was removed, and the residue was purified by flash chromatography on a silica gel column (6:1 EtOAc/MeOH), affording 3,4,5,6-tetrahydro-2H-[1,3']bipyridinyl 1'-oxide as a pale yellow solid (2.20 g, 67%). $^1H$ NMR ($CDCl_3$) δ 1.59-1.67 (m, 6H), 3.14-3.18 (m, 4H), 6.78 (dd, 1H, J=2.1, 8.7 Hz), 7.03 (dd, 1H, J=6.3, 8.7 Hz), 7.63-7.66 (m, 1H), 7.85-7.86 (m, 1H).

A mixture of 3,4,5,6-tetrahydro-2H-[1,3']bipyridinyl 1'-oxide (1.30 g, 7.30 mmol), trimethylsilyl cyanide (1.45 g, 14.6 mmol) and triethyl amine (1.47 g, 14.6 mmol) in dry $CH_3CN$ (25 mL) was heated at reflux for 16 h, yielding a red solution. The reaction mixture was then cooled to room temperature, and saturated aqueous $NaHCO_3$ (20 mL) was added. After concentrated under reduced pressure the mixture was extracted with $CH_2Cl_2$ (4×30 mL). The extracts were combined and dried over anhydrous $Na_2SO_4$. After filtration the solvent was removed by evaporation under vacuum, and the residue was purified by flash chromatography on a silica gel column ($CH_2Cl_2$) to afford 3,4,5,6-tetrahydro-2H-[1,3']bipyridinyl-2'-carbonitrile as a pale yellow solid (1.26 g, 92%). $^1H$ NMR ($CDCl_3$) δ 1.58-1.66 (m, 2H), 1.75-1.83 (m, 4H), 3.21 (t, 4H, J=5.7 Hz), 7.34-7.38 (m, 2H), 8.19-8.22 (m, 1H).

A solution of 3,4,5,6-tetrahydro-2H-[1,3']bipyridinyl-2'-carbonitrile (0.980 g, 5.23 mmol) in MeOH (10 mL) was added to a flask charged with Raney Ni (pre-washed with methanol) (~1.0 g) in MeOH (10 mL). After saturated with $NH_3$ gas the mixture was shaken under $H_2$ (40 psi) for 3 h. The reaction mixture was then filtered through a celite cake, and the filtrate was concentrated under reduced pressure. The residue was purified by flash chromatography on a silica gel column (100:5:1 $CH_2Cl_2$/MeOH/$NH_4OH$), affording C-(3,4, 5,6-tetrahydro-2H-[1,3']bipyridinyl-2'-yl)-methylamine as a pale yellow oil (0.627 g, 63%). $^1$H NMR (CDCl$_3$) δ 1.53-1.61 (m, 2H), 1.65-1.74 (m, 4H), 2.82 (t, 4H, J=5.4 Hz), 3.99 (s, 2H), 7.11 (dd, 1H, J=4.8, 8.1 Hz), 7.31 (dd, 1H, J=1.5, 8.1 Hz), 8.27 (dd, 1H, J=1.5, 4.8 Hz).

Using General Procedure B: Reaction of C-(3,4,5,6-tetrahydro-2H-[1,3']bipyridinyl-2'-yl)-methylamine, 3,5-dimethyl-pyridine-2-carbaldehyde and NaBH(OAc)$_3$ gave (3,5-dimethyl-pyridin-2-ylmethyl)-(3,4,5,6-tetrahydro-2H-[1,3'] bipyridinyl-2'-ylmethyl)-amine. $^1$H NMR (CDCl$_3$) δ 1.50-1.57 (m, 2H), 1.63-1.72 (m, 4H), 2.24 (s, 3H), 2.28 (s, 3H), 2.82 (t, 4H, J=5.1 Hz), 3.91 (s, 2H), 4.01 (s, 2H), 7.07 (dd, 1H, J=4.5, 8.1 Hz), 7.20 (s, 1H), 7.28 (dd, 1H, J=1.2, 8.1 Hz), 8.20 (s, 1H), 8.23 (dd, 1H, J=1.2, 4.5 Hz). Further reaction of (3,5-dimethyl-pyridin-2-ylmethyl)-(3,4,5,6-tetrahydro-2H-[1,3']bipyridinyl-2'-ylmethyl)-amine, 4-(1,3-dioxo-1,3-dihydro-isoindol-2-yl)-butyraldehyde and NaBH(OAc)$_3$ following General Procedure B gave a colorless oil. Deprotection with NH$_2$NH$_2$.H$_2$O following General Procedure E, and subsequent conversion to the HBr salt, gave COMPOUND 202 as a yellow solid. $^1$H NMR (CD$_3$OD) δ 1.55-1.83 (m, 10H), 2.51 (s, br. 6H), 2.71-2.76 (m, 2H), 2.922 (t, 2H, J=7.5 Hz), 3.00-3.04 (m, 4H), 4.32 (s, 2H), 4.33 (s, 2H), 7.89 (dd, 1H, J=5.7, 8.4 Hz), 8.20 (d, 1H, J=8.4 Hz), 8.23 (s, 1H), 8.56 (d, 1H, J=5.7 Hz), 8.62 (s, 1H); $^{13}$C NMR (D$_2$O) δ 17.20, 17.45, 23.08, 23.45, 25.04, 25.73, 39.68, 52.55, 53.42, 54.35, 56.32, 126.47, 133.78, 135.55, 137.45, 137.74, 147.08, 147.50, 148.70, 150.86. ES-MS m/z 382 (M+H). Anal. Calcd. for C$_{23}$H$_{35}$N$_5$O.3.8HBr.0.9H$_2$O.0.3C$_4$H$_{10}$O: C, 39.96; H, 6.04; N, 9.63; Br, 41.74. Found: C, 39.93; H, 6.08; N, 9.64; Br, 41.68.

Example 203

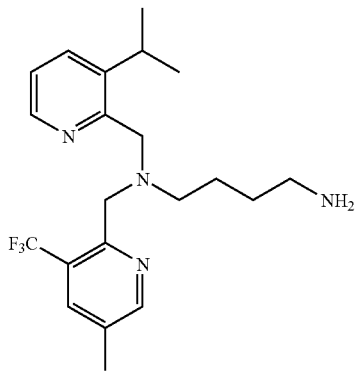

COMPOUND 203: N$^1$-(3-isopropyl-pyridin-2-ylmethyl)-N$^1$-(5-methyl-trifluoromethyl-pyridin-2-ylmethyl)-butane-1,4-diamine (HBr salt)

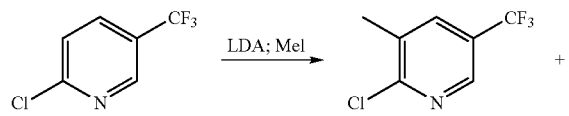

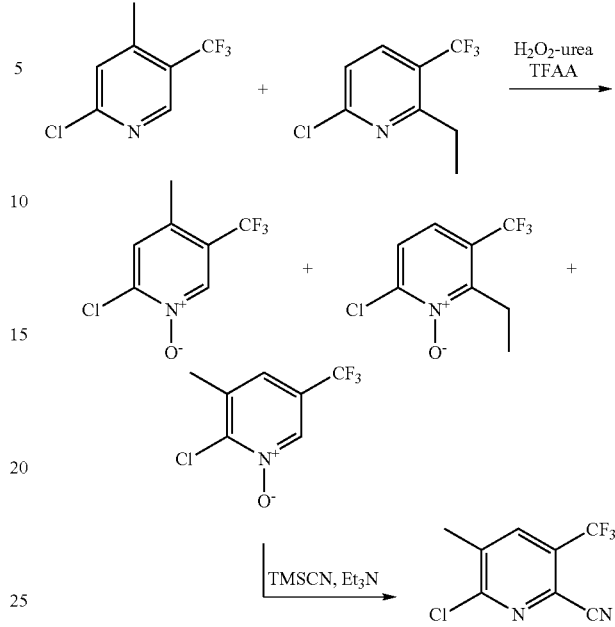

To a solution of 2-chloro-5-trifluoromethyl-pyridine (4.00 g, 22.0 mmol) in THF at −78° C. under N$_2$, was added LDA (2.0 M in heptane/benzene/THF, 11.5 mL, 23.0 mmol) slowly. After addition the mixture was stirred at −78° C. for 30 min, and MeI (3.55 g, 25.0 mmol) was added quickly. After the reaction mixture was stirred at −78° C. for 30 min water (30 mL) was added, and the mixture was extracted with EtOAc (4×40 mL). The extracts were combined and dried over anhydrous Na$_2$SO$_4$. After filtration the solvent was removed by evaporation under vacuum to afford a brown liquid (3.25 g) mainly containing the three species as shown in the Scheme. The brown liquid was dissolved in dry CH$_2$Cl$_2$ (40 mL), and H$_2$O$_2$-urea (ground, 4.0 g, 35 mmol) was added. The mixture was then cooled at 0° C., and TFAA (7.0 g, 33 mmol) was added. After addition the reaction mixture was warmed to room temperature and stirred overnight. The solid residue was filtered off, and saturated NaHCO$_3$ (50 mL) was added to the filtrate. The organic layer was collected, and the aqueous layer was extracted with CH$_2$Cl$_2$ (4×50 mL). The organic extracts were combined and dried over anhydrous Na$_2$SO$_4$. After filtration the solvent was removed by evaporation under vacuum, and the residue was purified by flash chromatography on a silica gel column (1:1 EtOAc/CH$_2$Cl$_2$) to afford 6-chloro-5-methyl-3-trifluoromethyl-pyridine-1-oxide as a pale yellow solid (1.03 g, 24% two steps). $^1$H NMR (CDCl$_3$) δ 2.51 (s, 3H), 7.32 (s, 1H), 8.51 (s, 1H).

A mixture of 6-chloro-5-methyl-3-trifluoromethyl-pyridine-1-oxide (1.03 g, 5.30 mmol), trimethylsilyl cyanide (1.57 g, 16.0 mmol) and Et$_3$N (1.34 g, 13.3 mmol) in dry CH$_3$CN (30 mL) was heated at reflux for 64 h. The reaction mixture was then cooled to room temperature, and saturated aqueous NaHCO$_3$ (20 mL) was added. After concentrated under reduced pressure the mixture was extracted with CH$_2$Cl$_2$ (3×30 mL). The extracts were combined and dried over anhydrous Na$_2$SO$_4$. After filtration the solvent was removed by evaporation under vacuum, and the residue was purified by flash chromatography on a silica gel column (6:1 hexanes/EtOAc) to afford 6-chloro-5-methyl-3-trifluoromethyl-pyridine-2-carbonitrile as a colorless oil (0.660 g, 56%). $^1$H NMR (CDCl$_3$) δ 2.56 (s, 3H), 7.95 (s, 1H).

A solution of 6-chloro-5-methyl-3-trifluoromethyl-pyridine-2-carbonitrile (0.300 g, 1.36 mmol) in MeOH (5 mL) was added to a flask charged with Raney Ni (pre-washed with methanol) (~0.6 g) in MeOH (5 mL). After saturated with NH$_3$ gas the mixture was shaken under H$_2$ (40 psi) for 2 h. The reaction mixture was then filtered through a celite cake, and the filtrate was concentrated by evaporation under vacuum. The residue was purified by flash chromatography on a silica gel column (200:10:1 CH$_2$Cl$_2$/MeOH/NH$_4$OH), affording C-(5-methyl-3-trifluoromethyl-pyridin-2-yl)-methylamine as a colorless oil (0.113 g, 44%). $^1$H NMR (CDCl$_3$) δ 2.39 (s, 3H), 4.07 (s, 2H), 7.71 (s, 1H), 8.56 (s, 1H).

Using General Procedure B: Reaction of C-(6-chloro-5-methyl-3-trifluoromethyl-pyridin-2-yl)-methylamine, 3-isopropyl-pyridine-2-carbaldehyde and NaBH(OAc)$_3$ gave (3-isopropyl-pyridin-2-ylmethyl)-(5-methyl-3-trifluoromethyl-pyridin-2'-ylmethyl)-amine. $^1$H NMR (CDCl$_3$) δ 1.23 (d, 6H, J=6.9 Hz), 2.38 (s, 3H), 3.21 (septet, 1H, J=6.9 Hz), 4.03 (s, 2H), 4.14 (s, 2H), 7.13 (dd, 1H, J=4.5, 8.1 Hz), 7.55 (dd, 1H, J=1.5, 8.1 Hz), 7.72 (s, 1H), 8.40 (dd, 1H, J=1.5, 4.5 Hz), 8.58 (s, 1H). Further reaction of (3-isopropyl-pyridin-2-ylmethyl)-(5-methyl-3-trifluoromethyl-pyridin-2'-ylmethyl)-amine, 4-(1,3-dioxo-1,3-dihydro-isoindol-2-yl)-butyraldehyde and NaBH(OAc)$_3$ following General Procedure B gave a colorless oil. Deprotection with NH$_2$NH$_2$.H$_2$O following General Procedure E and conversion to the HBr salt gave COMPOUND 203 as a white solid. $^1$H NMR (CD$_3$OD) δ 1.30 (d, 6H, J=6.9 Hz), 1.69-1.77 (m, 2H), 1.83-1.91 (m, 2H), 2.49 (s, 3H), 2.94 (t, 2H, J=7.5 Hz), 3.16 (septet, 1H, J=6.9 Hz), 3.20-3.33 (m, 2H), 4.73 (s, 2H), 4.81 (s, 2H), 7.60 (t, 1H, J=5.1 Hz), 8.09 (d, 1H, J=5.1 Hz), 8.15 (s, 1H), 8.58 (d, 1H, J=5.1 Hz), 8.79 (s, 1H); $^{13}$C NMR (D$_2$O) δ 17.71, 22.31, 22.45, 24.72, 28.32, 39.45, 54.45, 55.22, 55.34, 121.19, 124.81, 125.32, 125.77, 126.22, 126.66, 137.11, 140.83, 140.89, 141.65, 145.97, 147.97, 148.06, 148.86. ES-MS m/z 395 (M+H). Anal. Calcd. for C$_{21}$H$_{29}$F$_3$N$_4$.2.5HBr.0.6H$_2$O.0.6C$_4$H$_{10}$O: C, 43.10; H, 5.98; N, 8.59; Br, 30.64. Found: C, 43.07; H, 6.12; N, 8.54; Br, 30.68.

Example 204

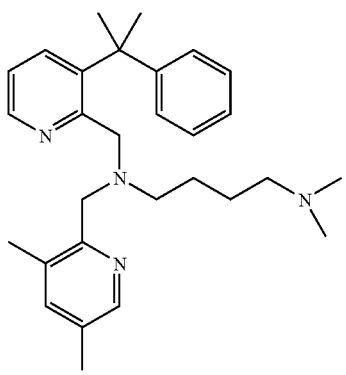

COMPOUND 204: N-(3,5-dimethyl-pyridin-2-ylmethyl)-N',N'-dimethyl-N-[3-(1-methyl-1-phenyl-ethyl)-pyridin-2-ylmethyl]-butane-1,4-diamine (HBr salt)

Using General Procedure B: Reaction of N-(3,5-dimethyl-pyridin-2-ylmethyl)-N-[3-(1-methyl-1-phenyl-ethyl)-pyridin-2-ylmethyl]-butane-1,4-diamine, paraformaldehyde and NaBH(OAc)$_3$ gave a colorless oil. Conversion to the HBr salt using General Procedure D gave a pale yellow solid. $^1$H NMR (CD$_3$OD) δ 1.47-1.63 (m, 4H), 1.81 (s, 6H), 2.27-2.33 (m, 2H), 2.35 (s, 3H), 2.51 (s, 3H), 2.85 (s, 6H), 3.04 (t, 2H, J=7.5 Hz), 3.57 (s, 2H), 3.85 (s, 2H), 7.28-7.31 (m, 2H), 7.33-7.44 (m, 3H), 8.11 (dd, 1H, J=6.0, 8.1 Hz), 8.59 (s, 1H), 8.91 (s, 1H), 8.92 (d, 1H, J=8.1 Hz), 8.96 (d, 1H, J=6.0 Hz); $^{13}$C NMR (CD$_3$OD) δ 17.42, 17.62, 22.17, 29.68, 43.14, 43.19, 52.71, 54.06, 54.55, 57.58, 126.50, 126.94, 127.61, 129.64, 136.82, 137.43, 138.21, 139.26, 145.28, 147.36, 147.53, 148.21, 149.31, 151.99. ES-MS m/z 445 (M+H). Anal. Calcd. for C$_{29}$H$_{40}$N$_4$.4.4HBr.4.2H$_2$O.0.4C$_4$H$_{10}$O: C, 40.57; H, 6.32; N, 6.18; Br, 38.81. Found: C, 40.39; H, 6.43; N, 6.23; Br, 39.10.

Example 205

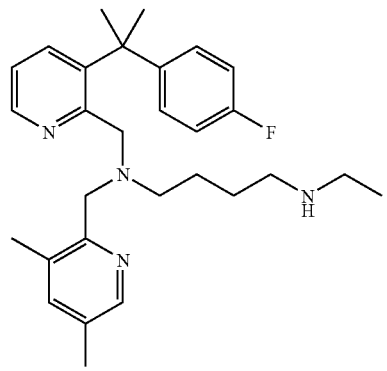

COMPOUND 205: N-(3,5-dimethyl-pyridin-2-ylmethyl)-N'-ethyl-N-{3-[1-(4-fluoro-phenyl)-1-methyl-ethyl]-pyridin-2-ylmethyl}-butane-1,4-diamine (HBr salt)

A mixture of (4-amino-butyl)-carbamic acid tert-butyl ester (0.360 g, 1.91 mmol), acetaldehyde (0.085 g, 1.91 mmol) and K$_2$CO$_3$ (0.264 g, 1.91) in MeOH (5 mL) was stirred for 6 h. The mixture was filtered through a celite cake. The filtrate was cooled at 0° C. and NaBH$_4$ (0.106 g, 2.08 mmol) was added. After the reaction mixture was stirred at 0° C. for 45 min water (20 mL) was added, and the mixture was extracted with CH$_2$Cl$_2$ (3×30 mL). The organic extracts were combined and dried over anhydrous Na$_2$SO$_4$. After filtration the solvent was removed by evaporation under vacuum, and the residue was purified by flash chromatography on a silica gel column (200:10:1 CH$_2$Cl$_2$/MeOH/NH$_4$OH), affording (4-ethylamino-butyl)-carbamic acid tert-butyl ester as a colorless oil (0.215 g, 52%).

To a solution of (4-ethylamino-butyl)-carbamic acid tert-butyl ester (0.215 g, 0.995 mmol) and Et$_3$N (0.151 g, 1.45 mmol) in dry CH$_2$Cl$_2$ (10 mL) was added 2-nitrobenzenesulfonyl chloride (0.265 g, 1.19 mmol). After the mixture was stirred for 2 h water (10 mL) was added, and the mixture was extracted with CH$_2$Cl$_2$ (3×20 mL). The organic extracts were combined and dried over anhydrous Na$_2$SO$_4$. After filtration the solvent was removed by evaporation under vacuum, and the residue was purified by flash chromatography on a silica gel column (4:1 CH$_2$Cl$_2$/EtOAc), affording 4-[ethyl-(2-nitro-benzenesulfonyl)-amino]-butyl}-carbamic acid tert-butyl ester as a pale blue oil (0.343 g, 86%).

Deprotection with TFA using General Procedure F gave (4-Amino-butyl)-N-ethyl-2-nitro-benzenesulfonamide was obtained as a colorless oil. $^1$H NMR (CDCl$_3$) δ 1.12 (t, 3H, J=6.9 Hz), 1.35-1.47 (m, 2H), 1.54-1.65 (m, 2H), 2.68 (t, 2H, J=6.9 Hz), 3.27-3.40 (m, 4H), 7.59-7.68 (m, 3H), 7.99-8.02 (m, 1H).

A mixture of (4-amino-butyl)-N-ethyl-2-nitro-benzenesulfonamide (0.252 g, 0.836 mmol), 3.5-dimethyl-pyridine-2-carbaldehyde (0.113 g, 0.836 mmol) and K$_2$CO$_3$ (0.115 g, 0.836) in MeOH (8 mL) was stirred for 5 h. Methanol was removed by evaporation under vacuum and CH$_2$Cl$_2$ (20 mL) was added. The mixture was filtered through a celite cake and NaBH(OAc)$_3$ (0.354 g, 1.67 mmol) was added to the filtrate. After the mixture was stirred for 5 h saturated aqueous NaHCO$_3$ (20 mL) was added, and the mixture was extracted with CH$_2$Cl$_2$ (2×30 mL). The organic extracts were combined and dried over anhydrous Na$_2$SO$_4$. After filtration the solvent was removed by evaporation under vacuum, and the residue was purified by flash chromatography on a silica gel column (500:25:1 CH$_2$Cl$_2$/MeOH/NH$_4$OH), affording N-{4-[(3,5-dimethyl-pyridin-2-ylmethyl)-amino]-butyl}-N-ethyl-2-nitro-benzenesulfonamide as a pale yellow oil (0.256 g, 73%). $^1$H NMR (CDCl$_3$) δ 1.13 (t, 3H, J=7.2 Hz), 1.50-1.66 (m, 4H), 2.67 (s, 6H), 2.68 (t, 2H, J=7.2 Hz), 3.29-3.40 (m, 4H), 3.81 (s, 2H), 7.24 (s, 1H), 7.58-7.69 (m, 3H), 7.97-8.02 (m, 1H), 8.20 (s, 1H).

Using General Procedure B: Reaction of N-{4-[(3,5-dimethyl-pyridin-2-ylmethyl)-amino]-butyl}-N-ethyl-2-nitro-benzenesulfonamide, 3-[1-(4-fluoro-phenyl)-1-methyl-ethyl]-pyridine-2-carbaldehyde and NaBH(OAc)$_3$ gave a pale yellow oil. The oil was dissolved in dry CH$_3$CN (5 mL), and Cs$_2$CO$_3$ (0.225 g, 0.690 mmol) and thiophenol (0.076 g, 0.69 mmol) were added. After the mixture was stirred for 2 h, CH$_3$CN was removed and water (20 mL) was added. The mixture was extracted with CH$_2$Cl$_2$ (3×20 mL). The organic extracts were combined and dried over anhydrous Na$_2$SO$_4$. After filtration the solvent was removed by evaporation under vacuum, and the residue was purified by flash chromatography on a silica gel column (500:25:1 CH$_2$Cl$_2$/MeOH/NH$_4$OH), affording the product as a colorless oil (0.095 g, 60% two steps). Conversion to the HBr salt using General Procedure D gave a white solid. $^1$H NMR (D$_2$O) δ 1.15-1.24 (m, 5H), 1.31-1.38 (m, 2H), 1.73 (s, 6H), 2.20-2.29 (m, 5H), 2.43 (s, 3H), 2.84 (t, 1H, J=7.8 Hz), 3.00 (q, 2H, J=7.2 Hz), 3.69 (s, 2H), 3.74 (s, 2H), 7.10 (t, 2H, J=8.7 Hz), 7.25-7.30 (m, 2H), 8.04 (dd, 1H, J=5.4, 8.4 Hz), 8.14 (s, 1H), 8.39 (s, 1H), 8.69 (d, 1H, J=5.4 Hz), 8.65 (d, 1H, J=8.4 Hz); $^{13}$C NMR (D$_2$O) δ 11.02, 17.28, 17.61, 22.32, 23.77, 29.77, 42.80, 43.30, 47.01, 52.78, 54.01, 54.53, 116.26 (d, J=21 Hz), 126.54, 128.82 (d, J=8 Hz), 136.80, 137.48, 138.27, 139.37, 143.47, 145.24, 147.34, 147.95, 149.28, 151.89, 161.74 (d, J=244 Hz). ES-MS m/z 463 (M+H). Anal. Calcd. for C$_{29}$H$_{39}$FN$_4$·3.2HBr·2.3H$_2$O·0.4C$_4$H$_{10}$O: C, 46.37; H, 6.46; N, 7.07; Br, 32.26. Found: C, 46.44; H, 6.50; N, 7.11; Br, 32.18.

Example 206

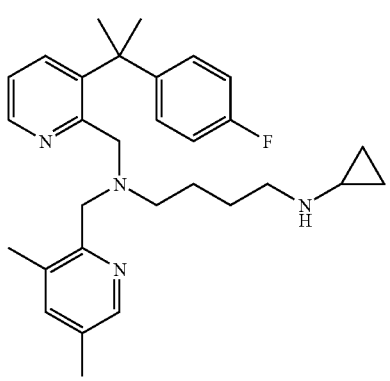

COMPOUND 206: N-cyclopropyl-N'-(3,5-dimethyl-pyridin-2-ylmethyl)-N'-{3-[1-(4-fluoro-phenyl)-1-methyl-ethyl]-pyridin-2-ylmethyl}-butane-1,4-diamine (HBr salt)

Using General Procedure B, cyclopropylamine, 4-(1,3-dioxo-1,3-dihydro-isoindol-2-yl)-butyraldehyde and NaBH(OAc)$_3$ were reacted to obtain a pale yellow oil. A mixture of the oil, Boc$_2$O, Et$_3$N in CH$_2$Cl$_2$ was stirred overnight. Aqueous workup and purification gave cyclopropyl-[4-(1,3-dioxo-1,3-dihydro-isoindol-2-yl)-butyl]-carbamic acid tert-butyl ester as a pale yellow oil. Deprotection with NH$_2$NH$_2$·H$_2$O using General Procedure E gave (4-Amino-butyl)-cyclopropyl-carbamic acid tert-butyl ester as a colorless oil. $^1$H NMR (CDCl$_3$) δ 0.54-0.59 (m, 2H), 0.70-0.75 (m, 2H), 1.32-1.45 (m, 11H), 1.52-1.65 (m, 2H), 2.44-2.50 (m, 1H), 2.71 (t, 2H, J=7.2 Hz), 3.20 (t, 2H, J=7.5 Hz).

Using General Procedure B, (4-amino-butyl)-cyclopropyl-carbamic acid tert-butyl ester and 3,5-dimethyl-pyridine-2-carbaldehyde in MeOH were reacted with NaBH$_4$ to obtain cyclopropyl-{4-[(3,5-dimethyl-pyridin-2-ylmethyl)-amino]-butyl}-carbamic acid tert-butyl ester as a colorless oil (0.217 g, 89%). $^1$H NMR (CDCl$_3$) δ 0.52-0.58 (m, 2H), 0.68-0.74 (m, 2H), 1.44 (s, 9H), 1.53-1.65 (m, 4H), 2.26 (s, 6H), 2.45-2.50 (m, 1H), 2.70 (t, 2H, J=6.9 Hz), 3.19 (t, 2H, J=7.2 Hz), 3.82 (s, 2H), 7.23 (s, 1H), 8.20 (s, 1H).

Using General Procedure B, cyclopropyl-{4-[(3,5-dimethyl-pyridin-2-ylmethyl)-amino]-butyl}-carbamic acid tert-butyl ester, 3-[1-(4-fluoro-phenyl)-1-methyl-ethyl]-pyridine-2-carbaldehyde and NaBH(OAc)$_3$ were reacted to obtain a pale yellow oil. Deprotection with TFA following General Procedure F, and conversion to the HBr salt gave COMPOUND 206 as a white solid. $^1$H NMR (D$_2$O) δ 0.76-0.85 (m, 4H), 1.11-1.17 (m, 2H), 1.34-1.42 (m, 2H), 1.74 (s, 6H), 2.20-2.32 (m, 5H), 2.43 (s, 3H), 2.62-2.66 (m, 1H), 2.93-2.98 (m, 2H), 3.71 (s, 2H), 3.75 (s, 2H), 7.08-7.15 (m, 2H), 7.23-7.30 (m, 2H), 8.00-8.08 (m, 1H), 8.15 (s, 1H), 8.39 (s, 1H), 869 (d, 1H, J=4.5 Hz), 8.86 (d, 1H, J=7.5 Hz); $^{13}$C NMR (D$_2$O) δ 3.41, 17.27, 17.60, 22.24, 23.57, 29.76, 30.36, 42.83, 48.05, 52.77, 53.96, 54.63, 116.18 (d, J=21 Hz), 126.57, 128.83 (d, J=8 Hz), 136.87, 137.57, 138.34, 139.38, 143.52, 145.28, 147.33, 148.00, 149.34, 151.91, 161.81 (d, J=244 Hz). ES-MS m/z 475 (M+H). Anal. Calcd. for C$_{30}$H$_{39}$FN$_4$·3.4HBr·1.0H$_2$O·0.4C$_4$H$_{10}$O: C, 47.60; H, 6.12; N, 7.03; Br, 34.07. Found: C, 47.54; H, 6.29; N, 7.09; Br, 34.23.

Example 207

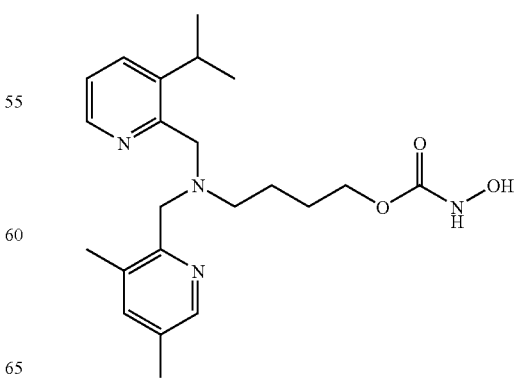

COMPOUND 207: hydroxylaminecarboxylic acid 4-[(3,5-dimethyl-pyridin-2-ylmethyl)-(3-isopropyl-pyridin-2-ylmethyl)-amino]-butyl ester Using General Procedure B, 4-amino-butan-1-ol and 3,5-dimethyl-pyridine-2-carbaldehyde in MeOH were reacted with NaBH$_4$ to give 4-[(3,5-dimethyl-pyridin-2-ylmethyl)-amino]-butan-1-ol as a pale yellow oil.

Using General Procedure B, 4-[(3,5-dimethyl-pyridin-2-ylmethyl)-amino]-butan-1-ol, 3-isopropoxy-pyridine-2-carbaldehyde and NaBH(OAc)$_3$ were reacted to obtain 4-[(3,5-dimethyl-pyridin-2-ylmethyl)-(3-isopropyl-pyridin-2-ylmethyl)-amino]-butan-1-ol as a colorless oil. $^1$H NMR (CDCl$_3$) δ 1.01 (d, 6H, J=6.9 Hz), 1.37-1.54 (m, 2H), 1.62-1.71 (m, 2H), 2.16 (s, 3H), 2.27 (s, 3H), 2.59 (t, 2H, J=7.2 Hz), 2.93 (septet, 1H, J=6.9 Hz), 3.47 (t, 2H, J=6.0 Hz), 3.74 (s, 2H), 3.75 (s, 2H), 7.14 (dd, 1H, J=4.5, 7.8 Hz), 7.24 (s, 1H), 7.52 (dd, 1H, J=1.2, 7.8 Hz), 8.19 (s, 1H), 8.33 (dd, 1H, J=1.2, 4.5 Hz).

To a mixture of 4-[(3,5-dimethyl-pyridin-2-ylmethyl)-(3-isopropyl-pyridin-2-ylmethyl)-amino]-butan-1-ol (0.230 g, 0.673 mmol) and Et$_3$N (0.136 g, 1.35 mmol) in dry CH$_2$Cl$_2$ (8 mL) was added 4-nitrophenyl chloroformate (0.163 g, 0.808 mmol). After the mixture was stirred overnight, water (20 mL) was added and the mixture was extracted with CH$_2$Cl$_2$ (3×20 mL). The extracts were combined, and dried over anhydrous Na$_2$SO$_4$ to afford a yellow oil. The oil was dissolved in CH$_2$Cl$_2$ (5 mL), and NH$_2$OH.HCl (0.046 g, 0.66 mmol) and Et$_3$N (0.101 g, 1.00 mmol) were added. The mixture was stirred for 24 h, and water (20 mL) was added. The mixture was extracted CH$_2$Cl$_2$ (3×20 mL). The extracts were combined and dried over anhydrous Na$_2$SO$_4$. After filtration the solvent was removed by evaporation under vacuum, and the residue was purified by flash chromatography on a silica gel column (6:1 EtOAc/MeOH), affording a pale yellow solid (0.113 g, 42%) after precipitation from CH$_2$Cl$_2$/hexanes by evaporation under vacuum. $^1$H NMR (CDCl$_3$) δ 0.99 (d, 6H, J=6.9 Hz), 1.46-1.61 (m, 4H), 2.17 (s, 3H), 2.27 (s, 3H), 2.52-2.57 (m, 2H), 2.96 (septet, 1H, J=6.9 Hz), 3.72 (s, 2H), 3.73 (s, 2H), 4.03 (t, 2H, J=5.7 Hz), 7.15 (dd, 1H, J=4.8, 7.8 Hz), 7.26 (s, 1H), 7.53 (dd, 1H, J=1.2, 7.8 Hz), 7.76 (s, br. 1H), 8.18 (s, 1H), 8.32 (dd, 1H, J=1.2, 4.8 Hz); $^{13}$C NMR (CDCl$_3$) δ 18.03, 22.48, 2.28, 26.88, 27.29, 54.03, 57.91, 58.58, 65.39, 123.10, 132.21, 133.21, 133.96, 139.18, 144.26, 145.51, 146.01, 153.81, 155.54, 159.25. ES-MS m/z 423 (M+Na). Anal. Calcd. for C$_{22}$H$_{32}$N$_4$O$_3$.0.3CH$_2$Cl$_2$.0.2C$_6$H$_{14}$: C, 63.68; H, 8.05; N, 12.64. Found: C, 63.58; H, 8.10; N, 12.82.

Example 208

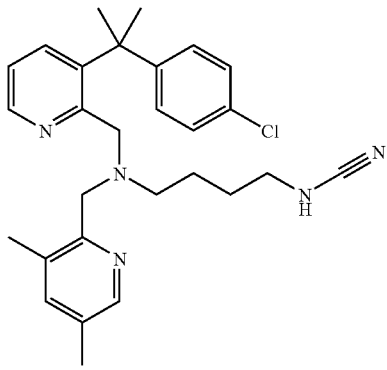

COMPOUND 208: 4-[{3-[1-(4-chloro-phenyl)-1-methyl-ethyl]-pyridin-2-ylmethyl}-(3,5-dimethyl-pyridin-2-ylmethyl)-amino]-butyl-cyanamide To a solution of N-{3-[1-(4-chloro-phenyl)-1-methyl-ethyl]-pyridin-2-ylmethyl-N-(3,5-dimethyl-pyridin-2-ylmethyl)-butane-1,4-diamine (0.200 g, 0.444 mmol) in dry MeOH (4 mL), at 0° C., was added NaOAc (0.106 g, 1.29 mmol) and BrCN (0.063 g, 0.59 mmol). The mixture was stirred at 0° C. for 30 min, then at room temperature for 2 h. Water (10 mL) was added, and the mixture was extracted with CH$_2$Cl$_2$ (3×20 mL). The organic extracts were combined and dried over anhydrous Na$_2$SO$_4$. After filtration the solvent was removed by evaporation under vacuum. The residue was purified by flash chromatography on a silica gel column (100:5:2 CH$_2$Cl$_2$/MeOH/NH$_4$OH), affording a pale yellow oil (0.13 g, 62%). $^1$H NMR (CDCl$_3$) δ 1.35-1.45 (m, 4H), 1.65 (s, 6H), 1.99 (s, 3H), 2.25 (s, 3H), 2.32-2.40 (m, 2H), 2.62-2.70 (m, 2H), 3.04 (s, 2H), 3.22 (s, 2H), 7.02 (d, 2H, J=8.1 Hz), 7.15-7.28 (m, 4H), 7.91 (d, 1H, J=7.8 Hz), 8.13 (s, 1H), 8.48 (s, br. 1H), 8.57 (d, 1H, J=3.9 Hz). ES-MS m/z 476 (M+H).

Example 209

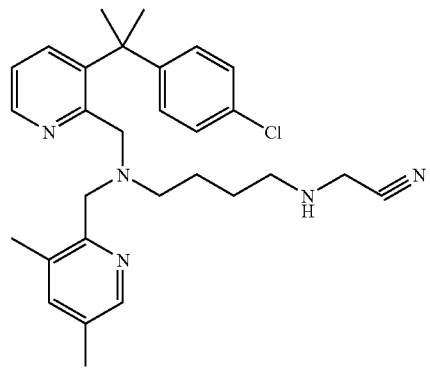

COMPOUND 209: {4-[{3-[1-(4-chloro-phenyl)-1-methyl-ethyl]-pyridin-2-ylmethyl}-(3,5-dimethyl-pyridin-2-ylmethyl)-amino]-butylamino}-acetonitrile A solution of N-{3-[1-(4-chloro-phenyl)-1-methyl-ethyl]-pyridin-2-ylmethyl-N-(3,5-dimethyl-pyridin-2-ylmethyl)-butane-1,4-diamine (0.200 g, 0.444 mmol) in MeOH (4 mL) was added to a mixture of formaldehyde (37% wt. in water, 0.041 g, 0.50 mmol) and NaHSO$_3$ (0.052 g, 0.5 mmol) in water (2 mL). Then NaCN (0.025 g, 0.50 mmol) was added, and the mixture was stirred for 5 h. Saturated aqueous NaHCO$_3$ (20 mL) was added, and the mixture was extracted with CH$_2$Cl$_2$ (3×30 mL). The organic extracts were combined, and dried over anhydrous Na$_2$SO$_4$. After filtration the solvent was removed by evaporation under vacuum. The residue was purified by flash chromatography on a silica gel column (40:2:1 CH$_2$Cl$_2$/MeOH/NH$_4$OH), affording the product as a pale yellow oil (0.088 g, 40%). $^1$H NMR (CDCl$_3$) δ 1.25-1.30 (m, 4H), 1.63 (s, 6H), 2.13 (s, 3H), 2.27 (s, 3H), 2.29-2.32 (m, 2H), 2.50-2.58 (m, 2H), 3.27 (s, 2H), 3.53 (s, 2H), 3.57 (s, 2H), 6.91-6.95 (m, 2H), 7.13-7.26 (m, 4H), 7.83-7.87 (m, 1H), 8.13 (s, 1H), 8.52-8.54 (m, 1H). ES-MS m/z 490 (M+H).

Example 210

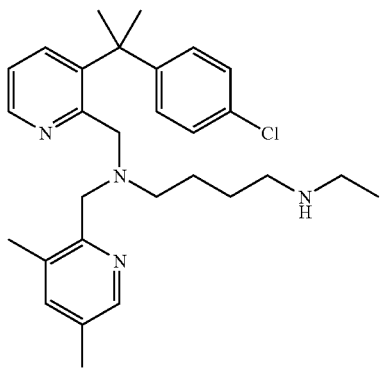

COMPOUND 210: N-{3-[1-(4-chloro-phenyl)-1-methyl-ethyl]-pyridin-2-ylmethyl}-N-(3,5-dimethyl-pyridin-2-ylmethyl)-N'-ethyl-butane-1,4-diamine (HBr salt)

A mixture of N-{3-[1-(4-chloro-phenyl)-1-methyl-ethyl]-pyridin-2-ylmethyl-N-(3,5-dimethyl-pyridin-2-ylmethyl)-butane-1,4-diamine (0.200 g, 0.444 mmol), acetaldehyde (0.020 g, 0.44 mmol) and K$_2$CO$_3$ (0.061 g, 0.44) in MeOH (2 mL) was stirred for 5 h. The mixture was filtered through a celite cake. The filtrate was cooled at 0° C., and NaBH$_4$ (0.017 g, 0.44 mmol) was added. After the reaction mixture was stirred at 0° C. for 30 min water (20 mL) was added, and the mixture was extracted with CH$_2$Cl$_2$ (3×20 mL). The organic extracts were combined and dried over anhydrous Na$_2$SO$_4$. After filtration the solvent was removed by evaporation under vacuum to give a pale yellow oil (0.181 g, 85%) without purification by chromatography. Conversion to the HBr salt using General Procedure D gave a pale yellow solid. $^1$H NMR (D$_2$O) δ 1.22 (t, 3H, J=7.5 Hz), 1.30-1.50 (m, 4H), 1.64 (s, 6H), 2.22 (s, 3H), 2.34 (s, 3H), 2.50-2.60 (m, 2H), 2.88-2.94 (m, 2H), 3.01 (q, 2H, J=7.5 Hz), 3.68 (s, 2H), 3.83 (s, 2H), 7.12 (d, 2H, J=8.1 Hz), 7.20 (d, 2H, J=8.1 Hz), 7.80-7.90 (m, 2H), 8.26 (s, 1H), 8.58 (d, 1H, J=8.1 Hz), 8.65 (d, 1H, J=4.8 Hz); $^{13}$C NMR (D$_2$O) δ 11.09, 17.40, 17.71, 22.25, 23.60, 29.67, 42.58, 43.34, 46.95, 53.40, 54.35, 55.15, 126.02, 128.56, 129.32, 132.29, 135.55, 136.62, 141.18, 141.93, 142.36, 146.19, 146.51, 146.53, 146.67, 150.56. ES-MS m/z 480 (M+H).

Example 211

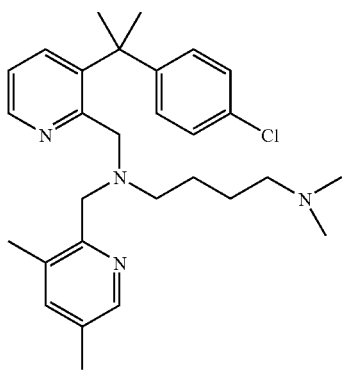

COMPOUND 211: N-{3-[1-(4-chloro-phenyl)-1-methyl-ethyl]-pyridin-2-ylmethyl}-N',N'-dimethyl-N-(3,5-dimethyl-pyridin-2-ylmethyl)-butane-1,4-diamine (HBr salt)

Using General Procedure B. N-{3-[1-(4-chloro-phenyl)-1-methyl-ethyl]-pyridin-2-ylmethyl-N-(3,5-dimethyl-pyridin-2-ylmethyl)-butane-1,4-diamine, paraformaldehyde and NaBH(OAc)$_3$ were reacted to obtain a colorless oil. Conversion to the HBr salt gave a pale yellow solid. $^1$H NMR (D$_2$O) δ 1.10-1.25 (m, 2H), 1.35-1.45 (m, 2H), 1.73 (s, 6H), 2.18-2.30 (m, 2H), 2.31 (s, 3H), 2.43 (s, 3H), 2.79 (s, 6H), 2.92-3.00 (m, 2H), 3.70 (s, 2H), 3.74 (s, 2H), 7.24 (d, 2H, J=7.5 Hz), 7.37 (2H, J=7.5 Hz), 8.00-8.10 (m, 1H), 8.16 (s, 1H), 8.38 (s, 1H), 8.60-8.70 (m, 1H), 8.86 (d, 1H, J=7.2 Hz). ES-MS m/z 480 (M+H).

Example 212

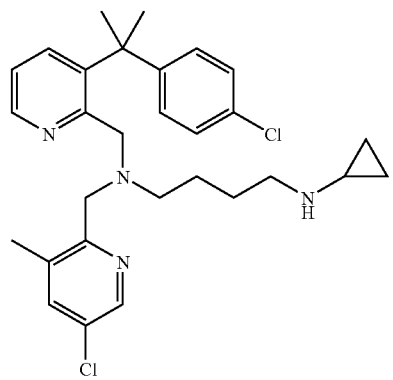

COMPOUND 212: N-(5-chloro-3-methyl-pyridin-2-ylmethyl)-N-{3-[1-(4-chloro-phenyl)-1-methyl-ethyl]-pyridin-2-ylmethyl}-N'-cyclopropyl-butane-1,4-diamine (HBr salt)

A mixture of (4-amino-butyl)-cyclopropyl-carbamic acid tert-butyl ester (0.228 g, 1.00 mmol), 5-chloro-3-methyl-pyridine-2-carbaldehyde (0.141 g, 1.00 mmol) and K$_2$CO$_3$ (0.138 g, 1.00) in MeOH (5 mL) was stirred for 16 h. The mixture was filtered through a celite cake and the filtrate was cooled at 0° C. NaBH$_4$ (0.038 g, 1.0 mmol) was added to the filtrate, and the mixture was stirred for 30 min. Saturated aqueous NaHCO$_3$ (20 mL) was added and MeOH was removed. The aqueous residue was extracted with CH$_2$Cl$_2$ (3×30 mL). The organic extracts were combined and dried over anhydrous Na$_2$SO$_4$. After filtration the solvent was removed by evaporation under vacuum, and the residue was purified by flash chromatography on a silica gel column (200:10:1 CH$_2$Cl$_2$/MeOH/NH$_4$OH), affording {4-[(5-chloro-3-methyl-pyridin-2-ylmethyl)-amino]-butyl}-cyclopropyl-carbamic acid tert-butyl ester as a pale yellow oil (0.155 g, 44%). $^1$H NMR (CDCl$_3$) δ 0.54-0.59 (m, 2H), 0.69-0.75 (m, 2H), 1.45 (s, 9H), 1.54-1.61 (m, 4H), 2.30 (s, 3H), 2.45-2.50 (m, 1H), 2.69-2.74 (m, 2H), 3.18-3.23 (m, 2H), 3.85 (s, 2H), 7.43 (s, 1H), 8.34 (s, 1H).

Using General Procedure B, {4-[(5-chloro-3-methyl-pyridin-2-ylmethyl)-amino]-butyl}-cyclopropyl-carbamic acid tert-butyl ester, 3-[1-(4-chloro-phenyl)-1-methyl-ethyl]-pyridine-2-carbaldehyde and NaBH(OAc)$_3$ were reacted to give a pale yellow oil. Deprotection with TFA using General Procedure F, and conversion to the HBr salt, gave a white solid. $^1$H NMR (D$_2$O) δ 0.83-0.85 (m, 4H), 1.50-1.59 (m, 10H), 2.21 (s, 3H), 2.67-2.72 (m, 1H), 2.78-2.84 (m, 2H), 3.02-3.10 (m, 2H), 3.70 (s, 2H), 4.05 (s, 2H), 7.02-7.12 (m, 4H), 7.73-7.78 (m, 1H), 7.89 (s, 1H), 8.29 (s, 1H), 8.43 (d, 1H, J=8.1 Hz), 8.61 (d, 1H, J=5.1 Hz); $^{13}$C NMR (D$_2$O) δ 3.49, 17.53, 22.14, 23.22, 29.62, 30.41, 42.37, 47.92, 54.07, 54.79, 55.78, 125.69, 128.48, 129.12, 132.09, 132.54, 136.64, 140.68, 141.98, 143.12, 143.25, 145.22, 146.79, 148.34, 149.52. ES-MS m/z 512 (M+H).

Example 213

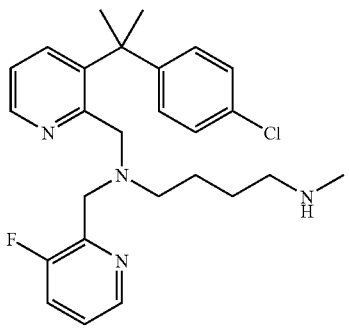

COMPOUND 213: N-{3-[1-(4-chloro-phenyl)-1-methyl-ethyl]-pyridin-2-ylmethyl}-N-(3-fluoro-pyridin-2-ylmethyl)-N'-methyl-butane-1,4-diamine (HBr salt)

A mixture of (4-amino-butyl)-methyl-carbamic acid tert-butyl ester (0.202 g, 1.00 mmol), 3-fluoro-pyridine-2-carbaldehyde (0.125 g, 1.00 mmol) and K$_2$CO$_3$ (0.138 g, 1.00) in MeOH (5 mL) was stirred for 16 h. The mixture was filtered through a celite cake and NaBH$_4$ (0.050 g, 1.3 mmol) was added to the filtrate, and the mixture was stirred for 30 min. Saturated aqueous NaHCO$_3$ (20 mL) was added, and MeOH was removed. The aqueous residue was extracted with CH$_2$Cl$_2$ (3×30 mL). The organic extracts were combined and dried over anhydrous Na$_2$SO$_4$. After filtration the solvent was removed by evaporation under vacuum, and the residue was purified by flash chromatography on a silica gel column (50:2:1 CH$_2$Cl$_2$/MeOH/NH$_4$OH), affording {4-[(3-fluoro-pyridin-2-ylmethyl)-amino]-butyl}-methyl-carbamic acid tert-butyl ester as a colorless oil (0.230 g, 74%). $^1$H NMR (CDCl$_3$) δ 1.42 (s, 9H), 1.48-1.54 (m, 4H), 2.61-2.68 (m, 2H), 2.80 (s, 3H), 3.14-3.22 (m, 2H), 3.96 (s, 2H), 7.11-7.20 (m, 1H), 7.30-7.36 (m, 1H), 8.33-8.38 (m, 1H).

Using General Procedure B, {4-[(3-fluoro-pyridin-2-ylmethyl)-amino]-butyl}-methyl-carbamic acid tert-butyl ester, 3-[1-(4-chloro-phenyl)-1-methyl-ethyl]-pyridine-2-carbaldehyde and NaBH(OAc)$_3$ were reacted to give a pale yellow oil. Deprotection with TFA using General Procedure F and conversion to the HBr salt using General Procedure D gave a white solid. $^1$H NMR (D$_2$O) δ 1.21-1.25 (m, 2H), 1.36-1.42 (m, 2H), 1.67 (s, 6H), 2.30-2.36 (m, 2H), 2.65 (s, 3H), 2.89-2.91 (m, 2H), 3.75 (s, 2H), 4.10 (s, 2H), 7.18 (d, 2H, J=8.4 Hz), 7.32 (d, 2H, J=8.4 Hz), 7.87-7.94 (m, 1H), 8.19 (t, 1H, J=8.7 Hz), 8.58 (d, 1H, J=5.1 Hz), 8.66 (dd, 1H, J=5.7, 8.7 Hz); $^{13}$C NMR (D$_2$O) δ 21.64, 23.34, 29.58, 33.16, 42.64, 48.88, 50.52, 53.30, 54.88, 126.15, 128.30 (d, J=7 Hz), 128.50, 129.41, 131.78 (d, J=19 Hz), 132.40, 140.91, 141.13, 141.21, 141.33, 143.16, 146.54 (d, J=4 Hz), 150.78, 158.93 (d, J=256 Hz). ES-MS m/z 455 (M+H).

Example 214

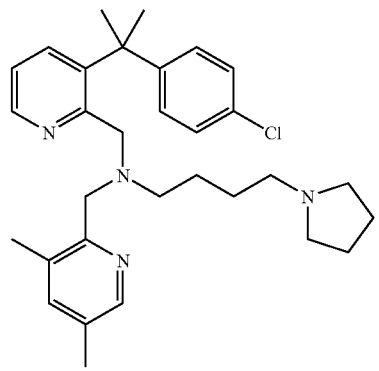

COMPOUND 214: {3-[1-(4-chloro-phenyl)-1-methyl-ethyl]-pyridin-2-ylmethyl}-(3,5-dimethyl-pyridin-2-ylmethyl)-(4-pyrrolidin-1-yl-butyl)-amine (HBr salt)

A mixture of 4-pyrrolidin-1-yl-butylamine (0.180 g, 1.27 mmol) (Seguin, H. et al. *Synth. Commun.* 1998, 28, 4257-4272), 3,5-dimethyl-pyridine-2-carbaldehyde (0.171 g, 1.27 mmol) and K$_2$CO$_3$ (0.175 g, 1.27) in MeOH (5 mL) was stirred for 20 h. The mixture was filtered through a celite cake and the filtrate was cooled at 0° C. NaBH$_4$ (0.048 g, 1.3 mmol) was added to the filtrate, and the mixture was stirred at for 1 h. Water (20 mL) was added and MeOH was removed. The aqueous residue was extracted with CH$_2$Cl$_2$ (3×20 mL). The organic extracts were combined and dried over anhydrous Na$_2$SO$_4$. After filtration the solvent was removed by evaporation under vacuum, and the residue was purified by flash chromatography on a silica gel column (100:5:3 CH$_2$Cl$_2$/MeOH/NH$_4$OH), affording (3,5-dimethyl-pyridin-2-ylmethyl)-(4-pyrrolidin-1-yl-butyl)-amine as a colorless oil (0.110 g, 33%). $^1$H NMR (CDCl$_3$) δ 1.54-1.58 (m, 4H), 1.72-1.76 (m, 4H), 2.24 (s, 3H), 2.25 (s, 3H), 2.39-2.46 (m, 6H), 2.66-2.71 (m, 2H), 3.81 (s, 2H), 7.21 (s, 1H), 8.18 (s, 1H).

Using General Procedure B, (3,5-dimethyl-pyridin-2-ylmethyl)-(4-pyrrolidin-1-yl-butyl)-amine, 3-[1-(4-chloro-phenyl)-1-methyl-ethyl]-pyridine-2-carbaldehyde and NaBH(OAc)$_3$ gave a colorless oil. Conversion to the HBr salt gave a white solid. $^1$H NMR (D$_2$O) δ 1.54 (s, 6H), 1.55-1.65 (m, 4H), 1.90-2.12 (m, 8H), 2.20 (s, 3H), 2.90-3.11 (m, 5H), 3.58-3.66 (m, 4H), 4.04 (s, 2H), 5.94-7.05 (m, 4H), 7.58 (s, 1H), 7.62-7.68 (m, 1H), 8.09 (s, 1H), 8.27 (d, 1H, J=7.2 Hz), 8.59 (d, 1H, J=3.3 Hz); $^{13}$C NMR (D$_2$O) δ 17.42, 17.75, 22.19, 23.10, 23.21, 29.69, 42.18, 54.25, 54.56, 54.79, 55.95, 125.31, 128.40, 129.09, 131.96, 134.06, 135.52, 138.98, 143.28, 144.32, 144.52, 144.66, 145.82, 147.15, 149.25. ES-MS m/z 506 (M+H).

Example 215

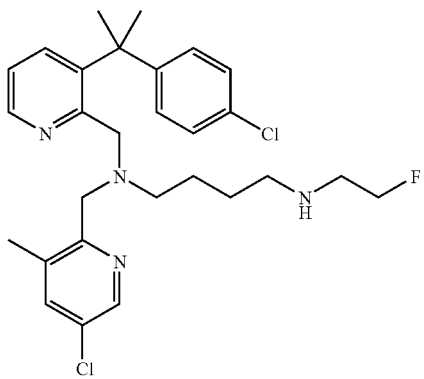

COMPOUND 215: N-(5-chloro-3-methyl-pyridin-2-ylmethyl)-N-{3-[1-(4-chloro-phenyl)-1-methyl-ethyl]-pyridin-2-ylmethyl}-N'-(2-fluoro-ethyl)-butane-1,4-diamine Using General Procedure B, FCH$_2$CH$_2$NH$_2$.HCl, 4-(1,3-dioxo-1,3-dihydro-isoindol-2-yl)-butyraldehyde, Et$_3$N and NaBH(OAc)$_3$ gave a pale yellow oil. A mixture of the oil, Boc$_2$O, Et$_3$N in CH$_2$Cl$_2$ was stirred for 2 h. Aqueous workup and purification gave (2-fluoro-ethyl)-[4-(1,3-dioxo-1,3-dihydro-isoindol-2-yl)-butyl]-carbamic acid tert-butyl ester as a pale yellow oil. Deprotection with NH$_2$NH$_2$.H$_2$O using General Procedure E gave (4-Amino-butyl)-(2-fluoro-ethyl)-carbamic acid tert-butyl ester as a colorless oil. $^1$H NMR (CDCl$_3$) δ 1.24-1.62 (m, 13H), 2.71 (t, 2H, J=6.9 Hz), 3.24-3.30 (m, 2H), 3.44-3.52 (m, 2H), 4.40-4.48 (m, 1H), 4.56-4.64 (m, 1H).

A mixture of (4-amino-butyl)-(2-fluoro-ethyl)-carbamic acid tert-butyl ester (0.190 g, 0.882 mmol), 5-chloro-3-methyl-pyridine-2-carbaldehyde (0.129 g, 0.882 mmol) and K$_2$CO$_3$ (0.122 g, 0.82) in MeOH (5 mL) was stirred for 16 h. The mixture was filtered through a celite cake and the filtrate was cooled at 0° C. NaBH$_4$ (0.038 g, 1.0 mmol) was added to the filtrate, and the mixture was stirred at for 30 min. Saturated aqueous NaHCO$_3$ (20 mL) was added and MeOH was removed. The aqueous residue was extracted with CH$_2$Cl$_2$ (3×30 mL). The organic extracts were combined and dried over anhydrous Na$_2$SO$_4$. After filtration the solvent was removed by evaporation under vacuum, and the residue was purified by flash chromatography on a silica gel column (200:10:1 CH$_2$Cl$_2$/MeOH/NH$_4$OH), affording {4-[(5-chloro-3-methyl-pyridin-2-ylmethyl)-amino]-butyl}-(2-fluoro-ethyl)-carbamic acid tert-butyl ester as a pale yellow oil (0.215 g, 72%). $^1$H NMR (CDCl$_3$) δ 1.45 (s, 9H), 1.53-1.66 (m, 4H), 2.30 (s, 3H), 2.71 (t, 2H, J=6.6 Hz), 3.24-3.30 (m, 2H), 3.42-3.52 (m, 2H), 3.84 (s, 2H), 4.40-4.48 (m, 1H), 4.56-4.64 (m, 1H), 7.43 (s, 1H), 8.34 (s, 1H).

Using General Procedure B, {4-[(5-chloro-3-methyl-pyridin-2-ylmethyl)-amino]-butyl}-(2-fluoro-ethyl)-carbamic acid tert-butyl ester, 3-[1-(4-chloro-phenyl)-1-methyl-ethyl]-pyridine-2-carbaldehyde and NaBH(OAc)$_3$ were reacted to obtain a pale yellow oil. Deprotection with TFA using General Procedure F gave a white solid. $^1$H NMR (CDCl$_3$) δ 1.53-1.63 (m, 2H), 1.64 (s, 6H), 1.78-1.86 (m, 2H), 2.07 (s, 3H), 2.26-2.30 (m, 2H), 3.01-3.05 (m, 2H), 3.29 (s, 2H), 3.40 (s, 2H), 3.40-3.45 (m, 1H), 3.49-3.52 (m, 1H), 4.70-4.75 (m, 1H), 4.84-4.91 (m, 1H), 6.96 (d, 2H, J=8.7 Hz), 7.15 (d, 2H, J=8.7 Hz), 7.25-7.29 (m, 1H), 7.40 (d, 1H, J=1.8 Hz), 7.87-7.90 (m, 1H), 8.34 (d, 1H, J=1.8 Hz), 8.63-8.65 (m, 1H). ES-MS m/z 517 (M+H).

Example 216

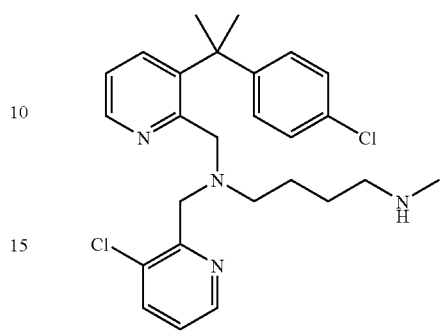

COMPOUND 216: N-{3-[1-(4-chloro-phenyl)-1-methyl-ethyl]-pyridin-2-ylmethyl}-N-(3-chloro-pyridin-2-ylmethyl)-N'-methyl-butane-1,4-diamine (HBr salt)

Using General Procedure B, (4-amino-butyl)-methyl-carbamic acid tert-butyl ester, 3-[1-(4-chloro-phenyl)-1-methyl-ethyl]-pyridine-2-carbaldehyde and NaBH(OAc)$_3$ were reacted to give [4-({3-[1-(4-chloro-phenyl)-1-methyl-ethyl]-pyridin-2-ylmethyl}-amino)-butyl]-methyl-carbamic acid tert-butyl ester as a colorless oil. $^1$H NMR (CDCl$_3$) δ 1.24-1.32 (m, 2H), 1.33-1.42 (m, 11H), 1.65 (s, 6H), 2.20-2.24 (m, 2H), 2.79 (s, 3H), 3.08-3.12 (m, 2H), 3.26 (s, 2H), 7.05-7.08 (m, 2H), 7.21-7.26 (m, 3H), 7.84-7.87 (m, 1H), 8.46-8.48 (m, 1H).

Using General Procedure B, [4-({3-[1-(4-chloro-phenyl)-1-methyl-ethyl]-pyridin-2-ylmethyl}-amino)-butyl]-methyl-carbamic acid tert-butyl ester, 3-chloro-pyridine-2-carbaldehyde and NaBH(OAc)$_3$ were reacted to give a pale yellow oil. Deprotection with TFA using General Procedure F gave a colorless oil. Conversion to the HBr salt gave a pale yellow solid. $^1$H NMR (D$_2$O) δ 1.25-1.32 (m, 2H), 1.35-1.45 (m, 2H), 1.68 (s, 6H), 2.47-2.52 (m, 2H), 2.64 (s, 3H), 2.84-2.91 (m, 2H), 3.85 (s, 2H), 4.02 (s, 2H), 7.20 (d, 2H, J=7.8 Hz), 7.33 (d, 2H, J=7.8 Hz), 7.73-7.80 (m, 1H), 7.85-7.90 (m, 1H), 8.33 (d, 1H, J=8.4 Hz), 8.61-8.69 (m, 3H); $^{13}$C NMR (D$_2$O) δ 21.59, 23.31, 29.57, 33.12, 42.58, 48.83, 53.88, 53.99, 55.11, 126.03, 126.85, 128.52, 129.47, 132.49, 133.63, 141.62, 142.68, 143.17, 144.72, 146.48, 146.57, 149.63, 150.50. ES-MS m/z 471 (M+H).

Example 217

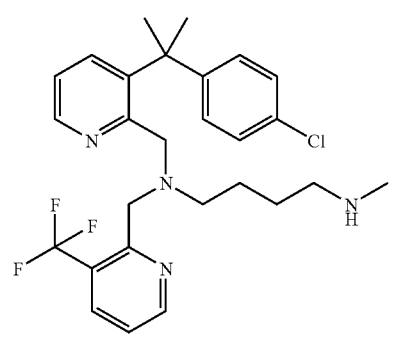

COMPOUND 217: N-{3-[1-(4-chloro-phenyl)-1-methyl-ethyl]-pyridin-2-ylmethyl}-N'-methyl-N-(3-trifluoromethyl-pyridin-2-ylmethyl)-butane-1,4-diamine (HBr salt)

To a solution of 2-methyl-3-trifluoromethyl-pyridine (0.850 g, 5.28 mmol) (Ashimori, A. et al. *Chem. Pharm. Bull.* 1990, 33, 2446-2458) in CCl₄ (30 mL) was added 1,1'-azobis(cyclohexanecarbonitrile) (0.193 g, 0.79 mmol) and NBS (1.96 g, 11.0 mmol). The mixture was stirred and heated at reflux for 24 h, and then cooled to room temperature. A solution of $Na_2S_2O_3$ (5 g) in $H_2O$ (100 mL) was added, and the organic layer was collected. The aqueous layer was extracted with $CH_2Cl_2$ (3×40 mL), and the extracts were combined and dried over anhydrous $Na_2SO_4$. After filtration the solvent was removed by evaporation under vacuum, and the residue was purified by flash chromatography on a silica gel column ($CH_2Cl_2$), affording 2-bromomethyl-3-trifluoromethyl-pyridine as a pale yellow liquid (0.180 g, 14%). ¹H NMR (CDCl₃) δ 4.69 (s, 2H), 7.37 (dd, 1H, J=4.5, 7.8 Hz), 7.96 (d, 1H, J=7.8 Hz), 8.78 (d, 1H, J=4.5 Hz).

Using General Procedure A, [4-({3-[1-(4-chloro-phenyl)-1-methyl-ethyl]-pyridin-2-ylmethyl}-amino)-butyl]-methyl-carbamic acid tert-butyl ester, 2-bromomethyl-3-trifluoromethyl-pyridine, DIPEA and KI in $CH_3CN$ were reacted to obtain a pale yellow oil. Deprotection with TFA using General Procedure F gave a colorless oil. Conversion to the HBr salt gave a pale yellow solid. ¹H NMR (D₂O) δ 1.33-1.42 (m, 2H), 1.45-1.55 (m, 2H), 1.64 (s, 6H), 2.64 (s, 3H), 2.70-2.76 (m, 2H), 2.85-2.95 (m, 2H), 3.81 (s, 2H), 4.22 (s, 2H), 7.13 (d, 2H, J=8.1 Hz), 7.23 (d, 2H, J=8.1 Hz), 7.76-7.83 (m, 2H), 8.46 (d, 1H, J=8.1 Hz), 8.50 (d, 1H, J=8.4 Hz), 8.61 (d, 1H, J=4.8 Hz), 8.79 (d, 1H, J=4.8 Hz). ES-MS m/z 505 (M+H).

Example 218

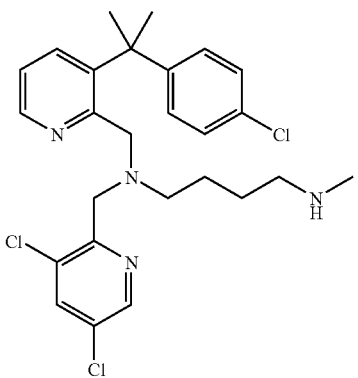

COMPOUND 218: N-{3-[1-(4-chloro-phenyl)-1-methyl-ethyl]-pyridin-2-ylmethyl}-N-(3,5-dichloro-pyridin-2-ylmethyl)-N'-methyl-butane-1,4-diamine (HBr salt)

Using General Procedure B, [4-({3-[1-(4-chloro-phenyl)-1-methyl-ethyl]-pyridin-2-ylmethyl}-amino)-butyl]-methyl-carbamic acid tert-butyl ester, 3,5-dichloro-pyridine-2-carbaldehyde and NaBH(OAc)₃ were reacted to obtain a pale yellow oil. Deprotection with TFA using General Procedure F gave a colorless oil. Conversion to the HBr salt gave a pale yellow solid. ¹H NMR (D₂O) δ 1.52 (s, 6H), 1.66 (s, br, 4H), 2.65 (s, 3H), 2.95-3.08 (m, 4H), 3.70 (s, br, 2H), 4.16 (s, 2H), 6.93 (s, 4H), 7.60-7.69 (m, 2H), 8.19-8.26 (m, 2H), 8.55-8.59 (m, 1H); ¹³C NMR (D₂O) δ 22.50, 23.16, 29.71, 33.24, 42.16, 48.77, 54.76, 55.21, 56.16, 125.35, 128.30, 128.94, 131.69, 131.82, 132.20, 137.99, 138.73, 144.14, 144.71, 146.44, 147.24, 147.44, 149.01. ES-MS m/z 507 (M+H).

Example 219

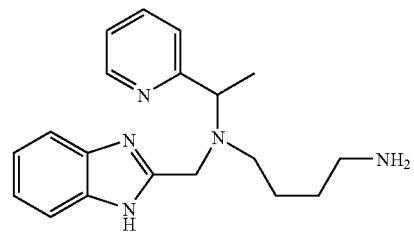

COMPOUND 219: N-(1H-benzimidazol-2-ylmethyl)-N-(1-pyridin-2-ylethyl)-butane-1,4-diamine (HBr salt)

Using General Procedure B, (4-aminobutyl)-carbamic acid tert-butyl ester and 2-acetylpyridine in $CH_2Cl_2$ and NaBH(OAc)₃ were reacted to obtain [4-(1-pyridin-2-ylethylamino)-butyl]-carbamic acid tert-butyl ester as a light brown oil.

Using General Procedure A, [4-(1-pyridin-2-ylethylamino)-butyl]-carbamic acid tert-butyl ester, N-(t-butoxycarbonyl)-2-chloromethylbenzimidazole, and KI in anhydrous $CH_3CN$ were reacted with DIPEA to obtain 2-{[(4-tert-butoxycarbonylaminobutyl)-(1-pyridin-2-ylethyl)-amino]-methyl}benzimidazole-1-carboxylic acid tert-butyl ester. Conversion to the HBr salt gave COMPOUND 219 as a white solid. ¹H NMR (D₂O) δ 1.55 (br, 4H), 1.63 (d, 3H, 6.9 Hz), 2.62 (m, 1H), 2.80 (m, 1H), 2.88 (br, 2H), 4.43 (d, 2H, J=2.4 Hz), 4.58 (m, 1H), 7.60 (m, 2H), 7.78 (m, 2H), 7.97 (t, 1H, J=6.6 Hz), 8.12 (d, 1H, J=8.1 Hz), 8.56 (t, 1H, J=8.0 Hz), 8.77 (d, 1H, J=5.7 Hz). ¹³C NMR (D₂O) δ 13.17, 24.44, 24.97, 39.57, 47.46, 52.31, 59.31, 114.26 (2C), 126.57, 126.74, 126.92 (2C), 130.92 (2C), 141.83, 148.12, 152.04, 156.52. ES-MS m/z 324 (M+H). Anal. Calcd. for $C_{19}H_{25}N_5 \cdot 3.1HBr \cdot 1.8H_2O \cdot 0.2C_4H_{10}O$: C, 38.26; H, 5.47; N, 11.27; Br, 39.85. Found: C, 38.22; H, 5.13; N, 11.16; Br, 40.00.

Example 220

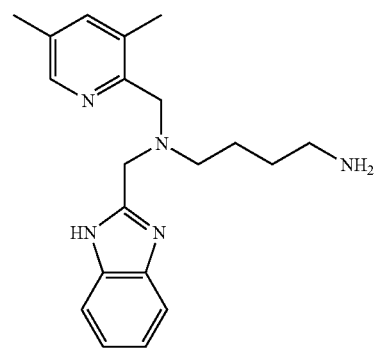

COMPOUND 220: N¹-(1H-benzoimidazol-2-ylmethyl)-N¹-(3,5-dimethyl-pyridine-2-ylmethyl)-butane-1,4-diamine (HBr salt)

Using General Procedure A, {4-[(3,5-dimethyl-pyridin-2-ylmethyl)-amino]-butyl}-carbamic acid tert-butyl ester, 2-chloromethyl-benzimidazole-1-carboxylic acid tert-butyl ester, DIPEA, and KI in CH₃CN were reacted to obtain a yellow oil. Deprotection with TFA using General Procedure F gave a pale yellow oil. ¹H NMR (CDCl₃) δ 1.46 (qn, 2H, J=7.5 Hz), 1.63 (qn, 2H, J=7.5 Hz), 2.34 (s, 3H), 2.39 (s, 3H), 2.58-2.68 (m, 4H), 3.78 (s, 2H), 3.84 (s, 2H), 7.21 (dd, 2H, J=6.0, 3.0 Hz), 7.36 (s, 1H), 7.64 (br s, 2H), 8.37 (d, 1H, J=3.0 Hz). Conversion to the HBr salt gave COMPOUND 220 as a pale yellow solid. ¹H NMR (D₂O) δ 1.59 (m, 4H), 2.34 (s, 3H), 2.40 (s, 3H), 2.80 (br s, 2H), 2.92 (br s, 2H), 4.25 (s, 2H), 4.43 (s, 2H), 7.51-7.55 (m, 2H), 7.69-7.72 (m, 2H), 8.06 (s, 1H), 8.36 (s, 1H). ¹³C NMR (D₂O) δ 14.57, 17.02, 17.54, 20.89, 23.47, 24.96, 39.64, 50.78, 53.99, 55.59, 66.44, 114.22, 127.01, 130.77, 136.76, 137.48, 148.21, 149.01, 150.50. ES-MS m/z 338 [M+H]⁺. Anal. Calcd. for C₂₀H₂₇N₅.3.7HBr.2.7H₂O.0.3C₄H₁₀O: C, 35.98; H, 5.57; N, 9.90; Br, 41.77. Found: C, 36.07; H, 5.57; N, 9.90; Br, 41.70.

Example 221

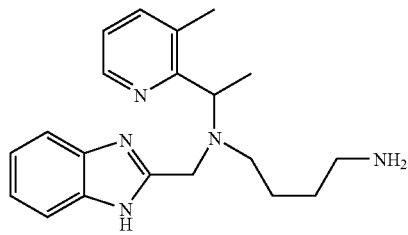

COMPOUND 221: N-(1H-benzimidazol-2-ylmethyl)-N-[1-(3-methylpyridin-2-yl)-ethyl]-butane-1,4-diamine (HBr salt)

Using General Procedure B, 1-(3-methylpyridin-2-yl)-ethanone (Sundberg, R J et al. *J. Am. Chem. Soc.* 1969, 91, 658-668), (4-aminobutyl)-carbamic acid tert-butyl ester and NaBH(OAc)₃ were reacted in CH₂Cl₂ to obtain {4-[1-(3-methylpyridin-2-yl)-ethylamino]-butyl}-carbamic acid tert-butyl ester.

Using General Procedure A: Reaction of the above secondary amine, N-(t-butoxycarbonyl)-2-chloromethylbenzimidazole, KI in anhydrous CH₃CN and DIPEA gave 2-({(4-tert-butoxycarbonylaminobutyl)-[1-(3-methylpyridin-2-yl)-ethyl]-amino}-methyl)-benzimidazole-1-carboxylic acid tert-butyl ester. ¹H NMR (CDCl₃) δ 1.12 (br, 1H), 1.29 (br, 3H), 1.40 (s, 9H), 1.47 (d, 3H, J=9.0 Hz), 1.69 (s, 9H), 2.17 (s, 3H), 2.58 (m, 1H), 2.73 (m, 1H), 2.87 (br, 2H), 4.31 (d, 1H, J=15.0 Hz), 4.45 (m, 1H), 4.47 (d, 1H, J=15.0 Hz), 4.59 (br, 1H, (NH)), 7.00 (m, 1H), 7.31 (m, 3H), 7.73 (m, 1H), 7.84 (m, 1H), 8.37 (d, 1H, J=3.0 Hz). Conversion to the HBr salt gave COMPOUND 221 as a white solid. ¹H NMR (D₂O) δ 1.41 (d, 3H, J=6.6 Hz), 1.49 (m, 2H), 1.58 (m, 2H), 2.57 (s, 3H), 2.69 (m, 2H), 2.89 (m, 2H), 4.37 (d, 1H, J=17.4 Hz), 4.63 (d, 1H, J=18.0 Hz), 4.70 (m, 2H), 7.60 (m, 2H), 7.77 (m, 2H), 7.83 (t, 1H, J=6.9 Hz), 8.37 (d, 1H, J=7.8 Hz), 8.60 (d, 1H, J=5.7 Hz). ¹³C NMR (D₂O) δ 17.31, 18.39, 22.81, 24.91, 39.57, 47.15, 53.80, 57.62, 114.23 (2C), 126.14, 126.92 (2C), 130.92 (2C), 137.40, 139.49, 149.54, 152.39, 155.23. ES-MS m/z 338 (M+H). Anal. Calcd. for C₂₀H₂₇N₅.3.5HBr.1.5H₂O.0.5C₄H₁₀O: C, 38.59; H, 5.67; N, 10.23; Br, 40.84. Found: C, 38.58; H, 5.50; N, 10.10; Br, 40.87.

Example 222

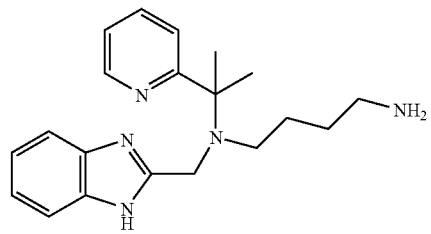

COMPOUND 222: N¹-(1H-Benzimidazol-2-ylmethyl)-N¹-(1-methyl-1-pyridin-2-yl-ethyl)-butane-1,4-diamine (HBr salt)

Using General Procedure B, reaction of 1-methyl-1-pyridin-2-yl-ethylamine (Chakravarty, P K et al. *Bioorg. Med. Chem. Lett.* 2003, 13, 147-150) with 4-(1,3-Dioxo-1,3-dihydroisoindole-2-yl)-butyraldehyde and NaBH(OAc)₃ gave 2-[4-(1-methyl-1-pyridin-2-yl-ethylamino)-butyl]-isoindole-1,3-dione as a colorless oil. ¹H NMR (CDCl₃) δ 1.46 (s, 6H), 1.50-1.56 (m, 2H), 1.60-1.74 (m, 2H), 2.31 (t, 2H, J=7.0 Hz), 3.65 (t, 2H, J=7.1 Hz), 7.07-7.14 (m, 1H), 7.39 (d, 1H, J=8.3 Hz), 7.63 (td, 1H, J=7.7, 1.8 Hz), 7.66-7.74 (m, 2H), 7.77-7.87 (m, 2H), 8.56 (d, 1H, J=3.9 Hz).

Using General Procedure A: Reaction of 2-[4-(1-methyl-1-pyridin-2-yl-ethylamino)-butyl]-isoindole-1,3-dione in dry CH₃CN, N-(tert-butoxycarbonyl)-2-chloromethylbenzimidazole, DIPEA and KI gave 2-{[[4-(1,3-Dioxo-1,3-dihydro-isoindol-2-yl)-butyl]-(1-methyl-1-pyridin-2-yl-ethyl)-amino]-methyl}-benzimidazole-1-carboxylic acid tert-butyl ester as a white foam. ¹H NMR (CDCl₃) δ 1.18-1.33 (m, 2H), 1.39-1.54 (m, 2H), 1.52 (s, 6H), 1.71 (s, 9H), 2.65 (t, 2H, J=7.5 Hz), 3.43 (t, 2H, J=7.2 Hz), 4.27 (s, 2H), 7.04 (t, 1H, J=4.8 Hz), 7.19-7.31 (m, 3H), 7.55 (td, 1H, J=7.7, 1.7 Hz), 7.62-7.70 (m, 2H), 7.70-7.78 (m, 2H), 7.81 (dd, 1H, J=6.6, 1.6 Hz), 8.06 (d, 1H, J=8.4 Hz), 8.47 (d, 1H, J=3.9 Hz). Deprotection with H₂NNH₂.H₂O using General Procedure E gave a colorless oil. Conversion to the HBr salt gave COMPOUND 222 as a white solid. ¹H NMR (D₂O) δ 1.36-1.51 (m, 4H), 1.60 (s, 6H), 2.46-2.59 (m, 2H), 2.72-2.84 (m, 2H), 4.56 (s, 2H), 7.54-7.64 (m, 2H), 7.74-7.84 (m, 2H), 8.03 (t, 1H, J=6.6 Hz), 8.21 (d, 1H, J=8.4 Hz), 8.64 (t, 1H, J=7.8 Hz), 8.85 (d, 1H, J=5.4 Hz); ¹³C NMR (D₂O) δ 23.21, 24.88, 26.01, 39.43, 45.77, 53.70, 63.80, 114.23, 125.75, 126.73, 126.84, 131.03, 142.12, 148.73, 153.74, 160.26; ES-MS m/z 338 (M+H). Anal. Calcd. for C₂₀H₂₇N₅.3.0HBr.1.4H₂O.0.3C₄H₁₀O: C, 40.57; H, 5.75; N, 11.16; Br, 38.19. Found: C, 40.48; H, 5.67; N, 11.01; Br, 38.18.

Example 223

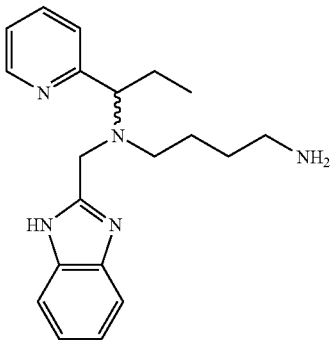

COMPOUND 223: N$^1$-(1H-benzimidazol-2-ylmethyl)-N$^1$-(1-pyridin-2-yl-propyl)-butane-1,4-diamine (HBr salt)

Using General Procedure B: Reaction of 2-(1-oxo-propyl)-pyridine (Teague et al *J. Am. Chem. Soc.* 1953, 75, 3429) and (4-amino-butyl)-carbamic acid tert-butyl ester with NaBH(OAc)$_3$ gave the secondary amine as a light yellow oil. $^1$H NMR (CDCl$_3$) δ 0.81 (t, 3H, J=7.4 Hz), 1.36-1.54 (m, 13H), 1.64-1.83 (m, 3H), 2.35-2.50 (m, 2H), 2.97-3.14 (m, 2H), 3.58 (dd, 1H, J=7.2, 6.3 Hz), 7.14 (ddd, 1H, J=7.4, 4.9, 1.0 Hz), 7.24 (d, 1H, J=7.8 Hz), 7.63 (td, 1H, J=7.6, 1.7 Hz), 8.56 (d, 1H, J=4.2 Hz).

Using General Procedure A: Reaction of the above secondary amine, 2-chloromethyl-benzimidazole-1-carboxylic acid tert-butyl ester, DIPEA and KI in CH$_3$CN gave the tertiary amine as a yellow foam. $^1$H NMR (CDCl$_3$) δ 0.78 (t, 3H, J=7.2 Hz), 1.29-1.39 (m, 4H), 1.41 (s, 9H), 1.72 (s, 9H), 1.92-2.04 (m, 2H), 2.43-2.56 (m, 1H), 2.67-2.79 (m, 1H), 2.89-3.05 (m, 2H), 3.88 (t, 1H, J=7.1 Hz), 4.11 (d, 1H, J=15.6 Hz), 4.48 (d, 1H, J=15.6 Hz), 4.70 (br. s, 1H), 7.14 (dd, 1H, J=6.8, 5.3 Hz), 7.28-7.38 (m, 3H), 7.59-7.64 (m, 1H), 7.71-7.79 (m, 1H), 7.81-7.88 (m, 1H), 8.57 (d, 1H, J=5.1 Hz). Deprotection with TFA using General Procedure F gave the free amine as a white foam. $^1$H NMR (CDCl$_3$) δ 0.86 (t, 3H, J=7.4 Hz), 1.25-1.49 (m, 4H), 1.99 (apparent quint, 2H, J=7.4 Hz), 2.44-2.72 (m, 4H), 3.81 (t, 1H, J=7.4 Hz), 3.98 (d, 1H, J=16.4 Hz), 4.17 (d, 1H, J=16.4 Hz), 7.21-7.29 (m, 4H), 7.55-7.63 (m, 2H), 7.70 (td, 1H, J=7.7, 1.7 Hz), 8.70 (d, 1H, J=4.8 Hz). Conversion to the HBr salt gave COMPOUND 223 as a yellow solid. $^1$H NMR (D$_2$O) δ 0.81 (t, 3H, J=7.4 Hz), 1.44-1.64 (m, 4H), 1.86-2.02 (m, 1H), 2.06-2.24 (m, 1H), 2.62-2.94 (m, 4H), 4.28 (dd, 1H, J=9.9, 4.5 Hz), 4.45 (s, 2H), 7.54-7.64 (m, 2H), 7.72-7.81 (m, 2H), 7.95 (t, 1H, J=6.8 Hz), 8.10 (d, 1H, J=7.8 Hz), 8.53 (t, 1H, J=8.0 Hz), 8.76 (d, 1H, J=5.4 Hz). $^{13}$C NMR (D$_2$O) δ 10.2, 23.7, 24.1, 24.9, 39.6, 47.2, 52.9, 66.4, 114.2, 126.8, 127.4, 129.0, 131.0, 142.5, 147.5, 152.5, 155.3. ES-MS m/z 338 (M+H). Anal. Calcd. for C$_{20}$H$_{27}$N$_5$.3.2HBr.1.2H$_2$O: C, 38.87; H, 5.32; N, 11.33; Br, 41.37. Found: C, 38.89; H, 5.29; N, 10.98; Br, 41.60.

Example 224

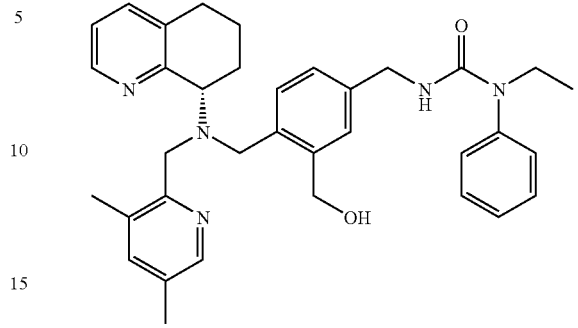

COMPOUND 224: 3-(4-{[(3,5-dimethyl-pyridin-2-ylmethyl)-(5,6,7,8-tetrahydro-quinolin-8-yl)-amino]-methyl}-3-hydroxymethyl-benzyl)-1-ethyl-1-phenyl-urea To a solution of N-ethylaniline (23 μL, 0.18 mmol) in toluene (3 mL) was added DIPEA (63 μL, 0.36 mmol) and phosgene (99 μL, 2.2M in toluene, 0.22 mmol). The mixture was stirred for 2 hours at room temperature under N$_2$ and then the solvent was removed under reduced pressure to give a white solid. A solution of (5-aminomethyl-2-{[(3,5-dimethyl-pyridin-2-ylmethyl)-(5,6,7,8-tetrahydro-quinolin-8-yl)-amino]-methyl}-phenyl)-methanol (0.075 g, 0.18 mmol) and DIPEA (63 μL, 0.36 mmol) in DMF (4 mL) was added to the white residue and the resulting mixture was stirred for 16 hours. The solvent was removed under reduced pressure and the resulting residue was suspended in CH$_2$Cl$_2$ (30 mL) and quenched with saturated aqueous NaHCO$_3$ (30 mL). The mixture was extracted with CH$_2$Cl$_2$ (3×30 mL) and the combined organic extracts were washed with brine (3×20 mL) and then dried (Na$_2$SO$_4$), filtered and concentrated under reduced pressure. Purification by column chromatography on silica gel (CH$_2$Cl$_2$/MeOH/NH$_4$OH, 93:5:2, v/v/v) afforded 3-(4-{[(3,5-dimethyl-pyridin-2-ylmethyl)-(5,6,7,8-tetrahydro-quinolin-8-yl)-amino]-methyl}-3-hydroxymethyl-benzyl)-1-ethyl-1-phenyl-urea as a white foamy solid (0.080 g, 78%). $^1$H NMR (CDCl$_3$) δ 1.10 (t, 3H, J=9.0 Hz), 1.60 (m, 1H), 1.99 (m, 1H), 2.19 (m, 2H), 2.20 (s 3H), 2.24 (s, 3H), 2.64 (m, 1H), 2.78 (m, 1H), 3.63 (d, 2H, J=12.0 Hz), 3.70-3.79 (m, 3H), 3.86 (t, 1H, J=7.5 Hz), 4.11 (m, 2H), 4.31 (d+m, 2H), 4.42 (m, 1H), 7.05 (m, 2H), 7.14-7.38 (m, 9H), 8.15 (s, 1H), 8.37 (d, 1H, J=3.0 Hz). HPLC: 99%.

Example 225

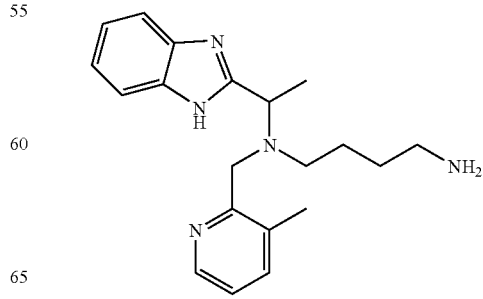

COMPOUND 225: N$^1$-[1-(1H-Benzimidazol-2-yl)-ethyl]-N$^1$-(3-methyl-pyridin-2-ylmethyl)-butane-1,4-diamine (HBr salt)

Using General Procedure B: Reaction of 1-(1H-Benzimidazol-2-yl)-ethanone (Vekariya, N A et al. *J. Indian Chem. Soc.* 2002, 79, 966-967) in dry MeOH, (4-Amino-butyl)-carbamic acid tert-butyl ester and NaBH$_4$ gave the desired amine as a beige foam.

Using General Procedure B: Reaction of the amine from above and 3-methyl-2-pyridinecarboxaldehyde in dry CH$_2$Cl$_2$ with NaBH(OAc)$_3$ gave the desired amine as a clear oil. Conversion to the HBr salt with simultaneous removal of the Boc group gave COMPOUND 225 as a white solid. $^1$H NMR (D$_2$O) δ 1.46-1.55 (m, 4H), 1.75 (d, 3H, J=6.9 Hz), 2.48 (s, 3H), 2.65-2.73 (m, 1H), 2.80-2.88 (m, 3H), 4.26 (d, 1H, J=18.3 Hz), 4.42 (d, 1H, J=18.3 Hz), 4.78-4.81 (m, 1H, overlap with HOD), 7.61 (dd, 2H, J=6, 3 Hz), 7.79 (dd, 2H, J=6, 3 Hz), 7.84 (dd, 1H, J=7.5, 6.3 Hz), 8.34 (d, 1H, J=7.8 Hz), 8.61 (d, 1H, J=5.7 Hz); $^{13}$C NMR (D$_2$O) δ 12.86, 16.97, 24.79, 25.00, 39.51, 51.24, 52.75, 55.67, 114.29, 125.89, 127.06, 131.00, 137.15, 138.20, 148.28, 152.13, 153.17. ES-MS m/z 338 (M+H). Anal. Calcd. for C$_{20}$H$_{27}$N$_5$.3.2HBr.1.0H$_2$O.0.5C$_4$H$_{10}$O: C, 40.56; H, 5.76; N, 10.75; Br, 39.25. Found: C, 40.63; H, 5.72; N, 10.84; Br, 39.06.

Example 226

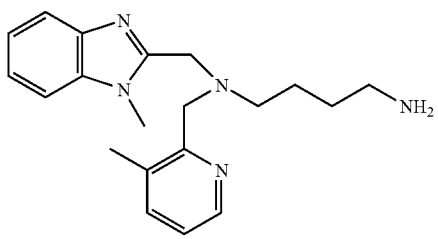

COMPOUND 226: N$^1$-(1-methyl-1H-benzoimidazol-2-ylmethyl)-N$^1$-(3-methyl-pyridin-2-ylmethyl)-butane-1,4-diamine Using General Procedure B, reaction of 1-methyl-1H-benzoimidazole-2-carbaldehyde and (4-amino-butyl)-carbamic acid tert-butyl ester in CH$_2$Cl$_2$ with NaBH(OAc)$_3$ gave {4-[(1-methyl-1H-benzoimidazol-2-ylmethyl)-amino]-butyl}-carbamic acid tert-butyl ester as a sticky white foam. $^1$H NMR (CDCl$_3$) δ 1.43 (s, 9H), 1.54-1.64 (m, 4H), 1.80-1.82 (m, 2H), 2.67-2.75 (m, 2H), 3.12-3.13 (m, 2H), 3.82 (s, 3H), 4.06 (s, 2H), 7.23-7.30 (m, 2H), 7.31-7.38 (m, 1H), 7.70-7.76 (m, 1H).

Using General Procedure B, reaction of {4-[(1-methyl-1H-benzoimidazol-2-ylmethyl)-amino]-butyl}-carbamic acid tert-butyl ester in CH$_2$Cl$_2$ and 3-methyl-pyridine-2-carbaldehyde in CH$_2$Cl$_2$ with NaBH(OAc)$_3$ gave {4-[(1-methyl-1H-benzoimidazol-2-ylmethyl)-(3-methyl-pyridin-2-ylmethyl)-amino]-butyl}-carbamic acid tert-butyl ester as a white solid. $^1$H NMR (CDCl$_3$) δ 1.42 (s, 9H), 1.50-1.60 (m, 2H), 1.78 (s, 2H), 2.27 (s, 3H), 2.60 (t, 2H, J=7.4 Hz), 2.96-3.00 (m, 2H), 3.55 (s, 3H), 3.82 (s, 2H), 3.90 (s, 2H), 4.79-4.80 (m, 1H), 7.09-7.13 (m, 1H), 7.23-7.25 (m, 3H), 7.43 (d, 1H, J=7.4 Hz), 7.70-7.73 (m, 1H), 8.40 (d, 1H, J=4.9 Hz). Deprotection with TFA using General Procedure F gave COMPOUND 226 as a white solid. $^1$H NMR (CDCl$_3$) δ 1.25-1.34 (m, 4H), 1.50-1.60 (m, 2H), 2.28 (s, 3H), 2.52-2.63 (m, 4H), 3.56 (s, 3H), 3.83 (s, 2H), 3.91 (s, 2H), 7.10-7.14 (m, 1H), 7.22-7.25 (m, 3H), 7.43 (d, 1H, J=7.5 Hz), 7.71-7.73 (m, 1H), 8.41 (d, 1H, J=3.6 Hz). $^{13}$C NMR (CDCl$_3$) δ 18.55, 23.95, 29.97, 31.79, 42.19, 51.70, 54.99, 59.43, 109.37, 119.91, 122.15, 122.80, 122.95, 133.34, 136.56, 138.44, 142.55, 146.68, 152.48, 157.02. ES-MS m/z 338 (M+H). Anal. Calcd. for C$_{20}$H$_{27}$N$_5$.0.1H$_2$O: C, 70.81; H, 8.08; N, 20.64. Found: C, 70.67; H, 8.02; N, 20.73.

Example 227

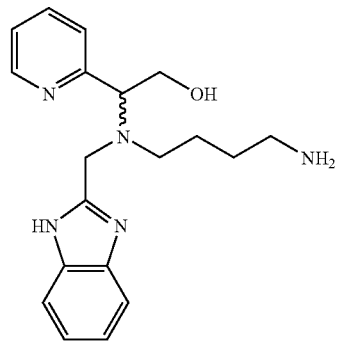

COMPOUND 227: 2-[(4-amino-butyl)-(1H-benzimidazol-2-ylmethyl)-amino]-2-pyridin-2-yl-ethanol (HBr salt)

Using General Procedure A: A solution of 2-(tert-butyl-dimethylsilanyloxy)-1-pyridin-2-yl-ethylamine (Uenishi, J. et al. *Heterocycles,* 2000, 52, 719-732), 2-chloromethyl-benzimidazole-1-carboxylic acid tert-butyl ester, DIPEA and KI in CH$_3$CN was reacted to obtain the secondary amine as a yellow foam.

Using General Procedure B: Reaction of the above amine and 4-(1,3-dioxo-1,3-dihydro-isoindol-2-yl)-butyraldehyde in CH$_2$Cl$_2$ with NaBH(OAc)$_3$ gave the tertiary amine as a yellow foam. $^1$H NMR (CDCl$_3$) δ −0.12 (s, 3H), −0.10 (s, 3H), 0.75 (s, 9H), 1.29-1.55 (m, 4H), 1.70 (s, 9H), 2.81 (t, 2H, J=6.9 Hz), 3.51 (t, 2H, J=6.9 Hz), 4.12 (dd, 1H, J=10.2, 6.0 Hz), 4.24 (dd, 1H, J=9.0, 6.0 Hz), 4.31-4.38 (m, 2H), 4.64 (d, 1H, J=16.8 Hz), 7.07 (ddd, 1H, J=6.6, 4.8, 1.8 Hz), 7.22-7.29 (m, 2H), 7.52-7.59 (m, 2H), 7.63-7.88 (m, 6H), 8.49 (d, 1H, J=4.5 Hz). Deprotection with H$_2$NNH$_2$.H$_2$O following General Procedure E gave a yellow oil. A solution of this material and KF (361 mg, 6.21 mmol) in 25% H$_2$O in MeOH (10 mL) was stirred at room temperature for 24 hours. The MeOH was evaporated under reduced pressure and the residue was taken up into saturated aqueous NaHCO$_3$ (10 mL). Extraction with CH$_2$Cl$_2$ (15 mL×3) and purification of the organic soluble material by flash column chromatography on silica (CH$_2$Cl$_2$/MeOH/NH$_4$OH, 9:1:0.05) gave recovered starting material (silane) as a yellow oil (27 mg, 0.06 mmol, 12%).

The aqueous solution from the extraction was concentrated under reduced pressure and the residual solid was extracted with MeOH until no UV active material remained in the residue. The extract was filtered through a cotton plug and the filtrate was concentrated under reduced pressure. Purification by flash column chromatography on silica (CH$_2$Cl$_2$/MeOH/NH$_4$OH, 9:1:0.1) gave the alcohol as a white foam (45 mg, 0.13 mmol, 26% from phthalimide). $^1$H NMR (CDCl$_3$) δ 1.32-1.56 (m, 4H), 2.41-2.53 (m, 1H), 2.56 (t, 2H, J=6.6 Hz), 2.68-2.81 (m, 1H), 3.91 (d, 1H, J=16.2 Hz), 3.99-4.10 (m, 2H), 4.18-4.26 (m, 1H), 4.28 (d, 1H, J=15.9 Hz), 4.85 (br. s, 2H), 7.13-7.24 (m, 3H), 7.30 (d, 1H, J=7.8 Hz), 7.47-7.59 (m, 2H), 7.66 (td, 1H, J=7.7, 1.8 Hz), 8.56 (d, 1H, J=4.2 Hz).

Conversion to the HBr salt gave COMPOUND 227 as a white powder. $^1$H NMR (D$_2$O) δ 1.44-1.67 (m, 4H), 2.69-2.97 (m, 4H), 4.04-4.13 (m, 1H), 4.16-4.27 (m, 1H), 4.42-4.62 (m, 3H), 7.53-7.64 (m, 2H), 7.71-7.81 (m, 2H), 7.90 (t, 1H, J=4.5 Hz), 8.05 (d, 1H, J=6.9 Hz), 8.46 (t, 1H, J=6.6 Hz), 8.74 (d, 1H, J=4.5 Hz). $^{13}$C NMR (D$_2$O) δ 23.6, 24.8, 39.5, 47.5, 53.0, 60.8, 65.8, 114.2, 126.7, 126.8, 127.0, 131.0, 143.2, 146.4, 154.5, 154.9. ES-MS m/z 340 (M+H). Anal. Calcd. for C$_{19}$H$_{25}$N$_5$O.2.9HBr.2.3H$_2$O: C, 37.08; H, 5.32; N, 11.38; Br, 37.65. Found: C, 37.34; H, 5.30; N, 11.03; Br, 37.37.

Example 228

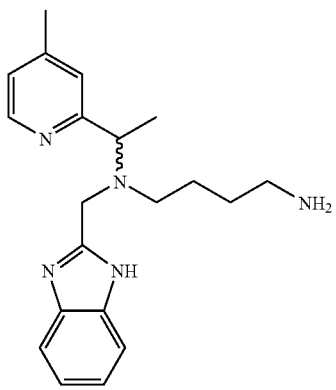

COMPOUND 228: N$^1$-(1H-Benzimidazol-2-ylmethyl)-N$^1$-[1-(4-methyl-pyridin-2-yl)-ethyl]-butane-1,4-diamine (HBr salt)

Using General Procedure B: To a stirred solution of 1-(4-methyl-pyridin-2-yl)-ethanone (Sundberg, R J et al. *J. Am. Chem. Soc.* 1969, 91, 658-668) and (4-amino-butyl)-carbamic acid tert-butyl ester in CH$_2$Cl$_2$ was added NaBH(OAc)$_3$ to give {4-[1-(4-methyl-pyridin-2-yl)-ethylamino]-butyl}-carbamic acid tert-butyl ester as a colorless oil. $^1$H NMR (CDCl$_3$) δ 1.35 (d, 3H, J=6.6 Hz), 1.42 (s, 9H), 1.46-1.49 (m, 4H), 1.80 (br, 1H), 2.34 (s, 3H), 2.40-2.51 (m, 2H), 3.06-3.09 (m, 2H), 3.78 (q, 1H, J=6.6 Hz), 4.89 (br, 1H), 6.96 (d, 1H, J=5.1 Hz), 7.08 (s, 1H), 8.39 (d, 1H, J=5.1 Hz).

Using General Procedure A: Reaction of {4-[1-(4-methyl-pyridin-2-yl)-ethylamino]-butyl}-carbamic acid tert-butyl ester in CH$_3$CN with DIPEA, KI and 2-chloromethyl-1H-benzimidazole gave the tertiary amine as a white foam. Deprotection with TFA using General Procedure F gave the desired free amine as a pale yellow oil. Conversion to the HBr salt gave COMPOUND 228 as a white powder. $^1$H NMR (CD$_3$OD) δ 1.59-1.79 (m, 7H), 2.63-2.71 (m, 4H), 2.79-2.87 (m, 1H), 2.91 (t, 1H, J=7.2 Hz), 4.48 (s, 2H), 4.60 (t, 1H, J=6.6 Hz), 7.59-7.63 (m, 2H), 7.85-7.90 (m, 2H), 8.10 (s, 1H), 8.78 (d, 1H, J=6.0 Hz). $^{13}$C NMR (D$_2$O) δ 14.37, 23.04, 25.96, 26.64, 40.86, 48.74, 53.73, 60.34, 115.52, 128.10, 128.35, 128.48, 132.61, 142.39, 153.90, 156.91, 163.98. ES-MS m/z 338 [M+H]$^+$. Anal. Calcd. for C$_{20}$H$_{27}$N$_5$.3.7HBr.1.8H$_2$O.0.5C$_4$H$_{10}$O: C, 37.41; H, 5.61; N, 9.91; Br, 41.72. Found: C, 37.44; H, 5.60; N, 9.91; Br, 41.72.

Example 229

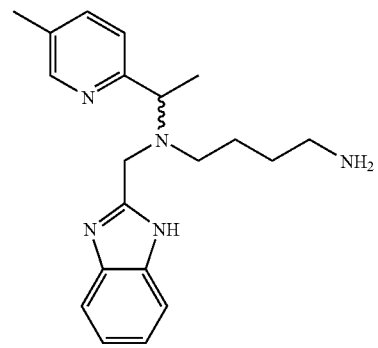

COMPOUND 229: N$^1$-(1H-Benzimidazol-2-ylmethyl)-N$^1$-[1-(5-methyl-pyridin-2-yl)-ethyl]-butane-1,4-diamine (HBr salt)

Using General Procedure B: Reaction of 1-(5-methyl-pyridin-2-yl)-ethanone (Sundberg, R J et al. *J. Am. Chem. Soc.* 1969, 91, 658-668) and (4-amino-butyl)-carbamic acid tert-butyl ester in CH$_2$Cl$_2$ with NaBH(OAc)$_3$ gave {4-[1-(5-methyl-pyridin-2-yl)-ethylamino]-butyl}-carbamic acid tert-butyl ester as a pale yellow oil.

Using General Procedure A: Reaction of {4-[1-(5-methyl-pyridin-2-yl)-ethylamino]-butyl}-carbamic acid tert-butyl ester in CH$_3$CN with DIPEA, KI and 2-chloromethyl-1H-benzimidazole gave the tertiary amine as a white foam. Conversion to the HBr salt gave COMPOUND 229 as a white powder. $^1$H NMR (CD$_3$OD) δ 1.59-1.79 (m, 7H), 2.57 (s, 3H), 2.61-2.69 (m, 1H), 2.79-2.84 (m, 1H), 2.89-2.93 (m, 2H), 3.30-3.32 (m, 1H), 4.48 (s, 2H), 4.60 (t, 1H, J=6.9 Hz), 7.58-7.64 (m, 2H), 7.85-7.91 (m, 2H), 8.15 (d, 1H, 8.4 Hz), 8.48 (dd, 1H, J=8.1, 1.5 Hz). 8.81 (s, 1H). $^{13}$C NMR (D$_2$O) δ 14.40, 18.54, 25.97, 26.64, 40.86, 48.74, 53.61, 60.12, 115.52, 127.40, 128.09, 132.61, 139.65, 142.94, 149.87, 153.93, 155.06. ES-MS m/z 338 [M+H]$^+$. Anal. Calcd. for C$_{20}$H$_{27}$N$_5$.3.4HBr.0.3H$_2$O.1.1C$_2$H$_6$O: C, 38.98; H, 5.22; N, 10.24; Br, 39.72. Found: C, 38.89; H, 5.44; N, 10.17; Br, 39.92.

Example 230

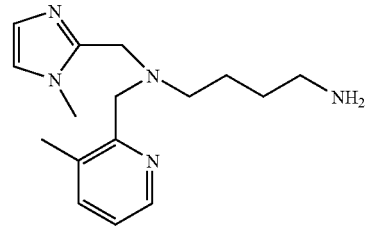

COMPOUND 230: N$^1$-(1-methyl-1H-imidazol-2-ylmethyl)-N$^1$-(3-methyl-pyridin-2-ylmethyl)-butane-1,4-diamine Using General Procedure B, reaction of 1-methyl-1H-imidazole-2-carbaldehyde and (4-amino-butyl)-carbamic acid tert-butyl ester in CH$_2$Cl$_2$ and NaBH(OAc)$_3$ gave {4-[(1-methyl-1H-imidazol-2-ylmethyl)-amino]-butyl}-carbamic acid tert-butyl ester as a sticky white foam. $^1$H NMR (CDCl$_3$) δ 1.43 (s, 9H), 1.50-1.59 (m, 4H), 2.01 (s, 3H), 2.04-2.06 (m, 2H), 2.62-2.73 (m, 2H), 3.08-3.17 (m, 2H), 3.79 (s, 2H), 6.85 (d, 1H, J=2.2 Hz), 7.11 (d, 1H, J=1.8 Hz).

Using General Procedure B, reaction of {4-[(1-methyl-1H-imidazol-2-ylmethyl)-amino]-butyl}-carbamic acid tert-butyl ester in $CH_2Cl_2$, 3-methyl-pyridine-2-carbaldehyde in $CH_2Cl_2$ and $NaBH(OAc)_3$ gave {4-[(1-methyl-1H-imidazol-2-ylmethyl)-(3-methyl-pyridin-2-ylmethyl)-amino]-butyl}-carbamic acid tert-butyl ester as a sticky white solid. $^1$H NMR ($CDCl_3$) δ 1.43 (s, 9H), 2.01 (s, 3H), 2.05-2.08 (m, 4H), 2.30 (s, 3H), 2.64 (t, 1H, J=7.5 Hz), 2.94-3.04 (m, 2H), 3.56 (s, 2H), 3.82 (s, 2H), 4.20 (s, 2H), 6.81 (d, 1H, J=1.7 Hz), 7.09-7.15 (m, 2H), 7.43-7.45 (m, 1H), 8.40 (d, 1H, J=3.5 Hz). Deprotection with TFA using General Procedure F gave COMPOUND 230 as a white solid. $^1$H NMR ($CDCl_3$) δ 1.22-1.32 (m, 2H), 1.41-1.49 (m, 4H), 2.21 (s, 3H), 2.48-2.55 (m, 4H), 3.41 (s, 3H), 3.64 (s, 2H), 3.72 (s, 2H), 6.76 (s, 1H), 6.87 (s, 1H), 7.06-7.10 (m, 1H), 7.40 (d, 1H, J=7.5 Hz), 8.35 (d, 1H, J=4.2 Hz). $^{13}$C NMR ($CDCl_3$) δ 16.98, 22.56, 30.18, 31.41, 40.63, 49.44, 53.11, 57.94, 120.31, 121.43, 125.99, 131.96, 136.99, 144.58, 145.13, 155.90. ES-MS m/z 288 (M+H). Anal. Calcd. for $C_{16}H_{25}N_5 \cdot 0.1H_2O \cdot 0.2CH_2Cl_2 \cdot 0.1CH_4O$: C, 63.28; H, 8.47; N, 22.64. Found: C, 63.59; H, 8.58; N, 22.30.

Example 231

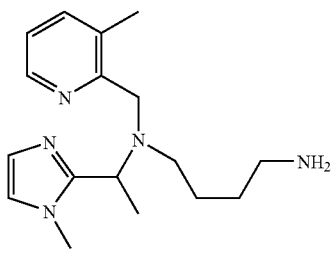

COMPOUND 231: N-[1-(1-Methyl-1H-Imidazol-2-yl)-ethyl]-N-(3-methylpyridin-2-ylmethyl)-butane-1,4-diamine (HBr salt)

The ketone 1-(N-methyl-imidazol-2-yl)-ethanone (0.65 g, 5.2 mmol) (Davies, D. et al. *J. Chem. Soc. Perkin Trans. I* 1991, 11, 2691-2698) and (4-aminobutyl)-carbamic acid tert-butyl ester (1.97 g, 10.5 mmol) were combined in toluene (80 mL) and heated for 16 hours at reflux with a Dean-Stark trap and condenser fitted to the reaction vessel. The solution was then cooled and the solvent removed under reduced pressure. Methanol (40 mL) was added and the solution was treated with $NaBH_4$ (0.40 g, 10.5 mmol) for 16 hours. The solvent was removed under reduced pressure and the residue partitioned between $CH_2Cl_2$ (50 mL) and saturated aqueous $NaHCO_3$ solution (40 mL). The organic phase was separated and the aqueous was extracted with $CH_2Cl_2$ (2×50 mL). The combined organics were then dried ($Na_2SO_4$) and concentrated under reduced pressure to provide, after column chromatography with silica gel (1:99 MeOH:$CH_2Cl_2$ ramping to 4:0.5:94.5 MeOH:$NH_4OH$:$CH_2Cl_2$), {4-[1-(1-methyl-1H-imidazol-2-yl)-ethylamino]-butyl}-carbamic acid tert-butyl ester as a light yellow oil (0.37 g, 24%).

Using General Procedure B, reaction of 3-methylpyridine-2-carboxaldehyde, {4-[1-(1-methyl-1H-imidazol-2-yl)-ethylamino]-butyl}-carbamic acid tert-butyl ester and $NaBH(OAc)_3$ in $CH_2Cl_2$ gave {4-[[1-(1-methyl-1H-imidazol-2-yl)-ethyl]-(3-methylpyridin-2-ylmethyl)-amino]-butyl}-carbamic acid tert-butyl ester as a light yellow oil. $^1$H NMR ($CDCl_3$) δ 1.10-1.35 (m, 4H), 1.37 (s, 9H), 1.53 (d, 3H, J=7.5 Hz), 2.11 (s, 3H), 2.51 (m, 1H), 2.62 (m, 1H), 2.90 (br, 2H), 3.37 (s, 3H), 3.62 (d, 1H, J=13.5 Hz), 3.95 (d, 1H, J=13.5 Hz), 4.04 (q, 1H, J=7.5 Hz), 4.57 (br, 1H, NH), 6.76 (s, 1H), 6.92 (s, 1H), 7.09 (m, 1H), 7.40 (d, 1H, J=7.5 Hz), 8.38 (d, 1H, J=4.5 Hz). Conversion to the HBr salt using General Procedure D gave COMPOUND 231 as a white solid. $^1$H NMR ($D_2O$) δ 1.50 (br, 4H), 1.52 (d, 3H, J=6.9 Hz), 2.44 (s, 3H), 2.72 (br, 2H), 2.89 (br t, 2H), 3.89 (s, 3H), 4.24 (s, 2H), 4.68 (q, 1H, J=6.9 Hz), 7.38 (d, 1H, J=1.8 Hz), 7.40 (d, 1H, J=1.8 Hz), 7.85 (t, 1H, J=6.6 Hz), 8.36 (d, 1H, J=7.8 Hz), 8.55 (d, 1H, J=5.7 Hz). $^{13}$C NMR ($D_2O$) δ 14.17, 16.90, 24.18, 25.00, 35.16, 39.54, 50.20, 52.57, 53.23, 119.09, 124.44, 125.99, 137.29, 138.34, 146.69, 148.46, 152.08. ES-MS m/z 302 (M+H). Anal. Calcd. for $C_{17}H_{27}N_5 \cdot 3.5HBr \cdot 1.9H_2O \cdot C_4H_{10}O$: C, 34.45; H, 5.95; N, 10.80; Br, 43.12. Found: C, 34.57; H, 5.73; N, 10.77; Br, 42.98.

Example 232

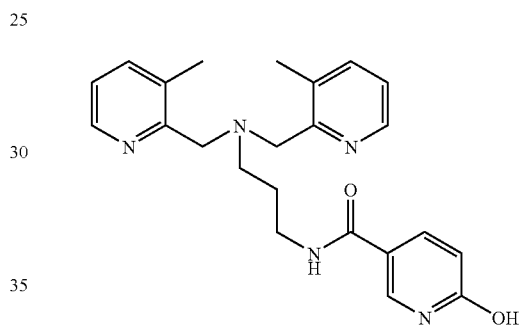

COMPOUND 232: N-{3-[Bis-(3-methyl-pyridin-2-ylmethyl)-amino]-propyl}-6-hydroxy-nicotinamide (HBr salt)

Using General Procedure G: To a solution of $N^1,N^1$-bis-(3-methyl-pyridin-2-ylmethyl)-propane-1,3-diamine (0.24 g, 0.84 mmol) in dry DMF (4 mL) was added 6-hydroxy-nicotinic acid (0.121 g, 0.87 mmol) followed by EDCI (0.182 g, 0.95 mmol), HOBT (0.128 g, 0.95 mmol), and DIPEA (0.25 mL, 1.44 mmol). Purification of the crude material by column chromatography on silica gel (10:1:1 $CH_2Cl_2$-MeOH—$NH_4OH$) provided 47 mg (14%) of the free base of the title compound as a colorless oil. Conversion to the HBr salt gave COMPOUND 232 (65 mg, 78%) as a white solid. $^1$H NMR ($D_2O$) δ 1.74-1.84 (m, 2H), 2.47 (s, 6H), 2.64-2.69 (m, 2H), 3.24 (dd, 2H, 6.3 Hz), 4.31 (s, 4H), 6.62 (d, 1H, J=9.6 Hz), 7.80-7.84 (m, 3H), 7.95 (d, 1H, J=2.1 Hz), 8.32 (d, 2H, J=8.1 Hz), 8.58 (d, 2H, J=6.0 Hz); $^{13}$C NMR ($D_2O$) δ 17.24, 25.16, 37.61, 51.91, 53.99, 115.32, 119.34, 126.02, 137.52, 137.87, 138.75, 140.81, 148.48, 150.88, 166.80; ES-MS m/z 406 (M+H). Anal. Calcd. for $C_{23}H_{27}N_5O_2 \cdot 3.2HBr \cdot 3.0H_2O$: C, 38.45; H, 5.08; N, 9.75; Br, 35.59. Found: C, 38.32; H, 4.94; N, 9.48; Br, 35.96.

Example 233

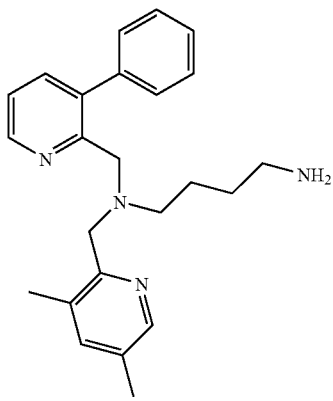

COMPOUND 233: $N^1$-(3,5-Dimethyl-pyridin-2-ylmethyl)-$N^1$-(3-phenyl-pyridin-2-ylmethyl)-butane-1,4-diamine (HBr salt)

An anhydrous MeOH solution (2.0 mL) of 3-phenyl-pyridine-2-carbaldehyde (38 mg, 0.21 mmol) (Iqbal, N. et al. *J. Med. Chem.* 1998, 41, 1827-1837) and (4-Amino-butyl)-carbamic acid tert-butyl ester (40 mg, 0.21 mmol) was stirred overnight at room temperature, after which NaBH₄ (16 mg, 0.41 mmol) was added and the reaction mixture stirred for an additional hour. The solvent was removed in vacuo and the residue dissolved in CH₂Cl₂ (15 mL) and treated with saturated aqueous NaHCO₃ (25 mL). The aqueous layer was separated and extracted with CH₂Cl₂ (2×15 mL). The combined organic extracts were dried (Na₂SO₄), filtered and concentrated in vacuo to afford {4-[(3-Phenyl-pyridin-2-ylmethyl)-amino]-butyl}-carbamic acid tert-butyl ester (59 mg, 0.17 mmol) as a yellow oil. The yellow oil was used without further purification.

Using General Procedure B, reaction of {4-[(3-Phenyl-pyridin-2-ylmethyl)-amino]-butyl}-carbamic acid tert-butyl ester, 3,5-Dimethyl-pyridine-2-carbaldehyde and NaBH(OAc)₃ gave {4-[(3,5-Dimethyl-pyridin-2-ylmethyl)-(3-phenyl-pyridin-2-ylmethyl)-amino]-butyl}-carbamic acid tert-butyl ester as a colorless oil. ¹H NMR (CDCl₃) δ 1.03-1.21 (m, 4H), 1.44 (s, 9H), 1.89 (s, 3H), 2.24 (s, 3H), 2.29-2.40 (m, 2H), 2.76-2.90 (m, 2H), 3.63 (s, 2H), 3.79 (s, 2H), 4.85 (s, 1H), 7.09 (s, 1H), 7.26 (dd, 1H, J=7.6, 4.5 Hz), 7.54 (dd, 1H, J=7.8, 1.8 Hz), 8.08 (s, 1H), 8.60 (dd, 1H, J=4.7, 1.2 Hz). Conversion to the HBr salt gave COMPOUND 233 as a white solid (40.3 mg, 88%). ¹H NMR (D₂O) δ 1.36-1.52 (m, 4H), 2.33 (s, 3H), 2.46 (s, 3H), 2.58-2.69 (m, 2H), 2.79-2.91 (m, 2H), 4.09 (s, 2H), 4.33 (s, 2H), 7.38-7.47 (m, 2H), 7.54-7.63 (m, 3H), 8.03 (dd, 1H, J=7.8, 6.0 Hz), 8.14 (s, 1H), 8.36 (s, 1H), 8.48 (dd, 1H, J=8.1, 1.2 Hz), 8.79 (dd, 1H, J=5.7, 1.2 Hz); ¹³C NMR (D₂O) δ 16.99, 17.50, 22.52, 24.92, 39.53, 53.74, 54.46, 54.73, 126.46, 129.58, 129.62, 130.23, 134.13, 136.97, 137.55, 138.16, 140.85, 141.09, 147.55, 148.07, 149.10, 150.39; ES-MS m/z 375 (M+H). Anal. Calcd. for C₂₄H₃₀N₄.3.4HBr. 3.1H₂O: C, 40.86; H, 5.66; N, 7.94; Br, 38.51. Found: C, 40.66; H, 5.89; N, 7.82; Br, 38.79.

Example 234

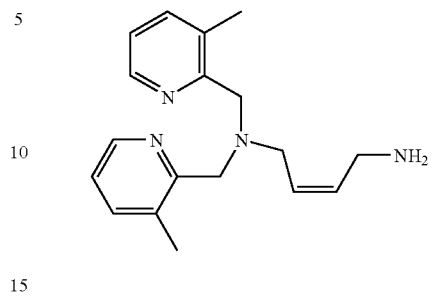

COMPOUND 234: N,N-Bis-(3-Methyl-pyridin-2-ylmethyl)-cis-but-2-ene-1,4-diamine (HBr salt)

Using General Procedure A: Reaction of bis-(3-methyl-pyridin-2-ylmethyl)-amine, (4-chloro-cis-but-2-enyl)-carbamic acid tert-butyl ester (Casara, P et al, *J. Am. Chem. Soc.* 1989, 111, 9111-9113), KI in anhydrous CH₃CN and DIPEA gave {4-[Bis-(3-methyl-pyridin-2-ylmethyl)-amino]-cis-but-2-enyl}-carbamic acid tert-butyl ester. ¹H NMR (CDCl₃) δ 1.46 (s, 9H), 2.13 (s, 6H), 3.18 (d, 2H, J=6.0 Hz), 3.63 (t, 2H, J=6.0 Hz), 3.74 (s, 4H), 5.69 (br, 2H), 5.80 (br, 1H, (NH)), 7.08 (m, 2H), 7.39 (d, 2H, J=6.0 Hz), 8.38 (d, 2H, J=3.6 Hz). Conversion to the HBr salt using General Procedure D gave COMPOUND 234 (56 mg) as a light beige solid. ¹H NMR (D₂O) δ 2.49 (s, 6H), 3.45 (d, 2H, J=6.9 Hz), 3.59 (d, 2H, J=6.9 Hz), 4.31 (s, 4H), 5.69 (m, 1H), 5.94 (m, 1H), 7.85 (t, 2H, J=6.9 Hz), 8.36 (d, 2H, J=7.8 Hz), 8.59 (d, 2H, J=5.4 Hz). ¹³C NMR (D₂O) δ 17.37 (2C), 36.60, 51.89, 54.10 (2C), 125.93, 126.18 (2C), 130.97, 137.94 (2C), 138.86 (2C), 148.65 (2C), 150.66 (2C). ES-MS m/z 297 (M+H). Anal. Calcd. for C₁₈H₂₄N₄.3.4HBr.1.9H₂O.0.2C₄H₁₀O: C, 36.39; H, 5.39; N, 9.03; Br, 43.78. Found: C, 36.61; H, 5.26; N, 9.00; Br, 43.49.

Example 235

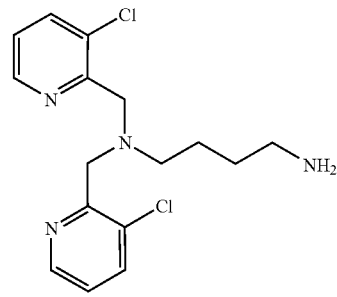

COMPOUND 235: $N^1,N^1$-Bis-(3-chloro-pyridin-2-ylmethyl)-butane-1,4-diamine (HBr salt)

Using General Procedure C: (3-Chloro-pyridin-2-yl)-methanol (167 mg, 1.17 mmol) (Iqbal, N. et al. *J. Med. Chem.* 1998, 41, 1827-1837) was dissolved in CH₂Cl₂ (10 mL) at 0° C. Et₃N (212 μL, 1.52 mmol) was added to the colorless solution followed by subsequent addition of MsCl (90 µL, 1.17 mmol). The reaction mixture was stirred at 0° C. for one hour and then the solvent was removed under reduced pressure. The resulting crude mesylate mixture was dissolved in CH₃CN (5 mL) and added to a mixture of {4-[(3-chloro-pyridin-2-ylmethyl)-amino]-butyl}-carbamic acid tert-butyl ester (265 mg, 0.88 mmol) and Et₃N (169 µL, 1.21 mmol) in CH₃CN (10 mL). The reaction mixture was stirred at 50° C. for 16 hours. The solvent was removed under reduced pressure and the brown oil was purified via column chromatography on silica gel (CH₂Cl₂:MeOH, 95:5, v/v) to give the product as a pale yellow oil (205 mg, 52%). ¹H NMR (CDCl₃) δ 1.35 (m, 2H), 1.43 (s, 9H), 1.55 (m, 2H), 2.67 (t, 2H, J=7.5 Hz), 2.98 (m, 2H), 3.98 (s, 4H), 4.86 (s, 1H), 7.11 (dd, 2H, J=9.0, 6.0 Hz), 7.61 (d, 2H, J=9.0 Hz), 8.45 (m, 2H). Conversion to the HBr salt using General Procedure D gave COMPOUND 235 as a white solid. ¹H NMR (D₂O) δ 1.75 (m, 2H), 1.97 (m, 2H), 3.02 (t, 2H, J=7.5 Hz), 3.52 (t, 2H, J=8.1 Hz), 4.80 (s, 2H), 4.82 (s, 2H), 7.42 (dd, 2H, J=8.4, 4.8 Hz), 7.92 (d, 2H, J=8.1 Hz), 8.45 (m, 2H). ¹³C NMR (D₂O) δ 21.51, 24.37, 39.25, 48.71, 55.98, 126.19, 131.75, 139.55, 147.09, 147.26. ES-MS m/z 339 [M+H]⁺. Anal. Calcd. for C₁₆H₂₀N₄Cl₂.3.5HBr.0.8H₂O: C, 30.18; H, 3.97; N, 8.80; Cl, 11.13; Br, 43.91. Found: C, 30.18; H, 4.04; N, 8.72; Cl, 10.77; Br, 44.05.

Example 236

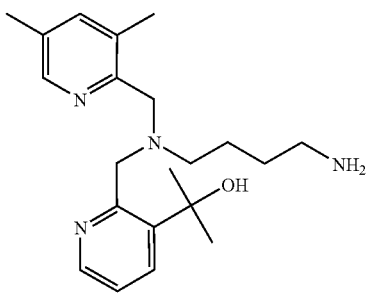

COMPOUND 236: 2-(2-{[(4-Amino-butyl)-(3,5-dimethyl-pyridin-2-ylmethyl)-amino]-methyl}-pyridin-3-yl)-propan-2-ol Acetic acid 1-(2-{[(4-tert-butoxycarbonylamino-butyl)-(3,5-dimethyl-pyridin-2-ylmethyl)-amino]-methyl}-pyridin-3-yl)-1-methyl-ethyl ester (285 mg, 0.57 mmol) was dissolved in MeOH (8 mL) and powdered K₂CO₃ (160 mg) was added. The mixture was stirred at room temperature for 18 hours. The solvent was removed under reduced pressure and the white residue was dissolved in water (20 mL) and extracted with CH₂Cl₂ (5×30 mL). The combined organic extracts were dried (Na₂SO₄), filtered, and concentrated in vacuo to afford a colorless oil. Deprotection with TFA using General Procedure F gave a colorless oil. ¹H NMR (CDCl₃) δ 1.23 (m, 2H), 1.34 (s, 6H), 1.57 (m, 2H), 1.75 (br s, 2H), 2.17 (s, 3H), 2.20 (s, 3H), 2.50 (m, 4H), 3.71 (s, 2H), 4.16 (s, 2H), 7.13 (dd, 1H, J=6.0, 3.0 Hz), 7.19 (s, 1H), 7.58 (d, 1H, J=7.5 Hz), 8.15 (s, 1H), 8.33 (d, 1H, J=3.0 Hz). ¹³C NMR (CDCl₃) δ 18.29, 18.87, 22.41, 31.68, 31.80, 42.02, 53.78, 57.06, 62.62, 71.79, 123.07, 132.40, 132.81, 134.86, 139.29, 144.76, 146.93, 147.05, 152.60, 155.25. ES-MS m/z 357 [M+H]⁺. Anal. Calcd. for C₂₁H₃₂N₄O.0.1TFA: C, 69.51; H, 8.84; N, 15.32. Found: C, 69.52; H, 8.79; N, 15.31.

Example 237

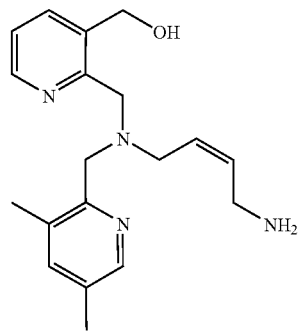

COMPOUND 237: N¹-(3,5-dimethyl-pyridin-2-ylmethyl)-N¹-(3-hydroxymethyl-pyridin-2-ylmethyl)-cis-but-2-ene-1,4-diamine (HBr salt)

Using General Procedure B: Reaction of (4-chloro-cis-but-2-enyl)-carbamic acid tert-butyl ester and 3,5-dimethyl-pyridine-2-carbaldehyde in CH₂Cl₂ with NaBH(OAc)₃ gave the desired secondary amine as a colorless oil.

Using General Procedure B: Reaction of the amine from above and 3-(tert-butyl-dimethylsiloxymethyl)-pyridine-2-carbaldehyde in CH₂Cl₂ with NaBH(OAc)₃ gave the protected amine. Deprotection with 6 N HCl (20 mL) and conversion to the HBr salt using General Procedure D gave COMPOUND 237 as a white solid. ¹H NMR (D₂O) δ 2.45 (s, 3H), 2.46 (s, 3H), 3.44 (d, 2H, J=6.6 Hz), 3.61 (d, 2H, J=6.6 Hz), 4.26 (s, 2H), 4.35 (s, 2H), 4.87 (s, 2H), 5.64-5.73 (m, 1H), 5.89-5.98 (m, 1H), 8.00 (t, 1H, J=6.9 Hz), 8.20 (s, 1H), 8.44 (s, 1H), 8.59 (d, 1H, J=7.8 Hz), 8.71 (d, 1H, J=6.7 Hz). ¹³C NMR (D₂O) δ 17.21, 17.56, 36.59, 51.90, 53.66, 53.75, 59.32, 125.94, 126.75, 130.94, 137.09, 137.70, 138.33, 139.52, 140.41, 146.17, 149.29, 150.90. ES-MS m/z 327 (M+H). Anal. Calcd. for C₁₉H₂₆N₄O.3HBr.2H₂O: C, 37.71; H, 5.50; N, 9.26. Found: C, 37.59; H, 5.19; N, 9.23.

Example 238

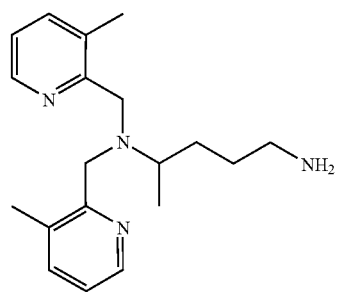

COMPOUND 238: N⁴,N⁴-bis-(3-methyl-pyridin-2-ylmethyl)-pentane-1,4-diamine (HBr salt)

Using General Procedure B: Reaction of 2-(4-oxo-pentyl)-isoindole-1,3-dione in CH₂Cl₂ and (3-methyl-pyridin-2-yl)- methylamine (Lu, Z et al. *Bioorg. Med. Chem. Lett.* 2003, 13, 1821-1824) with NaBH(OAc)₃ gave 2-{4-[(3-methyl-pyridin-2-ylmethyl)-amino]-pentyl}-isoindole-1,3-dione as a colorless oil.

Using General Procedure B: Reaction of 2-{4-[(3-methyl-pyridin-2-ylmethyl)-amino]-pentyl}-isoindole-1,3-dione in CH₂Cl₂ and 3-methyl-pyridine-2-carbaldehyde with NaBH(OAc)₃ gave a colorless oil. Deprotection with NH₂NH₂ using General Procedure E gave a colorless oil. Conversion to the HBr salt using General Procedure D gave COMPOUND 238. ¹H NMR (D₂O) δ 1.24 (d, 3H, J=6.6 Hz), 1.55-1.70 (m, 3H), 1.86-1.95 (m, 1H), 2.50 (s, 6H), 2.84-2.90 (m, 1H), 2.96-3.02 (m, 2H), 4.29 (s, 4H), 7.82 (dd, 2H, J=5.7, 7.8 Hz), 8.32 (d, 2H, J=7.8 Hz), 8.56 (d, 2H, J=5.7 Hz); ¹³C NMR (D₂O) δ 17.54, 24.96, 29.47, 39.96, 49.38, 50.59, 57.69, 126.10, 138.00, 138.83, 148.60, 151.25. ES-MS m/z 313 (M+H). Anal. Calcd. for C₁₉H₂₈N₄.3.1HBr.1.6H₂O.0.2C₄H₁₀O: C, 39.18; H, 6.03; N, 9.23; Br, 40.81. Found: C, 39.22; H, 5.86; N, 9.10; Br, 40.78.

Example 239

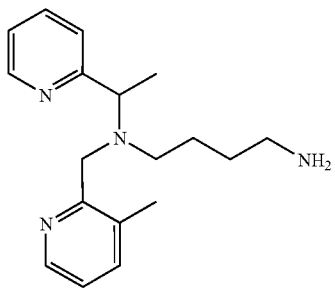

COMPOUND 239: N¹-(3-methyl-pyridin-2-ylmethyl)-N¹-(1-pyridin-2-yl-ethyl)-butane-1,4-diamine (HBr salt)

Using General Procedure B: Reaction of 3-methyl-pyridine-2-carbaldehyde in CH₂Cl₂ and 1-pyridin-2-yl-ethylamine with NaBH(OAc)₃ gave (3-methyl-pyridin-2-ylmethyl)-(1-pyridin-2-yl-ethyl)-amine as a pale yellow oil. ¹H NMR (CDCl₃) δ 1.48 (d, 3H, J=6.9 Hz), 2.19 (s, 3H), 3.70-3.83 (m, 2H), 4.02 (q, 1H, J=6.9 Hz), 7.06 (dd, 1H, J=5.4, 7.5 Hz), 7.13-7.18 (m, 1H), 7.36-7.40 (m, 1H), 7.47 (d, 1H, J=7.8 Hz), 7.66 (dt, 1H, J=1.8, 7.8 Hz), 8.40 (d, 1H, J=3.9 Hz), 8.55-8.57 (m, 1H).

Using General Procedure B: Reaction of 4-(1,3-dioxo-1,3-dihydro-isoindol-2-yl)-butyraldehyde and (3-methyl-pyridin-2-ylmethyl)-(1-pyridin-2-yl-ethyl)-amine with NaBH(OAc)₃ gave a colorless oil. Deprotection with NH₂NH₂ using General Procedure E gave a colorless oil. Conversion to the HBr salt using General Procedure D gave COMPOUND 239 as a white solid. ¹H NMR (CD₃OD) δ 1.43-1.51 (m, 7H), 2.28 (s, 3H), 2.48-2.55 (m, 1H), 2.61-2.82 (m, 3H), 3.80-3.90 (m, 2H), 4.10 (q, 1H, J=6.9 Hz), 7.22 (dd, 1H, J=5.1, 7.5 Hz), 7.28-7.32 (m, 1H), 7.47 (d, 1H, J=7.8 Hz), 7.57 (d, 1H, J=7.5 Hz), 7.79 (dt, 1H, J=1.8, 7.8 Hz), 8.28-8.30 (m, 1H), 8.50-8.52 (m, 1H); ¹³C NMR (D₂O) δ 13.48, 17.55, 22.92, 24.96, 39.46, 50.76, 53.75, 61.96, 123.95, 123.98, 124.28, 133.95, 138.46, 140.24, 145.21, 148.52, 153.90, 159.41. ES-MS m/z 299 (M+H). Anal. Calcd. for C₁₈H₂₆N₄.1.3HBr.1.2H₂O.0.2C₄H₁₀O: C, 51.31; H, 7.26; N, 12.73; Br, 23.60. Found: C, 51.15; H, 6.94; N, 12.61; Br, 23.78.

Example 240

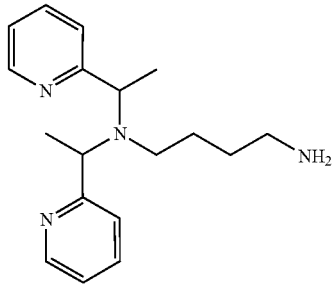

COMPOUND 240: N¹,N¹-bis-(1-pyridin-2-yl-ethyl)-butane-1,4-diamine (HBr salt)

To a stirred solution of 1-pyridin-2-yl-ethanol (156 mg, 1.27 mmol) (Mandal, S. K. et al. *J. Org. Chem.* 2003, 68, 4600-4603) and Et₃N (0.27 mL, 1.94 mmol) in CH₂Cl₂ (5 mL) was added methanesulphonyl chloride (0.11 mL, 1.29 mmol) and the solution was stirred for 70 minutes. The solution was diluted with CH₂Cl₂ (20 mL) and washed with saturated aqueous NaHCO₃ (2×15 mL) and brine (1×15 mL). The combined aqueous phase was extracted with CH₂Cl₂ (1×15 mL). The combined organic phase was dried (Na₂SO₄), filtered and concentrated under reduced pressure to give crude methanesulphonic acid 1-pyridin-2-yl-ethyl ester as a yellow oil (269 mg, 100%). ¹H NMR (CDCl₃) δ 1.77 (d, 3H, J=6.6 Hz), 2.94 (s, 3H), 5.79 (q, 1H, J=6.6 Hz), 7.28 (ddd, 1H, J=7.4, 7.1, 1.3 Hz), 7.47 (d, 1H, J=7.9 Hz), 7.76 (td, 1H, J=7.6, 1.7 Hz), 8.61 (d, 1H, J=4.9 Hz).

Using General Procedure A: To a stirred solution of methanesulphonic acid 1-pyridin-2-yl-ethyl ester (269 mg, 1.34 mmol) and 2-[4-(1-pyridin-2-yl-ethylamino)-butyl]-isoindole-1,3-dione (356 mg, 1.10 mmol) in CH₃CN (5 mL) at room temperature was added DIPEA (0.30 mL, 1.72 mmol) and KI (13 mg, 0.078 mmol). After 3 hours the temperature was increased to 60° C. and the mixture stirred for another 17 hours. KI (23 mg, 0.139 mmol) and DMAP (35 mg, 0.286 mmol) were added and the reaction stirred for a further 2 hours. Work up and purification by flash chromatography (35:1:1 CH₂Cl₂:MeOH:NH₄OH) afforded pure 2-{4-[bis-(1-pyridin-2-yl-ethyl)-amino]-butyl}-isoindole-1,3-dione as a mixture of diastereomers (139 mg, 30%). ¹H NMR (CDCl₃) δ 1.18-1.49 (m, 10H) containing 1.27 (d, 3H, J=7.0 Hz) and 1.42 (d, 3H, J=7.1 Hz), 2.51-2.80 (m, 2H), 3.44-3.52 (m, 2H), 4.03-4.12 (m, 2H), 6.98-7.07 (m, 2H), 7.31 (d, 1H, J=7.9 Hz), 7.45-7.61 (m, 3H) containing 7.47 (d, 1H, J=7.9 Hz), 7.66-7.70 (m, 2H), 7.76-7.81 (m, 2H), 8.43-8.48 (m, 2H). ES-MS m/z 429 [M+H].

Deprotection with H₂NNH₂.H₂O using General Procedure E gave N¹,N¹-bis-(1-pyridin-2-yl-ethyl)-butane-1,4-diamine. Conversion to the HBr salt using General Procedure D gave COMPOUND 240. ¹H NMR (D₂O) Mixture of diastereomers δ 1.05-1.15 (m) and 1.28-1.39 (m) and 1.48-1.57 (m) and 2.63-2.75 (m) and 2.85-2.91 (m) (total 8H), 1.53 (d, J=6.6 Hz) and 1.67 (d, J=6.5 Hz) (total 6H), 4.60 (q, J=6.9 Hz) and 4.70 (q, J=6.7 Hz) (total 2H), 7.95-8.01 (m) and 8.09-8.14 (m) and 8.54-8.61 (m) and 8.75-8.79 (m) (total 8H). ¹³C NMR (D₂O) Mixture of diastereomers δ 15.15, 15.37, 25.03, 25.13, 25.80, 26.00, 39.31, 39.51, 49.12, 49.34, 57.34, 57.76, 126.28, 126.48, 126.63, 126.67, 141.99, 147.92, 147.95, 157.39, 157.62. ES-MS m/z 299 (M+H). Anal. Calcd. for C₁₈H₂₆N₄.3.4HBr.2.3H₂O: C, 35.16; H, 5.57; N, 9.11; Br, 44.18. Found: C, 35.41; H, 5.24; N, 8.89; Br, 44.27.

Example 241

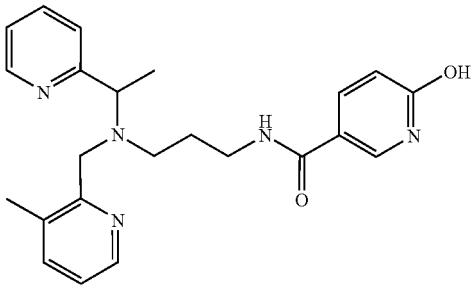

COMPOUND 241: 6-Hydroxy-N-{3-[(3-methyl-pyridin-2-ylmethyl)-(1-pyridin-2-yl-ethyl)-amino]-propyl}-nicotinamide (HBr salt)

Using General Procedure B: Reaction of 2-acetyl-pyridine and (3-amino-propyl)-carbamic acid tert-butyl ester with NaBH(OAc)₃ in CH₂Cl₂ gave [3-(1-pyridin-2-yl-ethylamino)-propyl]-carbamic acid tert-butyl ester as a colorless oil.

Using General Procedure B: Reaction of [3-(1-pyridin-2-yl-ethylamino)-propyl]-carbamic acid tert-butyl ester and 3-methyl-pyridine-2-carboxaldehyde with NaBH(OAc)₃ in CH₂Cl₂ gave {3-[(3-methyl-pyridin-2-ylmethyl)-(1-pyridin-2-yl-ethyl)-amino]-propyl}-carbamic acid tert-butyl ester as a colorless oil.

The oil (0.45 g) was dissolved in THF (5 mL) and treated with 6N HCl (5 mL). The resultant solution was stirred at room temperature overnight. The solution was neutralized with solid K₂CO₃ (5 g), diluted with water (5 mL) and extracted with CH₂Cl₂ (3×20 mL). The combined organic extracts were dried (Na₂SO₄) and concentrated and provided 0.38 g of N¹-(3-Methyl-pyridin-2-ylmethyl)-N¹-(1-pyridin-2-yl-ethyl)-propane-1,3-diamine as a yellow oil.

Using General Procedure G: To a solution of N-(3-Methyl-pyridin-2-ylmethyl)-N¹-(1-pyridin-2-yl-ethyl)-propane-1,3-diamine (0.33 g, 1.16 mmol) in dry DMF (3 mL) was added 6-hydroxy-nicotinic acid (0.174 g, 1.24 mmol) followed by EDCI (0.257 g, 1.34 mmol), HOBT (0.183 g, 1.35 mmol), and DIPEA (0.40 mL, 2.30 mmol). Purification of the crude material by column chromatography on silica gel (10:1:1 CH₂Cl₂-MeOH—NH₄OH) provided 177 mg (38%) of the free base of the title compound as a colorless oil. Conversion to the HBr salt gave COMPOUND 241 (270 mg, 83%) as a white solid. ¹H NMR (D₂O) δ 1.55 (d, 3H, J=6.6 Hz), 1.67 (quintet; 2H, J=7.2 Hz), 2.43 (s, 3H), 2.48-2.58 (m, 1H), 2.63-2.74 (m, 1H), 3.12-3.31 (m, 2H), 4.28 (s, 2H), 456 (q, 1H, J=6.6 Hz), 6.61 (d, 1H, J=9.3 Hz), 7.78-7.83 (m, 2H), 7.89-7.94 (m, 2H), 8.11 (d, 1H, J=8.1 Hz), 8.30 (d, 1H, J=8.1 Hz), 8.49-8.58 (m, 2H), 8.74 (d, 1H, J=5.7 Hz); ¹³C NMR (D₂O) δ 15.07, 16.98, 26.37, 37.59, 50.21, 50.95, 59.83, 115.31, 119.32, 125.82, 126.75, 126.83, 137.21, 137.53, 138.40, 140.83, 142.09, 148.06, 148.24, 152.11, 156.20, 165.43, 166.77; ES-MS m/z 406 (M+H). Anal. Calcd. for C₂₃H₂₇N₅O₂.3.3HBr.4.2H₂O: C, 36.92; H, 5.21; N, 9.36; Br, 35.24. Found: C, 36.85; H, 5.39; N, 9.04; Br, 35.63.

Example 242

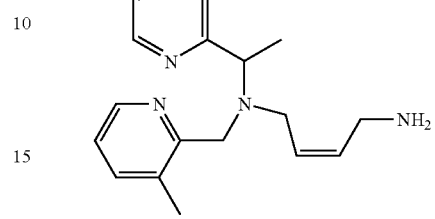

COMPOUND 242: N-(3-Methyl-pyridin-2-ylmethyl)-N-(1-pyridin-2-ylethyl)-cis-but-2-ene-1,4-diamine (HBr salt)

Using General Procedure B, reaction of 1-Pyridin-2-yl-ethylamine and 3-methylpyridine-2-carbaldehyde in MeOH with NaBH₄ gave (3-Methyl-pyridin-2-ylmethyl)-(1-pyridin-2-ylethyl)-amine as a pale yellow oil (0.21 g, 60%).

Using General Procedure A: Reaction of the above secondary amine, (4-chloro-cis-but-2-enyl)-carbamic acid tert-butyl ester, and KI in anhydrous CH₃CN with DIPEA gave {4-[(3-Methyl-pyridin-2-ylmethyl)-(1-pyridin-2-ylethyl)-amino]-cis-but-2-enyl}-carbamic acid tert-butyl ester. ¹H NMR (CDCl₃) δ 1.45 (s, 9H), 1.50 (d, 3H, J=6.0 Hz), 2.26 (s, 3H), 3.14 (m, 2H), 3.58 (m, 2H), 3.72 (d, 1H, J=13.5 Hz), 3.85 (d, 1H, J=13.5 Hz), 4.11 (q, 1H, J=6.0 Hz), 5.57 (br, 2H), 5.62 (br, 1H, (NH)), 7.07 (m, 1H), 7.15 (m, 1H), 7.38 (d, 2H, J=6.0 Hz), 7.63 (t, 1H, J=6.0 Hz), 8.36 (d, 1H, J=3.0 Hz), 8.57 (d, 1H, J=3.0 Hz). Conversion to the HBr salt using General Procedure D gave COMPOUND 242 as a white solid. ¹H NMR (D₂O) δ 1.61 (d, 3H, J=6.9 Hz), 2.45 (s, 3H), 3.32 (dd, 1H, J=15.0, 6.5 Hz), 3.48 (m, 1H), 3.55 (br, 2H), 4.27 (s, 2H), 4.59 (q, 1H, J=6.8 Hz), 5.57 (m, 1H), 5.84 (m, 1H), 7.84 (t, 1H, J=6.9 Hz), 8.00 (t, 1H, J=6.9 Hz), 8.14 (d, 1H, J=8.1 Hz), 8.33 (d, 1H, J=7.8 Hz), 8.58 (m, 2H), 8.78 (d, 1H, J=6.0 Hz). ¹³C NMR (D₂O) δ 14.34, 17.08, 36.54, 49.48, 50.71, 59.70, 125.25, 125.95, 126.77, 126.92, 131.56, 137.33, 138.54, 142.27, 148.04, 148.36, 151.74, 156.02. ES-MS m/z 297 (M+H). Anal. Calcd. For C₁₈H₂₄N₄.3.4HBr.1.2H₂O.0.3C₄H₁₀O: C, 37.48; H, 5.37; N, 9.10; Br, 44.15. Found: C, 37.44; H, 5.42; N, 9.07; Br, 44.10.

Example 243

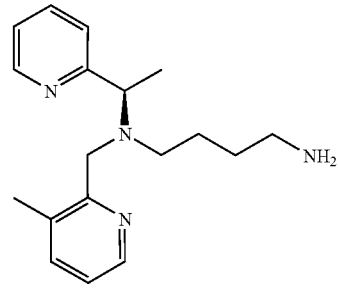

COMPOUND 243: (R)—N¹-(3-methyl-pyridin-2-ylmethyl)-N¹-(1-pyridin-2-yl-ethyl)-butane-1,4-diamine (HBr salt)

Using General Procedure B, reaction of (R)-1-pyridin-2-yl-ethylamine (Shin, C-G et al, *Bull. Chem. Soc. Jpn.* 2002, 75, 1583-1596) in $CH_2Cl_2$ and 4-(1,3-dioxo-1,3-dihydro-isoindol-2-yl)-butyraldehyde with $NaBH(OAc)_3$ gave 2-[4-(1-pyridin-2-yl-ethylamino)-butyl]-isoindole-1,3-dione as a yellow oil. $^1H$ NMR ($CDCl_3$) δ 1.37 (d, 3H, J=6.0 Hz), 1.51-1.54 (m, 1H), 1.66-1.71 (m, 2H), 2.02-2.03 (m, 2H), 2.41-2.45 (m, 1H), 2.52-2.57 (m, 1H), 3.66 (t, 2H, J=7.5 Hz), 3.81-3.88 (m, 1H), 7.12-7.14 (m, 1H), 7.28-7.30 (m, 1H), 7.63-7.64 (m, 1H), 7.68-7.71 (m, 2H), 7.81-7.84 (m, 2H), 8.53-8.54 (m, 1H).

Using General Procedure B, reaction of (R)-2-[4-(1-pyridin-2-yl-ethylamino)-butyl]-isoindole-1,3-dion and 3-methyl-pyridine-2-carbaldehyde in $CH_2Cl_2$ with $NaBH(OAc)_3$ gave 2-{4-[(3-methyl-pyridin-2-ylmethyl)-(1-pyridin-2-yl-ethyl)-amino]-butyl}-isoindole-1,3-dione. $^1H$ NMR ($CDCl_3$) δ 1.21-1.32 (m, 2H), 1.38-1.47 (m, 5H), 2.25 (s, 3H), 2.35-2.54 (m, 1H), 2.54-2.60 (m, 1H), 3.48 (t, 2H, J=7.5 Hz), 3.79 (s, 2H), 3.94-4.00 (m, 1H), 6.97-6.99 (m, 1H), 7.05-7.10 (m, 1H), 7.29-7.36 (m, 2H), 7.56-7.57 (m, 1H), 7.66-7.69 (m, 2H), 7.78-7.81 (m, 2H), 8.27 (d, 1H, J=3.5 Hz), 8.49 (d, 1H, J=3.5 Hz). Deprotection with $H_2NNH_2.H_2O$ following General Procedure E gave $N^1$-(3-methyl-pyridin-2-ylmethyl)-$N^1$-(1-pyridin-2-yl-ethyl)-butane-1,4-diamine as a beige oil. $^1H$ NMR ($CDCl_3$) δ 1.03 (s, 1H), 1.20-1.26 (m, 2H), 1.31-1.37 (m, 2H), 1.49 (d, 3H, J=6.0 Hz), 2.31 (s, 3H), 2.39-2.56 (m, 4H), 3.83 (s, 2H), 3.97-4.04 (m, 1H), 7.07-7.09 (m, 2H), 7.39 (d, 2H, J=9.0 Hz), 7.61-7.62 (m, 1H), 8.34-8.36 (m, 1H), 8.53-8.55 (m, 1H). Conversion to the HBr salt using General Procedure D gave COMPOUND 243 as a white solid. $^1H$ NMR ($D_2O$) 1.47-1.49 (m, 4H), 1.59 (d, 3H, 6.6 Hz), 2.45 (s, 3H), 2.60-2.66 (m, 1H), 2.70-2.77 (m, 1H), 2.85-2.86 (m, 2H), 4.30 (s, 2H), 4.57-4.60 (m, 2H), 7.81-7.85 (m, 1H), 7.99 (t, 1H, J=6.6 Hz), 8.13 (d, 1H, J=9.0 Hz), 8.32 (d, 1H, J=7.2 Hz), 8.56-8.58 (m, 2H), 8.77 (d, 1H, J=5.1 Hz). $^{13}C$ NMR ($D_2O$) δ 15.00, 17.00, 23.97, 25.01, 39.52, 51.06, 52.70, 59.88, 125.85, 126.82, 126.88, 137.10, 138.28, 142.11, 148.19, 148.25, 152.29, 156.10. ES-MS m/z 299 (M+H). Anal. Calcd. for $C_{18}H_{26}N_4.3.4HBr.0.3C_4H_{10}O.2.3H_2O$: C, 36.19; H, 5.85; N, 8.79; Br, 42.64. Found: C, 36.11; H, 5.54; N, 8.75; Br, 42.65.

Example 244

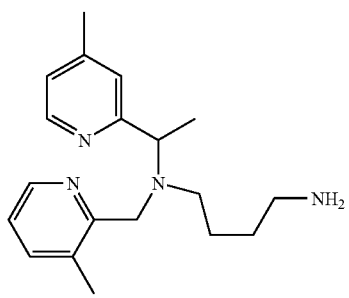

COMPOUND 244: N-[1-(4-Methylpyridin-2-yl)-ethyl]-N-(3-methylpyridin-2-ylmethyl)-butane-1,4-diamine (HBr salt)

Using General Procedure B, reaction of {4-[(3-Methyl-pyridin-2-ylmethyl)-amino]-butyl}-carbamic acid tert-butyl ester, 1-(4-methylpyridin-2-yl)-ethanone and $NaBH(OAc)_3$ in $CH_2Cl_2$ gave {4-[[1-(4-methyl-pyridin-2-yl)-ethyl]-(3-methylpyridin-2-ylmethyl)-amino]-butyl}-carbamic acid tert-butyl ester as a pale yellow oil. Conversion to the HBr salt using General Procedure D gave COMPOUND 244 as a white solid. $^1H$ NMR ($D_2O$) δ 1.47 (br, 4H), 1.54 (d, 3H, J=6.0 Hz), 2.45 (s, 3H), 2.60 (m, 1H), 2.63 (s, 3H), 2.71 (m, 1H), 2.85 (br, 2H), 4.27 (s, 2H), 4.49 (q, 1H, J=6.0 Hz), 7.78 (d, 1H, J=6.3 Hz), 7.83 (t, 1H, J=7.2 Hz), 7.95 (s, 1H), 8.33 (d, 1H, J=7.8 Hz), 8.56 (m, 2H). $^{13}C$ NMR ($D_2O$) δ 15.08, 17.10, 22.38, 24.01, 25.03, 39.57, 51.07, 52.81, 59.73, 125.84, 127.25, 127.40, 137.08, 138.22, 140.83, 148.27, 152.41, 154.85, 162.82. ES-MS m/z 313 (M+H). Anal. Calcd. for $C_{19}H_{28}N_4.4.3HBr.3.5H_2O$: C, 31.55; H, 5.48; N, 7.74; Br, 47.49. Found: C, 31.64; H, 5.63; N, 7.43; Br, 47.61.

Example 245

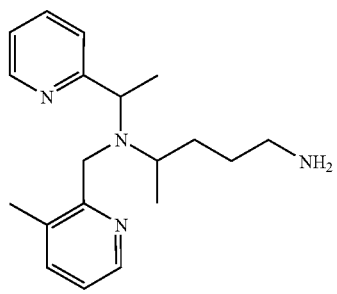

COMPOUND 245A and 245B: $N^4$-(3-methyl-pyridin-2-ylmethyl)-$N^4$-(1-pyridin-2-yl-ethyl)-pentane-1,4-diamine (HBr salts); COMPOUND 245A one diastereoisomer and COMPOUND 245B a mixture of diastereomers (41% COMPOUND 245A and 57% the other diastereoisomer)

Using General Procedure B: Reaction of 2-(4-oxo-pentyl)-isoindole-1,3-dione (Abdel-Monem, M M et al. *J. Med. Chem.* 1974, 17, 447-451) in $CH_2Cl_2$ and 1-pyridin-2-yl-ethylamine with $NaBH(OAc)_3$ gave 2-[4-(1-pyridin-2-yl-ethylamino)-pentyl]-isoindole-1,3-dione as a colorless oil.

Using General Procedure B: Reaction of 3-methyl-pyridine-2-carbaldehyde and 2-[4-(1-pyridin-2-yl-ethylamino)-pentyl]-isoindole-1,3-dione in $CH_2Cl_2$ with $NaBH(OAc)_3$ gave 2-{4-[(3-methyl-pyridin-2-ylmethyl)-(1-pyridin-2-yl-ethyl)-amino]-pentyl}-isoindole-1,3-dione, as (one diastereoisomer (0.101 g) and a mixture of two diastereoisomers (0.0770 g), with a total yield of 58%. Deprotection with $H_2NNH_2.H_2O$ using General Procedure E gave a colorless oil. Conversion to the HBr salt using General Procedure D gave a white solid, which was isolated as a pure diastereoisomer. $^1H$ NMR ($D_2O$) δ 1.08 (d, 3H, J=6.3 Hz), 1.32 (d, 3H, J=6.6 Hz), 1.37-1.59 (m, 3H), 1.61-1.85 (m, 1H), 2.50 (s, 3H), 2.71-2.76 (m, 1H), 2.90-2.95 (m, 2H), 4.35 (s, 2H), 4.68 (q, 1H, J=6.6 Hz), 7.84 (t, 1H, J=6.6 Hz), 8.01 (t, 1H, J=6.9 Hz), 8.20 (d, 1H, J=8.1 Hz), 8.34 (d, 1H, J=7.8 Hz), 8.56-8.63 (m, 2H), 8.81 (d, 1H, J=5.7 Hz); $^{13}C$ NMR ($D_2O$) δ 17.01, 17.19, 19.97, 24.75, 27.37, 39.88, 46.16, 56.59, 59.71, 125.76, 127.08, 127.18, 136.58, 138.12, 142.58, 148.25, 148.62, 153.57, 156.65. ES-MS m/z 313 (M+H). Anal. Calcd. for $C_{19}H_{28}N_4.3.1HBr.0.4H_2O$: C, 40.00; H, 5.64; N, 9.82; Br, 43.42. Found: C, 39.93; H, 5.66; N, 9.71; Br, 43.54.

The mixture of two isomers was treated in the same way, and the HBr salt was isolated as white solid containing two isomers with a ratio of 0.414:0.568. ES-MS m/z 313 (M+H). Anal. Calcd. for $C_{19}H_{28}N_4 \cdot 3.6HBr \cdot 3.4H_2O \cdot 0.2C_4H_{10}O$: C, 34.98; H, 5.99; N, 8.24; Br, 42.31. Found: C, 34.94; H, 5.95; N, 8.27; Br, 42.38.

Example 246

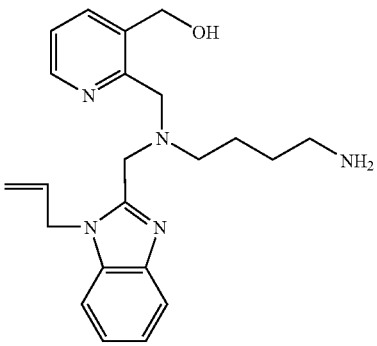

COMPOUND 246: (2-{[1-Allyl-1H-benzoimidazol-2-ylmethyl)-(4-amino-butyl)-amino]-methyl}-pyridin-3-yl)-methanol (HBr salt)

Using General Procedure B: Reaction of (4-amino-butyl)-carbamic acid tert-butyl ester in $CH_2Cl_2$ and 1-allyl-1H-benzimidazole-2-carbaldehyde gave {4-[(1-allyl-1H-benzoimidazol-2-ylmethyl)-amino]-butyl}-carbamic acid tert-butyl ester as a colorless oil (0.10 g, 30%). $^1$H NMR (CDCl$_3$) δ 1.43 (s, 9H), 1.54 (s, 4H), 2.71 (m, 2H), 3.11 (m, 2H), 4.04 (s, 2H), 4.87 (d, 2H, J=5.3 Hz), 5.02 (d, 1H, J=17.1 Hz), 5.19 (d, 1H, J=11.0 Hz), 5.98 (m, 1H), 7.30 (m, 3H), 7.73 (m, 1H)

Using General Procedure B: Reaction of {4-[(1-allyl-1H-benzoimidazol-2-ylmethyl)-amino]-butyl}-carbamic acid tert-butyl ester in $CH_2Cl_2$ and 2-(tert-butyl-dimethyl-silanyloxymethyl)-benzaldehyde with NaBH(OAc)$_3$ gave (2-{[1-allyl-1H-benzoimidazol-2-ylmethyl)-(4-amino-butyl)-amino]-methyl}-pyridin-3-yl)-methanol as a colorless oil. $^1$H NMR (CDCl$_3$) δ 1.34 (m, 2H), 1.65 (m, 2H), 2.65 (m, 4H), 3.82 (s, 2H), 4.06 (s, 2H), 4.59 (s, 2H), 4.70 (d, 2H, J=5.3 Hz), 4.76 (d, 1H, J=16.7 Hz), 5.10 (d, 1H, J=10.1 Hz), 5.77 (m, 1H), 7.20 (m, 4H), 7.63 (dd, 1H, J=7.45, 1.75 Hz), 7.66 (m, 1H), 8.45 (dd, 1H, J=4.82, 1.3 Hz). Conversion to the HBr salt using General Procedure D gave COMPOUND 246 as a white solid. $^1$H NMR (D$_2$O) δ 1.36 (m, 2H), 1.68 (m, 2H), 2.91 (m, 4H), 3.35 (s, 2H), 4.50 (s, 2H), 4.62 (s, 2H), 5.25 (s, 2H), 5.32 (d, 1H, J=18.0 Hz), 5.40 (d, 1H, 10.1 Hz), 6.11 (m, 1H), 7.64 (m, 2H), 7.87 (m, 1H), 8.02 (m, 2H), 8.66 (m, 1H), 8.92 (m, 1H); $^{13}$C NMR (D$_2$O) δ 25.98, 26.56, 27.30, 40.81, 51.77, 55.22, 55.46, 56.92, 60.57, 114.50, 115.95, 120.59, 127.50, 127.93, 128.18, 128.48, 131.83, 141.30, 142.13, 143.18, 146.76, 149.27, 152.55. ES-MS m/z 380 (M+H). Anal. Calcd. for $C_{22}H_{29}N_5O \cdot 3.49HBr \cdot 1.87H_2O$: C, 38.00; H, 5.25; N, 10.07; Br, 40.06. Found: C, 38.04; H, 5.22; N, 9.93; Br, 40.06.

Example 247

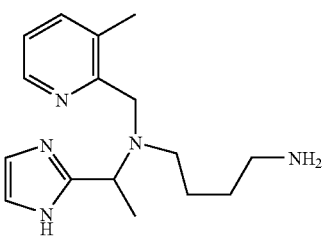

COMPOUND 247: N-[1-(1H-Imidazol-2-yl)-ethyl]-N-(3-methylpyridin-2-ylmethyl)-butane-1,4-diamine (HBr salt)

A solution of imidazole-2-carboxaldehyde (0.70 g, 7.3 mmol) in DMF (25 mL) was treated with DIPEA (1.90 mL, 10.9 mmol) and 2-(trimethylsilyl)ethoxymethyl chloride (1.46 g, 8.7 mmol) for 24 hours. Ethyl acetate (50 mL) was added and the solution was washed with brine (5×50 mL). The organic phase was then dried (MgSO$_4$), filtered, and concentrated under reduced pressure to afford, after column chromatography with silica gel (2:98 MeOH:CH$_2$Cl$_2$), 1-(2-trimethylsilanylethoxymethyl)-1H-imidazole-2-carboxaldehyde as a pale yellow oil (0.90 g, 55%).

To a solution of the above aldehyde (0.90 g, 4.0 mmol) in Et$_2$O (40 mL) at 0° C. was added MeMgBr (3.0 M in Et$_{20}$, 1.7 mL, 5.2 mmol) and the mixture stirred for 1 hour. Saturated aqueous NH$_4$Cl solution (40 mL) and Et$_2$O (40 mL) was added and the aqueous phase was extracted with Et$_2$O (2×40 mL). The organic phase was then washed with brine (20 mL), dried (Na$_2$SO$_4$), and concentrated under reduced pressure to give 1-[1-(2-trimethylsilanylethoxymethyl)-1H-imidazol-2-yl]-ethanol as a pale yellow oil (0.96 g, 100%). $^1$H NMR (CDCl$_3$) δ −0.01 (s, 9H), 0.91 (t, 2H, J=7.5 Hz), 1.65 (d, 3H, J=7.5 Hz), 3.53 (t, 2H, J=7.5 Hz), 4.99 (q, 1H, J=7.5 Hz), 5.32 (d, 1H, J=10.5 Hz), 5.37 (d, 1H, J=10.5 Hz), 6.97 (s, 2H).

Using General Procedure C: Methanesulfonyl chloride (0.46 mL, 5.9 mmol) and Et$_3$N (1.1 mL, 7.9 mmol) were added to a solution of the above oil (0.96 g, 3.9 mmol) in CH$_2$Cl$_2$ (39 mL) at room temperature and stirred 1 hour. This gave, after aqueous work up, the crude methanesulfonate (1.13 g, 91%) as a brown oil that was used immediately in the next reaction.

A solution of the above methanesulfonate (~3.9 mmol) in DMF (20 mL) was treated with NaN$_3$ (0.63 g, 10.0 mmol) and stirred at 60° C. for 16 h. The solution was then cooled to room temperature and EtOAc (50 mL), brine (20 mL), and water (10 mL) was added. The organic phase was separated, washed with brine (4×20 mL), and dried (MgSO$_4$) and concentrated under reduced pressure. This gave 2-(1-azidoethyl)-1-(2-trimethylsilanylethoxymethyl)-1H-imidazole (0.81 g) that was used unpurified in the next reaction.

The crude material from above (~3.0 mmol) was dissolved in anhydrous MeOH (20 mL) and the reaction vessel was purged with N$_2$. 10% Palladium on carbon (200 mg) was added and the mixture stirred under an atmosphere of hydrogen (30 psi) for 3 hour. The reaction mixture was then filtered through celite to give 1-[1-(2-trimethylsilanylethoxymethyl)-1H-imidazol-2-yl]-ethylamine as a yellow oil (0.72 g, 77% 3 steps) which was used without further purification in the next reaction. $^1$H NMR (CDCl$_3$) δ −0.01 (s, 9H), 0.90 (t, 2H, J=7.5 Hz), 1.53 (d, 3H, J=7.5 Hz), 1.92 (br, 2H, NH$_2$), 3.50, (t, 2H, J=7.5 Hz), 4.21 (q, 1H, J=7.5 Hz), 5.29 (d, 1H, J=12.0 Hz), 5.35 (d, 1H, J=12.0 Hz), 6.92 (s, 1H), 6.96 (s, 1H).

Using General Procedure B, reaction of the above primary amine, 3-methylpyridine-2-carboxaldehyde and NaBH(OAc)$_3$ in CH$_2$Cl$_2$ gave (3-methylpyridin-2-ylmethyl)-1-[1-(2-trimethylsilanylethoxymethyl)-1H-imidazol-2-yl]-ethyl}amine as a yellow oil.

Using General Procedure B, reaction of the above secondary amine, 4-(1,3-dioxo-1,3-dihydroisoindol-2-yl)-butyraldehyde and NaBH(OAc)$_3$ in CH$_2$Cl$_2$ gave 2-[4-((3-methylpyridin-2-ylmethyl)-{1-[1-(2-trimethylsilanylethoxymethyl)-1H-imidazol-2-yl]-ethyl}-amino)-butyl]-isoindole-1,3-dione as a yellow oil. $^1$H NMR (CDCl$_3$) δ −0.07 (s, 9H), 0.71 (t, 2H, J=7.5 Hz), 1.13-1.45 (br m, 4H), 1.52 (d, 3H, J=7.5 Hz), 1.79 (br, 1H), 2.06 (s, 3H), 2.57 (m, 2H), 3.19 (m, 2H), 3.47 (br t, 2H), 3.61 (d, 1H, J=13.5 Hz), 3.92 (d, 1H, J=13.5 Hz), 4.18 (q, 1H, J=7.5 Hz), 4.98 (d, 1H, J=12.0 Hz), 5.32 (d, 1H, J=12.0 Hz), 6.90 (d, 2H, J=6.0 Hz), 7.02 (m, 1H), 7.33 (d, 1H, J=7.5 Hz), 7.71 (m, 2H), 7.82 (m, 2H), 8.32 (d, 1H, J=3.0 Hz).

A solution of the above material (0.57 g, 1.0 mmol) was stirred in 4N HCl (5 mL) at 50° C. for 4 hours. K$_2$CO$_3$ (5.5 g, 40 mmol) was added slowly and the mixture was diluted with water (10 mL). The aqueous was then extracted with CH$_2$Cl$_2$ (2×25 mL) and the organic phase dried (Na$_2$SO$_4$) and concentrated under reduced pressure to give, after column chromatography with silica gel (3:1:96 MeOH:NH$_4$OH:CH$_2$Cl$_2$), 2-{4-[[1-(1H-imidazol-2-yl)-ethyl]-(3-methylpyridin-2-ylmethyl)-amino]-butyl}-isoindole-1,3-dione (0.30 g, 70%).

Deprotection with H$_2$NNH$_2$·H$_2$O using General Procedure E gave N-[1-(1H-imidazol-2-yl)-ethyl]-N-(3-methylpyridin-2-ylmethyl)-butane-1,4-diamine as a yellow oil. $^1$H NMR (CDCl$_3$) δ 1.38 (br, 4H), 1.47 (d, 3H, J=7.5 Hz), 2.19 (m, 1H), 2.39 (s, 3H), 2.55 (t, 2H, J=6.0 Hz), 2.80 (m, 1H), 3.53 (d, 1H, J=12.0 Hz), 3.86 (d, 1H, J=15.0 Hz), 3.92 (q, 1H, J=7.5 Hz), 7.03 (s, 2H), 7.15 (m, 1H), 7.48 (d, 1H, J=7.5 Hz), 8.47 (d, 1H, J=4.5 Hz). Conversion to the HBr salt using General Procedure D gave COMPOUND 247 166 mg) as a white solid. $^1$H NMR (D$_2$O) δ 1.35-1.60 (br, 4H), 1.61 (d, 3H, J=6.9 Hz), 2.45 (s, 3H), 2.58 (m, 1H), 2.73 (m, 1H), 2.87 (t, 2H, J=7.2 Hz), 4.13 (d, 1H, J=18.3 Hz), 4.30 (d, 1H, J=18.6 Hz), 4.57 (q, 1H, J=6.9 Hz), 7.43 (s, 2H), 7.85 (t, 1H, J=6.8 Hz), 8.34 (d, 1H, J=7.8 Hz), 8.57 (d, 1H, J=5.7 Hz). $^{13}$C NMR (D$_2$O) δ 13.10, 16.90, 24.72, 25.00, 39.53, 50.87, 52.48, 54.71, 119.67 (2C), 125.87, 137.10, 138.14, 147.21, 148.25, 152.30. ES-MS m/z 288 (M+H). Anal. Calcd. for C$_{16}$H$_{25}$N$_5$·3.2HBr·1.1H$_2$O: C, 33.94; H, 5.41; N, 12.37; Br, 45.16. Found: C, 34.25; H, 5.54; N, 12.22; Br, 44.88.

Example 248

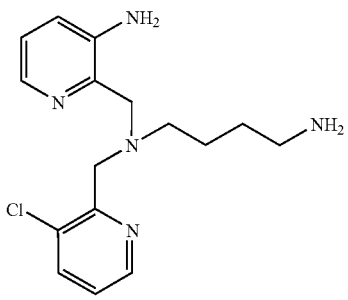

COMPOUND 248: N$^1$-(3-Aminopyridin-2-ylmethyl)-N$^1$-(3-chloropyridin-2-ylmethyl)-butane-1,4-diamine (HBr salt)

Using General Procedure B: Reaction of (4-Aminobutyl)-carbamic acid tert-butyl ester and (2-formylpyridin-3-yl)carbamic acid tert-butyl ester in MeOH with NaBH$_4$ gave {2-[(4-tert-butoxycarbonylamino-butylamino)-methyl]-pyridin-3-yl}-carbamic acid tert-butyl ester as a clear residue. $^1$H NMR (CDCl$_3$): δ 1.44 (s, 9H), 1.53 (s, 9H), 1.55 (m, 4H), 2.67 (m, 2H), 3.13 (m, 2H), 4.07 (s, 2H), 4.53 (m, 1H), 7.15 (dd, 1H, J=6.3 Hz), 8.11 (dd, 1H, J=6.3 Hz), 8.33 (d, 1H, J=9 Hz), 10.09 (s, 1H).

Using General Procedure B: Reaction of the secondary amine from above and 3-chloropyridine-2-carbaldehyde in CH$_2$Cl$_2$ with NaBH(OAc)$_3$ gave (2-{[4-tert-butoxycarbonylamino-butyl)-(3-chloropyridin-2-ylmethyl)-amino]-methyl}-pyridin-3-yl)-carbamic acid tert-butyl ester as a white foam. Conversion to the HBr salt yielded COMPOUND 244 as a white solid. $^1$H NMR (D$_2$O): 1.62-1.87 (m, 2H), 1.87-2.01 (m, 2H), 3.04 (t, 2H, J=6.6 Hz), 3.30 (t, 2H, J=7.2 Hz), 4.52 (s, 2H), 4.63 (s, 2H), 7.51-7.70 (m, 3H), 8.00 (d, 1H, J=3.9 Hz), 8.12 (d, 1H, J=7.8 Hz), 8.55 (d, 1H, J=4.2 Hz). $^{13}$C NMR (D$_2$O): 21.98, 24.69, 39.42, 53.17, 54.49, 56.21, 126.50, 128.01, 129.08, 131.58 (2 carbons), 132.15, 142.44, 144.65, 146.92, 149.84. ES-MS 320.4 m/z [M+H]$^+$; Anal. Calcd. for (C$_{16}$H$_{22}$N$_5$Cl×3.4HBr×1.4 MeOH): C, 32.69; H, 4.92; N, 10.89; Br, 42.25. Found: C, 32.33; H, 4.88; N, 11.25; Br, 41.92.

Example 249

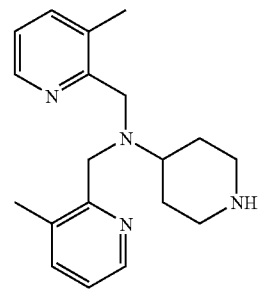

COMPOUND 249: Bis-(3-methyl-pyridin-2-ylmethyl)-piperidin-4-yl-amine

Using General Procedure B, reaction of 4-oxo-piperidine-1-carboxylic acid tert-butyl ester, C-(3-methyl-pyridine-2-yl)-methylamine and NaBH(OAc)$_3$ in CH$_2$Cl$_2$ gave 4-[(3-methyl-pyridin-2-ylmethyl)-amino]-piperidine-1-carboxylic acid tert-butyl ester as a yellow oil. $^1$H NMR (CDCl$_3$) δ 1.45 (s, 9H), 1.89-1.93 (m, 5H), 2.30 (s, 3H), 2.68-2.71 (m, 1H), 2.73-2.87 (m, 2H), 3.90 (s, 2H), 4.02-4.04 (m, 2H), 7.06-7.10 (m, 1H), 7.41-7.44 (m, 1H), 8.38 (d, 1H, J=3.0 Hz).

Using General Procedure B, reaction of 4-[(3-methyl-pyridin-2-ylmethyl)-amino]-piperidine-1-carboxylic acid tert-butyl ester, 3-methyl-pyridine-2-carbaldehyde and NaBH(OAc)$_3$ in CH$_2$Cl$_2$ gave 4-[bis-(3-methyl-pyridin-2-ylmethyl)-amino]-piperidine-1-carboxylic acid tert-butyl ester as a yellow oil. $^1$H NMR (CDCl$_3$) δ 1.45 (s, 9H), 1.84-1.88 (m, 4H), 2.09 (s, 6H), 2.50-2.66 (m, 3H), 3.81 (s, 4H), 4.14-4.17 (m, 2H), 7.05-7.09 (m, 2H), 7.36 (d, 2H, J=9.0 Hz), 8.34 (d, 2H, J=3.0 Hz). Deprotection with TFA using General Procedure F gave COMPOUND 249 as a white solid. $^1$H NMR (CDCl$_3$) δ 1.56-1.70 (m, 2H), 1.75 (s, 1H), 1.90 (d, 2H, J=12.0 Hz), 2.10 (s, 6H), 2.31-2.51 (m, 2H), 2.55-2.58 (m, 1H), 3.12 (d, 2H, J=12.0 Hz), 3.84 (s, 4H), 7.05-7.09 (m, 2H), 7.35 (d, J=7.5 Hz), 8.34 (d, 2H, J=3.0 Hz). $^{13}$C NMR (CDCl$_3$) δ 18.42, 28.86, 47.07, 55.13, 58.17, 122.64, 133.81, 138.29, 146.21, 157.93. ES-MS m/z 311 (M+H). Anal. Calcd. for C$_{19}$H$_{26}$N$_4$.0.3H$_2$O: C, 72.25; H, 8.49; N, 17.74. Found: C, 72.11; H, 8.41; N, 17.58.

Example 250

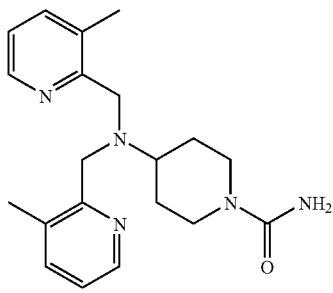

COMPOUND 250 4-[bis-(3-methyl-pyridin-2-yl)-amino]-piperidine-1-carboxylic acid amide To a solution of COMPOUND 249 (0.2036 g, 0.66 mmol) in 2-propanol (7 mL) under Ar was added trimethylsilyl isocyanate (0.124 mL, 0.92 mmol). The reaction was stirred at room temperature for 16 hours, and then concentrated. Purification of the crude material by column chromatography on silica gel (25:1:1 CH$_2$Cl$_2$-MeOH—NH$_4$OH) provided 0.1778 g (76%) of COMPOUND 250 as a white solid. $^1$H NMR (CDCl$_3$) δ 1.62-1.70 (m, 3H), 1.90-1.94 (m, 2H), 2.09 (s, 6H), 2.68 (t, 2H, J=12.0 Hz), 3.82 (s, 4H), 4.00 (d, 2H, J=12.0 Hz), 4.43 (s, 2H), 7.07-7.11 (m, 2H), 7.37 (d, 2H, J=6.0 Hz), 8.34 (d, 2H, J=3.0 Hz). $^{13}$C NMR (CDCl$_3$) δ 16.97, 25.94, 43.44, 53.59, 56.28, 121.42, 132.41, 137.04, 144.89, 156.12, 156.81. ES-MS m/z 377 (M+Na$^+$). Anal. Calcd. for C$_{20}$H$_{27}$N$_5$O.0.13CH$_2$Cl$_2$: C, 66.31; H, 7.54; N, 19.21. Found: C, 66.33; H, 7.69; N, 19.12.

Example 251

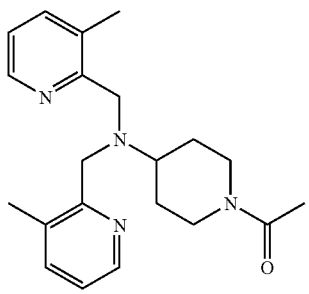

COMPOUND 251: 1-{4-[bis-(3-methyl-pyridin-2-ylmethyl)-amino]-piperidin-1-yl}-ethanone Using General Procedure B, to a solution of COMPOUND 249 (0.1331 g, 0.43 mmol) in CH$_3$CN (5 mL) was added Ac$_2$O (0.05 mL, 0.51 mmol), Et$_3$N (0.09 mL, 0.65 mmol), and KI (0.0116 g, 0.04 mmol). Purification of the crude material by column chromatography on silica gel (50:1:1 CH$_2$Cl$_2$-MeOH—NH$_4$OH) provided 83.5 mg (53%) of COMPOUND 251 as a white solid. $^1$H NMR (CDCl$_3$) δ 1.53-1.69 (m, 2H), 1.78-1.85 (m, 2H), 2.08 (s, 9H), 2.35 (t, 1H, J=13.0 Hz), 2.72 (t, 1H, J=12.0 Hz), 2.91 (t, 1H, J=12.0 Hz), 3.73-3.90 (m, 5H), 4.69 (d, 1H, J=24.0 Hz), 7.06-7.11 (m, 2H), 7.36 (d, 2H, J=9.0 Hz), 8.35 (d, 2H, J=3.0 Hz). $^{13}$C NMR (CDCl$_3$) δ 18.35, 21.86, 27.09, 28.19, 42.05, 46.79, 54.99, 57.78, 122.82, 133.77, 138.43, 146.31, 157.49, 169.14. ES-MS m/z 353 (M+H). Anal. Calcd. for C$_{21}$H$_{28}$N$_4$O.H$_2$O: C, 69.43; H, 8.10; N, 15.42. Found: C, 69.52; H, 7.82; N, 15.28.

Example 252

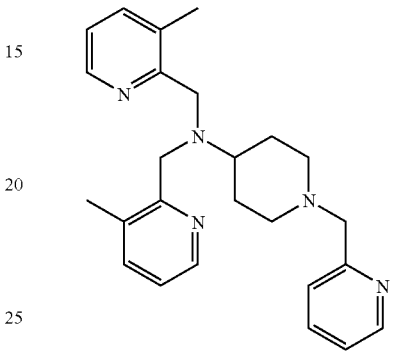

COMPOUND 252: bis-(3-methyl-pyridin-2-ylmethyl)-(1-pyridin-2-ylmethyl-piperidin-4-yl)-amine Using General Procedure B, reaction of COMPOUND 249, pyridine-2-carboxaldehyde and NaBH(OAc)$_3$ in CH$_2$Cl$_2$ gave COMPOUND 252 as an amber solid. $^1$H NMR (CDCl$_3$) δ 1.84-1.87 (m, 4H), 1.92-2.00 (m, 2H), 2.09 (s, 6H), 2.45-2.50 (m, 1H), 2.95 (d, 2H, J=10.2 Hz), 3.60 (s, 2H), 3.84 (s, 4H), 7.04-7.09 (m, 2H), 7.12-7.17 (m, 1H), 7.33-7.39 (m, 2H), 7.61-7.67 (m, 1H), 8.34 (d, 2H, J=3.0 Hz), 8.55 (d, 1H, J=6.0 Hz). $^{13}$C NMR (CDCl$_3$) δ 18.39, 27.28, 54.32, 55.20, 57.77, 64.99, 122.26, 122.61, 123.50, 133.78, 136.69, 138.26, 146.19, 149.60, 157.92, 159.31. ES-MS m/z 402 (M+H). Anal. Calcd. for C$_{25}$H$_{31}$N$_5$.1.0H$_2$O: C, 71.57; H, 7.93; N, 16.69. Found: C, 71.73; H, 7.99; N, 16.54.

Example 253

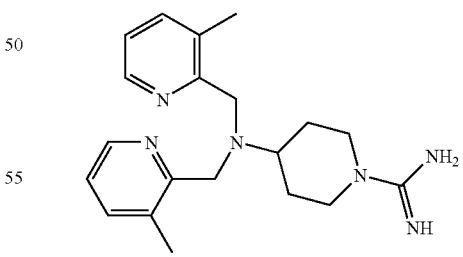

COMPOUND 253: 4-[Bis-(3-methyl-pyridin-2-ylmethyl)-amino]-piperidine-1-carboxamidine (HBr salt)

4-Hydroxypiperidine (0.25 g, 2.5 mmol) and (tert-butoxycarbonylimino-pyrazol-1-yl-methyl)-carbamic acid tert-butyl ester (0.78 g, 2.2 mmol) (Drake, B. et al. *Synthesis* 1994, 6, 579-582) were dissolved in THF (1 mL) and stirred for 1 hour. The solvent was removed under reduced pressure and EtOAc (20 mL) was added. The organic was washed with an aqueous solution of 15% NaOH (5×15 mL), dried (Na$_2$SO$_4$) and concentrated under reduced pressure to afford [tert-butoxycarbonylimino-(4-hydroxy-piperidin-1-yl)-methyl]-carbamic acid tert-butyl ester as a white solid (0.47 g, 55%).

A solution of the above alcohol (0.47 g, 1.2 mmol) in CH$_2$Cl$_2$ (6 mL) was treated with molecular sieves (0.60 g), N-methylmorpholine oxide (0.22 g, 1.8 mmol), and TPAP (43 mg, 0.12 mmol). The mixture was stirred for 16 hours and then filtered through silica, washing with an excess of Et$_2$O. The filtrate was then concentrated under reduced pressure to afford, after column chromatography with silica gel (1:1 EtOAc:hexanes), the desired [tert-butoxycarbonylimino-(4-oxo-piperidin-1-yl)-methyl]-carbamic acid tert-butyl ester (0.31 g, 66%). $^1$H NMR (CDCl$_3$) δ 1.50 (s, 18H), 2.59 (t, 4H, J=6.0 Hz), 3.83 (t, 4H, J=6.0 Hz), 10.30 (br, 1H, NH).

Using General Procedure B, reaction of [tert-butoxycarbonylimino-(4-oxo-piperidin-1-yl)-methyl]-carbamic acid tert-butyl ester, C-(3-methylpyridin-2-yl)-methylamine and NaBH(OAc)$_3$ in CH$_2$Cl$_2$ gave (tert-butoxycarbonylimino-{4-[(3-methyl-pyridin-2-ylmethyl)-amino]-piperidin-1-yl}-methyl)-carbamic acid tert-butyl ester as a white solid.

Using General Procedure B, reaction of the above secondary amine, 3-methylpyridine-2-carboxaldehyde and NaBH(OAc)$_3$ in CH$_2$Cl$_2$ (2.0 mL) gave ({4-[bis-(3-methyl-pyridin-2-ylmethyl)-amino]-piperidin-1-yl}-tert-butoxycarbonylimino-methyl)-carbamic acid tert-butyl ester. $^1$H NMR (CDCl$_3$) δ 1.50 (s, 18H), 1.63 (br, 2H), 1.77 (m, 2H), 1.95 (br, 2H), 2.08 (s, 6H), 2.75 (m, 3H), 3.81 (s, 4H), 7.08 (m, 2H), 7.37 (d, 2H, J=7.5 Hz), 8.35 (d, 2H, J=3.0 Hz), 10.10 (br, 1H, NH). Conversion to the HBr salt using General Procedure D gave COMPOUND 253 as a white solid. $^1$H NMR (D$_2$O) δ 1.74 (dq, 2H, J=12.3, 3.6 Hz), 2.10 (d, 2H, J=11.7 Hz), 2.48 (s, 6H), 3.01 (m, 3H), 3.91 (d, 2H, J=13.5 Hz), 4.33 (s, 4H), 7.79 (m, 2H), 8.29 (d, 2H, J=7.8 Hz), 8.52 (d, 2H, J=5.4 Hz). $^{13}$C NMR (D$_2$O) δ 17.30 (2C), 27.15 (2C), 45.53 (2C), 51.02 (2C), 59.66, 126.13 (2C), 137.80 (2C), 138.92 (2C), 148.51 (2C), 151.09 (2C), 156.27. ES-MS m/z 353 (M+H). Anal. Calcd. for C$_{20}$H$_{28}$N$_6$·3.3HBr·2.8H$_2$O: C, 35.86; H, 5.55; N, 12.54; Br, 39.36. Found: C, 35.85; H, 5.21; N, 12.35; Br, 39.50.

Example 254

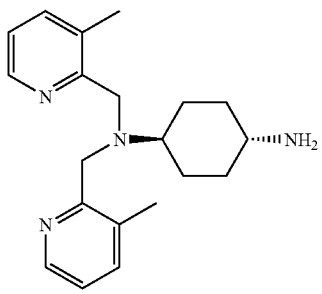

COMPOUND 254: N,N-Bis-(3-methyl-pyridin-2-ylmethyl)-cyclohexane-1,4-diamine (HBr salt)

Using General Procedure B, reaction of 3-methyl-pyridine-2-carbaldehyde and (4-Amino-cyclohexyl)-carbamic acid tert-butyl ester in CH$_2$Cl$_2$ with NaBH(OAc)$_3$ gave the tertiary amine as a colorless oil. Conversion to the HBr salt using General Procedure D gave COMPOUND 254 as a white powder. $^1$H NMR (D$_2$O) δ 1.38-1.59 (m, 4H), 2.08-2.14 (m, 4H), 2.49 (s, 6H), 2.73 (tt, 1H, J=7.8, 2.3 Hz), 3.16 (tt, 1H, J=8.1, 2.3 Hz), 4.36 (s, 4H), 7.81 (t, 2H, J=6.0 Hz), 8.32 (d, 2H, J=6.0 Hz), 8.54 (d, 2H, J=5.1 Hz). $^{13}$C NMR (D$_2$O) δ 15.85, 24.42, 27.96, 48.18, 49.67, 57.22, 58.86, 124.51, 136.25, 137.12, 145.83, 147.06, 149.75. ES-MS m/z 325 [M+H]$^+$. Anal. Calcd. for C$_{20}$H$_{28}$N$_4$·3.7HBr·2.6H$_2$O: C, 36.16; H, 5.64; N, 7.84; Br, 44.75. Found: C, 36.18; H, 5.35; N, 7.78; Br, 44.82.

Example 255

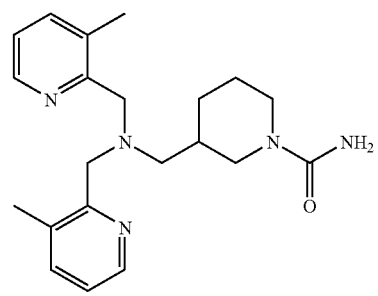

COMPOUND 255: 3-{[Bis-(3-methyl-pyridin-2-ylmethyl)-amino]-methyl}-piperidine-1-carboxylic acid amide (HBr salt)

A solution of Bis-(3-methyl-pyridin-2-ylmethyl)-piperidin-3-ylmethyl-amine) (0.16 g, 0.50 mmol) in anhydrous i-PrOH (3.3 mL) was treated with trimethylsilylisocyanate (94 μL, 0.69 mmol) for 16 h at room temperature. The solvent was then removed under reduced pressure to afford, after column chromatography with silica gel (3:0.5:96.5 MeOH:NH$_4$OH:CH$_2$Cl$_2$), 3-{[Bis-(3-methyl-pyridin-2-ylmethyl)-amino]-methyl}-piperidine-1-carboxylic acid amide (0.12 g, 67%). Conversion to the HBr salt using General Procedure D gave COMPOUND 255 as a white solid. $^1$H NMR (D$_2$O) δ 1.13 (m, 1H), 1.35 (m, 1H), 1.51 (m, 1H), 1.64 (m, 1H), 1.76 (m, 1H), 2.50 (s, 6H), 2.52 (m, 2H), 2.59 (m, 1H), 2.92 (td, 1H, J=12.0, 3.3 Hz), 3.45 (dt, 1H, J=13.2, 4.2 Hz), 3.74 (br d, 1H, J=13.2 Hz), 4.23 (s, 4H), 7.87 (m, 2H), 8.37 (d, 2H, J=7.8 Hz), 8.61 (d, 1H, J=5.4 Hz). $^{13}$C NMR (D$_2$O) δ 17.42 (2C), 23.76, 28.58, 33.69, 45.58, 47.77, 54.77 (2C), 58.96, 126.28 (2C), 138.37 (2C), 139.03 (2C), 148.83 (2C), 150.57 (2C), 160.50. ES-MS m/z 368 (M+H). Anal. Calcd. for C$_{21}$H$_{29}$N$_5$·3.1HBr·2.7H$_2$O: C, 37.82; H, 5.67; N, 10.50; Br, 37.14. Found: C, 37.89; H, 5.90; N, 10.45; Br, 37.14.

Example 256

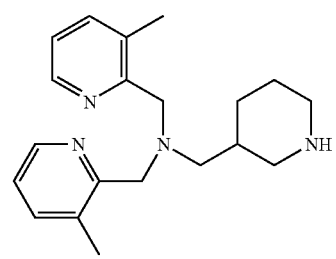

COMPOUND 256: Bis-(3-methyl-pyridin-2-ylmethyl)-piperidin-3-ylmethyl-amine (HBr salt)

Using General Procedure B, reaction of 3-formylpiperidine-1-carboxylic acid tert-butyl ester (Wacker, D. A. et al. *Bioorg. Med. Chem. Lett.* 2002, 12, 1785-1790), C-(3-methylpyridin-2-yl)-methylamine and NaBH(OAc)$_3$ in CH$_2$Cl$_2$ gave 3-{[(3-methyl-pyridin-2-ylmethyl)-amino]-methyl}-piperidine-1-carboxylic acid tert-butyl ester as a white solid.

Using General Procedure B, reaction of the above secondary amine, 3-methylpyridine-2-carboxaldehyde and NaBH(OAc)$_3$ in CH$_2$Cl$_2$ gave 3-{[Bis-(3-methyl-pyridin-2-ylmethyl)-amino]-methyl}-piperidine-1-carboxylic acid tert-butyl ester. $^1$H NMR (CDCl$_3$) δ 0.67 (m, 1H), 1.31 (m, 1H), 1.44 (s, 9H), 1.48 (br, 2H), 1.60 (br, 1H), 2.17 (s, 6H), 2.38 (m, 2H), 2.42 (br, 2H), 3.63 (br d, 2H), 3.83 (br, 4H), 7.10 (m, 2H), 7.40 (d, 2H, J=7.5 Hz), 8.36 (d, 2H, J=3.0 Hz). Deprotection with TFA using General Procedure F gave Bis-(3-methyl-pyridin-2-ylmethyl)-piperidin-3-ylmethyl-amine. Conversion to the HBr salt using General Procedure D gave COMPOUND 256 as a white solid. $^1$H NMR (D$_2$O) δ 1.10 (m, 1H), 1.60 (m, 1H), 1.86 (m, 1H), 1.92 (m, 1H), 2.04 (m, 1H), 2.49 (s, 6H), 2.51 (m, 1H), 2.59 (m, 2H), 2.80 (td, 1H, J=12.9, 2.9 Hz), 3.36 (br t, 2H, J=15.0 Hz), 4.23 (s, 4H), 7.88 (m, 2H), 8.38 (d, 2H, J=7.8 Hz), 8.61 (d, 1H, J=5.1 Hz). $^{13}$C NMR (D$_2$O) δ 17.67 (2C), 21.82, 27.08, 31.84, 44.54, 47.40, 54.59 (2C), 59.00, 126.46 (2C), 138.54 (2C), 139.17 (2C), 149.05 (2C), 150.16 (2C). ES-MS m/z 325 (M+H). Anal. Calcd. for C$_{20}$H$_{28}$N$_4$.3.2HBr.2.6H$_2$O: C, 38.12; H, 5.82; N, 8.89; Br, 40.57. Found: C, 38.30; H, 6.02; N, 8.57; Br, 40.54.

Example 257

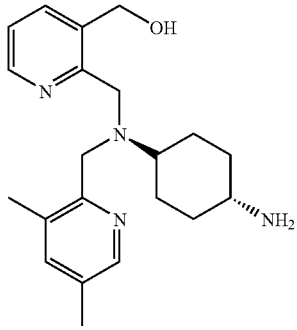

COMPOUND 257: N-(3,5-Dimethyl-pyridin-2-ylmethyl)-N-(3-hydroxymethyl-pyridin-2-ylmethyl)-trans-cyclohexane-1,4-diamine (HBr salt)

To a stirred solution of trans-(4-amino-cyclohexyl)-carbamic acid tert-butyl ester (300 mg, 1.4 mmol) and 3,5-dimethyl-pyridine-2-carbaldehyde (180 mg, 1.3 mmol) in anhydrous THF (1.3 mL) was added K$_2$CO$_3$ powder (180 mg, 1.3 mmol). The mixture was stirred for 3 h at room temperature, under a N$_2$ atmosphere. NaBH$_4$ (50 mg, 1.3 mmol) was added and stirring was continued for 1 h. The reaction was quenched with saturated NaHCO$_3$ solution (10 mL) and extracted with CH$_2$Cl$_2$ (3×20 mL). The organic layers were combined, dried over Na$_2$SO$_4$, and concentrated. Purification of the resultant milky oil by column chromatography (CH$_2$Cl$_2$/MeOH/NH$_4$OH, 50:1:1) gave the desired secondary amine (130 mg, 30%) as a clear oil.

Using General Procedure B: Reaction of {trans-4-[(3,5-dimethyl-pyridin-2-ylmethyl)-amino]-cyclohexyl}-carbamic acid tert-butyl ester and 3-(tert-butyl-dimethylsiloxymethyl)-pyridine-2-carbaldehyde in CH$_2$Cl$_2$ (4 mL) with NaBH(OAc)$_3$ gave the crude material. Deprotection with 6 N HCl gave the amine as a white foamy solid. Conversion to the HBr salt using General Procedure D gave COMPOUND 257 as a white solid. $^1$H NMR (D$_2$O) δ 1.33-1.62 (m, 4H), 2.06-2.13 (m, 4H), 2.40 (s, 3H), 2.41 (s, 3H), 2.74 (t br, 1H, J=11.4 Hz), 3.14 (t br, 1H, J=11.4 Hz), 4.20 (s, 2H), 4.35 (s, 2H), 4.84 (s, 2H), 7.89 (dd, 1H, J=7.8, 5.1 Hz), 8.10 (s, 1H), 8.32 (s, 1H), 8.48 (d, 1H, J=7.8 Hz), 8.61 (d, 1H, J=5.1 Hz). $^{13}$C NMR (D$_2$O) δ 17.05, 17.44, 25.86 (2), 29.48 (2), 49.67, 50.68, 51.02, 59.43, 60.73, 126.55, 136.72, 137.44, 138.30, 139.13, 140.83, 145.85, 148.11, 148.86, 151.63. ES-MS m/z 355 (M+H). Anal. Calcd. for C$_{21}$H$_{30}$N$_4$O.2.9HBr.1.8H$_2$O: C, 40.58; H, 5.92; N, 9.01; Br, 37.28. Found: C, 40.28; H, 6.04; N, 8.79; Br, 37.52.

Example 258

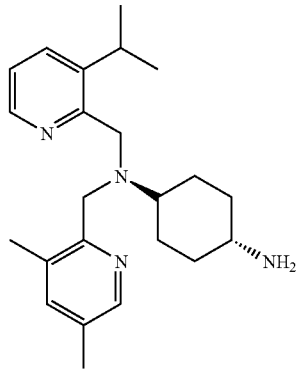

COMPOUND 258: N-(3,5-Dimethyl-pyridin-2-ylmethyl)-N-(3-isopropyl-pyridin-2-ylmethyl)-trans-cyclohexane-1,4-diamine (HBr salt)

Using General Procedure B: Reaction of {trans-4-[(3,5-dimethyl-pyridin-2-ylmethyl)-amino]-cyclohexyl}-carbamic acid tert-butyl ester and 3-isopropyl-pyridine-2-carbaldehyde in CH$_2$Cl$_2$ with NaBH(OAc)$_3$ gave the desired amine as a white solid. Conversion to the HBr salt using General Procedure D gave COMPOUND 258 as an off-white solid. $^1$H NMR (D$_2$O) δ 1.27 (d, 6H, J=7.0 Hz), 1.37-1.65 (m, 4H), 2.09-2.16 (m, 4H), 2.44 (s, 3H), 2.47 (s, 3H), 2.75 (t br, 1H, J=11.4 Hz), 3.16 (t br, 1H, J=11.4 Hz), 3.32 (h, 1H, J=7.0 Hz), 4.28 (s, 2H), 4.39 (s, 2H), 7.90 (dd, 1H, J=7.8, 5.1 Hz), 8.17 (s, 1H), 8.40 (s, 1H), 8.50 (d, 1H, J=7.8 Hz), 8.57 (d, 1H, J=5.1 Hz). $^{13}$C NMR (D$_2$O) δ 17.22, 17.48, 22.15 (2), 25.97 (2), 28.28, 29.54 (2), 49.75, 50.31, 50.76, 60.49, 126.60, 137.17, 137.69, 138.19, 138.80, 144.83, 147.32, 148.03, 149.31, 150.12. ES-MS m/z 367 (M+H). Anal. Calcd. for C$_{23}$H$_{34}$N$_4$.2.9HBr.1.7H$_2$O: C, 43.72; H, 6.43; N, 8.87; Br, 36.68. Found: C, 43.94; H, 6.40; N, 8.48; Br, 36.43.

Example 259

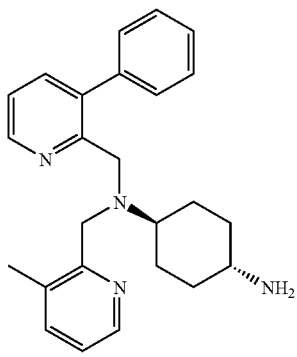

COMPOUND 259: N-(3-methyl-pyridine-2-ylmethyl)-N-(3-phenyl-pyridine-2-ylmethyl)-cyclohexane-1,4-diamine (HBr salt)

Using General Procedure B: Reaction of 3-phenyl-2-pyridinecarboxaldehyde and (4-amino-cyclohexyl)-carbamic acid tert-butyl ester in MeOH with NaBH$_4$ gave {4-[(3-phenyl-pyridin-2-ylmethyl)-amino]-cyclohexyl}-carbamic acid tert-butyl ester as a pale yellow oil. $^1$H NMR (CDCl$_3$) δ 0.96-1.25 (m, 4H), 1.40 (s, 9H), 1.81 (d, 2H, J=12.3 Hz), 1.92 (d, 2H, J=11.1 Hz), 2.29-2.39 (m, 1H), 2.56 (s, 1H), 3.36 (br s, 1H), 3.83 (s, 2H), 4.08-4.41 (br m, 1H), 7.20 (dd, 1H, J=7.8, 4.8 Hz), 7.30-7.33 (m, 2H), 7.36-7.43 (m, 3H), 7.52 (dd, 1H, J=7.7, 1.5 Hz), 8.53 (dd, 1H, J=4.8, 1.8 Hz).

Using General Procedure B: Reaction of the above amine and 3-methyl-2-pyridinecarboxaldehyde in CH$_2$Cl$_2$ with NaBH(OAc)$_3$ gave {4-[(3-methyl-pyridine-2-ylmethyl)-(3-phenyl-pyridin-2-ylmethyl)-amino]-cyclohexyl}-carbamic acid tert-butyl ester as a pale yellow oil. $^1$H NMR (CDCl$_3$) δ 0.86 (q, 2H, J=10.8 Hz), 1.14 (q, 2H, J=11. Hz), 1.41 (s, 9H), 1.58 (d, 2H, J=11.7 Hz), 1.85 (s, 2H), 1.91 (s, 3H), 2.11 (s, 1H), 2.21 (s, 1H), 3.19 (br s, 1H), 3.80 (s, 2H), 3.84 (s, 2H), 4.23 (br s, 1H), 7.00 (dd, 1H, J=7.4, 5.1 Hz), 7.21-7.30 (m, 7H), 7.49 (dd, 1H, 7.8, 1.5 Hz), 8.25 (d, 1H, J=3.9 Hz), 8.53 (dd, 1H, J=4.8, 1.8 Hz). Conversion to the HBr salt using General Procedure D gave COMPOUND 259 as a pale yellow solid. $^1$H NMR (D$_2$O) δ 1.29-1.48 (m, 4H), 1.90 (d, 2H, J=10.2 Hz), 2.02 (d, 2H, J=9.6 Hz), 2.37 (s, 3H), 2.66 (br t, 1H, J=8.1 Hz), 3.09 (br s, 1H), 4.12 (s, 2H), 4.35 (s, 2H), 7.42 (d, 2H, J=4.5 Hz), 7.59 (s, 3H), 7.81 (t, 1H, J=6.6 Hz), 8.01 (t, 1H, J=6.3 Hz), 8.28 (d, 1H, J=7.8 Hz), 8.45 (d, 1H, J=7.8 Hz), 8.51 (d, 1H, J=5.7 Hz), 8.77 (d, 1H, J=5.7 Hz). $^{13}$C NMR (D$_2$O) δ 14.56, 17.18, 25.80, 29.46, 49.67, 50.80, 51.86, 60.40, 126.08, 126.54, 129.68, 130.35, 133.97, 137.79, 138.70, 140.93, 141.18, 148.35, 148.41, 150.54, 151.18. ES-MS m/z 387 [M+H]$^+$. Anal. Calcd. for C$_{25}$H$_{30}$N$_4$.3.3HBr.2.2CH$_3$OH: C, 45.12; H, 5.86; N, 7.74; Br, 36.42. Found: C, 45.22; H, 5.69; N, 7.97; Br, 36.19.

Example 260

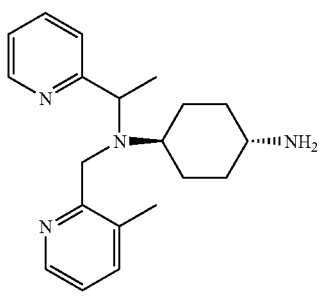

COMPOUND 260: N-(3-methyl-pyridin-2-ylmethyl)-N-(1-pyridin-2-yl-ethyl)-cyclohexane-1,4-diamine (HBr salt)

Using General Procedure B: Reaction of 1-pyridin-2-yl-ethanone and (4-Amino-cyclohexyl)-carbamic acid tert-butyl ester (Ducruet, A P et al. *Bioorg. Med. Chem.* 2000, 8, 1451-1466) in CH$_2$Cl$_2$ (30 mL) with NaBH(OAc)$_3$ gave the secondary amine as a colorless oil. $^1$H NMR (CDCl$_3$) δ 0.97-1.03 (m, 2H), 1.19-1.27 (m, 3H), 1.37 (d, 3H, J=6.0 Hz), 1.41 (s, 9H), 1.74-1.80 (m, 1H), 1.90-2.01 (m, 3H), 2.20-2.32 (m, 1H), 3.35 (br, 1H), 4.03 (q, 1H, J=6.0 Hz), 4.29 (br, 1H), 7.15 (dd, 1H, J=6.0, 3.0 Hz), 7.28 (dd, 1H, J=6.0, 3.0 Hz), 7.63 (t, 1H, J=6.0 Hz), 8.54 (d, 1H, J=6.0 Hz).

Using General Procedure B: Reaction of 3-methyl-pyridine-2-carbaldehyde and [4-(1-pyridin-2-yl-ethylamino)-cyclohexyl]-carbamic acid tert-butyl ester in CH$_2$Cl$_2$ with NaBH(OAc)$_3$ gave the tertiary amine as a colorless oil. Conversion to the HBr salt using General Procedure D gave COMPOUND 260 as a white powder. $^1$H NMR (D$_2$O) δ 1.24-1.43 (m, 2H), 1.47 (d, 3H, J=6.6 Hz), 1.57-1.73 (m, 2H), 1.98-2.19 (m, 4H), 2.62 (s, 3H), 2.71 (tt, 1H, J=10.2, 3.0 Hz), 3.16 (tt, 1H, J=8.1, 3.6 Hz), 3.29-3.32 (m, 1H), 4.46 (A part of AB, 1H, J=19.5 Hz), 4.58 (B part of AB, 1H, J=19.5, Hz), 4.23-4.33 (m, 2H), 4.82 (q, 1H, J=6.6 Hz), 7.93 (t, 1H, J=6.0 Hz), 8.09 (t, 1H, J=6.9 Hz), 8.40 (t, 2H, J=9.3 Hz), 8.67 (td, 1H, J=7.8, 1.5 Hz), 8.92 (dd, 2H, J=16.8 Hz). $^{13}$C NMR (D$_2$O) δ 16.93, 19.14, 24.79, 28.01, 29.22, 29.46, 46.70, 49.35, 49.58, 49.67, 59.15, 125.81, 127.00, 136.64, 138.05, 142.43, 144.97, 148.36, 148.57, 153.38, 156.63. ES-MS m/z 325 [M+H]$^+$. Anal. Calcd. for C$_{20}$H$_{28}$N$_4$.3.7HBr.2.6H$_2$O: C, 35.82; H, 5.55; N, 8.35; Br, 44.08. Found: C, 35.89; H, 5.41; N, 8.31; Br, 43.95.

Example 261

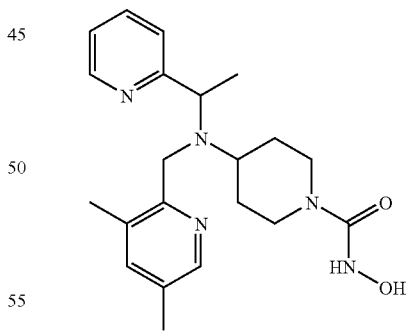

COMPOUND 261: 4-[(3,5-Dimethyl-pyridin-2-ylmethyl)-(1-pyridin-2-yl-ethyl)-amino]-piperidine-1-carboxylic acid hydroxyamide Using General Procedure B: Reaction of 1-Pyridin-2-yl-ethylamine and 1-Boc-4-piperidone with NaBH(OAc)$_3$ in CH$_2$Cl$_2$ gave 4-(1-Pyridin-2-yl-ethylamino)-piperidine-1-carboxylic acid tert-butyl ester as a colorless oil.

217

Using General Procedure B: Reaction of 4-(1-Pyridin-2-yl-ethylamino)-piperidine-1-carboxylic acid tert-butyl ester and 3,5-dimethyl-pyridine-2-carboxaldehyde with NaBH(OAc)$_3$ in CH$_2$Cl$_2$ gave 4-[(3,5-Dimethyl-pyridin-2-ylmethyl)-(1-pyridin-2-yl-ethyl)-amino]-piperidine-1-carboxylic acid tert-butyl ester as a white solid. Deprotection with TFA using General Procedure F gave (3,5-dimethyl-pyridin-2-ylmethyl)-piperidin-4-yl-(1-pyridin-2-yl-ethyl)-amine as a pale yellow oil.

To a solution of (3,5-Dimethyl-pyridin-2-ylmethyl)-piperidin-4-yl-(1-pyridin-2-yl-ethyl)-amine (0.124 g, 0.38 mmol) in dry THF (4 mL) was added N-(phenoxycarbonyl)hydroxylamine (Stewart, A. O. et al. *J. Org. Chem.* 1992, 57, 5020-5023) (0.116 g, 0.76 mmol) and the resultant solution was stirred at 60° C. overnight. The mixture was cooled to room temperature and concentrated. Purification of the crude material by radial chromatography on silica gel (1 mm plate, 15:1:1 CH$_2$Cl$_2$-MeOH—NH$_4$OH) provided 59 mg (38%) of COMPOUND 261 as a white solid. $^1$H NMR (CDCl$_3$) δ 0.97-1.02 (m, 1H), 1.39-1.47 (m, 3H), 1.61-1.67 (m, 3H), 1.83-1.86 (m, 1H), 2.27 (s, 3H), 2.28 (s, 3H), 2.53-2.61 (m, 1H), 2.71-2.80 (m, 1H), 2.92-3.00 (m, 1H), 3.79-3.99 (m, 4H), 6.48-6.85 (m, 2H), 7.11-7.15 (m, 1H), 7.23 (br s, 1H), 7.34-7.40 (m, 1H), 7.58-7.63 (m, 1H), 8.19 (br s, 1H), 8.51 (d, 1H, J=3.9 Hz); $^{13}$C NMR (CDCl$_3$) δ 16.42, 18.31, 18.68, 30.14, 30.52, 44.12, 44.18, 51.88, 55.29, 58.52, 122.25, 123.99, 132.19, 133.15, 136.48, 139.60, 146.63, 148.84, 155.08, 161.12, 162.90; ES-MS m/z 384 (M+H). Anal. Calcd. For C$_{21}$H$_{29}$N$_5$O$_2$.0.1CH$_2$Cl$_2$.1.0H$_2$O: C, 61.81; H, 7.67; N, 17.08. Found: C, 62.17; H, 7.33; N, 16.74.

Example 262

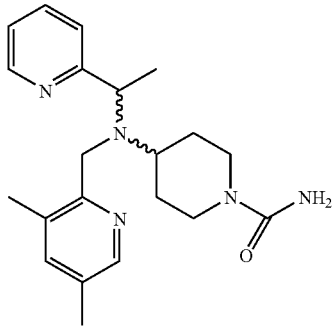

COMPOUND 262: 4-[(3,5-Dimethyl-pyridin-2-ylmethyl)-(1-pyridin-2-yl-ethyl)-amino]-piperidine-1-carboxylic acid amide To a solution of (3,5-Dimethyl-pyridin-2-ylmethyl)-piperidin-4-yl-(1-pyridin-2-yl-ethyl)-amine (194 mg, 0.60 mmol) in 2-propanol (3 mL) was added trimethylsilyl-isocyanate (85 μL, 0.63 mmol). The resultant solution was stirred at room temperature overnight then concentrated. Purification of the crude material by column chromatography on silica gel (10:1:1 CH$_2$Cl$_2$-MeOH—NH$_4$OH) gave COMPOUND 262 (200 mg, 88%) as a white solid. $^1$H NMR (CDCl$_3$) δ 0.96-1.02 (m, 1H), 1.45-1.49 (m, 4H), 1.52-1.86 (m, 2H), 2.26 (s, 3H), 2.27 (s, 3H), 2.53-2.62 (m, 1H), 2.71-2.80 (m, 1H), 2.89-2.96 (m, 1H), 3.77-3.97 (m, 5H), 4.37 (s, 2H), 7.10-7.25 (m, 2H), 7.39 (d, 1H, J=7.8 Hz), 7.57-7.62 (m, 1H), 8.19 (br s, 1H), 8.51 (d, 1H, J=3.9 Hz); $^{13}$C NMR (CDCl$_3$) δ 13.61, 15.79, 16.16, 27.90, 28.13, 42.22, 42.27, 49.35, 52.87, 55.61, 119.60, 121.54, 129.51, 130.57, 133.80, 136.93, 144.14, 146.25, 152.72, 156.04, 160.52; ES-MS m/z 368 (M+H). Anal. Calcd. For C$_{21}$H$_{29}$N$_5$O.0.8H$_2$O: C, 66.05; H, 8.08; N, 18.34. Found: C, 65.9281; H, 7.73; N, 18.18.

Example 263

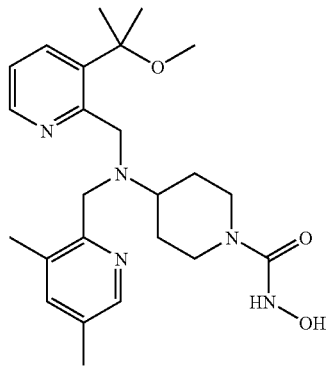

COMPOUND 263: 4-{(3,5-Dimethyl-pyridin-2-ylmethyl)-[3-(1-methoxy-1-methyl-ethyl)-pyridin-2-ylmethyl]-amino}-piperidine-1-carboxylic acid hydroxyamide Using General Procedure B: Reaction of 4-[(3,5-Dimethyl-pyridin-2-ylmethyl)-amino]-piperidine-1-carboxylic acid tert-butyl ester and 3-(1-Methoxy-1-methyl-ethyl)-pyridine-2-carbaldehyde with NaBH(OAc)$_3$ in CH$_2$Cl$_2$ gave a white solid. Deprotection with TFA using General Procedure F gave (3,5-Dimethyl-pyridin-2-ylmethyl)-[3-(1-methoxy-1-methyl-ethyl)-pyridin-2-ylmethyl]-piperidin-4-yl-amine as a pale yellow oil.

To a solution of (3,5-Dimethyl-pyridin-2-ylmethyl)-[3-(1-methoxy-1-methyl-ethyl)-pyridin-2-ylmethyl]-piperidin-4-yl-amine (0.245 g, 0.64 mmol) in dry THF (4 mL) was added N-(phenoxycarbonyl)hydroxylamine (0.193 g, 1.26 mmol) and the resultant solution was stirred at 60° C. overnight. The mixture was cooled to room temperature and concentrated. Purification of the crude material by column chromatography on silica gel (10:1:1 CH$_2$Cl$_2$-MeOH—NH$_4$OH) provided 177 mg (54%) of COMPOUND 263 as a white solid. $^1$H NMR (CDCl$_3$) δ 1.52-1.74 (m, 8H), 1.94-1.98 (m, 2H), 2.10 (s, 3H), 2.25 (s, 3H), 2.67 (t, 2H, J=12.6 Hz), 2.77-2.95 (m, 4H), 3.93-4.02 (m, 4H), 4.16 (s, 2H), 6.80 (s, 1H), 7.13-7.18 (m, 2H), 7.62 (d, 1H, J=8.1 Hz), 8.14 (s, 1H), 8.49 (dd, 1H, J=4.5, 1.5 Hz); $^{13}$C NMR (CDCl$_3$) δ 18.31, 18.54, 27.87, 28.29, 44.05, 50.79, 54.01, 54.53, 54.86, 58.20, 122.10, 131.99, 133.18, 135.73, 139.25, 139.97, 146.56, 147.36, 161.04; ES-MS m/z 442 (M+H). Anal. Calcd. For C$_{24}$H$_{35}$N$_5$O$_3$.0.8CH$_2$Cl$_2$: C, 58.46; H, 7.24; N, 13.75. Found: C, 58.40; H, 7.20; N, 13.89.

Example 264

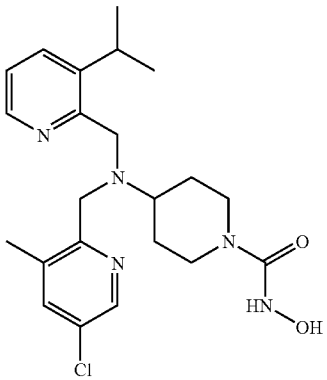

COMPOUND 264: 4-[(5-Chloro-3-methyl-pyridin-2-ylmethyl)-(3-isopropyl-pyridin-2-ylmethyl)-amino]-piperidine-1-carboxylic acid hydroxyamide Using General Procedure B: Reaction of 4-[(5-Chloro-3-methyl-pyridin-2-ylmethyl)-amino]-piperidine-1-carboxylic acid tert-butyl ester and 3-Isopropyl-pyridine-2-carbaldehyde with NaBH(OAc)$_3$ in CH$_2$Cl$_2$ gave 4-[(5-Chloro-3-methyl-pyridin-2-ylmethyl)-(3-isopropyl-pyridin-2-ylmethyl)-amino]-piperidine-1-carboxylic acid tert-butyl ester as a white solid. Deprotection with TFA using General Procedure F gave (5-Chloro-3-methyl-pyridin-2-ylmethyl)-(3-isopropyl-pyridin-2-ylmethyl)-piperidin-4-yl-amine as a colorless oil.

To a solution of (5-Chloro-3-methyl-pyridin-2-ylmethyl)-(3-isopropyl-pyridin-2-ylmethyl)-piperidin-4-yl-amine (0.263 g, 0.71 mmol) in dry THF (7 mL) was added N-(phenoxycarbonyl)hydroxylamine (0.216 g, 1.41 mmol) and the resultant solution was stirred at 60° C. overnight. The mixture was cooled to room temperature and concentrated. Purification of the crude material by column chromatography on silica gel (10:1:1 CH$_2$Cl$_2$-MeOH—NH$_4$OH) provided 241 mg (64%) of COMPOUND 264 as a white solid. $^1$H NMR (CDCl$_3$) δ 0.99 (d, 6H, J=6.9 Hz), 1.60-1.66 (m, 2H), 1.92 (d, 2H, J=11.1 Hz), 2.14 (s, 3H), 2.66-2.88 (m, 4H), 3.78 (s, 2H), 3.81 (s, 2H), 4.04 (d, 2H, J=12.9 Hz), 6.65 (br s, 1H), 6.81 (br s, 1H), 7.16 (dd, 1H, J=7.8, 4.8 Hz), 7.42 (d, 1H, J=1.5 Hz), 7.52 (dd, 1H, J=7.8, 1.5 Hz), 8.32-8.34 (m, 2H); $^{13}$C NMR (CDCl$_3$) δ 19.64, 24.80, 28.47, 28.74, 45.43, 55.31, 58.83, 124.66, 132.29, 135.42, 136.61, 139.11, 145.69, 146.12, 147.20, 156.93, 162.45; ES-MS m/z 432 ($^{35}$Cl) & 434 ($^{37}$Cl) (M+H). Anal. Calcd. For C$_{22}$H$_{30}$N$_5$O$_2$Cl.0.2CH$_2$Cl$_2$.0.5H$_2$O: C, 58.22; H, 6.91; N, 15.29; Cl, 10.84. Found: C, 58.51; H, 6.68; N, 15.29; Cl, 10.55.

Example 265

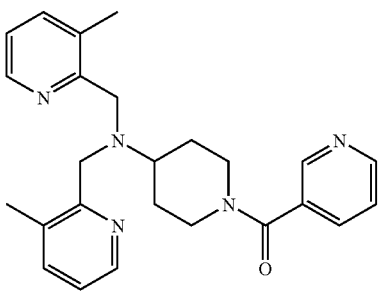

COMPOUND 265: {4-[Bis-(3-methyl-pyridin-2-ylmethyl)-amino]-piperidin-1-yl}-pyridin-3-yl-methanone To a solution of COMPOUND 249 (65 mg, 0.21 mmol) in THF (2 mL) was added nicotinoyl chloride hydrochloride (60 mg, 0.34 mmol) followed by DIPEA (0.10 mL, 0.57 mmol). The resultant mixture was stirred at room temperature for 40 minutes. The mixture was treated with 1.0 N NaOH (5 mL) and extracted with CH$_2$Cl$_2$ (4×10 mL). The combined organic extracts were dried (Na$_2$SO$_4$) and concentrated under reduced pressure. Purification of the crude material by radial chromatography on silica gel (1 mm plate, 20:1:1 CH$_2$Cl$_2$-MeOH—NH$_4$OH) provided 75 mg (86%) of COMPOUND 265 as a white solid. $^1$H NMR (CDCl$_3$) δ 1.61-1.75 (m, 2H), 1.90-1.99 (m, 2H), 2.09 (s, 6H), 2.55-3.00 (m, 3H), 3.75-3.90 (m, 5H), 4.75-4.80 (m, 1H), 7.09 (dd, 2H, J=7.5, 4.8 Hz), 7.34-7.39 (m, 3H), 7.75 (dt, 1H, J=6.0, 1.8 Hz), 8.35 (d, 2H, J=4.8 Hz), 8.65 (s, 2H); ES-MS m/z 416 (M+H).

Example 266

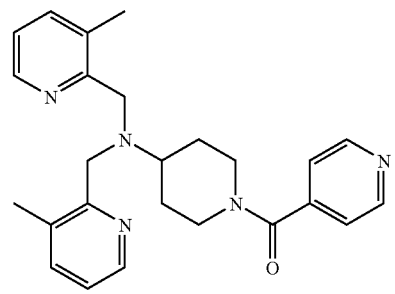

COMPOUND 266: {4-[Bis-(3-methyl-pyridin-2-ylmethyl)-amino]-piperidin-1-yl}-pyridin-4-yl-methanone To a cold (0° C.), stirred, mixture of isonicotinic acid (130 mg, 1.05 mmol) in CH$_2$Cl$_2$ (10 mL) was added DMF (1 mL) followed by oxalyl chloride (0.46 mL, 5.27 mmol). The mixture was warmed to room temperature. After 15 minutes the mixture was concentrated under reduced pressure and provided a white solid. To a solution of COMPOUND 249 (60 mg, 0.19 mmol) in THF (7 mL) was added the white solid from above followed by DIPEA (1.20 mL, 6.88 mmol). The resultant mixture was stirred at room temperature for 2.5 hours then diluted with 1.0 N NaOH (10 mL) and EtOAc (50 mL). The phases were separated and the organic phase was washed with 1.0 N NaOH (3×10 mL) and brine (10 mL), dried (Na$_2$SO$_4$), and concentrated. Purification of the crude material by radial chromatography on silica gel (1 mm plate, 50:1:1 CH$_2$Cl$_2$-MeOH—NH$_4$OH) provided 33 mg (42%) of COMPOUND 266 as a white solid. $^1$H NMR (CDCl$_3$) δ 1.50-1.76 (m, 2H), 1.80-2.04 (m, 2H), 2.09 (s, 6H), 2.57-3.02 (m, 3H), 3.65-3.91 (m, 5H), 4.76-4.84 (m, 1H), 7.09 (dd, 2H, J=7.5, 4.8 Hz), 7.27 (d, 2H, J=5.7 Hz), 7.38 (d, 2H, J=7.5 Hz), 8.35 (d, 2H, J=4.8 Hz), 8.69 (d, 2H, J=5.7 Hz); ES-MS m/z 416 (M+H).

Example 267

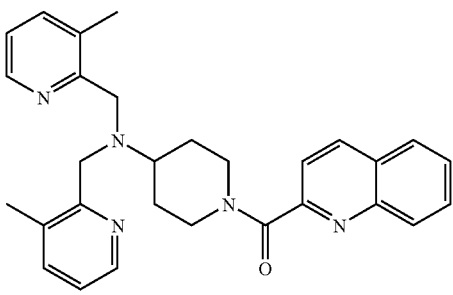

COMPOUND 267: {4-[Bis-(3-methyl-pyridin-2-ylmethyl)-amino]-piperidin-1-yl}-quinolin-2-yl-methanone To a cold (0° C.), stirred, mixture of quinaldic acid (89 mg, 0.52 mmol) in CH$_2$Cl$_2$ (5 mL) was added DMF (0.1 mL) followed by oxalyl chloride (0.22 mL, 2.52 mmol). The mixture was warmed to room temperature. After 15 minutes the mixture was concentrated under reduced pressure and provided a pink solid. To a solution of COMPOUND 249 (62 mg, 0.20 mmol) in THF (10 mL) was added the pink solid from above followed by DIPEA (0.50 mL, 2.87 mmol). The resultant mixture was stirred at room temperature for 2 hours then diluted with 1.0 N NaOH (10 mL) and EtOAc (30 mL). The phases were separated and the organic phase was washed with 1.0 N NaOH (3×10 mL), dried (Na$_2$SO$_4$), and concentrated. Purification of the crude material by radial chromatography on silica gel (1 mm plate, 50:1:1 CH$_2$Cl$_2$-MeOH—NH$_4$OH) provided 56 mg (60%) of COMPOUND 267 as a yellow solid. $^1$H NMR (CDCl$_3$) δ 1.73-2.03 (m, 4H), 2.10 (s, 6H), 2.64-2.86 (m, 2H), 2.97-3.05 (m, 1H), 3.79 (d, 2H, J=12.3 Hz), 3.92 (d, 2H, J=12.3 Hz), 4.09 (d, 1H, J=13.2 Hz), 4.89 (d, 1H, J=13.2 Hz), 7.09 (dd, 2H, J=7.5, 5.1 Hz), 7.37 (d, 2H, J=7.5 Hz), 7.58-7.69 (m, 2H), 7.77 (td, 1H, J=7.5, 1.2 Hz), 7.86 (d, 1H, J=7.8 Hz), 8.10 (d, 1H, J=8.4 Hz), 8.26 (d, 1H, J=8.7 Hz), 8.35 (d, 2H, J=3.6 Hz); ES-MS m/z 466 (M+H).

Example 268

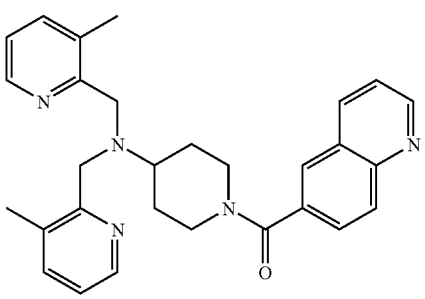

COMPOUND 268: {4-[Bis-(3-methyl-pyridin-2-ylmethyl)-amino]-piperidin-1-yl}-quinolin-6-yl-methanone To a cold (0° C.), stirred, mixture of 6-quinoline carboxylic acid (101 mg, 0.59 mmol) in CH$_2$Cl$_2$ (5 mL) was added DMF (0.5 mL) followed by oxalyl chloride (0.25 mL, 2.87 mmol). The mixture was warmed to room temperature. After 15 minutes the mixture was concentrated under reduced pressure and provided a white solid. To a solution of COMPOUND 249 (68 mg, 0.22 mmol) in THF (10 mL) was added the white solid from above followed by DIPEA (0.60 mL, 3.44 mmol). The resultant mixture was stirred at room temperature for 2.5 hours then diluted with 1.0 N NaOH (10 mL) and EtOAc (40 mL). The phases were separated and the organic phase was washed with 1.0 N NaOH (3×10 mL), dried (Na$_2$SO$_4$), and concentrated. Purification of the crude material by column chromatography on silica gel (20:1:1 CH$_2$Cl$_2$-MeOH—NH$_4$OH) followed by radial chromatography on silica gel (1 mm plate, 100:1:1 CH$_2$Cl$_2$-MeOH—NH$_4$OH) provided 30 mg (29%) of COMPOUND 268 as a yellow solid. $^1$H NMR (CDCl$_3$) δ 1.65-2.03 (m, 4H), 2.10 (s, 6H), 2.64-3.05 (m, 3H), 3.66-3.90 (m, 5H), 4.80-4.88 (m, 1H), 7.10 (dd, 2H, J=7.5, 4.8 Hz), 7.38 (d, 2H, J=7.5 Hz), 7.46 (dd, 1H, J=8.4, 4.2 Hz), 7.72 (dd, 1H, J=8.4, 1.5 Hz), 7.90 (s, 1H), 8.13-8.21 (m, 2H), 8.35 (d, 2H, J=3.6 Hz), 8.97 (d, 1H, J=3.6 Hz); ES-MS m/z 466 (M+H).

Example 269

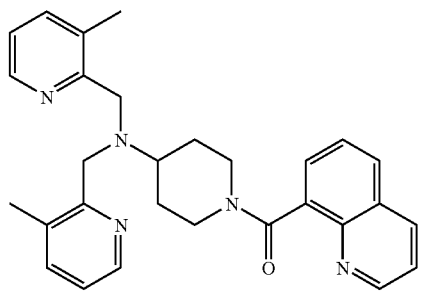

COMPOUND 269: {4-[Bis-(3-methyl-pyridin-2-ylmethyl)-amino]-piperidin-1-yl}-quinolin-8-yl-methanone To a cold (0° C.), stirred, mixture of 8-quinoline carboxylic acid (177 mg, 1.02 mmol) in CH$_2$Cl$_2$ (10 mL) was added DMF (0.5 mL) followed by oxalyl chloride (0.45 mL, 5.16 mmol). The mixture was warmed to room temperature. After 20 minutes the mixture was concentrated under reduced pressure and provided a pink solid. To a solution of COMPOUND 249 (93 mg, 0.30 mmol) in THF (20 mL) was added the pink solid from above followed by DIPEA (1.10 mL, 6.31 mmol). The resultant mixture was stirred at room temperature for 2.5 hours then diluted with 1.0 N NaOH (20 mL) and EtOAc (60 mL). The phases were separated and the organic phase was washed with 1.0 N NaOH (3×10 mL), dried (Na$_2$SO$_4$), and concentrated. Purification of the crude material by column chromatography on silica gel (20:1:1 CH$_2$Cl$_2$-MeOH—NH$_4$OH) followed by radial chromatography on silica gel (1 mm plate, 100:1:1 CH$_2$Cl$_2$-MeOH—NH$_4$OH) provided 36 mg (26%) of COMPOUND 269 as a white foam. $^1$H NMR (CDCl$_3$) δ 1.50-2.00 (m, 4H), 2.09 (s, 6H), 2.62-2.99 (m, 3H), 3.30-3.40 (m, 1H), 3.69-3.98 (m, 4H), 4.99-5.10 (m, 1H), 7.09 (dd, 2H, J=7.5, 4.8 Hz), 7.35-7.45 (m, 3H), 7.52-7.61 (m, 2H), 7.83-7.87 (m, 1H), 8.14-8.18 (m, 1H), 8.32 (d, 2H, J=3.9 Hz), 8.90-8.95 (m, 1H); ES-MS m/z 488 (M+Na).

Example 270

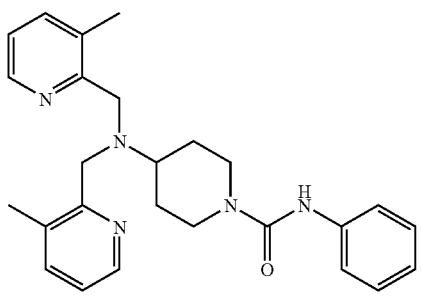

COMPOUND 270: 4-[Bis-(3-methyl-pyridin-2-ylmethyl)-amino]-piperidine-1-carboxylic acid phenylamide To a cold (0° C.), stirred solution of COMPOUND 249 (66 mg, 0.21 mmol) in CH$_2$Cl$_2$ (2 mL) was added phenyl isocyanate (30 μL, 0.28 mmol). After 15 minutes, the cooling bath was removed and the reaction mixture was warmed to room temperature. After an additional 45 minutes, the mixture was concentrated under reduced pressure. Purification of the crude material by radial chromatography on silica gel (1 mm plate, 25:1:1 CH$_2$Cl$_2$-MeOH—NH$_4$OH) provided 84 mg (84%) of COMPOUND 270 as a white solid. $^1$H NMR (CDCl$_3$) δ 1.62-1.78 (m, 2H), 1.95-1.99 (m, 2H), 2.09 (s, 6H), 2.68-2.79 (m, 3H), 3.83 (s, 4H), 4.14 (d, 2H, J=13.5 Hz), 6.39 (br s, 1H), 6.99-7.12 (m, 3H), 7.25-7.39 (m, 6H), 8.34 (d, 2H, J=3.6 Hz); $^{13}$C NMR (CDCl$_3$) δ 18.39, 27.45, 44.86, 54.98, 57.83, 120.41, 122.86, 123.17, 129.13, 133.86, 138.50, 139.80, 146.23, 155.40, 157.50; ES-MS m/z 430 (M+H). Anal. Calcd. For C$_{26}$H$_{31}$N$_5$O.0.5CH$_2$Cl$_2$: C, 67.43; H, 6.83; N, 14.84. Found: C, 67.77; H, 6.99; N, 14.90.

Example 271

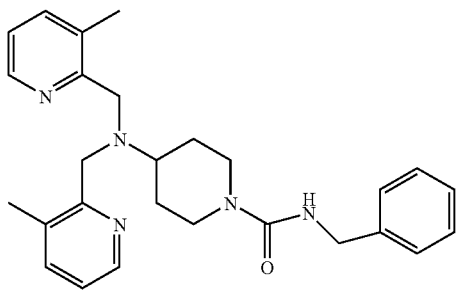

COMPOUND 271: 4-[Bis-(3-methyl-pyridin-2-ylmethyl)-amino]-piperidine-1-carboxylic acid benzylamide To a cold (0° C.), stirred solution of COMPOUND 249 (69 mg, 0.22 mmol) in CH$_2$Cl$_2$ (2 mL) was added benzyl isocyanate (35 μL, 0.28 mmol). After 15 minutes, the cooling bath was removed and the reaction mixture was warmed to room temperature. After an additional 45 minutes, the mixture was concentrated under reduced pressure. Purification of the crude material by radial chromatography on silica gel (1 mm plate, 25:1:1 CH$_2$Cl$_2$-MeOH—NH$_4$OH) provided 93 mg (87%) of COMPOUND 271 as a white solid. $^1$H NMR (CDCl$_3$) δ 1.60-1.71 (m, 2H), 1.88-1.93 (m, 2H), 2.08 (s, 6H), 2.61-2.69 (m, 3H), 3.81 (s, 4H), 4.05 (d, 2H, J=12.9 Hz), 4.42 (d, 2H, J=5.4 Hz), 4.74 (br t, 1H, J=5.4 Hz), 7.08 (dd, 2H, J=7.5, 5.1 Hz), 7.25-7.38 (m, 7H), 8.34 (d, 2H, J=3.6 Hz); $^{13}$C NMR (CDCl$_3$) δ 18.36, 27.35, 44.58, 45.30, 54.99, 57.83, 122.81, 127.47, 128.03, 128.87, 133.82, 138.45, 140.13, 146.20, 157.52, 157.83; ES-MS m/z 444 (M+H). Anal. Calcd. For C$_{27}$H$_{33}$N$_5$O.0.4.CH$_2$Cl$_2$: C, 68.91; H, 7.13; N, 14.66. Found: C, 69.19; H, 7.37; N, 14.64.

Example 272

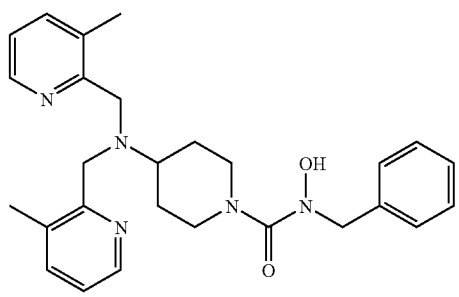

COMPOUND 272: 4-[Bis-(3-methyl-pyridin-2-ylmethyl)-amino]-piperidine-1-carboxylic acid benzyl-hydroxy-amide To a solution of COMPOUND 249 (0.115 g, 0.37 mmol) in toluene (4 mL) was added DIPEA (0.16 mL, 0.92 mmol) followed by phosgene solution (20% in toluene, 0.20 mL, 0.44 mmol). The resultant mixture was stirred at room temperature for 90 minutes then concentrated under reduced pressure. The residue was dissolved in DMF (4 mL) and treated with DIPEA (0.60 mL, 3.44 mmol) followed by N-benzylhydroxylamine hydrochloride (0.194 g, 1.22 mmol) and the resultant mixture was stirred at room temperature overnight. The mixture was concentrated and the residue was partitioned between CH$_2$Cl$_2$ (50 mL) and saturated aqueous NaHCO$_3$ (15 mL). The phases were separated and the aqueous phase was extracted with CH$_2$Cl$_2$ (3×15 mL). The combined organic extracts were dried (Na$_2$SO$_4$) and concentrated. Purification of the crude material by radial chromatography on silica gel (1 mm plate, 25:1:1 CH$_2$Cl$_2$-MeOH—NH$_4$OH) provided 131 mg (74%) of COMPOUND 272 as a white solid. $^1$H NMR (CDCl$_3$) δ 1.64-1.76 (m, 2H), 1.918-1.96 (m, 2H), 2.08 (s, 6H), 2.68-2.79 (m, 3H), 3.81 (s, 4H), 4.20 (d, 2H, J=13.2 Hz), 4.30 (s, 2H), 6.81 (s, 1H), 7.08 (dd, 2H, J=7.5, 4.8 Hz), 7.27-7.38 (m, 7H), 8.32 (d, 2H, J=3.6 Hz); $^{13}$C NMR (CDCl$_3$) δ 18.35, 27.54, 46.12, 54.86, 57.74, 59.70, 122.87, 127.94, 128.68, 129.35, 133.88, 136.61, 138.59, 146.15, 157.28, 164.68; ES-MS m/z 460 (M+H).

Anal. Calcd. For $C_{27}H_{33}N_5O_2 \cdot 0.2CH_2Cl_2$: C, 68.55; H, 7.06; N, 14.70. Found: C, 68.85; H, 7.21; N, 14.79.

Example 273

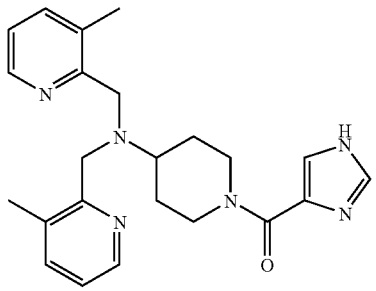

COMPOUND 273: {4-[Bis-(3-methyl-pyridin-2-ylmethyl)-amino]-piperidin-1-yl}-(1H-imidazol-4-yl)-methanone To a solution of COMPOUND 249 (93 mg, 0.30 mmol) in dry DMF (3 mL) was added imidazole-4-carboxylic acid (50 mg, 0.45 mmol) followed by EDCI (84 mg, 0.44 mmol), and DMAP (112 mg, 0.92 mmol). The mixture was stirred at room temperature overnight. The mixture was diluted with water (10 mL) and brine (10 mL) and extracted with $CH_2Cl_2$ (5×20 mL). The combined organic extracts were dried ($Na_2SO_4$) and concentrated. Purification of the crude material by column chromatography on silica gel (10:1:1 $CH_2Cl_2$-MeOH—$NH_4OH$) provided 36 mg (30%) of COMPOUND 273 as a white solid. $^1H$ NMR ($CDCl_3$) δ 1.60-1.76 (m, 4H), 1.95-2.09 (m, 8H), 2.60-3.02 (m, 3H), 3.83 (br s, 3H), 4.73 (br s, 1H), 7.09 (dd, 2H, J=7.2, 4.8 Hz), 7.36-7.54 (m, 3H), 7.65 (br s, 1H), 8.34 (d, 2H, J=4.2 Hz); ES-MS m/z 405 (M+H).

Example 274

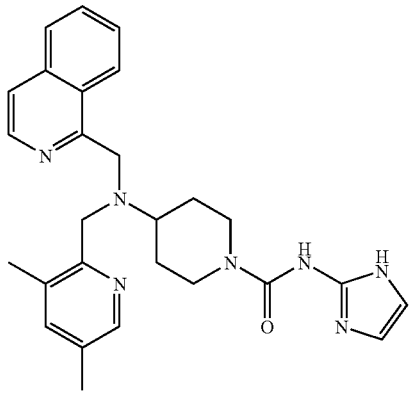

COMPOUND 274: 4-[(3,5-Dimethyl-pyridin-2-ylmethyl)-isoquinolin-1-ylmethyl-amino]-piperidine-1-carboxylic acid (1H-imidazol-2-yl)-amide Using General Procedure B: Reaction of 4-[(3,5-Dimethyl-pyridin-2-ylmethyl)-amino]-piperidine-1-carboxylic acid tert-butyl ester and 1-isoquinoline-carbaldehyde with NaBH(OAc)$_3$ in $CH_2Cl_2$ gave 4-[(3,5-Dimethyl-pyridin-2-ylmethyl)-isoquinolin-1-ylmethyl-amino]-piperidine-1-carboxylic acid tert-butyl ester as a colorless oil. Deprotection with TFA using General Procedure F gave (3,5-Dimethyl-pyridin-2-ylmethyl)-isoquinolin-1-ylmethyl-piperidin-4-yl-amine as a white foam.

To a stirred suspension of 2-aminoimidazole sulfate (667 mg, 5.05 mmol) in $CH_2Cl_2$ (25 mL) was added 1,1'-carbonyldiimidazole followed by DIPEA (2.70 mL, 15.50 mmol). The resultant mixture was stirred at room temperature overnight then concentrated under reduced pressure and provided 1.53 g of imidazole-1-carboxylic acid (1H-imidazol-2-yl)-amide as a brown solid.

To a warm (70° C.), stirred, solution of (3,5-Dimethyl-pyridin-2-ylmethyl)-isoquinolin-1-ylmethyl-piperidin-4-yl-amine (0.101 g, 0.28 mmol) and DIPEA (0.29 mL, 1.67 mmol) in DMF (3 mL) was added freshly prepared imidazole-1-carboxylic acid (1H-imidazol-2-yl)-amide (2 equivs). After 1 hour, the mixture was cooled to room temperature, diluted with brine (5 mL) and extracted with $CH_2Cl_2$ (4×10 mL). The combined organic extracts were washed with water (5×10 mL), dried ($Na_2SO_4$) and concentrated. Purification of the crude material by column chromatography on silica gel (20:1:1 $CH_2Cl_2$-MeOH—$NH_4OH$) provided 102 mg (75%) of COMPOUND 274 as a white solid. $^1H$ NMR ($CDCl_3$) δ 1.60-1.79 (m, 2H), 1.96-2.03 (m, 5H), 2.27 (s, 3H), 2.66-2.75 (m, 3H), 3.85 (s, 2H), 4.26-4.30 (m, 4H), 6.69 (s, 2H), 7.22-7.26 (m, 2H), 7.32-7.37 (m, 1H), 7.53-7.62 (m, 2H), 7.75 (d, 1H, J=8.1 Hz), 7.87 (d, 1H, J=8.7 Hz), 8.18 (s, 1H), 8.40 (d, 1H, J=6.0 Hz); $^{13}C$ NMR ($CDCl_3$) δ 18.32, 18.49, 27.57, 44.75, 54.92, 55.42, 58.07, 120.85, 126.62, 126.77, 127.23, 128.09, 130.13, 132.31, 133.26, 136.67, 139.17, 141.76, 145.51, 146.85, 154.35, 155.80, 159.42; ES-MS m/z 470 (M+H). Anal. Calcd. For $C_{27}H_{31}N_7O \cdot 1.0H_2O$: C, 66.51; H, 6.82; N, 20.11. Found: C, 66.34; H, 6.68; N, 19.74.

Example 275

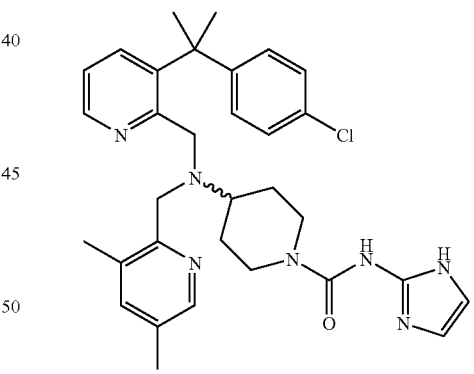

COMPOUND 275: 4-{[3-[1-(4-Chloro-phenyl)-1-methyl-ethyl]-pyridin-2-ylmethyl}-(3,5-dimethyl-pyridin-2-ylmethyl)-amino]-piperidine-1-carboxylic acid (1H-imidazol-2-yl)-amide Using General Procedure B: Reaction of 4-[(3,5-Dimethyl-pyridin-2-ylmethyl)-amino]-piperidine-1-carboxylic acid tert-butyl ester and 3-[1-(4-Chloro-phenyl)-1-methyl-ethyl]-pyridine-2-carbaldehyde with NaBH(OAc)$_3$ in $CH_2Cl_2$ gave 4-[{3-[1-(4-Chloro-phenyl)-1-methyl-ethyl]-pyridin-2-ylmethyl}-(3,5-dimethyl-pyridin-2-ylmethyl)-amino]-piperidine-1-carboxylic acid tert-butyl ester as a white solid. Deprotection with TFA using General Procedure F gave {3-[1-(4-Chloro-phenyl)-1-methyl-ethyl]-pyridin-2-ylmethyl}-(3,5-dimethyl-pyridin-2-ylmethyl)-piperidin-4-yl-amine as a white solid.

To a warm (70° C.), stirred, solution of {3-[1-(4-Chlorophenyl)-1-methyl-ethyl]-pyridin-2-ylmethyl}-(3,5-dimethyl-pyridin-2-ylmethyl)-piperidin-4-yl-amine (0.141 g, 0.30 mmol) and DIPEA (0.32 mL, 1.84 mmol) in DMF (3 mL) was added imidazole-1-carboxylic acid (1H-imidazol-2-yl)-amide (2 equivs). After 1.5 hours, the mixture was cooled to room temperature and concentrated under reduced pressure. The residue was dissolved in $CH_2Cl_2$ (30 mL) and washed with water (5×10 mL). The organic phase was dried ($Na_2SO_4$) and concentrated. Purification of the crude material by column chromatography on silica gel (20:1:1 $CH_2Cl_2$-MeOH—$NH_4OH$) provided 157 mg (85%) of COMPOUND 275 as a white solid. $^1H$ NMR ($CDCl_3$) δ 1.28-1.39 (m, 2H), 1.58 (s, 6H), 1.65-1.71 (m, 2H), 2.24 (s, 3H), 2.29 (s, 3H), 2.56-2.65 (m, 3H), 3.36 (s, 2H), 3.68 (s, 2H), 4.10-4.14 (m, 2H), 6.68 (s, 2H), 6.83-6.85 (m, 2H), 7.07-7.10 (m, 2H), 7.17-7.21 (m, 2H), 7.81 (d, 1H, J=6.9 Hz), 8.09 (s, 1H), 8.50 (d, 1H, J=3.3 Hz); $^{13}C$ NMR ($CDCl_3$) δ 18.78, 19.21, 28.81, 31.76, 43.11, 45.08, 55.15, 55.65, 58.55, 122.21, 127.81, 129.21, 132.10, 132.30, 133.51, 134.67, 139.48, 143.61, 145.93, 147.15, 147.46, 149.05, 155.28, 156.16, 158.91; ES-MS m/z 572 (M+1) & 574 (M+1). Anal. Calcd. For $C_{32}H_{38}N_7OCl.0.4CH_2Cl_2$: C, 64.20; H, 6.45; N, 16.18; Cl, 10.53. Found: C, 63.83; H, 6.43; N, 15.88; Cl, 10.92.

Example 276

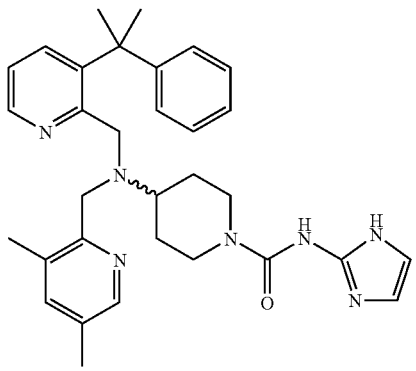

COMPOUND 276: 4-{(3,5-Dimethyl-pyridin-2-ylmethyl)-[3-(1-methyl-1-phenyl-ethyl)-pyridin-2-ylmethyl]-amino}-piperidine-1-carboxylic acid (1H-imidazol-2-yl)-amide Using General Procedure B: Reaction of 4-[(3,5-Dimethyl-pyridin-2-ylmethyl)-amino]-piperidine-1-carboxylic acid tert-butyl ester and 3-(1-Methyl-1-phenyl-ethyl)-pyridine-2-carbaldehyde with NaBH(OAc)$_3$ in $CH_2Cl_2$ gave 4-{(3,5-Dimethyl-pyridin-2-ylmethyl)-[3-(1-methyl-1-phenyl-ethyl)-pyridin-2-ylmethyl]-amino}-piperidine-1-carboxylic acid tert-butyl ester as a white solid. Deprotection with TFA using General Procedure F gave (3,5-Dimethyl-pyridin-2-ylmethyl)-[3-(1-methyl-1-phenyl-ethyl)-pyridin-2-ylmethyl]-piperidin-4-yl-amine as a white solid.

To a warm (70° C.), stirred, solution of (3,5-Dimethyl-pyridin-2-ylmethyl)-[3-(1-methyl-1-phenyl-ethyl)-pyridin-2-ylmethyl]-piperidin-4-yl-amine (0.211 g, 0.49 mmol) and DIPEA (0.51 mL, 2.92 mmol) in DMF (5 mL) was added imidazole-1-carboxylic acid (1H-imidazol-2-yl)-amide (2 equivs). After 2 hours, the mixture was cooled to room temperature and concentrated under reduced pressure. The residue was dissolved in $CH_2Cl_2$ (50 mL) and washed with water (5×10 mL). The organic phase was dried ($Na_2SO_4$) and concentrated. Purification of the crude material by column chromatography on silica gel (20:1:1 $CH_2Cl_2$-MeOH—$NH_4OH$) provided 213 mg (76%) of COMPOUND 276 as a white solid. $^1H$ NMR ($CDCl_3$) δ 1.13-1.27 (m, 2H), 1.54-1.62 (m, 8H), 2.26 (s, 6H), 2.47-2.595 (m, 3H), 3.37 (s, 2H), 3.62 (s, 2H), 4.03-4.07 (m, 2H), 6.69 (s, 2H), 6.99-7.10 (m, 3H), 7.14-7.20 (m, 4H), 7.84 (d, 1H, J=7.2 Hz), 8.08 (s, 1H), 8.50 (d, 1H, J=3.6 Hz); $^{13}C$ NMR ($CDCl_3$) δ 17.31, 17.84, 27.16, 30.28, 41.87, 43.64, 53.13, 54.60, 57.03, 120.55, 125.05, 125.26, 127.82, 130.57, 132.31, 133.09, 138.09, 142.53, 144.49, 145.58, 145.90, 148.90, 154.11, 154.58, 157.80; ES-MS m/z 538 (M+1). Anal. Calcd. For $C_{32}H_{39}N_7O.0.4H_2O.0.3CH_2Cl_2$: C, 68.02; H, 7.14; N, 17.19. Found: C, 67.67; H, 7.01; N, 17.32.

Example 277

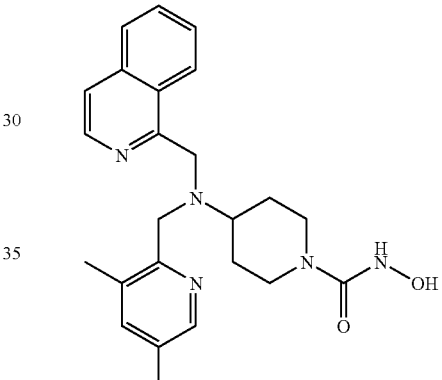

COMPOUND 277: 4-[(3,5-Dimethyl-pyridin-2-ylmethyl)-isoquinolin-1-ylmethyl-amino]-piperidine-1-carboxylic acid hydroxyamide To a solution of (3,5-dimethyl-pyridin-2-ylmethyl)-isoquinolin-1-ylmethyl-piperidin-4-yl-amine (118 mg, 0.327 mmol) in anhydrous THF (3.5 mL) was added N-(phenoxycarbonyl)hydroxylamine (57.5 mg, 0.344 mmol). The mixture was warmed to reflux and stirred for 17 h, then cooled to ambient temperature and concentrated to a yellow solid. Purification by column chromatography on silica gel (eluted with $CH_2Cl_2$/MeOH/$NH_4OH$) follow by purification by radial chromatography (eluted with $CH_2Cl_2$/MeOH/$NH_4OH$ 94:5:1) afforded 4-[(3,5-Dimethyl-pyridin-2-ylmethyl)-isoquinolin-1-ylmethyl-amino]-piperidine-1-carboxylic acid hydroxyamide (86 mg, 61%) as a yellow solid. $^1H$ NMR ($CDCl_3$) δ 1.69-1.79 (m, 2H), 1.96 (d, 1H, J=11.1 Hz), 2.04 (s, 3H), 2.27 (s, 3H), 2.63-2.77 (m, 3H), 3.85 (s, 2H), 4.05 (d, 2H, J=12.7 Hz), 4.25 (s, 2H), 6.88 (s, 1H), 7.22 (s, 1H), 7.35 (t, 1H, J=7.7 Hz), 7.54 (d, 1H, J=5.9 Hz), 7.59 (t, 1H, J=7.5 Hz), 7.75 (d, 1H, J=8.1 Hz), 7.87 (d, 1H, J=8.5 Hz), 8.18 (s, 1H), 8.39 (d, 1H, J=5.7 Hz); $^{13}C$ NMR ($CDCl_3$) δ 17.9, 18.1, 26.9, 43.8, 53.4, 54.6, 57.7, 120.6, 126.3, 126.9, 127.7, 129.8, 132.0, 132.9, 136.3, 138.9, 141.3, 146.4, 153.8, 158.9, 160.7;

ES-MS m/z 420 (M+H). Anal Calcd. For $C_{24}H_{29}N_5O_2 \cdot 0.1$ $(CH_2Cl_2)$: C, 67.63; H, 6.88; N, 16.36. Found: C, 67.59; H, 6.99; N, 16.02.

Example 278

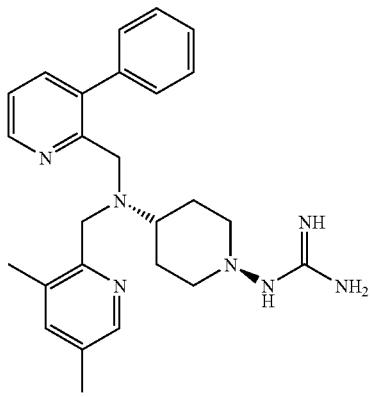

COMPOUND 278: N-{4-trans-[(3,5-Dimethyl-pyridin-2-ylmethyl)-(3-phenyl-pyridin-2-ylmethyl)-amino]-cyclohexyl}-guanidine (HBr salt)

Following General Procedure B: Reaction of {4-[(3-phenyl-pyridin-2-ylmethyl)-amino]-cyclohexyl}-carbamic acid tert-butyl ester and 3,5-dimethylpyridine-2-carbaldehyde in dry $CH_2Cl_2$ (7 mL) with $NaBH(OAc)_3$ gave the desired tertiary amine as a white foam. Deprotection with $CH_2Cl_2$/TFA using General Procedure F gave a yellow oil.

To a solution of the amine from above (66 mg) in THF (2.5 mL) was added N,N'-bis-(tert-butoxycarbonyl)-1H-pyrazole-1-carboxamidine (70 mg, 0.23 mmol) and the reaction stirred at room temperature overnight. The mixture was concentrated and purified by radial chromatography on silica gel (1 mm plate, $CH_2Cl_2$/MeOH/$NH_4OH$, 100:1:1 then 50:1:1 then 25:1:1) to afford the Boc-protected guanidine (80 mg, 68% over 2 steps) as a colourless oil.

Using General Procedure D: Conversion to the HBr salt gave COMPOUND 278 as a white solid. $^1H$ NMR ($D_2O$) δ 1.24-1.36 (m, 2H), 1.40-1.48 (m, 2H), 1.86-1.90 (m, 2H), 1.98-2.02 (m, 2H), 2.32 (s, 3H), 2.44 (s, 3H), 2.65-2.72 (m, 1H), 3.23-3.31 (m, 1H), 4.08 (s, 2H), 4.33 (s, 2H), 7.38-7.42 (m, 2H), 7.58-7.62 (m, 3H), 7.98 (dd, 1H, J=7.8, 6 Hz), 8.10 (s, 1H), 8.31 (s, 1H), 8.44 (dd, 1H, J=7.8, 1.2 Hz), 8.75 (dd, 1H, J=5.4, 1.2 Hz). $^{13}C$ NMR ($D_2O$) δ 17.02, 17.46, 26.32, 31.11, 50.29, 50.56, 51.91, 61.21, 126.34, 129.66, 130.30, 134.00, 137.04, 137.56, 138.26, 140.91, 141.04, 147.87, 147.94, 148.97, 150.75, 156.23. ES-MS m/z 443 (M+H). Anal. Calcd. for $C_{27}H_{34}N_6 \cdot 3.1HBr \cdot 1.7H_2O \cdot 0.4C_4H_{10}O$: C, 45.58; H, 5.95; N, 11.15; Br, 32.86. Found: C, 45.49; H, 5.89; N, 11.13; Br, 32.92.

Example 279

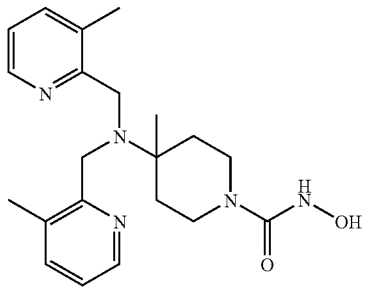

COMPOUND 279: 4-[Bis-(3-methyl-pyridin-2-ylmethyl)-amino]-4-methyl-piperidine-1-carboxylic acid hydroxyamide To a solution of 1-Boc-4-piperidone (2.61 g, 13.03 mmol) in 1,2-dichloroethane (25 mL) was added diallyl amine (1.7 mL, 13.77 mmol) and the mixture cooled to 0° C. Titanium (IV) isopropoxide (3.9 mL, 13.3 mmol) was then added and the reaction warmed to room temperature and stirred for 2.5 d. The resultant orange mixture was then cooled to 0° C. and diethylaluminum cyanide added (1 M in toluene, 16 mL, 16 mmol) The reaction was warmed to room temperature, stirred for 3.5 h then diluted with $CH_2Cl_2$ (30 mL) and EtOAc (25 mL). The mixture was cooled to 0° C., quenched with water (7 mL) and filtered through celite, washing with $CH_2Cl_2$ and MeOH. The resultant filtrate was concentrated, diluted with $CH_2Cl_2$ (150 mL), dried ($Na_2SO_4$), concentrated and purified by flash chromatography on silica gel (Hexanes/EtOAc, 3:1 then 1:1) to afford the diallylamino-cyanide intermediate (2.79 g, 70%) as a yellow oil.

To a solution of the cyanide from above (2.79 g, 9.15 mmol) in THF (30 mL) at 0° C. was added MeMgBr (3.0 m in $Et_2O$, 10 mL, 30 mmol) and the reaction stirred at 0° C. for 1 h then warmed to room temperature and stirred an additional 3 h. The mixture was quenched with water (20 mL), diluted with EtOAc (50 mL) and saturated aqueous $NaHCO_3$ (40 mL). The layers were separated and the aqueous layer was washed with EtOAc (2×30 mL). The combined organic extracts were washed with brine (1×50 mL), dried (Na2SO4), concentrated and purified by column chromatography on silica gel (Hexanes/EtOAc, 3:1) to afford 4-diallylamino-4-methyl-piperidine-1-carboxylic acid tert-butyl ester (2.016 g, 75%) as a colorless oil.

To a solution of the N,N-diallyl-protected amine from above (2.01 g, 6.84 mmol) in $CH_2Cl_2$ (30 mL) was added 1,3-dimethylbarbituric acid (5.3232 g, 34.09 mmol) and $Pd(PPh_3)_4$ (548 mg, 0.47 mmol) and the reaction stirred under Ar overnight. The mixture was concentrated and purified by column chromatography on silica gel ($CH_2Cl_2$/MeOH/$NH_4OH$, 96:4:0 then 94:4:2 then 88:10:2) to give 4-Amino-4-methyl-piperidine-1-carboxylic acid tert-butyl ester (0.91 g, 62%) as an orange oil. $^1H$ NMR ($CDCl_3$) δ 1.17 (s, 3H), 1.45 (s, 9H), 1.47-1.54 (m, 4H), 1.66 (br s, 2H), 3.42-3.47 (m, 4H). $^{13}C$ NMR ($CDCl_3$) δ 27.92, 28.76, 38.60, 47.26, 53.05, 78.72, 154.18. ES-MS m/z 237 (M+Na).

Using General Procedure B: Reaction of 4-Amino-4-methyl-piperidine-1-carboxylic acid tert-butyl ester and 3-methyl-2-pyridinecarboxaldehyde in $CH_2Cl_2$ with NaBH$(OAc)_3$ gave the secondary amine as an orange oil.

Using General Procedure C: To a solution of 3-methyl-2-hydroxymethylpyridine (498 mg, 4.05 mmol) and $Et_3N$ (1.1 mL, 7.89 mmol) in $CH_2Cl_2$ (10 mL) at −78° C. was added MsCl (0.40 mL, 5.17 mmol) and the reaction stirred at −78° C. for 15 min. then warmed to room temperature.

Using General Procedure A: Reaction of the resultant crude mesylate, the amine from above in DMF with DIPEA and KI gave a beige foam. Deprotection with $CH_2Cl_2$/TFA using General Procedure F gave the deprotected piperidine as a brown oil.

To a solution of the piperidine from above (122 mg, 0.38 mmol) in THF (5 mL) was added N-(phenoxycarbonyl)hydroxylamine (74 mg, 0.48 mmol) and the resultant mixture stirred at 65° C. for 2.5 d. The mixture was concentrated and purified by column chromatography on silica gel (CH$_3$CN/MeOH/NH$_4$OH, 25:1:1 then 15:1:1) followed by radial chromatography on silica gel (1 mm plate, CH$_2$Cl$_2$/MeOH/NH$_4$OH, 25:1:1 then 10:1:1) to give COMPOUND 279 (50 mg, 34%) as a white foam: $^1$H NMR (CDCl$_3$) δ 1.23 (s, 3H), 1.60-1.67 (m, 2H), 1.78 (br s, 1H), 1.93-2.01 (m, 2H), 2.10 (s, 6H), 3.15-3.22 (m, 2H), 3.76-3.84 (m, 2H), 3.90 (s, 4H), 6.83 (dd, 2H, J=7.5, 4.8 Hz), 7.02 (d, 2H, J=7.5 Hz), 7.08 (br s, 1H), 8.20 (d, 2H, J=4.8 Hz). $^{13}$C NMR (CDCl$_3$) δ 17.02, 19.05, 36.57, 40.77, 53.05, 57.21, 122.02, 133.02, 137.50, 146.04, 158.18, 161.89. ES-MS m/z 384 (M+H). Anal. Calcd. for C$_{21}$H$_{29}$N$_5$O$_2$.0.5H$_2$O: C, 64.26; H, 7.70; N, 17.84. Found: C, 64.33; H, 7.52; N, 17.46.

Example 280

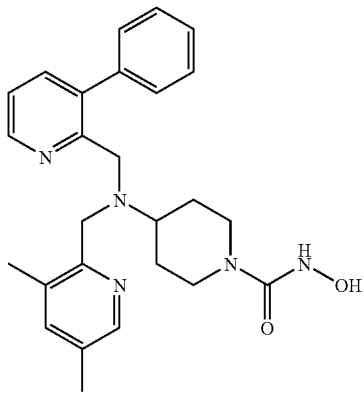

COMPOUND 280: 4-[(3,5-Dimethyl-pyridin-2-ylmethyl)-(3-methyl-pyridin-2-ylmethyl)-amino]-piperidine-1-carboxylic acid hydroxyamide Under General Procedure B: Reaction of 3-phenyl-pyridine-2-carbaldehyde and 4-amino-piperidine-1-carboxylic acid tert-butyl ester (Huang, Y. et al. *J. Med. Chem.* 2001, 44, 4404-4415) in MeO$_4$ with NaBH$_4$ gave 4-[(3-phenyl-pyridin-2-ylmethyl)-amino]-piperidine-1-carboxylic acid tert-butyl ester. $^1$H NMR (CDCl$_3$) δ 1.22 (m, 3H), 1.41 (s, 9H), 1.70 (m, 2H), 2.52 (m, 1H), 2.72 (m, 3H), 3.84 (s, 2H), 7.21 (q, 1H, J=4.03 Hz), 7.32 (m, 2H), 7.40 (m, 3H), 7.53 (dd, 1H, J=7.79, 1.72 Hz), 8.54 (m, 1H) ppm.

Using General Procedure B: Reaction of the amine from above and 3,5-dimethyl-2-pyridinecarboxaldehyde in CH$_2$Cl$_2$ with NaBH(OAc)$_3$ gave 4-[(3,5-dimethyl-pyridin-2-ylmethyl)-(3-phenyl-pyridin-2-ylmethyl)-amino]-piperidine-1-carboxylic acid tert-butyl ester. $^1$H NMR (CDCl$_3$) δ 1.20 (m, 3H), 1.40 (s, 9H), 1.84 (s, 3H), 2.20 (s, 3H), 2.34 (m, 2H), 2.75 (m, 4H), 3.69 (s, 2H), 3.79 (s, 2H), 7.04 (s, 1H), 7.22 (m, 6H), 7.46 (dd, 1H, J=7.27, 1.7 Hz), 8.01 (s, 1H), 8.49 (dd, 1H, J=4.8, 1.7 Hz) ppm. Deprotection with CH$_2$Cl$_2$/TFA using General Procedure F gave (3,5-dimethyl-pyridin-2-ylmethyl)-(3-phenyl-pyridin-2-ylmethyl)-piperidin-4-yl-amine. $^1$H NMR (CDCl$_3$) δ 1.72 (m, 2H), 1.92 (m, 2H), 2.34 (s, 3H), 2.44 (s, 3H), 2.70 (m, 3H), 3.25 (m, 2H), 4.16 (m, 4H), 7.28 (m, 2H), 7.45 (m, 3H), 7.58 (q, 1H, J=4.38 Hz), 7.86 (m, 2H), 8.49 (s, 1H), 8.80 (d, 1H, J=3.38 Hz) ppm.

To a solution of the piperidine from above (72 mg, 0.19 mmol) in THF (5 mL) was added N-(phenoxycarbonyl)hydroxylamine (47 mg, 0.31 mmol) and the resultant mixture stirred at 70° C. for 2.5 d. The mixture was concentrated and purified by radial chromatography on silica gel (1 mm plate, CH$_2$Cl$_2$/MeOH/NH$_4$OH, 25:1:1 then 10:1:1) to give COMPOUND 280 (20 mg, 34%) as a yellow oil: $^1$H NMR (CDCl$_3$) δ 1.20-1.30 (m, 2H), 1.51-1.54 (m, 2H), 1.83 (br s, 1H), 1.85 (s, 3H), 2.24 (s, 3H), 2.40-2.56 (m, 3H), 3.73 (s, 2H), 3.82 (s, 2H), 3.84-3.89 (m, 2H), 6.88 (s, 1H), 7.08 (s, 1H), 7.23-7.32 (m, 6H), 7.51 (dd, 2H, J=7.8, 1.5 Hz), 8.06 (s, 1H), 8.55 (dd, 1H, J=4.8, 1.5 Hz). $^{13}$C NMR (CDCl$_3$) δ 18.21, 18.30, 27.03, 44.06, 53.96, 54.44, 57.59, 122.55, 127.72, 128.62, 129.38, 131.97, 133.18, 138.58, 138.99, 139.44, 139.87, 146.23, 147.79, 154.32, 156.76, 161.08. ES-MS m/z 446 (M+H). Anal. Calcd. for C$_{26}$H$_{31}$N$_5$O$_2$.0.7CH$_2$Cl$_2$: C, 63.50; H, 6.47; N, 13.87. Found: C, 63.62; H, 6.57; N, 13.56.

Example 281

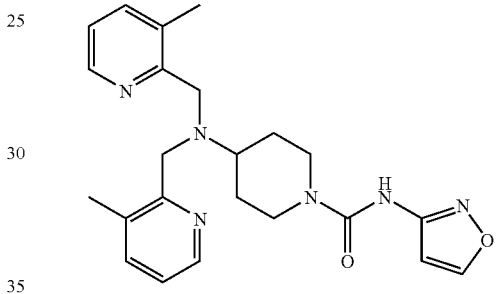

COMPOUND 281: 4-[Bis-(3-methyl-pyridin-2-ylmethyl)-amino]-piperidine-1-carboxylic acid isoxazol-3-ylamide To a solution of 2-aminothiazole (69 mg, 0.82 mmol) in CH$_2$Cl$_2$ (5 mL) was added 1,1'-carbonyldiimidazole (149 mg, 0.92 mmol) and the reaction stirred at room temperature for 4 h before the mixture was concentrated and diluted with CH$_3$CN (5 mL). COMPOUND 249 (120 mg, 0.387 mmol) was added and the reaction stirred at 60° C. for 2 hours. The solution was concentrated to dryness, treated with saturated aqueous NaHCO$_3$ (30 mL) and extracted with CH$_2$Cl$_2$ (3×15 mL). The combined organic extracts were dried (Na$_2$SO$_4$), filtered, and concentrated. Purification of the crude material by flash chromatography on silica gel (CH$_2$Cl$_2$/MeOH/NH$_4$OH, 96:4:0 then 94:4:2) provided COMPOUND 281 (148 mg, 91%) as a white solid: $^1$H NMR (CDCl$_3$) δ 1.68-1.82 (m, 2H), 1.97-2.01 (m, 2H), 2.08 (s, 6H), 2.70-2.82 (m, 3H), 3.83 (s, 4H), 4.23-4.27 (m, 2H), 7.00 (d, 1H, J=1.8 Hz), 7.09 (dd, 2H, J=7.5, 4.8 Hz), 7.37 (d, 2H, J=7.5 Hz), 8.20 (d, 1H, J=1.8 Hz), 8.35 (dd, 2H, J=4.8, 0.9 Hz), 8.60 (br s, 1H). $^{13}$C NMR (CDCl$_3$) δ 18.37, 27.50, 44.81, 54.89, 57.75, 100.15, 122.93, 133.88, 138.61, 146.16, 153.88, 157.36, 158.96, 160.25. ES-MS m/z 443 (M+Na). Anal. Calcd. for C$_{23}$H$_{28}$N$_6$O$_2$.0.5H$_2$O: C, 64.32; H, 6.81; N, 19.57. Found: C, 64.36; H, 6.82; N, 19.26.

Example 282

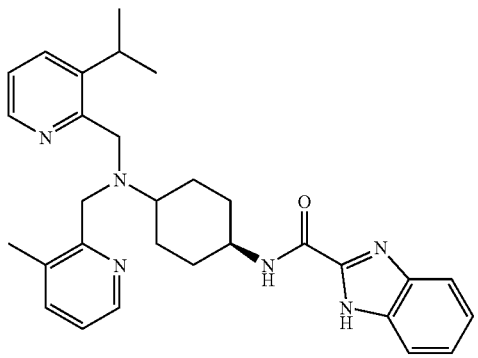

COMPOUND 282: 1H-Benzoimidazole-2-carboxylic acid {4-trans-[(3-isopropyl-pyridin-2-ylmethyl)-(3-methyl-pyridin-2-ylmethyl)-amino]-cyclohexyl}-amide To a solution of COMPOUND 117 (148 mg, 0.42 mmol), 1-H-benzimidazole-2-carboxylic acid (98 mg, 0.60 mmol), HOBT (97 mg, 0.72 mmol) and DIPEA (0.25 mL, 1.44 mmol) in DMF (2 mL) was added EDCII (309 mg, 1.61 mmol) and the reaction stirred at room temperature overnight. The mixture was concentrated and purified by column chromatography on silica gel ($CH_2Cl_2$/MeOH/$NH_4OH$, 96:4:0 then 94:4:2) to give COMPOUND 282 (110 mg, 53%) as a white solid: $^1H$ NMR ($CDCl_3$) δ 0.96 (d, 6H, J=6.9 Hz), 1.18-1.35 (m, 2H), 1.60-1.72 (m, 2H), 2.03-2.07 (m, 2H), 2.15-2.19 (m, 2H), 2.26 (s, 3H), 2.55-2.63 (m, 1H), 2.85-2.94 (m, 1H), 3.88 (s, 4H), 3.91-3.96 (m, 1H), 7.10-7.18 (m, 2H), 7.32-7.35 (m, 2H), 7.42-7.45 (m, 2H), 7.49-7.55 (m, 2H), 7.75 (br s, 1H), 8.35 (dd, 1H, J=4.8, 1.5 Hz), 8.37 (d, 1H, J=6 Hz). $^{13}C$ NMR ($CDCl_3$) δ 18.86, 23.80, 26.69, 27.64, 32.90, 49.77, 54.87, 55.34, 58.60, 113.02, 120.90, 123.10, 123.42, 123.94, 125.33, 134.08, 138.55, 144.58, 145.78, 146.24, 146.57, 156.46, 157.73, 159.37. ES-MS m/z 497 (M+H). Anal. Calcd. for $C_{30}H_{36}N_6O \cdot 1.0H_2O$: C, 70.01; H, 7.44; N, 16.33. Found: C, 70.17; H, 7.40; N, 15.96.

Example 283

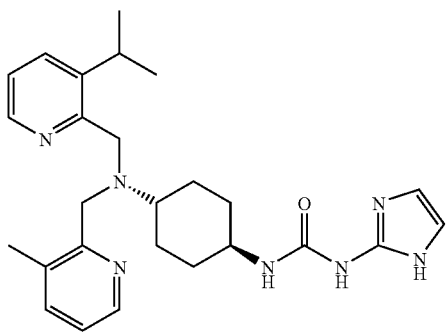

COMPOUND 283: 1-(1H-Imidazol-2-yl)-3-{4-trans-[(3-isopropyl-pyridin-2-ylmethyl)-(3-methyl-pyridin-2-ylmethyl)-amino]-cyclohexyl}-urea To a solution of 2-aminoimidazole sulfate (150 mg, 1.135 mmol) in DMF (2.4 mL) was added DIPEA (0.60 mL, 3.45 mmol) and 1,1'-carbonyldiimidazole (199 mg, 1.23 mmol) and the reaction stirred at room temperature for 2 h 40 min. after which COMPOUND 117 (148 mg, 0.418 mmol) was added and the reaction stirred at 60° C. overnight. The solution was cooled, treated with saturated aqueous $NaHCO_3$ (25 mL) and extracted with $CH_2Cl_2$ (3×20 mL). The combined organic extracts were washed with brine ((2×20 mL), dried ($Na_2SO_4$), filtered, and concentrated. Purification of the crude material by radial chromatography on silica gel (1 mm plate, $CH_2Cl_2$/MeOH/$NH_4OH$, 50:1:1 then 25:1:1 then 10:1:1) provided COMPOUND 283 (126 mg, 65%) as a white solid: $^1H$ NMR ($CDCl_3$) δ 0.92 (d, 6H, J=6.9 Hz), 1.05-1.17 (m, 2H), 1.51-1.63 (m, 2H), 1.95-2.07 (m, 4H), 2.22 (s, 3H), 2.45-2.53 (m, 1H), 2.81-2.88 (m, 1H), 3.45-3.57 (m, 1H), 3.80 (s, 2H), 3.81 (s, 2H), 6.65 (s, 2H), 7.08-7.15 (m, 2H), 7.42 (d, 1H, J=6.9 Hz), 7.48 (dd, 1H, J=7.8, 1.5 Hz), 8.30 (dd, 1H, J=4.8, 1.5 Hz), 8.34 (d, 1H, J=6 Hz). $^{13}C$ NMR ($CDCl_3$) δ 18.61, 23.51, 26.45, 27.32, 33.16, 49.33, 54.55, 54.91, 58.37, 117.80, 122.90, 123.23, 134.03, 138.48, 143.92, 144.58, 145.79, 146.12, 155.19, 156.28, 157.58. ES-MS m/z 462 (M+H). Anal. Calcd. for $C_{26}H_{35}N_7O \cdot 0.2H_2O$: C, 67.13; H, 7.67; N, 21.08. Found: C, 67.18; H, 7.77; N, 21.00.

Example 284

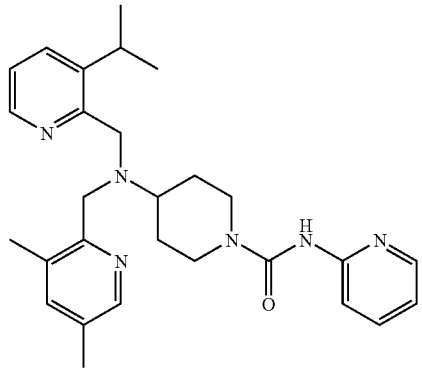

COMPOUND 284: 4-[(3,5-Dimethyl-pyridin-2-ylmethyl)-(3-isopropyl-pyridin-2-ylmethyl)-amino]-piperidine-1-carboxylic acid pyridin-2-ylamide To a solution of 2-aminopyridine (69 mg, 0.73 mmol) in $CH_2Cl_2$ (5 mL) was added 1,1'-carbonyldiimidazole (122 mg, 0.75 mmol) and the reaction stirred at reflux for 2 h 15 min. after which a solution of (3,5-dimethyl-pyridin-2-ylmethyl)-(3-isopropyl-pyridin-2-ylmethyl)-piperidine-4-yl-amine (87 mg, 0.247 mmol) in $CH_2Cl_2$ (3 mL) was added and the reaction stirred at reflux for 2.5 h. The solution was cooled, treated with saturated aqueous $NaHCO_3$ (25 mL) and extracted with $CH_2Cl_2$ (3×20 mL). The combined organic extracts were dried ($Na_2SO_4$), filtered, and concentrated. Purification of the

235 crude material by radial chromatography on silica gel (1 mm plate, $CH_2Cl_2/MeOH/NH_4OH$, 100:1:1 then 50:1:1) provided COMPOUND 284 (94 mg, 81%) as a colorless oil: $^1H$ NMR (CDCl$_3$) δ 0.92 (d, 6H, J=6.9 Hz), 1.62-1.75 (m, 2H), 1.92-1.98 (m, 3H), 2.16 (s, 3H), 2.28 (s, 3H), 2.72-2.85 (m, 4H), 3.77 (s, 2H), 3.83 (s, 2H), 4.17-4.21 (m, 2H), 6.92 (dd, 1H, J=6.6, 5.4 Hz), 7.14 (dd, 1H, J=7.8, 4.8 Hz), 7.24 (br s, 2H), 7.50 (dd, 1H, J=7.8, 1.2 Hz), 7.63 (dt, 1H, J=6.9, 1.8 Hz), 8.01 (d, 1H, J=8.4 Hz), 8.19 (s, 1H), 8.33 (dd, 1H, J=4.8, 1.5 Hz). $^{13}C$ NMR (CDCl$_3$) δ 18.29, 18.45, 23.60, 27.45, 44.80, 54.32, 57.34, 113.61, 118.62, 123.18, 132.28, 133.19, 133.86, 138.48, 139.06, 144.39, 146.08, 146.65, 147.81, 153.27, 154.03, 154.42, 156.23. ES-MS m/z 495 (M+Na). Anal. Calcd. for $C_{28}H_{36}N_6O \cdot 0.8CH_2Cl_2$: C, 63.99; H, 7.01; N, 15.55. Found: C, 64.33; H, 7.28; N, 15.68.

Example 285

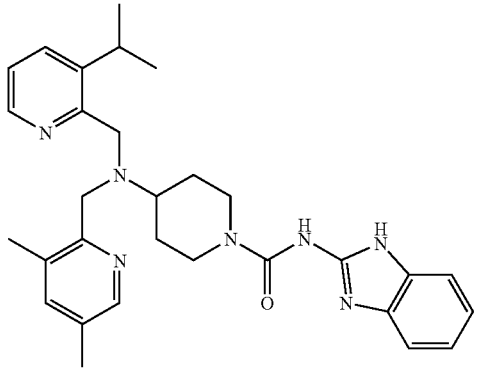

COMPOUND 285: 4-[(3,5-Dimethyl-pyridin-2-ylmethyl)-(3-isopropyl-pyridin-2-ylmethyl)-amino]-piperidine-1-carboxylic acid (1H-benzoimidazol-2-yl)-amide To a suspension of 2-aminobenzimidazole (81 mg, 0.61 mmol) in $CH_2Cl_2$ (5 mL) and DMF (0.5 mL) was added 1,1'-carbonyldiimidazole (99 mg, 0.61 mmol) and the reaction stirred at reflux for 30 min. then at room temperature for 2 h after which a solution of (3,5-dimethyl-pyridin-2-ylmethyl)-(3-isopropyl-pyridin-2-ylmethyl)-piperidine-4-yl-amine (109 mg, 0.31 mmol) in DMF (1 mL) was added and the reaction stirred at 65° C. overnight. The solution was cooled, treated with saturated aqueous NaHCO$_3$ (25 mL) and extracted with $CH_2Cl_2$ (3×20 mL). The combined organic extracts were washed with brine (1×30 mL), dried (Na$_2$SO$_4$), filtered, and concentrated. Purification of the crude material by radial chromatography on silica gel (1 mm plate, $CH_2Cl_2$/MeOH/NH$_4$OH, 100:1:1 then 50:1:1 then 25:1:1) provided COMPOUND 285 (158 mg, 99%) as a white foam: $^1H$ NMR (CDCl$_3$) δ 0.90 (d, 6H, J=6.9 Hz), 1.60-1.70 (m, 2H), 1.87-1.92 (m, 2H), 2.14 (s, 3H), 2.27 (s, 3H), 2.67-2.80 (m, 4H), 3.74 (s, 2H), 3.81 (s, 2H), 4.39-4.44 (m, 2H), 7.10-7.17 (m, 3H), 7.23 (s, 1H), 7.30 (dd, 2H, J=6, 3.3 Hz), 7.48 (dd, 1H, J=7.8, 1.5 Hz), 8.17 (s, 1H), 8.31 (dd, 1H, J=4.8, 1.5 Hz). $^{13}C$ NMR (CDCl$_3$) δ 17.80, 18.00, 23.09, 26.85, 27.07, 44.32, 53.78, 56.96, 121.63, 122.66, 131.76, 132.74, 133.37, 138.57, 143.90, 145.53, 146.09, 151.84, 153.97, 155.79, 157.81. ES-MS m/z 512 (M+H). Anal. Calcd. for $C_{30}H_{37}N_7O \cdot 1.0CH_2Cl_2$: C, 62.41; H, 6.59; N, 16.43. Found: C, 62.18; H, 6.60; N, 16.27.

236

Example 286

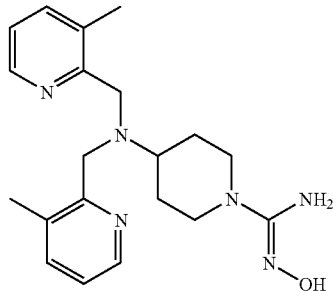

COMPOUND 286: 4-[bis-(3-methyl-pyridin-2-ylmethyl)-amino]-N-hydroxy-piperidine-1-carboxamidine To a solution of COMPOUND 249 (0.5021 g, 1.6 mmol) and anhydrous NaOAc (0.3775 g, 4.6 mmol) in MeOH (16 mL) was added at 0° C. cyanogen bromide (0.2315 g, 2.2 mmol), and stirred at for 2 hours at 0° C., then for another 3 hours at room temperature. Distilled water (20 mL) was added and extracted with $CH_2Cl_2$ (3×150 mL). The combined organic extracts were washed with brine (2×75 mL), dried (Na$_2$SO$_4$), filtered, and concentrated to provide 0.5137 g (96%) of 4-[bis-(3-methyl-pyridin-2-ylmethyl)-amino]-piperidine-1-carbonitrile as a beige solid. $^1H$ NMR (CDCl$_3$) δ 1.77-1.90 (m, 2H), 1.95-1.99 (m, 2H), 2.11 (s, 6H), 2.66 (t, 1H, J=12.0 Hz), 2.88-2.97 (m, 2H), 3.45-3.49 (m, 2H), 3.87 (s, 4H), 7.09-7.13 (m, 2H), 7.39 (d, 2H, J=6.0 Hz), 8.36 (d, 2H, J=3.0 Hz).

To a solution of 4-[bis-(3-methyl-pyridin-2-ylmethyl)-amino]-piperidine-1-carbonitrile (0.2413 g, 0.72 mmol) in DMF (7 mL) was added NH$_2$OH·HCl (0.1127 g, 1.44 mmol) and DIPEA (0.25 mL, 1.44 mmol), and stirred at 60° C. for 16 hours. Saturated NaHCO$_3$ (15 mL) was added and extracted with $CH_2Cl_2$ (3×50 mL). The combined organic extracts were washed with brine (2×50 mL), dried (Na$_2$SO$_4$), filtered, and concentrated. Purification of the crude material by column chromatography on silica gel (20:1:1 $CH_2Cl_2$-MeOH—NH$_4$OH) provided 66.1 mg (58%) of COMPOUND 286 as a yellow solid. $^1H$ NMR (CD$_3$OD) 1.70-1.87 (m, 4H), 2.15 (s, 6H), 2.36-2.58 (m, 3H), 3.71 (d, 2H), 3.82 (s, 4H), 7.19-7.24 (m, 2H), 7.53 (d, 2H, J=7.5 Hz), 8.25 (d, 2H, J=4.8 Hz). $^{13}C$ NMR (CD$_3$OD) δ 18.70, 28.15, 48.19, 55.78, 59.90, 124.62, 136.04, 140.60, 146.72, 158.48, 160.89. ES-MS m/z 369.3 (M+H). Anal. Calcd. for $C_{20}H_{28}N_6O \cdot 0.9H_2O$: C, 62.44; H, 7.81; N, 21.85. Found: C, 62.60; H, 7.82; N, 21.74.

Example 287

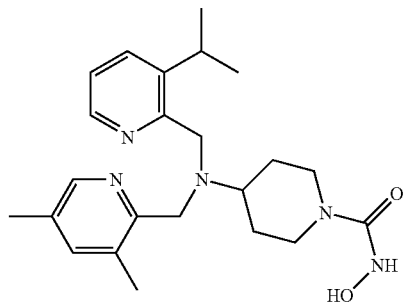

COMPOUND 287: 4-[(3,5-Dimethyl-pyridin-2-ylmethyl)-(3-isopropyl-pyridin-2-ylmethyl)-amino]-piperidine-1-carboxylic acid hydroxyamide A solution of (3,5-dimethyl-pyridin-2-ylmethyl)-(3-isopropyl-pyridin-2-ylmethyl)-piperidin-4-yl-amine (130 mg, 0.37 mmol) in toluene (3.7 mL) was treated with $Et_3N$ (82 μL, 0.59 mmol) and phosgene (0.25 mL, 2.2 M in toluene, 0.56 mmol) at 0° C. for 1.5 hours. The reaction was then warmed to room temperature and the solvent removed under reduced pressure. The residue was dissolved in $CH_2Cl_2$ (3.7 mL) and treated with $NH_2OH \cdot HCl$ (40 mg, 0.56 mmol) and $Et_3N$ (0.15 mL, 1.1 mmol) for 18 hours. Brine (10 mL) was added and the phases separated. The organic phase was then washed with brine (2×10 mL) and the organic dried ($Na_2SO_4$) and concentrated under reduced pressure to afford, after column chromatography with silica gel (50:1:0.1 $CH_2Cl_2$/MeOH/$NH_4OH$), COMPOUND 287 as a pale yellow solid (59 mg, 39%). $^1H$ NMR ($CDCl_3$) δ 0.93 (d, 6H, J=6.6 Hz), 1.67 (m, 2H), 1.92 (d, 2H, J=12.6 Hz), 2.16 (s, 3H), 2.28 (s, 3H), 2.73 (m, 4H), 3.77 (s, 2H), 3.83 (s, 2H), 4.03 (d, 2H, J=12.3 Hz), 6.60 (br, 1H(OH)), 6.75 (br, 1H(NH)), 7.15 (m, 1H), 7.25 (s, 1H), 7.50 (d, 1H, J=7.8 Hz), 8.19 (s, 1H), 8.32 (d, 1H, J=3.6 Hz). $^{13}C$ NMR ($CDCl_3$) δ 18.25, 18.40, 23.56 (2C), 27.26 (2C), 27.34, 44.30 (2C), 54.20 (2C), 57.48, 123.27, 132.39, 133.38, 134.09, 139.28, 144.53, 145.87, 146.38, 154.19, 155.98, 161.26. ES-MS m/z 412 (M+H). Anal. Calcd. for $C_{23}H_{33}N_5O_2 \cdot 0.3CH_2Cl_2$: C, 64.04; H, 7.75; N, 16.03. Found: C, 63.75; H, 7.68; N, 15.68.

Example 288

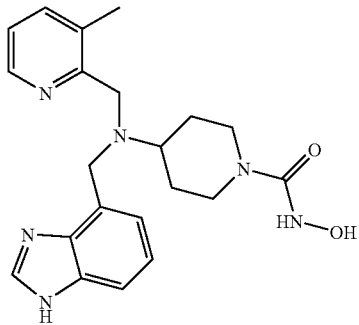

COMPOUND 288: 4-[(1H-Benzoimidazol-4-ylmethyl)-(3-methyl-pyridin-2-ylmethyl)-amino]-piperidine-1-carboxylic acid hydroxyamide Using General Procedure A: Reaction of 4-[(3-Methyl-pyridin-2-ylmethyl)-amino]-piperidine-1-carboxylic acid tert-butyl ester in dry $CH_3CN$ with 4-Bromomethyl-benzoimidazole-1-carboxylic acid tert-butyl ester, DIPEA and KI gave 4-{[(1-tert-Butoxycarbonyl-piperidin-4-yl)-(3-methyl-pyridin-2-ylmethyl)-amino]-methyl}-benzoimidazole-1-carboxylic acid tert-butyl ester as a white foam. Deprotection with TFA using General Procedure F gave (1H-Benzoimidazol-4-ylmethyl)-(3-methyl-pyridin-2-ylmethyl)-piperidin-4-yl-amine.

To a THF solution (3 mL) of the amine from above (100 mg, 0.300 mmol) was added N-(Phenoxycarbonyl)hydroxylamine (54.8 mg, 0.360 mmol), and the resultant solution was heated to 80° C. for 7 h and stirred at room temperature for 66 h. The solution was concentrated to dryness and the crude material was purified by flash chromatography on silica gel ($CH_2Cl_2$/MeOH/$NH_4OH$, 80:10:10) to afford COMPOUND 288 (49 mg, 55%) as a white solid. $^1H$ NMR ($CDCl_3$) δ 1.36-1.55 (m, 2H), 1.75 (d, 2H, J=11.7 Hz), 2.34 (s, 3H), 2.50-2.74 (m, 3H), 3.92 (s, 2H), 3.95 (d, 2H, J=15 Hz), 4.02 (s, 2H), 6.83 (br s, 1H), 7.04 (d, 1H, J=7.2 Hz), 7.11-7.23 (m, 2H), 7.52 (d, 1H, J=7.2 Hz), 7.74 (d, 1H, J=7.8 Hz), 8.18 (s, 1H), 8.53 (d, 1H, J=4.5 Hz); $^{13}C$ NMR ($CDCl_3$) δ 18.78, 27.46, 43.88, 52.09, 53.87, 54.58, 56.25, 118.67, 121.91, 122.15, 122.64, 124.55, 132.19, 133.51, 139.04, 141.08, 143.03, 145.87, 157.78, 161.25; ES-MS m/z 395 (M+H). Anal. Calcd. for $C_{21}H_{26}N_6O \cdot 0.5H_2O \cdot 0.2 CH_2Cl_2$: C, 58.76; H, 6.41; N, 19.21. Found: C, 58.65; H, 6.36; N, 19.19.

Example 289

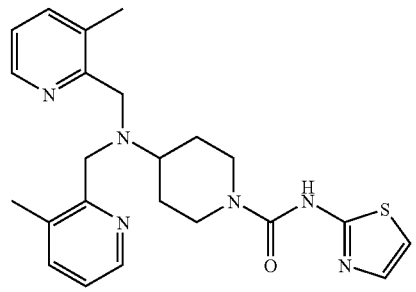

COMPOUND 289: 4-[Bis-(3-methyl-pyridin-2-ylmethyl)-amino]-piperidine-1-carboxylic acid thiazol-2-ylamide A solution of 1,1'-carbonyldiimidazole (79.6 mg, 0.491 mmol), 2-aminothiazole (48.2 mg, 0.481 mmol), and DIPEA (0.17 mL, 0.97 mmol) in $CH_2Cl_2$ (5 mL) and DMF (2 mL) was stirred at room temperature for 4 h. The mixture was concentrated to a minimum volume, diluted with DMF (3 mL), and COMPOUND 249 (150 mg, 0.482 mmol) was added and stirred at 60° C. for 20 hours. The solution was concentrated to dryness, treated with saturated aqueous $NaHCO_3$ (30 mL) and $H_2O$ (10 mL), and extracted with $CH_2Cl_2$ (3×10 mL). The combined organic extracts were dried ($Na_2SO_4$), filtered, and concentrated. Purification of the crude material by flash chromatography on silica gel ($CH_2Cl_2$/MeOH/$NH_4OH$, 90:5:5) followed by radial chromatography on a 1 mm TLC grade silica gel plate ($CH_2Cl_2$/MeOH/$NH_4OH$, 96:2:2) provided COMPOUND 289 (27 mg, 13%) as a white solid. $^1H$ NMR ($CDCl_3$) δ 1.57-1.82 (m, 4H), 1.97 (d, 2H, J=11.7 Hz), 2.08 (s, 6H), 2.64-2.84 (m, 3H), 3.81 (s, 4H), 4.20 (d, 2H, J=12.9 Hz), 6.85 (d, 1H, J=3.6 Hz), 7.09 (dd, 2H, J=7.2, 5.1 Hz), 7.31 (d, 1H, J=3.6 Hz), 7.37 (d, 2H, J=7.5 Hz), 8.34 (d, 2H, J=4.5 Hz), 9.47 (br s, 1H); $^{13}C$ NMR ($CDCl_3$) 18.37, 27.47, 44.83, 54.97, 57.59, 113.16, 122.87, 133.78, 137.00, 138.47, 146.35, 153.46, 157.43, 161.07; ES-MS m/z 459 (M+Na). Anal. Calcd. for $C_{23}H_{28}N_6OS \cdot 0.3H_2O \cdot 0.2 CH_2Cl_2$: C, 60.71; H, 6.37; N, 18.31. Found: C, 61.05; H, 6.61; N, 17.94.

Example 290

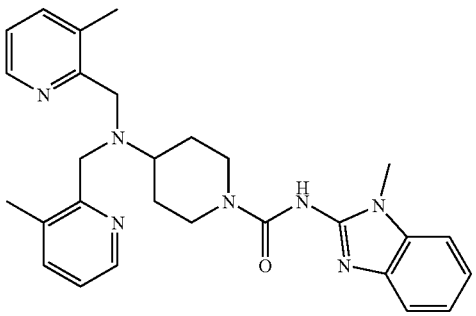

COMPOUND 290: 4-[Bis-(3-methyl-pyridin-2-ylmethyl)-amino]-piperidine-1-carboxylic acid (1-methyl-1H-benzoimidazol-2-yl)-amide A solution of 1,1'-carbonyldiimidazole (80.1 mg, 0.494 mmol), 2-amino-1-methylbenzimidazole (70.8 mg, 0.481 mmol), and DIPEA (0.17 mL, 0.97 mmol) in DMF (5 mL) was stirred at room temperature for 2.5 h. To this solution was added DIPEA (0.17 mL, 0.97 mmol) and COMPOUND 249 (149 mg, 0.479 mmol), and the resultant solution was stirred at 60° C. overnight. The solution was concentrated to dryness, treated with saturated aqueous NaHCO$_3$ (30 mL), and extracted with CH$_2$Cl$_2$ (3×15 mL). The combined organic extracts were dried (Na$_2$SO$_4$), filtered, and concentrated. Purification of the crude material by flash chromatography on silica gel (CH$_2$Cl$_2$/MeOH/NH$_4$OH, 92:4:4) provided COMPOUND 290 (62 mg, 27%) as a white solid. $^1$H NMR (CDCl$_3$) δ 1.63-1.76 (m, 2H), 1.80-2.05 (m, 2H), 2.10 (s, 6H), 2.43-2.80 (m, 3H), 3.54 (s, 3H), 3.83 (s, 4H), 4.61 (br s, 1H), 4.90 (br s, 1H), 7.04-7.20 (m, 6H), 7.36 (d, 2H, J=7.2 Hz), 8.35 (d, 2H, J=1.2 Hz); $^{13}$C NMR (CDCl$_3$) 18.43, 27.22, 28.22, 42.96, 45.27, 55.07, 58.34, 108.42, 110.29, 122.33, 122.36, 122.72, 129.12, 131.10, 133.84, 138.37, 146.25, 154.51, 157.80, 163.72; ES-MS m/z 506 (M+Na). Anal. Calcd. for C$_{28}$H$_{33}$N$_7$O.0.9H$_2$O: C, 67.28; H, 7.02; N, 19.62. Found: C, 67.19; H, 6.97; N, 19.50.

Example 291

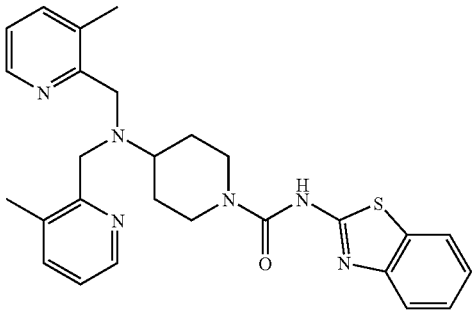

COMPOUND 291: 4-[Bis-(3-methyl-pyridin-2-ylmethyl)-amino]-piperidine-1-carboxylic acid benzothiazol-2-ylamide A solution of 1,1'-carbonyldiimidazole (86.2 mg, 0.531 mmol), 2-aminobenzothiazole (72.6 mg, 0.483 mmol), and DIPEA (0.17 mL, 0.97 mmol) in CH$_2$Cl$_2$ (5 mL) and DMF (3 mL) was stirred at room temperature for 4 h. The mixture was concentrated to a minimum volume, diluted with DMF (3 mL), and COMPOUND 249 (150 mg, 0.482 mmol) was added and stirred at 60° C. for 16 hours. The solution was concentrated to dryness, treated with saturated aqueous NaHCO$_3$ (30 mL) and H$_2$O (10 mL), and extracted with CH$_2$Cl$_2$ (3×15 mL). The combined organic extracts were dried (Na$_2$SO$_4$), filtered, and concentrated. Purification of the crude material by flash chromatography on silica gel (CH$_2$Cl$_2$/MeOH/NH$_4$OH, 90:5:5) provided COMPOUND 291 (107 mg, 45%) as a white solid. $^1$H NMR (CDCl$_3$) δ 1.57-1.76 (m, 2H), 1.94 (d, 2H, J=11.7 Hz), 2.05 (s, 6H), 2.62-2.84 (m, 3H), 3.79 (s, 4H), 4.26 (d, 2H, J=11.7 Hz), 7.02-7.11 (m, 2H), 7.16-7.27 (m, 1H), 7.29-7.40 (m, 3H), 7.58 (d, 1H, J=7.8 Hz), 7.74 (d, 1H, J=7.5 Hz), 8.33 (d, 2H, J=3.9 Hz), 9.91 (br s, 1H); $^{13}$C NMR (CDCl$_3$) 18.36, 27.44, 44.89, 54.89, 57.59, 119.09, 121.83, 122.84, 123.55, 126.34, 131.83, 133.77, 138.46, 146.27, 147.01, 154.75, 157.37, 163.38; ES-MS m/z 509 (M+Na). Anal. Calcd. for C$_{27}$H$_{30}$N$_6$OS.1.0 CH$_2$Cl$_2$: C, 58.84; H, 5.64; N, 14.70. Found: C, 58.69; H, 5.57; N, 14.82.

Example 292

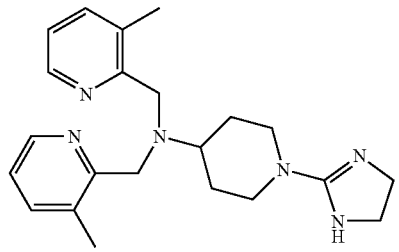

COMPOUND 292: [1-(4,5-Dihydro-1H-imidazol-2-yl)-piperidin-4-yl]-bis-(3-methyl-pyridin-2-ylmethyl)-amine (HBr salt)

Imidazolidine-2-thione (0.31 g, 3.0 mmol) was dissolved in acetone (15 mL) and treated with MeI (0.28 mL, 4.6 mmol). The solution was stirred at reflux for 4 hours and then the solvent removed under reduced pressure to afford 2-methysulfanyl-4,5-dihydro-1H-limidazole (hydroiodide salt) (730 mg, 100%). $^1$H NMR (D$_2$O) 3.93 (s, 4H), 2.61 (s, 3H).

COMPOUND 249 (0.23 g, 0.74 mmol) and 2-methysulfanyl-4,5-dihydro-1H-imidazole (hydroiodide salt) (0.27 g, 1.1 mmol) were dissolved in anhydrous CH$_3$CN (7.0 mL) and DIPEA (0.13 mL, 0.73 mmol) was added. The suspension was stirred at 60° C. for 16 hours. The mixture was then concentrated under reduced pressure and the residue partitioned between CH$_2$Cl$_2$ (20 mL) and brine (15 mL). The organic phase was separated and the aqueous phase was extracted with CH$_2$Cl$_2$ (2×15 mL). The combined organic phases were then dried (Na$_2$SO$_4$), filtered, and concentrated under reduced pressure to give, after purification by column chromatography with silica gel (10:1:0.1 CH$_2$Cl$_2$/MeOH/NH$_4$OH), [1-(4,5-Dihydro-1H-imidazol-2-yl)-piperidin-4-yl]-bis-(3-methyl-pyridin-2-ylmethyl)-amine (66 mg, 24%). Conversion to the HBr salt using General Procedure D gave COMPOUND 292 as a white solid. $^1$H NMR (D$_2$O) δ 1.73 (dq, 2H, J=12.3, 3.9 Hz), 2.11 (br d, 2H, J=11.7 Hz), 2.49 (s, 6H), 3.00 (m, 1H), 3.10 (br t, 2H, J=12.6 Hz), 3.69 (s, 4H), 3.76 (br d, 2H, J=13.5 Hz), 4.34 (s, 4H), 7.82 (t, 1H, J=6.9 Hz), 8.32 (d, 1H, J=7.8 Hz), 8.54 (d, 1H, J=5.7 Hz). $^{13}$C NMR (D$_2$O) δ 17.43 (2C), 27.14 (2C), 43.32 (2C), 46.30 (2C), 51.06 (2C), 59.34, 126.19 (2C), 137.93, 138.79 (2C), 148.72 (2C), 151.01, 159.75. ES-MS m/z 379 (M+H). Anal. Calcd. for C$_{22}$H$_{30}$N$_6$.3.6HBr.3.4H$_2$O.0.3C$_4$H$_{10}$O: C, 36.99; H, 5.81; N, 11.16; Br, 38.19. Found: C, 36.74; H, 5.53; N, 11.07; Br, 38.56.

Example 293

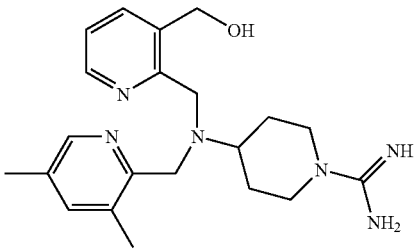

COMPOUND 293: 4-[(3,5-Dimethyl-pyridin-2-ylmethyl)-(3-hydroxymethyl-pyridin-2-ylmethyl)-amino]-piperidine-1-carboxamidine To a solution of 3-hydroxymethyl-2-methylpyridine (2.18 g, 17.7 mmol) (Blank et al. *J. Med. Chem.* 1979, 22, 840) in CH$_2$Cl$_2$ (90 mL) was added Et$_3$N (3.7 mL, 26.6 mmol), DMAP (0.22 g, 1.8 mmol), and tert-butyldimethylchlorosilane (3.2 g, 21.2 mmol) and the reaction was stirred for 2 hours. Brine (60 mL) was added, and the phases were separated. The organic phase was washed again with brine, dried (Na$_2$SO$_4$), and concentrated under reduced pressure to give, after column chromatography with silica gel (1:2 EtOAc: hexanes), 3-(tert-Butyldimethylsilanyloxymethyl)-2-methylpyridine (3.64 g, 86%). $^1$H NMR (CDCl$_3$) δ 0.13 (s, 6H), 0.95 (s, 9H), 2.47 (s, 3H), 4.70 (s, 2H), 7.14 (m, 1H), 7.73 (d, 1H, J=7.5 Hz), 8.38 (d, 1H, J=4.5 Hz).

The above compound (3.64 g, 15.3 mmol) was dissolved in CH$_2$Cl$_2$ (76 mL) and treated with meta-chloroperoxybenzoic acid (5.27 g, 30.5 mmol) over 5.5 hours. The reaction was then quenched with saturated aqueous NaHCO$_3$ (50 mL), the phases separated and the aqueous extracted with CH$_2$Cl$_2$ (70 mL). The combined organic phases were then dried (Na$_2$SO$_4$) and concentrated under reduced pressure to yield, after column chromatography with silica gel (2:98 MeOH:CH$_2$Cl$_2$), the desired N-oxide as a white crystalline solid (3.33 g, 86%).

A solution of the above compound in Ac$_2$O (25 mL, 260 mmol) was heated to 90° C. for 18 h followed by concentration under reduced pressure. This provided the rearranged 2-acetoxymethyl-3-(tert-butyldimethylsilanyloxymethyl)-pyridine as a crude brown oil that was again used immediately in the next reaction.

A solution of the above compound in anhydrous MeOH (50 mL) was treated with K$_2$CO$_3$ and stirred at room temperature for 2 h. The mixture was concentrated under reduced pressure and water (100 ml) was added. The aqueous solution was then extracted with CH$_2$Cl$_2$ (3×120 mL) and the combined organic phases were dried (Na$_2$SO$_4$), filtered, and concentrated under reduced pressure. This gave, after column chromatography with silica gel (2:98 MeOH:CH$_2$Cl$_2$), [3-(tert-Butyldimethylsilanyloxymethyl)-pyridin-2-yl]-methanol as a brown liquid (1.2 g, 36% 2 steps). $^1$H NMR (CDCl$_3$) δ 0.11 (s, 6H), 0.95 (s, 9H), 4.66 (s, 2H), 4.70 (s, 2H), 4.72 (br, 1H, OH), 7.25 (m, 1H), 7.76 (d, 1H, J=7.5 Hz), 8.47 (d, 1H, J=6.0 Hz).

[3-(tert-Butyldimethylsilanyloxymethyl)-pyridin-2-yl]-methanol (1.20 g, 4.7 mmol) was then dissolved in anhydrous CH$_2$Cl$_2$ (24 mL) and treated with MnO$_2$ (4.1 g, 47 mmol) for 18 h at room temperature. The black mixture was filtered through a celite pad and concentrated under reduced pressure. This gave, after column chromatography with silica gel (2:98 MeOH:CH$_2$Cl$_2$), the desired 3-(tert-Butyldimethylsilanyloxymethyl)-pyridine-2-carbaldehyde (1.07 g, 90%).

Using General Procedure B, reaction of 4-[(3,5-Dimethyl-pyridin-2-ylmethyl)-amino]-piperidine-1-carboxylic acid tert-butyl ester, 3-(tert-butyldimethylsilanyloxymethyl)-pyridine-2-carbaldehyde and NaBH(OAc)$_3$ in CH$_2$Cl$_2$ gave (tert-butoxycarbonylimino-{4-[[3-(tert-butyl-dimethylsilanyloxymethyl)-pyridin-2-ylmethyl]-(3,5-dimethyl-pyridin-2-ylmethyl)-amino]-piperidin-1-yl}-methyl)-carbamic acid tert-butyl ester as a yellow oil. Deprotection with 6N HCl gave COMPOUND 293 as a brown crystalline solid. $^1$H NMR (CDCl$_3$) δ 1.79 (qt, 2H, J=12.0 Hz), 2.00 (br d, 2H, J=11.7 Hz), 2.16 (s, 3H), 2.28 (s, 3H), 2.76 (m, 1H), 2.90 (t, 2H, J=12.6 Hz), 3.77 (s, 2H), 3.93 (br, 2H), 3.96 (s, 2H), 4.51 (s, 2H), 7.35 (m, 1H), 7.39 (s, 1H), 7.83 (d, 1H, J=6.6 Hz), 8.11 (s, 1H), 8.35 (dd, 1H, J=5.0, 1.7 Hz). $^{13}$C NMR (CDCl$_3$) δ 18.24, 18.66, 28.14 (2C), 47.14 (2C), 54.20, 56.09, 59.26, 62.15, 125.04, 134.46, 134.60, 138.77, 139.17, 141.26, 147.29, 148.27, 154.68, 157.92, 158.16. ES-MS m/z 383 (M+H). Anal. Calcd. for C$_{21}$H$_{30}$N$_6$O.0.9CH$_2$Cl$_2$.1.8H$_2$O: C, 53.53; H, 7.26; N, 17.10. Found: C, 53.62; H, 7.25; N, 17.16.

Example 294

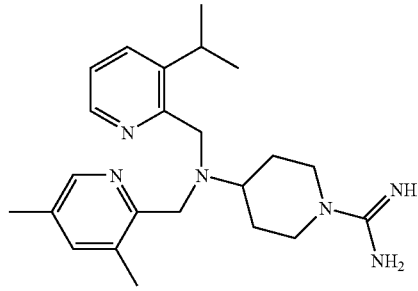

COMPOUND 294: 4-[(3,5-Dimethyl-pyridin-2-ylmethyl)-(3-isopropyl-pyridin-2-ylmethyl)-piperidine]-1-carboxamidine (HBr salt)

Using General Procedure B, reaction of N-Boc-4-piperidone, C-(3,5-dimethylpyridin-2-yl)-methylamine and NaBH(OAc)$_3$ in CH$_2$Cl$_2$ gave 4-[(3,5-dimethyl-pyridin-2-ylmethyl)-amino]-piperidine-1-carboxylic acid tert-butyl ester.

Using General Procedure B, reaction of the compound above, 3-isopropyl-pyridine-2-carbaldehyde and NaBH(OAc)$_3$ in CH$_2$Cl$_2$ gave 4-[(3,5-dimethyl-pyridin-2-ylmethyl)-(3-isopropyl-pyridin-2-ylmethyl)-amino]-piperidine-1-carboxylic acid tert-butyl ester as a yellow oil. $^1$H NMR (CDCl$_3$) δ 0.93 (d, 6H, J=7.5 Hz), 1.45 (s, 9H), 1.58 (br, 2H), 1.83 (br, 2H), 2.18 (s, 3H), 2.28 (s, 3H), 2.59 (m, 3H), 2.81 (qt, 1H, J=7.5 Hz), 3.77 (s, 2H), 3.83 (s, 2H), 4.15 (br, 2H), 7.13 (m, 1H), 7.24 (s, 1H), 7.50 (d, 1H, J=7.0 Hz), 8.18 (s, 1H), 8.32 (d, 1H, J=4.5 Hz). Deprotection with TFA using General Procedure F gave (3,5-dimethyl-pyridin-2-ylmethyl)-(3-isopropyl-pyridin-2-ylmethyl)-piperidin-4-yl-amine.

The secondary amine from above (120 mg, 0.34 mmol) and (tert-butoxycarbonylimino-pyrazol-1-yl-methyl)-carbamic acid tert-butyl ester (110 mg, 0.31 mmol) was stirred in THF (0.5 mL) for 16 hours. The solvent was removed under reduced pressure, CH$_2$Cl$_2$ (10 mL) was added and the organic phase washed with 15% aqueous NaOH solution (5×5 mL). The organic phase was then dried (Na$_2$SO$_4$) and concentrated under reduced pressure to afford, after column chromatography with silica gel (33:1:0.1 CH$_2$Cl$_2$/MeOH:NH$_4$OH), (tert-butoxycarbonylimino-{4-[(3,5-dimethyl-pyridin-2-ylmethyl)-(3-isopropyl-pyridin-2-ylmethyl)-amino]-piperidin-1-yl}-methyl)-carbamic acid tert butyl ester as a sticky solid (157 mg, 78%). Conversion to the HBr salt using General Procedure D gave COMPOUND 294 as a white solid. $^1$H NMR (D$_2$O) δ 1.25 (d, 6H, J=6.9 Hz), 1.72 (dq, 2H, J=12.3, 3.6 Hz), 2.12 (br d, 2H, J=11.4 Hz), 2.42 (s, 3H), 2.45 (s, 3H), 3.04 (t, 2H, J=12.0 Hz), 3.27 (sept, 1H, J=6.9 Hz), 3.92 (d, 2H, J=13.5 Hz), 4.27 (s, 2H), 4.38 (s, 2H), 7.89 (t, 1H, J=6.9 Hz), 8.15 (s, 1H), 8.38 (s, 1H), 8.48 (d, 1H, J=8.4 Hz), 8.54 (d, 1H, J=5.1 Hz). $^{13}$C NMR (D$_2$O) δ 17.25, 17.49, 22.15 (2C), 27.21, 28.32, 45.58 (2C), 50.12, 50.61, 59.61, 126.73, 137.31, 137.86, 138.26, 138.89, 145.00, 147.40, 147.76, 149.45, 149.88, 156.28. ES-MS m/z 395 (M+H). Anal. Calcd. for C$_{23}$H$_{34}$N$_6$·3.3HBr·1.1H$_2$O·0.5C$_4$H$_{10}$O: C, 41.79; H, 6.24; N, 11.70; Br, 36.70. Found: C, 41.66; H, 6.25; N, 11.61; Br, 36.78.

Example 295

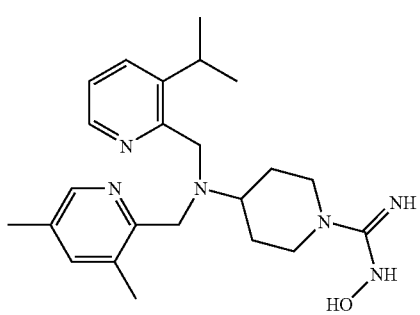

COMPOUND 295: 4-[(3,5-Dimethyl-pyridin-2-ylmethyl)-(3-isopropyl-pyridin-2-ylmethyl)-amino]-N-hydroxypiperidine-1-carboxamidine (3,5-Dimethyl-pyridin-2-ylmethyl)-(3-isopropyl-pyridin-2-ylmethyl)-piperidin-4-yl-amine (0.16 g, 0.45 mmol) was dissolved in MeOH (4 mL) and cooled to 0° C. NaOAc (112 mg, 1.4 mmol) and CNBr (68 mg, 0.64 mmol) were added and the solution was slowly warmed to room temperature and stirred for 6 hours. H$_2$O (15 mL) was added and the solution was extracted with CH$_2$Cl$_2$ (3×30 mL). The combined organics were dried (Na$_2$SO$_4$) and concentrated under reduced pressure to afford 4-[(3,5-dimethyl-pyridin-2-ylmethyl)-(3-isopropyl-pyridin-2-ylmethyl)-amino]-piperidine-1-carbonitrile (134 mg, 79%).

The compound from above (130 mg, 0.35 mmol) was dissolved in DMF (3 mL) and treated with NH$_2$OH.HCl (48 mg, 0.69 mmol) and DIPEA (0.15 mL, 0.87 mmol) at 60° C. for 16 hours. The solution was cooled, CH$_2$Cl$_2$ (15 mL) was added and the organic phase washed with brine (5×15 mL). The organic was then dried (Na$_2$SO$_4$) and concentrated under reduced pressure to afford, after purification by column chromatography with silica gel (20:1:0.1 CH$_2$Cl$_2$/MeOH/NH$_4$OH), COMPOUND 295 as a pale yellow solid (75 mg, 53%). $^1$H NMR (CDCl$_3$) δ 0.93 (d, 6H, J=6.9 Hz), 1.72 (dq, 2H, J=12.3, 3.8 Hz), 1.86 (br d, 2H, J=10.5 Hz), 2.18 (s, 3H), 2.28 (s, 3H), 2.51 (br t, 2H, J=11.1 Hz), 2.59 (m, 1H), 2.82 (sept, 1H, J=6.9 Hz), 3.63 (br d, 2H, J=12.6 Hz), 3.79 (s, 2H), 3.83 (s, 2H), 4.31 (br, 2H), 7.13 (m, 1H), 7.24 (s, 1H), 7.48 (dd, 1H, J=7.8, 1.5 Hz), 8.18 (s, 1H), 8.31 (dd, 1H, J=4.7, 1.5 Hz). $^{13}$C NMR (CDCl$_3$) δ 18.26, 18.47, 23.56 (2C), 26.84 (2C), 27.28, 47.63 (2C), 54.35 (2C), 57.52, 123.06, 132.12, 133.25, 133.79, 139.03, 144.37, 145.97, 146.51, 154.65, 156.41, 157.09. ES-MS m/z 411 (M+H). Anal. Calcd. for C$_{23}$H$_{34}$N$_6$O.0.2CH$_2$Cl$_2$: C, 65.18; H, 8.11; N, 19.66. Found: C, 64.88; H, 8.26; N, 19.37.

Example 296

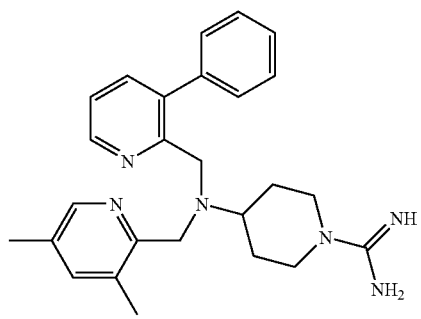

COMPOUND 296: 4-[(3,5-Dimethyl-pyridin-2-ylmethyl)-(3-phenyl-pyridin-2-ylmethyl)-piperidine]-1-carboxamidine (HBr salt)

The secondary amine (3,5-dimethyl-pyridin-2-ylmethyl)-(3-phenyl-pyridin-2-ylmethyl)-piperidin-4-yl-amine (122 mg, 0.32 mmol) and (tert-butoxycarbonylimino-pyrazol-1-yl-methyl)-carbamic acid tert-butyl ester (100 mg, 0.29 mmol) was stirred in THF (0.5 mL) for 16 hours. The solvent was removed under reduced pressure, CH$_2$Cl$_2$ (10 mL) was added and the organic phase washed with 15% aqueous NaOH solution (5×5 mL). The organic phase was then dried (Na$_2$SO$_4$) and concentrated under reduced pressure to afford, after column chromatography with silica gel (33:1:0.1 CH$_2$Cl$_2$/MeOH:NH$_4$OH), (tert-butoxycarbonylimino-{4-[(3,5-dimethyl-pyridin-2-ylmethyl)-(3-phenyl-pyridin-2-ylmethyl)-amino]-piperidin-1-yl}-methyl)-carbamic acid tert butyl ester as a sticky solid (104 mg, 58%), Using General Procedure D: The above material (100 mg, 0.24 mmol) was converted to the HBr salt to provide COMPOUND 296 (96 mg) as a white solid. $^1$H NMR (D$_2$O) δ 1.54 (dq, 2H, J=12.3, 3.6 Hz), 1.89 (d, 2H, J=11.7 Hz), 2.32 (s, 3H), 2.44 (s, 3H), 2.97 (t, 2H, J=12.8 Hz), 3.83 (d, 2H, J=13.5 Hz), 4.08 (s, 2H), 4.33 (s, 2H), 7.39 (m, 2H), 7.61 (m, 3H), 7.96 (m, 1H), 8.09 (s, 1H), 8.31 (s, 1H), 8.39 (dd, 1H, J=8.1, 1.4 Hz), 8.74 (dd, 1H, J=5.7, 1.5 Hz). $^{13}$C NMR (D$_2$O) δ 17.02, 17.46, 27.10 (2C), 45.52 (2C), 50.61, 51.67, 59.84, 126.36, 129.70 (4C), 130.29, 134.11, 137.07, 137.63, 138.29, 140.89, 141.36, 147.76, 147.87, 149.02, 150.80, 156.17. ES-MS m/z 429 (M+H). Anal. Calcd. for C$_{26}$H$_{32}$N$_6$·3.0HBr·2.1H$_2$O: C, 44.04; H, 5.57; N, 11.85; Br, 33.80. Found: C, 44.11; H, 5.57; N, 11.59; Br, 33.74.

Example 297

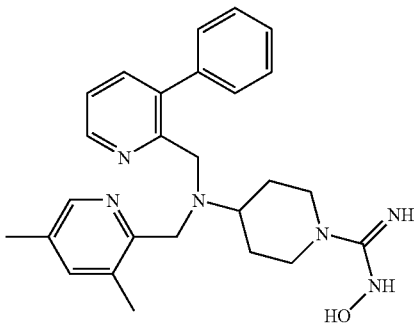

COMPOUND 297: 4-[(3,5-Dimethyl-pyridin-2-ylmethyl)-(3-phenyl-pyridin-2-ylmethyl)-amino]-N-hydroxypiperidine-1-carboxamidine (3,5-Dimethyl-pyridin-2-ylmethyl)-(3-phenyl-pyridin-2-ylmethyl)-amino]-piperidin-4-yl-amine (0.23 g, 0.60 mmol) was dissolved in MeOH (6 mL) and cooled to 0° C. NaOAc (112 mg, 1.4 mmol) and CNBr (68 mg, 0.64 mmol) were added and the solution was slowly warmed to room temperature and stirred for 5 hours. $H_2O$ (20 mL) was added and the solution was extracted with $CH_2Cl_2$ (3×25 mL). The combined organics were then dried ($Na_2SO_4$) and concentrated under reduced pressure to afford 4-[(3,5-dimethyl-pyridin-2-ylmethyl)-(3-phenyl-pyridin-2-ylmethyl)-amino]-piperidine-1-carbonitrile (208 mg, 85%).

The compound from above (204 mg, 0.50 mmol) was dissolved in DMF (5 mL) and treated with $NH_2OH.HCl$ (68 mg, 0.97 mmol) and DIPEA (0.21 mL, 1.22 mmol) at 60° C. for 16 hours. The solution was cooled, $CH_2Cl_2$ (15 mL) was added and the organic phase washed with brine (5×15 mL). The organic was then dried ($Na_2SO_4$) and concentrated under reduced pressure to afford, after purification by column chromatography with silica gel (50:1:0.1 $CH_2Cl_2$/MeOH/$NH_4OH$), COMPOUND 297 as a pale yellow solid (116 mg, 53%). $^1H$ NMR (CDCl$_3$) δ 1.31 (dq, 2H, J=12.0, 3.6 Hz), 1.49 (br d, 2H, J=11.4 Hz), 1.87 (s, 3H), 2.24 (s, 3H), 2.36 (br t, 2H, J=11.1 Hz), 3.46 (br d, 2H, J=12.9 Hz), 3.75 (s, 2H), 3.83 (s, 2H), 4.25 (br, 2H(NH$_2$)), 7.06 (s, 1H), 7.21-7.30 (m, 6H), 7.48 (dd, 1H, J=7.7, 1.6 Hz), 8.06 (s, 1H), 8.53 (dd, 1H, J=4.8, 1.6 Hz). $^{13}$C NMR (CDCl$_3$) δ 18.27 (2C), 26.79 (2C), 47.47 (2C), 54.05, 54.63, 57.78, 122.35, 127.57, 128.52 (2C), 129.41 (2C), 131.70, 133.07, 138.40, 138.93, 139.19, 140.04, 146.31, 147.81, 154.68, 157.11, 157.34. ES-MS m/z 445 (M+H). Anal. Calcd. for $C_{26}H_{32}N_6O.0.4.CH_2Cl_2$: C, 66.26; H, 6.91; N, 17.56. Found: C, 65.91; H, 6.82; N, 17.24.

Example 298

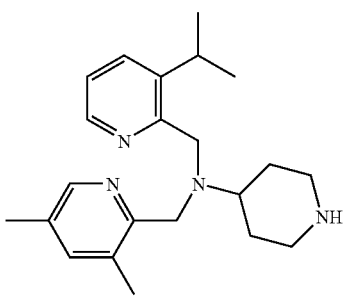

COMPOUND 298: (3,5-Dimethyl-pyridin-2-ylmethyl)-(3-isopropyl-pyridin-2-ylmethyl)-piperidin-4-yl-amine (HBr salt)

Using General Procedure D: Conversion of (3,5-Dimethyl-pyridin-2-ylmethyl)-(3-isopropyl-pyridin-2-ylmethyl)-piperidin-4-yl-amine to the HBr salt gave COMPOUND 298 as a white solid. $^1H$ NMR (D$_2$O) δ 1.24 (d, 6H, J=6.6 Hz), 1.95 (q, 2H, J=12.6 Hz), 2.30 (d, 2H, J=13.2 Hz), 2.42 (s, 3H), 2.46 (s, 3H), 3.00 (t, 2H, J=12.6 Hz), 3.10 (m, 1H), 3.25 (sept, 1H, J=6.6 Hz), 3.55 (d, 2H, J=7.8 Hz), 4.29 (s, 2H), 4.39 (s, 2H), 7.89 (m, 1H), 8.14 (s, 1H), 8.37 (s, 1H), 8.47 (d, 1H, J=8.4 Hz), 8.54 (d, 1H, J=5.7 Hz). $^{13}$C NMR (D$_2$O) δ 17.29, 17.49, 22.16 (2C), 25.02 (2C), 28.33, 44.03 (2C), 50.03, 50.45, 57.77, 126.81, 137.42, 137.98, 138.39, 138.98, 145.03, 147.46 (2C), 149.52 (2C). ES-MS m/z 353 (M+H). Anal. Calcd. for $C_{22}H_{32}N_4.3.2HBr.2.4H_2O.0.3C_4H_{10}O$: C, 41.17; H, 6.40; N, 8.28; Br, 37.77. Found: C, 41.15; H, 6.23; N, 8.21; Br, 37.77.

Example 299

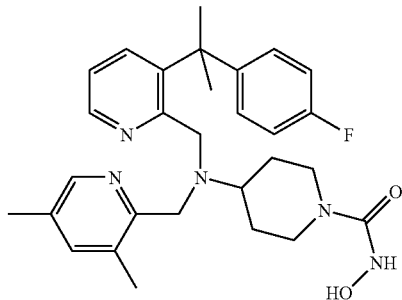

COMPOUND 299: 4-((3,5-Dimethyl-pyridin-2-ylmethyl)-{3-[1-(4-fluoro-phenyl)-1-methyl-ethyl]-pyridin-2-ylmethyl}-amino)-piperidine-1-carboxylic acid hydroxyamide The secondary amine (3,5-Dimethyl-pyridin-2-ylmethyl)-{3-[1-(4-fluoro-phenyl)-1-methyl-ethyl]-pyridin-2-ylmethyl}-piperidin-4-yl-amine (125 mg, 0.28 mmol) and N-(phenoxycarbonyl)hydroxylamine (56 mg, 0.36 mmol) were stirred in THF (3 mL) for 16 hours. The solvent was removed under reduced pressure and the residue purified by radial chromatography with silica gel (15:1:0.1 $CH_2Cl_2$/MeOH:NH$_4$OH), COMPOUND 299 as a sticky solid (66 mg, 47%). $^1H$ NMR (CDCl$_3$) δ 1.25 (q, 2H, J=8.7 Hz), 1.60 (s, 6H), 1.63 (br, 2H), 2.22 (s, 3H), 2.27 (s, 3H), 2.55 (m, 3H), 3.37 (s, 2H), 3.62 (s, 2H), 3.87 (d, 2H, J=12.6 Hz), 6.76 (br, 1H(NH)), 6.88 (m, 4H), 7.20 (m, 2H), 7.83 (d, 1H, J=8.1 Hz), 8.09 (s, 1H), 8.50 (d, 1H, J=3.9 Hz). $^{13}$C NMR (CDCl$_3$) δ 16.26, 16.73, 25.88 (2C), 29.43 (2C), 40.48, 41.98 (2C), 52.39, 52.65, 55.94, 113.46 (d, 2C, J=83 Hz), 119.88, 125.54 (d, 2C, J=30 Hz), 129.87, 131.04, 132.30, 137.28, 141.45, 143.72, 144.62, 144.96, 152.35, 156.10, 159.05, 159.27 (d, 1C, J=974 Hz). ES-MS m/z 506 (M+H). Anal. Calcd. for $C_{29}H_{36}N_5O_2.0.4CH_2Cl_2$: C, 65.44; H, 6.87; N, 12.98. Found: C, 65.28; H, 7.04; N, 12.95.

Example 300

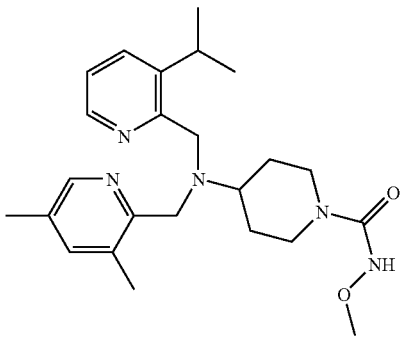

COMPOUND 300: 4-[(3,5-Dimethyl-pyridin-2-ylmethyl)-(3-isopropyl-pyridin-2-ylmethyl)-amino]-piperidine-1-carboxylic acid methoxy-amide Phenylchloroformate (14.78 g, 94.4 mmol) was dissolved in Et$_2$O (375 mL) and methoxylamine hydrochloride (7.88 g, 94.4 mmol), K$_2$CO$_3$ (15.66 g, 113.3 mmol), and water (18 mL) were added and the solution stirred over 64 hours. Solids were filtered, the phases separated, and the organic component concentrated under reduced pressure. The crude liquid was purified by column chromatography with silica gel (1:4 EtOAc/hexanes) to afford N-(phenoxycarbonyl)methoxylamine as a white solid (14.18 g, 90%).

(3,5-Dimethyl-pyridin-2-ylmethyl)-(3-isopropyl-pyridin-2-ylmethyl)-piperidin-4-yl-amine (125 mg, 0.36 mmol) and N-(phenoxycarbonyl)methoxylamine (120 mg, 0.71 mmol) were stirred in THF (3.5 mL) for 16 hours. The solvent was removed under reduced pressure and the residue purified by column chromatography with silica gel (20:1:0.2 CH$_2$Cl$_2$/MeOH:NH$_4$OH), COMPOUND 300 as a sticky solid (110 mg, 72%). $^1$H NMR (CDCl$_3$) δ 0.93 (d, 6H, J=6.9 Hz), 1.62 (dq, 2H, J=12.3, 3.8 Hz), 1.89 (br d, 2H, J=12.3 Hz), 2.16 (s, 3H), 2.28 (s, 3H), 2.64 (br t, 2H, J=12.3 Hz), 2.74 (m, 1H), 2.78 (sept, 1H, J=6.9 Hz), 3.71 (s, 3H), 3.77 (s, 2H), 3.82 (s, 2H), 4.02 (br d, 2H, J=12.0 Hz), 7.13 (br, 1H(NH)), 7.16 (m, 1H), 7.24 (s, 1H), 7.50 (d, 1H, J=7.2 Hz), 8.18 (s, 1H), 8.32 (d, 1H, J=3.9 Hz). $^{13}$C NMR (CDCl$_3$) δ 18.30, 18.45, 23.59 (2C), 27.30 (2C), 27.38, 44.40 (2C), 54.35 (2C), 57.24, 64.49, 123.20, 132.30, 133.23, 133.88, 139.09, 144.42, 146.05, 146.63, 154.42, 156.24, 159.06. ES-MS m/z 426 (M+H). Anal. Calcd. for C$_{24}$H$_{35}$N$_5$O$_2$.0.3CH$_2$Cl$_2$: C, 64.71; H, 7.96; N, 15.53. Found: C, 64.94; H, 8.09; N, 15.88.

Example 301

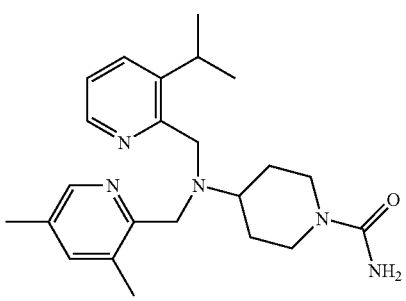

COMPOUND 301: 4-[(3,5-Dimethyl-pyridin-2-ylmethyl)-(3-isopropyl-pyridin-2-ylmethyl)-amino]-piperidine-1-carboxylic acid amide (3,5-Dimethyl-pyridin-2-ylmethyl)-(3-isopropyl-pyridin-2-ylmethyl)-piperidin-4-yl-amine (145 mg, 0.41 mmol) was dissolved in i-PrOH (4 mL) and treated with trimethylsilyl-isocyanate (78 μL, 0.58 mmol) at room temperature for 16 hours. The solution was then concentrated under reduced pressure and dried in vacuo. The crude material was purified by column chromatography with silica gel (15:1:0.1 CH$_2$Cl$_2$/MeOH/NH$_4$OH) to give COMPOUND 301 as a colorless oil (118 mg, 73%). $^1$H NMR (CDCl$_3$) δ 0.93 (d, 6H, J=6.6 Hz), 1.66 (q, 2H, J=11.1 Hz), 1.89 (br d, 2H, J=12.3 Hz), 2.17 (s, 3H), 2.28 (s, 3H), 2.68 (br t, 3H, J=12.3 Hz), 2.82 (sept, 1H, J=6.6 Hz), 3.77 (s, 2H), 3.83 (s, 2H), 4.00 (br d, 2H, J=12.6 Hz), 4.45 (br, 2H(NH$_2$)), 7.15 (m, 1H), 7.24 (s, 1H), 7.50 (d, 1H, J=7.2 Hz), 8.19 (s, 1H), 8.32 (d, 1H, J=3.6 Hz). $^{13}$C NMR (CDCl$_3$) δ 17.91, 18.07, 23.21 (2C), 26.93 (2C), 27.00, 44.49 (2C), 53.97 (2C), 56.89, 122.79, 131.89, 132.84, 133.47, 138.68, 144.03, 145.03, 146.26, 154.10, 155.91, 157.78. ES-MS m/z 396 (M+H). Anal. Calcd. for C$_{23}$H$_{33}$N$_5$O.0.8CH$_2$Cl$_2$: C, 67.39; H, 8.51; N, 17.08. Found: C, 67.33; H, 8.23; N, 17.27.

Example 302

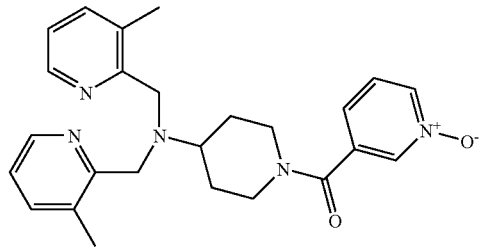

COMPOUND 302: {4-[Bis-(3-methyl-pyridin-2-ylmethyl)-amino]-piperidin-1-yl}-(1-oxy-pyridin-3-yl)-methanone Nicotinic acid N-oxide (405 mg, 2.9 mmol) was dissolved in thionyl chloride (2.9 mmol) and heated to 60° C. for 10 minutes. The solvent was then removed in vacuo and THF (3 mL), COMPOUND 249 (300 mg, 0.96 mmol), and DIPEA (0.50 mL, 2.9 mmol) added. The solution was stirred for 1 hour and diluted with CH$_2$Cl$_2$ (10 mL). The organic was washed with saturated aqueous NaHCO$_3$ solution (15 mL), the phases separated, and the aqueous extracted with CH$_2$Cl$_2$ (3×15 mL). The combined organic phases were dried (Na$_2$SO$_4$) and concentrated under reduced pressure to afford, after column chromatography with silica gel (20:1:0.1 CH$_2$Cl$_2$/MeOH/NH$_4$OH), COMPOUND 302 as a pale yellow solid (253 mg, 61%). $^1$H NMR (CDCl$_3$) δ 1.35 (br, 1H), 1.61 (br, 1H), 2.00 (br, 2H), 2.09 (s, 6H), 2.62 (br, 1H), 2.82 (m, 1H), 2.95 (br, 1H), 3.74 (br, 1H), 3.82 (d, 4H, J=12.6 Hz), 4.72 (br, 1H), 7.10 (m, 2H), 7.26 (m, 1H), 7.32 (d, 1H, J=6.9 Hz), 7.38 (d, 2H, J=7.8 Hz), 8.22 (m, 2H), 8.35 (d, 2H, J=3.9 Hz). ES-MS m/z 432 (M+H).

Example 303

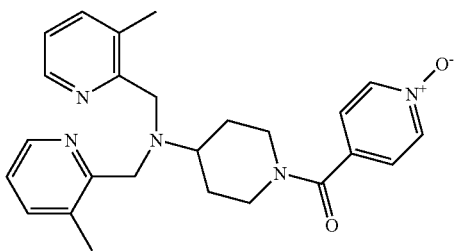

COMPOUND 303: {4-[Bis-(3-methyl-pyridin-2-ylmethyl)-amino]-piperidin-1-yl}-(1-oxy-pyridin-4-yl)-methanone Isonicotinic acid N-oxide (75 mg, 0.54 mmol) was dissolved in thionyl chloride (0.5 mmol) and heated to 60° C. for 10 minutes. The solvent was then removed in vacuo and THF (0.5 mL), COMPOUND 249 (134 mg, 0.43 mmol), and DIPEA (0.10 mL, 0.54 mmol) added. The solution was stirred for 1 hour and diluted with $CH_2Cl_2$ (5 mL). The organic was washed with saturated aqueous $NaHCO_3$ solution (5 mL), the phases separated, and the aqueous extracted with $CH_2Cl_2$ (3×5 mL). The combined organic phases were dried ($Na_2SO_4$) and concentrated under reduced pressure to afford, after column chromatography with silica gel (20:1:0.1 $CH_2Cl_2$/MeOH/$NH_4OH$), COMPOUND 303 as a pale yellow solid (144 mg, 78%). $^1$H NMR (CDCl$_3$) δ 1.67 (br, 2H), 2.00 (br, 2H, J=11.7 Hz), 2.09 (s, 6H), 2.63 (br, 1H), 2.82 (m, 1H), 2.99 (br, 1H), 3.83 (br, 5H), 4.71 (br, 1H), 7.10 (m, 2H), 7.32 (d, 2H, J=6.9 Hz), 7.38 (d, 2H, J=7.5 Hz), 8.21 (d, 2H, J=6.9 Hz), 8.35 (d, 2H, J=3.6 Hz). ES-MS m/z 432 (M+H).

Example 304

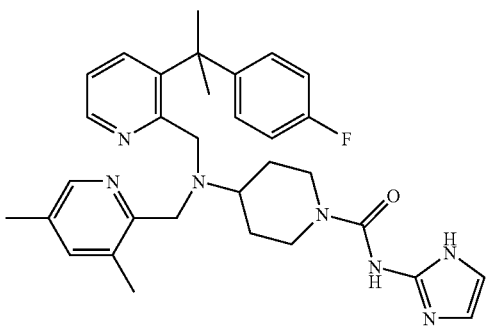

COMPOUND 304: 4-((3,5-Dimethyl-pyridin-2-ylmethyl)-{3-[1-(4-fluoro-phenyl)-1-methyl-ethyl]-pyridin-2-ylmethyl}-amino)-piperidine-1-carboxylic acid (1H-imidazol-2-yl)-amide 2-Aminoimidazole sulfate (87 mg, 0.66 mmol) was dissolved in $CH_2Cl_2$ (7 mL) and treated with 1,1-carbonyldiimidazole (0.112 mg, 0.69 mmol) and DIPEA (0.35 mL, 2.0 mmol). The solution was stirred at room temperature for 16 hours and then concentrated under reduced pressure to afford crude imidazole-1-carboxylic acid (1H-imidazol-2-yl)-amide. DMF (3.5 mL), (3,5-dimethyl-pyridin-2-ylmethyl)-{3-[1-(4-fluoro-phenyl)-1-methyl-ethyl]-pyridin-2-ylmethyl}-piperidine-4-yl-amine (148 mg, 0.33 mmol), and DIPEA (0.35 mL, 2.0 mmol) were then added and the solution heated to 75° C. for 2.5 hours. The reaction was diluted with $CH_2Cl_2$ (5 mL) and washed with brine solution (5 mL), and the organic phase separated. The aqueous was extracted with $CH_2Cl_2$ (2×5 mL) and the combined organics dried ($Na_2SO_4$) and concentrated under reduced pressure to afford, after column chromatography with silica gel (10:1:0.1 $CH_2Cl_2$:MeOH:$NH_4OH$), COMPOUND 304 (90 mg, 49%). $^1$H NMR (CDCl$_3$): δ 1.30 (q, 2H, J=11.1 Hz), 1.59 (s, 6H), 1.68 (d, 2H, J=12.3 Hz), 2.22 (s, 3H), 2.27 (s, 3H), 2.60 (br, 3H), 3.36 (s, 2H), 3.65 (s, 2H), 4.14 (d, 2H, J=12.9 Hz), 6.68 (s, 2H), 6.84 (m, 4H), 7.18 (br, 2H), 7.82 (d, 1H, J=7.5 Hz), 8.08 (s, 1H), 8.50 (d, 1H, J=3.9 Hz). $^{13}$C NMR (CDCl$_3$) δ 18.30, 18.81, 28.24 (2C), 31.49 (2C), 42.53, 44.64 (2C), 54.30, 54.75, 58.03, 115.50 (d, 2C, J=84 Hz), 121.85, 127.53 (d, 2C, J=30 Hz), 131.77, 133.00, 134.29, 139.20, 143.47, 145.43 (2C), 145.75, 146.73, 146.99 (2C), 154.60, 155.69, 158.34, 161.29 (d, 1C, 974 Hz). ES-MS m/z 556 (M+H). Anal. Calcd. for $C_{32}H_{38}N_7OF·0.8H_2O·0.3CH_2Cl_2$: C, 65.14; H, 6.80; N, 16.46; F, 3.19. Found: C, 64.82; H, 6.69; N, 16.59; F, 3.11.

Example 305

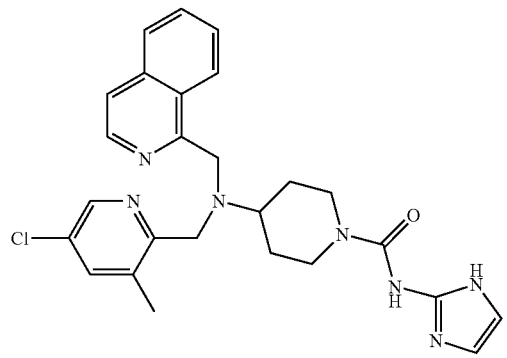

COMPOUND 305: 4-[(5-Chloro-3-methyl-pyridin-2-ylmethyl)-isoquinolin-1-ylmethyl-amino]-piperidine-1-carboxylic acid (1H-imidazol-2-yl)-amide Using General Procedure B, reaction of 5-chloro-3-methylpyridine-2-carbaldehyde, 4-aminopiperidine-1-carboxylic acid tert-butyl ester and NaBH(OAc)$_3$ in $CH_2Cl_2$ gave 4-[(5-chloro-3-methyl-pyridin-2-ylmethyl)-amino]-piperidine-1-carboxylic acid tert-butyl ester as a beige liquid. $^1$H NMR (CDCl$_3$): δ 1.39 (m, 2H), 1.45 (s, 9H), 1.89 (d, 2H, J=12.0 Hz), 2.30 (s, 3H), 2.69 (m, 1H), 2.83 (t, 2H, J=12.0 Hz), 3.87 (s, 2H), 4.03 (br, 2H), 7.44 (s, 1H), 8.34 (s, 1H).

Using General Procedure B, reaction of isoquinoline-1-carbaldehyde, the secondary amine from above and NaBH(OAc)$_3$ in $CH_2Cl_2$ gave 4-[(5-Chloro-3-methyl-pyridin-2-ylmethyl)-isoquinolin-1-ylmethyl-amino]-piperidine-1-carboxylic acid tert-butyl ester. Deprotection with TFA using General Procedure F gave (5-Chloro-3-methyl-pyridin-2-ylmethyl)-isoquinolin-1-ylmethyl-piperidine-4-yl-amine as a white solid.

The amine above (101 mg, 0.27 mmol) and imidazole-1-carboxylic acid (1H-imidazol-2-yl)-amide (159 mg, 0.54 mmol) were combined in DMF (3.0 mL) and treated with DIPEA (0.28 mL, 1.6 mmol). The solution was stirred at 75° C. for 2 hours and then concentrated under reduced pressure. This afforded, after column chromatography with silica gel (50:1:0.1 $CH_2Cl_2$:MeOH:$NH_4OH$), COMPOUND 305 as a light beige solid (89 mg, 69%). $^1$H NMR ($CDCl_3$): δ 1.75 (q, 2H, J=11.1 Hz), 1.96 (s, 3H), 1.99 (br, 2H), 2.75 (br, 3H), 3.86 (s, 2H), 4.26 (s, 2H), 4.36 (d, 2H, J=12.9 Hz), 6.70 (s, 2H), 7.31 (s, 1H), 7.40 (t, 1H, J=7.2 Hz), 7.54 (d, 1H, J=5.7 Hz), 7.61 (t, 1H, J=7.8 Hz), 7.77 (d, 1H, J=8.1 Hz), 7.96 (d, 1H, J=8.4 Hz), 8.26 (br, 1H), 8.44 (d, 1H, J=5.7 Hz). $^{13}$C NMR ($CDCl_3$) δ 18.43, 27.69 (2C), 44.71 (2C), 54.85, 55.59, 58.61, 120.96, 126.46 (2C), 126.85, 127.39, 128.02, 130.24, 130.90, 135.20, 136.67, 137.75, 141.78, 145.10 (2C), 145.50, 155.66, 155.83, 158.97. ES-MS m/z 491 (M+H). Anal. Calcd. for $C_{26}H_{28}N_7OCl.0.3H_2O.0.3CH_2Cl_2$: C, 60.64; H, 5.65; N, 18.82; Cl, 10.89. Found: C, 60.63; H, 5.65; N, 18.82; Cl, 10.82.

Example 306

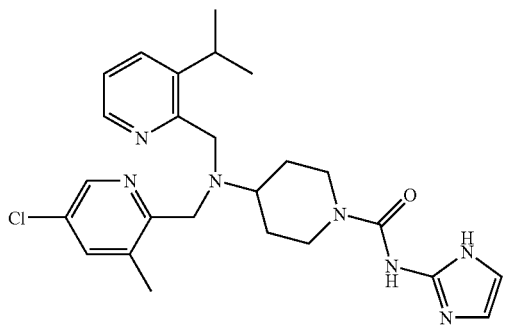

COMPOUND 306: 4-[(5-Chloro-3-methyl-pyridin-2-ylmethyl)-(3-isopropyl-pyridin-2-ylmethyl)-amino]-piperidine-1-carboxylic acid (1H-imidazol-2-yl)-amide The amine (5-Chloro-3-methyl-pyridin-2-ylmethyl)-(3-isopropyl-pyridin-2-ylmethyl)-piperidin-4-yl-amine (161 mg, 0.41 mmol), and imidazole-1-carboxylic acid (1H-imidazol-2-yl)-amide (246 mg, 0.82 mmol) were combined in DMF (4.0 mL) and treated with DIPEA (0.43 mL, 2.5 mmol). The solution was stirred at 75° C. for 2 hours and then concentrated under reduced pressure. This afforded, after column chromatography with silica gel (50:1:0.1 $CH_2Cl_2$:MeOH:$NH_4OH$), COMPOUND 306 as a white solid (66 mg, 33%). $^1$H NMR ($CDCl_3$): δ 0.99 (d, 6H, J=6.6 Hz), 1.65 (q, 2H, J=11.1 Hz), 1.93 (d, 2H, J=11.4 Hz), 2.14 (s, 3H), 2.74 (t, 3H, J=12.0 Hz), 2.84 (sept, 1H), 3.79 (s, 2H), 3.82 (s, 2H), 4.32 (d, 2H, J=12.0 Hz), 6.70 (s, 2H), 7.17 (m, 1H), 7.42 (s, 1H), 7.52 (d, 1H, J=7.2 Hz), 8.33 (d, 1H, J=6.0 Hz). $^{13}$C NMR ($CDCl_3$) δ 18.40, 23.60 (2C), 27.59, 27.61 (2C), 44.72 (2C), 54.09, 54.29, 57.67, 123.30, 130.98, 133.91, 135.23, 137.74, 144.26, 144.98 (2C), 145.50, 146.14 (2C), 155.81, 155.86, 155.93. ES-MS m/z 483 (M+H). Anal. Calcd. for $C_{25}H_{32}N_7OCl.0.2CH_2Cl_2$: C, 60.66; H, 6.54; N, 19.65; Cl, 9.95. Found: C, 60.60; H, 6.57; N, 19.80; Cl, 9.69.

Example 307

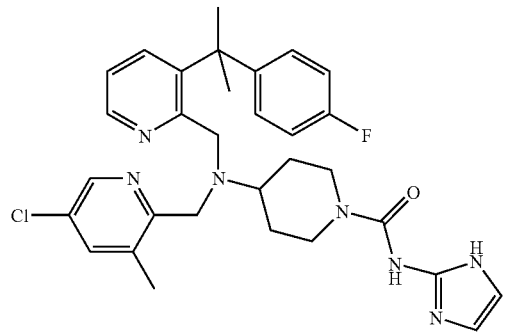

COMPOUND 307: 4-((5-Chloro-3-methyl-pyridin-2-ylmethyl)-{3-[1-(4-fluoro-phenyl)-1-methyl-ethyl]-pyridin-2-ylmethyl}-amino)-piperidine-1-carboxylic acid (1H-imidazol-2-yl)-amide Using General Procedure B, reacting of 3-[1-(4-fluoro-phenyl)-1-methyl-ethyl]-pyridine-2-carbaldehyde, 4-[(5-chloro-3-methyl-pyridin-2-ylmethyl)-amino]-piperidine-1-carboxylic acid tert-butyl ester and $NaBH(OAc)_3$ in $CH_2Cl_2$ gave 4-((5-chloro-3-methyl-pyridin-2-ylmethyl)-{3-[1-(4-fluoro-phenyl)-1-methyl-ethyl]-pyridin-2-ylmethyl}-amino)-piperidine-1-carboxylic acid tert-butyl ester. $^1$H NMR ($CDCl_3$): δ 1.22 (br, 2H), 1.44 (s, 9H), 1.59 (br, 2H), 1.60 (s, 6H), 2.27 (s, 3H), 2.47 (m, 3H), 3.34 (s, 2H), 3.65 (s, 2H), 4.03 (br, 2H), 6.87 (m, 4H), 7.18 (m, 1H), 7.36 (s, 1H), 7.82 (d, 1H, J=7.2 Hz), 8.21 (s, 1H), 8.48 (d, 1H, J=3.9 Hz). Deprotection with TFA using General Procedure F gave (5-chloro-3-methyl-pyridin-2-ylmethyl)-{3-[1-(4-fluoro-phenyl)-1-methyl-ethyl]-pyridin-2-ylmethyl}-piperidine-4-yl-amine as a white solid.

The amine from above (131 mg, 0.28 mmol), and imidazole-1-carboxylic acid (1H-imidazol-2-yl)-amide (168 mg, 0.56 mmol) were combined in DMF (4.0 mL) and treated with DIPEA (0.29 mL, 1.7 mmol). The solution was stirred at 75° C. for 2 hours and then concentrated under reduced pressure. This afforded, after column chromatography with silica gel (25:1:0.1 $CH_2Cl_2$:MeOH:$NH_4OH$), COMPOUND 307 (72 mg, 45%). $^1$H NMR ($CDCl_3$): δ 1.30 (q, 2H, J=11.1 Hz), 1.59 (s, 6H), 1.66 (d, 2H, J=12.3 Hz), 2.26 (s, 3H), 2.61 (br t, 3H, J=11.7 Hz), 3.35 (s, 2H), 3.65 (s, 2H), 4.14 (d, 2H, J=13.2 Hz), 6.68 (s, 2H), 6.86 (m, 4H), 7.19 (br, 2H), 7.37 (s, 1H), 7.82 (d, 1H, J=7.5 Hz), 8.20 (s, 1H), 8.48 (br d, 1H). $^{13}$C NMR ($CDCl_3$) δ 18.40, 18.81, 28.08 (2C), 31.12 (2C), 42.14, 44.20 (2C), 54.06, 54.67, 58.01, 115.13 (d, 2C, J=84 Hz), 121.44, 127.07 (d, 2C, J=30 Hz), 130.07, 133.81, 134.84, 137.31, 142.96, 144.59 (2C), 145.07, 145.36, 146.61 (2C), 155.31, 155.96, 157.96, 161.91 (d, 1C, 975 Hz). ES-MS m/z 577 (M+H). Anal. Calcd. for $C_{31}H_{35}N_7OClF.0.2CH_2Cl_2.0.2H_2O$: C, 62.46; H, 6.02; N, 16.32; Cl, 8.85; F, 3.16. Found: C, 62.60; H, 6.02; N, 16.09; Cl, 8.79; F, 2.94.

Example 308

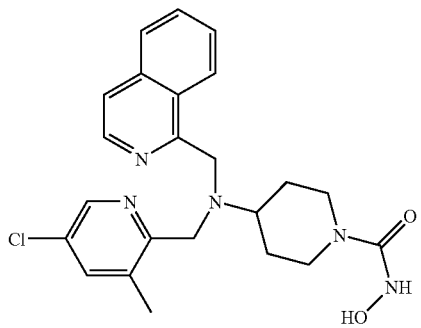

COMPOUND 308: 4-[(5-Chloro-3-methyl-pyridin-2-ylmethyl)-isoquinolin-1-ylmethyl-amino]-piperidine-1-carboxylic acid hydroxyamide A solution of (5-Chloro-3-methyl-pyridin-2-ylmethyl)-isoquinolin-1-ylmethyl-piperidine-4-yl-amine (140 mg, 0.37 mmol) and N-(phenoxycarbonyl)hydroxylamine (112 mg, 0.74 mmol) in anhydrous THF (4 mL) was stirred for 16 hours at 70° C. The solution was then cooled and concentrated under reduced pressure and dried in vacuo. The crude material was purified by column chromatography with silica gel (50:1:0.1 $CH_2Cl_2$/MeOH/$NH_4OH$) to give COMPOUND 308 as a white solid (82 mg, 51%). $^1H$ NMR ($CDCl_3$): δ 1.73 (q, 2H, J=11.1 Hz), 1.96 (s, 3H), 1.99 (br, 2H), 2.70 (br, 3H), 3.85 (s, 2H), 4.05 (d, 2H, J=13.2 Hz), 4.26 (s, 2H), 6.65 (br, 1H(OH)), 6.81 (br s, 1H(NH)), 7.33 (s, 1H), 7.42 (t, 1H, J=7.2 Hz), 7.54 (d, 1H, J=4.8 Hz), 7.62 (t, 1H, J=7.8 Hz), 7.77 (d, 1H, J=7.8 Hz), 7.95 (d, 1H, J=7.2 Hz), 8.26 (s, 1H), 8.39 (d, 1H, J=3.6 Hz). $^{13}C$ NMR ($CDCl_3$) δ 18.75, 28.62 (2C), 45.17 (2C), 56.17, 56.61, 61.23, 122.76, 127.88, 128.44, 128.59, 129.29, 132.10, 132.65, 137.35, 138.33, 139.35, 141.74, 145.51, 156.93, 160.35, 162.80. ES-MS m/z 441 (M+H). Anal. Calcd. for $C_{23}H_{26}N_5O_2Cl.0.2H_2O$: C, 62.28; H, 6.00; N, 15.79; Cl, 7.99. Found: C, 62.31; H, 5.83; N, 15.50; Cl, 8.06.

Example 309

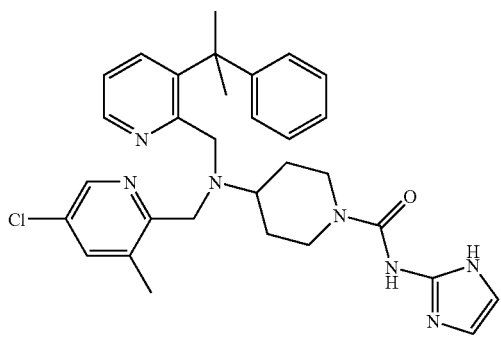

COMPOUND 309: 4-{(5-Chloro-3-methyl-pyridin-2-ylmethyl)-[3-(1-methyl-1-phenyl-ethyl)-pyridin-2-ylmethyl]-amino}-piperidine-1-carboxylic acid (1H-imidazol-2-yl)-amide Using General Procedure B, reaction of 3-(1-methyl-1-phenyl-ethyl)-pyridine-2-carbaldehyde, 4-[(5-chloro-3-methyl-pyridin-2-ylmethyl)-amino]-piperidine-1-carboxylic acid tert-butyl ester and NaBH(OAc)$_3$ in $CH_2Cl_2$ gave 4-{(5-Chloro-3-methyl-pyridin-2-ylmethyl)-[3-(1-methyl-1-phenyl-ethyl)-pyridin-2-ylmethyl]-amino}-piperidine-1-carboxylic acid tert-butyl ester as a white solid. $^1H$ NMR ($CDCl_3$): δ 1.13 (q, 2H, J=11.1 Hz), 1.44 (s, 9H), 1.50 (br, 2H), 1.62 (s, 6H), 2.28 (s, 3H), 2.43 (m, 3H), 3.34 (s, 2H), 3.61 (s, 2H), 3.98 (br, 2H), 6.98 (m, 2H), 7.17 (m, 4H), 7.35 (s, 1H), 7.85 (d, 1H, J=7.2 Hz), 8.20 (s, 1H), 8.48 (d, 1H, J=3.9 Hz). Deprotection with TFA using General Procedure F gave (5-Chloro-3-methyl-pyridin-2-ylmethyl)-[3-(1-methyl-1-phenyl-ethyl)-pyridin-2-ylmethyl]-piperidin-4-yl-amine as a white solid.

The amine from above (230 mg, 0.50 mmol), and imidazole-1-carboxylic acid (1H-imidazol-2-yl)-amide (300 mg, 1.0 mmol) were combined in DMF (2.5 mL) and treated with DIPEA (0.52 mL, 3.0 mmol). The solution was stirred at 75° C. for 3 hours and then concentrated under reduced pressure. This afforded, after column chromatography with silica gel (50:1:0.2 $CH_2Cl_2$:MeOH:$NH_4OH$), COMPOUND 309 (180 mg, 65%). $^1H$ NMR ($CDCl_3$): δ 1.17 (q, 2H, J=12.3 Hz), 1.55 (d, 2H, J=12.3 Hz), 1.61 (s, 6H), 2.29 (s, 3H), 2.53 (m, 3H), 3.36 (s, 2H), 3.64 (s, 2H), 4.08 (d, 2H, J=12.9 Hz), 6.68 (s, 2H), 7.00 (d, 2H, J=7.5 Hz), 7.08 (m, 1H), 7.19 (m, 3H), 7.36 (s, 1H), 7.85 (d, 1H, J=7.5 Hz), 8.20 (s, 1H), 8.48 (br d, 1H, J=3.3 Hz). $^{13}C$ NMR ($CDCl_3$) δ 18.87, 28.30 (2C), 31.29 (2C), 42.88, 44.58 (2C), 54.13, 55.33, 58.30, 121.67, 126.02 (2C), 126.32, 128.88 (2C), 130.40, 134.13, 135.41, 137.73, 143.49, 144.91 (2C), 145.48, 146.91 (2C), 149.84, 155.60, 156.53, 158.59. ES-MS m/z 559 (M+H). Anal. Calcd. for $C_{31}H_{36}N_7OCl.0.3CH_2Cl_2$: C, 64.42; H, 6.32; N, 16.80; Cl, 9.72. Found: C, 64.26; H, 6.35; N, 16.64; Cl, 9.47.

Example 310

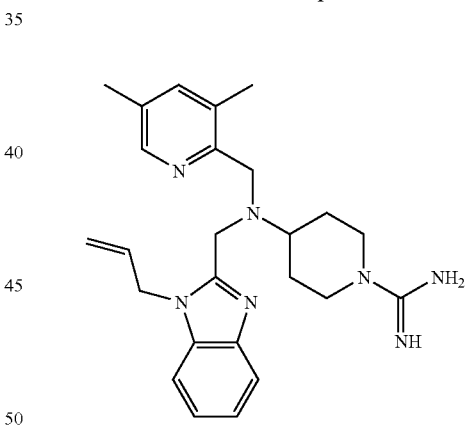

COMPOUND 310: 4-[(1-allyl-1H-benzomidazol-2-ylmethyl)-(3,5-dimethyl-pyridin-2-ylmethyl)-amino]-piperidine-1-carboxamidine Using General Procedure B: Reaction of the 4-[(3,5-dimethyl-pyridin-2-ylmethyl)-amino]-piperidine-1-carboxylic acid tert-butyl ester and 1-allyl-1H-benzoimidazole-2-carbaldehyde in $CH_2Cl_2$ with NaBH(OAc)$_3$ gave 4-[(1-allyl-1H-benzoimidazol-2-ylmethyl)-(3,5-dimethyl-pyridin-2-ylmethyl)-amino]-piperidine-1-carboxylic acid tert-butyl ester as white foam. $^1H$ NMR ($CDCl_3$) δ 1.44 (s, 9H), 1.57-1.65 (m, 2H), 1.86-1.89 (m, 2H), 2.25 (s, 3H), 2.27 (s, 3H), 2.57 (t, 2H, J=12.0 Hz), 2.72 (td, 2H, J=10.5, 3.0 Hz), 3.78 (s, 2H), 3.98 (s, 2H), 4.15-4.17 (m, 2H), 4.53 (d, 2H, J=3.0 Hz), 4.65 (d, 1H, J=18.0 Hz), 4.98 (d, 1H, J=9.0 Hz), 5.51-5.63 (m, 1H), 7.20-7.24 (m, 4H), 7.70-7.73 (m, 1H), 8.19 (s, 1H). Deprotection with TFA using General Procedure F gave (1-allyl-1H-benzoimidazol-2-ylmethyl)-(3,5-dimethyl-pyridin-2-ylmethyl)-piperidin-4-yl-amine as a yellow solid. $^1$H NMR (CDCl$_3$) δ 1.72 (br t, 2H, J=10.5 Hz), 1.93 (d, 2H, J=11.1 Hz), 2.25 (s, 3H), 2.26 (s, 3H), 2.54 (t, 2H, J=12.0 Hz), 2.69 (t, 1H, J=11.4 Hz), 3.17 (d, 2H, J=11.4 Hz), 3.38 (br s, 2H), 3.82 (s, 2H), 3.99 (s, 2H), 4.55 (s, 2H), 4.65 (d, 1H, J=17.4 Hz), 4.97 (d, 1H, J=10.2 Hz), 5.53-5.62 (m, 1H), 7.20-7.23 (m, 4H), 7.71 (d, 1H, J=4.8 Hz), 8.18 (s, 1H).

To a solution of the above amine (81 mg, 0.21 mmol) in THF (3 mL) was added (tert-butoxycarbonylimino-pyrazol-1-yl-methyl)-carbamic acid tert-butyl ester (64 mg, 0.21 mmol) and the mixture was stirred overnight. Then the solvent was removed under reduced pressure. The residue was dissolved in CH$_2$Cl$_2$ (20 mL) and washed with NaOH (15%, 3×15 mL). The organic layer was dried (MgSO$_4$), filtered, and concentrated to afford a pale yellow foam. Purification by radial chromatography on silica gel (1 mm plate; using NH$_4$—OH/MeOH/CH$_2$Cl$_2$; 1:1:100) afforded the product as an impure yellow oil (87 mg), which was used without further purification. Deprotection of the above amide with TFA using General Procedure F gave COMPOUND 310 as a yellow oil. $^1$H NMR (CDCl$_3$) δ 1.69 (br s, 2H), 1.89 (br s, 2H), 2.16 (s, 3H), 2.20 (s, 3H), 2.73 (br d, 3H, J=9.0 Hz), 3.45 (s, 1H), 3.68 (s, 2H), 3.89 (s, 2H), 4.11 (br s, 2H), 4.47 (s, 2H), 4.60 (d, 2H, J=18.0 Hz), 4.94 (d, 2H, J=12.0 Hz), 5.49-5.59 (m, 1H), 7.16 (s, 4H), 7.6317-7.68 (m, 4H), 8.08 (s, 1H). $^{13}$C NMR (CDCl$_3$) δ 18.24, 18.64, 26.87, 45.85, 46.22, 47.22, 53.76, 57.37, 110.28, 116.85, 119.70, 122.36, 123.04, 132.54, 132.96, 135.87, 139.46, 142.35, 146.81, 151.90, 153.69, 156.73. ES-MS m/z 432 [M+H]$^+$. Anal. Calcd. for C$_{25}$H$_{33}$N$_7$.1.4CH$_2$Cl$_2$.0.4NH$_4$OH: C, 56.17; H, 6.75; N, 18.36. Found: C, 55.91; H, 6.59; N, 18.25.

Example 311

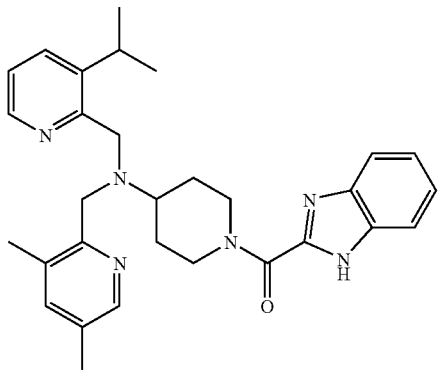

COMPOUND 311: (1H-benzoimidazol-2-yl)-{4-[(3,5-dimethyl-pyridin-2-ylmethyl)-(3-isopropyl-pyridin-2-ylmethyl)-amino]-piperidin-1-yl}-methanone A mixture of the (3,5-dimethyl-pyridin-2-ylmethyl)-(3-isopropyl-pyridin-2-ylmethyl)-piperidin-4-yl-amine (211 mg, 0.60 mmol), 1H-benzimidazole-2-carboxylic acid (107 mg, 0.66 mmol), HOBT (97 mg, 0.72 mmol), EDCI (142 mg, 0.72 mmol), and DIPEA (142 mg, 0.72 mmol) in DMF (5 mL) was stirred at room temperature overnight. The mixture was then diluted with CH$_2$Cl$_2$ (25 mL) and saturated NaHCO$_3$ (3×20 mL). The organic layer was dried (MgSO$_4$), filtered, and concentrated to afford a yellow oil. Purification by radial chromatography on silica gel (2 mm plate; using CH$_2$Cl$_2$/MeOH/NH$_4$OH; 100:1:1→25:1:1) afforded the product as a white foam (160 mg, 54%). $^1$H NMR (CDCl$_3$) δ 0.93 (t, 2H, J=6.9 Hz), 1.69-1.92 (m, 2H), 2.09 (br t, 3H, J=14.7 Hz), 2.18 (s, 3H), 2.27 (s, 3H), 2.68-2.83 (m, 2H), 2.87-2.94 (m, 1H), 3.04-3.13 (m, 1H), 3.79 (d, 2H, J=5.1 Hz), 3.86 (s, 2H), 4.94 (d, 1H, J=13.5 Hz), 6.16 (d, 1H, J=12.9 Hz), 7.15 (dd, 1H, J=7.8, 4.8 Hz), 7.25 (s, 1H), 7.31 (d, 2H, J=3.9 Hz), 7.50 (d, 2H, J=6.6 Hz), 7.82 (br s, 1H), 8.19 (s, 1H), 8.34 (dd, 1H, J=4.7, 1.2 Hz). $^{13}$C NMR (CDCl$_3$) δ 18.31, 18.53, 23.60, 23.68, 27.35, 27.42, 28.66, 44.20, 47.20, 54.34, 57.35, 112.35, 121.26, 123.22, 125.11, 132.31, 133.26, 133.61, 133.92, 139.10, 143.52, 144.45, 145.85, 146.09, 146.64, 154.45, 156.28, 159.23. ES-MS m/z 497 [M+H]$^+$. Anal. Calcd. for C$_{30}$H$_{36}$N$_6$O.—0.8CH$_2$Cl$_2$: C, 65.52; H, 6.71; N, 14.88. Found: C, 65.54; H, 6.62; N, 15.11.

Example 312

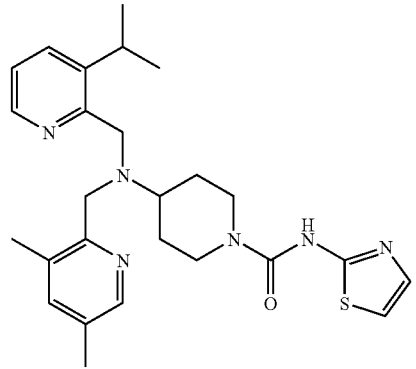

COMPOUND 312: 4-[(3,5-dimethyl-pyridin-2-ylmethyl)-(3-isopropyl-pyridin-2-ylmethyl)-amino]-piperidine-1-carboxylic acid thiazol-2-ylamide To a solution of 2-aminothiazole (48 mg, 0.45 mmol) in CH$_2$Cl$_2$ (5 mL) was added 1,1'-carbonyldiimidazole (90 mg, 0.55 mmol) and the reaction was stirred at room temperature for 4 h. The reaction mixture was concentrated and dried in vacuo. The tan residue was dissolved in a solution of the (3,5-dimethyl-pyridin-2-ylmethyl)-(3-isopropyl-pyridin-2-ylmethyl)-piperidine-4-yl-amine (80 mg, 0.23 mmol) in CH$_3$CN (5 mL) and warmed to 60° C. After 2 h at 60° C., the mixture was cooled and diluted with CH$_2$Cl$_2$/saturated NaHCO$_3$ (1:1, 60 mL). The aqueous layer was extracted with CH$_2$Cl$_2$ (2×20 mL). The combined organic layer was dried (MgSO$_4$), filtered, and concentrated to afford a yellow oil. Purification by radial chromatography on silica gel (1 mm plate; using CH$_2$Cl$_2$/MeOH/NH$_4$OH; 100:1:1→25:1:1) afforded the product as a yellow oil (40 mg, 19%). $^1$H NMR (CDCl$_3$) δ 0.94 (d, 6H, J=6.0 Hz), 1.63 (br m, 2H), 1.96 (d, 2H, J=12.0 Hz), 2.16 (s, 3H), 2.28 (s, 3H), 2.74-2.82 (m, 4H), 3.77 (s, 2H), 3.83 (s, 2H), 4.17 (s, 1H), 4.21 (s, 1H), 6.86 (d, 1H, J=3.0 Hz), 7.11-7.17 (m, 1H), 7.26 (s, 1H), 7.33 (d, 1H, J=3.0 Hz), 7.51 (d, 1H, J=9.0 Hz), 8.19 (s, 1H), 8.33 (d, 1H, J=3.0 Hz), 9.16 (br s, 1H). $^{13}$C NMR (CDCl$_3$) δ 18.30, 18.47, 23.61, 27.44, 27.50, 30.09, 44.86, 53.85, 54.30, 113.09, 122.38, 123.26, 132.39, 133.25, 133.96, 135.57, 136.72, 139.16, 144.45, 146.06, 146.63, 153.93, 154.34, 156.16, 162.92. ES-MS m/z 479 [M+H]$^+$. Anal. Calcd. for C$_{26}$H$_{34}$N$_6$—SO.0.7CH$_2$Cl$_2$.0.7CH$_3$CN: C, 59.54; H, 6.67; N, 16.56; S, 5.66. Found: C, 59.40; H, 6.91; N, 16.49; S, 5.46.

Example 313

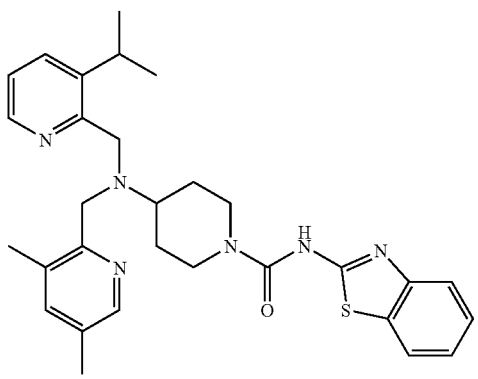

COMPOUND 313: 4-[(3,5-dimethyl-pyridin-2-ylmethyl)-(3-isopropyl-pyridin-2-ylmethyl)-amino]-piperidine-1-carboxylic acid benzothiazol-2-ylamide To a solution of 1,1'-carbonyldiimidazole (125 mg, 0.77 mmol) in $CH_2Cl_2$ (5 mL) was added 2-aminobenzothiazole (95 mg, 0.64 mmol). The resulting suspension was stirred for 2 h and then concentrated under reduced pressure. The residue was dissolved in $CH_3CN$ (5 mL) and was treated with (3,5-dimethyl-pyridin-2-ylmethyl)-(3-isopropyl-pyridin-2-ylmethyl)-piperidine-4-yl-amine (112 mg, 0.32 mmol) and the reaction mixture was stirred at 60° C. overnight. Then the mixture was cooled and diluted with $CH_2Cl_2$/saturated $NaHCO_3$ (1:1, 40 mL). The aqueous layer was extracted with $CH_2Cl_2$ (2×20 mL). The combined organic layers were dried ($MgSO_4$), filtered, and concentrated to afford a pink foam. Purification by radial chromatography on silica gel (2 mm plate; using $CH_2Cl_2$/MeOH/$NH_4OH$; 50:1:1) afforded the product as a white solid (84 mg, 50%). $^1$H NMR ($CDCl_3$) δ 0.91 (d, 6H, J=6.9 Hz), 1.60-1.72 (m, 2H), 1.91 (d, 2H, J=11.4 Hz), 2.14 (s, 3H), 2.27 (s, 3H), 2.68-2.80 (m, 4H), 3.74 (s, 2H), 3.81 (s, 2H), 4.24 (br s, 1H), 4.28 (br s, 1H), 7.13 (dd, 1H, J=7.8, 4.8 Hz), 7.148-7.24 (m, 2H), 7.35 (t, 1H, J=7.2 Hz), 7.48 (dd, 1H, J=7.8, 1.5 Hz), 7.58 (br d, 1H, J=8.1 Hz), 7.74 (br d, 1H, J=7.8 Hz), 8.18 (s, 1H), 8.31 (dd, 1H, J=4.5, 1.5 Hz). $^{13}$C NMR ($CDCl_3$) δ 18.30, 18.47, 23.61, 27.41, 27.65, 44.94, 54.31, 57.18, 119.37, 121.81, 123.20, 123.58, 126.35319 132.04, 132.31, 133.18, 133.87, 139.07, 144.38, 146.11, 146.68, 147.39, 154.36, 156.18, 162.71. ES-MS m/z 529 [M+H]$^+$. Anal. Calcd. for $C_{30}H_{36}N_6OS \cdot 0.1CH_2Cl_2$: C, 67.30; H, 6.79; N, 15.64; S, 5.97. Found: C, 67.56; H, 6.86; N, 15.52; S, 5.89.

Example 314

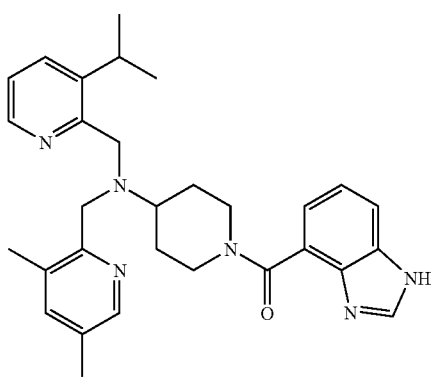

COMPOUND 314: (1H-benzoimidazol-2-yl)-{4-[(3,5-dimethyl-pyridin-2-ylmethyl)-(3-isopropyl-pyridin-2-ylmethyl)-amino]-piperidin-1-yl}-methanone To a solution of (3,5-dimethyl-pyridin-2-ylmethyl)-(3-isopropyl-pyridin-2-ylmethyl)-piperidine-4-yl-amine (101 mg, 0.29 mmol) and 1H-benzoimidazole-4-carbonyl chloride (55 mg, 0.30 mmol) in $CH_2Cl_2$ (5 mL) was added $Et_3N$ (80 μL, 0.58 mmol) and the mixture was stirred at room temperature overnight. The mixture was heated to 60° C. for 2 h when the TLC indicated the reaction had not completed. Then the reaction mixture was cooled, diluted with $CH_2Cl_2$ (20 mL), and washed with saturated $NaHCO_3$ (3×20 mL). The organic layer was dried ($MgSO_4$), filtered, and concentrated to afford a pale yellow foam. Purification by radial chromatography on silica gel (1 mm plate; using $CH_2Cl_2$/MeOH/$NH_4OH$; 100:1:1→25:1:1) afforded the product as a yellow oil (45 mg, 31%). $^1$H NMR ($CDCl_3$) δ 0.95 (d, 6H, J=9.0 Hz), 1.70-1.72 (m, 2H), 1.90-1.92 (m, 2H), 2.19 (s, 3H), 2.29 (s, 3H), 2.79-2.83 (m, 4H), 3.82 (s, 2H), 3.87 (s, 2H), 7.17 (dd, 1H, J=6.0, 3.0 Hz), 7.26 (s, 1H), 7.30 (s, 2H), 7.52 (d, 1H, J=9.0 Hz), 7.89 (d, 1H, J=3.0 Hz), 8.09 (s, 1H), 8.19 (s, 1H), 8.34 (d, 1H, J=3.0 Hz). $^{13}$C NMR ($CDCl_3$) δ 18.30, 18.47, 23.59, 27.42, 30.08, 53.83, 54.44, 54.76, 58.03, 122.04, 123.32, 132.42, 133.32, 134.05, 139.19, 142.22, 144.51, 145.96, 146.15, 146.56, 154.40, 156.23, 168.84. ES-MS m/z 497 [M+H]$^+$. Anal. Calcd. for $C_{30}H_{36}N_6O \cdot 0.7CH_2Cl_2$: C, 66.31; H, 6.78; N, 15.11. Found: C, 66.26; H, 6.93; N, 14.96.

Example 315

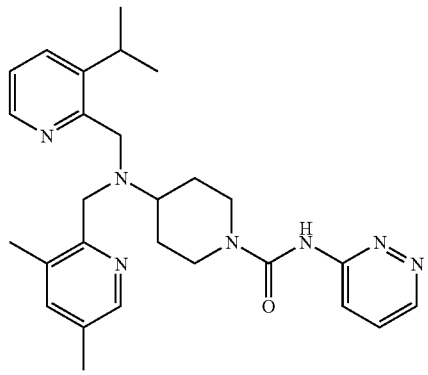

COMPOUND 315: 4-[(3,5-dimethyl-pyridin-2-ylmethyl)-(3-isopropyl-pyridin-2-ylmethyl)-amino]-piperidine-1-carboxylic acid pyridazin-3-ylamide To a solution of 3-aminopyridazine (62 mg, 0.65 mmol) (Wermuth, C.-G. *J. Het. Chem.* 1998, 35, 1091-1100) in $CH_2Cl_2$ (5 mL) was added 1,1'carbonyldiimidazole (128 mg, 0.79 mmol). After stirring at room temperature for 1.5 h, the mixture was heated to 50° C. After 45 min, (3,5-dimethyl-pyridin-2-ylmethyl)-(3-isopropyl-pyridin-2-ylmethyl)-piperidine-4-yl-amine (115 mg, 0.33 mmol) was added and stirring was continued for 50° C. After 2 h, the reaction mixture was cooled, diluted with $CH_2Cl_2$ (20 mL), and washed with saturated $NaHCO_3$ (3×20 mL). The organic layer was dried (MgSO₄), filtered, and concentrated to afford a pale yellow oil. Purification by radial chromatography on silica gel (1 mm plate; using CH₂Cl₂/MeOH/NH₄OH; 50:1:1) afforded COMPOUND 315 as a pale yellow oil (44 mg, 28%). ¹H NMR (CDCl₃) δ 0.93 (d, 6H, J=6.0 Hz), 1.64-1.75 (m, 2H), 1.96-1.99 (m, 2H), 2.16 (s, 3H), 2.28 (s, 3H), 2.75-2.84 (m, 4H), 3.78 (s, 2H), 3.84 (s, 2H), 4.21 (s, 1H), 4.26 (s, 1H), 7.15-7.17 (m, 1H), 7.38-7.42 (m, 1H), 7.50 (dd, 1H, J=6.0, 3.0 Hz), 7.99 (s, 1H), 8.18 (s, 1H), 8.32 (d, 1H, J=3.0 Hz), 8.33 (d, 1H, J=3.0 Hz), 8.80 (s, 1H). ¹³C NMR δ 18.30, 18.46, 23.61, 27.46, 44.89, 53.83, 54.34, 57.27, 118.83, 123.22, 128.28, 132.33, 133.19, 133.88, 139.08, 144.40, 146.12, 146.70, 147.89, 153.74, 154.38, 156.21, 156.96. ES-MS m/z 496 [M+H]⁺. Anal. Calcd. for $C_{27}H_{35}N_7O \cdot 1.4CH_2Cl_2 \cdot 0.5H_2O$: C, 56.71; H, 6.50; N, 16.30. Found: C, 56.48; H, 6.32; N, 16.54.

Example 316

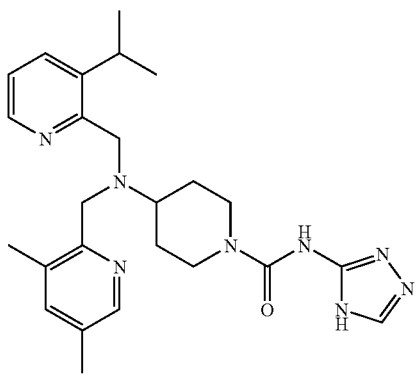

COMPOUND 316: 4-[(3,5-dimethyl-pyridin-2-ylmethyl)-(3-isopropyl-pyridin-2-ylmethyl)-amino]-piperidine-1-carboxylic acid triazol-3-ylamide To a solution of 3-amino-1,2,4-triazole (95 mg, 1.13 mmol) in CH₂Cl₂ (5 mL) was added 1,1'-carbonyldiimidazole (222 mg, 1.37 mmol) and the reaction mixture was stirred at 50° C. After stirring for 2 h, (3,5-dimethyl-pyridin-2-ylmethyl)-(3-isopropyl-pyridin-2-ylmethyl)-piperidine-4-yl-amine (200 mg, 0.57 mmol) was added and the reaction mixture was continued stirring at 50° C. After 2.5 h, the mixture was cooled, diluted with CH₂Cl₂ (20 mL), and washed with saturated NaHCO₃ (3×20 mL). The organic layer was dried (MgSO₄), filtered, and concentrated to afford a yellow foam. Purification by flash column chromatography on silica gel using CH₂Cl₂/MeOH/NH₄OH (50:1:1) afforded the product as a pale yellow oil (27 mg, 10%). ¹H NMR (CDCl₃) δ 0.93 (d, 6H, J=6.0 Hz), 1.72-1.86 (m, 2H), 1.97-2.01 (m, 2H), 2.19 (s, 3H), 2.28 (s, 3H), 2.73-2.86 (m, 4H), 3.80 (s, 2H), 3.85 (s, 2H), 4.64-4.72 (br s, 2H), 5.94 (s, 2H), 7.16 (dd, 1H, J=6.0, 3.0 Hz), 7.44 (s, 1H), 7.50 (dd, 1H, J=6.0, 3.0 Hz), 8.19 (s, 1H), 8.34 (dd, 1H, J=6.0, 3.0 Hz). ¹³C NMR (CDCl₃) δ 18.30, 18.51, 23.61, 27.42, 27.58, 47.14, 53.83, 54.33, 57.14, 123.19, 132.31, 133.19, 133.86, 139.06, 144.39, 146.12, 146.71, 149.43, 151.89, 154.41, 156.25, 158.62. ES-MS m/z 463 [M+H]⁺. Anal. Calcd. for $C_{25}H_{34}N_8O \cdot 0.3CH_3OH$: C, 64.35; H, 7.51; N, 23.73. Found: C, 64.42; H, 7.31; N, 23.61.

Example 317

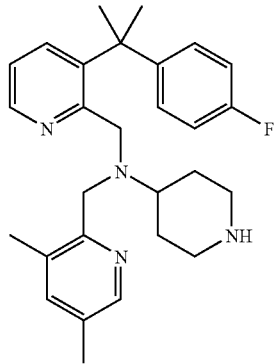

COMPOUND 317: (3,5-dimethyl-pyridin-2-ylmethyl)-{3-[1-(4-fluoro-phenyl)-1-methyl-ethyl]-pyridin-2-ylmethyl}-piperidin-4-yl-amine Using General Procedure B: Reaction of 4-amino-piperidine-1-carboxylic acid tert-butyl ester in CH₂Cl₂ with 3-[1-(4-fluoro-phenyl)-1-methyl-ethyl]-pyridine-2-carbaldehyde and NaBH(OAc)₃ gave the amine. ¹H NMR (CDCl₃) δ 1.10 (m, 2H), 1.43 (s+m, 12H), 1.66 (s, 6H), 2.21 (m, 1H), 2.62 (m, 2H), 3.33 (m, 1H), 3.87 (br d, 2H), 6.97 (t, 2H, J=7.5 Hz), 7.11 (dd, 2H, J=9.0, 3.0 Hz), 7.25 (dd, 1H, J=7.5, 3.0 Hz), 7.86 (d, 1H, J=9.0 Hz), 8.46 (d, 1H, J=3.0 Hz).

Using General Procedure B: Reaction of 4-({3-[1-(4-fluoro-phenyl)-1-methyl-ethyl]-pyridin-2-ylmethyl}-amino)-piperidine-1-carboxylic acid tert-butyl ester in CH₂Cl₂ with 3,5-dimethyl-pyridine-2-carbaldehyde and NaBH(OAc)₃ gave 4-((3,5-dimethyl-pyridin-2-ylmethyl)-{3-[1-(4-fluoro-phenyl)-1-methyl-ethyl]-pyridin-2-ylmethyl}-amino)-piperidine-1-carboxylic acid tert-butyl ester as a white foam. ¹H NMR (CDCl₃) δ 1.25 (m, 3H), 1.43 (s, 9H), 1.61 (s+m, 8H), 2.24 (s, 3H), 2.28 (s, 3H), 2.39-2.47 (m, 3H), 3.35 (m, 1H), 3.66 (s, 2H), 4.02 (s, 2H), 6.87 (m, 4H), 7.19 (s, 2H), 7.82 (d, 1H, J=9.0 Hz), 8.10 (s, 1H), 8.51 (s, 1H). Deprotection with TFA using General Procedure F gave (3,5-dimethyl-pyridin-2-ylmethyl)-{3-[1-(4-fluoro-phenyl)-1-methyl-ethyl]-pyridin-2-ylmethyl}-piperidin-4-yl-amine as a pale yellow foam. ¹H NMR (CDCl₃) δ 1.56 (s+m, 9H), 1.76 (d, 2H, J=12.0 Hz), 2.21 (s, 3H), 2.28 (s, 3H), 2.52-2.67 (m, 3H), 3.18 (m, 1H), 3.41 (s, 2H), 3.57 (s, 2H), 6.83-6.90 (m, 4H), 7.20 (m, 2H), 7.82 (d, 1H, J=9.0 Hz), 8.09 (s, 1H), 8.49 (d, 1H, J=3.0 Hz). ¹³C NMR (CDCl₃) δ 17.9, 18.4, 27.9, 31.1, 41.9, 42.2, 53.4, 54.1, 54.5, 57.0, 114.9, 115.2, 127.1, 127.2, 131.3, 132.7, 133.8, 138.7, 143.1, 145.5, 146.3, 146.6, 154.4, 158.1, 159.3, 162.5. HPLC: 90%. ES-MS m/z 447 [M+H]⁺. Anal. Calcd. for $C_{28}H_{35}N_4F \cdot 0.2 CH_2Cl_2$: C, 73.06; H, 7.70; N, 12.09. Found: C, 73.19; H, 7.79; N, 12.10.

Example 318

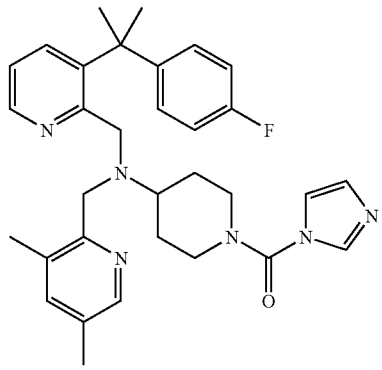

261

COMPOUND 318: [4-((3,5-dimethyl-pyridin-2-ylmethyl)-{3-[1-(4-fluoro-phenyl)-1-methyl-ethyl]-pyridin-2-ylmethyl}-amino)-piperidin-1-yl]-imidazol-1-yl-methanone (3,5-Dimethyl-pyridin-2-ylmethyl)-{3-[1-(4-fluoro-phenyl)-1-methyl-ethyl]-pyridin-2-ylmethyl}-piperidin-4-yl-amine (0.270 g, 0.60 mmol) and 1,1'-carbonyldiimidazole (0.098 g, 0.60 mmol) were combined in THF (6 mL) and the mixture was stirred at room temperature for one hour. The solvent was removed under reduced pressure to give a colorless oil that was resuspended in DMF (5 mL), followed by addition of N,N-diisopropylamine (527 μL, 3.02 mmol) and $NH_2OH \cdot HCl$ (0.168 g, 2.40 mmol). The mixture was stirred at room temperature for 16 hours and then the solvent was removed under reduced pressure. The yellow oil was resuspended in $CH_2Cl_2$ (30 mL), washed with brine (3×20 mL) and the organic layer was dried ($Na_2SO_4$), filtered and concentrated in vacuo to give a yellow oil. Purification by column chromatography on silica gel ($CH_2Cl_2$:MeOH:$NH_4OH$, 85:10:5, v/v/v) afforded COMPOUND 318 as a white foamy solid (0.087 g, 27%). $^1$H NMR (CDCl$_3$) δ 1.29-1.42 (m, 2H), 1.62 (s, 6H), 1.76 (d, 2H, J=12.0 Hz), 2.22 (s, 3H), 2.29 (s+m, 4H), 2.75-2.84 (m, 3H), 3.42 (m, 1H), 3.71 (br s, 2H), 4.02 (d, 2H, J=12.0 Hz), 6.87 (t, 2H, J=9.0 Hz), 7.07 (s, 2H), 7.15 (s, 1H), 7.23 (s, 1H), 7.23 (s, 1H), 7.81 (s, 1H), 7.88 (m, 1H), 8.15 (s, 1H), 8.54 (s, 1H). $^{13}$C NMR (CDCl$_3$) δ 17.9, 18.2, 28.2, 31.0, 42.1, 46.3, 54.2, 115.0, 115.3, 118.0, 127.3, 129.6, 132.6, 136.9, 146.5, 150.7, 159.3. HPLC: 91%. ES-MS m/z 541 [M+H]$^+$. Anal. Calcd. for $C_{32}H_{37}N_6OF \cdot 0.15 \, CH_2Cl_2$: C, 69.78; H, 6.79; N, 15.19. Found: C, 69.74; H, 6.83; N, 15.03.

Example 319

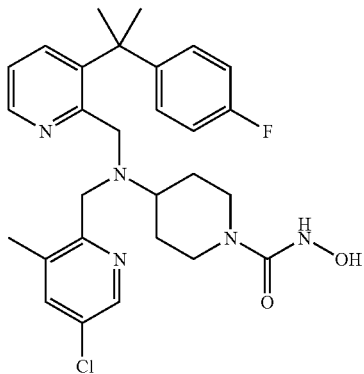

COMPOUND 319: 4-((5-chloro-3-methyl-pyridin-2-ylmethyl)-{3-[1-(4-fluoro-phenyl)-1-methyl-ethyl]-pyridin-2-ylmethyl}-amino)-piperidine-1-carboxylic acid hydroxyamide (5-Chloro-3-methyl-pyridin-2-ylmethyl)-{3-[1-(4-fluoro-phenyl)-1-methyl-ethyl]-pyridin-2-ylmethyl}-piperidin-4-yl-amine (0.160 g, 0.34 mmol) and N-(phenoxycarbonyl)-hydroxylamine (0.068 g, 0.44 mmol) were combined in THF (4 mL) and the mixture was stirred at 70° C. for 2 hours and then 45° C. for 48 hours. The solvent was removed under reduced pressure and the residue was purified by column chromatography on silica gel ($CH_2Cl_2$:MeOH:$NH_4OH$, 85:10:5, v/v/v) to give 4-((5-chloro-3-methyl-pyridin-2-ylm-

262 ethyl)-{3-[1-(4-fluoro-phenyl)-1-methyl-ethyl]-pyridin-2-ylmethyl}-amino)-piperidine-1-carboxylic acid hydroxyamide (0.082 g, 45%) as a white solid. $^1$H NMR (CDCl$_3$) δ 1.25-1.37 (m, 2H), 1.61 (s+m, 8H), 2.26 (s, 3H), 2.55 (t, 2H. J=12.0 Hz), 2.64 (m, 1H), 3.45 (s, 2H), 3.73 (s, 2H), 3.92 (d, 2H, J=12.0 Hz), 6.89-6.95 (m, 4H), 7.21 (m, 1H), 7.39 (s, 1H), 7.87 (d, 1H, J=9.0 Hz), 8.21 (d, 1H, J=3.0 Hz), 8.50 (d, 1H, J=6.0 Hz). $^{13}$C NMR (CDCl$_3$) δ 18.7, 27.9, 31.3, 42.5, 43.7, 54.4, 58.7, 115.5, 115.7, 121.8, 122.3, 127.6, 127.7, 129.7, 130.8, 134.6, 135.0, 138.0, 143.5, 145.0, 146.9, 161.0, 163.0. HPLC: 90%. ES-MS m/z 527 [M+H]$^+$. Anal. Calcd. for $C_{28}H_{33}N_5O_2ClF \cdot 0.6 H_2O \cdot 0.1 \, CH_2Cl_2$: C, 61.89; H, 6.36; N, 12.84; Cl, 7.80. Found: C, 61.83; H, 6.19; N, 12.62; Cl, 8.06.

Example 320

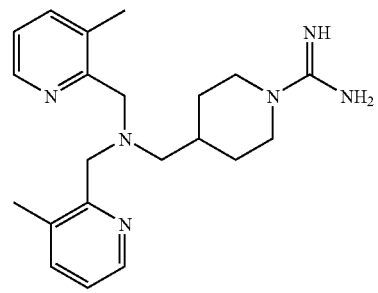

COMPOUND 320: 4-{[Bis-(3-methyl-pyridin-2-ylmethyl)-amino]-methyl}-piperidine-1-carboxamidine (HBr salt)

Using General Procedure B, reaction of 4-formylpiperidine-1-carboxylic acid tert-butyl ester (*Bioorg. Med. Chem. Lett.* 2002, 12, 1785-1790), C-(3-methylpyridin-2-yl)-methylamine and NaBH(OAc)$_3$ in CH$_2$Cl$_2$ gave 4-{[(3-methyl-pyridin-2-ylmethyl)-amino]-methyl}-piperidine-1-carboxylic acid tert-butyl ester as a clear oil.

Using General Procedure B, reaction of the above secondary amine, 3-methylpyridine-2-carboxaldehyde and NaBH(OAc)$_3$ in CH$_2$Cl$_2$ gave 4-{[bis-(3-methyl-pyridin-2-ylmethyl)-amino]-methyl}-piperidine-1-carboxylic acid tert-butyl ester. Deprotection with TFA using General Procedure F gave bis-(3-methyl-pyridin-2-ylmethyl)-piperidin-4-ylmethyl-amine. $^1$H NMR (CDCl$_3$) δ 0.64-0.78 (m, 2H), 1.40-1.47 (m, 1H), 1.53-1.58 (m, 2H), 2.14 (s, 6H), 2.28-2.48 (m, 6H), 2.87-2.95 (m, 2H), 3.73 (s, 4H), 7.08 (dd, 2H, J=4.8, 7.5 Hz), 7.39 (d, 2H, J=7.5 Hz), 8.36 (d, 2H, J=4.8 Hz).

Bis-(3-methyl-pyridin-2-ylmethyl)-piperidin-4-ylmethylamine (170 mg, 0.24 mmol) and (tert-butoxycarbonylimino-pyrazol-1-yl-methyl)-carbamic acid tert-butyl ester (182 g, 0.52 mmol) were dissolved in THF (6 mL) and stirred for 17 hours at room temperature. The solvent was removed under reduced pressure and CH$_2$Cl$_2$ (10 mL) was added. The organic was washed with an aqueous solution of 1N NaOH (5×15 mL), dried (MgSO$_4$) and concentrated under reduced pressure to afford, after column chromatography on silica gel (20:1:0.1 CH$_2$Cl$_2$:MeOH:NH$_4$OH)) [(4-{[bis-(3-methyl-pyridin-2-ylmethyl)-amino]-methyl}-piperidin-1-yl)-tert-butoxycarbonyliminomethyl]-carbamic acid tert-butyl ester (152 mg, 51%). Conversion to the HBr salt using General Procedure D gave COMPOUND 320 as a white solid. $^1$H NMR (D$_2$O) δ 1.08-1.14 (m, 2H), 1.80-1.87 (m, 2H), 2.50 (s, 6H), 2.56-2.61 (m, 2H), 2.95-3.06 (m, 2H), 3.73-3.79 (m, 2H), 4.27 (s, 4H), 7.85-7.88 (m, 2H), 8.37-8.41 (m, 2H), 8.61 (d, 2H, J=5.7 Hz); $^{13}$C NMR (D$_2$O) δ 14.6, 17.6, 29.8, 33.1, 46.0, 54.7, 61.5, 66.5, 126.4, 138.4, 139.0, 148.9, 150.6, 156.9; ES-MS m/z 367 (M+H). Anal. Calcd. for C$_{21}$H$_{30}$N$_6$.3.4HBr.1.2H$_2$O.0.2C$_4$H$_{10}$O: C, 38.62; H, 5.62; N, 12.39; Br, 40.07. Found: C, 38.47; H, 5.62; N, 12.26; Br, 40.16.

Example 321

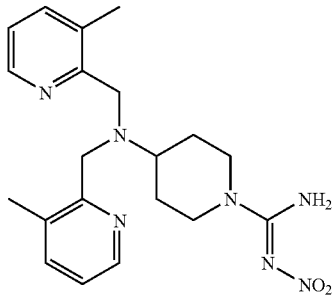

COMPOUND 321: 4-[Bis-3-methyl-pyridin-2-ylmethyl)-amino]-N-nitro-piperidine-1-carboxamidine A mixture of COMPOUND 249 (163 mg, 0.525 mmol) and N-nitro-3,5-dimethylpyrazole-1-carboxamidine (*Biochem. Biophys. Acta* 1964, 93, 533-543) (96 mg, 0.525 mmol) in MeOH (5 mL) was heated at reflux for 17 hours. Solvent was removed under reduced pressure and the crude material was purified by flash column chromatography on silica gel (9:1: 0.2 CH$_2$Cl$_2$:MeOH:NH$_4$OH) to give COMPOUND 321 as a white solid (98 mg, 47%). $^1$H NMR (CDCl$_3$) δ 1.60-1.79 (m, 4H), 1.95-2.09 (m, 2H), 2.09 (s, 6H), 2.75-2.84 (m, 3H), 3.82 (s, 4H), 4.24-4.31 (m, 2H), 7.11 (dd, 2H, J=4.5, 7.5 Hz), 7.39 (d, 2H, J=7.5 Hz), 7.63 (br s, 1H), 8.34 (d, 2H, J=4.5 Hz); $^{13}$C NMR (DMSO-d$_6$) δ 17.7, 26.7, 44.7, 54.5, 57.1, 122.9, 133.2, 138.2, 146.0, 157.2, 157.7; ES-MS m/z 398 (M+H); Anal. Calcd. for C$_{21}$H$_{28}$N$_6$O$_2$.0.3H$_2$O: C, 59.63; H, 6.90; N, 24.34. Found: C, 59.58; H, 6.80; N, 24.67.

Example 322

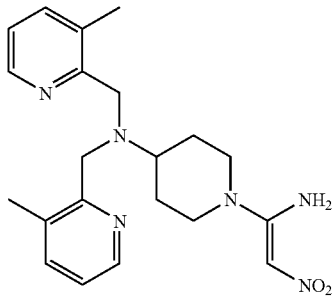

COMPOUND 322: [1-(1-Amino-2-nitro-vinyl)-piperidin-4-yl]-bis-(3-methyl-pyrin-2-ylmethyl)-amine A mixture of COMPOUND 249 (238 mg, 0.766 mmol) and 1,1-bis(methylthio)-2-nitroethylene (253 mg, 1.51 mmol) in MeOH (10 mL) was heated at reflux for 1.5 hours. Solvent was removed under reduced pressure (high vac.) and the crude material was dissolved in MeOH (10 mL) and NH$_4$OH (3 mL). The mixture was heated in a sealed tube at 40° C. for 1 hour. Solvent was removed and the product was recrystallized from CH$_2$Cl$_2$ to give COMPOUND 322 as a yellow solid (120 mg, 39%). $^1$H NMR (CDCl$_3$) δ 1.60-1.79 (m, 3H), 1.95-2.09 (m, 2H), 2.09 (s, 6H), 2.81-2.22 (m, 3H), 3.83 (s, 4H), 3.77-4.84 (m, 2H), 6.68 (br s, 1H), 7.11 (dd, 2H, J=4.5, 7.5 Hz), 7.39 (d, 2H, J=7.5 Hz), 8.34 (d, 2H, J=4.5 Hz); $^{13}$C NMR (CDCl$_3$) δ 18.3, 27.2, 46.5, 54.9, 100.3, 123.0, 133.8, 138.6, 146.3, 157.0, 157.5; ES-MS m/z 397 (M+H); Anal. Calcd. for C$_{21}$H$_{28}$N$_6$O$_2$.1.4H$_2$O: C, 59.81; H, 7.36; N, 19.93. Found: C, 59.80; H, 7.58; N, 19.73.

Example 323

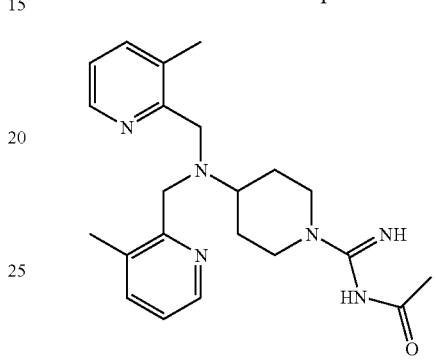

COMPOUND 323: N-({4-[Bis-(3-methyl-pyridin-2-ylmethyl)-amino]-piperidin-1-yl}-imino-methyl)-acetamide To a solution of 4-[bis-(3-methyl-pyridin-2-ylmethyl)-amino]-piperidine-1-carboxyamidine (0.575 mmol) in CH$_2$Cl$_2$ (10 mL) and DIPEA (2 mL) was added Ac$_2$O (1 mL). White precipitate formed immediately. Water was added (10 mL) and the mixture was extracted with excess CH$_2$Cl$_2$. The extracts were dried over Na$_2$SO$_4$, were filtered and concentrated. Trituration of the crude material with EtOAc and removal of the solvent with a pipette, followed by removal of the residual solvent under reduced pressure provided COMPOUND 323 as white solid (109 mg, 48%). $^1$H NMR (CD$_3$OD) δ 1.70-1.82 (m, 2H), 1.91-2.00 (m, 2H), 2.02 (s, 3H), 2.14 (s, 6H), 2.67-2.80 (m, 3H), 3.83 (s, 4H), 4.25-4.36 (m, 2H), 7.24 (dd, 2H, J=4.8, 7.5 Hz), 7.54 (d, 2H, J=7.5 Hz), 8.27 (d, 2H, J=4.8 Hz); $^{13}$C NMR (DMSO-d$_6$) δ18.3, 27.4, 29.3, 43.9, 55.0, 58.0, 123.3, 133.7, 138.6, 146.5, 157.9, 159.8, 183.7; ES-MS m/z 395 (M+H). Anal. Calcd. for C$_{22}$H$_{30}$N$_6$O.0.5H$_2$O.0.1C$_4$H$_8$O$_2$: C, 65.25; H, 7.77; N, 20.38. Found: C, 65.13; H, 7.53; N, 20.16.

Example 324

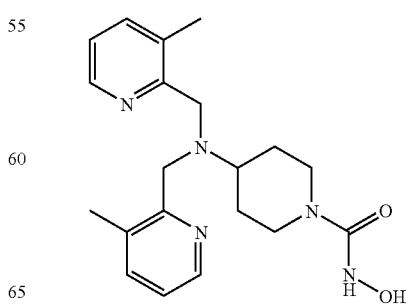

COMPOUND 324: 4-[Bis-(3-methyl-pyridin-2-ylm-ethyl)-amino]-piperidine-1-carboxylic acid hydroxyamide To a 0° C. solution of COMPOUND 249 (144 mg, 0.465 mmol) in toluene (20 mL) and Et$_3$N (0.40 mL, 3.34 mmol) was added phosgene solution in toluene (20 wt %, 0.317 mL, 0.697 mmol). The mixture was stirred at 0° C. for 3 hours, was then warmed up to room temperature and solvent was removed under reduced pressure (high vac.) to yield a yellow solid. The solid was dissolved in CH$_2$Cl$_2$ (15 mL) and Et$_3$N (0.194 mL, 1.40 mmol) was added followed by NH$_2$OH.HCl (48 mg, 0.700 mmol). The mixture was stirred at room temperature for 17 hours. Solvent was removed under reduced pressure and the residue was purified by radial chromatography on silica gel (9:1:0.2 CH$_2$Cl$_2$:MeOH:NH$_4$OH) to provide COMPOUND 324 as white solid (112 mg, 60%). $^1$H NMR (CDCl$_3$) δ 1.61-1.73 (m, 3H), 1.92-2.00 (m, 2H), 2.08 (s, 6H), 2.65-2.72 (m, 3H), 3.81 (s, 4H), 4.01-4.06 (m, 2H), 6.72 (br s, 1H), 7.09 (dd, 2H, J=4.8, 7.8 Hz), 7.37 (d, 2H, J=7.8 Hz), 8.34 (d, 2H, J=4.8 Hz); $^{13}$C NMR (CDCl$_3$) δ 18.0, 26.9, 43.8, 54.6, 57.3, 122.5, 133.4, 138.1, 145.9, 157.0, 160.7; ES-MS m/z 370 (M+H). Anal. Calcd. for C$_{20}$H$_{27}$N$_5$O$_2$.0.4 CH$_2$Cl$_2$: C, 60.73; H, 6.95; N, 17.36. Found: C, 61.07; H, 7.19; N, 17.09.

Example 325

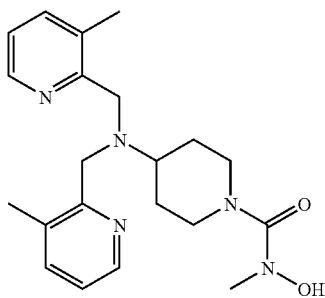

COMPOUND 325: 4-[Bis-(3-methyl-pyridin-2-ylm-ethyl)-amino]-piperidine-1-carboxylic acid hydroxy-methyl-amide To a 0° C. solution of COMPOUND 249 (236 mg, 0.760 mmol) in toluene (20 mL) and Et$_3$N (0.45 mL, 3.42 mmol) was added phosgene solution in toluene (20 wt %, 0.519 mL, 1.14 mmol). The mixture was stirred at 0° C. for 2 hours, was then warmed up to room temperature and solvent was removed under reduced pressure (high vac.) to yield a yellow solid. Half of the solid (0.380 mmol) was dissolved in CH$_2$Cl$_2$ (10 mL) and DIPEA (0.5 mL) was added followed by N-methylhydroxylamine hydrochloride (48 mg, 0.57 mmol). The mixture was stirred at room temperature for 17 hours. Solvent was removed under reduced pressure and the residue was dissolved in CH$_2$Cl$_2$ (20 mL), extracted with saturated NaHCO$_3$ (20 mL), dried over MgSO4, filtered and concentrated. The crude material was purified by column chromatography on silica gel (9:1:0.1 CH$_2$Cl$_2$:MeOH:NH$_4$OH) to provide COMPOUND 325 as white solid (81 mg, 55%). $^1$H NMR (CDCl$_3$) δ 1.60-1.73 (m, 3H), 1.92-2.00 (m, 2H), 2.09 (s, 6H), 2.65-2.76 (m, 3H), 2.95 (s, 3H), 3.83 (s, 4H), 4.12-4.18 (m, 2H), 7.09 (dd, 2H, J=4.2, 7.5 Hz), 7.37 (d, 2H, J=7.5 Hz), 8.34 (d, 2H, J=4.2 Hz); $^{13}$C NMR (CDCl$_3$) δ 18.0, 27.1, 44.3, 45.5, 54.6, 57.4, 122.5, 133.4, 138.2, 145.9, 157.0, 165.8; ES-MS m/z 384 (M+H). Anal. Calcd. for C$_{21}$H$_{29}$N$_5$O$_2$.0.2H$_2$O.0.5 CH$_2$Cl$_2$: C, 60.12; H, 7.13; N, 16.30. Found: C, 60.06; H, 7.09; N, 16.32.

Example 326

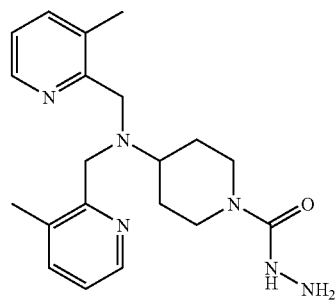

COMPOUND 326: 4-[Bis-(3-methyl-pyridin-2-ylm-ethyl)-amino]-piperidine-1-carboxylic acid hydrazide (HBr salt)

To a 0° C. solution of COMPOUND 249 (106 mg, 0.341 mmol) in toluene (5 mL) and DIPEA (0.12 mL, 0.68 mmol) was added phosgene solution in toluene (20 wt %, 0.185 mL, 0.375 mmol). After one hour the TLC of the reaction mixture showed that starting material was still present, and additional phosgene solution (0.050 mL) and DIPEA (0.100 mL) were added. After 30 min, excess anhydrous hydrazine (0.2 mL) was added and the mixture was warmed to room temperature and was stirred for 30 minutes. Reaction mixture was concentrated under reduced pressure and the residue was purified by radial chromatography (19:1:0.1 CH$_2$Cl$_2$:MeOH: NH$_4$OH) on silica gel twice, however complete purification was not achieved. The material (41 mg, 33%, 0.103 mmol) was dissolved in THF, and Et$_3$N (0.200 mL) and Boc$_2$O (100 mg, 0.50 mmol) were added. The mixture was stirred at room temperature for 2 days. The solvent was removed and the crude material was purified by radial chromatography (20:1:1 CH$_2$Cl$_2$:MeOH:NH$_4$OH) to provide 21 mg (43%) of mono-Boc protected product.

Using General Procedure D, 21 mg (72%) of COMPOUND 326 was obtained. $^1$H NMR (D$_2$O) δ 1.60-1.68 (m, 1H), 2.04-2.08 (m, 1H), 2.48 (s, 6H), 2.82-2.97 (m, 3H), 3.96-4.03 (m, 2H), 4.33 (s, 4H), 7.81 (dd, 2H, J=6.0, 7.8 Hz), 8.31 (d, 1H, J=7.8 Hz), 8.54 (d, 2H, J=6.0 Hz); $^{13}$C NMR (D$_2$O) δ 17.3, 27.4, 43.6, 51.0, 60.0, 126.0, 137.8, 138.8, 148.5, 151.2, 157.1; ES-MS m/z 369 (M+H). Anal. Calcd. for C$_{20}$H$_{28}$N$_4$O.2.9HBr.2.9H$_2$O: C, 36.65; H, 5.64; N, 12.82, Br.25.36. Found: C, 36.87; H, 5.48; N, 12.42, Br.35.23.

Example 327

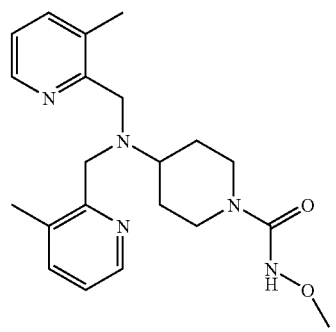

COMPOUND 327: 4-[Bis-(3-methyl-pyridin-2-ylmethyl)-amino]-piperidine-1-carboxylic acid methoxyamide To a solution of methoxyamine hydrochloride (115 mg, 1.37 mmol) in CH$_3$CN (10 mL) was added DIPEA (0.5 mL) and 1,1'-carbonyldiimidazole (223 mg, 1.37 mmol). The mixture was stirred at room temperature for 1 hour. To this solution COMPOUND 249 (44 mg, 0.1417 mmol) was added and the reaction was stirred for 17 hours. The solvent was removed under reduced pressure and saturated NaHCO$_3$ was added (10 mL) and the mixture was extracted with CH$_2$Cl$_2$ (3×30 mL). The extracts were dried (MgSO$_4$), filtered and concentrated and the crude material was purified by radial chromatography on silica gel (19:1:1 CH$_2$Cl$_2$:MeOH:NH$_4$OH). The obtained product contained some imidazole impurity, which was removed by dissolving the material in CH$_2$Cl$_2$ (50 mL) and washing with 2 N NaOH solution (2×10 mL). The organic layer was dried (MgSO$_4$) and concentrated to provide COMPOUND 327 as a white solid (36 mg, 66%). $^1$H NMR (CDCl$_3$) δ 1.57-1.68 (m, 2H), 1.87-1.93 (m, 2H), 2.07 (s, 6H), 2.57-2.66 (m, 3H), 3.68 (s, 3H), 3.79 (s, 4H), 3.98-4.04 (m, 2H), 7.07 (dd, 2H, J=3.6, 7.5 Hz), 7.35 (d, 2H, J=7.5 Hz), 8.31 (d, 2H, J=3.6 Hz); $^{13}$C NMR (CDCl$_3$) δ18.3, 27.3, 44.4, 54.9, 57.6, 64.4, 122.8, 133.8, 138.4, 146.3, 157.5, 159.0; ES-MS m/z 406 (M+Na). Anal. Calcd. for C$_{21}$H$_{29}$N$_5$O$_2$: C, 65.77; H, 7.62; N, 18.26. Found: C, 65.72; H, 7.69; N, 17.96.

Example 328

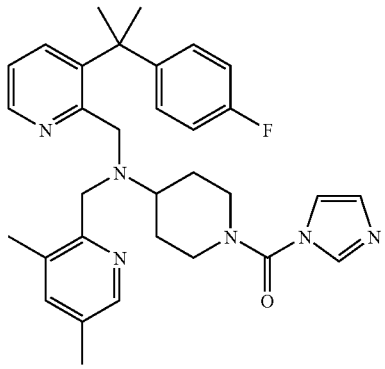

COMPOUND 328: [4-((3,5-dimethyl-pyridin-2-ylmethyl)-{3-[1-(4-fluoro-phenyl)-1-methyl-ethyl]-pyridin-2-ylmethyl}-amino)-piperidin-1-yl]-imidazol-1-yl-methanone (3,5-Dimethyl-pyridin-2-ylmethyl)-{3-[1-(4-fluoro-phenyl)-1-methyl-ethyl]-pyridin-2-ylmethyl}-piperidin-4-yl-amine (0.270 g, 0.60 mmol) and 1,1'-carbonyldiimidazole (0.098 g, 0.60 mmol) were combined in THF (6 mL) and the mixture was stirred at room temperature for one hour. The solvent was removed under reduced pressure to give a colorless oil that was resuspended in DMF (5 mL), followed by addition of N,N-diisopropylamine (527 µL, 3.02 mmol) and NH$_2$OH.HCl (0.168 g, 2.40 mmol). The mixture was stirred at room temperature for 16 hours and then the solvent was removed under reduced pressure. The yellow oil was resuspended in CH$_2$Cl$_2$ (30 mL), washed with brine (3×20 mL) and the organic layer was dried (Na$_2$SO$_4$), filtered and concentrated in vacuo to give a yellow oil. Purification by column chromatography on silica gel (CH$_2$Cl$_2$:MeOH:NH$_4$OH, 85:10:5, v/v/v) afforded two major products. The first band to elute from the column was [4-((3,5-dimethyl-pyridin-2-ylmethyl)-{3-[1-(4-fluoro-phenyl)-1-methyl-ethyl]-pyridin-2-ylmethyl}-amino)-piperidin-1-yl]-imidazol-1-yl-methanone isolated as a white foamy solid (COMPOUND 328, 0.087 g, 27%). $^1$H NMR (CDCl$_3$) δ 1.29-1.42 (m, 2H), 1.62 (s, 6H), 1.76 (d, 2H, J=12.0 Hz), 2.22 (s, 3H), 2.29 (s+m, 4H), 2.75-2.84 (m, 3H), 3.42 (m, 1H), 3.71 (br s, 2H), 4.02 (d, 2H, J=12.0 Hz), 6.87 (t, 2H, J=9.0 Hz), 7.07 (s, 2H), 7.15 (s, 1H), 7.23 (s, 1H), 7.23 (s, 1H), 7.81 (s, 1H), 7.88 (m, 1H), 8.15 (s, 1H), 8.54 (s, 1H). $^{13}$C NMR (CDCl$_3$) δ 17.9, 18.2, 28.2, 31.0, 42.1, 46.3, 54.2, 115.0, 115.3, 118.0, 127.3, 129.6, 132.6, 136.9, 146.5, 150.7, 159.3. HPLC: 91%. ES-MS m/z 541 [M+H]$^+$. Anal. Calcd. for C$_{32}$H$_{37}$N$_6$OF.0.15 CH$_2$Cl$_2$: C, 69.78; H, 6.79; N, 15.19. Found: C, 69.74; H, 6.83; N, 15.03.

Example 329

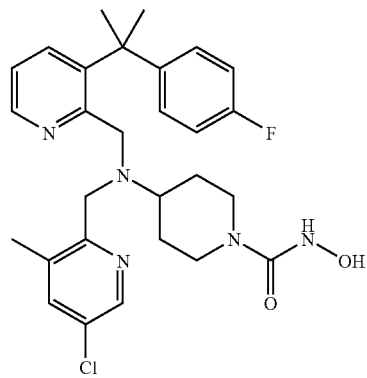

COMPOUND 329: 4-((5-chloro-3-methyl-pyridin-2-ylmethyl)-{3-[1-(4-fluoro-phenyl)-1-methyl-ethyl]-pyridin-2-ylmethyl}-amino)-piperidine-1-carboxylic acid hydroxyamide Using General Procedure B: Reaction of 4-({3-[1-(4-fluoro-phenyl)-1-methyl-ethyl]-pyridin-2-ylmethyl}-amino)-piperidine-1-carboxylic acid tert-butyl ester in CH$_2$Cl$_2$ with 5-chloro-3-methyl-pyridine-2-carbaldehyde and NaBH(OAc)$_3$ gave 4-((5-chloro-3-methyl-pyridin-2-ylmethyl)-{3-[1-(4-fluoro-phenyl)-1-methyl-ethyl]-pyridin-2-ylmethyl}-amino)-piperidine-1-carboxylic acid tert-butyl ester 0.558 g, 66%) as a white foam. $^1$H NMR (CDCl$_3$) δ 1.21 (m, 2H), 1.44 (s, 9H), 1.60 (s+m, 9H), 2.24 (s, 3H), 2.39-2.51 (m, 3H), 3.33 (s, 2H), 3.66 (s, 2H), 4.02 (br s, 2H), 6.88 (m, 4H), 7.21 (dd, 1H, J=7.5, 3.0 Hz), 7.36 (s, 1H), 7.81 (d, 1H, J=9.0 Hz), 8.21 (d, 1H, J=3.0 Hz), 8.48 (d, 1H, J=3.0 Hz). Deprotection with TFA using General Procedure F gave (5-chloro-3-methyl-pyridin-2-ylmethyl)-{3-[1-(4-fluoro-phenyl)-1-methyl-ethyl]-pyridin-2-ylmethyl}-piperidin-4-yl-amine as a pale yellow foam. $^1$H NMR 1.25-1.33 (m, 2H), 1.61 (s+m, 9H), 2.22 (s, 3H), 2.34-2.49 (m, 4H), 3.03 (d, 2H, J=12.0 Hz), 3.37 (s, 2H), 3.60 (s, 2H), 6.90 (m, 4H), 7.21 (dd, 1H, J=7.5, 3.0 Hz), 7.36 (s, 1H), 7.81 (d, 1H, J=9.0 Hz), 8.21 (d, 1H, J=3.0 Hz), 8.48 (d, 1H, J=3.0 Hz).

(5-Chloro-3-methyl-pyridin-2-ylmethyl)-{3-[1-(4-fluoro-phenyl)-1-methyl-ethyl]-pyridin-2-ylmethyl}-piperidin-4-yl-amine (0.160 g, 0.34 mmol) and N-(phenoxycarbonyl)-hydroxylamine (0.068 g, 0.44 mmol) were combined in THF (4 mL) and the mixture was stirred at 70° C. for 2 hours and then 45° C. for 48 hours. The solvent was removed under reduced pressure and the residue was purified by column chromatography on silica gel (CH$_2$Cl$_2$:MeOH:NH$_4$OH, 85:10:5, v/v/v) to give 4-((5-chloro-3-methyl-pyridin-2-ylmethyl)-{3-[1-(4-fluoro-phenyl)-1-methyl-ethyl]-pyridin-2-ylmethyl}-amino)-piperidine-1-carboxylic acid hydroxamide (0.082 g, 45%) as a white solid. $^1$H NMR (CDCl$_3$) δ 1.25-1.37 (m, 2H), 1.61 (s+m, 8H), 2.26 (s, 3H), 2.55 (t, 2H. J=12.0 Hz), 2.64 (m, 1H), 3.45 (s, 2H), 3.73 (s, 2H), 3.92 (d, 2H, J=12.0 Hz), 6.89-6.95 (m, 4H), 7.21 (m, 1H), 7.39 (s, 1H), 7.87 (d, 1H, J=9.0 Hz), 8.21 (d, 1H, J=3.0 Hz), 8.50 (d, 1H, J=6.0 Hz). $^{13}$C NMR (CDCl$_3$) δ 18.7, 27.9, 31.3, 42.5, 43.7, 54.4, 58.7, 115.5, 115.7, 121.8, 122.3, 127.6, 127.7, 129.7, 130.8, 134.6, 135.0, 138.0, 143.5, 145.0, 146.9, 161.0, 163.0. HPLC: 90%. ES-MS m/z 527 [M+H]$^+$. Anal. Calcd. for C$_{28}$H$_{33}$N$_5$O$_2$ClF.0.6H$_2$O.0.1 CH$_2$Cl$_2$: C, 61.89; H, 6.36; N, 12.84; Cl, 7.80. Found: C, 61.83; H, 6.19; N, 12.62; Cl, 8.06.

Example 330

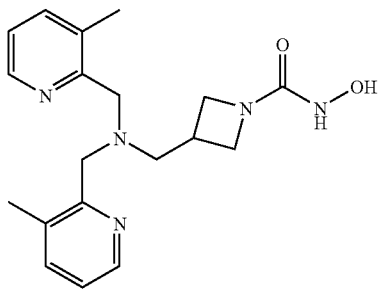

COMPOUND 330: 3-{[Bis-(3-methyl-pyridin-2-ylmethyl)-amino]-methyl}-azetidine-1-carboxylic acid hydroxyamide Using General Procedure B, reaction of tert-butyl 3-(aminomethyl)-1-azetidinecarboxylate (*J. Med. Chem.* 2001, 44, 94-104), 3-methylpyridine-2-carbaldehyde, and NaBH(OAc)$_3$ in CH$_2$Cl$_2$ gave an amine, which was further reacted with 3-methylpyridine-2-carbaldehyde and NaBH(OAc)$_3$ to give 3-{[bis-(3-methyl-pyridin-2-ylmethyl)-amino]-methyl}-azetidine-1-carboxylic acid tert-butyl ester. $^1$H NMR (CDCl$_3$) δ 1.37 (s, 9H), 2.10 (s, 6H), 2.66-2.76 (m, 3H), 3.25 (dd, 2H, J=5.1, 8.7 Hz), 3.73 (s, 4H), 3.78-3.84 (m, 2H), 7.11 (dd, 2H, J=4.8, 7.5 Hz), 7.39 (d, 2H, J=7.5 Hz), 8.36 (d, 2H, J=4.8 Hz). Deprotection with TFA using General Procedure F gave azetidin-3-ylmethyl-bis(3-methyl-pyridin-2-ylmethyl)-amine. $^1$H NMR (CDCl$_3$) δ 2.08 (s, 6H), 2.26 (br s, 1H), 2.75 (d, 2H, J=6.9 Hz), 2.90-3.00 (m 1H), 3.12 (t, 2H, J=7.2 Hz), 3.55 (t, 2H, J=7.8 Hz), 3.72 (s, 4H), 3.78-3.84 (m, 2H), 7.09 (dd, 2H, J=4.8, 7.5 Hz), 7.38 (d, 2H, J=7.5 Hz), 8.36 (d, 2H, J=4.8 Hz).

To a 0° C. solution of azetidin-3-ylmethyl-bis(3-methyl-pyridin-2-ylmethyl)-amine from above (134 mg, 0.452 mmol) in toluene (5 mL) and DIPEA (0.20 mL, 0.90 mmol) was added phosgene solution in toluene (20 wt %, 0.247 mL, 0.543 mmol). The reaction mixture was warmed to room temperature and was stirred for 1.5 hours. The volatiles were removed under reduced pressure and the remaining yellow solid was dissolved in DMF (5 mL). DIPEA (1 mL) and NH$_2$OH.HCl (180 mg, 2.56 mmol) were added and the mixture was stirred for 17 hours at room temperature. Saturated NaHCO$_3$ (15 mL) was added and the mixture was extracted with CH$_2$Cl$_2$ (3×30 mL). The combined organic extracts were dried (MgSO$_4$), filtered and concentrated. The crude material was purified by radial chromatography (10:1:0.2 CH$_2$Cl$_2$:MeOH:NH$_4$OH) on silica gel to provide COMPOUND 330 (61 mg, 38%) as a white solid. $^1$H NMR (MeOH-d$_4$) δ 2.14 (s, 6H), 2.69-2.72 (m, 2H), 2.82-2.85 (m, 1H), 3.25-3.31 (m, 2H), 3.73 (s, 4H), 3.93 (dd, 2H, J=8.4, 8.4 Hz), 7.26 (dd, 2H, J=4.5, 7.5 Hz), 7.59 (d, 2H, J=7.5 Hz), 8.29 (d, 2H, J=4.5 Hz); $^{13}$C NMR (DMSO-d$_6$) δ 18.5, 29.3, 55.3, 60.3, 60.6, 124.9, 136.0, 140.8, 146.9, 157.8, 164.2; ES-MS m/z 378 (M+Na). Anal. Calcd. for C$_{19}$H$_{25}$N$_5$O$_2$.0.6H$_2$O.0.9 CH$_2$Cl$_2$: C, 53.99; H, 6.37; N, 15.82. Found: C, 54.27; H, 6.33; N, 16.10.

Example 331

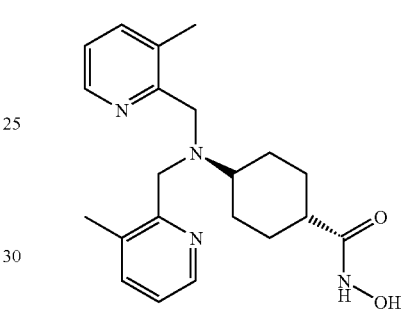

COMPOUND 331: trans-4-[Bis-(3-methyl-pyridin-2-ylmethyl)-amino]-cyclohexanecarboxylic acid hydroxyamide Using General Procedure B, a 4:1 mixture of trans- and cis-4-amino-cyclohexanecarboxylic acid methyl ester (1.1 g, 7.0 mmol), 3-methylpyridine-2-carbaldehyde (931 mg, 7.68 mmol), NaBH(OAc)$_3$ (2.22 g, 10.4 mmol) in CH$_2$Cl$_2$ (30 mL) were stirred at room temperature for 17 hours. Saturated NaHCO$_3$ (20 mL) was added and the mixture was extracted with CH$_2$Cl$_2$ (3×50 mL). The combined organic extracts were dried (MgSO$_4$), filtered and concentrated. Column chromatography of the material on silica gel (20:1:1 CH$_2$Cl$_2$:MeOH:NH$_4$OH) provided trans-4-[(3-methyl-pyridin-2-ylmethyl)-amino]-cyclohexanecarboxylic acid methyl ester (80% by LC-MS with 12% of the cis-isomer) (763 mg, 42%).

The material was dissolved in CH$_2$Cl$_2$ (15 mL) and 3-methylpyridine-2-carbaldehyde (387 mg, 3.19 mmol) and NaBH(OAc)$_3$ (922 mg, 4.35 mmol) were added. The reaction mixture was stirred at room temperature for 5 days. Saturated NaHCO$_3$ (20 mL) was added and the mixture was extracted with CH$_2$Cl$_2$ (3×50 mL). The combined organic extracts were dried (MgSO$_4$), filtered and concentrated.

The crude material was purified by flash column chromatography on silica gel (25:1:1 CH$_2$Cl$_2$:MeOH:NH$_4$OH) to give 862 mg (81%) of trans-4-[bis-(3-methyl-pyridin-2-ylmethyl)-amino]-cyclohexanecarboxylic acid methyl ester. $^1$H NMR (CDCl$_3$) δ 1.28-1.43 (m, 4H), 1.71 (br s, 2H), 1.94-2.04 (m, 4H), 2.11 (s, 6H), 2.16-2.23 (m, 1H), 2.42-2.57 (m, 1H), 3.63 (s, 3H), 3.81 (s, 4H), 7.06 (dd, 2H, J=4.5, 6.9 Hz), 7.34 (d, 2H, J=6.9 Hz), 8.33 (d, 2H, J=4.5 Hz).

To the methyl ester (134 mg, 0.364 mmol) above was added a solution (0.88M, 3.3 mL) of NH$_2$OH.HCl in KOH and MeOH (prepared by dissolving 1.0 g of $NH_2OH \cdot HCl$ in 10.2 mL MeOH, and adding a solution of 1.36 g of KOH in 6.0 mL MeOH at 40° C.). The mixture was stirred at room temperature for 17 hr. The solution was neutralized (pH 7) with 1N HCl and was extracted with $CH_2Cl_2$ (3×50 mL). The combined organic extracts were dried ($MgSO_4$), filtered and concentrated. The crude material was purified by radial chromatography on silica gel (10:1:0.5 $CH_2Cl_2$:MeOH:$NH_4OH$) to give 68 mg of white solid The material displayed very broad $^1H$ NMR spectrum and was dissolved in $CH_2Cl_2$ (20 mL), washed with $NaHCO_3$ (10 ml), dried ($MgSO_4$) and concentrated to provide COMPOUND 331 (42 mg, 31%) as a white solid that contained 9% of the cis-isomer by LC-MS.

$^1H$ NMR ($CDCl_3$) δ 1.36-1.50 (m, 4H), 1.75-1.80 (m, 2H), 1.89-2.01 (m, 2H), 2.09 (s, 6H), 2.09-2.11 (m, 1H), 2.34-2.50 (m, 1H), 3.82 (br s, 4H), 7.05 (dd, 2H, J=4.8, 7.5 Hz), 7.34 (d, 2H, J=7.5 Hz), 8.27 (d, 2H, J=4.8 Hz); $^{13}C$ NMR ($CDCl_3$) δ18.4, 27.0, 29.3, 42.2, 55.1, 59.2, 122.9, 133.9, 138.7, 145.9, 157.1, 173.8; LS-MS m/z 369 (M+H) (90%)+369 (M+H) (9%). Anal. Calcd. for $C_{21}H_{28}N_4O_2 \cdot 0.7\,CH_2Cl_2$: C, 60.91; H, 6.92; N, 13.09. Found: C, 60.82; H, 7.03; N, 12.75.

Example 332

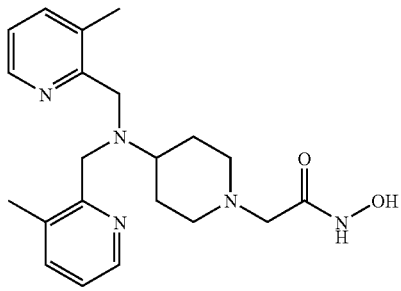

COMPOUND 332: 2-{4-[Bis-(3-methyl-pyridin-2-ylmethyl)-amino]-piperidin-1-yl}-N-hydroxyacetamide To a 0° C. solution of a solution of COMPOUND 249 (150 mg, 0.483 mmol) in $CH_2Cl_2$ (10 mL) and DIPEA (0.170 mL, 0.966 mmol) was added methyl bromoacetate (0.055 mL, 0.579 mmol), and the reaction mixture was stirred for 17 hr at room temperature. Saturated $NaHCO_3$ (10 mL) was added to the reaction mixture, which was then extracted with $CH_2Cl_2$ (3×30 mL). The combined organic extracts were dried ($MgSO_4$), filtered and concentrated. The residue was purified by radial chromatography on silica gel (20:1:0.5 $CH_2Cl_2$:MeOH:$NH_4OH$) to give {4-[bis-(3-methyl-pyridin-2-ylmethyl)-amino]-piperidin-1-yl}-acetic acid methyl ester (154 mg, 83%). $^1H$ NMR ($CDCl_3$) δ 1.86-1.92 (m, 4H), 1.98-2.07 (m, 2H), 2.08 (s, 6H), 2.45-2.50 (m, 1H), 2.96-2.99 (m, 2H), 3.17 (s, 2H), 3.71 (s, 3H), 3.83 (s, 4H), 7.07 (dd, 2H, J=4.8, 7.5 Hz), 7.34 (d, 2H, J=7.5 Hz), 8.33 (d, 2H, J=4.8 Hz).

To the methyl ester (154 mg, 0.4026 mmol) above was added a 0.88 M solution (3.7 mL) of $NH_2OH \cdot HCl$ in KOH and MeOH (prepared by dissolving 1.0 g of $NH_2OH \cdot HCl$ in 10.2 mL MeOH, and adding a solution of 1.36 g of KOH in 6.0 mL MeOH at 40° C.). The mixture was stirred at room temperature for 17 hr. The solution was neutralized (pH 7) with 1N HCl and was extracted with $CH_2Cl_2$ (3×50 mL). The combined organic extracts were dried ($MgSO_4$), filtered and concentrated. The white powder required no purification and AMD12962 was obtained (115 mg, 75%). $^1H$ NMR (MeOH-$d_4$) δ 1.84-2.02 (m, 6H), 2.14 (s, 6H), 2.35-2.51 (m, 1H), 2.93-2.97 (m, 2H), 2.96 (s, 2H) 3.83 (s, 4H), 7.22 (dd, 2H, J=4.8, 7.8 Hz), 7.54 (d, 2H, J=7.8 Hz), 8.25 (d, 2H, J=4.8 Hz); $^{13}C$ NMR (DMSO-$d_6$) δ 17.8, 26.5, 53.6, 54.5, 57.0, 59.5, 122.7, 133.1, 138.1, 145.9, 157.4, 166.3; ES-MS m/z 385 (M+H). Anal. Calcd. for $C_{21}H_{29}N_5O_2 \cdot 1.5H_2O$: C, 61.44; H, 7.86; N, 17.06. Found: C, 61.44; H, 7.61; N, 16.95.

Example 333

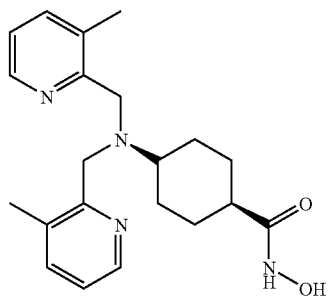

COMPOUND 333: cis-4-[Bis-(3-methyl-pyridin-2-ylmethyl)-amino]-cyclohexanecarboxylic acid hydroxyamide Using General Procedure B, reaction of cis-4-amino-cyclohexanecarboxylic acid methyl ester, 3-methylpyridine-2-carbaldehyde, and $NaBH(OAc)_3$ in $CH_2Cl_2$ gave an amine, which was further reacted in $CH_2Cl_2$ with 3-methylpyridine-2-carbaldehyde and $NaBH(OAc)_3$ to give cis-4-[bis-(3-methyl-pyridin-2-ylmethyl)-amino]-cyclohexanecarboxylic acid methyl ester. $^1H$ NMR ($CDCl_3$) δ 1.30-1.43 (m, 2H), 1.52-1.60 (m, 2H), 1.82-1.90 (m, 2H), 2.09 (s, 6H), 2.16-2.25 (m, 2H), 2.40-2.49 (m, 1H), 2.52-2.62 (m, 1H), 3.70 (s, 3H), 3.80 (s, 4H), 7.06 (dd, 2H, J=3.6, 6.9 Hz), 7.34 (d, 2H, J=6.9 Hz), 8.32 (d, 2H, J=3.6 Hz).

To the methyl ester (116 mg, 0.316 mmol) above was added a solution (0.88 M, 2.8 mL) of $NH_2OH \cdot HCl$ in KOH and MeOH (prepared by dissolving 1.0 g of $NH_2OH \cdot HCl$ in 10.2 mL MeOH, and adding a solution of 1.36 g of KOH in 6.0 mL MeOH at 40° C.). The mixture was stirred at room temperature for 4 hr. The solution was neutralized (pH 7) with 1N HCl and was extracted with $CH_2Cl_2$ (3×50 mL). The combined organic extracts were dried ($MgSO_4$), filtered and concentrated. The crude material was purified by recrystallization from $CH_2Cl_2$ to provide COMPOUND 333 (14 mg, 12%). $^1H$ NMR (MeOH-$d_4$) δ 1.36-1.45 (m, 2H), 1.73-1.80 (m, 2H), 1.89-2.08 (m, 4H), 2.14 (s, 6H), 2.34-2.50 (m, 2H), 3.82 (s, 4H), 7.20 (dd, 2H, J=4.8, 7.5 Hz), 7.53 (d, 2H, J=7.5 Hz), 8.24 (d, 2H, J=4.8 Hz); $^{13}C$ NMR (DMSO-$d_6$) δ 17.8, 23.9, 27.7, 35.8, 54.4, 57.9, 122.7, 133.0, 138.1, 145.9, 157.5, 172.0; ES-MS m/z 391 (M+Na). Anal. Calcd. for $C_{21}H_{28}N_4O_2 \cdot 0.2H_2O$: C, 67.79; H, 7.69; N, 15.06. Found: C, 67.67; H, 7.58; N, 14.96.

Example 334

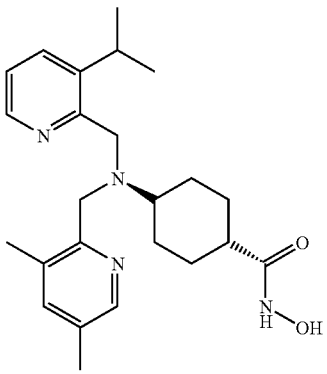

COMPOUND 334: trans-4-[(3,5-dimethyl-pyridin-2-ylmethyl)-(3-isopropyl-pyridin-2-ylmethyl)-amino]-cyclohexanecarboxylic acid hydroxyamide Using General Procedure B, a 1:1 mixture of trans- and cis-4-amino-cyclohexanecarboxylic acid methyl ester (1.06 g, 6.72 mmol), 3,5-dimethylpyridine-2-carbaldehyde (605 mg, 4.48 mmol), NaBH(OAc)$_3$ (1.42 g, 6.72 mmol) in CH$_2$Cl$_2$ (25 mL) were stirred at room temperature for 17 hours. Saturated NaHCO$_3$ (20 mL) was added and the mixture was extracted with CH$_2$Cl$_2$ (3×50 mL). The combined organic extracts were dried (MgSO$_4$), filtered and concentrated. Column chromatography of the material on silica gel (20:1:1 CH$_2$Cl$_2$:MeOH:NH$_4$OH) followed by radial chromatography of the most polar material provided clean trans-4-[(3,5-dimethyl-pyridin-2-ylmethyl)-amino]-cyclohexanecarboxylic acid methyl ester (133 mg, 11%) along with 1.13 g of mixed cis and trans compound. $^1$H NMR (CDCl$_3$) δ 1.14-1.26 (m, 2H), 1.40-1.53 (m, 2H), 1.95-2.08 (m, 4H), 2.09-2.30 (m, 2H), 2.24 (s, 6H), 2.16-2.23 (m, 1H), 2.46-2.53 (m, 1H), 3.64 (s, 3H), 3.83 (s, 2H), 7.21 (s, 1H), 8.18 (s, 1H).

Using General Procedure B: Reaction of the material above, 3-isopropylpyridine-2-carbaldehyde and NaBH(OAc)$_3$ gave trans-4-[(3,5-dimethyl-pyridin-2-ylmethyl)-(3-isopropyl-pyridin-2-ylmethyl)-amino]-cyclohexanecarboxylic acid methyl ester. $^1$H NMR (CDCl$_3$) δ 0.93 (d, 6H, J=6.6 Hz), 1.28-1.50 (m, 4H), 1.95-2.03 (m, 4H), 2.20-2.23 (m, 1H), 2.20 (s, 3H), 2.28 (s, 3H), 2.44-2.52 (m, 1H), 2.85-2.95 (m, 1H), 3.63 (s, 3H), 3.78 (s, 2H), 3.82 (s, 2H), 7.12 (dd, 1H, J=3.9, 7.5 Hz), 7.23 (s, 1H), 7.48 (d, 1H, J=7.5 Hz), 8.18 (s, 1H), 8.32 (d, 1H, J=3.9 Hz).

To the methyl ester (74 mg, 0.1816 mmol) above was added a solution (0.88 M, 1.65 mL) of NH$_2$OH.HCl in KOH and MeOH (prepared by dissolving 1.0 g of NH$_2$OH.HCl in 10.2 mL MeOH, and adding a solution of 1.36 g of KOH in 6.0 mL MeOH at 40° C.). The mixture was stirred at room temperature for 17 hr. The solution was neutralized (pH 7) with 1N HCl and was extracted with CH$_2$Cl$_2$ (3×50 mL). The combined organic extracts were dried (MgSO$_4$), filtered and concentrated. The crude material was recrystallized from CH$_2$Cl$_2$ give to provide COMPOUND 334 (45 mg, 60%) as a white solid. $^1$H NMR (MeOH-d$_4$) δ 0.93 (d, 6H, J=6.6 Hz), 1.25-1.60 (m, 4H), 1.80-1.86 (m, 2H), 1.97-2.03 (m, 3H), 2.29 (s, 3H), 2.31 (s, 3H), 2.41-2.52 (m, 1H), 2.83-2.90 (m, 1H), 3.80 (s, 4H), 7.28 (dd, 1H, J=4.8, 8.1 Hz), 7.48 (s, 1H), 7.68 (d, 1H, J=8.1 Hz), 8.13 (s, 1H), 8.24 (d, 1H, J=4.8 Hz); $^{13}$C NMR (MeOH-d$_4$) δ18.2, 18.9, 23.8, 28.2, 28.5, 30.5, 43.5, 55.1, 55.2, 60.0, 125.0, 134.7, 135.6, 136.3, 141.3, 146.6, 146.6, 146.8, 155.5, 157.1, 175.9; ES-MS m/z 411 (M+H); Anal. Calcd. for C$_{24}$H$_{34}$N$_4$O$_2$.0.7H$_2$O: C, 68.12; H, 8.43; N, 13.24. Found: C, 68.03; H, 8.28; N, 13.12.

Example 335

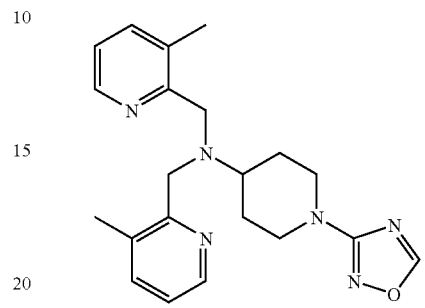

COMPOUND 335: Bis-(3-methyl-pyridin-2-ylmethyl)-(1-[1,2,4]oxadiazol-3-yl-piperidine-4-yl)-amine A mixture of 4-[bis-(3-methyl-pyridin-2-ylmethyl)-amino]-N-hydroxy-piperidine-1-carboxamidine (50 mg, 0.13 mmol), dioxane (2 ml) and ethyl orthoformate (2 ml) were heated for 17 hours at 100° C. The volatiles were removed in vacuo, and the residue was purified using radial chromatography on silica gel (20:1:1 CH$_2$Cl$_2$:MeOH:NH$_4$OH) to provide COMPOUND 335 as a yellow oil (34.2 mg, 69%). $^1$H NMR (CHCl$_3$) δ 1.70-1.82 (m, 5H), 1.96-2.00 (m, 2H), 2.10 (s, 6H), 2.68-2.86 (m, 3H), 3.83 (s, 4H), 4.08-4.13 (m, 2H), 7.09 (dd, 2H, J=5.7, 8.4 Hz), 7.37 (d, 2H, J=8.4 Hz), 8.29 (s, 1H), 8.34 (d, 2H, J=5.7 Hz); $^{13}$C NMR (CHCl$_3$) δ 18.4, 26.7, 46.9, 55.0, 57.6, 122.8, 133.8, 138.4, 146.3, 157.6, 164.3, 169.9; ES-MS m/z 401 (M+Na). Anal. Calcd. for C$_{21}$H$_{26}$N$_6$.0.2H$_2$O.0.4CH$_2$Cl$_2$: C, 61.78; H, 6.59; N, 20.20. Found: C, 61.77; H, 6.59; N, 19.93.

Example 336

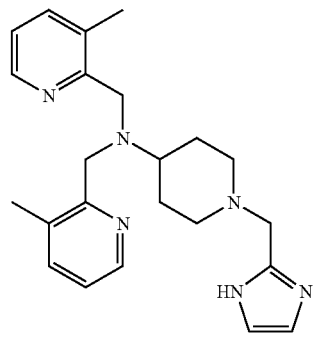

COMPOUND 336: [1-(1H-imidazol-2-ylmethyl)-piperidin-4-yl]-bis-(3-methyl-pyridin-2-ylmethyl)-amine To a solution of COMPOUND 249 (0.1182 g, 0.38 mmol) in MeOH (8 mL) was added NaBH$_3$CN (0.0477, 0.76 mmol)

and 2-imidazole carboxaldehyde (0.0438 g, 0.46 mmol), and stirred at room temperature for 24 hours then concentrated. Saturated NaHCO$_3$ (15 mL) was added and extracted with CH$_2$Cl$_2$ (2×40 mL). The combined organic extracts were dried (Na$_2$SO$_4$), filtered, and concentrated. Purification of the crude material by column chromatography on silica gel (20:1:1 CH$_2$Cl$_2$-MeOH—NH$_4$OH) provided 0.0486 g (31%) of COMPOUND 336 as a white solid. $^1$H NMR (CDCl$_3$) δ 1.67-1.87 (m, 4H), 1.99 (t, 2H, J=11.3 Hz), 2.08 (s, 6H), 2.47-2.55 (m, 1H), 2.87 (d, 2H, J=11.1 Hz), 3.58 (s, 2H), 3.82 (s, 4H), 6.98 (s, 2H), 7.02-7.09 (m, 2H), 7.35 (d, 2H, J=7.2 Hz), 8.33 (d, 2H, J=3.9 Hz). $^{13}$C NMR (CDCl$_3$) δ 18.39, 27.23, 54.15, 55.31, 56.25, 57.94, 121.88, 122.77, 127.09, 133.81, 138.42, 146.20, 157.67. ES-MS m/z 377 (M+Na$^+$). Anal. Calcd. for C$_{23}$H$_{30}$N$_6$.0.6CH$_4$O: C, 69.18; H, 7.97; N, 20.51. Found: C, 69.05; H, 7.78; N, 20.39.

Example 337

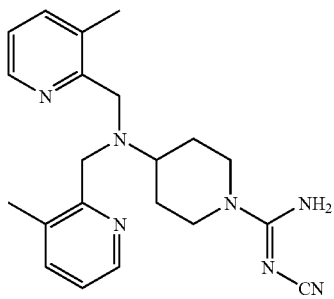

COMPOUND 337: 4-[bis-(3-methyl-pyridin-2-ylmethyl)-amino]-N-cyano-piperidine-1-carboxamidine To a solution of COMPOUND 249 (0.2469 g, 0.80 mmol) in MeOH (8 mL) was added dimethyl N-cyanodithioiminocarbonate (0.1489 g, 0.87 mmol) and stirred at 65° C. for 2 hours, then concentrated. The crude was dissolved in MeOH (10 mL) and NH$_4$OH (3 mL) was added, and stirred at 40° C. for 2 hours, then concentrated. Recrystallization from CH$_2$Cl$_2$ followed by radial chromatography (20:1:1 CH$_2$Cl$_2$-MeOH—NH$_4$OH) provided 0.0156 g (5%) of COMPOUND 337 as a white solid. $^1$H NMR (CD$_3$OD) δ 1.67-1.75 (m, 2H), 1.89-1.94 (m, 2H), 2.14 (s, 6H), 2.70 (t, 3H, J=12.0 Hz), 3.82 (s, 4H), 4.21 (d, 2H, J=12.6 Hz), 7.20-7.24 (m, 2H), 7.54 (d, 2H, J=7.5 Hz), 8.25-8.26 (m, 2H). $^{13}$C NMR (CD$_3$OD) δ 18.67, 28.32, 46.62, 55.71, 59.44, 120.77, 124.69, 136.09, 140.65, 146.77, 158.31, 161.88. ES-MS m/z 378.4 (M+H). Anal. Calcd. for C$_{21}$H$_{27}$N$_7$.0.2CH$_2$Cl$_2$: C, 64.55; H, 7.00; N, 24.85. Found: C, 64.64; H, 7.09; N, 24.46.

Example 338

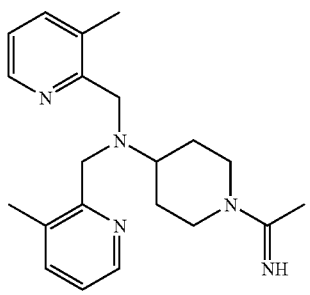

COMPOUND 338: [1-(1-imino-ethyl)-piperidin-4-yl]-bis-(3-methyl-pyridin-2-ylmethyl)-amine To a solution of COMPOUND 249 (0.1054 g, 0.34 mmol) in MeOH (4 mL) was added Et$_3$N (0.1 mL, 0.68 mmol) and ethyl acetimidate hydrochloride (0.0549 g, 0.41 mmol), and stirred at room temperature for 24 hours then concentrated. Saturated NaHCO$_3$ (15 mL) was added and extracted with CH$_2$Cl$_2$ (2×40 mL). Purification of the crude material by column chromatography on silica gel (15:1:1 CH$_2$Cl$_2$-MeOH—NH$_4$OH) followed by radial chromatography on silica gel (50:3:2 CH$_2$Cl$_2$-MeOH—NH$_4$OH) provided 0.0408 g (34%) of COMPOUND 338 as a white solid. $^1$H NMR (CDCl$_3$) δ 1.60-1.72 (m, 2H), 1.90-1.95 (m, 2H), 2.09 (s, 6H), 2.12 (s, 3H), 2.47-2.68 (m, 4H), 3.82 (s, 4H), 4.17 (d, 2H, J=12.3 Hz), 7.06-7.10 (m, 2H), 7.37 (d, 2H, J=7.2 Hz), 8.34 (d, 2H, J=4.5 Hz). $^{13}$C NMR (CDCl$_3$) δ 18.39, 23.92, 27.33, 45.64, 55.06, 57.89, 122.77, 133.81, 138.40, 146.29, 157.63, 164.64. ES-MS m/z 352.5 (M+H).

Example 339

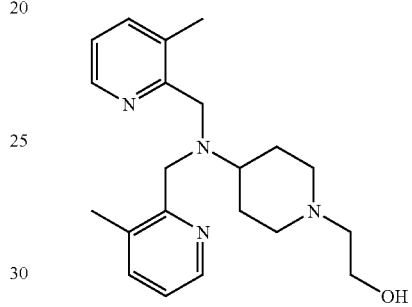

COMPOUND 339: 2-{4-[bis-(3-methyl-pyridin-2-ylmethyl)-amino]-piperidin-1-yl}-ethanol To a solution of COMPOUND 249 (0.1189 g, 0.38 mmol) in CH$_3$CN (4 mL) was added Et$_3$N (0.08 mL, 0.57 mmol), KI (0.0063 g, 0.04 mmol), and 2-bromoethanol (0.03 mL, 0.46 mmol), and stirred at room temperature for 23 hours. Saturated NaHCO$_3$ (10 mL) was added and extracted with CH$_2$Cl$_2$ (3×30 mL), and the combined organic extracts were dried (Na$_2$SO$_4$), filtered, and concentrated. Purification of the crude material by column chromatography on silica gel (25:1:1 CH$_2$Cl$_2$-MeOH—NH$_4$OH) provided 0.0946 g (66%) of COMPOUND 339 as a pale yellow oil. $^1$H NMR (CDCl$_3$) δ 1.71-1.98 (m, 6H), 2.09 (s, 6H), 2.46 (t, 3H, J=5.1 Hz), 2.94 (d, 3H, J=10.8 Hz), 3.56 (t, 2H, J=5.1 Hz), 3.82 (s, 4H), 7.04-7.08 (m, 2H), 7.34 (d, 2H, J=7.5 Hz), 8.33 (d, 2H, J=4.2 Hz). $^{13}$C NMR (CDCl$_3$) δ 18.35, 27.34, 53.93, 55.13, 57.82, 58.52, 59.74, 122.63, 133.76, 138.29, 146.15, 157.80. ES-MS m/z 355.5 (M+H). Anal. Calcd. for C$_{21}$H$_{30}$N$_4$O.0.3CH$_2$Cl$_2$: C, 67.33; H, 8.12; N, 14.74. Found: C, 67.46; H, 8.43; N, 14.93.

Example 340

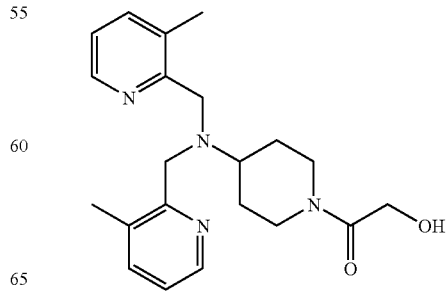

COMPOUND 340: 1-{4-[bis-(3-methyl-pyridin-2-ylmethyl)-amino]-piperidin-1-yl}-2-hydroxy-ethanone To a solution of COMPOUND 249 (0.3543 g, 1.14 mmol) in CH$_2$Cl$_2$ (11 mL) was added acetoxyacetyl chloride (0.18 mL, 1.71 mmol) and DIPEA (0.60 mL, 3.42 mmol), and stirred at room temperature for 60 hours. Saturated NaHCO$_3$ (15 mL) was added and extracted with CH$_2$Cl$_2$ (3×40 mL). The combined organic extracts were dried (Na$_2$SO$_4$), filtered and concentrated. Purification of the crude material by column chromatography on silica gel (50:1:1 CH$_2$Cl$_2$-MeOH—NH$_4$OH) provided 0.2161 g (46%) of 2-{4-[bis-(3-methyl-pyridin-2-ylmethyl)-amino]-piperidin-1-yl}-2-oxo-ethyl ester as a pale yellow solid. $^1$H NMR (CDCl$_3$) δ 1.58-1.66 (m, 2H), 1.83-1.87 (m, 1H), 2.06 (s, 6H), 2.13 (s, 1H), 2.16 (s, 3H), 2.41 (t, 1H, J=12.0 Hz), 2.68-2.73 (m, 1H), 2.90 (t, 1H, J=12.0 Hz), 3.66-3.87 (m, 5H), 4.63 (d, 1H, J=15.0 Hz), 4.71 (d, 2H, J=3.0 Hz), 7.05-7.09 (m, 2H), 7.35 (d, 2H, J=6.0 Hz), 8.33 (d, 2H, J=3.0 Hz).

To a solution of 2-{4-[bis-(3-methyl-pyridin-2-ylmethyl)-amino]-piperidin-1-yl}-2-oxo-ethyl ester (0.2161 g, 0.53 mmol) in MeOH (5 mL) was added K$_2$CO$_3$ (0.2930 g, 2.12 mmol), and stirred at room temperature for 1 hour. The mixture was concentrated, and water (10 mL) was added and extracted with CH$_2$Cl$_2$ (3×35 mL). The combined organic extracts were dried (Na$_2$SO$_4$), filtered, and concentrated. Purification of the crude material by column chromatography on silica gel (50:1:1 CH$_2$Cl$_2$-MeOH—NH$_4$OH) provided 0.1474 mg (73%) of COMPOUND 340 as a white solid. $^1$H NMR (CDCl$_3$) δ 1.53-1.71 (m, 2H), 1.88-1.93 (m, 1H), 2.02 (s, 1H), 2.07 (s, 6H), 2.51 (t, 1H, J=12.0 Hz), 2.71-2.88 (m, 2H), 3.52 (d, 1H, J=12.6 Hz), 3.66 (s, 1H), 3.73-3.90 (m, 4H), 4.08-4.20 (m, 2H), 4.65 (d, 1H, J=13.2 Hz), 7.06-7.10 (m, 2H), 7.36 (d, 2H, J=7.5 Hz), 8.33 (d, 2H, J=3.0 Hz). $^{13}$C NMR (CDCl$_3$) δ 16.51, 21.79, 24.00, 26.09, 26.86, 28.30, 29.59, 43.07, 49.81, 50.48, 62.30, 65.47, 111.39, 119.16, 121.70, 122.15, 122.66, 137.72, 147.18, 157.09. ES-MS m/z 369.3 (M+H). Anal. Calcd. for C$_{21}$H$_{28}$N$_4$O$_2$.0.1(CH$_2$Cl$_2$).0.2H$_2$O: C, 66.59; H, 7.57; N, 14.72. Found: C, 66.53; H, 7.51; N, 14.75.

Example 341

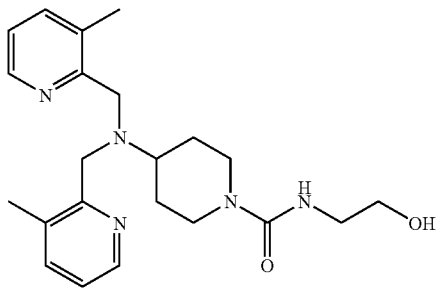

COMPOUND 341: 4-[bis-(3-methyl-pyridin-2-ylmethyl)-amino]-piperidine-1-carboxylic acid (2-hydroxy-ethyl)-amide To a solution of COMPOUND 249 (0.2345 g, 0.76 mmol) in CH$_2$Cl$_2$ (8 mL) was added DIPEA (3.9 mL, 22.80 mmol) and 1,1'-carbonyldiimidazole (0.6162 g, 3.80 mmol). After stirring at room temperature for 2 hours, ethanolamine (0.69 mL, 11.40 mmol) was added, and stirred at room temperature for 16 hours. Saturated NaHCO$_3$ (20 mL) was added and extracted with CH$_2$Cl$_2$ (3×30 mL). The combined organic extracts were dried (Na$_2$SO$_4$), filtered and concentrated. Purification of the crude material by column chromatography on silica gel (50:1:1 CH$_2$Cl$_2$-MeOH—NH$_4$OH) provided 0.2917 g of intermediate {4-[bis-(3-methyl-pyridin-2-ylmethyl)-amino]-piperidin-1-yl}-imidazol-1-yl-methanone as a colorless oil. The intermediate was dissolved in DMF (5 mL) and ethanolamine (1.0 mL, 16.5 mmol) was added, and stirred at 80° C. for 20 hours. The mixture was concentrated, and saturated NaHCO$_3$ (10 mL) was added and extracted with CH$_2$Cl$_2$ (3×30 mL). The combined organic extracts were washed with brine (3×20 mL), dried (Na$_2$SO$_4$), filtered and concentrated. Purification of the crude material by column chromatography on silica gel (50:1:1 then 20:1:1 CH$_2$Cl$_2$-MeOH—NH$_4$OH) provided 58.5 mg (19%) of COMPOUND 341 as a white solid. $^1$H NMR (CDCl$_3$) δ 1.60-1.65 (m, 2H), 1.87-1.91 (m, 2H), 2.08 (s, 6H), 2.64 (t, 3H, J=12.6 Hz), 3.35-3.40 (m, 2H), 3.70 (t, 2H, J=4.8 Hz), 3.80 (s, 4H), 4.01 (d, 2H, J=13.2 Hz), 5.15 (t, 1H, J=6.0 Hz), 7.05-7.10 (m, 2H), 7.36 (d, 2H, J=7.5 Hz), 8.32 (d, 2H, J=4.5 Hz). $^{13}$C NMR (CDCl$_3$) δ 18.68, 28.51, 44.61, 45.46, 55.72, 59.88, 62.95, 124.66, 136.08, 140.64, 146.73, 158.40, 160.45. ES-MS m/z 398.2 (M+H). Anal. Calcd. for C$_{22}$H$_{31}$N$_5$O$_2$.0.1CH$_2$Cl$_2$: C, 65.38; H, 7.75; N, 17.25. Found: C, 65.01; H, 7.89; N, 17.21.

Example 342

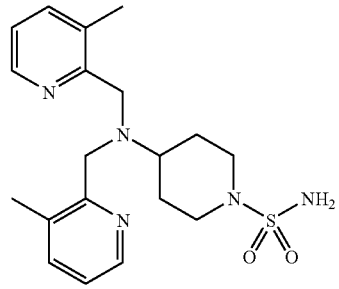

COMPOUND 342: 4-[bis-(3-methyl-pyridin-2-ylmethyl)-amino]-piperidine-1-sulfonic acid amide To a solution of COMPOUND 249 (0.1882 g, 0.61 mmol) in 1,4-dioxane (25 mL) was added sulfamide (0.5826 g, 6.06 mmol), and stirred at 100° C. for 4 hours. The mixture was concentrated and water (20 mL) was added and extracted with CH$_2$Cl$_2$ (2×75 mL). The combined organic extracts were washed with water (2×30 mL), dried (Na$_2$SO$_4$), filtered and concentrated. Purification of the crude material by column chromatography on silica gel (33:1:1 CH$_2$Cl$_2$-MeOH—NH$_4$OH) provided 0.1461 g (59%) of COMPOUND 342 as a white solid. $^1$H NMR (CDCl$_3$) δ 1.80-1.88 (m, 2H), 1.95-2.00 (m, 2H), 2.08 (s, 6H), 2.48-2.58 (m, 3H), 3.76-3.82 (m, 6H), 4.76 (s, 2H), 7.06-7.11 (m, 2H), 7.37 (d, 2H, J=7.2 Hz), 8.33 (d, 2H, J=3.0 Hz). $^{13}$C NMR (CDCl$_3$) δ 21.23, 30.29, 50.70, 58.21, 61.67. ES-MS m/z 390.4 (M+H). Anal. Calcd. for $C_{19}H_{27}N_5O_2S \cdot 0.2(CH_2Cl_2)$: C, 56.73; H, 6.79; N, 17.23. Found: C, 56.44; H, 7.06; N, 17.08.

Example 343

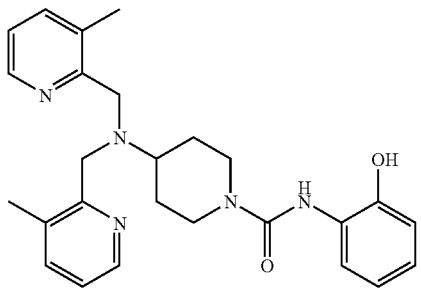

COMPOUND 343: 4-[bis-(3-methyl-pyridin-2-ylmethyl)-amino]-piperidine-1-carboxylic acid (2-hydroxy-phenyl)-amide To a solution of COMPOUND 249 (0.1537 g, 0.50 mmol) in toluene (5 mL) was added DIPEA (0.17 mL, 1.00 mmol), and at 0° C. was added a 20% phosgene solution in toluene (0.27 mL, 0.59 mmol). The reaction was stirred at room temperature for 2 hours, then concentrated. The remaining solid was dissolved in DMF (5 mL), and DIPEA (0.17 mL, 1.00 mmol) and 2-aminophenol (0.2353 g, 2.50 mmol) were added, and stirred at room temperature for 20 hours. The mixture was concentrated, and saturated NaHCO$_3$ (20 mL) was added and extracted with CH$_2$Cl$_2$ (3×40 mL). The combined organic extracts were washed with brine (2×30 mL), dried (Na$_2$SO$_4$), filtered, and concentrated. Purification of the crude material by column chromatography on silica gel (50:1:1 then 20:1:1 CH$_2$Cl$_2$-MeOH—NH$_4$OH) followed by radial chromatography (20:1:1 CH$_2$Cl$_2$-MeOH—NH$_4$OH) provided 56.0 mg (24%) of COMPOUND 343 as a brown solid. $^1$H NMR (CD$_3$OD) δ 1.70-1.78 (m, 2H), 1.91-1.95 (m, 2H), 2.15 (s, 6H), 2.68 (t, 3H, J=12.6 Hz), 3.85 (s, 4H), 4.23 (d, 2H, J=14.1 Hz), 6.68-6.71 (m, 2H), 7.08-7.11 (m, 2H), 7.21-7.25 (m, 2H), 7.55 (d, 2H, J=7.8 Hz), 8.27 (d, 2H, J=4.5 Hz). $^{13}$C NMR (DMSO) δ 17.76, 27.09, 44.12, 54.56, 57.81, 115.03, 122.36, 122.84, 128.41, 132.36, 133.23, 138.16, 145.97, 152.75, 155.37, 157.39. ES-MS m/z 446.5 (M+H). Anal. Calcd. for $C_{26}H_{31}N_5O_2 \cdot 0.3(CH_2Cl_2) \cdot 0.2H_2O$: C, 67.06; H, 6.76; N, 14.87. Found: C, 67.17; H, 6.83; N, 14.58.

Example 344

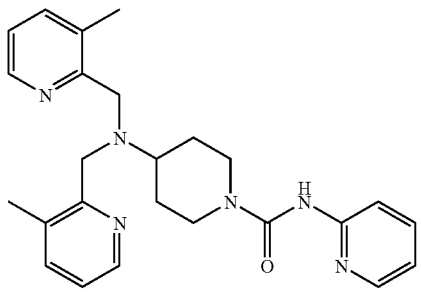

COMPOUND 344: 4-[bis-(3-methyl-pyridin-2-ylmethyl)-amino]-piperidine-1-carboxylic acid pyridin-2-ylamide A solution of 1,1'-carbonyldiimidazole (0.0924 g, 0.57 mmol), 2-aminopyridine (0.0489 g, 0.52 mmol), and DIPEA (0.18 mL, 1.04 mmol) in CH$_2$Cl$_2$ (6 mL) was stirred at room temperature for 4.5 hours. The mixture was concentrated, then dissolved in DMF (6 mL), and DIPEA (0.18 mL, 1.04 mmol) and COMPOUND 249 (0.1614 g, 0.52 mmol) were added. The mixture stirred at 60° C. for 20 hours, then concentrated. Saturated NaHCO$_3$ (10 mL) was added and extracted with CH$_2$Cl$_2$ (3×40 mL). The combined organic extracts were dried (Na$_2$SO$_4$), filtered and concentrated. Purification of the crude material by column chromatography on silica gel (50:1:1 CH$_2$Cl$_2$-MeOH—NH$_4$OH) provided 0.1148 g (46%) COMPOUND 344 as a white solid. $^1$H NMR (CDCl$_3$) δ 1.61-1.74 (m, 2H), 1.95 (d, 2H, J=12.0 Hz), 2.07 (s, 6H), 2.68-2.77 (m, 3H), 3.80 (s, 4H), 4.17 (d, 2H, J=13.2 Hz), 6.88-6.92 (m, 1H), 7.05-7.09 (m, 2H), 7.35-7.37 (m, 2H), 7.58-7.65 (m, 2H), 7.98 (d, 1H, J=8.4 Hz), 8.17 (d, 1H, J=4.8 Hz), 8.32 (d, 2H, J=6.0 Hz). $^{13}$C NMR (CDCl$_3$) 18.37, 27.49, 44.78, 54.96, 57.77, 113.67, 118.68, 122.36, 122.88, 133.82, 135.55, 138.51, 146.26, 147.82, 153.23, 154.14, 157.41. ES-MS m/z 431.3 (M+H). Anal. Calcd. for $C_{25}H_{30}N_6O \cdot 0.5H_2O \cdot 0.6C_3H_4N_2$: C, 67.00; H, 7.01; N, 20.99. Found: C, 67.11; H, 6.94; N, 21.04.

Example 345

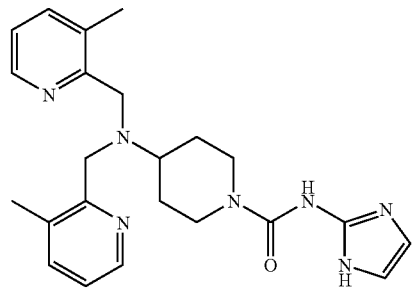

COMPOUND 345: 4-[bis-(3-methyl-pyridin-2-ylmethyl)-amino]-piperidine-1-carboxylic acid (1H-imidazol-2-yl)-amide A solution of 1,1'-carbonyldiimidazole (0.0924 g, 0.57 mmol), 2-aminoimidazole sulfate (0.0687 g, 0.52 mmol), and DIPEA (0.36 mL, 2.08 mmol) in CH$_2$Cl$_2$ (6 mL) and DMF (6 mL) was stirred at room temperature for 4.5 hours. The mixture was concentrated to rid of CH$_2$Cl$_2$, and DIPEA (0.36 mL, 2.08 mmol) and COMPOUND 249 (0.1614 g, 0.52 mmol) were added. The mixture stirred at 60° C. for 19 hours, then concentrated. Saturated NaHCO$_3$ (15 mL) was added and extracted with CH$_2$Cl$_2$ (3×30 mL). The combined organic extracts were dried (Na$_2$SO$_4$), filtered and concentrated. Purification of the crude material by column chromatography on silica gel (50:1:1 CH$_2$Cl$_2$-MeOH—NH$_4$OH) provided 37.1 mg (16%) COMPOUND 345 as a white solid. $^1$H NMR (CDCl$_3$) δ 1.66-1.70 (m, 2H), 1.93-1.97 (m, 2H), 2.08 (s, 6H), 2.72 (t, 3H, J=10.8 Hz), 3.82 (s, 4H), 4.32 (d, 2H, J=11.4 Hz), 6.70 (s, 2H), 7.07-7.09 (m, 2H), 7.36 (d, 2H, J=7.2 Hz), 8.34 (s, 2H). $^{13}$C NMR (CDCl$_3$) 18.37, 27.61, 44.75, 54.96, 57.81, 122.81, 133.79, 138.43, 145.43, 146.30, 155.71, 157.54. ES- MS m/z 420.1 (M+H). Anal. Calcd. for C$_{23}$H$_{29}$N$_7$O.0.3CH$_2$Cl$_2$: C, 62.89; H, 6.70; N, 22.03. Found: C, 62.84; H, 6.93; N, 21.82.

Example 346

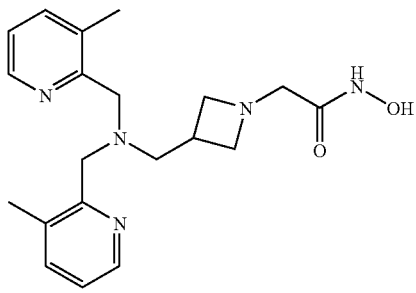

COMPOUND 346: 2-(3-{[bis-(3-methyl-pyridin-2-ylmethyl)-amino]-methyl}-azetidin-1-yl)-N-hydroxy-acetamide Using General Procedure B: Reaction of 3-aminomethyl-azetidine-1-carboxylic acid tert-butyl ester (Falgueyret, J.-P. et al. *J. Med. Chem.* 2001, 44, 94-104) in CH$_2$Cl$_2$ with 3-methyl-pyridine-2-carbaldehyde and NaBH(OAc)$_3$ gave 3-{[(3-methyl-pyridin-2-ylmethyl)-amino]-methyl}-azetidine-1-carboxylic acid tert-butyl ester as a yellow oil. $^1$H NMR (CDCl$_3$) δ 1.44 (s, 9H), 2.30 (s, 3H), 2.66-2.75 (m, 1H), 2.92 (d, 2H, J=6.0 Hz), 3.61-3.66 (m, 2H), 3.88 (s, 2H), 4.02 (t, 2H, J=9.0 Hz).

Using General Procedure B: Reaction of 3-{[(3-methyl-pyridin-2-ylmethyl)-amino]-methyl}-azetidine-1-carboxylic acid tert-butyl ester in CH$_2$Cl$_2$ with 3-methyl-pyridine-2-carbaldehyde and NaBH(OAc)$_3$ gave 3{[bis-(3-methyl-pyridin-2-ylmethyl)-amino]-methyl}-azetidine-1-carboxylic acid tert-butyl ester as a sticky colorless oil. $^1$H NMR (CDCl$_3$) δ 1.36 (s, 9H), 2.06 (s, 6H), 2.64-2.75 (m, 3H), 3.22-3.26 (m, 2H), 3.72 (s, 4H), 3.80 (t, 2H, J=7.5 Hz), 7.08-7.12 (m, 2H), 7.39 (d, 2H, J=6.0 Hz), 8.36 (d, 2H, J=3.0 Hz). Deprotection with TFA using General Procedure F gave azetidin-3-ylmethyl-bis-(3-methyl-pyridin-2-ylmethyl)-amine as a pale yellow sticky oil. $^1$H NMR (CDCl$_3$) δ 1.85 (s, 1H), 2.10 (s, 6H), 2.73 (d, 2H, J=9.0 Hz), 2.94-2.99 (m, 1H), 3.09-3.12 (m, 2H), 3.49-3.54 (m, 2H), 3.70 (s, 4H), 7.08-7.12 (m, 2H), 7.39 (d, 2H, J=6.0 Hz), 8.37 (d, 2H, J=6.0 Hz).

To a solution of azetidin-3-ylmethyl-bis-(3-methyl-pyridin-2-ylmethyl)-amine (0.4739 g, 1.6 mmol) in CH$_2$Cl$_2$ (16 mL) were added DIPEA (0.56 mL, 3.2 mmol), and methyl bromoacetate (0.18 mL, 1.9 mmol). The mixture was stirred at room temperature for 19 hours, and then saturated NaHCO$_3$ (15 mL) was added and extracted with CH$_2$Cl$_2$ (3×50 mL). The combined organic extracts were dried (Na$_2$SO$_4$), filtered, and concentrated. Purification of the crude material by column chromatography on silica gel (100:1:1 CH$_2$Cl$_2$-MeOH—NH$_4$OH) provided 0.1411 g (24%) of (3-{[bis-(3-methyl-pyridin-2-ylmethyl)-amino]-methyl}-azetidin-1-yl)-acetic acid methyl ester as a yellow sticky oil. $^1$H NMR (CDCl$_3$) δ 2.09 (s, 6H), 2.53-2.58 (m, 2H), 2.65-2.78 (m, 3H), 3.10 (s, 2H), 3.51 (t, 2H, J=6.0 Hz), 3.65 (s, 3H), 3.68 (s, 4H), 7.06-7.10 (m, 2H), 7.38 (d, 2H, J=9.0 Hz), 8.35 (d, 2H, J=6.0 Hz).

Hydroxylamine hydrochloride (1.0 g, 14.3 mmol) was dissolved in MeOH (6 mL) with slight heating. In a separate flask, KOH (1.36 g, 21.3 mmol) was dissolved in MeOH (6 mL) with heating to 60° C., then this was added to the above solution at 40° C. KCl precipitated out, and was cooled to 0° C. The clear portion of this suspension (3.2 mL) was added to (3-{[bis-(3-methyl-pyridin-2-ylmethyl)-amino]-methyl}-azetidin-1-yl)-acetic acid methyl ester (0.1411 g, 0.38 mmol) and stirred at room temperature for 24 hours. 1N HCl (3 mL) was added until neutral, and extracted with CH$_2$Cl$_2$ (3×40 mL). The combined organic extracts were dried (Na$_2$SO$_4$), filtered, and concentrated. Purification of the crude material by column chromatography on silica gel (25:1:1 then 10:1:1 CH$_2$Cl$_2$-MeOH—NH$_4$OH) provided 67.3 mg (48%) of COMPOUND 346 as a white solid. $^1$H NMR (CDCl$_3$) δ 2.07 (s, 6H), 2.57-2.73 (m, 5H), 3.03 (s, 2H), 3.32 (t, 2H, J=6.0 Hz), 3.69 (s, 4H), 7.09-7.13 (m, 2H), 7.40 (d, 2H, J=7.5 Hz), 8.36 (d, 2H, J=3.9 Hz). $^{13}$C NMR (CDCl$_3$) δ 18.23, 29.15, 58.56, 59.63, 60.28, 60.69, 123.06, 133.80, 138.65, 146.22, 156.94, 167.02. ES-MS m/z 370.5 (M+H). Anal. Calcd. for C$_{20}$H$_{27}$N$_5$O$_2$.0.6CH$_4$O.0.5H$_2$O: C, 62.21; H, 7.70; N, 17.61. Found: C, 62.06; H, 7.61; N, 17.49.

Example 347

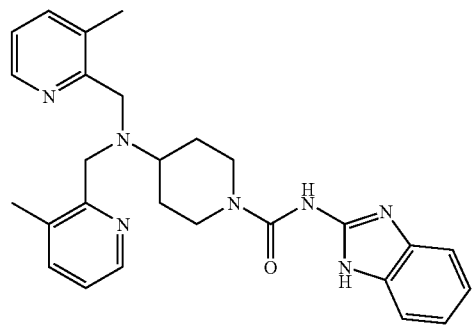

COMPOUND 347: 4-[bis-(3-methyl-pyridin-2-ylmethyl)-amino]-piperidine-1-carboxylic acid (1H-benzoimidazol-2-yl)-amide A solution of 1,1'-carbonyldiimidazole (0.0713 g, 0.44 mmol), 2-aminobenzimidazole (0.0533 g, 0.40 mmol), and DIPEA (0.14 mL, 0.80 mmol) in CH$_2$Cl$_2$ (4 mL) was stirred at room temperature for 2.5 hours. The mixture was concentrated, then dissolved in DMF (4 mL), and DIPEA (0.14 mL, 0.80 mmol) and COMPOUND 249 (0.1242 g, 0.40 mmol) were added. The mixture stirred at 60° C. for 20 hours, then concentrated. Saturated NaHCO$_3$ (15 mL) was added and extracted with CH$_2$Cl$_2$ (3×40 mL). The combined organic extracts were washed with brine (2×30 mL), dried (Na$_2$SO$_4$), filtered and concentrated. Purification of the crude material by column chromatography on silica gel (75:1:1 then 50:1:1 CH$_2$Cl$_2$-MeOH—NH$_4$OH) provided 0.0919 g (43%) of COMPOUND 347 as a white solid. $^1$H NMR (CDCl$_3$) δ 1.66-1.70 (m, 4H), 1.94 (d, 2H, J=12.6 Hz), 2.07 (s, 6H), 2.69-2.77 (m, 3H), 3.81 (s, 4H), 4.41 (d, 2H, J=13.5 Hz), 7.06-7.15 (m, 4H), 7.29-7.31 (m, 2H), 7.36 (d, 2H, J=7.5 Hz), 8.33 (d, 2H, J=3.0 Hz). $^{13}$C NMR (CDCl$_3$) 18.36, 27.60, 44.78, 54.93, 57.89, 112.76, 122.11, 122.77, 133.77, 138.41, 146.22, 152.31, 157.51, 158.32. ES-MS m/z 470.3 (M+H). Anal. Calcd. for C$_{27}$H$_{31}$N$_7$O.0.7CH$_2$Cl$_2$.0.1CH$_4$O: C, 62.74; H, 6.21; N, 18.42. Found: C, 63.02; H, 6.24; N, 18.22.

Example 348

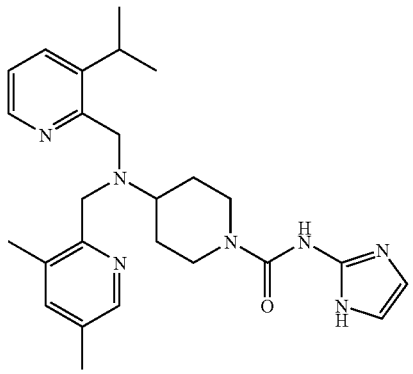

COMPOUND 348: 4-[(3,5-dimethyl-pyridin-2-ylmethyl)-(3-isopropyl-pyridin-2-ylmethyl)-amino]-piperidine-1-carboxylic acid (1H-imidazol-2-yl)-amide A solution of 1,1'-carbonyldiimidazole (0.1054 g, 0.65 mmol), 2-aminoimidazole sulfate (0.0859 g, 0.65 mmol), and DIPEA (0.45 mL, 2.60 mmol) in DMF (7 mL) was stirred at room temperature for 4 hours. (3,5-Dimethyl-pyridin-2-ylmethyl)-(3-isopropyl-pyridin-2-ylmethyl)-piperidin-4-yl-amine (0.2301 g, 0.65 mmol) was added and stirred at 60° C. for 22 hours, then concentrated. Saturated NaHCO$_3$ (15 mL) was added and extracted with CH$_2$Cl$_2$ (3×30 mL). The combined organic extracts were dried (Na$_2$SO$_4$), filtered and concentrated. Purification of the crude material by column chromatography on silica gel (50:1:1 CH$_2$Cl$_2$-MeOH—NH$_4$OH) followed by radial chromatography on silica (100:1:1 CH$_2$Cl$_2$-MeOH—NH$_4$OH) provided 30.2 mg (10%) COMPOUND 348 as a yellow solid. $^1$H NMR (CDCl$_3$) δ 0.93 (d, 6H, J=9.0 Hz), 1.61-1.72 (m, 2H), 1.93 (d, 2H, J=11.1 Hz), 2.16 (s, 3H), 2.28 (s, 3H), 2.68-2.79 (m, 4H), 3.80 (d, 4H, J=18.3 Hz), 4.33 (d, 2H, J=12.9 Hz), 6.70 (s, 2H), 7.12-7.16 (m, 1H), 7.24 (s, 1H), 7.50 (d, 1H, J=7.5 Hz), 8.18 (s, 1H), 8.32 (d, 1H, J=4.5 Hz). $^{13}$C NMR (CDCl$_3$) 18.29, 18.46, 23.60, 27.39, 27.59, 44.78, 54.32, 57.40, 123.16, 132.26, 133.21, 133.85, 139.06, 144.40, 145.46, 146.07, 146.64, 154.49, 155.70, 156.31. ES-MS m/z 463.1 (M+H). Anal. Calcd. for C$_{26}$H$_{35}$N$_7$O.0.3CH$_2$Cl$_2$: C, 64.85; H, 7.37; N, 20.13. Found: C, 64.72; H, 7.63; N, 19.74.

Example 349

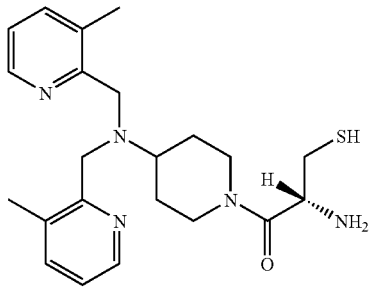

COMPOUND 349: L-2-amino-1-{4-[bis-(3-methyl-pyridin-2-ylmethyl)-amino]-piperidin-1-yl}-3-mercapto-propan-1-one (HBr salt)

To a solution of L-cysteine (1.0218 g, 8.4 mmol) in water (8 mL) and THF (8 mL) were added Et$_3$N (4.68 mL, 33.6 mmol) and Boc$_2$O (3.6884 g, 16.9 mmol) and stirred at room temperature for 48 hours. Et$_2$O (20 mL) was added and extracted with 10% Et$_3$N in water (3×30 mL). The combined aqueous extracts were acidified to pH 4 with citric acid, then extracted with Et$_2$O (3×50 mL). The combined organic extracts were washed with 0.5 M citric acid (1×40 mL) and water (1×40 mL), dried (Na$_2$SO$_4$), filtered, and concentrated to provide 2.4232 g (85%) of 2-tert-butoxycarbonylamino-3-tert-butoxycarbonylsulfanyl-propionic acid as a white solid. $^1$H NMR (CDCl$_3$) δ 1.45 (s, 9H), 1.49 (s, 9H), 3.21-3.25 (m, 1H), 4.16-4.32 (m, 2H), 5.45 (d, 1H, J=6.0 Hz).

Using General Procedure G: To a solution of COMPOUND 249 (0.1233 g, 0.40 mmol) in DMF (5 mL) were added 2-tert-butoxycarbonylamino-3-tert-butoxycarbonylsulfanyl-propionic acid (0.1414 g, 0.44 mmol), DIPEA (0.14 mL, 0.80 mmol), EDCI (0.0920 g, 0.48 mmol), and HOBT (0.0649 g, 0.48 mmol), and stirred at room temperature for 16 hours. Purification of the crude material by column chromatography on silica gel (100:1:1 CH$_2$Cl$_2$-MeOH—NH$_4$OH) provided 0.1652 g (67%) of thiocarbonic acid S-(3-{4-[bis-(3-methyl-pyridin-2-ylmethyl)-amino]-piperidin-1-yl}-2-tert-butoxycarbonylamino-3-oxo-propyl) ester O-tert-butyl ester as a white solid. $^1$H NMR (CDCl$_3$) δ 1.43 (s, 9H), 1.47 (s, 9H), 1.67 (s, 5H), 2.08 (d, 6H, J=6.0 Hz), 2.39-2.43 (m, 1H), 2.75-3.14 (m, 3H), 3.80-3.83 (m, 4H), 4.13 (d, 1H, J=15.0 Hz), 4.65 (d, 1H, J=15.0 Hz), 4.88-4.89 (m, 1H), 5.52-5.55 (m, 1H), 7.07-7.11 (m, 2H), 7.37 (d, 2H, J=6.0 Hz), 8.34 (d, 2H, J=3.0 Hz).

Conversion to the HBr salt using General Procedure D gave COMPOUND 349 as a white solid. $^1$H NMR (D$_2$O) 1.62-1.64 (m, 2H), 2.10-2.12 (m, 2H), 2.48 (s, 6H), 2.72-3.20 (m, 5H), 3.96-3.97 (m, 1H), 4.34 (s, 4H), 4.48-4.50 (m, 2H), 7.81-7.82 (m, 2H), 8.32 (d, 2H, J=5.7 Hz), 8.54-8.55 (m, 2H). $^{13}$C NMR (D$_2$O) 17.35, 24.60, 27.40, 42.73, 45.42, 50.98, 52.29, 59.73, 126.16, 137.88, 138.74, 148.67, 151.08, 166.29. ES-MS m/z 414.3 (M+H). Anal. Calcd. for C$_{22}$H$_{31}$N$_5$OS.3.6HBr.4.8H$_2$O: C, 33.39; H, 5.63; N, 8.85; Br, 36.35; S, 4.05. Found: C, 33.45; H, 5.58; N, 8.72; Br, 36.31; 4.18.

Example 350

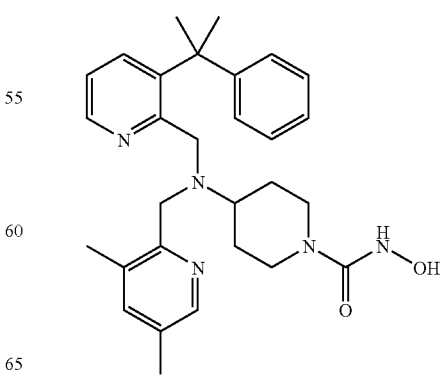

COMPOUND 350: 4-{(3,5-Dimethyl-pyridin-2-ylmethyl)-[3-(1-methyl-1-phenyl-ethyl)-pyridin-2-ylmethyl]-amino}-piperidine-1-carboxylic acid hydroxamide A stirred solution of (3,5-dimethyl-pyridin-2-ylmethyl)-[3-(1-methyl-1-phenyl-ethyl)-pyridin-2-ylmethyl]-piperidin-4-yl-amine (1.20 g, 2.8 mmol) and N-(phenoxycarbonyl)-hydroxylamine (515 mg, 3.4 mmol) in THF (28 mL) was heated at reflux for 16 hours. The mixture was cooled to room temperature, concentrated, and purified on a silica gel column (40 g, eluted with 5% $NH_4OH$/10% MeOH/$CH_3CN$) to afford COMPOUND 350 (1.12 g, 82%), as a white solid. $^1$H NMR ($CDCl_3$) δ 1.10-1.26 (m, 2H), 1.51 (d, 2H, J=11.5 Hz), 1.62 (s, 6H), 2.23 (s, 3H), 2.25 (s, 3H), 2.48 (t, 3H, J=11.5), 3.41 (s, 2H), 3.60 (s, 2H), 3.86 (d, 2H, J=12.0 Hz), 7.03 (d, 2H, J=7.5 Hz), 7.12-7.25 (m, 5H), 7.87 (d, 1H, J=8.0 Hz), 8.10 (s, 1H), 8.50 (d, 1H, J=3.5 Hz); $^{13}$C NMR ($CDCl_3$) δ 18.31, 18.76, 27.73(2), 31.23 (2), 42.86, 43.94(2), 54.18, 54.78, 58.20, 121.96, 126.15(2), 126.42, 128.93(2), 131.98, 133.14, 134.44, 139.45, 143.75, 146.51, 146.89, 149.75, 161.05; ES-MS m/z 488 (M+H). Anal. Calcd. For $C_{29}H_{37}N_5O_2$.0.6$H_2O$: C, 69.88; H, 7.72; N, 14.05. Found: C, 69.51; H, 7.55; N, 14.12.

Example 351

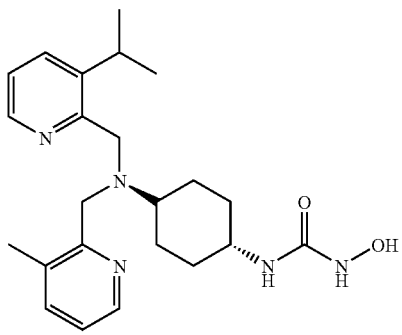

COMPOUND 351: 1-{trans-4-[(3-Isopropyl-pyridin-2-ylmethyl)-(3-methyl-pyridin-2-ylmethyl)-amino]-cyclohexyl}-3-hydroxy-urea A solution of COMPOUND 117 (159 mg, 0.45 mmol) and 1,1'-carbonyl-diimidazole (73 mg, 0.45 mmol) in anhydrous THF (5 mL) was stirred at room temperature, under a $N_2$ atmosphere, for 45 minutes. The mixture was concentrated on a rotary evaporator. To the resultant residue were added DMF (3 mL), $NH_2OH$.HCl (125 mg, 1.8 mmol), and DIPEA (0.40 mL, 2.3 mmol). The mixture was stirred for 16 hours and concentrated. The colorless oily residue was dissolved in EtOAc (15 mL), washed with brine (4×10 mL), dried over $Na_2SO_4$, and concentrated. Purification of the crude material by silica gel column chromatography (10 g silica, eluted with 10% $NH_4OH$/10% MeOH/$CH_2Cl_2$) provided COMPOUND 351 (85 mg, 46%), as a white solid. $^1$H NMR ($CDCl_3$) δ 0.91 (d, 6H, J=7.5 Hz), 1.01-1.16 (m, 2H), 1.59-1.70 (m, 2H), 1.97 (d, 2H, J=11.5 Hz), 2.18 (d, 2H, J=11.5 Hz), 2.21 (s, 3H), 2.44 (t, 1H, J=10.5 Hz), 2.71-2.80 (m, 1H), 3.58-3.70 (m, 1H), 3.79 (s, 4H), 5.82 (d, 1H, J=8.0 Hz), 6.60 (s, 1H), 7.10-7.18 (m, 2H), 7.45 (d, 1H, J=7.5 Hz), 7.53 (dd, 1H, J=8.0, 1.5 Hz), 8.35 (ddd, 2H, J=12.5, 5.0, 1.5 Hz), 9.94 (s br, 1H); $^{13}$C NMR ($CDCl_3$) δ 18.57, 23.52(2), 26.40 (2), 27.39, 33.71(2), 49.12, 53.81, 54.31, 58.24, 123.07, 123.51, 134.19, 134.60, 138.67, 144.95, 145.85(2), 146.28 (2), 161.77; ES-MS m/z 412 (M+H). Anal. Calcd. For $C_{23}H_{33}N_5O_2$.0.1$H_2O$: C, 66.83; H, 8.10; N, 16.94. Found: C, 66.63; H, 8.18; N, 16.94.

Example 352

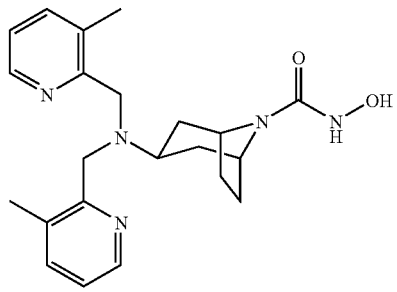

COMPOUND 352: 3-[Bis-(3-methyl-pyridin-2-ylmethyl)-amino]-8-aza-bicyclo[3.2.1]octane-8-carboxylic acid hydroxyamide A solution of tropan-3-endo-ylamine (2.8 g, 20 mmol) (Allegretti, M., et al. Tetrahedron Lett. 2001, 42, 4257-4260) and phthalic anhydride (5.9 g, 40 mmol) in toluene (60 mL) was refluxed under a Dean-Stark apparatus for 64 hours. The mixture was cooled to room temperature and concentrated. The residue was partitioned between saturated $NaHCO_3$ solution (20 mL) and chloroform (20 mL). The aqueous layer was extracted with chloroform (3×20 mL), and the combined organic extracts were dried over $Na_2SO_4$ and concentrated. Purification of the crude material by column chromatography (80 g silica gel, eluted with 5% $NH_4OH$/EtOAc) gave 3-endo-phthalamido-tropane (2.4 g, 44%) as a pale-yellow solid.

A stirred solution of 3-endo-phthalamido-tropane (1.0 g, 3.7 mmol) and vinyl chloroformate (0.70 mL, 8.2 mmol) in 1,2-dichloroethane (15 mL) was heated at reflux for 16 hours under a $N_2$ atmosphere. The mixture was cooled to room temperature, quenched with saturated $NaHCO_3$ solution (10 mL), and extracted with $CH_2Cl_2$ (3×10 mL). The organic extracts were combined, dried over $Na_2SO_4$, and concentrated. The pale-yellow foamy residue was dissolved in $CH_2Cl_2$ (10 mL) and anhydrous HCl was bubbled through the stirred solution for 10 minutes. The solution was concentrated, taken up in MeOH (10 mL), and heated at reflux for 15 minutes. The solution was allowed to cool to room temperature and saturated $NaHCO_3$ solution (10 mL) was added. The mixture was stirred for 1 hour and the layers were separated. The aqueous layer was extracted with $CH_2Cl_2$ (2×10 mL). The combined organic layers were dried over $Na_2SO_4$ and concentrated to give 2-(8-aza-bicyclo[3.2.1]oct-3-yl)-isoindole-1,3-dione (0.80 g, 84%) as a pale-yellow solid.

Deprotection with $H_2NNH_2.H_2O$ following General Procedure E gave 3-endo-amino-8-aza-bicyclo[3.2.1]octane-8-carboxylic acid tert-butyl ester as a colorless oil.

Using General Procedure B: Reaction of 3-endo-Amino-8-aza-bicyclo[3.2.1]octane-8-carboxylic acid tert-butyl ester with 3-methyl-pyridine-2-carbaldehyde gave 3-endo-[bis-(3-methyl-pyridin-2-ylmethyl)-amino]-8-aza-bicyclo[3.2.1]octane-8-carboxylic acid tert-butyl ester as a yellow solid. Deprotection with TFA using General Procedure F gave (endo-8-aza-bicyclo[3.2.1]oct-3-yl)-bis-(3-methyl-pyridin-2-ylmethyl)-amine as a pale-yellow oil.

A stirred solution of (endo-8-aza-bicyclo[3.2.1]oct-3-yl)-bis-(3-methyl-pyridin-2-ylmethyl)-amine (225 mg, 0.67 mmol) and N-(phenoxycarbonyl)-hydroxylamine (120 mg, 0.80 mmol) in THF (10 mL) was heated at reflux for 4 hours. The mixture was cooled to room temperature, concentrated, and purified on a silica gel column (5 g silica gel, eluted with 10% $NH_4OH$/10% $MeOH$/$CH_3CN$) to afford COMPOUND 352 (91 mg, 34%), as a white solid. $^1H$ NMR ($CDCl_3$) δ 1.40-1.47 (m, 2H), 1.76-1.95 (m, 6H), 2.08 (s, 6H), 3.08-3.20 (m, 1H), 3.79 (s, 4H), 4.27 (s, 2H), 6.89 (s, 1H), 7.10 (dd, 2H, J=7.5, 4.5 Hz), 7.37 (d, 2H, J=7.5 Hz), 8.36 (d, 2H, J=4.5 Hz); $^{13}C$ NMR δ 18.13(2), 28.14 (2), 31.91 (2), 51.11, 53.59(2), 54.56 (2), 123.24 (2), 134.10(2), 139.14 (2), 145.71 (2), 156.44, 159.14; ES-MS m/z 418 (M+Na); Anal. Calcd. For $C_{22}H_{29}N_5O_2 \cdot 0.3H_2O$: C, 65.91; H, 7.44; N, 17.47. Found: C, 65.67; H, 7.46; N, 17.67.

Example 353

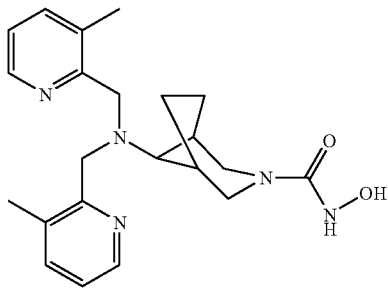

COMPOUND 353: 8-[bis-(3-methyl-pyridin-2-ylmethyl)-amino]-3-aza-bicyclo[3.2.1]octane-3-carboxylic acid hydroxyamide A mixture of 3-benzyl-3-aza-bicyclo[3.2.1]octan-8-one (0.560 g, 2.60 mmol) (Lowe, J. A. et al. *J. Med. Chem.* 1994, 37, 2831-2840), $NH_4OAc$ (2.3 g, 30 mmol) and $NaBH_3CN$ (0.245 g, 3.90 mmol) in MeOH (15 mL) was stirred and heated at reflux for 72 h. The mixture was cooled to room temperature, and the solvent was removed. Aqueous NaOH (1 N, 10 mL) was added, and the aqueous suspension was extracted with $CH_2Cl_2$ (3×30 mL). The combined extract was washed with water (30 mL) and dried over anhydrous $Na_2SO_4$. After filtration the solvent was removed by evaporation under vacuum, and the residue was dissolved in dry $CH_2Cl_2$ (30 mL). $Et_3N$ (3 mL) and $Boc_2O$ (0.872 g, 4.00 mmol) were added, and the mixture was stirred for 16 h. Water (30 mL) was then added, and the mixture was extracted with $CH_2Cl_2$ (4×30 mL). The organic extracts were combined and dried over anhydrous $Na_2SO_4$. After filtration the solvent was removed by evaporation under vacuum, and the residue was purified by flash chromatography on a silica gel column (1:1 $CH_2Cl_2$/hexanes), affording an impure solid mainly containing (3-benzyl-3-aza-bicyclo[3.2.1]oct-8-yl)-carbamic acid tert-butyl ester. A mixture of the solid and Pd/C (10% in wt, 0.20 g, 0.188 mmol) in MeOH/EtOAc (40 mL, 3:1) was stirred under $H_2$ atmosphere (1 atm) overnight. $CH_2Cl_2$ (20 mL) was then added, and the mixture was filtered through a celite cake. The filtrate was concentrated by evaporation under vacuum, and the residue was purified by flash chromatography on a silica gel column (100:5:1 $CH_2Cl_2$/MeOH/$NH_4OH$), affording (3-aza-bicyclo[3.2.1]oct-8-yl)-carbamic acid tert-butyl ester as a white solid (0.277 g, 50%). $^1H$ NMR ($CDCl_3$) δ 1.45 (s, 9H), 1.62-1.68 (m, 2H), 1.81-1.85 (m, 2H), 2.02 (s, br. 2H), 2.49-2.55 (m, 2H), 2.96-3.01 (m, 2H), 3.67-3.80 (m, 1H), 5.04 (s, br. 1H).

To a solution of (3-aza-bicyclo[3.2.1]oct-8-yl)-carbamic acid tert-butyl ester (0.277 g, 1.22 mmol) and $Et_3N$ (0.185 g, 1.83 mmol) in dry $CH_2Cl_2$ (10 mL) was added 2-nitrobenzenesulfonyl chloride (0.326 g, 1.47 mmol). After the mixture was stirred for 4 h water (20 mL) was added, and the mixture was extracted with $CH_2Cl_2$ (3×20 mL). The extracts were combined and dried over anhydrous $Na_2SO_4$. After filtration the solvent was removed by evaporation under vacuum, and the residue was purified by flash chromatography on a silica gel column ($CH_2Cl_2$), affording a pure white solid. Deprotection with TFA using General Procedure F gave 3-(2-Nitrobenzenesulfonyl)-3-aza-bicyclo[3.2.1]oct-8-ylamine as a pale yellow solid. $^1H$ NMR ($CDCl_3$) δ 1.76-1.79 (m, 4H), 1.95-2.03 (m, 2H), 3.16 (t, 1H, J=4.8 Hz), 3.37-4.45 (m, 4H), 7.57-7.60 (m, 1H), 7.65-7.69 (m, 2H), 7.92-7.95 (m, 1H).

Using General Procedure B: Reaction of 3-(2-nitro-benzenesulfonyl)-3-aza-bicyclo[3.2.1]oct-8-ylamine, 3-methyl-pyridine-2-carbaldehyde and $NaBH(OAc)_3$ gave a white solid The solid (0.129, 0.247 mmol) was dissolved in dry $CH_3CN$ (5 mL), and $Cs_2CO_3$ (0.242 g, 0.742 mmol) and thiophenol (0.082 g, 0.74 mmol) were added. After the mixture was stirred for 3 h $CH_3CN$ was removed, and water (10 mL) was added. The aqueous suspension was extracted with $CH_2Cl_2$ (3×20 mL). The extracts were combined and dried over anhydrous $Na_2SO_4$. After filtration the solvent was removed by evaporation under vacuum, and the residue was purified by flash chromatography on a silica gel column (100:5:4 $CH_2Cl_2$/MeOH/$NH_4OH$), affording (3-aza-bicyclo[3.2.1]oct-8-yl)-bis-(3-methyl-pyridin-2-ylmethyl)-amine as a colorless oil (0.064 g, 77%). $^1H$ NMR ($CDCl_3$) δ 1.77-1.81 (m, 2H), 2.00-2.08 (m, 2H), 2.16-2.22 (m, 2H), 2.24 (s, 6H), 2.41-2.48 (m, 2H), 2.98 (t, 1H, J=4.2 Hz), 3.16 (s, 1H), 3.21 (s, 1H), 3.96 (s, 4H), 6.98 (dd, 2H, J=4.8, 7.5 Hz), 7.27 (d, 2H, J=7.5 Hz), 8.31 (d, 2H, J=4.8 Hz).

A mixture of (3-aza-bicyclo[3.2.1]oct-8-yl)-bis-(3-methyl-pyridin-2-ylmethyl)-amine (0.064 g, 0.19 mmol) and hydroxylaminecarboxylic acid phenyl ester (PhOCONHOH) (0.058 g, 0.38 mmol) in dry THF (4 mL) was heated at reflux overnight. Water (10 mL) was then added, and the mixture was extracted with EtOAc (20 mL) and $CH_2Cl_2$ (2×20 mL). The extracts were combined and dried over anhydrous $Na_2SO_4$. After filtration the solvent was removed by evaporation under vacuum, and the residue was purified by flash chromatography on a silica gel column (100:5:4 $CH_2Cl_2$/MeOH/$NH_4OH$), affording the product as a white solid (0.056 g, 75%). $^1H$ NMR ($CDCl_3$) δ 1.51-1.58 (m, 2H), 1.74-1.77 (m, 2H), 2.14 (s, 6H), 2.25 (s, br. 2H), 3.15 (t, 1H, J=4.2 Hz), 3.24-3.29 (m, 2H), 3.37-3.42 (m, 2H), 3.96 (s, 4H), 6.93 (s, br. 1H), 6.98 (dd, 2H, J=4.8, 7.5 Hz), 7.25 (d, 2H, J=7.5 Hz), 8.33 (d, 2H, J=4.8 Hz); $^{13}C$ NMR ($CDCl_3$) δ 18.93, 26.08, 35.82, 44.58, 57.64, 67.11, 122.19, 132.69, 137.86, 146.39, 157.51, 163.07. ES-MS m/z 396 (M+H). Anal. Calcd. for $C_{22}H_{29}N_5O_2 \cdot 0.4CH_2Cl_2$: C, 62.65; H, 6.99; N, 16.31. Found: C, 62.50; H, 7.35; N, 16.10.

Example 354

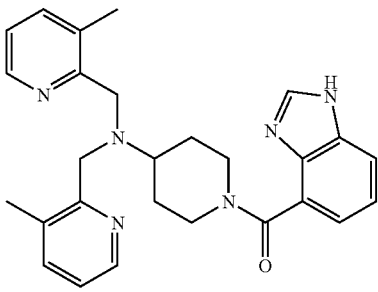

COMPOUND 354: (3H-benzoimidazol-4-yl)-{4-[bis-(3-methyl-pyridin-2-ylmethyl)-amino]-piperidin-1-yl}-methanone (HBr salt)

To a solution of COMPOUND 249 (0.100 g, 0.322 mmol) in CH$_2$Cl$_2$ (5 mL) was added 1H-benzoimidazole-4-carbonyl chloride (0.118 g, 0.653 mmol) (White, A. W. et al. J. Med. Chem. 2000, 43, 4084-4097) and Et$_3$N (0.37 g, 0.37 mmol). After the mixture was stirred overnight water (10 mL) was added, and the mixture was extracted with CH$_2$Cl$_2$ (3×20 mL). The extracts were combined and dried over anhydrous Na$_2$SO$_4$. After filtration the solvent was removed by evaporation under vacuum, and the residue was purified by flash chromatography on silica gel columns (column 1, 6:1 EtOAc/MeOH; column 2, 100:5:1 CH$_2$Cl$_2$/MeOH/NH$_4$OH), affording a white solid (0.080 g, 56%). Conversion to the HBr salt using General Procedure D gave a white solid. $^1$H NMR (D$_2$O) δ 1.55-1.84 (m, 2H), 1.95-1.99 (m, 1H), 2.18-2.22 (m, 1H), 2.45 (s, 6H), 2.88-3.20 (m, 3H), 3.72-3.77 (m, 1H), 4.32 (s, 4H), 4.63-4.70 (m, 1H), 7.61-7.67 (m, 2H), 7.74-7.80 (m, 2H), 7.89-7.93 (m, 1H), 8.28 (d, 2H, J=8.1 Hz), 8.50 (d, 2H, J=5.7 Hz), 9.20 (s, 1H); $^{13}$C NMR (D$_2$O) δ 17.41, 27.50, 28.20, 42.48, 47.56, 51.01, 60.02, 117.02, 121.50, 125.51, 126.16, 127.09, 127.71, 131.38, 137.93, 138.77 140.71, 148.67, 151.08, 167.43. ES-MS m/z 455 (M+Na). Anal. Calcd. for C$_{27}$H$_{30}$N$_6$O.3.5HBr.0.25H$_2$O.0.3C$_4$H$_{10}$O: C, 42.07; H, 5.20; N, 10.44; Br, 34.74. Found: C, 41.86; H, 5.18; N, 10.39; Br, 34.98.

Example 355

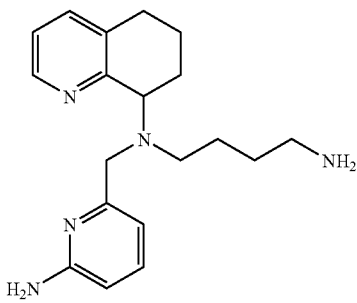

COMPOUND 355: N$^1$-(6-amino-pyridin-2-ylmethyl)-N$^1$-(5,6,7,8-tetrahydro-quinolin-8-yl)-butane-1,4-diamine (HBr salt)

Using General Procedure A: Reaction of 2-[4-(5,6,7,8-tetrahydro-quinolin-8-ylamino)-butyl]-isoindole-1,3-dione, 2-(6-bromomethyl-pyridin-2-yl)-isoindole-1,3-dione (Goswami, S. et al. J. Am. Chem. Soc. 1989, 111, 3425-6), and DIPEA in CH$_3$CN gave 2-{4-[[6-(1,3-dioxo-1,3-dihydro-isoindol-2-yl)-pyridin-2-ylmethyl]-(5,6,7,8-tetrahydro-quinolin-8-yl)-amino]-butyl}-isoindole-1,3-dione as a tan solid. Deprotection with hydrazine following General Procedure E gave the free base. Conversion to the HBr salt using General Procedure D gave COMPOUND 355 as a white solid. $^1$H NMR (D$_2$O) δ 1.51-1.55 (m, 4H), 1.71-1.85 (m, 1H), 1.91-2.03 (m, 1H), 2.13-2.18 (m, 1H), 2.32-2.36 (m, 1H), 2.46-2.54 (m, 1H), 2.67-2.74 (m, 1H), 2.90-2.99 (m, 4H), 3.98 (s, 2H), 4.38 (dd, 1H, J=5.7, 10.8 Hz), 6.90-6.96 (m, 2H), 7.80-7.86 (m, 2H), 8.30 (br d, 1H, J=8.1 Hz), 8.58 (br d, 1H, J=5.7 Hz); $^{13}$C NMR (D$_2$O) δ 20.00, 20.43, 25.14, 25.26, 27.63, 39.57, 51.24, 52.88, 59.64, 113.08, 113.21, 125.70, 139.29, 140.38, 145.05, 146.08, 147.71, 151.86, 154.94; ES-MS m/z 326 (M+H). Anal. Calcd. for C$_{19}$H$_{27}$N$_5$.3.4HBr.1.8H$_2$O: C, 36.05; H, 5.41; N, 11.06; Br, 42.92. Found: C, 35.93; H, 5.24; N, 10.91; Br, 43.14.

Example 356

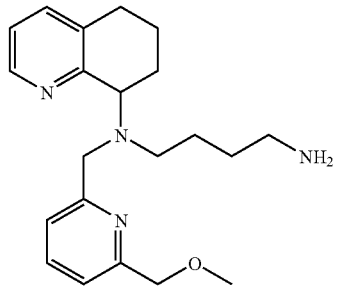

COMPOUND 356: N$^1$-(6-methoxymethyl-pyridin-2-ylmethyl)-N$^1$-(5,6,7,8-tetrahydro-quinolin-8-yl)-butane-1,4-diamine (HBr salt)

Using General Procedure A: Reaction of 2-[4-(5,6,7,8-tetrahydro-quinolin-8-ylamino)-butyl]-isoindole-1,3-dione, 2-bromomethyl-6-methoxymethyl-pyridine (Gillespie, R. J. et al. PCT Int. Appl. (2002), WO 2002055083), and DIPEA in CH$_3$CN gave 2-{4-[(6-methoxymethyl-pyridin-2-ylmethyl)-(5,6,7,8-tetrahydro-quinolin-8-yl)-amino]-butyl}-isoindole-1,3-dione as a yellow oil. Deprotection with H$_2$NNH$_2$.H$_2$O following General Procedure E gave the free base. Conversion to the HBr salt using General Procedure D gave COMPOUND 356 as a white solid. $^1$H NMR (D$_2$O) δ 1.52-1.70 (m, 4H), 1.75-1.89 (m, 1H), 1.98-2.10 (m, 1H), 2.16-2.22 (m, 1H), 2.39-2.43 (m, 1H), 2.59-2.68 (m, 1H), 2.84-3.02 (m, 5H), 3.53 (s, 3H), 4.28 (d, 1H, J=15.9 Hz), 4.36 (d, 1H, J=15.9 Hz), 4.49 (dd, 1H, J=5.7, 10.5 Hz), 4.88 (s, 2H), 7.80 (dd, 1H, J=5.7, 7.8 Hz), 7.91 (d, 1H, J=7.8 Hz), 8.08 (d, 1H, J=7.8 Hz), 8.26 (d, 1H, J=8.1 Hz), 8.47 (dd, 1H, J=7.8, 8.1 Hz), 8.57 (d, 1H, J=5.7 Hz); $^{13}$C NMR (D$_2$O) δ 20.42 (2 carbons), 24.93, 25.01, 27.62, 39.53, 51.42, 53.24, 59.28, 60.01, 70.38, 125.20, 125.72, 126.27, 140.04, 140.29, 146.84, 146.93, 151.24, 153.50, 153.82; ES-MS m/z 355 (M+H). Anal. Calcd.

for $C_{21}H_{30}N_4O \cdot 3.4HBr \cdot 1.2H_2O$: C, 38.73; H, 5.54; N, 8.60; Br, 41.72. Found: C, 39.06; H, 5.54; N, 8.44; Br, 41.42.

Example 357

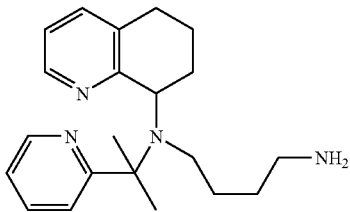

COMPOUND 357: N-(1-methyl-1-pyridin-2-yl-ethyl)-(5,6,7,8-tetrahydroquinolin-8-yl)-butane-1,4-diamine (HBr salt)

The primary amine 1-methyl-1-pyridin-2-yl-ethylamine (2.24 g, 16.4 mmol) and 6,7-Dihydro-5H-quinolin-8-one (1.21 g, 8.2 mmol) were dissolved in toluene (80 mL) and the reaction flask fitted with a Dean-Stark trap. The trap was filled to the mark with toluene (~35 mL) and a condensor placed on top. The vessel was then heated with a heating mantle to a strong reflux for 16 hours and cooled to room temperature. The solvent was then removed under reduced pressure and the solid dried in vacuo. Methanol (65 mL) was added and the solution was treated with $NaBH_4$ (0.62 g, 16.4 mmol), stirring for 20 minutes. The solvent was then removed under reduced pressure and the residue was partitioned between $CH_2Cl_2$ (100 mL) and $NaHCO_3$ (75 mL). The aqueous phase was extracted with $CH_2Cl_2$ (2×60 mL) and the combined organics dried ($Na_2SO_4$) and concentrated under reduced pressure to provide, after column chromatography with silica gel (saturated $NH_3$ in $Et_2O$), (1-Methyl-1-pyridin-2-yl-ethyl)-(5,6,7,8-tetrahydroquinolin-8-yl)-amine (1.47 g, 67%).

Using General Procedure B, reaction of the above secondary amine, 4-(1,3-dioxo-1,3-dihydroisoindol-2-yl)-butyraldehyde and $NaBH(OAc)_3$ in $CH_2Cl_2$ gave 2-{4-[(1-Methyl-1-pyridin-2-yl-ethyl)-(5,6,7,8-tetrahydroquinolin-8-yl)-amino]-butyl}-isoindole-1,3-dione. $^1H$ NMR ($CDCl_3$) δ 0.90 (m, 2H), 1.23 (q, 2H, J=7.5 Hz), 1.54 (s, 3H), 1.65 (s, 3H), 1.67 (br, 1H), 2.00 (m, 2H), 2.07 (m, 2H), 2.45 (m, 1H), 2.50-2.70 (m, 4H), 3.29 (t, 2H, J=7.5 Hz), 4.35 (m, 1H), 6.91 (m, 1H), 7.09 (m, 2H), 7.65 (t, 1H, J=7.5 Hz), 7.69 (m, 2H), 7.80 (m, 2H), 8.27 (d, 1H, J=6.0 Hz), 8.45 (m, 2H). Deprotection with $H_2NNH_2 \cdot H_2O$ following General Procedure E gave N-(1-Methyl-1-pyridin-2-yl-ethyl)-(5,6,7,8-tetrahydroquinolin-8-yl)-butane-1,4-diamine. Conversion to the HBr salt using General Procedure D gave COMPOUND 357 as a pale yellow solid. $^1H$ NMR ($D_2O$) δ 0.94 (br, 2H), 1.29 (q, 2H, J=7.8 Hz), 1.77 (s, 3H), 1.98 (s, 3H), 1.98 (m, 1H), 2.16 (m, 2H), 2.40 (br, 2H), 2.58 (t, 2H, J=7.8 Hz), 2.94 (m, 1H), 3.00 (br, 2H), 7.72 (t, 1H, J=6.8 Hz), 7.89 (t, 1H, J=6.8 Hz), 8.06 (d, 1H, J=7.8 Hz), 8.14 (d, 1H, J=7.5 Hz), 8.45 (dt, 1H, J=7.8, 1.5 Hz), 8.60 (d, 1H, J=4.5 Hz), 8.82 (dd, 1H, J=5.6, 1.0 Hz). $^{13}C$ NMR ($D_2O$) δ 21.00, 21.49, 24.92, 25.08, 26.11, 27.36, 27.83, 39.09, 47.00, 56.56, 65.40, 124.93, 125.51, 126.35, 138.35, 140.15, 143.92, 146.36, 146.84, 153.39, 159.90. ES-MS m/z 339 (M+H). Anal. Calcd. for $C_{21}H_{30}N_4 \cdot 3.1HBr \cdot 1.8H_2O \cdot 0.4C_4H_{10}O$: C, 41.67; H, 6.30; N, 8.60; Br, 38.03. Found: C, 41.97; H, 6.06; N, 8.53; Br, 37.70.

Example 358

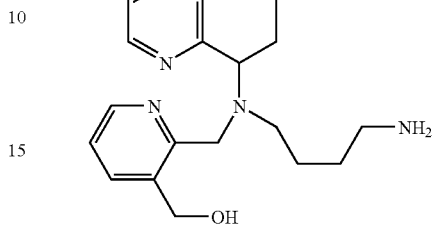

COMPOUND 358: (2-{[(4-Aminobutyl)-(5,6,7,8-tetrahydroquinolin-8-yl)-amino]-methyl}-pyridin-3-yl)-methanol (HBr salt)

Using General Procedure B, reaction of 3-(tert-Butyldimethylsilanyloxymethyl)-pyridine-2-carbaldehyde, 2-[4-(5,6,7,8-Tetrahydroquinolin-8-ylamino)-butyl]-isoindole-1,3-dione and $NaBH(OAc)_3$ in $CH_2Cl_2$ gave 2-{4-[[3-(tert-Butyldimethylsilanyloxymethyl)-pyridin-2-ylmethyl]-(5,6,7,8-tetrahydroquinolin-8-yl)-amino]-butyl}-isoindole-1,3-dione as a light brown solid. $^1H$ NMR ($CDCl_3$) δ 0.11 (s, 6H), 0.95 (s, 9H), 1.31 (m, 2H), 1.49 (quintet, 2H, J=7.5 Hz), 1.59 (m, 1H), 1.85-2.08 (m, 3H), 2.47 (m, 1H), 2.59 (m, 2H), 2.67 (m, 1H), 3.49 (t, 2H, J=7.5 Hz), 3.90 (m, 1H), 3.96 (d, 1H, J=12.0 Hz), 4.11 (d, 1H, J=12.0 Hz), 4.98 (d, 1H, J=15.0 Hz), 5.20 (d, 1H, J=15.0 Hz), 6.99 (m, 1H), 7.13 (m, 1H), 7.28 (d, 1H, J=7.5 Hz), 7.68 (m, 2H), 7.80 (m, 2H), 7.82 (d, 1H, J=7.5 Hz), 8.32 (d, 1H, J=3.0 Hz), 8.42 (d, 1H, J=3.0 Hz).

The above compound (0.56 g, 0.95 mmol) was dissolved in THF (1 mL) and treated with 4N HCl (2 mL) at room temperature for 5.5 hours. $K_2CO_3$ (1.4 g, 10 mmol) and water (10 mL) was added and the aqueous solution was extracted with $CH_2Cl_2$ (3×15 mL). The combined organic phases were dried ($Na_2SO_4$) and concentrated under reduced pressure to afford crude 2-{4-[(3-Hydroxymethyl-pyridin-2-ylmethyl)-(5,6,7,8-tetrahydroquinolin-8-yl)-amino]-butyl}-isoindole-1,3-dione that was used in the next reaction without further purification. Deprotection with $H_2NNH_2 \cdot H_2O$ following General Procedure E gave (2-{[(4-Aminobutyl)-(5,6,7,8-tetrahydroquinolin-8-yl)-amino]-methyl}-pyridin-3-yl)-methanol free base. $^1H$ NMR ($CDCl_3$) δ 1.30 (m, 2H), 1.57 (m, 3H), 1.78 (m, 1H), 2.00 (m, 1H), 2.27 (m, 1H), 2.39 (m, 2H), 2.55 (t, 2H, J=6.0 Hz), 2.70 (m, 2H), 3.71 (m, 1H), 3.92 (d, 1H, J=15.0 Hz), 4.38 (d, 1H, J=15.0 Hz), 4.42 (d, 1H, J=15.0 Hz), 4.97 (d, 1H, J=15.0 Hz), 7.01 (m, 1H), 7.22 (m, 1H), 7.30 (d, 1H, J=6.0 Hz), 7.71 (d, 1H, J=6.0 Hz), 8.36 (d, 1H, J=4.5 Hz), 8.43 (d, 1H, J=4.5 Hz). Conversion to the HBr salt using General Procedure D gave COMPOUND 358 as a white solid. $^1H$ NMR ($D_2O$) δ 1.49 (br, 4H), 1.82 (br m, 1H), 2.06 (m, 1H), 2.17 (br m, 1H), 2.45 (br m, 1H), 2.52 (m, 1H), 2.78 (br m, 1H), 2.84 (br d, 2H, J=6.9 Hz), 2.99 (br d, 2H), 4.33 (d, 1H, J=17.1 Hz), 4.44 (m, 1H), 4.49 (d, 1H, J=17.4 Hz), 7.81 (t, 1H, J=6.9 Hz), 7.97 (t, 1H, J=6.9 Hz), 8.28 (d, 1H, J=7.2 Hz), 8.56 (m, 2H), 8.72 (d, 1H, J=5.4 Hz). $^{13}C$ NMR ($D_2O$) δ 20.46, 20.56, 25.08, 25.31, 27.78, 39.44, 51.60, 51.76, 59.38, 61.04, 125.87, 126.59, 139.08, 139.57, 140.23, 140.58, 146.14, 147.88, 150.98, 151.90. ES-MS m/z 341 (M+H).

Anal. Calcd. for $C_{20}H_{28}N_4O.3.3HBr.0.9H_2O.0.3C_4H_{10}O$: C, 39.42; H, 5.63; N, 8.67; Br, 40.82. Found: C, 39.40; H, 5.52; N, 8.64; Br, 40.87.

Example 359

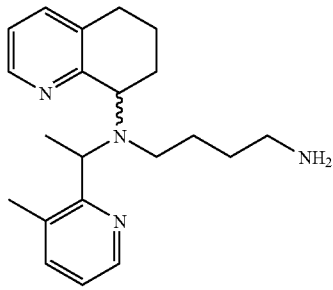

COMPOUND 359: $N^1$-[1-(3-methyl-pyridin-2-yl)-ethyl]-$N^1$-(5,6,7,8-tetrahydro-quinolin-8-yl)-butane-1,4-diamine (HBr salt)

A solution of 1-(3-methyl-pyridin-2-yl)-ethanol (330 mg, 2.41 mmol) (Kawasaki et al. *Nippon Kagaku Zasshi* 1962, 83, 949) and NEt$_3$ (0.50 mL, 3.6 mmol) in CH$_2$Cl$_2$ (10 mL) was cooled to 0° C. under N$_2$. MsCl (0.22 mL, 2.8 mmol) was added and the reaction was stirred at 0° C. for 15 minutes. The reaction was diluted with saturated aqueous NaHCO$_3$ (10 mL), the layers were separated and the aqueous solution was extracted with CH$_2$Cl$_2$ (10 mL×2). The combined organic solution was dried (MgSO$_4$), filtered and concentrated under reduced pressure, giving the crude methanesulfonic acid 1-(3-methyl-pyridin-2-yl)-ethyl ester as an orange oil (484 mg, 2.25 mmol, 93%). $^1$H NMR (CDCl$_3$) δ 1.76 (d, 3H, J=6.6 Hz), 2.45 (s, 3H), 2.84 (s, 3H), 6.07 (q, 1H, J=6.6 Hz), 7.20 (dd, 1H, J=7.8, 4.8 Hz), 7.51 (dd, 1H, J=7.8, 0.9 Hz), 8.51 (dd, 1H, J=4.8, 0.9 Hz).

A solution of the above mesylate (484 mg, 2.25 mmol) and NaN$_3$ (225 mg, 3.46 mmol) in DMF under N$_2$ was stirred for 45 minutes, while slowly heated to 50° C. Once cooled, the resulting cloudy pink mixture was diluted with saturated aqueous NaHCO$_3$ (10 mL) and H$_2$O (10 mL). The solution was extracted with CH$_2$Cl$_2$ (10 mL×3) and the combined organic solution was dried (MgSO$_4$), filtered and concentrated under reduced pressure, giving the crude 2-(1-azido-ethyl)-3-methyl-pyridine as a yellow liquid (254 mg, 1.57 mmol, 70%). $^1$H NMR (CDCl$_3$) δ 1.65 (d, 3H, J=6.6 Hz), 2.38 (s, 3H), 4.73 (q, 1H, J=6.6 Hz), 7.15 (dd, 1H, J=7.5, 4.8 Hz), 7.48 (dd, 1H, J=7.7 Hz, 0.9 Hz), 8.48 (dd, 1H, J=4.5, 0.9 Hz).

A solution of the above azide (254 mg, 1.57 mmol) and PPh$_3$ (828 mg, 3.16 mmol) in 10% aqueous THF (10 mL) was stirred at room temperature for 15 hours. The solvent was removed under reduced pressure and the residue was purified by flash column chromatography on silica (CH$_2$Cl$_2$/MeOH, 9:1), giving 1-(3-methyl-pyridin-2-yl)-ethylamine as a yellow liquid (163 mg, 1.20 mmol, 76%). $^1$H NMR (CDCl$_3$) δ 1.35 (d, 3H, J=6.6 Hz), 2.00 (s, 2H), 2.33 (s, 3H), 4.30 (q, 1H, J=6.6 Hz), 7.05 (dd, 1H, J=7.5, 4.8 Hz), 7.40 (d, 1H, J=7.5 Hz), 8.41 (d, 1H, J=4.2 Hz).

Using General Procedure B: Reaction of the above amine and 6,7-dihydro-5H-quinolin-8-one in MeOH with NaBH$_4$ gave the secondary amine as a 1:1 mixture of diastereomers (94 mg, 31%).

To a solution of the above amine and 4-(1,3-dioxo-1,3-dihydro-isoindol-2-yl)-butyraldehyde (127 mg, 0.58 mmol) in CH$_2$Cl$_2$ (2.5 mL) was added NaBH(OAc)$_3$ (117 mg, 0.55 mmol) and the reaction was stirred at room temperature under N$_2$ for 16 hours. The mixture was diluted with saturated aqueous NaHCO$_3$ (10 mL) and was extracted with CH$_2$Cl$_2$ (10 mL×3). The combined organic solution was dried (MgSO$_4$), filtered and concentrated under reduced pressure. Purification by flash column chromatography on silica (CH$_2$Cl$_2$/MeOH, 9:1) gave 2-{4-[[1-(3-methyl-pyridin-2-yl)-ethyl]-(5,6,7,8-tetrahydro-quinolin-8-yl)-amino]-butyl}-isoindole-1,3-dione as a 1:1 mixture of two diastereomers (72 mg, 0.15 mmol, 43%) along with some single diastereomer (33 mg, 0.07 mmol, 20%).

Data for the single diastereomer: $^1$H NMR (CDCl$_3$) δ 0.80-0.99 (m, 1H), 1.06-1.38 (m, 4H), 1.49-1.63 (m, 1H), 1.54 (d, 3H, J=6.6 Hz), 1.69-1.82 (m, 2H), 1.90-2.03 (m, 1H), 2.29 (s, 3H), 2.52-2.68 (m, 3H), 2.71-2.84 (m, 1H), 3.40 (t, 2H, J=7.1 Hz), 4.17 (t, 1H, J=6.0 Hz), 4.36 (q, 1H, J=6.0 Hz), 6.89 (dd, 1H, J=7.4, 4.8 Hz), 6.98 (dd, 1H, J=7.4, 4.8 Hz), 7.26 (d, 2H, J=7.2 Hz), 7.68-7.71 (m, 2H), 7.79-7.82 (m, 2H), 8.31 (d, 1H, J=3.6 Hz), 8.40 (d, 1H, J=3.6 Hz). Deprotection with H$_2$NNH$_2$.H$_2$O following General Procedure E gave the deprotected amine as a cloudy oil. Conversion to the HBr salt using General Procedure D gave a 60:40 mixture of diastereomers as an off-white solid. $^1$H NMR (D$_2$O) δ 0.87-1.04 and 1.21-1.39 (m, 3H), 1.46-1.98 (m, 5H), 2.05-2.27 (m, 2H), 2.34-2.70 (m, 5H), 2.76-3.21 (m, 5H), 4.34-4.49 and 4.86-4.99 (m, 2H), 7.61-7.81 (m, 2H), 8.01-8.29 (m, 2H), 8.53-8.66 (m, 2H). $^{13}$C NMR (D$_2$O) δ 17.4, 19.7, 20.2, 20.4, 20.6, 20.8, 21.0, 25.0, 25.3, 25.7, 26.4, 27.6, 27.8, 39.1, 39.5, 51.6, 56.5, 56.9, 57.1, 59.2, 125.6, 126.0, 136.8, 139.6, 139.9, 140.7, 147.1, 147.4, 148.8, 149.1, 152.4, 155.1. ES-MS m/z 339 (M+H). Anal. Calcd. for $C_{21}H_{30}N_4.2.8HBr.3.7H_2O.0.2C_4H_{10}O$: C, 40.50; H, 6.58; N, 8.67; Br, 34.60. Found: C, 40.44; H, 6.23; N, 8.61; Br, 34.78.

Example 360

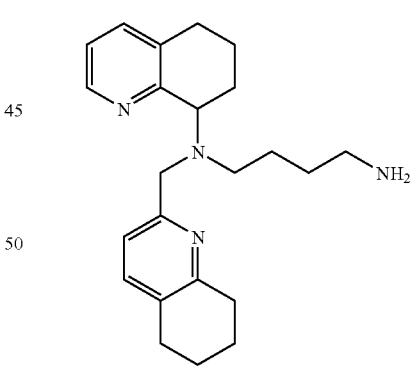

COMPOUND 360: $N^1$-(5,6,7,8-tetrahydroquinolin-8-yl)-$N^1$-(5,6,7,8-tetrahydroquinolin-3-ylmethyl)-butane-1,4-diamine (HBr salt)

The alcohol (5,6,7,8-tetrahydroquinolin-2-yl)-methanol (0.396 g, 2.43 mmoles) (Guay, D. et al. *Bioorg. Med. Chem. Lett.* 1998, 8, 453-458) was dissolved in CH$_2$Cl$_2$ (24 mL) and cooled to 0° C. Et$_3$N (0.51 mL, 3.65 mmoles) followed by MsCl (0.23 mL, 2.91 mmoles) were added. After 30 minutes, the solution was washed with saturated NH$_4$Cl (3×10 mL), dried (Na$_2$SO$_4$) and concentrated to form the desired mesylate as a beige oil (0.432 g, 74%).

Reaction of the mesylate from above, 2-[4-(5,6,7,8-Tetrahydroquinolin-8-ylamino)-butyl]-isoindole-1,3-dione and KI in CH$_3$CN and DIPEA gave the desired amine as a foam. $^1$H NMR (CDCl$_3$): 1.27 (m, 2H), 1.46 (m, 4H), 1.75 (m, 5H), 1.85 (m, 1H), 2.20 (m, 1H), 2.64 (m, 4H), 2.81 (m, 4H), 3.57 (d, 1H, J=18.6 Hz), 3.59 (m, 2H), 3.75 (d, 1H, J=15.6 Hz), 6.95 (dd, 1H, J=4.8, 7.5 Hz), 7.26 (d, 1H, J=9.9 Hz), 7.48 (d, 1H, J=7.8 Hz), 7.67 (dd, 2H, J=4.5, 6.9 Hz), 7.77 (dd, 2H, J=3.3, 5.4 Hz), 8.42 (d, 1H, J=4.5 Hz) ppm. Deprotection with hydrazine gave N$^1$-(5,6,7,8-tetrahydroquinolin-8-yl)-N$^1$-(5,6,7,8-tetrahydroquinolin-3-ylmethyl)-butane-1,4-diamine. Conversion to the HBr salt using General Procedure D gave COMPOUND 360. $^1$H NMR (D$_2$O): 1.53 (m, 4H), 1.82 (m, 3H), 1.91 (m, 2H), 2.00 (m, 1H), 2.06 (m, 1H), 2.32 (m, 1H), 2.50 (m, 1H), 2.70 (m, 1H), 2.89 (m, 4H), 2.96 (m, 2H), 3.10 (m, 2H), 4.14 (s, 2H), 4.38 (m, 1H), 7.81 (d, 2H, J=7.2 Hz), 8.17 (d, 1H, J=8.1 Hz), 8.29 (d, 1H, J=8.1 Hz), 8.54 (d, 1H, J=4.8 Hz). $^{13}$C NMR (D$_2$O): 20.14, 20.47, 20.93, 21.11, 25.14, 25.27, 27.44, 27.65 (2 carbons), 39.61, 51.27, 52.81, 59.59, 124.25, 125.74, 137.89, 139.29, 140.48, 147.40, 147.79, 150.19, 151.82, 153.64. ES-MS m/z 365.4 (M+H); Anal. Calcd. for (C$_{23}$H$_{32}$N$_4$×3.7HBr×1.6H$_2$O×0.3C$_4$H$_{10}$O): C, 40.65; H, 5.91; N, 7.84 Br.41.35. Found: C, 40.78; H, 6.05; N, 7.86; Br, 41.07.

Example 361

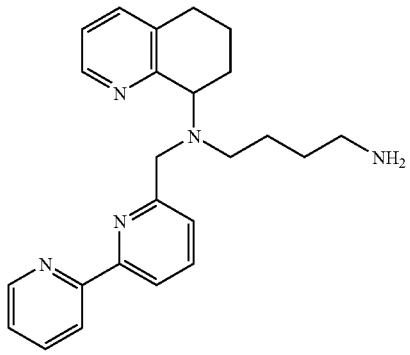

COMPOUND 361: N$^1$-[2,2']Bipyridinyl-6-ylmethyl-N$^1$-(5,6,7,8-tetrahydro-quinolin-8-yl)-butane-1,4-diamine Using General Procedure C: To a solution of [2,2']bipyridinyl-6-yl-methanol (70 mg, 0.38 mmol) (Uenishi, J. et al. *J. Org. Chem.* 1993, 58, 4382-4388) in CH$_2$Cl$_2$ (5 mL) at −78° C. was added MsCl (0.05 mL, 0.65 mmol) and Et$_3$N (0.15 mL, 1.08 mmol) and the mixture stirred for 15 min then quenched at −78° C. with water (5 mL) and saturated aqueous NaHCO$_3$ (20 mL). The resultant crude methanesulfonic acid [2,2']bipyridinyl-6-ylmethyl ester was used without further purification in the next reaction.

Using the general alkylation procedure A: Reaction of the mesylate from above and 2-[4-(5,6,7,8-tetrahydro-quinolin-8-ylamino)-butyl]-isoindole-1,3-dione in dry CH$_3$CN and DIPEA gave the desired amine as a yellow oil. Deprotection with hydrazine following General Procedure E gave COMPOUND 361 as a colorless oil. $^1$H NMR (CDCl$_3$) δ 1.42-1.58 (m, 4H), 1.63-1.72 (m, 1H), 1.86-2.04 (m, 2H), 2.14-2.19 (m, 1H), 2.08-2.19 (m, 2H), 2.60 (t, 2H, J=6.9 Hz), 2.65-2.90 (m, 4H), 3.83 (d, 1H, J=15.6 Hz), 3.99 (d, 1H, J=13.2 Hz), 4.18 (dd, 1H, J=9, 6 Hz), 7.03 (dd, 1H, J=7.8, 4.8 Hz), 7.25-7.33 (m, 2H), 7.74-7.82 (m, 3H), 8.15 (d, 1H, J=8.1 Hz), 8.34 (d, 1H, J=8.1 Hz), 8.51 (d, 1H, J=3.6 Hz), 8.66 (d, 1H, J=3.6 Hz); $^{13}$C NMR (CDCl$_3$) δ 21.83, 26.64, 26.79, 29.72, 31.82, 42.40, 53.27, 58.48, 61.50, 119.30, 121.54, 121.86, 123.30, 123.82, 134.59, 136.81, 137.24, 137.52, 147.58, 149.56, 155.27, 156.91, 158.64, 162.20. ES-MS m/z 388 (M+H). Anal. Calcd. for C$_{24}$H$_{29}$N$_5$.1.3CH$_2$Cl$_2$: C, 61.03; H, 6.40; N, 14.06. Found: C, 61.25; H, 6.36; N, 13.98.

Example 362

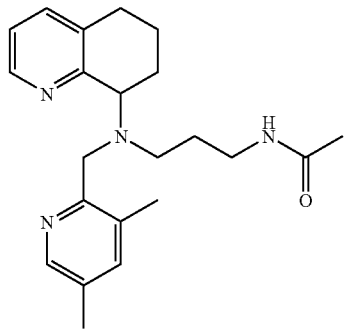

COMPOUND 362: N-{3-[(3,5-Dimethyl-pyridin-2-ylmethyl)-(5,6,7,8-tetrahydro-quinolin-8-yl)-amino]-propyl}-acetamide (HBr salt)

Using General Procedure B: Reaction of 5,6,7,8-Tetrahydro-quinolin-8-ylamine and 3,5-dimethyl-pyridine-2-carboxaldehyde with NaBH(OAc)$_3$ in CH$_2$Cl$_2$ gave (3,5-Dimethyl-pyridin-2-ylmethyl)-(5,6,7,8-tetrahydro-quinolin-8-yl)-amine as a colorless oil.

Using General Procedure B: Reaction of N-(tert-butoxycarbonyl)-3-propionaldehyde and (3,5-Dimethyl-pyridin-2-ylmethyl)-(5,6,7,8-tetrahydro-quinolin-8-yl)-amine with NaBH(OAc)$_3$ in CH$_2$Cl$_2$ gave a white foam. Deprotection with TFA following General Procedure F gave N$^1$-(3,5-Dimethyl-pyridin-2-ylmethyl)-N$^1$-(5,6,7,8-tetrahydro-quinolin-8-yl)-propane-1,3-diamine as a colorless oil. $^1$H NMR (CDCl$_3$) δ 1.44-2.09 (m, 8H), 2.25 (s, 3H), 2.37 (s, 3H), 2.56-2.69 (m, 6H), 3.84-4.04 (m, 3H), 7.03 (dd, 1H, J=4.8, 7.2 Hz), 7.21 (s, 1H), 7.33 (d, 1H, J=7.2 Hz), 8.18 (s, 1H), 8.47 (d, 1H, J=4.8 Hz).

To a solution of N$^1$-(3,5-Dimethyl-pyridin-2-ylmethyl)-N$^1$-(5,6,7,8-tetrahydro-quinolin-8-yl)-propane-1,3-diamine (78 mg, 0.23 mmol) in CH$_2$Cl$_2$ (2.5 mL) was added Et$_3$N (100 μL, 0.72 mmol) followed by Ac$_2$O (40 μL, 0.43 mmol). The resultant solution was stirred at room temperature for 45 minutes. The mixture was diluted with CH$_2$Cl$_2$ (20 mL), washed with brine (3×5 mL), dried (Na$_2$SO$_4$), and concentrated. Purification of the crude material by column chromatography on silica gel (20:1:1 CH$_2$Cl$_2$-MeOH—NH$_4$OH) provided 60 mg (71%) of the free base of the title compound as a white foam. Conversion of the foam to the HBr salt gave COMPOUND 362 as a white solid. $^1$H NMR (D$_2$O) δ 1.42-1.47 (m, 2H), 1.71-1.80 (m, 4H), 1.99-2.17 (m, 2H), 2.32-2.39 (m, 2H), 2.41 (s, 3H), 2.45 (s, 3H), 2.62-2.72 (m, 1H), 2.92-2.97 (m, 4H), 4.11 (d, 1H, J=17.1 Hz), 4.33 (d, 1H, J=17.1 Hz), 4.45 (dd, 1H, J=10.5, 5.7 Hz), 7.84 (dd, 1H, J=8.1, 5.4 Hz), 8.19 (s, 1H), 8.32 (d, 1H, J=8.1 Hz), 8.42 (s, 1H), 8.57 (d, 1H, J=5.4 Hz); $^{13}$C NMR (D$_2$O) δ 17.13, 17.56, 20.45, 20.65, 22.17, 27.85, 28.05, 37.58, 49.78, 52.00, 61.10, 125.88, 136.64, 137.42, 137.79, 139.39, 140.75, 148.15, 148.73, 149.28, 151.16, 174.37; ES-MS m/z 367 (M+H). Anal. Calcd. For $C_{22}H_{30}N_4O\cdot2.9HBr\cdot3.7H_2O$: C, 39.57; H, 6.08; N, 8.39; Br, 34.70. Found: C, 39.62; H, 5.85; N, 8.04; Br, 34.70.

Example 363

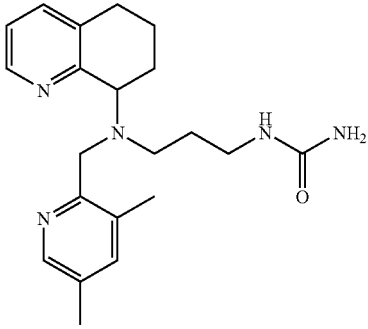

COMPOUND 363: {3-[(3,5-Dimethyl-pyridin-2-ylmethyl)-(5,6,7,8-tetrahydro-quinolin-8-yl)-amino]-propyl}-urea (HBr salt)

To a solution of $N^1$-(3,5-Dimethyl-pyridin-2-ylmethyl)-$N^1$-(5,6,7,8-tetrahydro-quinolin-8-yl)-propane-1,3-diamine (101 mg, 0.31 mmol) in 2-propanol (4 mL) was added trimethylsilyl-isocyanate (65 µL, 0.48 mmol). The resultant solution was stirred at room temperature overnight then concentrated. Purification of the crude material by radial chromatography on silica gel (1 mm plate, 20:1:1 $CH_2Cl_2$-MeOH—$NH_4OH$) provided 83 mg (73%) of the free base of the title compound as a white foam. Conversion of the white foam to the HBr salt gave COMPOUND 363 as a white solid. $^1H$ NMR ($D_2O$) δ 1.40-1.50 (m, 2H), 1.71-1.84 (m, 1H), 1.99-2.23 (m, 2H), 2.34-2.40 (m, 2H), 2.41 (s, 3H), 2.44 (s, 3H), 2.63-2.73 (m, 1H), 2.88 (t, 2H, J=6.3 Hz), 2.95-2.98 (m, 2H), 4.12 (d, 1H, J=17.4 Hz), 4.33 (d, 1H, J=17.4 Hz), 4.45 (dd, 1H, J=5.7, 10.5 Hz), 7.83 (dd, 1H, J=7.8, 5.4 Hz), 8.18 (s, 1H), 8.32 (d, 1H, J=7.8 Hz), 8.42 (s, 1H), 8.57 (d, 1H, J=5.4 Hz); $^{13}C$ NMR ($D_2O$) δ 17.06, 17.52, 20.46, 20.62, 27.83, 28.80, 37.85, 49.55, 51.95, 61.05, 125.86, 136.65, 137.41, 137.78, 139.38, 140.73, 148.09, 148.74, 149.24, 151.20; ES-MS m/z 368 (M+H). Anal. Calcd. For $C_{21}H_{29}N_5O\cdot3.0HBr\cdot2.9H_2O$: C, 38.07; H, 5.75; N, 10.57; Br, 36.18. Found: C, 38.05; H, 5.86; N, 10.68; Br, 36.20.

Example 364

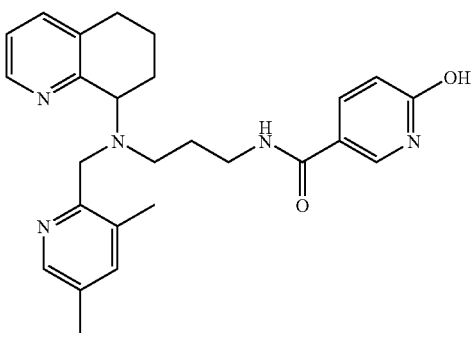

COMPOUND 364: N-{3-[(3,5-Dimethyl-pyridin-2-ylmethyl)-(5,6,7,8-tetrahydro-quinolin-8-yl)-amino]-propyl}-6-hydroxy-nicotinamide (HBr salt)

Using General Procedure G: To a solution of $N^1$-(3,5-Dimethyl-pyridin-2-ylmethyl)-$N^1$-(5,6,7,8-tetrahydro-quinolin-8-yl)-propane-1,3-diamine (270 mg, 0.839 mmol) in dry DMF (8.5 mL) was added 6-hydroxy-nicotinic acid (171 mg, 1.23 mmol) followed by EDCI (242 mg, 1.26 mmol), HOBT (166 mg, 1.22 mmol), and DIPEA (0.45 mL, 2.58 mmol). Purification of the crude material by column chromatography on silica gel (20:1:1 $CH_2Cl_2$-MeOH—$NH_4OH$) provided 136 mg (37%) of the free base of the title compound as a white foam. Conversion to the HBr salt COMPOUND 364 as a white solid. $^1H$ NMR ($D_2O$) δ 1.56-1.12 (m, 2H), 1.71-1.81 (m, 1H), 2.00-2.18 (m, 2H), 2.30-2.45 (m, 8H), 2.61-2.73 (m, 1H), 2.91-2.97 (m, 2H), 3.10-3.23 (m, 2H), 4.13 (d, 1H, J=16.2 Hz), 4.32 (d, 1H, J=16.2 Hz), 4.45-4.49 (m, 1H), 6.61 (d, 1H, J=9.6 Hz), 7.76-7.79 (m, 2H), 7.92 (s, 1H), 8.15 (s, 1H), 8.30 (d, 1H, J=8.1 Hz), 8.39 (s, 1H), 8.55 (d, 1H, J=5.4 Hz); $^{13}C$ NMR ($D_2O$) δ 17.10, 17.46, 20.40, 20.74, 27.81, 28.10, 37.64, 49.40, 51.72, 60.88, 115.21, 119.32, 125.75, 136.80, 137.36, 137.50, 137.77, 139.33, 140.73, 148.00, 148.59, 149.19, 151.20, 165.34, 166.58; ES-MS m/z 446 (M+H). Anal. Calcd. For $C_{26}H_{31}N_5O_2\cdot2.9HBr\cdot1.7H_2O$: C, 43.93; H, 5.29; N, 9.85; Br, 32.60. Found: C, 43.92; H, 5.56; N, 9.52; Br, 32.86.

Example 365

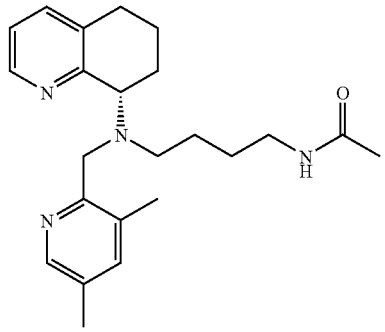

COMPOUND 365: (S)-N-{4-[(3,5-Dimethyl-pyridin-2-ylmethyl)-(5,6,7,8-tetrahydro-quinolin-8-yl)-amino]-butyl}-acetamide (HBr salt)

To a solution of (S)-($N^1$-(3,5-dimethyl-pyridin-2-ylmethyl)-$N^1$-(5,6,7,8-tetrahydro-quinolin-8-yl)-butane-1,4-diamine (HCl salt) (440 mg, 0.83 mmol) in water (2 mL) was added 1.0 N NaOH (5 mL). The mixture was extracted with $CH_2Cl_2$ (5×10 mL). The combined organic extracts were dried ($Na_2SO_4$) and concentrated and provided (S)-$N^1$-(3,5-Dimethyl-pyridin-2-ylmethyl)-$N^1$-(5,6,7,8-tetrahydro-quinolin-8-yl)-butane-1,4-diamine in quantitative yield.

To a solution of (S)-N¹-(3,5-Dimethyl-pyridin-2-ylmethyl)-N¹-(5,6,7,8-tetrahydro-quinolin-8-yl)-butane-1,4-diamine (56 mg, 0.17 mmol) in CH$_2$Cl$_2$ (3 mL) was added Et$_3$N (70 µL, 0.50 mmol) followed by Ac$_2$O (30 µL, 0.32 mmol). The resultant solution was stirred at room temperature for 70 minutes. The mixture was diluted with CH$_2$Cl$_2$ (20 mL), washed with brine (3×5 mL), dried (Na$_2$SO$_4$), and concentrated. Purification of the crude material by radial chromatography on silica gel (1 mm plate, 40:1:1 CH$_2$Cl$_2$-MeOH—NH$_4$OH) provided 27 mg (43%) of the free base of the title compound as a colorless oil. Using General Procedure D: Conversion of the oil to the HBr salt gave COMPOUND 365 as a white solid. ¹H NMR (D$_2$O) δ 1.11-1.39 (m, 4H), 1.82-1.85 (m, 4H), 1.97-2.27 (m, 2H), 2.41-2.49 (m, 8H), 2.65-2.72 (m, 1H), 2.98 (br s, 4H), 4.17 (d, 1H, J=17.7 Hz), 4.36 (d, 1H, J=17.7 Hz), 4.48 (dd, 1H, J=5.4, 10.2 Hz), 7.86 (dd, 1H, J=7.8, 5.7 Hz), 8.22 (s, 1H), 8.34 (d, 1H, J=7.8 Hz), 8.44 (s, 1H), 8.59 (d, 1H, J=5.7 Hz); ¹³C NMR (D$_2$O) δ 16.95, 17.50, 20.48, 20.60, 22.17, 25.55, 26.51, 27.82, 38.95, 52.01, 52.43, 61.54, 125.80, 136.33, 137.29, 137.53, 139.25, 140.56, 148.02, 149.11, 151.32, 174.09; ES-MS m/z 381 (M+H). Anal. Calcd. For C$_{23}$H$_{32}$N$_4$O.3.0HBr.3.0H$_2$O: C, 40.79; H, 6.10; N, 8.27; Br, 35.39. Found: C, 40.73; H, 6.04; N, 8.02; Br, 35.61.

Example 366

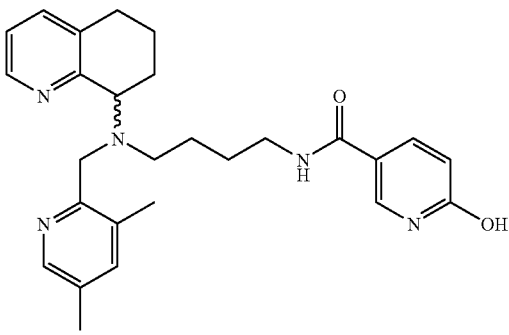

COMPOUND 366: N-{4-[(3,5-Dimethyl-pyridin-2-ylmethyl)-(5,6,7,8-tetrahydro-quinolin-8-yl)-amino]-butyl}-6-hydroxy-nicotinamide (HBr salt)

Using General Procedure G: To a solution of N¹-(3,5-Dimethyl-pyridin-2-ylmethyl)-N¹-(5,6,7,8-tetrahydro-quinolin-8-yl)-butane-1,4-diamine (202 mg, 0.60 mmol) in dry DMF (3 mL) was added 6-hydroxy-nicotinic acid (108 mg, 0.78 mmol) followed by EDCI (149 mg, 0.78 mmol), HOBT (106 mg, 0.78 mmol), and DIPEA (0.21 mL, 1.21 mmol). Purification of the crude material by radial chromatography on silica gel (1 mm plate, 10:1:1 CH$_2$Cl$_2$-MeOH—NH$_4$OH) provided 54 mg (20%) of the free base of the title compound as a white foam. Using General Procedure D: Conversion to the HBr salt gave COMPOUND 366 as a white solid. ¹H NMR (D$_2$O) δ 1.29-1.42 (m, 2H), 1.49-1.58 (m, 2H), 1.90-2.01 (m, 1H), 2.22-2.35 (m, 2H), 2.54 (s, 3H), 2.56 (s, 3H), 2.57-2.67 (m, 2H), 2.79-2.87 (m, 1H), 3.11-3.15 (m 2H), 3.29-3.40 (m, 2H), 4.33 (d, 1H, J=18.0 Hz), 4.52 (d, 1H, J=18.0 Hz), 4.63 (dd, 1H, J=10.8, 5.7 Hz), 6.82 (d, 1H, J=9.6 Hz), 7.96-8.01 (m, 2H), 8.10 (d, 1H, J=2.1 Hz), 8.23 (s, 1H), 8.46 (d, 1H, J=8.1 Hz), 8.55 (s, 1H), 8.73 (d, 1H, J=5.1 Hz); ¹³C NMR (D$_2$O) δ 16.89, 17.47, 20.49, 20.74, 25.72, 26.63, 27.82, 39.10, 52.31, 52.90, 62.08, 115.63, 119.37, 125.79, 136.06, 137.16, 137.16, 137.29, 137.49, 139.30, 140.49, 140.88, 147.96, 148.85, 149.33, 151.25, 165.45, 166.46; ES-MS m/z 460 (M+H). Anal. Calcd. For C$_{27}$H$_{33}$N$_5$O$_2$.3.0HBr.3.5H$_2$O: C, 42.37; H, 5.66; N, 9.15; Br, 31.32. Found: C, 42.16; H, 5.50; N, 9.26; Br, 31.61.

Example 367

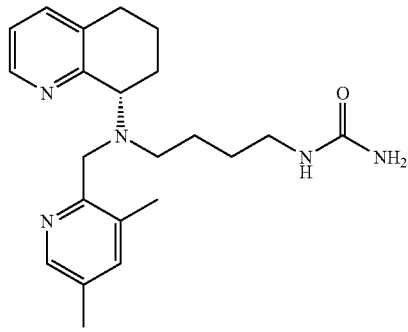

COMPOUND 367: (S)-{4-[(3,5-Dimethyl-pyridin-2-ylmethyl)-(5,6,7,8-tetrahydro-quinolin-8-yl)-amino]-butyl}-urea (HBr salt)

To a solution of (S)-N¹-(3,5-Dimethyl-pyridin-2-ylmethyl)-N¹-(5,6,7,8-tetrahydro-quinolin-8-yl)-butane-1,4-diamine (103 mg, 0.30 mmol) in 2-propanol (1.5 mL) was added trimethylsilyl-isocyanate (50 µL, 0.378 mmol). The resultant solution was stirred at room temperature overnight then concentrated. Purification of the crude material by radial chromatography on silica gel (1 mm plate, 25:1:1 CH$_2$Cl$_2$-MeOH—NH$_4$OH) provided 34 mg (29%) of the free base of the title compound as a white foam. Using General Procedure D: Conversion of the white foam to the HBr salt gave COMPOUND 367 (47 mg, 81%) as a white solid. ¹H NMR (D$_2$O) δ 1.15-1.29 (m, 4H), 1.75-1.91 (m, 1H), 2.06-2.22 (m, 2H), 2.41-2.50 (m, 8H), 2.66-2.74 (m, 1H), 2.90-3.03 (m, 4H), 4.19 (d, 1H, J=17.7 Hz), 4.38 (d, 1H, J=17.7 Hz), 4.50 (dd, 1H, J=10.5, 5.1 Hz), 7.88 (dd, 1H, J=7.8, 6.0 Hz), 8.23 (s, 1H), 8.36 (d, 1H, J=7.8 Hz), 8.46 (s, 1H), 8.62 (d, 1H, J=5.1 Hz); ¹³C NMR (D$_2$O) δ 16.97, 17.51, 20.49, 20.62, 25.43, 27.23, 27.83, 39.41, 52.08, 52.46, 61.55, 125.80, 136.35, 137.32, 137.59, 139.28, 140.55, 148.02, 149.13, 151.35; ES-MS m/z 382 (M+H). Anal. Calcd. For C$_{22}$H$_{31}$N$_5$O.3.0HBr.1.8H$_2$O: C, 40.24; H, 5.77; N, 10.66; Br, 36.50. Found: C, 40.22; H, 5.63; N, 10.62; Br, 36.50.

Example 368

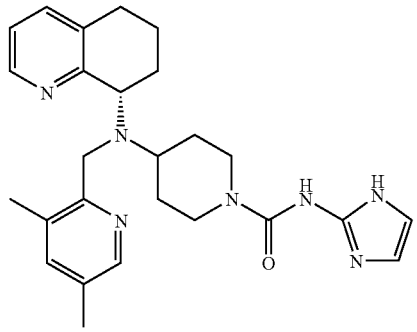

COMPOUND 368: 4-[(3,5-Dimethyl-pyridin-2-ylmethyl)-(5,6,7,8-tetrahydro-quinolin-8-yl)-amino]-piperidine-1-carboxylic acid (1H-imidazol-2-yl)-amide Using General Procedure B: Reaction of 6,7-Dihydro-5H-quinolin-8-one and 4-Amino-piperidine-1-carboxylic acid tert-butyl ester with $NaBH(OAc)_3$ in $CH_2Cl_2$ gave 4-(5,6,7,8-Tetrahydro-quinolin-8-ylamino)-piperidine-1-carboxylic acid tert-butyl ester as a colorless oil.

Using General Procedure B: Reaction of 4-(5,6,7,8-Tetrahydro-quinolin-8-ylamino)-piperidine-1-carboxylic acid tert-butyl ester and 3,5-dimethyl-pyridine-2-carbaldehyde with $NaBH(OAc)_3$ in $CH_2Cl_2$ gave 4-[(3,5-Dimethyl-pyridin-2-ylmethyl)-(5,6,7,8-tetrahydro-quinolin-8-yl)-amino]-piperidine-1-carboxylic acid tert-butyl ester as a white solid. Deprotection with TFA using General Procedure F gave (3,5-dimethyl-pyridin-2-ylmethyl)-piperidin-4-yl-(5,6,7,8-tetrahydro-quinolin-8-yl)-amine as a yellow oil.

To a warm (70° C.), stirred, solution of (3,5-dimethyl-pyridin-2-ylmethyl)-piperidin-4-yl-(5,6,7,8-tetrahydro-quinolin-8-yl)-amine (0.43 g, 0.41 mmol) and DIPEA (0.43 mL, 2.47 mmol) in DMF (4 mL) was added imidazole-1-carboxylic acid (1H-imidazol-2-yl)-amide (2 equivs). After 1 hour, the mixture was cooled to room temperature, diluted with brine (5 mL) and extracted with $CH_2Cl_2$ (4×10 mL). The combined organic extracts were washed with water (5×10 mL), dried ($Na_2SO_4$) and concentrated. Purification of the crude material by radial chromatography on silica gel (1 mm plate, 25:1:1 $CH_2Cl_2$-MeOH—$NH_4OH$) provided 70 mg (31%) of COMPOUND 368 as a white solid. $^1H$ NMR ($CDCl_3$) δ 1.52-2.06 (m, 8H), 2.21 (s, 3H), 2.38 (s, 3H), 2.56-2.79 (m, 5H), 3.91-4.21 (m, 5H), 6.68 (s, 2H), 6.96 (dd, 1H, J=7.5, 4.5 Hz), 7.12 (s, 1H), 7.23-7.27 (m, 1H), 8.09 (s, 1H), 8.41 (d, 1H, J=3.6 Hz); $^{13}C$ NMR ($CDCl_3$) δ 18.27, 19.02, 22.26, 29.28, 29.81, 30.93, 31.98, 44.84, 44.98, 53.77, 58.48, 60.37, 112.13, 121.44, 123.44, 131.64, 133.40, 132.32, 136.38, 139.06, 145.49, 146.39, 147.30, 155.71, 155.77, 159.01; ES-MS m/z 460 (M+H). Anal. Calcd. For $C_{26}H_{33}N_7O.1.1CH_2Cl_2$: C, 58.86; H, 6.42; N, 17.73. Found: C, 59.01; H, 6.32; N, 17.68.

Example 369

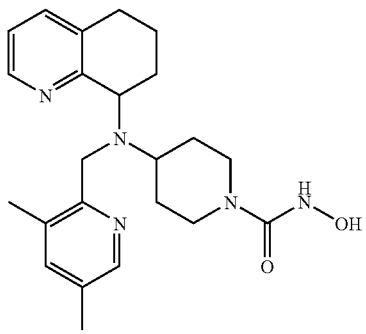

COMPOUND 369: 4-[(3,5-Dimethyl-pyridin-2-ylmethyl)-(5,6,7,8-tetrahydro-quinolin-8-yl)-amino]-piperidine-1-carboxylic acid hydroxyamide To a solution of (3,5-dimethyl-pyridin-2-ylmethyl)-piperidin-4-yl-(5,6,7,8-tetrahydro-quinolin-8-yl)-amine (150.0 mg, 0.428 mmol) in THF (5 mL) was added hydroxylamine carboxylic acid phenyl ester (75 mg, 0.449 mmol) and stirred for 17.5 h at reflux. The mixture was cooled to ambient temperature and concentrated in vacuo. Purification by flash chromatography on silica gel using $CH_2Cl_2$/MeOH/$NH_4OH$ (89:10:1) followed by purification by radial chromatography using $CH_2Cl_2$/MeOH/$NH_4OH$ (94:5:1) afforded COMPOUND 369 (59 mg, 34%) as white solid. $^1H$ NMR ($CDCl_3$) δ1.54-1.72 (m, 3H), 1.81-2.05 (m, 5H), 2.23 (s, 3H), 2.37 (s, 3H), 2.53-2.79 (m, 5H), 3.85-4.07 (m, 5H), 6.95-7.00 (m, 2H), 7.14 (s, 1H), 7.25 (d, 1H, J=4.2 Hz), 8.10 (s, 1H), 8.40 (d, 1H, J=3.7 Hz); $^{13}C$ NMR ($CDCl_3$) δ 17.90, 18.58, 21.71, 29.04, 29.37, 30.08, 31.25, 43.84, 53.30, 57.64, 60.19, 121.29, 131.51, 133.03, 134.11, 136.25, 138.92, 145.97, 146.88, 158.41, 160.63; ES-MS m/z 410 (M+H). Anal Calcd. For $C_{23}H_{31}N_5O_2.0.1(H2O).0.3CH_2Cl_2$): C, 64.07; H, 7.34; N, 16.03. Found: C, 64.13; H, 7.44; N, 15.69.

Example 370

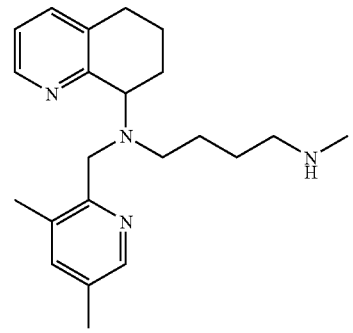

COMPOUND 370: N-(3,5-Dimethyl-pyridin-2-ylmethyl)-N'-methyl-N-(5,6,7,8-tetrahydro-quinolin-8-yl)-butane-1,4-diamine HBr salt Using General Procedure B: Reaction of 6,7-dihydro-5H-quinolin-8-one, (4-amino-butyl)-methyl-carbamic acid tert-butyl ester and $NaBH(OAc)_3$ in $CH_2Cl_2$ gave methyl-[4-(5,6,7,8-tetrahydro-quinolin-8-ylamino)-butyl]-carbamic acid tert-butyl ester as a yellow oil. $^1H$ NMR ($CDCl_3$) δ 1.45 (s, 9H), 1.50-1.60 (m, 4H), 1.72-1.81 (m, 2H), 1.95-2.20 (m, 4H), 2.67-2.78 (m, 4H), 2.83 (s, 3H), 3.17-3.24 (m, 2H), 3.75-3.79 (m, 1H), 7.06 (dd, 1H, J=7.6, 4.7 Hz), 7.36 (d, 1H, J=7.7 Hz), 8.38 (d, 1H, J=4.5 Hz).

Using General Procedure B: Reaction of methyl-[4-(5,6,7,8-tetrahydro-quinolin-8-ylamino)-butyl]-carbamic acid tert-butyl ester, 3,5-dimethyl-pyridine-2-carbaldehyde and $NaBH(OAc)_3$ in $CH_2Cl_2$ gave {4-[(3,5-Dimethyl-pyridin-2-ylmethyl)-(5,6,7,8-tetrahydro-quinolin-8-yl)-amino]-butyl}-methyl-carbamic acid tert-butyl ester as a yellow oil. $^1H$ NMR ($CDCl_3$) δ 1.20-1.29 (m, 4H), 1.41 (s, 9H), 1.60-1.65 (m, 1H), 1.86 (s, 3H), 1.93-2.00 (m, 3H), 2.25 (s, 3H), 2.38 (s, 3H), 2.45-2.890 (m, 7H), 2.96-3.04 (m, 2H), 3.94-4.05 (m, 3H), 7.01 (dd, 1H, J=7.6, 4.6 Hz), 7.19 (s, 1H), 7.30 (d, 1H, J=7.8 Hz), 8.15 (s, 1H), 8.45 (d, 1H, J=3.8 Hz). Conversion to the HBr salt according to General Procedure D gave COMPOUND 370 as a white solid. $^1H$ NMR ($D_2O$) δ 1.39-1.49 (m, 4H), 1.78-1.85 (m, 1H), 2.03-2.21 (m, 2H), 2.40-2.55 (m, 8H), 2.62 (s, 3H), 2.71-2.80 (m, 1H), 2.86-2.91 (m, 2H), 3.00-3.04 (m, 2H), 4.13 (d, 1H, J=17.7 Hz), 4.38 (d, 1H, J=17.8 Hz), 4.47-4.51 (m, 1H), 7.84-7.89 (m, 1H), 8.21

(s, 1H), 8.35 (d, 1H, J=7.9 Hz), 8.46 (s, 1H), 8.60 (d, 1H, J=5.7 Hz); $^{13}$C NMR (D$_2$O) δ 19.41, 19.92, 22.88, 23.03, 26.19, 27.77, 30.23, 35.44, 51.34, 54.26, 63.52, 128.25, 138.90, 139.74, 140.04, 141.74, 143.13, 150.52, 151.24, 151.60, 153.54; ES-MS m/z 353 (M+H). Anal Calcd. For C$_{22}$H$_{32}$N$_4$.4.3(HBr).3.3(H$_2$O).0.5(C$_4$H$_{10}$O): C, 36.17; H, 6.06; N, 7.03; Br, 43.11. Found: C, 36.31; H, 5.93; N, 6.95; Br, 42.84.

Example 371

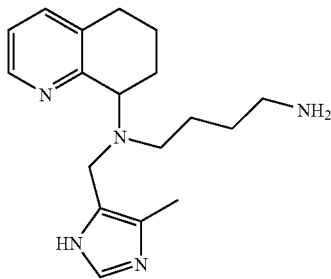

COMPOUND 371: N$^1$-(5-Methyl-3H-imidazol-4-ylmethyl)-N$^1$-(5,6,7,8-tetrahydro-quinolin-8-yl)-butane-1,4-diamine (HBr salt)

To a stirred solution of 4-methyl-5-imidazolemethanol (587 mg, 3.96 mmol) in anhydrous DMF (13 mL) was added DIPEA (2.1 mL, 11.9 mmol) followed by 2-(trimethylsilyl)ethoxymethyl chloride (793 mg, 4.76 mmol). The resultant solution was heated to 80° C. for 3 h then cooled to room temperature. The reaction mixture was poured into brine (15 mL), and diluted with H$_2$O (6 mL) and EtOAc (40 mL). The phases were mixed vigorously for 10 minutes and separated. The organic phase was washed with brine (4×20 mL), dried (Na$_2$SO$_4$), and concentrated under reduced pressure. Purification of the crude orange oil by flash chromatography on silica gel (CH$_2$Cl$_2$/MeOH/NH$_4$OH, 95:4:1) provided [5-Methyl-1-(2-trimethylsilanyl-ethoxymethyl)-1H-imidazol-4-yl]-methanol (535 mg, 56%) as a mixture of regioisomers.

To a stirred solution of [5-Methyl-1-(2-trimethylsilanyl-ethoxymethyl)-1H-imidazol-4-yl]-methanol (535 mg, 2.21 mmol) in CH$_2$Cl$_2$ (11 mL) was added manganese oxide (1.92 g, 22.1 mmol, 10 Equiv.) and the reaction mixture was allowed to stir for 3.5 h at room temperature. The mixture was concentrated under reduced pressure and the crude material filtered through a short plug of silica gel (EtOAc) to provide the desired aldehyde as a colorless oil (187 mg, 35%). $^1$H NMR (CDCl$_3$) δ –0.01 (s, 9H), 0.91 (t, 2H, J=8.1 Hz), 2.60 (s, 3H), 3.50 (t, 2H, J=8.1 Hz), 5.27 (s, 2H), 7.55 (s, 1H), 9.98 (s, 1H).

Using General Procedure B: Reaction of 5-Methyl-1-(2-trimethylsilanyl-ethoxymethyl)-1H-imidazole-4-carbaldehyde from above with 2-[4-(5,6,7,8-Tetrahydro-quinolin-8-ylamino)-butyl]-isoindole-1,3-dione and NaBH(OAc)$_3$ gave 2-{4-[[5-Methyl-3-(2-trimethylsilanyl-ethoxymethyl)-3H-imidazol-4-ylmethyl]-(5,6,7,8-tetrahydro-quinolin-8-yl)-amino]-butyl}-isoindole-1,3-dione as a white foam. $^1$H NMR (CDCl$_3$) δ –0.04 (s, 9H), 0.87 (t, 2H, J=8.1 Hz), 1.38-1.53 (m, 2H), 1.54-1.71 (m, 3H), 1.90-2.11 (m, 3H), 2.22 (s, 3H), 2.50-2.86 (m, 4H), 3.43 (t, 2H, J=8.3 Hz), 3.52-3.65 (m, 3H), 3.75 (d, 1H, J=13.1 Hz), 4.03-4.13 (m, 1H), 5.15 (s, 2H), 7.00 (dd, 1H, J=7.6, 4.7 Hz), 7.30 (d, 1H, J=6.2 Hz), 7.40 (s, 1H), 7.66-7.72 (m, 2H), 7.77-7.85 (m, 2H), 8.45 (dd, 1H, J=4.4, 1.5 Hz).

The white foam from above was dissolved in 4N HCl (6 mL) and heated to 60° C. with stirring for 4.5 h. The reaction was cooled to room temperature, diluted with H$_2$O (20 mL), basicified with K$_2$CO$_3$ and extracted with CH$_2$Cl$_2$ (3×15 mL). The combined organic extracts were dried (Na$_2$SO$_4$), filtered and concentrated under reduced pressure to afford the crude material (202 mg), which was used without further purification in the next reaction. Deprotection with H$_2$NNH$_2$.H$_2$O gave the free base as a colorless oil. Conversion to the HBr salt using General Procedure D gave COMPOUND 371 as a white solid. $^1$H NMR (D$_2$O) δ 1.46-1.88 (m, 5H), 1.89-2.09 (m, 1H), 2.10-2.22 (m, 1H), 2.24-2.36 (m, 1H), 2.31 (s, 3H), 2.54-2.67 (m, 1H), 2.73-2.85 (m, 1H), 2.86-2.99 (m, 4H), 4.01 (s, 2H), 4.37 (dd, 1H, J=10.5, 5.1 Hz), 7.73 (dd, 1H, J=7.8, 5.7 Hz), 8.19 (d, 1H, J=6.9 Hz), 8.53 (dd, 1H, J=5.7, 1.2 Hz), 8.59 (s, 1H); $^{13}$C NMR (D$_2$O) δ 8.72, 20.12, 20.52, 24.80, 25.08, 27.53, 39.57, 44.13, 50.68, 59.40, 124.28, 125.44, 128.99, 133.18, 139.40, 140.51, 146.22, 151.85; ES-MS m/z 314 (M+H). Anal. Calcd. for C$_{18}$H$_{27}$N$_5$.3.9HBr.1.7H$_2$O.0.3C$_4$H$_{10}$O: C, 33.82; H, 5.51; N, 10.27; Br, 45.70. Found: C, 33.68; H, 5.63; N, 10.34; Br, 45.87.

Example 372

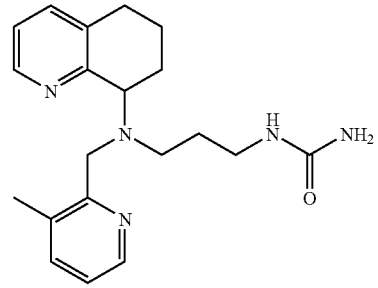

COMPOUND 372: {3-[(3-methyl-pyridin-2-yl)-(5,6,7,8-tetrahydro-quinolin-8-yl)-amino]-propyl}-urea (HBr salt)

Using General Procedure B, reaction of (3-amino-propyl)-carbamic acid tert-butyl ester, 6,7-dihydro-5H-quinolin-8-one and NaBH(OAc)$_3$ in CH$_2$Cl$_2$ gave [3-(5,6,7,8-tetrahydro-quinolin-8-ylamino)-propyl]-carbamic acid tert-butyl ester as a light brown oil plus ~15% impurity. $^1$H NMR (CDCl$_3$) δ 1.43 (s, 9H), 1.77 (m, 4H), 2.00 (m, 2H), 2.80 (m, 4H), 3.24 (m, 2H), 3.74 (t, 1H, J=7.5 Hz), 5.36 (br, 1H(NH)), 7.06 (m, 1H), 7.37 (d, 1H, J=7.5 Hz), 8.39 (d, 1H, J=4.5 Hz).

Using General Procedure B, reaction of the above material, 3-methylpyridine-2-carboxaldehyde and NaBH(OAc)$_3$ in CH$_2$Cl$_2$ gave {3-[(3-methyl-pyridin-2-yl)-(5,6,7,8-tetrahydro-quinolin-8-yl)-amino]-propyl}-carbamic acid tert-butyl ester plus ~20% impurity as a yellow oil. Deprotection with TFA using General Procedure F gave N'-(3-methyl-pyridin-2-yl)-N'-(5,6,7,8-tetrahydro-quinolin-8-yl)-propane-1,3-diamine which was used immediately in the next reaction. $^1$H NMR (CDCl$_3$) δ 1.55 (m, 1H), 1.73 (m, 1H), 1.92 (m, 2H), 2.08 (m, 1H), 2.29 (br, 1H), 2.36 (s, 3H), 2.62 (dt, 1H, J=10.5, 3.6 Hz), 2.70-2.90 (m, 4H), 3.16 (dt, 1H), 3.80 (d, 1H, J=14.4

Hz), 3.89 (m, 1H), 3.99 (d, 1H, J=14.4 Hz), 7.10 (m, 2H), 7.38 (d, 1H, J=7.8 Hz), 7.42 (d, 1H, J=7.2 Hz), 8.48 (d, 1H, J=3.9 Hz), 8.53 (d, 1H, J=3.9 Hz).

The amine from above was dissolved in i-PrOH (3 mL) and treated with trimethylsilylisocyanate (85 µL, 0.63 mmol) at room temperature for 16 hours. The solution was concentrated under reduced pressure and dried in vacuo. The crude material was then purified by column chromatography with silica gel (20:1:0.1 $CH_2Cl_2$/MeOH/$NH_4OH$) to give {3-[(3-methyl-pyridin-2-yl)-(5,6,7,8-tetrahydro-quinolin-8-yl)-amino]-propyl}-urea as a colorless oil (34 mg, 21%).

Using General Procedure D: Conversion to the HBr salt gave COMPOUND 372 as a white solid. $^1$H NMR ($D_2O$) δ 1.50 (m, 2H), 1.81 (m, 1H), 2.10 (m, 2H), 2.44 (br, 2H), 2.50 (s, 3H), 2.75 (m, 1H), 2.92 (t, 2H, J=6.3 Hz), 3.01 (br, 2H), 4.21 (d, 1H, J=17.7 Hz), 4.43 (d, 1H, J=18.0 Hz), 4.51 (m, 1H), 7.88 (t, 2H, J=5.7 Hz), 8.37 (t, 2H, J=6.7 Hz), 8.62 (t, 1H, J=5.4 Hz). $^{13}$C NMR ($D_2O$) δ 17.23, 20.47, 20.69, 27.85, 28.80, 37.89, 49.66, 52.36, 61.14, 125.91 (2C), 137.49, 138.41, 139.42, 140.77, 148.15, 148.47, 151.10, 151.82, 161.67. ES-MS m/z 354 (M+H). Anal. Calcd. for $C_{20}H_{27}N_5O\cdot3.3HBr\cdot2.1H_2O\cdot0.2C_4H_{10}O$: C, 37.11; H, 5.47; N, 10.40; Br, 39.17. Found: C, 37.36; H, 5.44; N, 10.46; Br, 38.87.

Example 373

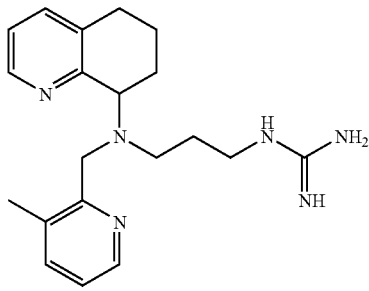

COMPOUND 373: {3-[(3-methyl-pyridin-2-yl)-(5,6,7,8-tetrahydro-quinolin-8-yl)-amino]-propyl}-guanidine (HBr salt)

$N^1$-(3-methyl-pyridin-2-yl)-$N^1$-(5,6,7,8-tetrahydro-quinolin-8-yl)-propane-1,3-diamine (63 mg, 0.20 mmol) and (tert-butoxycarbonylimino-pyrazol-1-yl-methyl)-carbamic acid tert-butyl ester (110 mg, 0.31 mmol) was stirred in THF (0.3 mL) for 16 hours. The solvent was removed under reduced pressure, $CH_2Cl_2$ (10 mL) was added and the organic phase washed with 15% aqueous NaOH solution (5×5 mL). The organic phase was then dried ($Na_2SO_4$) and concentrated under reduced pressure to afford, after column chromatography with silica gel (33:1:0.1 $CH_2Cl_2$/MeOH:$NH_4OH$), ({3-[(3-methyl-pyridin-2-ylmethyl)-(5,6,7,8-tetrahydro-quinolin-8-yl)-amino]-propyl}-tert-butoxycarbonyliminomethyl)-carbamic acid tert butyl ester as a pale brown sticky solid (50 mg, 49%), Using General Procedure D: Conversion to the HBr salt gave COMPOUND 373 as a light beige solid. $^1$H NMR ($D_2O$) δ 1.66 (m, 2H), 1.83 (m, 1H), 2.13 (m, 2H), 2.49 (s, 3H), 2.51 (m, 2H), 2.82 (m, 1H), 3.04 (m, 4H), 4.24 (d, 1H, J=17.7 Hz), 4.47 (d, 1H, J=17.7 Hz), 4.56 (m, 1H), 7.86 (m, 2H), 8.35 (t, 2H, J=7.7 Hz), 8.63 (t, 1H, J=6.5 Hz). $^{13}$C NMR ($D_2O$) δ 17.26, 20.45, 20.79, 27.51, 27.85, 39.23, 49.56, 52.24, 61.17, 125.97 (2C), 137.48, 138.63, 139.60, 140.76, 148.10, 148.43, 150.93, 151.65, 156.99. ES-MS m/z 353 (M+H). Anal. Calcd. for $C_{20}H_{28}N_6\cdot3.2HBr\cdot2.5H_2O\cdot0.3C_4H_{10}O$: C, 37.52; H, 5.82; N, 12.38; Br, 37.68. Found: C, 37.38; H, 5.66; N, 12.42; Br, 37.83.

Example 374

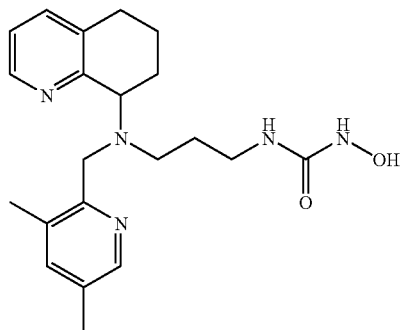

COMPOUND 374: N-{3-[(3,5-dimethyl-pyridin-2-yl)-(5,6,7,8-tetrahydro-quinolin-8-yl)-amino]-propyl}-N'-hydroxyurea Using General Procedure B, reaction of [3-(5,6,7,8-tetrahydro-quinolin-8-ylamino)-propyl]-carbamic acid tert-butyl ester, 3,5-dimethylpyridine-2-carboxaldehyde and NaBH($OAc$)$_3$ in $CH_2Cl_2$ gave {3-[(3,5-dimethyl-pyridin-2-yl)-(5,6,7,8-tetrahydro-quinolin-8-yl)-amino]-propyl}-carbamic acid tert-butyl ester as a pale beige sticky solid. $^1$H NMR (CDCl$_3$) δ 1.75 (m, 4H), 2.18 (br t, 1H), 2.27 (s, 3H), 2.30 (s, 3H), 2.37 (br, 1H), 2.56 (t, 1H, J=10.5 Hz), 2.83 (m, 4H), 3.38 (br, 1H), 3.68 (d, 1H, J=15.0 Hz), 3.84 (br, 1H), 4.04 (d, 1H, J=15.0 Hz), 7.13 (m, 1H), 7.26 (s, 1H), 7.41 (d, 1H, J=7.0 Hz), 8.33 (s, 1H), 8.53 (d, 1H, J=4.5 Hz). Deprotection with TFA using General Procedure F gave N'-(3,5-dimethyl-pyridin-2-yl)-N'-(5,6,7,8-tetrahydro-quinolin-8-yl)-propane-1,3-diamine as a white solid.

A solution of the free amine from above (0.22 g, 0.68 mmol) and 1,1-carbonyldiimidazole (110 mg, 0.68 mmol) in THF (7 mL) was stirred for 30 minutes at room temperature. The solvent was then removed under reduced pressure and the residue dissolved in DMF (3.5 mL). The solution was then treated with $NH_2OH\cdot HCl$ (190 mg, 2.7 mmol) and DIPEA (0.60 mL, 3.4 mmol) and stirred at room temperature for 16 hours. The reaction was then partitioned between $CH_2Cl_2$ (15 mL) and brine (10 mL) and separated. The organic phase was then washed several times with brine (4×10 mL) and the organic phase dried ($Na_2SO_4$) and concentrated under reduced pressure to afford, after column chromatography with silica gel (50:1:0.1 $CH_2Cl_2$:MeOH:$NH_4OH$), COMPOUND 374 as a white solid (144 mg, 52%). $^1$H NMR (CDCl$_3$) δ 1.54 (m, 2H), 1.70 (m, 1H), 1.95 (m, 2H), 2.14 (m, 1H), 2.27 (s, 3H), 2.32 (s, 3H), 2.73 (m, 4H), 3.16 (m, 1H), 3.50 (m, 1H), 3.72 (d, 1H, J=13.5 Hz), 4.02 (d, 1H, J=13.2 Hz), 4.06 (m, 1H), 6.50 (s, 1H), 7.08 (m, 1H), 7.26 (s, 1H), 7.37 (d, 1H, J=7.5 Hz), 8.22 (s, 1H), 8.41 (d, 1H, J=4.5 Hz), 8.91 (br, 1H), 10.77 (br, 1H). $^{13}$C NMR (CDCl$_3$) δ 17.87, 18.82, 21.74, 24.54, 25.54, 29.46, 40.82, 51.91, 53.54, 59.52, 121.71, 131.68, 132.61, 134.99, 137.07, 139.58, 146.63, 146.69, 153.39, 157.39, 162.64. ES-MS m/z 384 (M+H). Anal. Calcd. for $C_{21}H_{29}N_5O_2\cdot0.4CH_2Cl_2$: C, 61.57; H, 7.19; N, 16.78. Found: C, 61.22; H, 7.21; N, 16.74.

Example 375

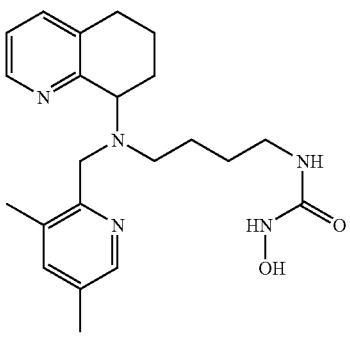

COMPOUND 375: N-{4-[(3,5-dimethyl-pyridin-2-yl)-(5,6,7,8-tetrahydro-quinolin-8-yl)-amino]-butyl}-N-hydroxyurea A solution of N'-(3,5-dimethyl-pyridin-2-yl)-N'-(5,6,7,8-tetrahydro-quinolin-8-yl)-butane-1,4-diamine (0.15 g, 0.42 mmol) and 1,1-carbonyldiimidazole (68 mg, 0.42 mmol) in THF (4.2 mL) was stirred for 30 minutes at room temperature. The solvent was then removed under reduced pressure and the residue dissolved in DMF (3.0 mL). The solution was then treated with NH$_2$OH.HCl (117 mg, 1.7 mmol) and DIPEA (0.37 mL, 2.1 mmol) and stirred at room temperature for 16 hours. The reaction was partitioned between CH$_2$Cl$_2$ (15 mL) and brine (10 mL) and then separated. The organic phase was washed several times with brine (4×10 mL) and the organic phase dried (Na$_2$SO$_4$) and concentrated under reduced pressure to afford, after column chromatography with silica gel (20:1:0.1 CH$_2$Cl$_2$:MeOH:NH$_4$OH), COMPOUND 375 as a white solid (114 mg, 65%). $^1$H NMR (CDCl$_3$) δ 1.46 (br, 4H), 1.67 (m, 1H), 1.99 (m, 4H), 2.18 (m, 1H), 2.25 (s, 3H), 2.29 (s, 3H), 2.52 (m, 1H), 2.69 (m, 1H), 2.79 (m, 2H), 3.15 (m, 2H), 3.78 (d, 1H, J=12.9 Hz), 3.87 (d, 1H, J=12.9 Hz), 4.16 (m, 1H), 6.90 (br, 1H), 7.05 (m, 1H), 7.14 (br, 1H), 7.24 (s, 1H), 7.34 (d, 1H, J=7.5 Hz), 8.18 (s, 1H), 8.44 (d, 2H, J=3.9 Hz), 10.50 (br, 1H). $^{13}$C NMR (CDCl$_3$) δ 17.90, 18.61, 21.53, 25.22, 25.64, 27.65, 29.30, 39.12, 50.29, 55.29, 60.56, 121.62, 131.74, 132.97, 134.56, 136.73, 139.34, 146.15, 146.70, 154.11, 157.83, 162.47. ES-MS m/z 398 (M+H). Anal. Calcd. for C$_{22}$H$_{31}$N$_5$O$_2$.0.6H$_2$O: C, 64.71; H, 7.95; N, 17.15. Found: C, 64.87; H, 7.78; N, 17.10.

Example 376

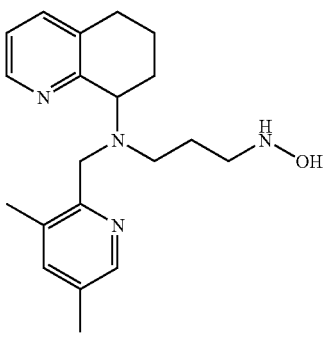

COMPOUND 376: N-{3-[(3,5-Dimethyl-pyridin-2-yl)-(5,6,7,8-tetrahydro-quinolin-8-yl)-amino]-propyl}-hydroxylamine (HBr salt)

A solution of NH$_2$OH.HCl (1.20 g, 17.3 mmol) in H$_2$O (12 mL) was cooled to 0° C. To this was added a solution of Boc$_2$O (7.73 g, 35.4 mmol) and Et$_3$N (5.1 mL, 36.3 mmol) in petroleum ether (10 mL) and MTBE (2 mL) via syringe pump over 45 minutes. The biphasic reaction mixture was stirred at 0° C. for 6 hours, and then stirred for an additional 16 hours at room temperature. The phases were separated and the aqueous washed with petroleum ether (15 mL). The combined organic phases were then washed with saturated aqueous NH$_4$Cl solution (20 mL), brine (20 mL) and dried (MgSO$_4$), filtered, and concentrated under reduced pressure to afford N,O-Bis-(tert-butoxycarbonyl)-hydroxylamine as a pale yellow oil (3.84 g, 95%). $^1$H NMR (CDCl$_3$) δ 1.50 (s, 9H), 1.53 (s, 9H), 7.50 (s, 1H(NH)).

Using General Procedure B, reaction of C-(3,5-dimethyl-pyridin-2-yl)-methylamine, 6,7-dihydro-5H-quinolin-8-one and NaBH(OAc)$_3$ in CH$_2$Cl$_2$ gave (3,5-dimethyl-pyridin-2-yl)-(5,6,7,8-tetrahydro-quinolin-8-yl)-amine as a light brown oil. $^1$H NMR (CDCl$_3$) δ 1.76 (m, 1H), 1.92 (m, 1H), 2.06 (m, 1H), 2.19 (m, 1H), 2.26 (s, 3H), 2.33 (s, 3H), 2.80 (m, 2H), 3.88 (t, 1H, J=7.2 Hz), 3.96 (d, 1H, J=12.0 Hz), 4.10 (d, 1H, J=12.5 Hz), 7.04 (m, 1H), 7.23 (s, 1H), 7.35 (d, 1H, J=7.5 Hz), 8.23 (s, 1H), 8.41 (d, 1H, J=4.5 Hz).

Using General Procedure B, the secondary amine from above, 3-(tert-butyl-dimethyl-silanyloxy)-propionaldehyde and NaBH(OAc)$_3$ were reacted in CH$_2$Cl$_2$ to give [3-(tert-butyl-dimethyl-silanyloxy)-propyl]-(3,5-dimethyl-pyridin-2-yl)-(5,6,7,8-tetrahydro-quinolin-8-yl)-amine.

The above compound was dissolved in THF (3 mL) and treated with 6N HCl (24 mL) for 4 hours. The solution was cooled to 0° C. and 15% aqueous NaOH solution (50 mL) was added slowly until the acid content was neutralized and the solution became basic (pH=8 to 12). The aqueous was extracted with CH$_2$Cl$_2$ (3×75 mL) and the combined organics were then dried (Na$_2$SO$_4$) and concentrated under reduced pressure to give, after column chromatography with silica gel (saturated NH$_3$/Et$_2$O), 3-[(3,5-dimethyl-pyridin-2-yl)-(5,6,7,8-tetrahydro-quinolin-8-yl)-amino]-propan-1-ol (1.19 g, 81%; 2 steps). $^1$H NMR (CDCl$_3$) δ 1.47 (m, 1H), 1.66 (m, 1H), 1.82 (m, 1H), 2.00 (m, 2H), 2.22 (m, 1H), 2.24 (s, 3H), 2.33 (s, 3H), 2.78 (m, 4H), 3.45 (m, 1H), 3.70 (d, 1H, J=13.9 Hz), 3.70 (br, 1H), 3.94 (d, 1H, J=13.9 Hz), 4.04 (m, 1H), 6.36 (br, 1H(OH)), 7.04 (m, 1H), 7.20 (s, 1H), 7.33 (d, 1H, J=7.5 Hz), 8.16 (s, 1H), 8.41 (d, 1H, J=4.5 Hz).

The above alcohol (0.76 g, 2.3 mmol), N,O-Bis-(tert-butoxycarbonyl)-hydroxylamine (0.60 g, 2.6 mmol), and PPh$_3$ (0.74 g, 2.8 mmol) were combined in THF (12 mL). The solution was cooled to 0° C. and a solution of DIAD (0.57 g, 2.8 mmol) in THF (1 mL) was added. The reaction was allowed to warm to room temperature while stirring over 6 hours. The solvent was then removed under reduced pressure and the crude material purified by column chromatography (first column: saturated NH$_3$/Et$_2$O; second column 1:1 EtOAc/hexanes) to give the desired fully Boc-protected hydroxylamine adduct as a white sticky solid (0.66 g, 52%).

Using General Procedure D: Conversion to the HBr salt gave COMPOUND 376 as a white solid. $^1$H NMR (D$_2$O) δ 1.82 (br, 3H), 2.06 (m, 1H), 2.17 (m, 1H), 2.42 (br, 1H), 2.45 (s, 3H), 2.48 (s, 3H), 2.58 (m, 1H), 2.84 (m, 1H), 3.00 (m, 2H), 3.14 (t, 2H, J=7.5 Hz), 4.16 (d, 1H, J=17.4 Hz), 4.40 (d, 1H, J=17.7 Hz), 4.50 (m, 1H), 7.87 (m, 1H), 8.22 (s, 1H), 8.35 (d, 1H, J=7.5 Hz), 8.47 (s, 1H), 8.60 (d, 1H, J=5.1 Hz). $^{13}$C NMR (D$_2$O) δ 17.13, 17.56, 20.43, 20.68, 22.69, 27.83, 48.65, 49.25, 51.52, 60.78, 125.97, 136.77, 137.54, 137.96, 139.53, 140.86, 148.24, 148.37, 149.38, 150.83. ES-MS m/z 341 (M+H). Anal. Calcd. for C$_{20}$H$_{28}$N$_4$O.3.0HBr.3.0H$_2$O: C, 37.70; H, 5.85; N, 8.79; Br, 37.62. Found: C, 37.54; H, 5.58; N, 8.45; Br, 37.91.

Example 377

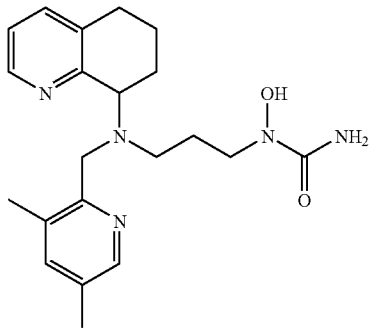

COMPOUND 377: N-{3-[(3,5-Dimethyl-pyridin-2-yl)-(5,6,7,8-tetrahydro-quinolin-8-yl)-amino]-propyl}-N-hydroxyurea (HBr salt)

N-{3-[(3,5-Dimethyl-pyridin-2-yl)-(5,6,7,8-tetrahydro-quinolin-8-yl)-amino]-propyl}-hydroxylamine (HBr salt) (138 mg, 0.22 mmol) was dissolved in H$_2$O (2 mL) and treated with sodium cyanate (42 mg, 0.65 mmol) for 3.5 hours. 15% aqueous NaOH solution (0.1 mL) was added and the aqueous was extracted with CH$_2$Cl$_2$ (3×5 mL). The combined organics were then dried (Na$_2$SO$_4$) and concentrated under reduced pressure to afford, after radial chromatographic purification on a silica gel plate (3% NH$_4$OH/CH$_3$CN) N-{3-[(3,5-dimethyl-pyridin-2-yl)-(5,6,7,8-tetrahydro-quinolin-8-yl)-amino]-propyl}-N-hydroxyurea (42 mg, 50%).

Using General Procedure D: Conversion to the HBr salt gave COMPOUND 377 as a white solid. $^1$H NMR (D$_2$O) δ 1.66 (m, 2H), 1.81 (m, 1H), 2.02 (m, 1H), 2.14 (m, 1H), 2.41 (m, 2H), 2.44 (s, 3H), 2.47 (s, 3H), 2.72 (m, 1H), 3.00 (m, 2H), 3.33 (t, 2H, J=6.6 Hz), 4.14 (d, 1H, J=17.7 Hz), 4.35 (d, 1H, J=17.4 Hz), 4.48 (m, 1H), 7.85 (m, 1H), 8.21 (s, 1H), 8.34 (d, 1H, J=7.5 Hz), 8.45 (s, 1H), 8.60 (d, 1H, J=5.4 Hz). $^{13}$C NMR (D$_2$O) δ 14.92, 15.35, 18.24, 18.35, 23.45, 25.61, 45.23, 47.12, 49.66, 58.66, 123.61, 134.41, 135.09, 135.55, 137.22, 138.49, 145.85, 146.48, 146.99, 148.90, 160.79. ES-MS m/z 384 (M+H). Anal. Calcd. for C$_{21}$H$_{29}$N$_5$O$_2$.3.4HBr.5.2H$_2$O: C, 33.50; H, 5.73; N, 9.31; Br, 36.11. Found: C, 33.51; H, 5.71; N, 9.28; Br, 36.12.

Example 378

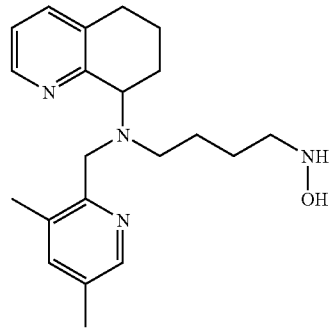

COMPOUND 378: N-{4-[(3,5-Dimethyl-pyridin-2-yl)-(5,6,7,8-tetrahydro-quinolin-8-yl)-amino]-butyl}-hydroxylamine (HBr salt)

Using General Procedure B, reaction of (3,5-dimethyl-pyridin-2-yl)-(5,6,7,8-tetrahydro-quinolin-8-yl)-amine, 4-(tert-butyl-dimethyl-silanyloxy)-butyraldehyde and NaBH(OAc)$_3$ in CH$_2$Cl$_2$ gave [4-(tert-butyl-dimethyl-silanyloxy)-butyl]-(3,5-dimethyl-pyridin-2-yl)-(5,6,7,8-tetrahydro-quinolin-8-yl)-amine.

The above compound was dissolved in THF (2 mL) and treated with 6N HCl (14 mL) for 2.5 hours. The solution was cooled to 0° C. and 15% aqueous NaOH solution (15 mL) was added slowly until the acid content was neutralized and the solution became basic (pH=8 to 12). The aqueous was extracted with CH$_2$Cl$_2$ (3×50 mL) and the combined organics were then dried (Na$_2$SO$_4$) and concentrated under reduced pressure to give, after column chromatography with silica gel (saturated NH$_3$/Et$_2$O), 4-[(3,5-dimethyl-pyridin-2-yl)-(5,6,7,8-tetrahydro-quinolin-8-yl)-amino]-butan-1-ol (0.78 g, 85%). $^1$H NMR (CDCl$_3$) δ 1.30-1.70 (m, 5H), 2.05 (m, 4H), 2.15 (s, 3H), 2.24 (s, 3H), 2.74 (m, 4H), 3.45 (m, 1H), 3.73 (d, 1H, J=13.9 Hz), 3.85 (d, 1H, J=14.2 Hz), 4.16 (m, 1H), 4.73 (br, 1H(OH)), 7.04 (m, 1H), 7.17 (s, 1H), 7.33 (d, 1H, J=7.5 Hz), 8.15 (s, 1H), 8.45 (d, 1H, J=4.5 Hz).

The above alcohol (0.74 g, 2.2 mmol), N,O-Bis-(tert-butoxycarbonyl)-hydroxylamine (0.56 g, 2.4 mmol), and PPh$_3$ (0.69 g, 2.6 mmol) were combined in THF (10 mL). The solution was cooled to 0° C. and a solution of DIAD (0.53 g, 2.6 mmol) in THF (1 mL) was added. The reaction was allowed to warm to room temperature while stirring over 16 hours. The solvent was then removed under reduced pressure and the crude material purified by column chromatography (first column: saturated NH$_3$/Et$_2$O; second column 1:1 EtOAc/hexanes) to give the desired fully Boc-protected hydroxylamine adduct as a white sticky solid (0.59 g, 49%).

Using General Procedure D: Conversion to the HBr salt gave COMPOUND 378 as a white solid. $^1$H NMR (D$_2$O) δ 1.42 (m, 2H), 1.54 (m, 2H), 1.77 (m, 1H), 2.03 (m, 1H), 2.15 (m, 1H), 2.38 (br, 2H), 2.40 (s, 3H), 2.44 (s, 3H), 2.71 (m, 1H), 2.97 (m, 2H), 3.09 (t, 2H, J=7.5 Hz), 4.12 (d, 1H, J=18.0 Hz), 4.35 (d, 1H, J=17.7 Hz), 4.46 (m, 1H), 7.82 (m, 1H), 8.17 (s, 1H), 8.31 (d, 1H, J=8.1 Hz), 8.41 (s, 1H), 8.56 (d, 1H, J=5.7 Hz). $^{13}$C NMR (D$_2$O) δ 16.99, 17.49, 20.46, 20.62, 21.34, 25.37, 27.81, 50.58, 51.85, 51.95, 61.18, 125.83, 136.47, 137.31, 137.63, 139.34, 140.69, 148.08, 148.83, 149.17, 151.12. ES-MS m/z 355 (M+H). Anal. Calcd. for C$_{21}$H$_{30}$N$_4$O.3.2HBr.2.6H$_2$O.C$_4$H$_{10}$O: C, 39.35; H, 6.19; N, 8.12; Br, 37.06. Found: C, 39.30; H, 5.90; N, 8.07; Br, 37.11.

Example 379

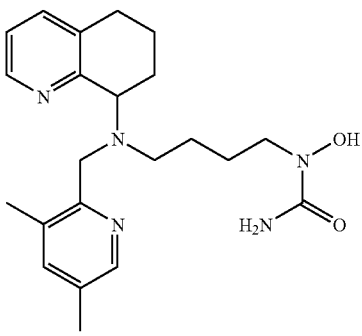

COMPOUND 379: N-{4-[(3,5-Dimethyl-pyridin-2-yl)-(5,6,7,8-tetrahydro-quinolin-8-yl)-amino]-butyl}-N-hydroxyurea (HBr salt)

N-{4-[(3,5-Dimethyl-pyridin-2-yl)-(5,6,7,8-tetrahydro-quinolin-8-yl)-amino]-butyl}-hydroxylamine (HBr salt) (180 mg, 0.25 mmol) was dissolved in H$_2$O (2.5 mL) and treated with sodium cyanate (65 mg, 1.0 mmol) for 2 hours. 15% aqueous NaOH solution (0.1 mL) was added and the aqueous was extracted with CH$_2$Cl$_2$ (3×5 mL). The combined organics were then dried (Na$_2$SO$_4$) and concentrated under reduced pressure to afford, after radial chromatographic purification on a silica gel plate (3% NH$_4$OH/CH$_3$CN) N-{4-[(3,5-dimethyl-pyridin-2-yl)-(5,6,7,8-tetrahydro-quinolin-8-yl)-amino]-butyl}-N-hydroxyurea (73 mg, 73%).

Using General Procedure D: Conversion to the HBr salt gave COMPOUND 379 as a white solid. $^1$H NMR (D$_2$O) δ 1.14 (m, 2H), 1.35 (m, 2H), 1.79 (m, 1H), 2.03 (m, 1H), 2.15 (m, 1H), 2.36 (br, 2H), 2.41 (s, 3H), 2.45 (s, 3H), 2.65 (m, 1H), 2.96 (m, 2H), 3.28 (m, 2H), 4.14 (d, 1H, J=17.7 Hz), 4.33 (d, 1H, J=18.0 Hz), 4.46 (m, 1H), 7.82 (t, 1H, J=6.7 Hz), 8.17 (s, 1H), 8.30 (d, 1H, J=8.1 Hz), 8.40 (s, 1H), 8.56 (d, 1H, J=5.4 Hz). $^{13}$C NMR (D$_2$O) δ 16.79, 17.31, 20.28, 20.38, 23.82, 25.04, 27.61, 48.07, 51.78, 52.34, 61.39, 125.55, 136.09, 137.01, 137.30, 139.03, 140.29, 147.79, 148.88 (2C), 151.10, 162.38. ES-MS m/z 398 (M+H). Anal. Calcd. for C$_{22}$H$_{31}$N$_5$O$_2$.3.2HBr.2.8H$_2$O: C, 37.38; H, 5.67; N, 9.91; Br, 36.17. Found: C, 37.46; H, 5.68; N, 9.65; Br, 36.06.

Example 380

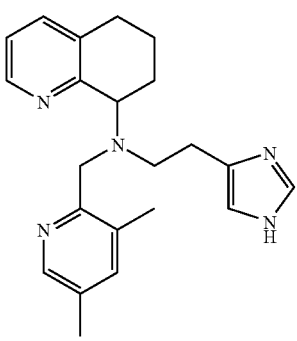

COMPOUND 380: (3,5-dimethyl-pyridin-2-ylmethyl)-(5,6,7,8-tetrahydro-quinolin-8-yl)-amine Using General Procedure B: Reaction of 6,7-dihydro-5H-quinolin-8-one in MeOH, 2-(1H-imidazol-4-yl)-ethylamine and NaBH$_4$ gave [2-(1H-imidazol-4-yl)-ethyl]-(5,6,7,8-tetrahydro-quinolin-8-yl)-amine. $^1$H NMR (CDCl$_3$) δ 1.75 (m, 2H), 1.91 (m, 1H), 2.10 (m, 1H), 2.72 (q, 2H, J=8.6 Hz), 2.82 (q, 2H, J=10.0 Hz), 3.01 (t, 2H, J=6.6 Hz), 3.81 (t, 1H, J=6.1 Hz), 6.73 (s, 1H), 7.04 (q, 1H, J=4.3 Hz), 7.35 (d, 1H, J=7.6 Hz), 7.43 (s, 1H), 8.36 (d, 1H, J=4.0 Hz).

Using General Procedure B: Reaction of [2-(1H-imidazol-4-yl)-ethyl]-(5,6,7,8-tetrahydro-quinolin-8-yl)-amine and 3,5-dimethyl-pyridine-2-carbaldehyde in CH$_2$Cl$_2$ with NaBH(OAc)$_3$ gave COMPOUND 380 as a yellow oil. $^1$H NMR (CDCl$_3$) δ 1.60 (m, 1H), 1.90 (m, 2H), 2.05 (m, 2H), 2.11 (s, 3H), 2.18 (s, 3H), 2.47 (m, 1H), 2.75 (m, 2H), 2.90 (m, 2H), 3.77 (d, 1H, J=12.0 Hz), 4.04 (m, 2H), 6.65 (s, 1H), 7.04 (t, 2H, J=6.0 Hz), 7.31 (d, 1H, J=9.0 Hz), 7.55 (s, 1H), 8.09 (s, 1H), 8.43 (d, 1H, J=3.0 Hz). $^{13}$C NMR (CDCl$_3$) δ 18.2, 18.4, 22.1, 23.2, 23.6, 29.7, 51.4, 55.1, 61.1, 122.1, 124.8, 130.4, 133.0, 134.9, 135.0, 137.1, 139.1, 146.4, 154.3, 158.3. ES-MS m/z 362 [M+H]$^+$. Anal. Calcd. for C$_{22}$H$_{27}$N$_5$.0.4H$_2$O.0.3CH$_2$Cl$_2$: C, 73.10; H, 7.53; N, 19.37. Found: C, 67.69; H, 7.28; N, 17.64.

Example 381

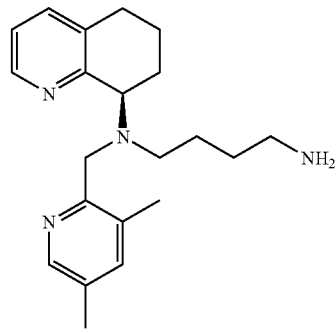

COMPOUND 381: (R)—N-(3,5-dimethyl-pyridin-2-ylmethyl)-N-(5,6,7,8-tetrahydro-quinolin-8-yl)-butane-1,4-diamine (HBr salt)

Using General Procedure B: Reaction of (R)-2-[4-(5,6,7,8-tetrahydro-quinolin-8-ylamino)-butyl]-isoindole-1,3-dione in CH$_2$Cl$_2$ with 3,5-dimethyl-2-pyridine-carbaldehyde and NaBH(OAc)$_3$ gave a pale yellow oil. Deprotection with H$_2$NNH$_2$.H$_2$O following General Procedure E gave N-(3,5-dimethyl-pyridin-2-ylmethyl)-N-(5,6,7,8-tetrahydro-quinolin-8-yl)-butane-1,4-diamine as a colorless oil. $^1$H NMR (CDCl$_3$) δ 1.35 (m, 4H), 1.66 (m, 1H), 1.94-2.05 (m, 4H), 2.25 (s, 3H), 2.35 (s, 3H), 2.52-2.79 (m, 7H), 3.92 (d, 2H, J=15.0, 12.0 Hz), 4.01 (t, 1H, J=6.0 Hz), 7.03 (dd, 1H, J=7.5, 4.5 Hz), 7.20 (s, 1H), 7.32 (d, 1H, J=9.0 Hz), 8.18 (s, 1H), 8.48 (d, 1H, J=3.0 Hz). Conversion to the HBr salt gave a pale yellow crystalline solid. $^1$H NMR (D$_2$O) δ 1.48 (m, 4H), 1.82 (m, 1H), 2.03-2.16 (m, 2H), 2.40-2.52 (m, 2H), 2.45 (s, 3H), 2.48 (s, 3H), 2.65-2.85 (m, 3H), 3.02 (m, 2H), 4.16 (d, 1H, J=18.0 Hz), 4.39 (d, 1H, J=18.0 Hz), 4.97 (m, 1H), 7.87 (t, 1H, J=6.0 Hz), 8.21 (s, 1H), 8.34 (d, 1H, J=9.0 Hz), 8.46 (s, 1H), 8.61 (d, 1H, J=6.0 Hz). HPLC: 93%. ES-MS m/z 339 [M+H]$^+$.

Example 382

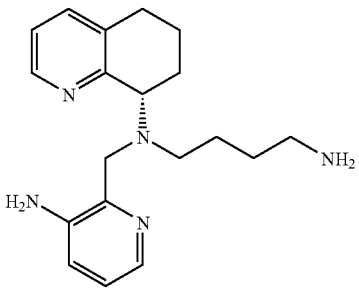

COMPOUND 382: $N^1$-(3-Amino-pyridin-2-ylmethyl)-$N^1$-(5,6,7,8-tetrahydro-quinolin-8-yl)-butane-1,4-diamine Using General Procedure B: Reaction of 2-[4-(5,6,7,8-tertrahydro-quinolin-8-ylamino)-butyl]-isoindole-1,3-dione in CH$_2$Cl$_2$ with (2-formyl-pyridin-3-yl)-carbamic acid tert-butyl ester (2.71 g, 11.5 mmol) and NaBH(OAc)$_3$ gave (2-{[[4-(1,3-dioxo-1,3-dihydro-isoindol-2-yl)-butyl]-(5,6,7,8-tetrahydroquinolin-8-yl)-amino]-methyl}-pyridin-3-yl)-carbamic acid tert-butyl ester as an off white solid. $^1$H NMR (CDCl$_3$) δ 1.69 (m, 9H), 1.85 (m, 4H), 2.05 (m, 1H), 2.18 (m, 1H), 2.52 (m, 2H), 2.82 (m, 2H), 3.54 (dd, 2H, J=5.3, 8.3 Hz), 3.77 (d, 1H, J=13.1 Hz), 4.01 (d, 1H, J=14.5 Hz), 4.09 (m, 1H), 7.03 (m, 2H), 7.34 (d, 1H, J=7.9 Hz), 7.70 (m, 2H), 7.82 (m, 2H), 8.07 (d, 1H, J=4.8 Hz), 8.52 (d, 1H, J=9.2 Hz), 8.54 (d, 1H, J=5.3 Hz). Deprotection with H$_2$NNH$_2$.H$_2$O following General Procedure E gave (2-{[(4-amino-butyl)-(5,6,7,8-tetrahydro-quinolin-8-yl)-amino]-methyl}-pyridin-3-yl)-carbamic acid tert-butyl ester as a colorless oil. $^1$H NMR (D$_2$O) δ 1.42 (m, 6H), 1.58 (s, 9H), 2.05 (m, 1H), 2.10 (m, 1H), 2.46 (m, 1H), 2.56 (m, 3H), 2.77 (m, 2H), 3.78 (d, 1H, J=13.2 Hz), 3.99 (d, 1H, J=13.6 Hz), 4.10 (m, 1H), 7.07 (dd, 1H, J=3.9, 7.0 Hz), 7.13 (dd, 1H, J=48, 8.3 Hz), 7.37 (d, 1H, J=7.5 Hz), 8.10 (d, 1H, J=4.8 Hz), 8.45 (d, 1H, J=8.8 Hz), 8.55 (d, 1H, J=4.4 Hz).

To a solution of (2-{[(4-amino-butyl)-(5,6,7,8-tetrahydro-quinolin-8-yl)-amino]-methyl}-pyridin-3-yl)-carbamic acid tert-butyl ester (2.32 g, 5.45 mmol) dissolved in THF (28 mL) add t-butoxycarbonyl (1.19 g, 5.45 mmol) and DIPEA (0.95 mL, 5.45 mmol). Stir the reaction for 30 min under a positive pressure of N$_2$. The reaction mixture was quenched with a solution of saturated NaHCO$_3$ (50 mL). Extract with CH$_2$Cl$_2$ (3×50 mL). The combined organic extracts were dried (Na$_2$SO$_4$), filtered, and concentrated in vacuo to afford a light yellow oil. Purification via column chromatography on silica gel (CH$_2$Cl$_2$:MeOH:NH$_4$OH, 96:3:1, v/v/v) afforded (2-{[(4-tert-butoxycarbonylamino-butyl)-(5,6,7,8-tetrahydro-quinolin-8-yl)-amino]-methyl}-pyridin-3-yl)-carbamic acid tert-butyl ester as a white solid (2.84 g, 99%). $^1$H NMR (CDCl$_3$) δ 1.43 (m, 4H), 1.59 (m, 16H), 1.80 (m, 2H), 2.03 (m, 1H), 2.19 (m, 1H), 2.41 (m, 1H), 2.59 (m, 1H), 2.77 (m, 2H), 2.97 (m, 2H), 3.74 (d, 1H, J=13.6 Hz), 3.96 (d, 1H, J=41 Hz), 4.11 (m, 1H), 7.07 (m, 1H), 7.14 (m, 1H), 7.38 (d, 1H, J=7.9 Hz), 8.08 (d, 1H, J=5.3 Hz), 8.50 (d, 1H, J=7.5 Hz), 8.56 (d, 1H, J=3.9 Hz).

To a solution of (2-{[(4-tert-butoxycarbonylamino-butyl)-(5,6,7,8-tetrahydro-quinolin-8-yl)-amino]-methyl}-pyridin-3-yl)-carbamic acid tert-butyl ester (2.84 g, 5.40 mmol) dissolved in MeOH (6 mL) add HCl-saturated MeOH (14 mL) and stir for 1.5 hours at room temperature under a N$_2$ atmosphere. The solution was added dropwise to Et$_2$O (1.0 L) to yield a chunky white precipitate. The white solid was isolated via suction filtration under a steady stream of N$_2$, washed with Et$_2$O and dried at 40° C. in vacuo overnight to afford COMPOUND 382 (2.02 g, 78%). $^1$H NMR (D$_2$O) δ 1.43 (m, 4H), 1.53 (m, 1H), 2.05 (m, 3H), 2.47 (m, 6H), 3.72 (s, 2H), 4.11 (m, 1H), 7.16 (dd, 1H, J=4.8, 8.3 Hz), 7.47 (d, 1H, J=7.9 Hz), 7.67 (m, 1H), 8.41 (d, 1H, J=4.8 Hz); $^{13}$C NMR (D$_2$O) δ 20.50, 20.53, 25.14, 25.26, 27.79, 39.50, 50.23, 52.15, 60.65, 125.83, 126.54, 129.74, 130.95, 136.43, 139.39, 140.58, 145.31, 147.95, 151.23. Anal. Calcd. For (C$_{19}$H$_{27}$N$_5$) 3.1 (HCl) 2.07 (H$_2$O): C, 47.97; H, 7.25; N, 14.72; Cl, 23.08. Found: C, 48.01; H, 7.12; N, 14.59; Cl, 23.07.

Example 383

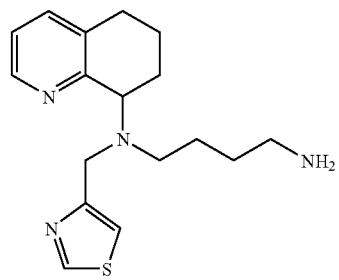

COMPOUND 383: $N^1$-(5,6,7,8-tetrahydro-quinolin-8-yl)-$N^1$-thiazol-4-ylmethyl-butane-1,4-diamine (HBr salt)

Using General Procedure A, reaction of 2-[4-(5,6,7,8-tetrahydro-quinolin-8-ylamino)-butyl]-isoindole-1,3-dione, 4-(chloromethyl) thiazole hydrochloride, KI and DIPEA in CH$_3$CN gave a pale yellow foam. Deprotection with NH$_2$NH$_2$.H$_2$O gave a pale yellow oil. Conversion to the HBr salt using General Procedure D gave an orange solid. $^1$H NMR (D$_2$O) δ 1.60-1.75 (m, 5H), 2.06-2.20 (m, 2H), 2.40-2.44 (m, 1H), 2.83-2.87 (m, 2H), 2.91-2.96 (m, 2H), 3.12-3.20 (m, 1H), 3.25-3.29 (m, 1H), 4.47 (s, 2H), 4.68-4.71 (m, 1H), 7.41 (dd, 1H, J=4.8, 7.8 Hz), 7.76 (s, 1H), 7.78 (d, 1H, J=7.8 Hz), 8.43 (d, 1H, J=4.8 Hz), 9.04 (s, 1H); $^{13}$C NMR (D$_2$O) δ 20.30, 20.78, 23.41, 24.61, 27.41, 39.30, 49.99, 51.62, 61.70, 122.77, 125.07, 137.17, 142.31, 144.45, 146.63, 149.57, 157.38. ES-MS m/z 317 (M+H). Anal. Calcd. for C$_{17}$H$_{24}$N$_4$S.3.2HBr.1.5H$_2$O.0.2C$_4$H$_{10}$O: C, 34.73; H, 5.28; N, 9.05; Br, 41.30; S, 5.18. Found: C, 34.66; H, 5.21; N, 8.98; Br, 41.28; S, 5.21.

Example 384

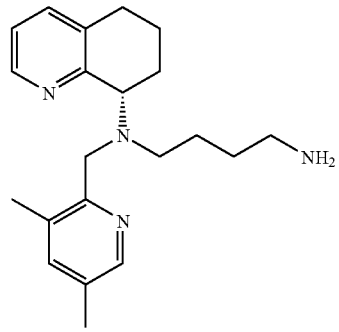

COMPOUND 384: (S)-(N[1]-(3,5-dimethyl-pyridin-2-ylmethyl)-N[1]-(5,6,7,8-tetrahydro-quinolin-8-yl)-butane-1,4-diamine (HCl salt)

Using General Procedure B, reaction of (S)-2-[4-(5,6,7,8-tetrahydro-quinolin-8-ylamino)-butyl]-isoindole-1,3-dione, 3,5-dimethyl-pyridine-2-carbaldehyde and NaBH(OAc)$_3$ gave a colorless oil. Deprotection with NH$_2$NH$_2$.H$_2$O gave a colorless oil. The oil was treated with HCl saturated MeOH (30 mL) to afford an HCl salt as a white solid (4.5 g, 64%). $^1$H NMR (D$_2$O) δ 1.36-1.44 (m, 4H), 1.77 (m, 1H), 2.40-2.50 (m, 8H), 2.71-2.81 (m, 3H), 2.97 (d, 1H, J=4.8 Hz), 4.11 (d, 1H, J=15 Hz), 4.33-4.47 (m, 3H), 7.83 (dd, 1H, J=14, 7.5 Hz), 8.17 (s, 1H), 8.30 (d, 1H, J=7.8 Hz), 8.42 (s, 1H), 8.56 (d, 1H, J=5.7 Hz); $^{13}$C NMR (D$_2$O) δ 16.89, 17.45, 20.45, 20.59, 25.08, 25.32, 27.79, 39.39, 51.81, 51.98, 61.07, 125.81, 136.45, 137.31, 137.63, 139.34, 140.67, 148.03, 148.82, 149.10, 151.13. ES-MS m/z 339.3 (M+H). Anal. Calcd. for C$_{21}$H$_{30}$N$_4$.3.5HCl.1.5H$_2$O.1.1CH$_4$O: C, 50.24; H, 7.80; N, 10.60; Cl, 23.48. Found: C, 50.60; H, 7.90; N, 10.87; Br, 23.20.

Example 385

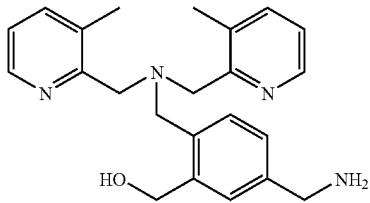

COMPOUND 385: (5-Aminomethyl-2-{[bis-(3-methyl-pyridin-2-ylmethyl)-amino]-methyl}-phenyl)-methanol Using General Procedure A: Reaction of bis-(3-methyl-pyridin-2-ylmethyl)-amine, 2-bromomethyl-5-cyano-benzoic acid methyl ester and DIPEA in CH$_3$CN gave 2-{[bis-(3-methyl-pyridin-2-ylmethyl)-amino]-methyl}-5-cyano-benzoic acid methyl ester as a colorless oil.

To a cold (0° C.) mixture of LiAlH$_4$ (195 mg, 5.12 mmol) in dry THF (6 mL) was added 2-{[bis-(3-methyl-pyridin-2-ylmethyl)-amino]-methyl}-5-cyano-benzoic acid methyl ester (0.22 g, 0.55 mmol) as a solution in THF (5 mL). The resultant mixture was stirred at room temperature for 5 hours then cooled in an ice water bath. The mixture was treated with saturated aqueous sodium-potassium tartrate (11 mL) and diluted with THF (11 mL). The phases were separated and the aqueous phase was extracted with THF (2×10 mL). The combined organic extracts were dried (Na$_2$SO$_4$) and concentrated. Purification of the crude material by column chromatography on silica gel (20:1:1 CH$_2$Cl$_2$-MeOH—NH$_4$OH) followed by radial chromatography on silica gel (1 mm plate, 50:1:1 CH$_2$Cl$_2$-MeOH—NH$_4$OH) gave COMPOUND 385 (56 mg, 26%) as a white solid. $^1$H NMR (CDCl$_3$) δ 2.12 (s, 6H), 3.72 (s, 4H), 3.82 (s, 2H), 3.89 (s, 2H), 4.25 (s, 2H), 6.54 (br s, 1H), 7.05 (dd, 2H, J=4.8, 7.5 Hz), 7.14-7.17 (m, 1H), 7.22-7.28 (m, 2H). 7.37 (d, 2H, J=7.2 Hz), 8.36 (d, 2H, J=3.6 Hz); $^{13}$C NMR (CDCl$_3$) δ 18.57, 46.53, 57.74, 59.20, 63.53, 122.76, 126.35, 130.26, 132.06, 133.38, 135.74, 138.46, 142.44, 143.79, 146.51, 156.35; ES-MS m/z 377 (M+H).

Anal. Calcd. for C$_{23}$H$_{28}$N$_4$O.0.2H$_2$O: C, 72.68; H, 7.53; N, 14.74. Found: C, 72.69; H, 7.52; N, 14.40.

Example 386

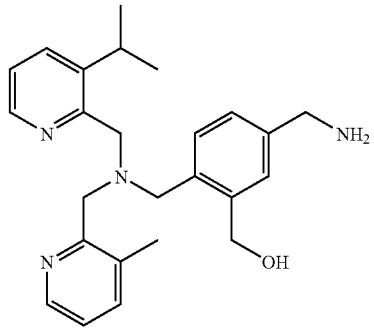

COMPOUND 386: (5-aminomethyl-2-{[(3-methyl-pyridin-2-ylmethyl)-(3-isopropyl-pyridin-2-ylmethyl)-amino]-methyl}-phenyl)-methanol Using General Procedure B: Reaction of C-(3-methyl-pyridin-2-yl)-methylamine and 3-isopropyl-pyridine-2-carboxaldehyde with NaBH(OAc)$_3$ in CH$_2$Cl$_2$ gave (3-isopropyl-pyridin-2-ylmethyl)-(3-methyl-pyridin-2-ylmethyl)-amine as a yellow oil.

Using General Procedure A: Reaction of (3-isopropyl-pyridin-2-ylmethyl)-(3-methyl-pyridin-2-ylmethyl)-amine, 2-bromomethyl-5-cyano-benzoic acid methyl ester, and DIPEA in CH$_3$CN gave 5-Cyano-2-{[(3-isopropyl-pyridin-2-ylmethyl)-(3-methyl-pyridin-2-ylmethyl)-amino]-methyl}-benzoic acid methyl ester as a yellow oil.

To a cold (0° C.) mixture of LiAlH$_4$ (226 mg, 5.94 mmol) in dry THF (6 mL) was added 5-cyano-2-{[(3-isopropyl-pyridin-2-ylmethyl)-(3-methyl-pyridin-2-ylmethyl)-amino]-methyl}-benzoic acid methyl ester (0.253 g, 0.59 mmol) as a solution in THF (5 mL). The resultant mixture was stirred at room temperature for 4 hours then cooled in an ice water bath. The mixture was treated with saturated aqueous sodium-potassium tartrate (5 mL) and diluted with THF (10 mL). The phases were separated and the aqueous phase was extracted with THF (2×10 mL). The combined organic extracts were dried (Na$_2$SO$_4$) and concentrated. Purification of the crude material by column chromatography on silica gel (20:1:1 CH$_2$Cl$_2$-MeOH—NH$_4$OH) followed by radial chromatography on silica gel (1 mm plate, 50:1:1 CH$_2$Cl$_2$-MeOH—NH$_4$OH) gave COMPOUND 386 (42 mg, 17%) as a white solid. $^1$H NMR (CDCl$_3$) δ 1.04 (d, 6H, J=6.0 Hz), 2.10 (s, 3H), 2.97 (septet, 1H), 3.73 (s, 2H), 3.76 (s, 2H), 3.82 (s, 2H), 3.90 (s, 2H), 4.24 (s, 2H), 6.38 (br s, 1H), 7.05-7.17 (m, 3H), 7.20-7.28 (m, 2H), 7.39 (d, 1H, J=7.2 Hz), 7.52 (dd, 1H, J=1.5, 7.8 Hz), 8.35-8.38 (m, 2H); $^{13}$C NMR (CDCl$_3$) δ 18.53, 23.46 (2 carbons), 27.99, 46.54, 56.73, 58.03, 59.15, 63.42, 122.81, 123.13, 126.37, 130.24, 132.05, 133.62, 135.75, 138.55, 142.41, 143.66, 143.76, 146.32, 146.51, 155.10, 156.35; ES-MS m/z 405 (M+H). Anal. Calcd. for C$_{25}$H$_{32}$N$_4$O.0.9H$_2$O: C, 71.36; H, 8.10; N, 13.32. Found: C, 71.58; H, 7.93; N, 12.95.

Example 387

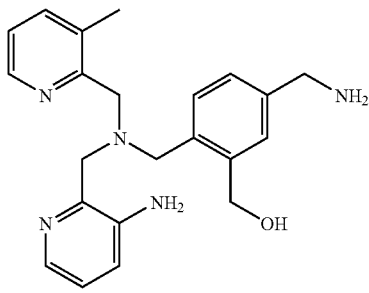

COMPOUND 387: (5-Aminomethyl-2-{[(3-amino-pyridin-2-ylmethyl)-(3-methyl-pyridin-2-ylmethyl)-amino]-methyl}-phenyl)-methanol Using General Procedure B: Reaction of C-(3-methyl-pyridin-2-yl)-methylamine and (2-formyl-pyridin-3-yl)-carbamic acid tert-butyl ester with NaBH(OAc)$_3$ in CH$_2$Cl$_2$ gave (2-{[(3-Methyl-pyridin-2-ylmethyl)-amino]-methyl}-pyridin-3-yl)-carbamic acid tert-butyl ester as a yellow oil.

Using General Procedure A: A solution (2-{[(3-methyl-pyridin-2-ylmethyl)-amino]-methyl}-pyridin-3-yl)-carbamic acid tert-butyl ester (0.220 g, 0.65 mmol), 2-bromomethyl-5-cyano-benzoic acid methyl ester (0.245 g, 0.97 mmol), and DIPEA (0.23 mL, 1.32 mmol) in CH$_3$CN (7 mL) was stirred at room temperature for 21 hours. Purification of the crude material by column chromatography on silica gel (20:1:1 CH$_2$Cl$_2$-MeOH—NH$_4$OH) provided 0.294 g (88%) of 2-{[(3-tert-Butoxycarbonylamino-pyridin-2-ylmethyl)-(3-methyl-pyridin-2-ylmethyl)-amino]-methyl}-5-cyano-benzoic acid methyl ester as a colorless oil. $^1$H NMR (CDCl$_3$) δ 1.58 (s, 9H), 2.20 (s, 3H), 3.76 (s, 2H), 3.86 (s, 3H), 4.05 (s, 2H), 4.09 (s, 2H), 7.09-7.16 (m, 2H), 7.44 (d, 1H, J=7.8 Hz), 7.55 (dd, 1H, J=8.1, 1.5 Hz), 7.89 (d, 1H, J=8.1 Hz), 8.04 (d, 1H, J=1.5 Hz), 8.09 (dd, 1H, J=1.5, 4.8 Hz), 8.51 (d, 1H, J=7.8 Hz), 8.63 (d, 1H, J=4.8 Hz).

To a cold (0° C.) solution of 2-{[(3-tert-Butoxycarbonylamino-pyridin-2-ylmethyl)-(3-methyl-pyridin-2-ylmethyl)-amino]-methyl}-5-cyano-benzoic acid methyl ester (0.388 g, 0.77 mmol) in MeOH (7 mL) was added LiBH$_4$ (107 mg, 4.91 mmol) and the mixture was allowed to warm to room temperature overnight. The mixture was concentrated and the residue was partitioned between CH$_2$Cl$_2$ (50 mL) and 1.0 N NaOH (15 mL). The phases were separated and the aqueous phase was extracted with CH$_2$Cl$_2$ (3×15 mL). The combined organic extracts were dried (Na$_2$SO$_4$) and concentrated and provided 0.36 g of (2-{[(4-Cyano-2-hydroxymethyl-benzyl)-(3-methyl-pyridin-2-ylmethyl)-amino]-methyl}-pyridin-3-yl)-carbamic acid tert-butyl ester as a white solid, which was used without further purification.

The intermediate from above (0.36 g, 0.77 mmol) was dissolved in NH$_3$ saturated MeOH (15 mL), treated with Raney nickel (90 mg), and placed under 50 psi H$_2$ on a Parr shaker, for 19 h. The mixture was filtered through celite and the cake was washed with methanol. The eluant was concentrated under reduced pressure. Purification of the crude material by column chromatography on silica gel (20:1:1 CH$_2$Cl$_2$-MeOH—NH$_4$OH) provided 0.34 g (89%) of (2-{[(4-Aminomethyl-2-hydroxymethyl-benzyl)-(3-methyl-pyridin-2-ylmethyl)-amino]-methyl}-pyridin-3-yl)-carbamic acid tert-butyl ester as a white solid.

The solid (0.33 g, 0.69 mmol) was dissolved in THF (4 mL) and treated with 6N HCl (4 mL). The resultant solution was stirred at room temperature overnight. The solution was neutralized with solid Na$_2$CO$_3$ (3 g), diluted with water (5 mL) and extracted with CH$_2$Cl$_2$ (5×20 mL). The combined organic extracts were dried (Na$_2$SO$_4$) and concentrated. Purification of the crude material by radial chromatography on silica gel (2 mm plate, 50:1:1 CH$_2$Cl$_2$-MeOH—NH$_4$OH) provided 0.144 g (53%) of COMPOUND 387 as a white solid. $^1$H NMR (CDCl$_3$) δ 2.20 (s, 3H), 3.64 (s, 2H), 3.77 (s, 2H), 3.81 (s, 2H), 3.84 (s, 2H), 4.30 (s, 2H), 5.11 (br s, 2H), 6.38 (br s, 1H), 6.95 (dd, 1H, J=7.8, 1.5 Hz), 7.01-7.09 (m, 2H), 7.16-7.19 (m, 1H), 7.24-7.28 (m, 2H), 7.38 (d, 1H, J=7.5 Hz), 7.92 (dd, 1H, J=4.5, 1.5 Hz), 8.33 (d, 1H, J=3.9 Hz); $^{13}$C NMR (CDCl$_3$) δ 18.59, 46.39, 55.73, 59.29, 60.64, 63.62, 122.52 (2 carbons), 124.21, 126.65, 130.22, 132.16, 132.38, 135.41, 138.15, 138.69, 142.02, 142.41, 143.82 (2 carbons), 146.30, 156.10; ES-MS m/z 378 (M+H). Anal. Calcd. for C$_{22}$H$_{27}$N$_5$O.1.3H$_2$O: C, 65.91; H, 7.44; N, 17.47. Found: C, 65.87; H, 7.37; N, 17.10.

Example 388

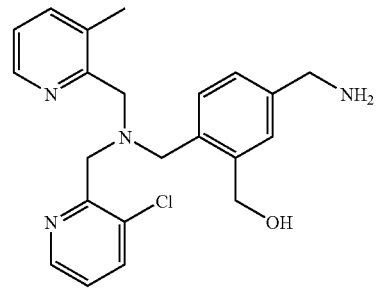

COMPOUND 388: (5-Aminomethyl-2-{[(3-chloro-pyridin-2-ylmethyl)-(3-methyl-pyridin-2-ylmethyl)-amino]-methyl}-phenyl)-methanol Using General Procedure B: Reaction of C-(3-methyl-pyridin-2-yl)-methylamine and 3-chloro-pyridine-2-carboxaldehyde with NaBH(OAc)$_3$ in CH$_2$Cl$_2$ gave (3-chloro-pyridin-2-ylmethyl)-(3-methyl-pyridin-2-ylmethyl)-amine as a yellow oil. Using General Procedure A: Reaction of (3-chloro-pyridin-2-ylmethyl)-(3-methyl-pyridin-2-ylmethyl)-amine, 2-bromomethyl-5-cyano-benzoic acid methyl ester, and DIPEA in CH$_3$CN gave 2-{[(3-chloro-pyridin-2-ylmethyl)-(3-methyl-pyridin-2-ylmethyl)-amino]-methyl}-5-cyano-benzoic acid methyl ester as a colorless oil. $^1$H NMR (CDCl$_3$) δ 2.12 (s, 3H), 3.85 (s, 3H), 3.90 (s, 2H), 3.97 (s, 2H), 4.22 (s, 2H), 7.03 (dd, 1H, J=7.8, 4.8 Hz), 7.13 (dd, 1H, J=7.8, 4.8 Hz), 7.32 (d, 1H, J=6.9 Hz), 7.52-7.63 (m, 2H), 7.71 (d, 1H, J=8.1 Hz), 7.94 (d, 1H, J=1.5 Hz), 8.30 (d, 1H, J=4.5 Hz), 8.42 (dd, 1H, J=4.8, 1.5 Hz).

To a cold (0° C.) solution of 2-{[(3-Chloro-pyridin-2-ylmethyl)-(3-methyl-pyridin-2-ylmethyl)-amino]-methyl}-5-cyano-benzoic acid methyl ester (0.314 g, 0.75 mmol) in MeOH (7 mL) was added LiBH$_4$ (106 mg, 4.89 mmol) and the mixture was allowed to warm to room temperature overnight. The mixture was concentrated and the residue was partitioned between CH$_2$Cl$_2$ (25 mL) and 1.0 N NaOH (10 mL). The phases were separated and the aqueous phase was extracted with CH$_2$Cl$_2$ (3×10 mL). The combined organic extracts were dried (Na$_2$SO$_4$) and concentrated. Purification of the crude material by column chromatography on silica gel (50:1:1 CH$_2$Cl$_2$-MeOH—NH$_4$OH) provided 0.19 g (65%) of 4-{[(3-Chloro-pyridin-2-ylmethyl)-(3-methyl-pyridin-2-ylmethyl)-amino]-methyl}-3-hydroxymethyl-benzonitrile as a white foam. The white foam from above (0.19 g, 0.48 mmol) was dissolved in NH$_3$ saturated MeOH (10 mL), treated with Raney nickel (80 mg), and placed under 50 psi H$_2$ on a Parr shaker, for 19 h. The mixture was filtered through celite and the cake was washed with methanol. The eluant was concentrated under reduced pressure. Purification of the crude material by column chromatography on silica gel (20:1:1 CH$_2$Cl$_2$-MeOH—NH$_4$OH) provided 0.15 g (82%) of a 1:1 mixture of (5-aminomethyl-2-{[(3-chloro-pyridin-2-ylmethyl)-(3-methyl-pyridin-2-ylmethyl)-amino]-methyl}-phenyl)-methanol and (5-aminomethyl-2-{[(3-methyl-pyridin-2-ylmethyl)-pyridin-2-ylmethyl-amino]-methyl}-phenyl)-methanol as a white solid.

The mixture (0.15 g) was dissolved in THF (9 mL) and treated with Boc$_2$O (0.217 g, 1.00 mmol) and water (1 mL). The resultant mixture was stirred at room temperature overnight then concentrated. Purification of the crude material column chromatography on silica gel (20:1:1 CH$_2$Cl$_2$-MeOH—NH$_4$OH) followed by radial chromatography on silica gel (1 mm plate, 100:1:1 CH$_2$Cl$_2$-MeOH—NH$_4$OH) provided 49.5 mg (25%) of (4-{[(3-chloro-pyridin-2-ylmethyl)-(3-methyl-pyridin-2-ylmethyl)-amino]-methyl}-3-hydroxymethyl-benzyl)-carbamic acid tert-butyl ester as a white solid.

The white solid (0.050 g, 0.10 mmol) was dissolved in THF (1 mL) and treated with 6N HCl (1 mL). The resultant solution was stirred at room temperature overnight. The solution was neutralized with solid Na$_2$CO$_3$ (0.6 g), diluted with water (4 mL) and extracted with CH$_2$Cl$_2$ (5×10 mL). The combined organic extracts were dried (Na$_2$SO$_4$) and concentrated. Purification of the crude material by radial chromatography on silica gel (1 mm plate, 20:1:1 CH$_2$Cl$_2$-MeOH—NH$_4$OH) provided 26 mg (64%) of COMPOUND 388 as a colorless oil. $^1$H NMR (CDCl$_3$) δ 2.15 (s, 3H), 3.80 (s, 2H), 3.82 (s, 2H), 3.93 (s, 2H), 3.96 (s, 2H), 4.31 (s, 2H), 6.28 (br s, 1H), 7.04-7.17 (m, 3H), 7.22-7.28 (m, 2H), 7.38 (d, 1H, J=6.9 Hz), 7.60 (dd, 1H, J=8.1, 1.5 Hz), 8.36 (m, 1H), 8.44 (dd, 1H, J=4.5, 1.5 Hz); $^{13}$C NMR (CDCl$_3$) δ 18.17, 46.14, 55.60, 57.72, 58.53, 63.33, 122.46, 123.16, 126.04, 129.86, 131.66, 131.99, 133.20, 135.33, 137.13, 138.07, 142.02, 143.47, 146.16, 146.89, 155.21, 155.66; ES-MS m/z 397 (M+H). Anal. Calcd. for C$_{22}$H$_{25}$N$_4$OCl.0.2H$_2$O.0.07CH$_2$Cl$_2$: C, 65.22; H, 6.33; N, 13.78; Cl, 9.94. Found: C, 65.32; H, 6.35; N, 13.55; Cl, 9.87.

Example 389

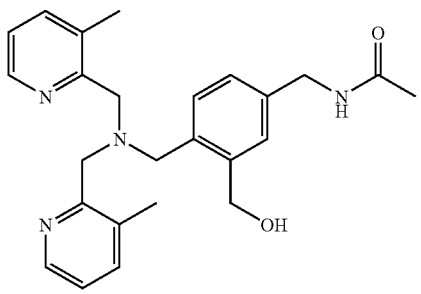

COMPOUND 389: N-(4-{[Bis-(3-methyl-pyridin-2-ylmethyl)-amino]-methyl}-3-hydroxymethyl-benzyl)-acetamide A mixture of 2-{[bis-(3-methyl-pyridin-2-ylmethyl)-amino]-methyl}-5-cyano-benzoic acid methyl ester (0.37 g, 0.92 mmol) in NH$_3$ saturated MeOH (10 mL) was treated with Raney nickel (0.50 g), and placed under 50 psi H$_2$ on a Parr shaker, for 18 h. The mixture was filtered through celite and the cake was washed with methanol. The eluant was concentrated under reduced pressure. Purification of the crude material by column chromatography on silica gel (10:1:1 CH$_2$Cl$_2$-MeOH—NH$_4$OH) provided 0.177 g (47%) of 5-aminomethyl-2-{[bis-(3-methyl-pyridin-2-ylmethyl)-amino]-methyl}-benzoic acid methyl ester as a yellow oil.

To a solution of 5-aminomethyl-2-{[bis-(3-methyl-pyridin-2-ylmethyl)-amino]-methyl}-benzoic acid methyl ester (0.177 g, 0.44 mmol) in CH$_2$Cl$_2$ (5 mL) was added Et$_3$N (0.20 mL, 1.43 mmol) followed by Ac$_2$O (0.10 mL, 1.06 mmol) and the resultant solution was stirred at room temperature for 2 hours. The mixture was diluted with CH$_2$Cl$_2$ (50 mL) and washed with brine (3×10 mL). The organic phase was dried (Na$_2$SO$_4$) and concentrated and provided 0.20 g of a yellow oil.

The yellow oil (0.20 g) was dissolved in cold (0° C.) MeOH (6 mL) and treated with LiBH$_4$ (0.110, 5.03 mmol). The mixture was allowed to warm to room temperature overnight. The mixture was concentrated and the residue was partitioned between CH$_2$Cl$_2$ (30 mL) and 1.0 N aqueous NaOH (5 mL). The phases were separated and the aqueous phase was extracted with CH$_2$Cl$_2$ (3×10 mL). The combined organic extracts were dried (Na$_2$SO$_4$) and concentrated. Purification of the crude material by radial chromatography on silica gel (1 mm plate, 50:1:1 CH$_2$Cl$_2$-MeOH—NH$_4$OH) provided 46 mg (24%) of COMPOUND 389 as a white foam. $^1$H NMR (CDCl$_3$) δ 1.99 (s, 3H), 2.14 (s, 6H), 3.70 (s, 4H), 3.89 (s, 2H), 4.24 (s, 2H), 4.38 (d, 2H, J=5.4 Hz), 5.75 (br s, 1H), 6.63 (br s, 1H), 7.03-7.08 (m, 2H), 7.13 (dd, 1H, J=7.8, 1.5 Hz), 7.22-7.26 (m, 2H), 7.38 (d, 2H, J=7.2 Hz), 8.35 (d, 2H, J=3.6 Hz); $^{13}$C NMR (CDCl$_3$) δ 18.56, 23.56, 43.70, 57.57, 59.09, 63.25, 122.81, 127.39, 130.92, 132.13, 133.33, 136.49, 138.50, 138.63, 142.48, 146.48, 156.16, 170.45; ES-MS m/z 419 (M+H). Anal. Calcd. For C$_{25}$H$_{30}$N$_4$O$_2$.1.1H$_2$O C, 68.50; H, 7.40; N, 12.78. Found: C, 68.60; H, 7.28; N, 12.72.

Example 390

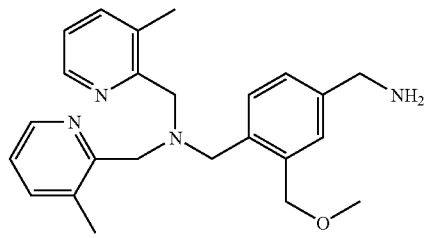

COMPOUND 390: (4-aminomethyl-2-methoxymethyl-benzyl)-bis-(3-methyl-pyridin-2-ylmethyl)-amine (HBr salt)

A solution of 2-{[bis-(3-methyl-pyridin-2-ylmethyl)-amino]-methyl}-5-cyano-benzoic acid methyl ester (0.37 g, 0.92 mmol) was dissolved in MeOH (10 mL) and treated with LiBH$_4$ (0.20 g, 9.2 mmol) at 0° C. for 0.5 h. The solution was then stirred at room temperature for 64 hours. The solvent was then removed under reduced pressure and CH$_2$Cl$_2$ (20 mL), and 1 N aqueous NaOH (10 mL) was added. The organic phase was separated, and the aqueous was extracted with CH$_2$Cl$_2$ (2×20 mL). The combined organic phases were then dried (Na$_2$SO$_4$), filtered, and concentrated under reduced pressure. This afforded 4-{[Bis-(3-methyl-pyridin-2-ylmethyl)-amino]-methyl}-3-hydroxymethyl-benzonitrile (0.33 g, 97%).

The product of above (0.33 g, 0.89 mmol) was dissolved in anhydrous THF (4 mL) and added to a suspension of NaH (30 mg, 1.2 mmol) in anhydrous THF (4 mL), stirring for 0.5 hours at 0° C. The reaction was then quenched with MeI (0.17 mL, 2.7 mmol) at 0° C. and allowed to warm to room temperature over 30 minutes. EtOAc (15 mL) and brine (15 mL) were added and the phases separated. The aqueous component was then extracted with EtOAc (2×20 mL) and the combined organic phases were then dried (MgSO$_4$), filtered, and concentrated under reduced pressure to yield, after column chromatography with silica gel (saturated NH$_3$/Et$_2$O), 4-{[Bis-(3-methyl-pyridin-2-ylmethyl)-amino]-methyl}-3-methoxymethyl-benzonitrile as a beige solid (79 mg, 23%). $^1$H NMR (CDCl$_3$) δ 1.81 (s, 6H), 3.14 (s, 3H), 3.75 (s, 6H), 3.99 (s, 2H), 7.11 (m, 2H), 7.37 (d, 3H, J=7.5 Hz), 7.46 (d, 1H, J=7.8 Hz), 7.67 (s, 1H), 8.38 (d, 2H, J=4.5 Hz).

A solution of the above compound (79 mg, 0.20 mmol) in anhydrous MeOH (5 mL) was transferred into a 100 mL Parr hydrogenator flask containing anhydrous solid Raney Nickel (~0.3 g). The mixture was then saturated with NH$_3$ gas and moved to a mechanical apparatus where the reaction vessel was purged three times (with hydrogen gas) and then pressurized to 50 psi (with H$_2$ gas) and shaken for 16 hours. The flask was then removed from the hydrogenator and filtered through a celite pad, washing several times with methanol. The filtrate was then concentrated and the residue purified by column chromatography with silica gel (3:0.5:96.5 MeOH:NH$_4$OH:CH$_2$Cl$_2$ ramping to 7:0.5:92.5 MeOH:NH$_4$OH:CH$_2$Cl$_2$) to afford (4-aminomethyl-2-methoxymethyl-benzyl)-bis-(3-methyl-pyridin-2-ylmethyl)-amine as a colorless film (30 mg, 37%). $^1$H NMR (CDCl$_3$) δ 1.76 (s, 6H), 3.06 (s, 3H), 3.64 (s, 2H), 3.72 (s, 4H), 3.83 (s, 2H), 3.99 (s, 2H), 7.10 (m, 3H), 7.22 (d, 1H, J=7.5 Hz), 7.30 (s, 1H), 7.36 (d, 2H, J=6.6 Hz), 8.38 (d, 2H, J=4.5 Hz).

Using General Procedure D: Conversion to the HBr salt gave COMPOUND 390 as a white solid. $^1$H NMR (D$_2$O) δ 2.44 (s, 6H), 3.34 (s, 3H), 3.92 (s, 2H), 4.04 (s, 2H), 4.36 (s, 4H), 4.40 (s, 2H), 7.25 (d, 1H, J=7.5 Hz), 7.26 (s, 1H), 7.45 (d, 1H, J=8.4 Hz), 7.80 (m, 2H), 8.30 (d, 2H, J=8.1 Hz), 8.54 (d, 2H, J=5.4 Hz). $^{13}$C NMR (D$_2$O) δ 17.45 (2C), 42.70, 55.28 (2C), 56.94, 58.74, 71.97, 126.18 (2C), 129.45, 131.33, 132.38, 133.51, 136.02, 137.21, 138.09 (2C), 138.92 (2C), 148.69 (2C), 150.54 (2C). ES-MS m/z 391 (M+H). Anal. Calcd. for C$_{24}$H$_{30}$N$_4$O.3.2HBr.2.2H$_2$O: C, 41.83; H, 5.50; N, 8.13; Br, 37.11. Found: C, 41.84; H, 5.62; N, 7.92; Br, 37.21.

Example 391

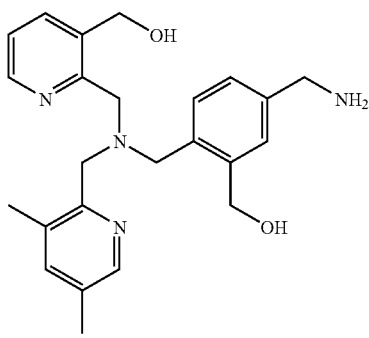

COMPOUND 391: (4-aminomethyl-2-hydroxymethyl-benzyl)-(3,5-dimethyl-pyridin-2-ylmethyl)-(3-hydroxymethyl-pyridin-2-ylmethyl)-amine Using General Procedure B: Reaction of C-(3,5-dimethyl-pyridin-2-yl)-methylamine and 3-(tert-butyl-dimethylsiloxymethyl)-pyridine-2-carbaldehyde in CH$_2$Cl$_2$ with NaBH(OAc)$_3$ gave the desired secondary amine as a yellow oil.

Using General Procedure A: Reaction of the amine from above, 2-bromomethyl-5-cyano-benzoic acid methyl ester, DIPEA, and CH$_3$CN gave the desired amine as a yellow oil.

The amine (410 mg, 0.75 mmol) from above was stirred in a 1:1 mixture of THF (7.5 mL) and deionized water (7.5 mL) for 1 h. The solution was washed with CH$_2$Cl$_2$ (3×10 mL) and the combined organic washes were discarded. Saturated NaHCO$_3$ solution was added to the aqueous layer (pH 8-9). The aqueous layer was extracted with CH$_2$Cl$_2$ (3×20 mL). The organic extracts were combined, dried over Na$_2$SO$_4$ and concentrated to give the desired alcohol (300 mg, 94%) as a colorless oil.

To a 0° C. stirred solution of the alcohol (300 mg, 0.70 mmol) from above in MeOH (7 mL) was added LiBH$_4$ (153 mg, 7.0 mmol). The solution was allowed to warm to ambient temperature and stirring was continued for 17 h. The solution was concentrated and the residue was partitioned between CH$_2$Cl$_2$ (50 mL) and 1 N NaOH (15 mL). The layers were separated and the aqueous layer was extracted with CH$_2$Cl$_2$ (2×15 mL). The combined organic extracts were dried over Na$_2$SO$_4$ and concentrated to provide the desired diol (290 mg, 100%) as a white solid.

Ammonia gas was bubbled through a solution of the diol (290 mg, 0.70 mmol) from above in MeOH (15 mL) until saturation was reached. The solution was added to a hydrogenation flask containing activated Raney nickel (300 mg) and shaken on a Parr apparatus under 30 psi of hydrogen for 17 h. The slurry was filtered through celite and concentrated. Purification of the crude material by column chromatography (CH$_2$Cl$_2$/MeOH/NH$_4$OH, 9:1:1) afforded COMPOUND 391 (213 mg, 70%) as a white solid. $^1$H NMR (CDCl$_3$) δ 2.13 (s, 3H), 2.25 (s, 3H), 3.70 (s, 2H), 3.79 (s, 2H), 3.85 (s, 2H), 3.88 (s, 2H), 4.26 (s, 2H), 4.28 (s, 2H), 7.18-7.28 (m, 4H), 7.36 (s, 1H), 7.75 (d, 1H, J=7.8 Hz), 8.22 (s, 1H), 8.43 (d, 1H, J=5.3). $^{13}$C NMR (CDCl$_3$) δ 18.27, 18.56, 46.42, 56.39, 58.19, 58.64, 61.10, 62.68, 123.56, 126.47, 129.88, 132.07, 132.30, 132.45, 134.84, 137.36, 138.69, 139.45, 141.95, 143.76, 146.97, 148.05, 152.80, 155.80. ES-MS m/z 407 (M+H). Anal. Calcd. for C$_{24}$H$_{30}$N$_4$O$_2$.0.2CH$_2$Cl$_2$: C, 68.63; H, 7.23; N, 13.23. Found: C, 68.69; H, 7.50; N, 13.34.

Example 392

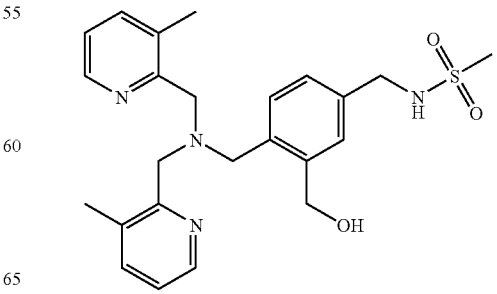

COMPOUND 392: The preparation of N-(4-{[bis-(3-methyl-pyridin-2-ylmethyl)-amino]-methyl}-3-hydroxymethyl-benzyl)-methanesulfonamide To a solution of 5-aminomethyl-2-{[bis-(3-methyl-pyridin-2-ylmethyl)-amino]-methyl}-benzoic acid methyl ester (0.382 g, 0.944 mmol) and Et$_3$N (0.191 g, 1.89 mmol) in dry THF (20 mL) was added MsCl (0.162 g, 1.42 mmol) at room temperature. After the addition the mixture was stirred at room temperature for 2 h saturated aqueous NaHCO$_3$ (20 mL) was added. THF was then removed, and the aqueous residue was extracted with CH$_2$Cl$_2$ (3×20 mL). The extracts were combined and dried over MgSO$_4$. After filtration the solvent was removed to afford 2-{[bis-(3-methyl-pyridin-2-ylmethyl)-amino]-methyl}-5-(methanesulfonylamino-methyl)-benzoic acid methyl ester as a pale yellow foam (0.460, 100%).

Under N$_2$, To a solution of 2-{[bis-(3-methyl-pyridin-2-ylmethyl)-amino]-methyl}-5-(methanesulfonylamino-methyl)-benzoic acid methyl ester (0.217 g, 0.450 mmol) in THF (20 mL) was added LiAlH$_4$ (1.0 M in THF, 0.67 mL, 0.67 mmol) at −78° C. After the addition the reaction mixture was brought to room temperature and stirred at room temperature for 30 min. H$_2$O (10 mL) was added, and THF removed. The aqueous residue was extracted with CH$_2$Cl$_2$ (3×20 mL), and the extracts were combined and dried over Na$_2$SO$_4$. After filtration the solvent was removed, and the residue was purified on silica gel column (500:25:1 CH$_2$Cl$_2$/MeOH/NH$_4$OH), affording a white foam (0.165 g, 81%). $^1$H NMR (CDCl$_3$) δ 2.13 (s, 6H), 2.87 (s, 3H), 3.71 (s, 4H), 3.90 (s, 2H), 4.25 (s, br, 2H), 4.28 (d, 2H, J=6.0 Hz), 4.59 (t, 1H, J=60 Hz), 6.65 (s, br, 1H), 7.06 (dd, 2H, J=4.8, 7.8 Hz), 7.21 (dd, 1H, J=1.5, 7.8 Hz), 7.26-7.31 (m, 2H), 7.38 (d, 2H, J=7.8 Hz), 8.35 (d, 2H, J=4.8 Hz); $^{13}$C NMR (CDCl$_3$) δ 18.26, 41.00, 46.84, 57.30, 58.68, 62.79, 122.60, 127.04, 130.68, 131.99, 133.12, 136.72, 137.03, 138.30, 142.35, 146.18, 155.87. ES-MS m/z 455 (M+H). Anal. Calcd. for C$_{24}$H$_{30}$N$_4$O$_3$S.0.21CH$_2$Cl$_2$: C, 61.55; H, 6.49; N, 11.86; S, 6.79. Found: C, 61.62; H, 6.58; N, 11.64; S, 6.77.

Example 393

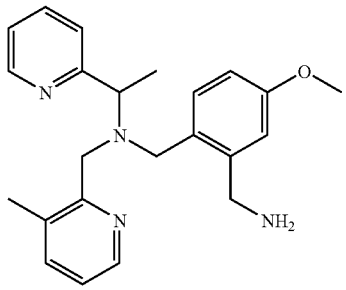

COMPOUND 393: (2-aminomethyl-4-methoxy-benzyl)-(3-methyl-pyridin-2-ylmethyl)-(1-pyridin-2-yl-ethyl)-amine Using General Procedure A: Reaction of (3-methyl-pyridin-2-ylmethyl)-(1-pyridin-2-yl-ethyl)-amine, 2-bromomethyl-5-methoxybenzonitrile (Ando, K. et al. *Bull. Chem. Soc. Jpn.* 1980, 53, 2885-2890), DIPEA and KI in CH$_3$CN gave 5-methoxy-2-{[(3-methyl-pyridin-2-ylmethyl)-(1-pyridin-2-yl-ethyl)-amino]-methyl}-benzonitrile as an orange oil. $^1$H NMR (CDCl$_3$) δ 1.60 (d, 3H, J=6.9 Hz), 2.08 (s, 3H), 3.73 (d, 1H, J=15.0 Hz), 3.74 (d, 1H, J=12.3 Hz), 3.78 (s, 3H), 3.92 (d 1H, J=12.3 Hz), 3.93 (d, 1H, J=15.0 Hz), 4.03 (q, 1H, J=6.9 Hz), 6.95-7.04 (m, 3H), 7.16 (ddd, 1H, J=7.5, 5.0, 1.0 Hz), 7.29 (t, 2H, J=6.6 Hz), 7.37 (d, 1H, J=7.8 Hz), 7.65 (td, 1H, J=7.7, 1.8 Hz), 8.32 (dd, 1H, J=4.8, 1.2 Hz), 8.58 (dd, 1H, J=4.8, 0.9 Hz).

A solution of the above nitrile (258 mg, 0.69 mmol) in MeOH saturated with NH$_3$ (15 mL) was hydrogenated (40 psi) over Raney-nickel for 4 hours. The mixture was filtered with suction through a pad of celite, washing with excess MeOH. The filtrate was concentrated under reduced pressure, giving the crude amine as a purple foam.

This material was taken up into 50% aqueous MeOH (10 mL) and NaCN (147 mg, 3.0 mmol) was added. The reaction was stirred at 45° C. for 30 minutes, and then the MeOH was evaporated under reduced pressure. The residue was taken up into saturated aqueous NaHCO$_3$ (10 mL) and was extracted with CH$_2$Cl$_2$ (20 mL×3). The combined organic solution was dried (Na$_2$SO$_4$), filtered and concentrated under reduced pressure. Purification by flash column chromatography on silica (CH$_2$Cl$_2$/MeOH/NH$_4$OH, 9:1:0.05) gave the primary amine as a colorless oil (179 mg, 0.48 mmol, 69%). $^1$H NMR (CDCl$_3$) δ 1.55 (d, 3H, J=6.9 Hz), 1.83 (br. s, 2H), 1.97 (s, 3H), 3.51 (s, 2H), 3.66 (d, 1H, J=13.5 Hz), 3.73 (d, 1H, J=13.5 Hz), 3.74 (d, 1H, J=12.6 Hz), 3.79 (s, 3H), 3.80 (d, 1H, J=12.6 Hz), 4.05 (q, 1H, J=6.8 Hz), 6.70 (dd, 1H, J=8.4, 2.7 Hz), 6.85 (d, 1H, J=2.7 Hz), 7.07 (dd, 1H, J=7.7, 4.7 Hz), 7.16 (dd, 1H, J=7.5, 4.8 Hz), 7.20 (d, 2H, J=8.4 Hz), 7.37 (d, 1H, J=7.5 Hz), 7.62 (td, 1H, J=7.7, 1.8 Hz), 8.36 (d, 1H, J=3.9 Hz), 8.58 (d, 1H, J=4.2 Hz). $^{13}$C NMR (CDCl$_3$) δ 11.5, 18.0, 43.6, 51.7, 53.6, 55.2, 58.3, 111.5, 114.1, 122.0, 122.3, 124.1, 128.7, 132.4, 133.1, 136.0, 138.1, 144.1, 146.0, 148.5, 157.3, 159.1, 161.6. ES-MS m/z 377 (M+H). Anal. Calcd. for C$_{23}$H$_{28}$N$_4$O.0.2CH$_2$Cl$_2$: C, 70.82; H, 7.27; N, 14.24. Found: C, 70.45; H, 7.24; N, 14.27.

Example 394

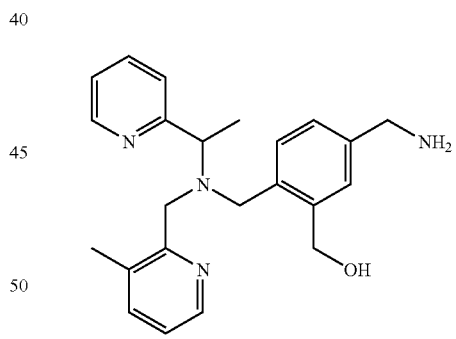

COMPOUND 394: (5-aminomethyl-2-{[(3-methyl-pyridin-2-ylmethyl)-(1-pyridin-2-yl-ethyl)-amino]-methyl}-phenyl)-methanol Using General Procedure A, reaction of (3-methyl-pyridin-2-ylmethyl)-(1-pyridin-2-yl-ethyl)-amine and 2-bromomethyl-5-cyano-benzoic acid methyl ester in CH$_3$CN with DMAP, KI, and DIPEA gave 5-cyano-2-{[(3-methyl-pyridin-2-ylmethyl)-(1-pyridin-2-yl-ethyl)-amino]-methyl}-benzoic acid methyl ester as an amber oil. $^1$H NMR (CDCl$_3$) δ 1.26 (t, 1H, J=7.3 Hz), 1.58 (d, 3H, J=6.7 Hz), 1.73 (s, 1H), 2.04 (s, 1H), 2.09 (s, 3H), 3.73-3.94 (m, 1H), 3.87 (s, 3H), 4.08-4.19 (m, 4H), 6.92-6.98 (m, 1H), 7.14-7.20 (m, 1H), 7.23 (d, 1H, J=8.0 Hz), 7.34 (d, 1H, J=7.8 Hz), 7.48-7.53 (m, 1H), 7.64-7.69 (m, 2H), 7.92 (d, 1H, J=1.6 Hz), 8.21 (d, 1H, J=3.0 Hz), 8.57 (d, 1H, J=4.8 Hz).

To a solution of 5-cyano-2-{[(3-methyl-pyridin-2-ylmethyl)-(1-pyridin-2-yl-ethyl)-amino]-methyl}-benzoic acid methyl ester (0.88 g, 2.2 mmol) in dry THF (11 mL) under Ar at 0° C. was slowly added 1.0 M LiAlH$_4$ in THF (22 mL, 22.0 mmol). The reaction was stirred at room temperature for 2 hours, then cooled to 0° C. Saturated aqueous KNa Tartrate (Rochelle's salt, 30 mL) was slowly added, and the phases were separated. The aqueous phase was extracted with THF (1×35 mL), and the organic extract was dried (MgSO$_4$) and concentrated. Purification of the crude material by column chromatography on silica gel (20:1:1 CH$_2$Cl$_2$-MeOH—NH$_4$OH) followed by radial chromatography twice on silica gel (33:1:1 and 50:1 CH$_2$Cl$_2$-MeOH—NH$_4$OH respectively) provided 75.1 mg (9%) of COMPOUND 394 as a white solid. $^1$H NMR (CDCl$_3$) δ 1.56 (d, 6H, J=6.9 Hz), 2.04 (s, 3H), 3.66-3.98 (m, 6H), 4.05-4.12 (m, 1H), 4.26 (s, 2H), 7.04-7.08 (m, 1H), 7.14-7.23 (m, 3H), 7.27-7.28 (m, 1H), 7.34-7.39 (m, 2H), 7.63-7.69 (m, 1H), 8.39 (d, 1H, J=4.5 Hz), 8.58 (d, 1H, J=4.5 Hz). $^{13}$C NMR (CDCl$_3$) δ 11.85, 18.43, 46.48, 52.54, 53.97, 58.89, 63.56, 122.53, 122.60, 124.15, 126.40, 130.15, 131.98, 132.93, 135.93, 136.65, 138.51, 142.48, 143.57, 146.57, 148.92, 156.73, 161.25. ES-MS m/z 377 (M+H). Anal. Calcd. for C$_{23}$H$_{28}$N$_4$O.0.1H$_2$O.0.3CH$_2$Cl$_2$: C, 69.31; H, 7.19; N, 13.88. Found: C, 69.56; H, 7.27; N, 13.70.

Example 395

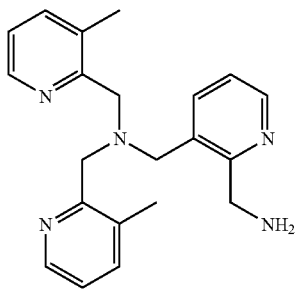

COMPOUND 395: (2-Aminoethyl-pyridin-3-ylmethyl)-bis-(3-methyl-pyridin-2-ylmethyl)-amine (HBr salt)

To a solution of 3-methylpicolinonitrile (1.0 g, 8.47 mmol) in CCl$_4$ (43 ml) was added NBS (1.81 g, 10.16 mmol) and benzoyl peroxide (32 mg, 1.27 mmol) and the mixture stirred at reflux for 16 hours. The reaction was concentrated in vacuo to afford a black oil. Purification via column chromatography on silica gel (EtOAc:hexane, 1:9, v/v) afforded 3-bromomethyl-pyridine-2-carbonitrile as a white solid (0.87 g, 48%). $^1$H NMR (CDCl$_3$) δ 4.64 (s, 2H), 7.53 (dd, 1H, J=4.4, 4.0 Hz), 7.94 (dd, 1H, J=6.1, 1.8 Hz), 8.66 (dd, 1H, J=2.6, 1.8 Hz).

Using General Procedure A: Reaction of bis-(3-methyl-pyridin-2-ylmethyl)-amine in CH$_3$CN with 2-cyano-3-bromomethyl-pyridine, KI and DIPEA gave 3-{[bis-(3-methyl-pyridin-2-ylmethyl)-amino]-methyl}-pyridine-2-carbonitrile as a dark red oil. $^1$H NMR (CDCl$_3$) δ 2.04 (s, 6H), 3.86 (s, 4H), 3.99 (s, 2H), 7.07 (m, 2H), 7.38 (m, 3H), 7.84 (d, 1H, J=9.0 Hz), 8.37 (m, 2H), 8.53 (m, 1H).

A solution of 3-{[bis-(3-methyl-pyridin-2-ylmethyl)-amino]-methyl}-pyridine-2-carbonitrile (0.72 g, 2.1 mmol) in MeOH (21 ml) was saturated with NH$_3$ gas for 18 min. A prewashed mixture of Raney Nickel (1 gram) was added to the nitrile and hydrogenated at 30 psi for 16 hours. The mixture was filtered through a sintered glass funnel containing celite and concentrated. Purification via column chromatography on silica gel (CH$_2$Cl$_2$:MeOH:NH$_4$OH, 94:5:1, v/v/v) afforded (2-aminoethyl-pyridin-3-ylmethyl)-bis-(3-methyl-pyridin-2-ylmethyl)-amine as a colorless oil (0.42 g, 58%). $^1$H NMR (CDCl$_3$) δ 1.68 (s, 2H), 1.81 (s, 6H), 3.45 (s, 2H), 3.71 (s, 6H), 7.10 (m, 3H), 7.39 (d, 2H, J=9 Hz), 7.55 (d, 1H, J=9 Hz), 8.36 (s, 2H), 8.38 (s, 1H). Conversion to the HBr salt gave a white solid. $^1$H NMR (D$_2$O) δ 2.42 (s, 6H), 3.93 (s, 2H), 4.29 (s, 6H), 7.31 (m, 1H), 7.89 (m, 3H), 8.33 (m, 2H), 8.42 (m, 1H), 8.60 (m, 2H); $^{13}$C NMR (D$_2$O) δ 17.52, 40.61, 54.73, 55.83, 124.22, 126.43, 130.09, 138.35, 1139.59, 139.76, 148.70, 149.03, 150.08, 150.43. ES-MS m/z 348 (M+H). Anal. Calcd. for C$_{21}$H$_{25}$N$_5$ 2.96HBr 1.46H$_2$O 0.23C$_4$H$_{10}$O: C, 41.78; H, 5.31; N, 11.11; Br, 37.51. Found: C, 41.79; H, 5.05; N, 11.02; Br, 37.48.

Example 396

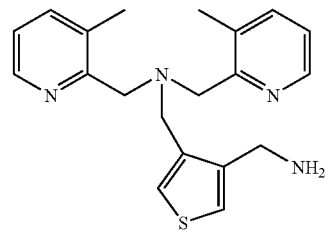

COMPOUND 396: (4-Aminomethyl-thiophen-3-ylmethyl)-bis-(3-methyl-pyridin-2-ylmethyl)-amine (HBr salt)

To a chilled (0° C.) solution of 4-methyl-tetrahydro-thiophene-3-carbonitrile (129 mg, 1.04 mmol) (Terpstra, J. W. et al. *J. Org. Chem.* 1986, 51, 230-238) in dry THF (5.0 mL) was added LAH (84.0 mg, 2.09 mmol). The mixture was stirred at room temperature for 4 h and saturated Rochelle's solution (10.0 mL) was added and the mixture was stirred at room temperature for an additional 30 min. By which time the two layers were separated and the organic layer was diluted with Et$_2$O (20 mL) and washed with brine (20 mL). The organic phase was dried using Na$_2$SO$_4$ (anh.) and concentrated to give 4 methyl-tetrahydro-thiophen-3-yl methylamine (119.0 mg, 90%) as slightly yellowish oil. This material was used directly in the next step without further purification. $^1$H NMR (CDCl$_3$) δ 2.20 (s, 3H), 3.78 (s, 2H), 6.91-6.92 (d, 1H, J=3.0 Hz), 7.07-7.08 (d, 1H, J=3.0 Hz).

The amine (12.0 g, 94.36 mmol) was dissolved in AcOH (200 mL). Phthalic anhydride (14.0 g, 94.4 mmol) was added in one portion. The mixture was heated at 130° C. for 15 h. After cooling to room temperature, the mixture was partitioned between water and CH$_2$Cl$_2$ (300 mL/300 mL). The CH$_2$Cl$_2$ layer was washed with NaOH (aq. 3.0 N, 3×200 mL) and dried over Na$_2$SO$_4$. Concentration in vacuo afford 2-(4-Methyl-tetrahydro-thiophen-3-ylmethyl)-isoindole-1,3-dione (19.45 g, 80%) as a white solid. $^1$H NMR (CDCl$_3$) δ 2.35 (s, 3H), 4.78 (s, 2H), 6.48 (m, 1H), 7.28 (m, 1H), 7.70-7.74 (m, 2H), 7.82-7.87 (m, 2H).

2-(4-Methyl-tetrahydro-thiophen-3-ylmethyl)-isoindole-1,3-dione (410.0 mg, 1.59 mmol) and NBS (312.0 mg, 1.75 mmol) were dissolved in CCl$_4$ (8.0 mL). AIBN (100 mg) was added in one portion. The mixture was heated at 85° C. under N$_2$ for 90 min. After cooling down, the mixture was passed through a short silica gel column (4×10 cm), eluted with CH$_2$Cl$_2$. The solution obtained was concentrated and the residue was recrystallized from EtOAc/Hexanes (5/1) to give 2-(4-Bromomethyl-thiophen-3-ylmethyl)-isoindole-1,3-dione (285 mg, 50%) as a white solid. $^1$H NMR (CDCl$_3$) δ 4.74 (s, 2H), 4.91 (s, 2H), 7.29-7.30 (d, 1H, J=3.3 Hz), 7.70-7.71 (d, 1H, J=3.3 Hz), 7.70-7.73 (m, 2H), 7.82-7.87 (m, 2H).

Using General Procedure A: Reaction of bis-(3-methyl-pyridin-2-ylmethyl)-amine, 2-(4-Bromomethyl-thiophen-3-ylmethyl)-isoindole-1,3-dione, and DIPEA in CH$_3$CN gave 2-(4-{[bis-(3-methyl-pyridin-2-ylmethyl)-amino]-methyl}-thiophen-3-ylmethyl)-isoindole-1,3-dione as a white foam. Deprotection with H$_2$NNH$_2$.H$_2$O using General Procedure E gave the free base as a pale yellow solid. Conversion to the HBr salt gave COMPOUND 396 as a beige solid. $^1$H NMR (D$_2$O) δ 2.43 (s, 6H), 3.88 (s, 2H), 3.99 (s, 2H), 4.31 (s, 4H), 7.29 (d, 1H, J=3 Hz), 7.48 (d, 1H, J=3 Hz), 7.79 (dd, 2H, J=6.0, 7.8 Hz), 8.31 (d, 2H, J=7.8 Hz), 8.55 (d, 2H, J=6.0 Hz); $^{13}$C NMR (D$_2$O) δ 17.39, 36.42, 53.37, 54.95, 126.10, 127.73, 128.48, 132.21, 134.97, 137.81, 139.23, 148.51, 150.64; ES-MS m/z 353 (M+H). Anal. Calcd. for C$_{20}$H$_{24}$N$_4$S.3.2HBr.1.5H$_2$O: C, 37.63; H, 4.77; N, 8.78; S, 5.02; Br, 40.05. Found: C, 37.52; H, 4.62; N, 8.68; S, 4.95; Br, 40.21.

Example 397

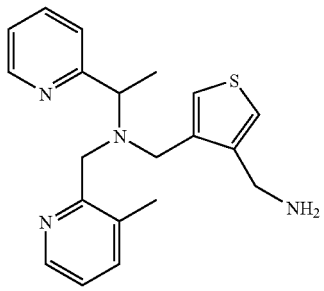

COMPOUND 397: The preparation of (4-aminomethyl-thiophen-3-ylmethyl)-(3-methyl-pyridin-2-ylmethyl)-(1-pyridin-2-yl-ethyl)-amine (HBr salt)

Using General Procedure A: Reaction of 2-(4-bromomethyl-thiophen-3-ylmethyl)-isoindole-1,3-dione, (3-methyl-pyridin-2-ylmethyl)-(1-pyridin-2-yl-ethyl)-amine, DIPEA and KI in CH$_3$CN gave a pale yellow oil. Deprotection with NH$_2$NH$_2$ using General Procedure E gave a colorless oil. Conversion to the HBr salt using General Procedure D gave COMPOUND 397 as a white solid. $^1$H NMR (CD$_3$OD) δ 1.70 (d, 3H, J=6.3 Hz), 2.30 (s, 3H), 4.07-4.20 (m, 6H), 4.39 (s, br, 1H), 7.30-7.57 (m, 5H), 7.72-7.76 (m, 1H), 7.89-7.94 (m, 1H), 8.51 (s, br, 1H), 8.71 (s, br, 1H); $^{13}$C NMR (D$_2$O) δ 12.84, 17.34, 36.63, 49.57, 51.45, 61.62, 123.90, 124.09, 124.15, 128.17, 132.77, 134.20, 136.03, 139.23, 142.73, 148.42, 153.98, 159.40. ES-MS m/z 353 (M+H). Anal. Calcd. for C$_{20}$H$_{24}$N$_4$S.1.55HBr.1.1H$_2$O.0.2C$_4$H$_{10}$O: C, 48.74; H, 5.85; N, 10.93; Br, 24.16; S, 6.25. Found: C, 48.80; H, 5.66; N, 10.69; Br, 24.01; S, 6.35.

Example 398

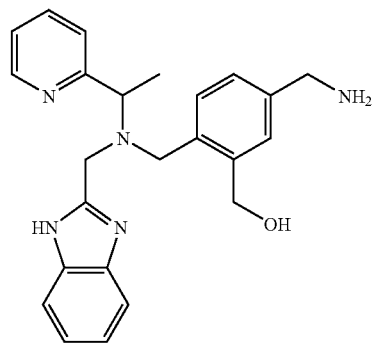

COMPOUND 398: (5-aminomethyl-2-{[(1H-benzoimidazol-2-ylmethyl)-(1-pyridin-2-yl-ethyl)-amino]-methyl}-phenyl)-methanol To a suspension of crushed and dried 3 A molecular sieves (1.0393 g) in DMF (15 mL) was added cesium hydroxide monohydrate (0.6272 g, 3.7 mmol) and DMAP (0.0366 g, 0.3 mmol), and the mixture was stirred at room temperature for 15 minutes. To this was added 1-pyridin-2-yl-ethylamine (0.4168 g, 3.4 mmol) in DMF (10 mL), and was stirred for 30 minutes. Then 2-chloromethyl-benzoimidazole-1-carboxylic acid tert-butyl ester (1.1050 g, 4.1 mmol) was added and the reaction was stirred at room temperature for 19 hours. The reaction mixture was filtered with CH$_2$Cl$_2$, concentrated, and diluted with 1N NaOH (75 mL) and CH$_2$Cl$_2$ (100 mL). The layers were separated and the aqueous phase was extracted with CH$_2$Cl$_2$ (4×150 mL). The combined organic layers were washed with brine (1×100 mL), dried (Na$_2$SO$_4$), and concentrated. Purification of the crude material by column chromatography on silica gel (33:1:1 CH$_2$Cl$_2$-MeOH—NH$_4$OH) provided 0.7260 g (61%) of 2-[(1-pyridin-2-yl-ethylamino)-methyl]-2,3-dihydro-benzoimidazole-1-carboxylic acid tert-butyl ester as an orange oil. $^1$H NMR (CDCl$_3$) δ 1.47 (d, 3H, J=6.0 Hz), 1.66 (s, 9H), 2.92 (d, 2H, J=31.0 Hz), 4.00-4.07 (m, 1H), 4.13-4.29 (m, 1H), 7.03-7.04 (m, 1H), 7.27-7.33 (m, 3H), 7.48-7.55 (m, 1H), 7.65-7.70 (m, 1H), 7.82-7.86 (m, 1H), 8.48 (d, 1H, J=4.8 Hz).

Using General Procedure A: Reaction of 2-bromomethyl-5-cyano-benzoic acid methyl ester and 2-[(1-pyridin-2-yl-ethylamino)-methyl]-2,3-dihydro-benzoimidazole-1-carboxylic acid tert-butyl ester in CH$_3$CN with DIPEA, KI, and DMAP gave 2-{[(4-cyano-2-methoxycarbonyl-benzyl)-(1-pyridin-2-yl-ethyl)-amino]-methyl}-benzoimidazole-1-carboxylic acid tert-butyl ester as a light yellow solid. $^1$H NMR (CDCl$_3$) δ 1.56-1.59 (m, 3H), 1.71 (s, 9H), 3.86 (s, 3H), 4.23 (s, 1H), 4.28-4.30 (m, 2H), 4.40-4.47 (m, 2H), 7.10-7.16 (m, 1H), 7.24-7.32 (m, 3H), 7.42-7.46 (m, 1H), 7.51-7.66 (m, 2H), 7.71-7.76 (m, 1H), 7.82 (d, 1H, J=1.7 Hz), 7.92 (d, 1H, J=8.0 Hz), 8.53 (d, 1H, J=4.8 Hz).

To a solution of 2-{[(4-cyano-2-methoxycarbonyl-benzyl)-(1-pyridin-2-yl-ethyl)-amino]-methyl}-benzoimidazole-1-carboxylic acid tert-butyl ester (0.5065 g, 1.0 mmol) in dry THF (5 mL) under Ar at 0° C. was slowly added 1.0 M LiAlH$_4$ in THF (9.6 mL, 9.6 mmol). The reaction was stirred at room temperature for 3 hours, then cooled to 0° C. Saturated aqueous KNa Tartrate (Rochelle's salt, 30 mL) was slowly added, and the phases were separated. The aqueous phase was extracted with $CH_2Cl_2$ (3×35 mL), and the combined organic extracts were dried ($Na_2SO_4$) and concentrated. Purification of the crude material by column chromatography on silica gel (25:1:1 $CH_2Cl_2$-MeOH—$NH_4OH$) provided 28.0 mg (7%) of COMPOUND 398 as a white solid. $^1H$ NMR ($CDCl_3$) δ 1.55 (d, 7H), 3.72 (s, 2H), 3.79-3.97 (m, 4H), 4.08-4.15 (m, 1H), 4.61 (s, 2H), 7.00-7.03 (m, 1H), 7.12-7.22 (m, 4H), 7.30-7.34 (m, 2H), 7.39-7.548 (m, 2H), 7.66-7.73 (m, 1H), 8.63 (d, 1H, J=4.3 Hz). $^{13}C$ NMR ($CDCl_3$) δ 12.64, 46.30, 48.93, 56.11, 60.76, 63.68, 122.24, 122.64, 123.03, 126.86, 130.49, 132.06, 135.86, 137.63, 140.79, 140.79, 143.92, 149.44, 153.77, 161.45. ES-MS m/z 402 (M+H). Anal. Calcd. for $C_{24}H_{27}N_5O.0.6H_2O.0.2CH_2Cl_2$: C, 67.71; H, 6.71; N, 16.31. Found: C, 68.05; H, 6.75; N, 16.38.

Example 399

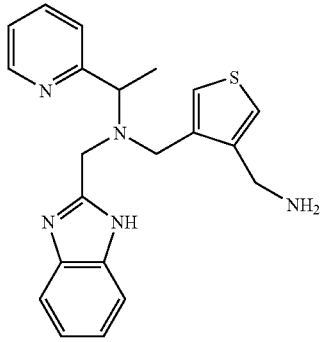

COMPOUND 399: The preparation of (4-aminomethyl-thiophen-3-ylmethyl)-(1H-benzimidazol-2-ylmethyl)-(1-pyridin-2-yl-ethyl)-amine (HBr salt)

Using General Procedure B: Reaction of 1-(2-trimethylsilanyl-ethoxymethyl)-1H-benzimidazole-2-carbaldehyde in $CH_2Cl_2$ with 1-pyridin-2-yl-ethylamine and $NaBH(OAc)_3$ gave (1-pyridin-2-yl-ethyl)-[1-(2-trimethylsilanyl-ethoxymethyl)-1H-benzimidazol-2-ylmethyl]-amine as a pale green oil.

Using General Procedure A: Reaction of 2-(4-bromomethyl-thiophen-3-ylmethyl)-isoindole-1,3-dione, (1-pyridin-2-yl-ethyl)-[1-(2-trimethylsilanyl-ethoxymethyl)-1H-benzimidazol-2-ylmethyl]-amine, DIPEA and KI in $CH_3CN$ gave 2-[4-({(1-pyridin-2-yl-ethyl)-[1-(2-trimethylsilanyl-ethoxymethyl)-1H-benzimidazol-2-ylmethyl]-amino}-methyl)-thiophen-3-ylmethyl]-isoindole-1,3-dione.

The above product (0.580 g, ~90%, g, 0.86 mmol) was dissolved in aqueous HCl (4 N, 10 mL), and the solution was stirred at 50° C. for 4 h. After that period of time the mixture was cooled down, and saturated aqueous $NaHCO_3$ (30 mL) was added. The mixture was extracted with $CH_2Cl_2$ (3×20 mL), and the organic extracts were combined and dried over $Na_2SO_4$. After filtration the solvent was removed, and the residue was purified on a silica gel column (80:2:1 $CH_2Cl_2$/MeOH/$NH_4OH$), affording a pale yellow sticky solid. Deprotection with $NH_2NH_2$ following General Procedure E gave (4-aminomethyl-thiophen-3-ylmethyl)-(1H-benzimidazol-2-ylmethyl)-(1-pyridin-2-yl-ethyl)-amine as a colorless oil. Conversion to the HBr salt gave a white solid. $^1H$ NMR ($CD_3OD$) δ 1.69 (d, 3H, J=6.9 Hz), 3.82-3.92 (m, 2H), 3.96-4.09 (m, 2H), 4.24-4.45 (m, 3H), 7.20 (d, 1H, J=2.1 Hz), 7.45-7.54 (m, 4H), 7.58-7.65 (m, 1H), 7.67-7.70 (m, 2H), 7.90-8.00 (m, 1H), 8.73 (d, 1H, J=2.1 Hz); $^{13}C$ NMR ($D_2O$) δ 13.56, 36.41, 47.94, 50.55, 62.90, 114.16, 124.20, 124.29, 125.66, 127.83, 128.04, 132.44, 132.48, 136.51, 140.08, 147.68, 152.88, 159.52. ES-MS m/z 378 (M+H). Anal. Calcd. for $C_{21}H_{23}N_5S.2.2HBr.0.3C_4H_{10}O.0.2CH_2Cl_2$: C, 45.24; H, 4.85; N, 11.78; Br, 29.56; S, 5.39. Found: C, 45.61; H, 5.09; N, 12.08; Br, 29.55; S, 5.34.

Example 400

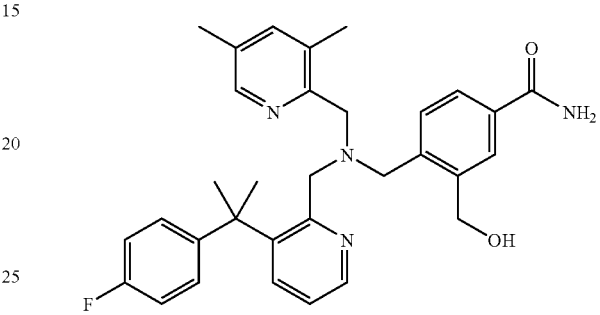

COMPOUND 400: 4-[((3,5-dimethyl-pyridin-2-ylmethyl)-{3-[1-(4-fluoro-phenyl)-1-methyl-ethyl]-pyridin-2-ylmethyl}-amino)-methyl]-3-hydroxymethyl-benzamide To a solution of N-(3,5-dimethyl-pyridin-2-ylmethyl)-2-nitro-benzenesulfonamide (0.60 g, 1.87 mmol) dissolved in $CH_3CN$ (10 mL) was added 2-bromomethyl-5-cyano-benzoic acid methyl ester (0.50 g, 1.96 mmol) and $K_2CO_3$ (0.72 g, 5.61 mmol). The mixture was stirred at 80° C. for 3 hours, then concentrated in vacuo and redissolved in $CH_2Cl_2$ (50 mL). Saturated aqueous $NaHCO_3$ (50 mL) was added and the mixture was extracted with $CH_2Cl_2$ (3×50 mL). The combined organic extracts were dried ($Na_2SO_4$), filtered, and concentrated in vacuo to give a brown oil. Purification via column chromatography on silica gel ($CH_2Cl_2$:MeOH, 99:1, v/v) afforded 5-cyano-2-{[(3,5-dimethyl-pyridin-2-ylmethyl)-(2-nitro-benzenesulfonyl)-amino]-methyl}-benzoic acid methyl ester as a yellow solid (0.90 g, 97%). $^1H$ NMR ($CDCl_3$) δ 2.15 (s, 3H), 2.22 (s, 3H), 3.88 (s, 2H), 5.15 (s, 2H), 7.05 (s, 1H), 7.61-7.72 (m, 5H), 7.83 (s, 1H), 7.95 (d, 1H, J=7.5 Hz), 8.06 (s, 1H).

To a solution of 5-cyano-2-{[(3,5-dimethyl-pyridin-2-ylmethyl)-(2-nitro-benzenesulfonyl)-amino]-methyl}-benzoic acid methyl ester (0.83 g, 1.68 mmol) dissolved in THF (30 mL) and MeOH (10 mL), $LiBH_4$ (0.37 g, 16.8 mmol) was slowly added. The mixture was stirred at room temperature for 3 hours. The mixture was concentrated in vacuo and redissolved in $CH_2Cl_2$ (50 mL). Water (50 mL) was added and the resulting mixture was extracted with $CH_2Cl_2$ (4×50 mL). The combined organic extracts were dried ($Na_2SO_4$), filtered, and concentrated in vacuo to give crude N-(4-cyano-2-hydroxymethyl-benzyl)-N-(3,5-dimethyl-pyridin-2-ylmethyl)-2-nitro-benzene-sulfonamide (0.82 g, 78%) as a yellow foam. $^1H$ NMR ($CDCl_3$) δ 2.16 (s, 3H), 2.25 (s, 3H), 4.58 (s, 2H), 4.67 (s, 2H), 4.76 (br s, 1H), 4.88 (s, 2H), 7.10 (s, 1H), 7.36 (m, 2H), 7.50 (m, 1H), 7.65-7.72 (m, 3H), 7.80 (s, 1H), 7.89 (d, 1H, J=7.5 Hz).

To a solution of N-(4-cyano-2-hydroxymethyl-benzyl)-N-(3,5-dimethyl-pyridin-2-ylmethyl)-2-nitro-benzene-sulfonamide (0.82 g, 1.76 mmol) dissolved in DMF (35 mL) was added $K_2CO_3$ (1.21 g, 8.75 mmol) and thiophenol (0.54 mL, 5.28 mmol). The mixture was stirred at room temperature for 3 hours then concentrated in vacuo and redissolved in $CH_2Cl_2$ (50 mL). The mixture was filtered through a celite plug and the filtrate was concentrated in vacuo to afford a yellow solid. Purification by column chromatography on silica gel (hexane:EtOAc, 4:1, v/v<EtOAc) afforded 4-{[(3,5-dimethyl-pyridin-2-ylmethyl)-amino]-methyl}-3-hydroxymethyl-benzonitrile (0.176 g, 35%) as a yellow solid. $^1$H NMR (CDCl$_3$) δ 2.20 (s, 3H), 2.28 (s, 3H), 3.82 (s, 2H), 3.99 (s, 2H), 4.65 (s, 2H), 7.26 (s, 1H), 7.36 (d, 1H, J=6.0 Hz), 7.55 (d, 1H, J=6.0 Hz), 7.64 (s, 1H), 8.20 (s, 1H).

Using General Procedure B: Reaction of 4-{[(3,5-dimethyl-pyridin-2-ylmethyl)-amino]-methyl}-3-hydroxymethyl-benzonitrile in $CH_2Cl_2$ with 3-[1-(4-fluoro-phenyl)-1-methyl-ethyl]-pyridine-2-carbaldehyde and NaBH(OAc)$_3$ gave 4-[((3,5-dimethyl-pyridin-2-ylmethyl)-{3-[1-(4-fluoro-phenyl)-1-methyl-ethyl]-pyridin-2-ylmethyl}-amino)-methyl]-3-hydroxymethyl-benzamide as a white foam. $^1$H NMR (CDCl$_3$) δ 1.62 (s, 6H), 2.24 (s, 3H), 2.26 (s, 3H), 3.05 (s, 2H), 3.21 (s, 2H), 3.47 (s, 1H), 3.59 (s, 2H), 4.18 (s, 2H), 5.75 (br s, 1H), 6.29 (br s, 1H), 6.89 (t, 1H, J=9.0 Hz), 7.02 (m, 3H), 7.21 (dd, 1H, J=7.5, 3.0 Hz), 7.26 (s, 1H), 7.61 (d, 1H, J=7.5 Hz), 7.66 (s, 1H), 7.87 (d, 1H, J=7.5 Hz), 8.15 (s, 1H), 8.45 (d, 1H, J=3.0 Hz). $^{13}$C NMR (CDCl$_3$) δ 18.3, 18.5, 31.3, 42.3, 51.1, 57.78, 58.4, 58.9, 63.1, 115.6, 115.8, 122.2, 127.1, 127.6, 127.7, 130.3, 131.8, 132.5, 133.5, 133.6, 134.3, 139.5, 141.7, 142.4, 143.5, 145.5, 146.8, 146.9, 152.7, 156.7, 159.9, 163.1, 169.5. HPLC: 98%. ES-MS m/z 527 [M+H]$^+$, 549 [M+Na]$^+$. Anal. Calcd. for $C_{32}H_{35}N_4O_2F$.0.4 $CH_2Cl_2$: C, 69.41; H, 6.44; N, 9.99. Found: C, 69.15; H, 6.35; N, 9.97.

Example 401

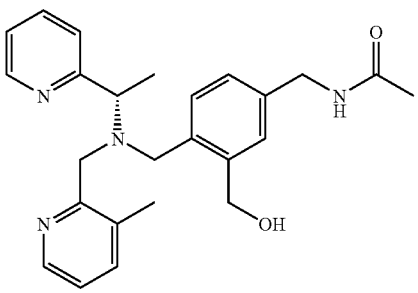

COMPOUND 401: N-(3-Hydroxymethyl-4-{[(3-methyl-pyridin-2-ylmethyl)-(1-pyridin-2-yl-ethyl)-amino]-methyl}-benzyl)-acetamide To a solution of (S)-(5-aminomethyl-2-{[(3-methyl-pyridin-2-ylmethyl)-(1-pyridin-2-yl-ethyl)-amino]-methyl}-phenyl)-methanol (0.0914 g, 0.24 mmol) in $CH_2Cl_2$ (3 mL) was added Ac$_2$O (0.0228 mL, 0.24 mmol), Et$_3$N (0.05 mL, 0.36 mmol), and KI (0.0033 g, 0.02 mmol), and stirred at room temperature for 18 hours. Saturated NaHCO$_3$ (10 mL) was added and extracted with $CH_2Cl_2$ (3×30 mL), and the combined organic extracts were dried (Na$_2$SO$_4$), filtered, and concentrated. Purification of the crude material by column chromatography on silica gel (50:1:1 $CH_2Cl_2$-MeOH—NH$_4$OH) provided 0.0750 g (64%) of COMPOUND 401 as a white solid. $^1$H NMR (CDCl$_3$) δ 1.55 (d, 3H, J=6.6 Hz), 1.71 (s, 2H), 1.99 (s, 3H), 2.05 (s, 3H), 3.63-3.77 (m, 2H), 3.81-3.96 (m, 2H), 4.02-4.09 (m, 1H), 4.20-4.29 (m, 2H), 4.37 (d, 2H, J=5.4 Hz), 5.76 (s, 1H), 6.87 (s, 1H), 7.04-7.23 (m, 3H), 7.33-7.39 (m, 2H), 7.66 (t, 1H, J=7.5 Hz), 8.38 (d, 2H, J=3.9 Hz), 8.57 (d, 2H, J=4.2 Hz). $^{13}$C NMR (CDCl$_3$) δ 11.93, 18.45, 23.58, 43.70, 52.43, 53.86, 58.92, 63.32, 122.57, 122.67, 124.03, 127.44, 130.86, 132.10, 132.86, 136.70, 137.05, 138.55, 142.57, 146.56, 148.93, 156.59, 161.08, 170.41. ES-MS m/z 441.4 (M+Na). Anal. Calcd. for $C_{25}H_{30}N_4O_2$.0.8$CH_2Cl_2$.0.8$H_2O$: C, 63.70; H, 6.55; N, 11.52. Found: C, 63.76; H, 6.56; N, 11.60.

Example 402

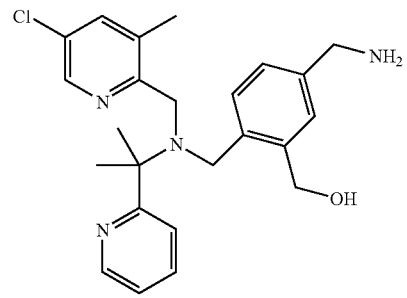

COMPOUND 402: (5-aminomethyl-2-{[(5-chloro-3-methyl-pyridin-2-ylmethyl)-(1-methyl-1-pyridin-2-yl-ethyl)-amino]-methyl}-phenyl)-methanol To a solution of 4-{[(5-chloro-3-methyl-pyridin-2-ylmethyl)-(1-methyl-1-pyridin-2-yl-ethyl)-amino]-methyl}-3-hydroxymethyl-benzonitrile (0.5371 g, 1.2 mmol) in THF (12 mL) at 0° C. was added LiBH$_4$ (0.2086 g, 9.6 mmol), then heated to 70° C. and stirred for 18 hours. 1N NaOH (25 mL) and $CH_2Cl_2$ (50 mL) were added and stirred for 10 minutes. The phases were separated and the aqueous phase was extracted with $CH_2Cl_2$ (3×50 mL). The combined organic extracts were dried (Na$_2$SO$_4$), filtered, and concentrated. Purification of the crude material by column chromatography on silica gel (75:1:1 $CH_2Cl_2$-MeOH—NH$_4$OH) provided 0.2330 g (48%) of COMPOUND 402 as a white solid. $^1$H NMR (CDCl$_3$) δ 1.61 (s, 5H), 2.07 (s, 6H), 3.69 (s, 2H), 3.73 (s, 2H), 3.91 (s, 2H), 4.55 (s, 2H), 6.69-6.78 (bs, 1H), 6.94-6.97 (m, 1H), 7.02-7.08 (m, 3H), 7.21 (d, 1H, J=1.5 Hz), 7.49-7.55 (m, 1H), 7.77 (d, 1H, J=8.1 Hz), 8.05 (d, 1H, J=2.1 Hz), 8.45-8.48 (m, 1H). $^{13}$C NMR (CDCl$_3$) δ 18.71, 24.43, 46.39, 51.43, 53.95, 63.49, 64.78, 122.10, 123.09, 126.25, 129.32, 130.26, 131.30, 132.25, 136.21, 137.16, 137.26, 141.33, 143.29, 144.59, 147.94, 156.80, 165.90. ES-MS m/z 425.4 (M+H). Anal. Calcd. for $C_{24}H_{29}N_4ClO$.0.3$H_2O$: C, 66.98; H, 6.93; N, 13.02; Cl, 8.24. Found: C, 67.11; H, 6.54; N, 12.13; Cl, 8.99.

Example 403

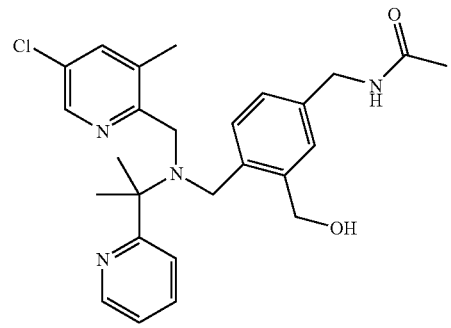

333

COMPOUND 403: N-(4-{[(5-chloro-3-methyl-pyridin-2-ylmethyl)-(1-methyl-1-pyridin-2-yl-ethyl)-amino]-methyl}-3-hydroxymethyl-benzyl)-acetamide To a solution of (5-aminomethyl-2-{[(5-chloro-3-methyl-pyridin-2-ylmethyl)-(1-methyl-1-pyridin-2-yl-ethyl)-amino]-methyl}-phenyl)-methane (0.0966 g, 0.23 mmol) in CH$_2$Cl$_2$ (3 mL) was added Ac$_2$O (0.0213 mL, 0.23 mmol), Et$_3$N (0.05 mL, 0.35 mmol), and KI (0.0038 g, 0.02 mmol), and stirred for 18 hours at room temperature. Saturated NaHCO$_3$ (10 mL) was added and extracted with CH$_2$Cl$_2$ (3×20 mL). The combined organic extracts were dried (Na$_2$SO$_4$), filtered, and concentrated. Purification of the crude material by column chromatography on silica gel (100:1:1 CH$_2$Cl$_2$-MeOH—NH$_4$OH) provided 0.0573 g (52%) of COMPOUND 403 as a white solid. $^1$H NMR (CDCl$_3$) δ 1.61 (s, 6H), 2.00 (s, 3H), 2.08 (s, 3H), 3.69 (s, 2H), 3.90 (s, 2H), 4.30 (d, 2H, J=5.4 Hz), 4.53 (s, 2H), 5.65 (s, 1H), 6.69 (s, 1H), 6.94 (d, 1H, J=7.5 Hz), 7.03-7.09 (m, 3H), 7.17 (s, 1H), 7.54 (t, 1H, J=7.8 Hz), 7.75 (d, 1H, J=8.1 Hz), 8.04 (s, 1H), 8.47 (d, 1H, J=6.0 Hz). $^{13}$C NMR (CDCl$_3$) δ 18.72, 23.66, 24.47, 43.62, 51.37, 53.92, 63.30, 64.75, 122.16, 122.99, 127.27, 129.31, 130.85, 131.46, 132.38, 136.22, 137.30, 138.04, 138.13, 141.45, 144.53, 147.99, 156.81, 165.70, 170.29. ES-MS m/z 467.2 (M+H). Anal. Calcd. for C$_{26}$H$_{31}$N$_4$ClO$_2$.0.1CH$_2$Cl$_2$.0.4H$_2$O: C, 64.94; H, 6.68; N, 11.61; Cl, 8.81. Found: C, 64.69; H, 6.58; N, 11.37; Cl, 9.18.

Example 404

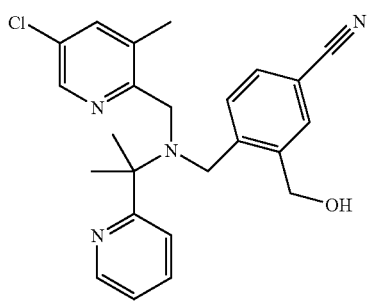

COMPOUND 404: 4-{[(5-chloro-3-methyl-pyridin-2-ylmethyl)-(1-methyl-1-pyridin-2-yl-ethyl)-amino]-methyl}-3-hydroxymethyl-benzonitrile Using General Procedure B: Reaction of 1-methyl-1-pyridin-2-yl-ethylamine and 5-chloro-3-methyl-pyridine-2-carbaldehyde in CH$_2$Cl$_2$ with NaBH(OAc)$_3$ gave (5-chloro-3-methyl-pyridin-2-ylmethyl)-(1-methyl-1-pyridin-2-yl-ethyl)-amine as a beige oil. $^1$H NMR (CDCl$_3$) δ 1.61 (s, 6H), 2.19 (s, 3H), 3.62 (s, 2H), 4.66 (s, 1H), 7.11-7.15 (m, 1H), 7.38 (s, 1H), 7.48 (d, 1H, J=6.0 Hz), 7.62-7.67 (m, 1H), 8.37 (s, 1H), 8.58 (d, 1H, J=6.0 Hz).

Using General Procedure A: Reaction of (5-chloro-3-methyl-pyridin-2-ylmethyl)-(1-methyl-1-pyridin-2-yl-ethyl)-amine in CH$_3$CN with 2-bromomethyl-5-cyano-benzoic acid methyl ester, KI, and DIPEA gave 2-{[(5-chloro-3-methyl-pyridin-2-ylmethyl)-(1-methyl-1-pyridin-2-yl-ethyl)-amino]-methyl}-5-cyano-benzoic acid methyl ester as a pale yellow solid. $^1$H NMR (CDCl$_3$) δ 1.60 (s, 6H), 2.17 (s, 3H), 3.80 (s, 2H), 3.91 (s, 3H), 4.24 (s, 2H), 7.10-7.12 (m, 2H), 7.47 (d, 1H, J=6.0 Hz), 7.63-7.65 (m, 1H), 7.77 (d, 2H, J=9.0 Hz), 7.88 (s, 1H), 8.03-8.09 (m, 2H), 8.56-8.57 (m, 1H).

To a solution of 2-{[(5-chloro-3-methyl-pyridin-2-ylmethyl)-(1-methyl-1-pyridin-2-yl-ethyl)-amino]-methyl}-5-cyano-benzoic acid methyl ester (0.4561 g, 1.0 mmol) in MeOH (5 mL) and THF (5 mL) at 0° C. was added LiBH$_4$. The reaction was stirred at room temperature for 3 hours, then 1N NaOH (25 mL) was added and stirred for 10 minutes. CH$_2$Cl$_2$ (35 mL) was added, the phases were separated, and the aqueous layer was extracted with CH$_2$Cl$_2$ (4×15 mL). The combined organic extracts were dried (Na$_2$SO4) and concentrated. Purification of the crude material by column chromatography on silica gel (100:1:1 CH$_2$Cl$_2$-MeOH—NH$_4$OH) provided 0.3847 g (91%) of COMPOUND 404 as a white solid. $^1$H NMR (CDCl$_3$) δ 1.61 (s, 6H), 2.09 (s, 3H), 3.71 (s, 2H), 3.98 (s, 2H), 4.50-4.51 (m, 2H), 6.39 (s, 1H), 7.09 (1H, J=6.0 Hz), 7.15 (s, 1H), 7.23-7.31 (m, 2H), 7.54-7.58 (m, 2H), 7.65-7.68 (m, 1H), 8.04 (s, 1H), 8.50 (d, 1H, J=3.0 Hz). $^{13}$C NMR (CDCl$_3$) δ 18.64, 24.64, 52.42, 53.30, 62.46, 64.46, 111.26, 119.08, 122.35, 122.53, 130.18, 130.98, 131.00, 133.10, 134.03, 136.42, 137.59, 141.71, 144.61, 144.95, 148.30, 155.91, 165.29. ES-MS m/z 422.2 (M+H). Anal. Calcd. for C$_{24}$H$_{25}$N$_4$ClO.0.1H$_2$O: C, 68.19; H, 6.01; N, 13.25; Cl, 8.39. Found: C, 68.01; H, 6.04; N, 13.20; Cl, 8.84.

Example 405

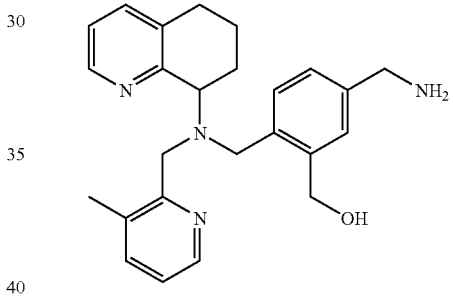

COMPOUND 405: (5-aminomethyl-2-{[(3-methyl-pyridin-2-ylmethyl)-(5,6,7,8-tetrahydro-quinolin-8-yl)-amino]-methyl}-phenyl)-methanol Using General Procedure B: Reaction of 5,6,7,8-tetrahydro-quinolin-8-ylamine in MeOH with 3-methyl-pyridine-2-carboxaldehyde and NaBH$_4$ gave a yellow oil.

Using General Procedure A: Reaction of the yellow oil, 2-bromomethyl-5-cyano-benzoic acid methyl ester and DIPEA in CH$_3$CN gave 5-cyano-2-{[(3-methyl-pyridin-2-ylmethyl)-(5,6,7,8-tetrahydro-quinolin-8-yl)-amino]-methyl}-benzoic acid methyl ester as a tan solid.

To a cold (0° C.) mixture of LiAlH$_4$ (187 mg, 4.93 mmol) in dry THF (5 mL) was added 5-cyano-2-{[(3-methyl-pyridin-2-ylmethyl)-(5,6,7,8-tetrahydro-quinolin-8-yl)-amino]-methyl}-benzoic acid methyl ester (245 mg, 0.57 mmol) as a solution in THF (6 mL). The resultant mixture was stirred at room temperature for 5 hours then cooled in an ice water bath. The mixture was treated with saturated aqueous sodium-potassium tartrate (11 mL) and diluted with THF (11 mL). The phases were separated and the aqueous phase was extracted with THF (2×11 mL). The combined organic extracts were dried (Na$_2$SO$_4$) and concentrated. Purification of the crude material by column chromatography on silica gel (20:1:1 CH$_2$Cl$_2$-MeOH—NH$_4$OH) followed by radial chromatography on silica gel (1 mm plate, 75:1:1 CH$_2$Cl$_2$-MeOH—NH$_4$OH) gave COMPOUND 405 (85 mg, 34%) as a white solid. $^1$H NMR (CDCl$_3$) δ 1.46-1.64 (m, 4H), 1.91-1.98 (m, 1H), 2.06-2.19 (m, 5H), 2.51-2.59 (m, 1H), 2.68-2.77 (m, 1H), 3.62 (d, 2H, J=12.3 Hz), 3.72-3.76 (m, 3H), 3.84 (dd, 1H, J=7.5, 7.8 Hz), 4.06-4.15 (m, 2H), 4.30 (d, 1H, J=11.4 Hz), 6.92-7.07 (m, 3H), 7.15-7.29 (m, 3H), 7.35 (d, 1H, J=7.5 Hz), 8.27-8.31 (m, 2H); $^{13}$C NMR (CDCl$_3$) δ 17.32, 19.78, 20.72, 28.66, 45.11, 53.06, 53.62, 56.48, 61.63, 120.59, 121.46, 124.93, 129.32, 130.07, 133.01, 133.58, 134.44, 135.60, 137.18, 141.23, 142.21, 144.76, 145.58, 155.32, 155.89; ES-MS m/z 403 (M+H). Anal. Calcd. for C$_{25}$H$_{30}$N$_4$O.1.0CH$_3$OH: C, 71.86; H, 7.89; N, 12.89. Found: C, 71.78; H, 7.59; N, 12.59.

Example 406

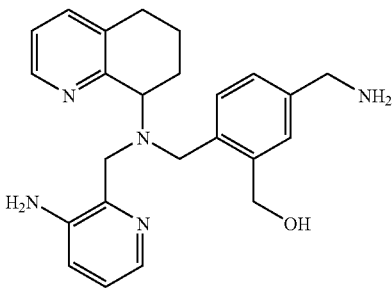

COMPOUND 406: (5-aminomethyl-2-{[(3-amino-pyridin-2-ylmethyl)-(5,6,7,8-tetrahydro-quinolin-8-yl)-amino]-methyl}-phenyl)-methanol Using General Procedure B: Reaction of 5,6,7,8-tetrahydro-quinolin-8-ylamine in CH$_2$Cl$_2$ with (2-formyl-pyridin-3-yl)-carbamic acid tert-butyl ester and NaBH(OAc)$_3$ gave {2-[(5,6,7,8-tetrahydro-quinolin-8-ylamino)-methyl]-pyridin-3-yl}-carbamic acid tert-butyl ester as a yellow oil. $^1$H NMR (CDCl$_3$) δ 1.51 (s, 9H), 1.85-1.94 (m, 2H), 1.98-2.08 (m, 2H), 2.78-2.84 (m, 2H), 3.82-3.86 (m, 1H), 4.19 (s, 2H), 7.11-7.19 (m, 2H), 7.42 (d, 1H, J=7.1 Hz), 8.15-8.17 (m, 1H), 8.28 (d, 1H, J=8.0 Hz), 8.44 (d, 1H, J=3.0 Hz), 10.17 (s, 1H).

Using General Procedure A: Reaction of {2-[(5,6,7,8-tetrahydro-quinolin-8-ylamino)-methyl]-pyridin-3-yl}-carbamic acid tert-butyl ester in CH$_3$CN with 2-bromomethyl-5-cyano-benzoic acid methyl ester, DIPEA, KI, and DMAP gave 2-{[(3-tert-butoxycarbonylamino-pyridin-2-ylmethyl)-(5,6,7,8-tetrahydro-quinolin-8-yl)-amino]-methyl}-5-cyano-benzoic acid methyl ester as a beige solid. $^1$H NMR (CDCl$_3$) δ 1.65 (s, 9H), 1.68-1.71 (m, 1H), 1.85-1.93 (m, 1H), 2.08-2.12 (m, 1H), 2.27-2.28 (m, 1H), 2.81-2.86 (m, 2H), 3.79-3.91 (m, 7H), 4.02-4.07 (m, 1H), 4.50 (d, 1H, J=18.0 Hz), 7.02-7.06 (m, 1H), 7.12-7.18 (m, 1H), 7.43 (d, 1H, J=6.8 Hz), 7.54-7.59 (m, 1H), 8.00-8.09 (m, 3H), 8.41 (d, 1H, J=9.0 Hz), 8.67-8.71 (m, 1H).

2-{[(3-tert-Butoxycarbonylamino-pyridin-2-ylmethyl)-(5,6,7,8-tetrahydro-quinolin-8-yl)-amino]-methyl}-5-cyano-benzoic acid methyl ester (0.4532 g, 0.86 mmol) was dissolved in dry THF (5 mL) and flushed with Ar. At 0° C., 1.0 M LiAlH$_4$ in THF (8.6 mL, 8.6 mmol) was added dropwise to the solution and was stirred at room temperature for 6 hours. The reaction was cooled to 0° C. and saturated aqueous KNa Tartrate (Rochelle's salt, 10 mL) was added slowly, and then CH$_2$Cl$_2$ (100 mL) was added. The phases were separated and the aqueous phase was extracted with CH$_2$Cl$_2$ (8×75 mL). The organic extracts were dried (Na$_2$SO$_4$) and concentrated. Purification of the crude material by column chromatography on silica gel (20:1:1 CH$_2$Cl$_2$-MeOH—NH$_4$OH) provided 0.1620 g (37%) of (2-{[(4-aminomethyl-2-hydroxymethyl-benzyl)-(5,6,7,8-tetrahydro-quinolin-8-yl)-amino]-methyl}-pyridin-3-yl)-carbamic acid tert-butyl ester as a yellow solid. $^1$H NMR (CDCl$_3$) δ 1.54 (s, 9H), 1.62 (s, 6H), 1.97-2.06 (m, 1H), 2.25-2.26 (m, 1H), 2.69-2.82 (m, 2H), 2.95-2.97 (m, 1H), 3.62-3.72 (m, 1H), 3.80 (s, 2H), 3.85-3.99 (m, 3H), 4.22-4.26 (m, 1H), 4.48-4.52 (m, 1H), 7.08-7.23 (m, 4H), 7.39-7.37 (m, 1H), 8.17-8.19 (m, 1H), 8.45-8.51 (m, 1H), 8.65-8.69 (m, 1H), 9.41-9.44 (m, 1H). Deprotection with TFA using General Procedure F gave COMPOUND 406 as a white solid. $^1$H NMR (CDCl$_3$) δ 1.64-1.68 (m, 4H), 2.02-2.13 (m, 2H), 2.17-2.26 (m, 1H), 2.64-2.69 (m, 1H), 2.77-2.88 (m, 1H), 3.61-3.69 (m, 3H), 3.82-3.88 (m, 3H), 4.06 (d, 1H, J=12.9 Hz), 4.18 (d, 1H, J=11.1 Hz), 4.58 (d, 1H, J=11.4 Hz), 4.92 (s, 2H), 6.93-6.96 (m, 1H), 6.99-7.04 (m, 1H), 7.06-7.10 (m, 1H), 7.13-7.16 (m, 1H), 7.22-7.29 (m, 2H), 7.37 (d, 1H, J=7.5 Hz), 7.91 (d, 1H, J=3.9 Hz), 8.35 (d, 1H, J=3.9 Hz). $^{13}$C NMR (CDCl$_3$) δ 19.54, 21.88, 29.55, 46.47, 54.64, 55.47, 58.18, 63.17, 122.36, 122.63, 124.08, 126.62, 130.67, 131.64, 135.21, 135.32, 137.99, 138.29, 142.08, 142.92, 143.78, 143.88, 146.91, 157.29. ES-MS m/z 404 (M+H). Anal. Calcd. for C$_{24}$H$_{29}$N$_5$O.0.8H$_2$O.0.1CH$_2$Cl$_2$: C, 67.88; H, 7.28; N, 16.42. Found: C, 67.85; H, 7.3; N, 16.27.

Example 407

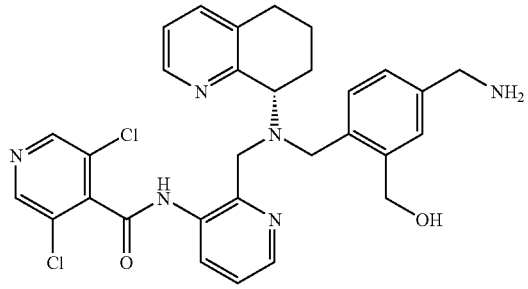

COMPOUND 407: N-(2-{[(S)-(4-aminomethyl-2-hydroxymethyl-benzyl)-5,6,7,8-tetrahydro-quinolin-8-yl-amino]-methyl}-pyridin-3-yl)-3,5-dichloro-isonicotinamide To a stirred suspension of 3,5-dichloro-isonicotinic acid (85 mg, 0.44 mmol) in CH$_2$Cl$_2$ (3 mL) was added DMF (1 drop) and oxalyl chloride (0.12 mL, 1.4 mmol). The suspension was stirred at room temperature for 2 h, then concentrated under reduced pressure. A solution of (5-aminomethyl-2-{[(3-amino-pyridin-2-ylmethyl)-((S)-5,6,7,8-tetrahydro-quinolin-8-yl)-amino]-methyl}-phenyl)-methanol (88 mg, 0.22 mmol) in THF (3 mL) was added to the acid chloride followed by Et$_3$N (0.04 mL, 0.3 mmol). The mixture was stirred for 1 h, then diluted with CH$_2$Cl$_2$ (10 mL) and washed with water (10 mL). The aqueous layer was extracted with CH$_2$Cl$_2$ (3×8 mL), and the combined organic layers were washed with saturated NaHCO$_3$ (20 mL), then dried (Na$_2$SO$_4$) and concentrated under reduced pressure. The residue was purified using flash chromatography on silica gel (97:2:1 CH$_2$Cl$_2$/MeOH/NH$_4$OH) to give COMPOUND 407 (21 mg, 17%), as a white foam.

COMPOUND 407: $^1$H NMR (CDCl$_3$) δ 1.49-1.55 (m, 1H), 1.86-2.15 (m, 3H), 2.58-2.62 (m, 1H), 2.81 (s, 2H), 3.03 (s, 2H), 3.75-3.91 (m, 4H), 4.10 (dd, 2H, J=50.6, 11.4 Hz), 4.60-4.64 (m, 2H), 6.54 (br. s, 1H), 6.91-7.07 (m, 3H), 7.17-7.36 (m, 4H), 8.14 (dd, 1H, J=4.7, 1.5 Hz), 8.29-8.31 (m, 1H), 8.45 (s, 2H); $^{13}$C NMR (CDCl$_3$) δ 22.44, 25.02, 29.86, 44.31, 52.19, 54.83, 58.36, 63.43, 121.45, 123.47, 126.94, 127.28, 129.41, 130.75, 132.39, 134.79, 136.40, 136.65, 138.48, 142.47, 143.35, 146.78, 148.04, 152.81, 154.01, 158.15, 162.39. ES-MS m/z 578 (M+H). Anal. Calcd. for (C$_{30}$H$_{30}$N$_6$Cl$_2$O$_2$).0.24(CH$_2$Cl$_2$).0.75(H$_2$O): C, 59.41; H, 5.27; N, 13.75; Cl, 14.37. Found: C, 59.33; H, 5.31; N, 14.08; Cl, 14.39.

Example 408

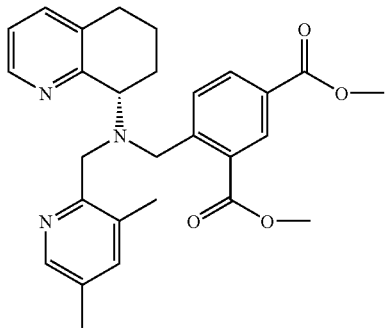

COMPOUND 408: (S)-4-{[(3,5-dimethyl-pyridin-2-ylmethyl)-(5,6,7,8-tetrahydro-quinolin-8-yl)-amino]-methyl}-isophthalic acid dimethyl ester Using General Procedure B: Reaction of (S)-5,6,7,8-tetrahydro-quinolin-8-ylamine in CH$_2$Cl$_2$ with 3,5-dimethyl-pyridine-2-carbaldehyde and NaBH(OAc)$_3$ gave (S)-(3,5-dimethyl-pyridin-2-ylmethyl)-(5,6,7,8-tetrahydro-quinolin-8-yl)-amine. $^1$H NMR (CDCl$_3$) δ 1.75 (m, 1H), 1.91 (m, 2H), 2.26 (s+m, 4H), 2.33 (s, 3H), 2.80 (m, 2H), 3.96 (t, 1H, J=6.0 Hz), 4.02 (d, 1H, J=15.0 Hz), 4.17 (d, 1H, J=15.0 Hz), 5.41 (br s, 1H), 7.06 (dd, 1H, J=7.5, 3.0 Hz), 7.25 (s, 1H), 7.37 (d, 1H, J=9.0 Hz), 8.24 (s, 1H), 8.40 (d, 1H, J=3.0 Hz).

Using General Procedure A: Reaction of (S)-(3,5-Dimethyl-pyridin-2-ylmethyl)-(5,6,7,8-tetrahydro-quinolin-8-yl)-amine, 4-bromomethyl-isophthalic acid dimethyl ester (Egbertson, M. S. et al. Bioorg. Med. Chem. Lett. 1996, 6, 2519-2524), DIPEA and KI in CH$_3$CN gave 4-{[(3,5-dimethyl-pyridin-2-ylmethyl)-(5,6,7,8-tetrahydro-quinolin-8-yl)-amino]-methyl}-isophthalic acid dimethyl ester as a tan oily foam. $^1$H NMR (CDCl$_3$) δ 1.64 (m, 1H), 2.01 (m, 2H), 2.14 (s+m, 4H), 2.27 (s, 3H), 2.68 (m, 1H), 2.79 (m, 1H), 3.89 (s, 6H), 3.92 (s, 2H), 4.09 (t, 1H, J=6.0 Hz), 4.26 (m, 2H), 6.97 (s, 1H), 7.03 (m, 1H), 7.30 (d, 1H, J=9.0 Hz), 7.89 (dd, 2H, J=7.5, 4.5 Hz), 8.02 (s, 1H), 8.25 (s, 1H), 8.50 (d, 1H, J=3.0 Hz). $^{13}$C NMR (CDCl$_3$) δ 18.1, 18.7, 22.2, 26.8, 29.7, 52.5, 54.7, 57.1, 63.3, 121.9, 128.0, 130.7, 131.4, 131.9, 133.3, 134.5, 136.7, 138.8, 146.3, 148.5, 166.8, 168.1. HPLC: 96%. ES-MS m/z 474 [M+H]$^+$, 496 [M+Na]$^+$. Anal. Calcd. for C$_{28}$H$_{31}$N$_3$O$_4$.1.1H$_2$O: C, 68.30; H, 6.59; N, 8.53. Found: C, 68.23; H, 6.41; N, 8.60.

Example 409

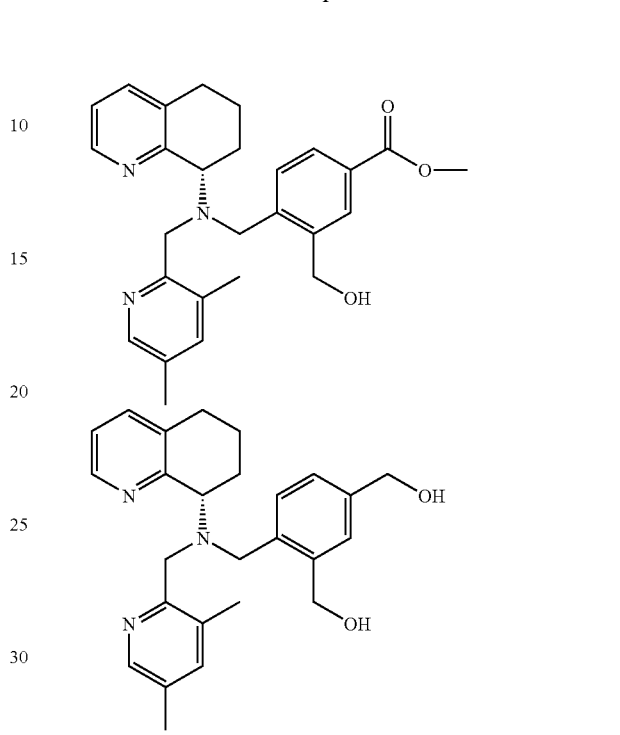

409A and 409B: 4-{[(3,5-dimethyl-pyridin-2-ylmethyl)-(5,6,7,8-tetrahydro-quinolin-8-yl)-amino]-methyl}-3-hydroxymethyl-benzoic acid methyl ester and (2-{[(3,5-Dimethyl-pyridin-2-ylmethyl)-(5,6,7,8-tetrahydro-quinolin-8-yl)-amino]-methyl}-5-hydroxymethyl-phenyl)-methanol, Respectively To a solution of (S)-4-{[(3,5-dimethyl-pyridin-2-ylmethyl)-(5,6,7,8-tetrahydro-quinolin-8-yl)-amino]-methyl}-isophthalic acid dimethyl ester (0.400 g, 0.85 mmol) in MeOH (50 mL) was slowly added LiBH$_4$ (370 mg, 16.8 mmol) and the mixture was stirred at room temperature for one hour. The mixture was concentrated under reduced pressure, diluted with CH$_2$Cl$_2$ (50 mL) and washed with 1N NaOH (15 mL). The aqueous was extracted with CH$_2$Cl$_2$ (3×30 mL) and the combined organic extracts were dried (Na$_2$SO$_4$), filtered and concentrated under reduced pressure. Purification by column chromatography on silica gel (EtOAc: NH$_4$OH, 95:5, v/v) afforded two major products. The first band to elute from the column was 4-{[(3,5-dimethyl-pyridin-2-ylmethyl)-(5,6,7,8-tetrahydro-quinolin-8-yl)-amino]-methyl}-3-hydroxymethyl-benzoic acid methyl ester (409A, 0.190 g, 50%) isolated as a white solid. $^1$H NMR (CDCl$_3$) δ 1.59 (m, 1H), 2.02 (m, 1H), 2.14 (m, 1H), 2.19 (s, 3H), 2.24 (s, 3H), 2.63 (m, 1H), 2.77 (m, 1H), 3.64 (d, 1H, J=12.0 Hz), 3.73 (d, 1H, J=12.0 Hz), 3.85 (s, 3H), 4.20 (d, 1H, J=12.0 Hz), 4.37 (d, 1H, J=12.0 Hz), 7.00 (dd, 1H, J=7.5, 3.0 Hz), 7.23 (s, 1H), 7.31 (d, 1H, J=9.0 Hz), 8.02 (d, 1H, J=3.0 Hz), 8.15 (d, 1H, J=3.0 Hz), 8.37 (d, 1H, J=4.5 Hz). $^{13}$C NMR (CDCl$_3$) δ 18.3, 18.6, 21.3, 22.1, 28.7, 29.8, 31.0, 52.3, 54.5, 54.6, 58.3, 62.8, 122.1, 128.9, 130.3, 131.3, 132.4, 133.2, 133.8, 135.0, 137.1, 139.4, 142.8, 142.9, 146.6, 147.0, 153.5, 157.0, 167.3.

HPLC: 94%. ES-MS m/z 446 [M+H]$^+$, 468 [M+Na]$^+$. Anal. Calcd. for $C_{27}H_{31}N_3O_3 \cdot 0.3H_2O$: C, 71.91; H, 7.06; N, 9.32. Found: C, 72.01; H, 6.95; N, 9.11. The second band to elute from the column was (2-{[(3,5-Dimethyl-pyridin-2-ylmethyl)-(5,6,7,8-tetrahydro-quinolin-8-yl)-amino]-methyl}-5-hydroxymethyl-phenyl)-methanol (409B, 0.115 g, 32%) isolated as a pale yellow solid. $^1$H NMR (CDCl$_3$) δ 1.59 (m, 1H), 2.02 (m, 1H), 2.14 (m, 1H), 2.20 (s, 3H), 2.24 (s, 3H), 2.63 (m, 1H), 2.79 (m, 1H), 3.62-3.72 (m, 3H), 3.87 (t, 1H, J=9.0 Hz), 4.08 (m, 1H), 4.12 (d, 1H, J=12.0 Hz), 4.35 (d, 1H, J=12.0 Hz), 4.62 (s, 2H), 7.02 (dd, 1H, J=7.5, 3.0 Hz), 7.19-7.34 (m, 5H), 8.15 (d, 1H, J=3.0 Hz), 8.35 (d, 1H, J=4.5 Hz). $^{13}$C NMR (CDCl$_3$) δ 18.3, 18.6, 21.0, 22.1, 29.8, 31.0, 54.4, 54.6, 57.8, 62.9, 65.3, 121.9, 126.3, 130.6, 131.5, 132.3, 133.8, 135.0, 136.7, 137.0, 139.4, 141.4, 142.6, 146.5, 147.0, 153.7, 157.3. HPLC: 94%. ES-MS m/z 418 [M+H]$^+$, 440 [M+Na]$^+$. Anal. Calcd. for $C_{26}H_{31}N_3O_2 \cdot 0.4H_2O$: C, 73.52; H, 7.55; N, 9.89. Found: C, 73.52; H, 7.55; N, 9.89.

Example 410

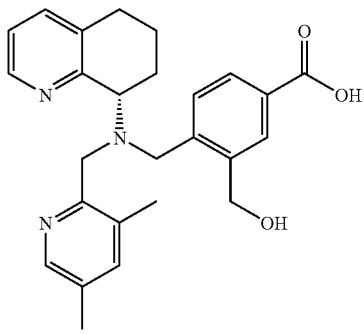

COMPOUND 410: 4-{[(3,5-dimethyl-pyridin-2-ylmethyl)-(5,6,7,8-tetrahydro-quinolin-8-yl)-amino]-methyl}-3-hydroxymethyl-benzoic acid A solution of 4-{[(3,5-dimethyl-pyridin-2-ylmethyl)-(5,6,7,8-tetrahydro-quinolin-8-yl)-amino]-methyl}-3-hydroxymethyl-benzoic acid methyl ester (0.513 g, 1.15 mmol) in THF (20 mL) was slowly added to a slurry of NaH (60% dispersion in oil, 0.048 g, 1.21 mmol) in THF (15 mL) at 0° C. After the bubbling subsided, the mixture was stirred at 0° C. for 30 minutes followed by the addition of tert-butyl-chloro-dimethyl-silane (0.182 g, 1.21 mmol). The mixture was warmed to room temperature for one hour then heated to 50° C. for 16 hours. The mixture was quenched with saturated aqueous NaHCO$_3$ (20 mL), extracted with CH$_2$Cl$_2$ (7×30 mL) and the combined organic extracts were dried (Na$_2$SO$_4$), filtered and concentrated under reduced pressure. Purification by column chromatography on silica gel (CH$_2$Cl$_2$:MeOH:NH$_4$OH, 80:15:5, v/v/v) afforded two major products. The first band to elute from the column was the TBDMS-protected acid compound followed by 4-{[(3,5-dimethyl-pyridin-2-ylmethyl)-(5,6,7,8-tetrahydro-quinolin-8-yl)-amino]-methyl}-3-hydroxymethyl-benzoic acid (COMPOUND 410, 0.235 g, 47%) isolated as a white solid. $^1$H NMR (CD$_3$OD) δ 1.67 (m, 1H), 2.08 (m, 1H), 2.19 (s, 3H), 2.23 (m, 1H), 2.28 (s, 3H), 2.75 (m, 1H), 2.85 (m, 1H), 3.93-4.12 (m, 4H), 4.23 (d, 1H, J=13.2 Hz), 4.40 (d, 1H, J=12.0 Hz), 4.52 (d, 1H, J=12.0 Hz), 7.18 (dd, 1H, J=7.5, 3.0 Hz), 7.42 (d, 1H, J=7.2 Hz), 7.49 (d, 1H, J=7.5 Hz), 7.79 (d, 1H, J=7.5 Hz), 7.90 (s, 1H), 8.17 (s, 1H), 8.35 (d, 1H, J=4.5 Hz). $^{13}$C NMR (CD$_3$OD) δ 18.2, 22.8, 23.5, 29.9, 54.0, 55.3, 62.5, 63.7, 124.4, 130.2, 132.2, 132.7, 135.1, 135.4, 136.9, 137.4, 139.5, 142.4, 145.7, 147.9, 152.1, 155.8, 173.0. HPLC: 98%. ES-MS m/z 432 [M+H]$^+$. Anal. Calcd. for $C_{26}H_{29}N_3O_3 \cdot 1.0H_2O \cdot 0.2 \ CH_2Cl_2$: C, 67.45; H, 6.78; N, 9.41. Found: C, 67.51; H, 6.64; N, 9.61.

Example 411

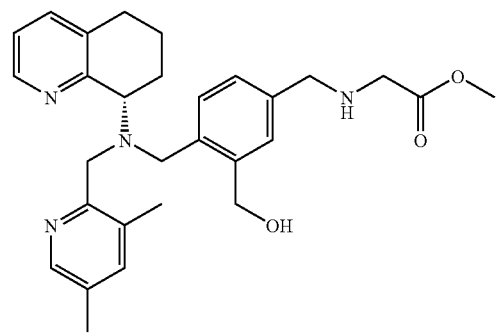

COMPOUND 411: (4-{[(3,5-Dimethyl-pyridin-2-ylmethyl)-(5,6,7,8-tetrahydro-quinolin-8-yl)-amino]-methyl}-3-hydroxymethyl-benzylamino)-acetic acid methyl ester Using General Procedure A: Reaction of (5-Aminomethyl-2-{[(3,5-dimethyl-pyridin-2-ylmethyl)-(5,6,7,8-tetrahydro-quinolin-8-yl)-amino]-methyl}-phenyl)-methanol, methyl-bromoacetate and DIPEA in CH$_2$Cl$_2$ gave (4-{[(3,5-Dimethyl-pyridin-2-ylmethyl)-(5,6,7,8-tetrahydro-quinolin-8-yl)-amino]-methyl}-3-hydroxymethyl-benzylamino)-acetic acid methyl ester as a white foamy solid. $^1$H NMR (CDCl$_3$) δ 1.60 (m, 1H), 1.80 (br s, 1H), 1.98 (m, 1H), 2.19 (m, 2H), 2.22 (s 3H), 2.25 (s, 3H), 2.64 (m, 1H), 2.79 (m, 1H), 3.40 (s, 2H), 3.63-3.77 (m, 8H), 3.91 (t, 1H, J=7.5 Hz), 4.15 (m, 2H), 4.36 (d, 1H, J=12.0 Hz), 7.01 (dd, 1H, J=7.5, 3.0 Hz), 7.16 (d, 1H, J=7.5 Hz), 7.21-7.31 (m, 4H), 8.16 (s, 1H), 8.37 (d, 1H, J=3.0 Hz). $^{13}$C NMR (CDCl$_3$) δ 18.3, 18.6, 21.1, 22.1, 29.8, 50.4, 52.1, 53.3, 54.4, 54.6, 57.9, 63.0, 121.9, 127.4, 131.4, 131.8, 132.2, 133.8, 134.9, 136.3, 136.9, 139.3, 139.7, 142.6, 146.5, 146.9, 153.7, 157.3, 173.2. HPLC: 98%. ES-MS m/z 489 [M+H]$^+$, 511 [M+Na]$^+$. Anal. Calcd. for $C_{29}H_{36}N_4O_3 \cdot 0.1 \ CH_2Cl_2$: C, 70.31; H, 7.34; N, 11.27. Found: C, 70.54; H, 7.48; N, 11.17.

Example 412

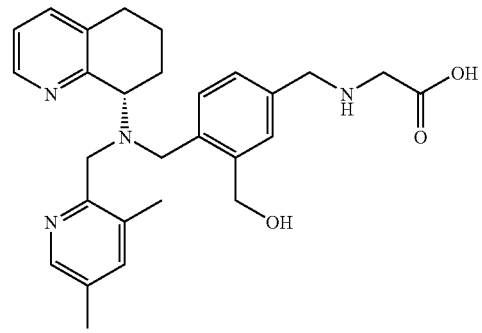

COMPOUND 412: (4-{[(3,5-Dimethyl-pyridin-2-ylmethyl)-(5,6,7,8-tetrahydro-quinolin-8-yl)-amino]-methyl}-3-hydroxymethyl-benzylamino)-acetic acid (4-{[(3,5-Dimethyl-pyridin-2-ylmethyl)-(5,6,7,8-tetrahydro-quinolin-8-yl)-amino]-methyl}-3-hydroxymethyl-benzylamino)-acetic acid methyl ester (0.140 g, 0.29 mmol) was dissolved in a mixture of EtOH (3 mL) and 3M NaOH (7 mL). The colorless mixture was stirred at 90° C. for 16 hours to give an orange/brown solution. 3M HCl was added until pH~2 followed by the addition of 3M NaOH until the pH~9 and a white precipitate formed. The white solid was removed via suction filtration and the filtrate was extracted with 95:5 (CHCl$_3$/MeOH) (9×30 mL) and the combined organic extracts were dried (Na$_2$SO$_4$), filtered and concentrated under reduced pressure. Purification by column chromatography on silica gel (MeCN:MeOH:NH$_4$OH, 6:3:1, v/v/v) afforded (4-{[(3,5-dimethyl-pyridin-2-ylmethyl)-(5,6,7,8-tetrahydro-quinolin-8-yl)-amino]-methyl}-3-hydroxymethyl-benzylamino)-acetic acid (0.106 g, 78%) as a pale yellow solid. $^1$H NMR (CD$_3$OD) δ 1.58 (m, 1H), 2.05 (m, 2H), 2.17 (s+m, 4H), 2.27 (s, 3H), 2.65 (m, 1H), 2.83 (m, 1H), 3.43 (s, 2H), 3.74 (m, 4H), 4.16-4.22 (m, 4H), 4.39 (d, 1H, J=11.1 Hz), 7.11 (m, 1H), 7.25-7.42 (m, 5H), 8.10 (s, 1H), 8.28 (s, 1H). $^{13}$C NMR (CD$_3$OD) δ 18.2, 18.9, 22.4, 23.2, 30.5, 52.0, 55.0, 55.1, 59.8, 63.2, 123.4, 130.5, 131.1, 133.1, 133.6, 133.8, 134.7, 135.8, 136.9, 138.7, 140.1, 141.3, 143.7, 146.9, 147.8, 154.5, 158.0, 171.5. HPLC: 97%. ES-MS m/z 475 [M+H]$^+$. Anal. Calcd. for C$_{28}$H$_{34}$N$_4$O$_3$·1.3H$_2$O: C, 67.53; H, 7.41; N, 11.25. Found: C, 67.65; H, 7.36; N, 11.09.

Example 413

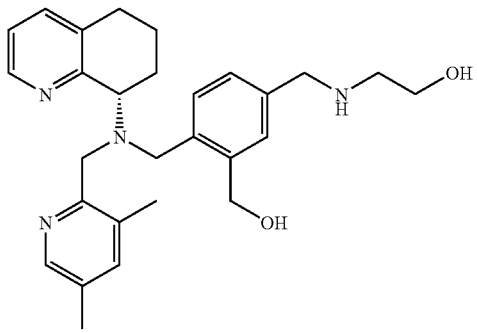

COMPOUND 413: 2-(4-{[(3,5-dimethyl-pyridin-2-ylmethyl)-(5,6,7,8-tetrahydro-quinolin-8-yl)-amino]-methyl}-3-hydroxymethyl-benzylamino)-ethanol To a solution of (4-{[(3,5-Dimethyl-pyridin-2-ylmethyl)-(5,6,7,8-tetrahydro-quinolin-8-yl)-amino]-methyl}-3-hydroxymethyl-benzylamino)-acetic acid methyl ester (0.128 g, 0.26 mmol) in THF was added LiAlH$_4$ (0.049 g, 1.30 mmol). The resulting slurry rapidly bubbled for the first minute and then gas production subsided. The mixture was stirred at room temperature for one hour and then was quenched with saturated aqueous NH$_4$Cl (20 mL) and extracted with 98:2 (CHCl$_3$/MeOH) (5×40 mL). The combined organic extracts were dried (Na$_2$SO$_4$), filtered and concentrated under reduced pressure to a pale yellow oil. Purification by column chromatography on silica gel (CH$_2$Cl$_2$:MeOH:NH$_4$OH, 85:10:5, v/v/v) afforded 2-(4-{[(3,5-dimethyl-pyridin-2-ylmethyl)-(5,6,7,8-tetrahydro-quinolin-8-yl)-amino]-methyl}-3-hydroxymethyl-benzylamino)-ethanol (0.045 g, 37%) as a colorless oil. $^1$H NMR (CDCl$_3$) δ 1.58 (m, 1H), 1.98 (m, 2H), 2.16 (m, 1H), 2.21 (s, 3H), 2.25 (s, 3H), 2.64 (m, 1H), 2.78 (m+t, 3H), 3.61 (t, 2H, J=4.5 Hz), 3.65-3.72 (m, 3H), 3.75 (s, 2H), 3.88 (t, 1H, J=9.0 Hz), 4.15 (d, 2H, J=12.0 Hz), 4.36 (d, 1H, J=9.0 Hz), 7.01 (dd, 1H, J=7.5, 3.0 Hz), 7.16 (d, 1H, J=6.0), 7.21-7.32 (m, 4H), 8.16 (s, 1H), 8.36 (d, 1H, J=3.0 Hz). $^{13}$C NMR (CDCl$_3$) δ 9.2, 26.5, 28.7, 28.8, 29.6, 42.9, 44.1, 79.7, 84.4, 86.5, 115.5, 121.8, 123.5, 124.6, 124.9, 130.8, 137.4, 140.1, 145.5, 155.1. HPLC: 99%. ES-MS m/z 461 [M+H]$^+$.

Example 414

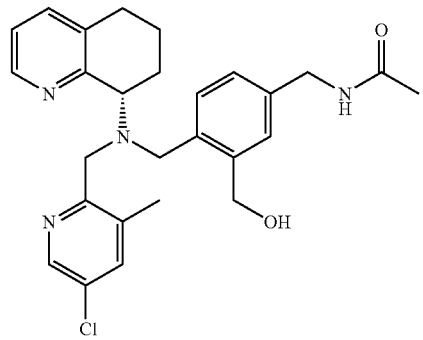

COMPOUND 414: N-(4-{[(5-chloro-3-methyl-pyridin-2-ylmethyl)-(5,6,7,8-tetrahydro-quinolin-8-yl)-amino]-methyl}-3-hydroxymethyl-benzyl)-acetamide To a solution of 5,6,7,8-tetrahydro-quinolin-8-ylamine (1.73 g, 12.0 mmol) dissolved in THF (80 mL) was added 2-nitrobenzenesulfonyl chloride (2.92 g, 13.0 mmol) and Et$_3$N (2.4 mL, 18.0 mmol). The mixture was stirred for 16 hours at room temperature under a positive pressure of N$_2$. The reaction mixture was quenched with saturated aqueous NaHCO$_3$ (100 mL) and extracted with CH$_2$Cl$_2$ (2×100 mL). The combined organic extracts were dried (Na$_2$SO$_4$), filtered, and concentrated in vacuo to afford 2-nitro-N-(5,6,7,8-tetrahydro-quinolin-8-yl)-benzenesulfonamide as a dark brown solid (3.72 g, 94%). $^1$H NMR (CDCl$_3$) δ 1.59 (m, 1H), 1.89 (m, 2H), 2.50 (m, 1H), 2.76 (m, 2H), 4.35 (m, 1H), 6.86 (m, 1H), 7.04 (m, 1H), 7.35 (m, 1H), 7.74 (m, 2H), 7.99 (m, 1H), 8.12 (m, 1H), 8.26 (m, 1H).

To a solution of 2-nitro-N-(5,6,7,8-tetrahydro-quinolin-8-yl)-benzenesulfonamide (3.72 g, 11.0 mmol) dissolved in CH$_3$CN (120 mL) was added 2-bromomethyl-5-cyano-benzoic acid methyl ester (2.79 g, 11.0 mmol) and K$_2$CO$_3$ (4.56 g, 33.0 mmol). The mixture was stirred for 18 hours at 80° C. under a positive pressure of N$_2$. The mixture was concentrated in vacuo and redissolved in CH$_2$Cl$_2$ (150 mL). Brine (150 mL) was added and the mixture was extracted with CH$_2$Cl$_2$ (2×150 mL). The combined organic extracts were dried (Na$_2$SO$_4$), filtered, and concentrated in vacuo to afford a black oil. Purification via column chromatography on silica gel (hexanes:EtOAc, 2:1, v/v) afforded 5-cyano-2-{[(2-nitro-benzenesulfonyl)-(5,6,7,8-tetrahydro-quinolin-8-yl)-amino]-methyl}-benzoic acid methyl ester as a yellow solid (2.89 g, 52%). $^1$H NMR (CDCl$_3$) δ 1.55 (m, 1H), 1.89 (m, 2H), 2.34 (m, 1H), 2.66 (m, 2H), 4.44 (d, 1H, J=18.9 Hz), 5.18

(d, 1H, J=18.9 Hz), 5.38 (m, 1H), 6.98 (dd, 1H, J=7.5, 4.8 Hz), 7.31 (d, 1H, J=7.5 Hz), 7.75 (m, 4H), 7.91 (d, 1H, J=4.4 Hz), 8.12 (m, 3H).

To a solution of 5-cyano-2-{[(2-nitro-benzenesulfonyl)-(5,6,7,8-tetrahydro-quinolin-8-yl)-amino}-methyl}-benzoic acid methyl ester (2.32 g, 5.72 mmol) dissolved in THF (50 mL) and MeOH (50 mL), LiBH$_4$ (1.26 g, 57.2 mmol) was slowly added. The mixture was stirred at room temperature under a positive pressure of N$_2$ for 2 hours. The mixture was concentrated in vacuo and redissolved in CH$_2$Cl$_2$ (50 mL). Brine (30 mL) was added and the resulting mixture was extracted with CH$_2$Cl$_2$ (2×50 mL). The combined organic extracts were dried (Na$_2$SO$_4$), filtered, and concentrated in vacuo to afford a yellow solid. Purification via column chromatography on silica gel (hexanes:EtOAc, 1:1, v/v) afforded N-(4-cyano-2-hydroxymethyl-benzyl)-2-nitro-N-(5,6,7,8-tetrahydro-quinolin-8-yl)-benzenesulfonamide as a yellow solid (2.32 g, 85%). $^1$H NMR (CDCl$_3$) δ 1.56 (s, 9H), 1.91 (m, 2H), 2.36 (m, 1H), 2.61 (m, 2H), 2.98 (m, 1H), 4.23 (d, 1H, J=16.7 Hz), 4.61 (m, 2H), 4.90 (d, 1H, J=16.2 Hz), 5.21 (m, 1H), 7.03 (dd, 1H, J=5.3, 9.7 Hz), 7.37 (m, 3H), 7.67 (m, 4H), 7.95 (d, 1H, J=7.9 Hz), 8.16 (d, 1H, J=4.4 Hz).

To a solution of N-(4-cyano-2-hydroxymethyl-benzyl)-2-nitro-N-(5,6,7,8-tetrahydro-quinolin-8-yl)-benzenesulfonamide (2.32 g, 4.85 mmol) dissolved in DMF (50 mL) was added K$_2$CO$_3$ (3.35 g, 24.3 mmol) and thiophenol (1.49 mL, 14.6 mmol). The solution was stirred at room temperature under a positive pressure of N$_2$ for 3 hours. The mixture was concentrated in vacuo and redissolved in CH$_2$Cl$_2$ (50 mL). The mixture was filtered through a sintered glass funnel containing celite. The solution was concentrated in vacuo to afford a yellow solid. Purification via column chromatography on silica gel (hexane:EtOAc, 1:1, v/v) afforded 3-hydroxymethyl-4-[(1,2,3,4-tetrahydro-naphthalen-1-ylamino)-methyl]-benzonitrile as a yellow solid (1.22 g, 86%). $^1$H NMR (CDCl$_3$) δ 1.92 (m, 3H), 2.26 (m, 1H), 2.77 (m, 2H), 3.86 (m, 1H), 4.02 (d, 1H, J=13.3 Hz), 4.17 (d, 1H, J=12.3 Hz), 4.51 (d, 1H. J=12.3 Hz), 4.80 (d, 1H, J=11.4 Hz), 7.09 (dd, 1H, J=8.3, 5.3 Hz), 7.42 (d, 1H, J=6.6 Hz), 7.49 (d, 1H, J=7.9 Hz), 7.59 (m, 1H), 7.64 (s, 1H), 8.35 (d, 1H, J=4.8 Hz).

To a solution of 3-hydroxymethyl-4-[(1,2,3,4-tetrahydro-naphthalen-1-ylamino)-methyl]-benzonitrile (1.22 g, 4.18 mmol) dissolved in THF (50 mL) was added t-butoxycarbonyl (0.91 g, 4.18 mmol) and DIPEA (0.58 mL). The solution was stirred for 16 hours under a positive pressure of N$_2$. The solution was concentrated in vacuo and redissolved in EtOAc (80 mL). Saturated aqueous NaHCO$_3$ (80 mL) was added and the resulting mixture was extracted with EtOAc (2×60 mL). The combined organic extracts were dried (Na$_2$SO$_4$), filtered, and concentrated to afford an off-white solid. Purification via column chromatography on silica gel (EtOAc) afforded (4-cyano-2-hydroxymethyl-benzyl)-(5,6,7,8-tetrahydro-quinolin-8-yl)-carbamic acid tert-butyl ester as a colorless oil (1.39 g, 85%). $^1$H NMR (CDCl$_3$) δ 1.06 (s, 9H), 1.28 (m, 2H), 2.04 (m, 3H), 2.29 (m, 1H), 2.74 (m, 2H), 3.97 (m, 2H), 4.46 (m, 1H), 5.02 (m, 1H), 5.59 (m, 1H), 7.04 (m, 1H), 7.35 (d, 1H, J=9.0 Hz), 7.50 (d, 1H, J=9.0 Hz), 7.82 (s, 1H), 8.19 (d, 1H, J=6.0 Hz).

Ammonia gas was bubbled through a solution of (4-cyano-2-hydroxymethyl-benzyl)-(5,6,7,8-tetrahydro-quinolin-8-yl)-carbamic acid tert-butyl ester (1.39 g, 3.55 mmol) in MeOH (40 mL) for 18 minutes. A prewashed mixture of Raney Nickel (~1 gram) was added to the nitrile and the mixture was shaken for 16 hours under 30 psi hydrogen. The mixture was filtered through a celite plug and the filtrate was concentrated under reduced pressure. Purification via column chromatography on silica gel (CH$_2$Cl$_2$:MeOH:NH$_4$OH, 94:5:1, v/v/v) afforded (4-aminomethyl-2-hydroxymethyl-benzyl)-(5,6,7,8-tetrahydro-quinolin-8-yl)-carbamic acid tert-butyl ester as an off-white solid (0.77 g, 55%). $^1$H NMR (CDCl$_3$) δ 1.05 (s, 9H), 1.76 (m, 2H), 2.25 (m, 2H), 2.67 (m, 2H), 3.85 (s, 2H), 3.92 (d, 1H, J=15.0 Hz), 4.27 (m, 1H), 4.37 (d, 1H, J=9.0 Hz), 5.02 (d, 1H, J=12.0 Hz), 5.43 (d, 1H, J=15.0 Hz), 7.00 (m, 1H), 7.19 (m, 2H), 7.22 (m, 1H), 7.45 (m, 1H), 8.14 (d, 1H, J=3.0 Hz).

To a solution of (4-aminomethyl-2-hydroxymethyl-benzyl)-(5,6,7,8-tetrahydro-quinolin-8-yl)-carbamic acid tert-butyl ester (0.86 g, 2.17 mmol) dissolved in CH$_2$Cl$_2$ (15 mL) was added Ac$_2$O (0.21 mL, 2.17 mmol) and Et$_3$N (0.31 mL, 2.17 mmol). The solution was stirred for 30 minutes under a positive pressure of N$_2$. The reaction mixture was quenched with saturated aqueous NaHCO$_3$ (25 mL) and extracted with CH$_2$Cl$_2$ (2×25 mL). The combined organic extracts were dried (Na$_2$SO$_4$), filtered, and concentrated to afford [4-(acetylamino-methyl)-2-hydroxymethyl-benzyl]-(5,6,7,8-tetrahydro-quinolin-8-yl)-carbamic acid tert-butyl ester as a white solid (0.95 g, 99%). $^1$H NMR (CDCl$_3$) δ 1.06 (s, 9H), 1.65 (m, 1H), 2.01 (m, 3H), 2.08 (m, 1H), 2.70 (m, 2H), 3.87 (d, 1H, J=15.0 Hz), 4.09 (m, 1H), 4.41 (d, 3H, J=6.0 Hz), 5.07 (d, 1H, J=12.0 Hz), 5.56 (d, 1H, J=12.0 Hz), 5.96 (m, 1H), 6.98 (m, 1H), 7.15 (s, 2H), 7.32 (d, 1H, J=6.0 Hz), 7.41 (s, 1H), 8.15 (d, 1H, J=3.0 Hz). Deprotection with TFA following General Procedure F gave N-{3-hydroxymethyl-4-{(5,6,7,8-tetrahydro-quinolin-8-ylamino)-methyl}-benzyl}-acetamide as an off-white solid. $^1$H NMR (CDCl$_3$) δ 1.79 (m, 2H), 1.94 (m, 1H), 2.00 (s, 3H), 2.26 (m, 1H), 2.77 (m, 2H), 3.89 (m, 2H), 4.13 (d, 1H, J=12.0 Hz), 4.41 (m, 3H), 4.79 (d, 1H, J=12.0 Hz), 7.05 (m, 1H), 7.20 (m, 1H), 7.31 (m, 1H), 7.40 (m, 2H), 8.33 (d, 1H, J=3.0 Hz).

Using General Procedure B: Reaction of N-{3-hydroxymethyl-4-[(5,6,7,8-tetrahydro-quinolin-8-ylamino)-methyl]-benzyl}-acetamide in CH$_2$Cl$_2$ with 5-chloro-3-methyl-pyridine-2-carbaldehyde and NaBH(OAc)$_3$ gave N-(4-{[(5-chloro-3-methyl-pyridin-2-ylmethyl)-(5,6,7,8-tetrahydro-quinolin-8-yl)-amino]-methyl}-3-hydroxymethyl-benzyl)-acetamide as a white foam. $^1$H NMR (CDCl$_3$) δ 1.58 (m, 1H), 2.03 (s, 3H), 2.04 (m, 1H), 2.18 (m, 1H), 2.24 (s, 3H), 2.65 (m, 1H), 2.79 (m, 1H), 3.69 (dd, 2H, J=12.0, 3.0 Hz), 3.79 (d, 1H, J=12.0 Hz), 3.89 (t, 1H, J=9.0 Hz), 4.12 (d, 1H, J=12.0 Hz), 4.21 (m, 1H), 4.39 (d, 2H, J=6.0 Hz), 4.41 (m, 1H), 5.67 (br s, 1H), 7.01 (dd, 1H, J=7.5, 3.0 Hz), 7.14 (d, 1H, J=6.0), 7.24-7.30 (m, 3H), 7.39 (s, 1H), 8.28 (s, 1H), 8.36 (d, 1H, J=3.0 Hz). $^{13}$C NMR (CDCl$_3$) δ 18.2, 20.8, 21.7, 23.3, 29.3, 43.4, 53.0, 54.0, 54.3, 57.7, 62.6, 65.9, 121.7, 127.1, 130.6, 131.1, 131.3, 134.6, 135.4, 136.1, 136.7, 137.6, 138.1, 142.4, 144.5, 146.6, 154.6, 156.7, 169.8. HPLC: 97%. ES-MS m/z 479 [M+H]$^+$, 501 [M+Na]$^+$. Anal. Calcd. for C$_{27}$H$_{31}$N$_4$O$_2$Cl.0.5 CH$_2$Cl$_2$: C, 62.69; H, 6.24; N, 10.63; Cl, 13.46. Found: C, 62.52; H, 6.18; N, 10.47; Cl, 13.59.

Example 415

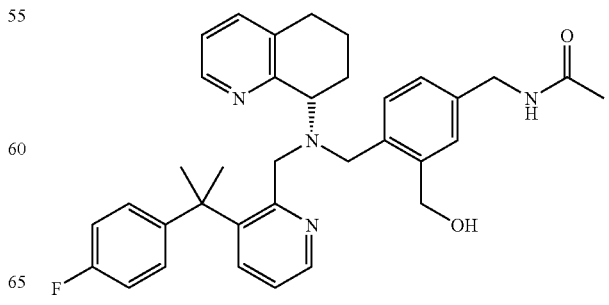

345

COMPOUND 415: N-(4-{[{3-[1-(4-fluoro-phenyl)-1-methyl-ethyl]-pyridin-2-ylmethyl}-(5,6,7,8-tetrahydro-quinolin-8-yl)-amino]-methyl}-3-hydroxymethyl-benzyl)-acetamide Using General Procedure B: Reaction of N-{3-hydroxymethyl-4-[(5,6,7,8-tetrahydro-quinolin-8-ylamino)-methyl]-benzyl}-acetamide in $CH_2Cl_2$ with 3-[1-(4-fluoro-phenyl)-1-methyl-ethyl]-pyridine-2-carbaldehyde and $NaBH(OAc)_3$ gave N-(4-{[{3-[1-(4-fluoro-phenyl)-1-methyl-ethyl]-pyridin-2-ylmethyl}-(5,6,7,8-tetrahydro-quinolin-8-yl)-amino]-methyl}-3-hydroxymethyl-benzyl)-acetamide as a white foam. $^1$H NMR (CDCl$_3$) δ 1.45 (m, 1H), 1.55 (s, 3H), 1.63 (s, 3H), 1.72 (m, 1H), 1.83 (m, 1H), 2.00 (s, 3H), 2.10 (m, 1H), 2.57 (m, 2H), 2.79 (m, 1H), 3.48 (s, 2H), 3.72-3.90 (m, 4H), 4.35 (d, 2H, J=6.0 Hz), 4.60 (d, 1H, J=12.0 Hz), 4.72 (d, 1H, J=12.0 Hz), 5.67 (br s, 1H), 6.79 (t, 2H, J=6.0 Hz), 6.91 (d, 1H, J=6.0), 7.03 (br s, 3H), 7.21 (m, 2H), 7.27 (d, 1H, J=9.0 Hz), 7.79 (d, 1H, J=9.0 Hz), 8.41 (d, 1H, J=3.0 Hz), 8.53 (d, 1H, J=3.0 Hz). $^{13}$C NMR (CDCl$_3$) δ 22.4, 23.6, 27.2, 29.4, 29.6, 32.6, 42.3, 43.8, 54.8, 55.2, 59.0, 63.7, 115.2, 115.5, 121.6, 121.8, 127.1, 127.4, 127.5, 130.7, 132.4, 133.9, 134.6, 136.8, 138.0, 142.9, 145.7, 146.8, 146.9, 157.6, 158.1, 159.5, 162.7, 170.3. HPLC: 95%. ES-MS m/z 567 [M+H]$^+$. Anal. Calcd. for $C_{35}H_{39}N_4O_2F \cdot 0.3\ CH_2Cl_2$: C, 71.60; H, 6.74; N, 9.46. Found: C, 71.48; H, 6.81; N, 9.58.

Example 416

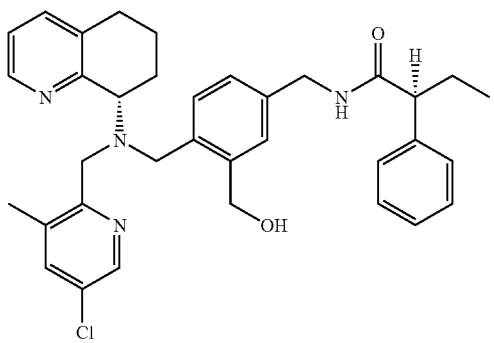

COMPOUND 416: N-(4-{[(5-chloro-3-methyl-pyridin-2-ylmethyl)-(5,6,7,8-tetrahydro-quinolin-8-yl)-(S)-amino]-methyl}-3-hydroxymethyl-benzyl)-(S)-2-phenyl-butyramide Using General Procedure B: Reaction of 3-hydroxymethyl-4-[(5,6,7,8-tetrahydro-quinolin-8-ylamino)-methyl]-benzonitrile in $CH_2Cl_2$ with 5-chloro-3-methyl-pyridine-2-carbaldehyde and $NaBH(OAc)_3$ gave 4-{[(5-chloro-3-methyl-pyridin-2-ylmethyl)-(5,6,7,8-tetrahydro-quinolin-8-yl)-amino]-methyl}-3-hydroxymethyl-benzonitrile as a colorless oil. $^1$H NMR (CDCl$_3$) δ 1.59 (m, 1H), 2.03 (m, 2H), 2.14 (m, 1H), 2.19 (s, 3H), 2.63 (m, 1H), 2.77 (m, 1H), 3.65 (d, 1H, J=12.0 Hz), 3.73-3.83 (m, 3H), 4.20 (d, 2H, J=12.0 Hz), 4.37 (d, 1H, J=12.0 Hz), 7.03 (dd, 1H, J=7.5, 3.0 Hz), 7.15-7.46 (m, 4H), 7.65 (s, 1H), 8.28 (s, 1H), 8.34 (s, 1H).

To a solution of 4-{[(5-chloro-3-methyl-pyridin-2-ylmethyl)-(5,6,7,8-tetrahydro-quinolin-8-yl)-amino]-methyl}-3-hydroxymethyl-benzonitrile (0.170 g, 0.39 mmol) dissolved in MeOH (8 mL) NH$_3$ gas was bubbled for 10 minutes. A prewashed mixture of Raney Nickel (~1 g) was added to the nitrile and the mixture was shaken on the hydrogenator at 35 psi for 2 hours. The mixture was filtered through a sintered glass funnel containing a celite plug and the filtrated was concentrated in vacuo to a pale yellow oil. Purification by column chromatography on silica gel (CH$_2$Cl$_2$:MeOH:NH$_4$OH, 87:8:5, v/v/v) afforded the product as a colorless oil (0.130 g, 76%). $^1$H NMR (CDCl$_3$) δ 1.56 (m, 1H), 2.02 (m, 1H), 2.17 (m, 2H), 2.25 (s, 3H), 2.62 (m, 1H), 2.76 (m, 1H), 3.64 (d, 2H, J=12.0 Hz), 3.79 (d, 2H, J=12.0 Hz), 3.82 (s, 1H), 3.91 (t, 1H, J=9.0 Hz), 4.11 (d, 2H, J=12.0 Hz), 4.22 (d, 1H, J=12.0 Hz), 4.40 (d, 1H, J=12.0 Hz), 7.02 (dd, 1H, J=7.5, 3.0 Hz), 7.15 (d, 1H, J=7.5 Hz), 7.23-7.31 (m, 3H), 7.39 (s, 1H), 8.28 (s, 1H), 8.34 (d, 1H, J=3.0 Hz).

(5-Aminomethyl-2-{[(5-chloro-3-methyl-pyridin-2-ylmethyl)-(5,6,7,8-tetrahydro-quinolin-8-yl)-amino]-methyl}-phenyl)-methanol (0.130 g, 0.30 mmol), S-(+)-2-phenylbutyric acid (56 µL, 0.36 mmol), HOBT (0.048 g, 0.36 mmol), EDCI (0.068 g, 0.36 mmol) and DIPEA (62 µL, 0.36 mmol) in CH$_2$Cl$_2$ (8 mL) were reacted according to General Procedure G. Purification by column chromatography on silica gel (CH$_2$Cl$_2$:MeOH:NH$_4$OH, 94:5:1, v/v/v) afforded N-(4-{[(5-chloro-3-methyl-pyridin-2-ylmethyl)-(5,6,7,8-tetrahydro-quinolin-8-yl)-(S)-amino]-methyl}-3-hydroxymethyl-benzyl)-(S)-2-phenyl-butyramide as a white solid (0.130 g, 75%). $^1$H NMR (CDCl$_3$) δ 0.86 (t, 3H, J=7.5 Hz), 1.58 (m, 1H), 1.82 (m, 1H), 2.05 (m, 1H), 2.18 (m, 1H), 2.24 (s, 3H), 2.66 (m, 1H), 2.77 (m, 1H), 3.22 (t, 1H, J=7.5 Hz), 3.64-3.88 (m, 4H), 4.11 (m, 2H), 4.34 (m, 3H), 5.62 (brt, 1H), 7.01 (m, 2H), 7.17-7.39 (m, 9H), 8.28 (s, 1H), 8.35 (d, 1H, J=3.0 Hz). HPLC: 96%. ES-MS m/z 583 [M+H]$^+$, 605 [M+Na]$^+$.

Example 417

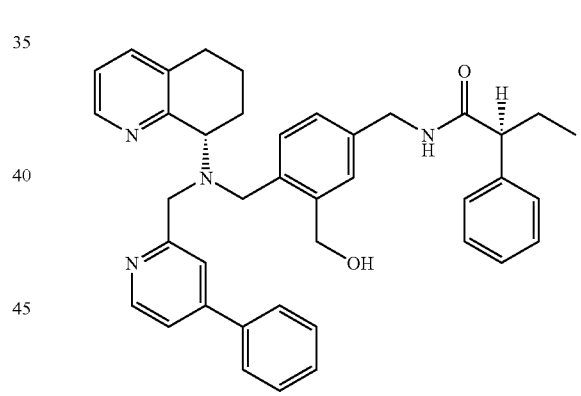

COMPOUND 417: N-(3-hydroxymethyl-4-{[(4-phenyl-pyridin-2-ylmethyl)-(5,6,7,8-tetrahydro-quinolin-8-yl)-(S)-amino]-methyl}-benzyl)-(S)-2-phenyl-butyramide Using General Procedure B: Reaction of 3-hydroxymethyl-4-[(5,6,7,8-tetrahydro-quinolin-8-ylamino)-methyl]-benzonitrile in CH$_2$Cl$_2$ with 4-phenyl-pyridine-2-carbaldehyde and NaBH(OAc)$_3$ gave 3-hydroxymethyl-4-{[(4-phenyl-pyridin-2-ylmethyl)-(5,6,7,8-tetrahydro-quinolin-8-yl)-amino]-methyl}-benzonitrile as a colorless oil. $^1$H NMR (CDCl$_3$) δ 1.63 (m, 1H), 2.08 (m, 2H), 2.29 (m, 1H), 2.72 (m, 1H), 2.81 (m, 1H), 3.61 (d, 1H, J=12.0 Hz), 3.73 (d, 1H, J=12.0 Hz), 3.85 (m, 3H), 4.08-4.23 (m, 3H), 4.43 (d, 1H, J=9.0 Hz), 7.06 (dd, 1H, J=7.5, 3.0 Hz), 7.36-7.64 (m, 8H), 7.86 (d, 2H, J=9.0 Hz), 8.00 (s, 1H), 8.51 (dd, 2H, J=12.0, 4.5 Hz).

To a solution of 3-hydroxymethyl-4-{[(4-phenyl-pyridin-2-ylmethyl)-(5,6,7,8-tetrahydro-quinolin-8-yl)-amino]-methyl}-benzonitrile (0.183 g, 0.40 mmol) dissolved in MeOH (8 mL) NH$_3$ gas was bubbled for 10 minutes. A prewashed mixture of Raney Nickel (~1 gram) was added to the nitrile and the mixture was shaken on the hydrogenator at 35 psi for 2 hours. The mixture was filtered through a sintered glass funnel containing a celite plug and the filtrate was concentrated in vacuo to a pale yellow oil. Purification by column chromatography on silica gel (CH$_2$Cl$_2$:MeOH:NH$_4$OH, 87:8:5, v/v/v) afforded (5-aminomethyl-2-{[(4-phenyl-pyridin-2-ylmethyl)-(5,6,7,8-tetrahydro-quinolin-8-yl)-amino]-methyl}-phenyl)-methanol as a colorless oil (0.036 g, 19%). $^1$H NMR (CDCl$_3$) δ 1.61 (m, 1H), 1.92-2.05 (m, 2H), 2.29 (m, 1H), 2.66 (m, 1H), 2.79 (m, 1H), 3.60 (d, 1H, J=12.0 Hz), 3.68-3.81 (m, 4H), 3.93 (m, 1H), 4.08 (m, 3H), 4.49 (d, 1H), 7.01 (dd, 1H, J=7.5, 3.0 Hz), 7.16 (d, 1H, J=7.5 Hz), 7.24-7.30 (m, 3H), 7.44 (m, 2H), 7.57 (t, 2H, J=7.5 Hz), 7.92 (d, 2H, J=6.0 Hz), 8.11 (s, 1H), 8.47 (d, 1H, J=3.0 Hz), 8.50 (d, 1H, J=4.5 Hz).

(5-Aminomethyl-2-{[(4-phenyl-pyridin-2-ylmethyl)-(5,6,7,8-tetrahydro-quinolin-8-yl)-amino]-methyl}-phenyl)-methanol (0.036 g, 0.08 mmol), S-(+)-2-phenylbutyric acid (14 μL, 0.09 mmol), HOBT (0.012 g, 0.09 mmol), EDCI (0.018 g, 0.09 mmol) and DIPEA (16 μL, 0.09 mmol) in CH$_2$Cl$_2$ (8 mL) were reacted according to General Procedure G. Purification by column chromatography on silica gel (CH$_2$Cl$_2$:MeOH:NH$_4$OH, 94:5:1, v/v/v) afforded COMPOUND 417 as a white solid (0.043 g, 91%). $^1$H NMR (CDCl$_3$) δ 0.86 (t, 3H, J=7.5 Hz), 1.62 (m, 1H), 1.80 (m, 1H), 1.91 (m, 1H), 2.02 (m, 2H), 2.23 (m, 1H), 2.69 (m, 1H), 2.77 (m, 1H), 3.20 (t, 1H, J=7.5 Hz), 3.61-3.70 (m, 3H), 3.88 (m, 1H), 4.09 (m, 2H), 4.30-4.42 (m, 3H), 5.60 (br t, 1H), 6.98 (m, 2H), 7.17-7.56 (m, 12H), 7.89 (m, 2H), 8.08 (m, 1H), 8.48 (m, 2H). HPLC: 98%. ES-MS m/z 611 [M+H]$^+$.

Example 418

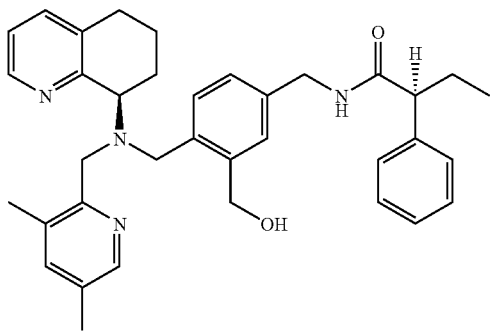

COMPOUND 418: N-(4-{[(3,5-dimethyl-pyridin-2-ylmethyl)-(5,6,7,8-tetrahydro-quinolin-8-yl)-(R)-amino]-methyl}-3-hydroxymethyl-benzyl)-(S)-2-phenyl-butyramide Using General Procedure B: Reaction of (R)-5,6,7,8-tetrahydro-quinolin-8-ylamine in CH$_2$Cl$_2$ (4 ml) with 3,5-dimethyl-pyridine-2-carbaldehyde and NaBH(OAc)$_3$ gave (R)-(3,5-dimethyl-pyridin-2-ylmethyl)-(5,6,7,8-tetrahydro-quinolin-8-yl)-amine as a brown oil. $^1$H NMR (CDCl$_3$) δ 1.78 (m, 1H), 2.03 (m, 1H), 2.10 (m, 1H), 2.26 (s+m, 4H), 2.33 (s, 3H), 2.81 (m, 2H), 3.96 (t, 1H, J=6.0 Hz), 4.02 (d, 1H, J=12.0 Hz), 4.17 (d, 1H, J=12.0 Hz), 5.41 (br s, 2H), 7.06 (dd, 1H, J=7.5, 3.0 Hz), 7.25 (s, 1H), 7.37 (d, 1H, J=9.0 Hz), 8.24 (s, 1H), 8.40 (d, 1H, J=3.0 Hz).

(R)-(3,5-Dimethyl-pyridin-2-ylmethyl)-(5,6,7,8-tetrahydro-quinolin-8-yl)-amine (0.40 g, 1.50 mmol), 2-bromomethyl-5-cyano-benzoic acid methyl ester (0.40 g, 1.57 mmol) and K$_2$CO$_3$ (0.58 g, 4.50 mmol) in CH$_3$CN (10 mL) were reacted according to General Procedure A. The crude 5-cyano-2-{[(3,5-dimethyl-pyridin-2-ylmethyl)-(5,6,7,8-tetrahydro-quinolin-8yl)-amino]-methyl}-benzoic acid methyl ester was isolated as an orange-brown oil (0.68 g, 100%) and used without purification in the next step of the synthesis.

To a solution of 5-cyano-2-{[(3,5-dimethyl-pyridin-2-ylmethyl)-(5,6,7,8-tetrahydro-quinolin-8yl)-(R)-amino]-methyl}-benzoic acid methyl ester (0.68 g, 1.55 mmol) dissolved in MeOH (30 mL) was added LiBH$_4$ (0.34 g, 15.5 mmol). The mixture was stirred for 16 hours under a positive pressure of N$_2$. The mixture was concentrated in vacuo and the white residue was quenched with saturated aqueous NaHCO$_3$ (30 ml) and then extracted with CH$_2$Cl$_2$ (4×30 mL). The combined organic extracts were dried (Na$_2$SO$_4$), filtered, and concentrated in vacuo to a yellow gum. Purification by column chromatography on silica gel (CH$_2$Cl$_2$:MeOH:NH$_4$OH, 96:3:1, v/v/v) afforded 4-{[(3,5-dimethyl-pyridin-2-ylmethyl)-(5,6,7,8-tetrahydro-quinolin-8-yl)-(R)-amino]-methyl}-3-hydroxy-methyl-benzonitrile as a white foam (0.38 g, 62%). $^1$H NMR (CDCl$_3$) δ 1.63 (m, 1H), 2.03 (m, 1H), 2.14 (m, 1H), 2.18 (s, 3H), 2.26 (s, 3H), 2.68 (m, 1H), 2.79 (m, 1H), 3.64 (d, 1H, J=12.0 Hz), 3.72-3.84 (m, 3H), 4.18 (m, 1H), 4.25 (d, 1H, J=12.0 Hz), 4.35 (d, 1H, J=12.0 Hz), 7.05 (dd, 1H, J=7.0, 5.7 Hz), 7.35 (d, 2H, J=6.0 Hz), 7.45 (d, 2H, J=9.0 Hz), 7.65 (s, 1H), 8.17 (s, 1H), 8.37 (d, 1H, J=3.0 Hz).

To a solution of 4-{[(3,5-dimethyl-pyridin-2-ylmethyl)-(5,6,7,8-tetrahydro-quinolin-8-yl)-(R)-amino]-methyl}-3-hydroxy-methyl-benzonitrile (0.38 g, 0.92 mmol) dissolved in MeOH (8 mL) NH$_3$ gas was bubbled for 10 minutes. A prewashed mixture of Raney Nickel (~1 gram) was added to the nitrile and the mixture was shaken on the hydrogenator at 35 psi for 2 hours. The mixture was filtered through a sintered glass funnel containing a celite plug and the filtrated was concentrated in vacuo to afford (5-aminomethyl-2-{[(3,5-dimethyl-pyridin-2-ylmethyl)-(5,6,7,8-tetrahydro-quinolin-8-yl)-(R)-amino]-methyl}-phenyl)-methanol as a pale yellow oil. Purification by column chromatography on silica gel (CH$_2$Cl$_2$:MeOH:NH$_4$OH, 85:10:5, v/v/v) afforded the product as a colorless oil (0.27 g, 69%). $^1$H NMR (CDCl$_3$) δ 1.60 (m, 1H), 1.99 (m, 1H), 2.16 (m, 2H), 2.22 (s, 3H), 2.25 (s, 3H), 2.64 (m, 1H), 2.80 (m, 1H), 3.63-3.72 (m, 3H), 3.81 (s, 3H), 3.90 (t, 1H, J=9.0 Hz), 4.14 (d, 2H, J=12.0 Hz), 4.37 (d, 1H, J=12.0 Hz), 7.01 (dd, 1H, J=7.5, 3.0 Hz), 7.14 (d, 1H, J=7.5 Hz), 7.21-7.32 (m, 4H), 8.16 (s, 1H), 8.36 (d, 1H, J=3.0 Hz).

(5-Aminomethyl-2-{[(3,5-dimethyl-pyridin-2-ylmethyl)-(5,6,7,8-tetrahydro-quinolin-8-yl)-(R)-amino]-methyl}-phenyl)-methanol (0.106 g, 0.26 mmol), S-(+)-2-phenylbutyric acid (48 μL, 0.31 mmol), HOBT (0.041 g, 0.31 mmol), EDCI (0.059 g, 0.31 mmol) and DIPEA (53 μL, 0.31 mmol) in CH$_2$Cl$_2$ (8 mL) were reacted according to General Procedure G. Purification by column chromatography on silica gel (CH$_2$Cl$_2$:MeOH:NH$_4$OH, 94:5:1, v/v/v) afforded N-(4-{[(3,5-dimethyl-pyridin-2-ylmethyl)-(5,6,7,8-tetrahydro-quinolin-8-yl)-(R)-amino]-methyl}-3-hydroxymethyl-benzyl)-(S)-2-phenyl-butyramide as a white solid (0.052 g, 36%). $^1$H NMR (CDCl$_3$) δ 0.86 (t, 3H, J=7.5 Hz), 1.61 (m, 1H), 1.79 (m, 1H), 2.05 (m, 1H), 2.17 (m, 1H), 2.21 (s, 3H), 2.25 (s, 3H), 2.65 (m, 1H), 2.79 (m, 1H), 3.21 (t, 1H, J=7.5 Hz), 3.62-3.75 (m, 3H), 3.86 (t, 1H, J=6.5 Hz), 4.10 (m, 2H), 4.30 (dd, 1H, J=12.0, 6.0 Hz), 4.35 (d, 1H, J=12.0 Hz), 4.43 (dd, 1H, J=12.0, 6.0 Hz), 5.65 (br t, 1H), 7.01 (m, 2H), 7.12-7.32 (m, 9H), 8.16 (s, 1H), 8.36 (d, 1H, J=3.0 Hz). HPLC: 98%. ES-MS m/z 563 [M+H]$^+$, 585 [M+Na]$^+$.

Example 419

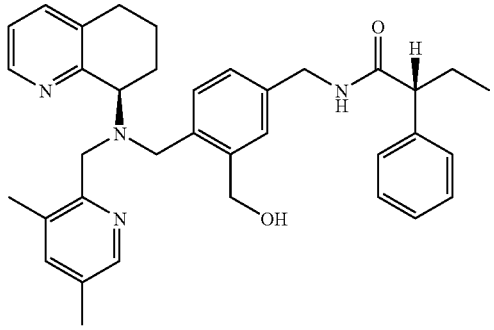

COMPOUND 419: N-(4-{[(3,5-dimethyl-pyridin-2-ylmethyl)-(5,6,7,8-tetrahydro-quinolin-8-yl)-(R)-amino]-methyl}-3-hydroxymethyl-benzyl)-(R)-2-phenyl-butyramide (5-Aminomethyl-2-{[(3,5-dimethyl-pyridin-2-ylmethyl)-(5,6,7,8-tetrahydro-quinolin-8-yl)-(R)-amino]-methyl}-phenyl)-methanol (0.110 g, 0.27 mmol), R-(−)-2-phenylbutyric acid (49 µL, 0.32 mmol), HOBT (0.043 g, 0.32 mmol), EDCI (0.061 g, 0.32 mmol) and DIPEA (55 µL, 0.32 mmol) in CH$_2$Cl$_2$ (8 mL) were reacted according to General Procedure G. Purification by column chromatography on silica gel (CH$_2$Cl$_2$:MeOH:NH$_4$OH, 94:5:1, v/v/v) afforded N-(4-{[(3,5-dimethyl-pyridin-2-ylmethyl)-(5,6,7,8-tetrahydro-quinolin-8-yl)-(R)-amino]-methyl}-3-hydroxymethyl-benzyl)-(R)-2-phenyl-butyramide as a white solid (0.050 g, 33%). $^1$H NMR (CDCl$_3$) δ 0.86 (t, 3H, J=7.5 Hz), 1.61 (m, 1H), 1.79 (m, 1H), 2.05 (m, 1H), 2.17 (m, 1H), 2.21 (s, 3H), 2.25 (s, 3H), 2.65 (m, 1H), 2.79 (m, 1H), 3.21 (t, 1H, J=7.5 Hz), 3.62-3.75 (m, 3H), 3.86 (t, 1H, J=6.5 Hz), 4.10 (m, 2H), 4.30 (dd, 1H, J=12.0, 6.0 Hz), 4.35 (d, 1H, J=12.0 Hz), 4.43 (dd, 1H, J=12.0, 6.0 Hz), 5.65 (br t, 1H), 7.01 (m, 2H), 7.12-7.32 (m, 9H), 8.16 (s, 1H), 8.36 (d, 1H, J=3.0 Hz). HPLC: 98%. ES-MS m/z 563 [M+H]$^+$, 585 [M+Na]$^+$.

Example 420

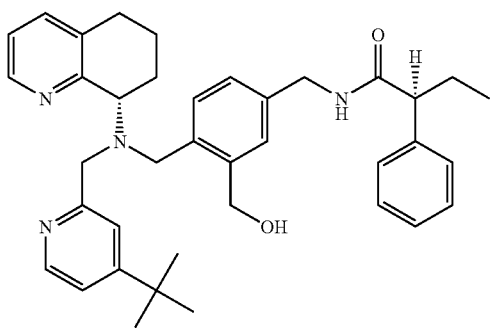

COMPOUND 420: N-(4-{[(4-tert-butyl-pyridin-2-ylmethyl)-(5,6,7,8-tetrahydro-quinolin-8-yl)-(S)-amino]-methyl}-3-hydroxymethyl-benzyl)-(S)-2-phenyl-butyramide Using General Procedure B: Reaction of 3-hydroxymethyl-4-[(5,6,7,8-tetrahydro-quinolin-8-ylamino)-methyl]-benzonitrile in CH$_2$Cl$_2$ with 4-tert-butyl-pyridine-2-carbaldehyde and NaBH(OAc)$_3$ gave 4-{[(4-tert-butyl-pyridin-2-ylmethyl)-(5,6,7,8-tetrahydro-quinolin-8-yl)-amino]-methyl}-3-hydroxymethyl-benzonitrile as a pale yellow oil. $^1$H NMR (CDCl$_3$) δ 1.38 (s, 9H), 1.70 (m, 1H), 1.91-2.04 (m, 2H), 2.21 (m, 1H), 2.71 (m, 1H), 2.81 (m, 1H), 3.52 (d, 1H, J=12.0 Hz), 3.64 (d, 1H, J=12.0 Hz), 3.73 (d, 1H, J=12.0 Hz), 3.80 (m, 1H), 4.07 (m, 1H), 4.13 (d, 1H, J=12.0 Hz), 4.34 (d, 1H, J=12.0 Hz), 7.03 (dd, 1H, J=7.5, 3.0 Hz), 7.19 (dd, 1H, J=4.5, 3.0 Hz), 7.36-7.52 (m, 4H), 7.63 (s, 1H), 7.78 (s, 1H), 8.36 (d, 1H, J=6.0 Hz), 8.51 (d, 1H, J=3.0 Hz).

To a solution of 4-{[(4-tert-butyl-pyridin-2-ylmethyl)-(5,6,7,8-tetrahydro-quinolin-8-yl)-amino]-methyl}-3-hydroxymethyl-benzonitrile (0.153 g, 0.34 mmol) dissolved in MeOH (8 mL) NH$_3$ gas was bubbled for 10 minutes. A prewashed mixture of Raney Nickel (~1 gram) was added to the nitrile and the mixture was shaken on the hydrogenator at 35 psi for 2 hours. The mixture was filtered through a sintered glass funnel containing a celite plug and the filtrate was concentrated in vacuo to a pale yellow oil. Purification by column chromatography on silica gel (CH$_2$Cl$_2$:MeOH:NH$_4$OH, 90:5:5, v/v/v) afforded (5-aminomethyl-2-{[(4-tert-butyl-pyridin-2-ylmethyl)-(5,6,7,8-tetrahydro-quinolin-8-yl)-amino]-methyl}-phenyl)-methanol as a pale yellow oil (0.085 g, 56%). $^1$H NMR (CDCl$_3$) δ 1.39 (s, 9H), 1.54 (m, 1H), 1.77 (br s, 2H), 1.82 (m, 1H), 1.99 (m, 1H), 2.22 (m, 1H), 2.68 (m, 1H), 2.79 (m, 1H), 3.51 (d, 1H, J=12.0 Hz), 3.63 (dd, 2H, J=13.5, 4.5 Hz), 3.80 (s, 2H), 3.87 (m, 1H), 4.06 (d, 2H, J=12.0 Hz), 4.41 (d, 1H, J=12.0 Hz), 7.05 (dd, 1H, J=7.5, 3.0 Hz), 7.15-7.27 (m, 4H), 7.32 (d, 1H, J=9.0 Hz), 7.89 (s, 1H), 8.35 (d, 1H, J=6.0 Hz), 8.50 (d, 1H, J=3.0 Hz).

(5-Aminomethyl-2-{[(4-tert-butyl-pyridin-2-ylmethyl)-(5,6,7,8-tetrahydro-quinolin-8-yl)-amino]-methyl}-phenyl)-methanol (0.038 g, 0.08 mmol), S-(+)-2-phenylbutyric acid (16 µL, 0.09 mmol), HOBT (0.014 g, 0.09 mmol), EDCI (0.020 g, 0.09 mmol) and DIPEA (18 µL, 0.09 mmol) in CH$_2$Cl$_2$ (8 mL) were reacted according to General Procedure G. Purification by column chromatography on silica gel (CH$_2$Cl$_2$:MeOH:NH$_4$OH, 94:5:1, v/v/v) afforded N-(4-{[(4-tert-butyl-pyridin-2-ylmethyl)-(5,6,7,8-tetrahydro-quinolin-8-yl)-(S)-amino]-methyl}-3-hydroxymethyl-benzyl)-(S)-2-phenyl-butyramide as a white solid (0.033 g, 65%). $^1$H NMR (CDCl$_3$) δ 0.87 (t, 3H, J=7.5 Hz), 1.39 (s, 9H), 1.59 (m, 1H), 1.77-1.89 (m, 2H), 2.00 (m, 1H), 2.20 (m, 1H), 2.68 (m, 1H), 2.77 (m, 1H), 3.21 (t, 1H, J=7.5 Hz), 3.51-3.65 (m, 3H), 3.81 (m, 1H), 3.99 (m, 2H), 4.29-4.38 (m, 3H), 5.73 (br t, 1H), 6.98 (d, 1H, J=9.0 Hz), 7.05 (dd, 1H, J=7.5, 3.0 Hz), 7.14-7.33 (m, 9H), 7.87 (s, 1H), 8.35 (d, 1H, J=6.0 Hz), 8.49 (d, 1H, J=3.0 Hz). HPLC: 95%. ES-MS m/z 613 [M+Na]$^+$.

Example 421

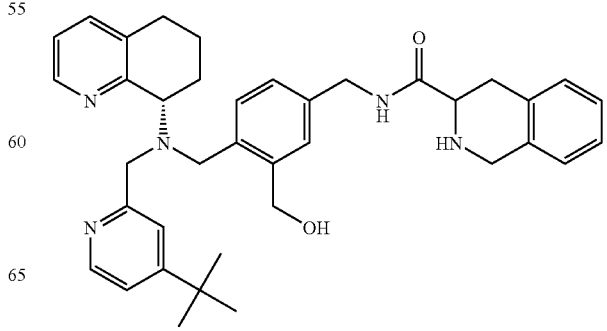

COMPOUND 421: 1,2,3,4-tetrahydro-isoquinoline-3-carboxylic acid 4-{[(4-tert-butyl-pyridin-2-ylmethyl)-(5,6,7,8-tetrahydro-quinolin-8-yl)-amino]-methyl}-3-hydroxymethyl-benzylamide (5-Aminomethyl-2-{[(4-tert-butyl-pyridin-2-ylmethyl)-(5,6,7,8-tetrahydro-quinolin-8-yl)-amino]-methyl}-phenyl)-methanol (0.047 g, 0.11 mmol), (±)-1,2,3,4-tetrahydro-3-isoquinoline carboxylic acid hydrochloride (0.027 g, 0.13 mmol), HOBT (0.017 g, 0.13 mmol), EDCI (0.024 g, 0.13 mmol) and DIPEA (40 μL, 0.26 mmol) in $CH_2Cl_2$ (8 mL) were reacted according to General Procedure G. Purification by column chromatography on silica gel ($CH_2Cl_2$:MeOH:$NH_4OH$, 94:5:1, v/v/v) afforded 1,2,3,4-tetrahydro-isoquinoline-3-carboxylic acid 4-{[(4-tert-butyl-pyridin-2-ylmethyl)-(5,6,7,8-tetrahydro-quinolin-8-yl)-amino]-methyl}-3-hydroxymethyl-benzylamide as a white solid (0.018 g, 28%). $^1$H NMR ($CDCl_3$) δ 1.40 (s, 9H), 1.59 (m, 1H), 1.89-2.02 (m, 2H), 2.22 (m, 1H), 2.69 (m, 1H), 2.79 (m, 1H), 3.22 (dt, 1H, J=12.0, 3.0 Hz), 3.55-3.66 (m, 4H), 3.87 (m, 1H), 3.94 (d, 2H, J=4.5 Hz), 4.06 (d, 2H, J=12.0 Hz), 4.40 (m, 3H), 7.04-7.24 (m, 9H), 7.36 (d, 1H, J=7.5 Hz), 7.52 (br t, 1H), 7.89 (s, 1H), 8.36 (d, 1H, J=6.0 Hz), 8.51 (d, 1H, J=3.0 Hz). HPLC: 89%. ES-MS m/z 604 [M+H]$^+$.

Example 422

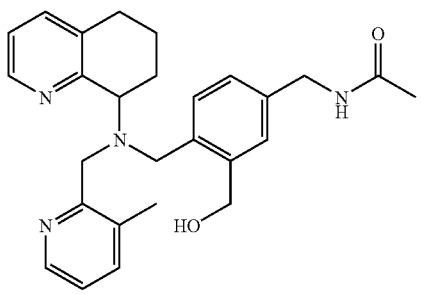

COMPOUND 422: N-(3-hydroxymethyl-4-{[(3-methyl-pyridin-2-ylmethyl)-(5,6,7,8-tetrahydro-quinolin-8-yl)-amino]-methyl}-benzyl)-acetamide To a solution of (5-aminomethyl-2-{[(3-methyl-pyridin-2-ylmethyl)-(5,6,7,8-tetrahydro-quinolin-8-yl)-amino]-methyl}-phenyl)-methanol (0.0980 g, 0.25 mmol) in $CH_2Cl_2$ (3 mL) was added $Et_3N$ (0.05 mL, 0.38 mmol), KI (0.0042 g, 0.03 mmol), and $Ac_2O$ (0.0237 mL, 0.25 mmol). After stirring at room temperature for 18 hours, saturated $NaHCO_3$ (10 mL) was added and extracted with $CH_2Cl_2$ (3×30 mL). The combined organic extracts were dried ($Na_2SO_4$), filtered, and concentrated. Purification of the crude material by column chromatography on silica gel (100:1:1 $CH_2Cl_2$-MeOH—$NH_4OH$) provided 74.0 mg (64%) of COMPOUND 422 as a white solid. $^1$H NMR ($CDCl_3$) δ 1.56-1.64 (m, 2H), 1.98 (s, 4H), 2.15-2.19 (m, 2H), 2.24 (s, 3H), 2.60-2.80 (m, 2H), 3.66-3.71 (m, 2H), 3.78-3.91 (m, 2H), 4.15 (d, 2H, J=12.3 Hz), 4.33-4.37 (m, 2H), 5.75 (s, 1H), 7.00-7.11 (m, 3H), 7.21 (s, 1H), 7.32 (d, 2H, J=7.5 Hz), 7.42 (d, 2H, J=7.2 Hz), 8.36 (t, 2H, J=5.1 Hz).

$^{13}$C NMR ($CDCl_3$) δ 18.72, 21.29, 22.11, 23.59, 29.76, 43.77, 54.39, 54.90, 57.93, 62.91, 122.08, 122.91, 127.40, 131.37, 131.65, 134.33, 135.04, 136.69, 137.08, 138.42, 138.62, 142.79, 146.20, 146.96, 156.64, 157.19, 170.33. ES-MS m/z 445.2 (M+H). Anal. Calcd. for $C_{27}H_{32}N_4O_2 \cdot 0.1CH_2Cl_2 \cdot 0.5H_2O$: C, 70.44; H, 7.24; N, 12.13. Found: C, 70.27; H, 7.26; N, 11.94.

Example 423

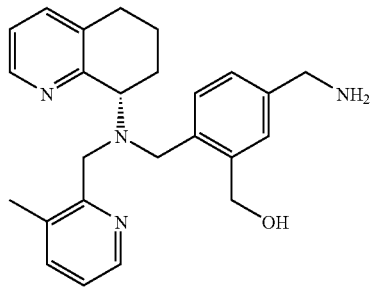

COMPOUND 423: N-(4-{[(3-Methyl-pyridin-2-ylmethyl)-(5,6,7,8-tetrahydro-quinolin-8-yl)-amino]-methyl}-3-hydroxymethyl-benzyl amine Using General Procedure B: Reaction of (S)-8-amino-5,6,7,8-tetrahydroquinoline with 3-methylpyridyl-2-aldehyde gave a secondary amine as a colorless oil. Using General Procedure A: Reaction of the secondary amine above with Methyl-5-cyano-2-bromethyl benzoate, DIPEA, KI and $CH_3CN$ gave a tertiary amine as a yellowish solid.

$LiAlH_4$ (4.0 g, 100.7 mmol) was weighted into a dry flask and cooled in ice bath. Dry THF (60 mL) was added slowly and the suspension was stirred under $N_2$ for 5 min. A solution of the above prepared tertiary amine in THF (15 mL plus 5 mL rinse) was added slowly over a period of 5 min. The reaction was continued at room temperature for 4 h. The mixture was then cooled in an ice bath, and satd. Rochelle's salt aqueous solution was added dropwise. In total 60 mL was added and the mixture was stirred at room temperature for 15 h. Layers was then separated. The aqueous layer was extracted further (2×60 mL) with THF. The organic layer were combined and concentrated to remove most of the solvent including water. The residue was columned using 20/1/1 $CH_2Cl_2$/MeOH/$NH_4OH$ to give COMPOUND 423 (3.9 g, 55%) as a pale yellow solid. $^1$H NMR ($CDCl_3$) δ 1.48-1.75 (m, 3H), 1.99-2.25 (m, 3H), 2.25 (s, 3H), 3.68 (d, 2H, J=12.0 Hz), 3.78-3.82 (m, 3H), 3.91 (t, 1H, J=6.0 Hz), 4.12-4.19 (m, 2H), 4.36 (d, 1H, J=12.0 Hz), 7.00-7.06 (m, 2H), 7.21-7.29 (m, 3H), 7.40 (d, 1H, J=9.0 Hz), 8.33-8.37 (m, 2H); $^{13}$C NMR ($CDCl_3$) δ 18.75, 21.20, 22.14, 29.81, 46.56, 54.49, 55.05, 57.90, 63.06, 122.00, 122.88, 126.33, 130.73, 131.49, 134.43, 135.00, 135.84, 137.01, 138.60, 142.66, 143.71, 146.19, 147.00, 156.75, 157.33; ES-MS m/z 403.3 (M+H); Anal. Calcd. for $C_{25}H_{30}N_4O \cdot 0.7CH_4O$: C, 72.73; H, 7.77; N, 13.22. Found: C, 72.62; H, 7.47; N, 13.39; HPLC e.e from ChiralPak AD-H, 98.8%.

Example 424

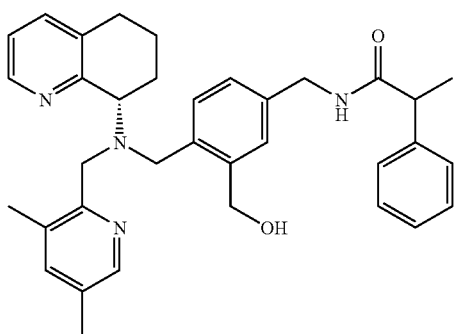

COMPOUND 424: N-(4-{[(3,5-Dimethyl-pyridin-2-ylmethyl)-(5,6,7,8-tetrahydro-quinolin-8-yl)-amino]-methyl}-3-hydroxymethyl-benzyl)-2-phenyl-propionamide Using General Procedure G: COMPOUND 436 (55 mg, 0.13 mmol) was reacted with 2-phenyl-propionic acid (24 mg, 0.16 mmol) to give COMPOUND 424 (52 mg, 74%) as a white solid. $^1$H NMR (CDCl$_3$) δ 1.52 (d, 3H, J=7.2 Hz), 1.55-1.66 (m, 2H), 1.98-2.05 (m, 1H), 2.11-2.17 (m, 1H), 2.20 (s, 3H), 2.25 (s, 3H), 2.57-2.66 (m, 1H), 2.75-2.83 (m, 1H), 3.54-3.74 (m, 4H), 3.85 (s br, 1H), 4.10 (t, 2H, J=10.0 Hz), 4.27-4.36 (m, 3H), 5.64 (s br, 1H), 6.97-7.03 (m, 2H), 7.11-7.20 (m, 2H), 7.23-7.32 (m, 7H), 8.16 (s, 1H), 8.37 (d, 1H, J=4.5 Hz); ES-MS m/z 549 (M+H).

Example 425

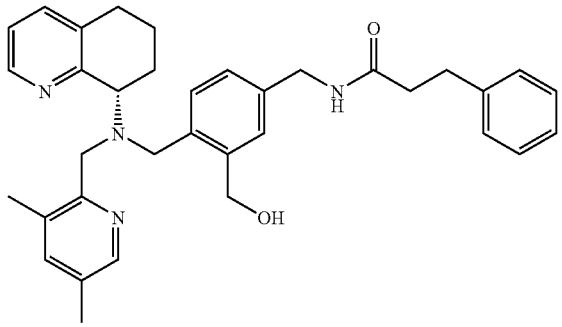

COMPOUND 425: N-(4-{[(3,5-Dimethyl-pyridin-2-ylmethyl)-(5,6,7,8-tetrahydro-quinolin-8-yl)-amino]-methyl}-3-hydroxymethyl-benzyl)-3-phenyl-propionamide Using General Procedure G: COMPOUND 436 (55 mg, 0.13 mmol) was reacted with 3-phenyl-propionic acid (24 mg, 0.16 mmol) to give COMPOUND 425 (46 mg, 65%) as a white solid. $^1$H NMR (CDCl$_3$) δ 1.51-1.64 (m, 1H), 2.04 (d, 2H, J=11.7 Hz), 2.09-2.16 (m, 1H), 2.21 (s, 3H), 2.25 (s, 3H), 2.47 (t, 2H, J=7.5 Hz), 2.57-2.67 (m, 1H), 2.74-2.86 (m, 1H), 2.97 (t, 2H, J=7.5 Hz), 3.61-3.75 (m, 3H), 3.86 (t, 1H, J=7.5 Hz), 4.09-4.17 (m, 2H), 4.30-4.36 (m, 3H), 5.62 (s br, 1H), 6.97-7.04 (m, 2H), 7.18-7.32 (m, 9H), 8.17 (s, 1H), 8.37 (d, 1H, J=4.5 Hz); ES-MS m/z 549 (M+H).

Example 426

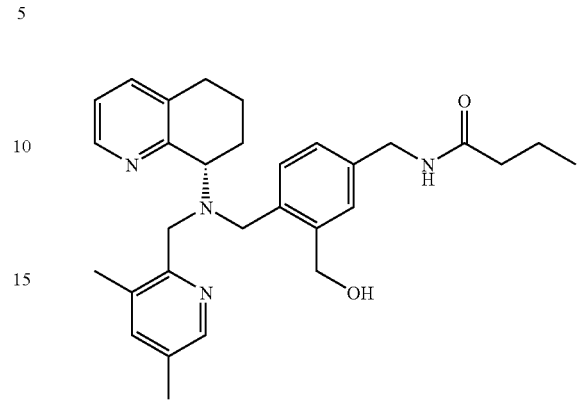

COMPOUND 426: N-(4-{[(3,5-Dimethyl-pyridin-2-ylmethyl)-(5,6,7,8-tetrahydro-quinolin-8-yl)-amino]-methyl}-3-hydroxymethyl-benzyl)-butyramide Using General Procedure G: COMPOUND 436 (55 mg, 0.13 mmol) was reacted with butyric acid (15 μL, 0.16 mmol) to give COMPOUND 426 (54 mg, 85%) as a white solid. $^1$H NMR (CDCl$_3$) δ 0.91-1.00 (m, 4H), 1.60-1.71 (m, 6H), 2.03 (d, 2H, J=9.0 Hz), 2.13-2.22 (m, 6H), 2.23 (s, 3H), 2.25 (s, 3H), 2.57-2.66 (m, 1H), 2.75-2.83 (m, 1H), 3.62-3.71 (m, 3H), 3.88 (t, 1H, J=7.5 Hz), 4.13-4.17 (m, 2H), 4.33-4.39 (m, 3H), 5.66 (s br, 1H), 7.00-7.04 (dd, 1H, J=6.0, 3.0 Hz), 7.10 (d, 1H, J=7.5 Hz), 7.21-7.26 (m, 3H), 7.32 (d, 1H, J=7.5 Hz), 8.17 (s, 1H), 8.38 (d, 1H, J=4.5 Hz); ES-MS m/z 487 (M+H).

Example 427

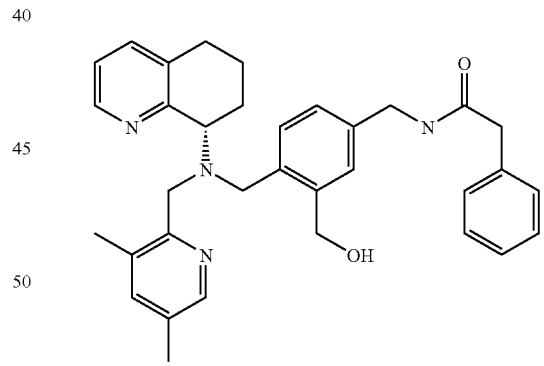

COMPOUND 427: N-(4-{[(3,5-Dimethyl-pyridin-2-ylmethyl)-(5,6,7,8-tetrahydro-quinolin-8-yl)-amino]-methyl}-3-hydroxymethyl-benzyl)-2-phenyl-acetamide Using General Procedure G: COMPOUND 436 (55 mg, 0.13 mmol) was reacted with 2-phenyl-acetic acid (22 mg, 0.16 mmol) to give COMPOUND 427 (61 mg, 88%) as a white solid. $^1$H NMR (CDCl$_3$) δ 1.49-1.65 (m, 1H), 2.03 (d, 2H, J=10 Hz), 2.09-2.15 (m, 1H), 2.20 (s, 3H), 2.25 (s, 3H), 2.57-2.66 (m, 1H), 2.74-2.85 (m, 1H), 3.59 (s, 2H), 3.60-3.74 (m, 3H), 3.85 (t, 1H, J=7.8 Hz), 4.11 (t, 2H, J=10.8 Hz), 4.30-4.37 (m, 3H), 5.69 (s br, 1H), 6.99-7.03 (m, 2H), 7.15-7.20 (m, 2H), 7.24-7.34 (m, 7H), 8.16 (s, 1H), 8.37 (d, 1H, J=4.5 Hz); ES-MS m/z 535 (M+H).

Example 428

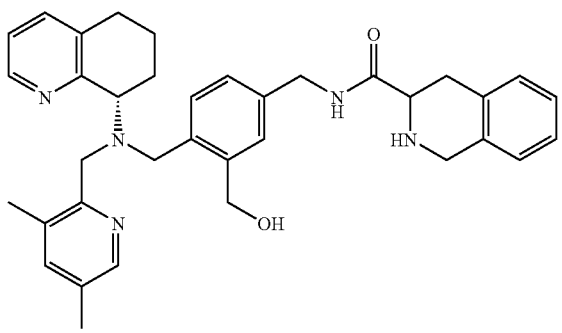

COMPOUND 428: 1,2,3,4-Tetrahydro-isoquinoline-3-carboxylic acid 4-{[(3,5-dimethyl-pyridin-2-ylmethyl)-(5,6,7,8-tetrahydro-quinolin-8-yl)-amino]-methyl}-3-hydroxymethyl-benzylamide Using General Procedure G: COMPOUND 436 (55 mg, 0.13 mmol) was reacted with 1,2,3,4-tetrahydro-isoquinoline-3-carboxylic acid (34 mg, 0.16 mmol) to give COMPOUND 428 (19 mg, 25%) as a white solid. $^1$H NMR (CDCl$_3$) δ 1.55-1.66 (m, 2H), 1.98-2.05 (m, 1H), 2.15-2.19 (m, 1H), 2.22 (s, 3H), 2.25 (s, 3H), 2.59-2.66 (m, 1H), 2.79-2.88 (m, 2H), 3.24-3.29 (m, 1H), 3.58-3.76 (m, 4H), 3.89 (t, 1H, J=7.5 Hz), 3.96 (s, 2H), 4.15 (d, 2H, J=12.0 Hz), 4.33-4.42 (m, 3H), 6.99-7.16 (m, 3H), 7.20 (s, 2H), 7.24-7.33 (m, 4H), 7.47 (s br, 1H), 8.17 (s, 1H), 8.37 (d, 1H, J=4.5 Hz); ES-MS m/z 576 (M+H).

Example 429

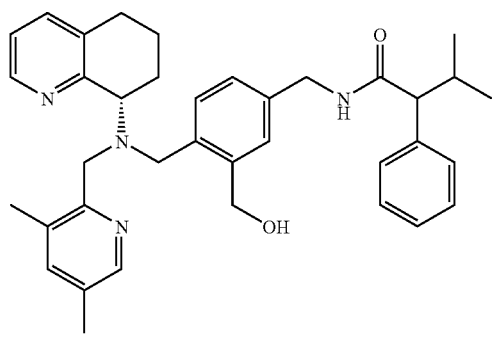

COMPOUND 429: N-(4-{[(3,5-Dimethyl-pyridin-2-ylmethyl)-(5,6,7,8-tetrahydro-quinolin-8-yl)-amino]-methyl}-3-hydroxymethyl-benzyl)-3-methyl-2-phenyl-butyramide Using General Procedure G: COMPOUND 436 (55 mg, 0.13 mmol) was reacted with 3-methyl-2-phenyl-butyric acid (29 mg, 0.16 mmol) to give COMPOUND 429 (71 mg, 95%) as a white solid. $^1$H NMR (CDCl$_3$) δ 0.67 (t, 3H, J=6.0 Hz), 0.99-1.06 (m, 3H), 1.53-1.64 (m, 1H), 1.95-2.08 (m, 1H), 2.11-2.17 (m, 1H), 2.19 (s, 3H), 2.24 (s, 3H), 2.37-2.42 (m, 1H), 2.57-2.64 (m, 1H), 2.75-2.86 (m, 2H), 3.59-3.73 (m, 3H), 3.83 (s br, 1H), 4.03-4.14 (m, 3H), 4.18-4.30 (m, 3H), 4.38-4.46 (m, 1H), 5.90-5.98 (m, 1H), 6.95-7.02 (m, 2H), 7.10-7.16 (m, 2H), 7.23-7.30 (m, 7H), 8.15 (s, 1H), 8.35 (d, 1H, J=4.5 Hz); ES-MS m/z 577 (M+H).

Example 430

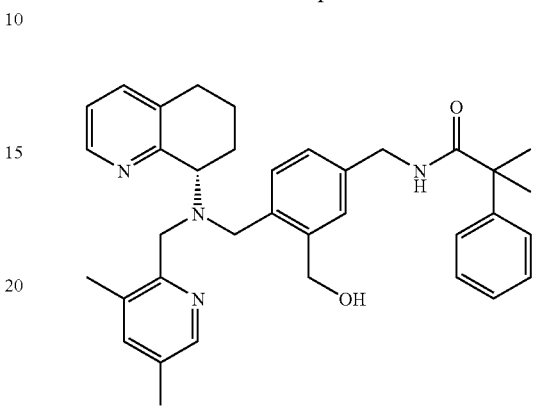

COMPOUND 430: N-(4-{[(3,5-Dimethyl-pyridin-2-ylmethyl)-(5,6,7,8-tetrahydro-quinolin-8-yl)-amino]-methyl}-3-hydroxymethyl-benzyl)-2-phenyl-isobutyramide Using General Procedure G: COMPOUND 436 (55 mg, 0.13 mmol) was reacted with 2-phenyl-isobutyric acid (26 mg, 0.16 mmol) to give COMPOUND 430 (70 mg, 96%) as a white solid. $^1$H NMR (CDCl$_3$) δ 1.50-1.63 (m, 7H), 1.95-2.05 (m, 2H), 2.07-2.17 (m, 1H), 2.19 (s, 3H), 2.24 (s, 3H), 2.55-2.66 (m, 1H), 2.72-2.85 (m, 1H), 3.60-3.73 (m, 3H), 3.83 (t, 1H, J=7.5 Hz), 4.02-4.13 (m, 2H), 4.23-4.40 (m, 3H), 5.43 (s br, 1H), 6.94 (d, 1H, J=7.5 Hz), 7.00 (dd, 1H, J=7.5, 4.8 Hz), 7.07 (s, 1H), 7.15 (d, 1H, J=7.5 Hz), 7.19-7.42 (m, 7H), 8.15 (s, 1H), 8.35 (d, 1H, J=4.5 Hz); ES-MS m/z 563 (M+H).

Example 431

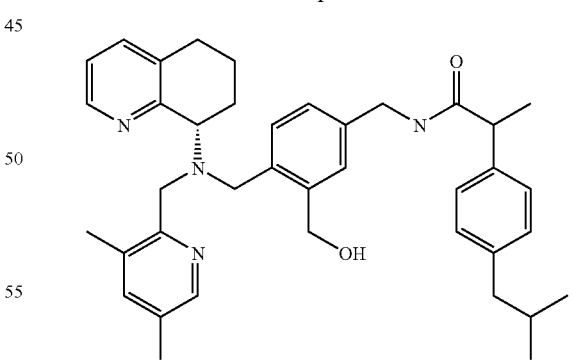

COMPOUND 431: N-(4-{[(3,5-Dimethyl-pyridin-2-ylmethyl)-(5,6,7,8-tetrahydro-quinolin-8-yl)-amino]-methyl}-3-hydroxymethyl-benzyl)-2-(4-isobutyl-phenyl)-propionamide Using General Procedure G: COMPOUND 436 (55 mg, 0.13 mmol) was reacted with 2-(4-isobutyl-phenyl)-propionic acid (33 mg, 0.16 mmol) to give COMPOUND 431 (63 mg, 81%) as a white solid. ¹H NMR (CDCl₃) δ 0.86 (d, 6H, J=7.2 Hz), 1.51 (d, 3H, J=7.2 Hz), 1.54-1.64 (m, 1H), 1.76-1.85 (m, 2H), 1.94-2.02 (m, 1H), 2.06-2.15 (m, 1H), 2.20 (s, 3H), 2.24 (s, 3H), 2.57-2.66 (m, 1H), 2.73-2.86 (m, 1H), 3.53 (q, 1H, J=7.2 Hz), 3.59-3.74 (m, 3H), 3.85 (s br, 1H), 4.03-4.15 (m, 2H), 4.21-4.43 (m, 3H), 5.61 (m, 1H), 6.94 (t, 1H, J=7.5 Hz), 7.00 (dd, 1H, J=7.5, 4.5 Hz), 7.07 (d, 2H, J=8.4 Hz), 7.12-7.20 (m, 4H), 7.23 (s, 1H), 7.30 (d, 1H, 7.2 Hz), 8.15 (s, 1H), 8.36 (d, 1H, J=4.5 Hz); ES-MS m/z 605 (M+H).

Example 432

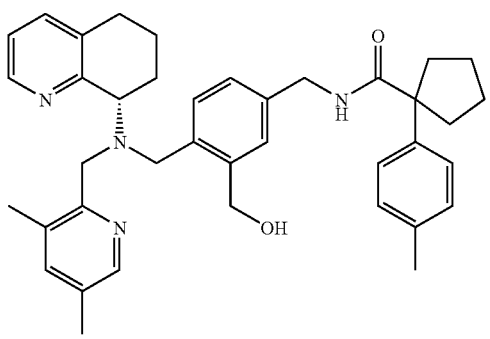

COMPOUND 432: 1-p-Tolyl-cyclopentanecarboxylic acid 4-{[(3,5-Dimethyl-pyridin-2-ylmethyl)-(5,6,7,8-tetrahydro-quinolin-8-yl)-amino]-methyl}-3-hydroxymethyl-benzylamide Using General Procedure G: COMPOUND 436 (50 mg, 0.12 mmol) was reacted with 1-p-tolyl-cyclopentanecarboxylic acid (31 mg, 0.15 mmol) to give COMPOUND 432 (65 mg, 90%) as a white solid. ¹H NMR (CDCl₃) δ 1.50-1.70 (m, 4H), 1.75-2.15 (m, 6H), 2.20 (s, 3H), 2.24 (s, 3H), 2.28 (s, 3H), 2.39-2.50 (m, 2H), 2.55-2.66 (m, 1H), 2.72-2.85 (m, 1H), 3.59-3.74 (m, 2H), 3.84 (t, 1H, J=7.5 Hz), 4.03-4.15 (m, 1H), 4.19-4.36 (m, 3H), 5.46 (s br, 1H), 6.88 (d, 1H, J=7.5 Hz), 7.00 (dd, 1H, J=7.5, 4.8 Hz), 7.04 (s, 1H), 7.07-7.15 (m, 3H), 7.19-7.32 (m, 4H), 8.15 (s, 1H), 8.36 (d, 1H, J=4.5 Hz); ES-MS m/z 603 (M+H).

Example 433

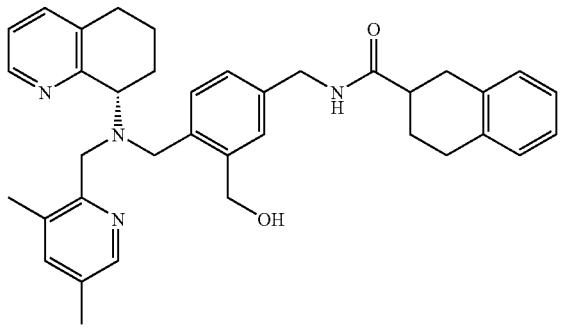

COMPOUND 433: 1,2,3,4-Tetrahydro-naphthalene-2-carboxylic acid 4-{[(3,5-dimethyl-pyridin-2-ylmethyl)-(5,6,7,8-tetrahydro-quinolin-8-yl)-amino]-methyl}-3-hydroxymethyl-benzylamide Using General Procedure G: COMPOUND 436 (50 mg, 0.12 mmol) was reacted with 1,2,3,4-tetrahydro-naphthalene-2-carboxylic acid (26 mg, 0.15 mmol) to give COMPOUND 433 (40 mg, 58%) as a white solid. ¹H NMR (CDCl₃) δ 1.50-1.64 (m, 1H), 1.77 (s br, 2H), 1.84-1.94 (m, 1H), 1.95-2.15 (m, 2H), 2.20 (s, 3H), 2.25 (s, 3H), 2.43-2.54 (m, 1H), 2.56-2.66 (m, 1H), 2.73-3.09 (m, 4H), 3.61-3.75 (m, 3H), 3.87 (t, 1H, J=7.5 Hz), 4.08-4.17 (m, 3H), 4.32-4.44 (m, 3H), 5.89 (s br, 1H), 6.99-7.12 (m, 6H), 7.21-7.33 (m, 4H), 8.16 (s, 1H), 8.37 (d, 1H, J=4.5 Hz); ES-MS m/z 575 (M+H).

Example 434

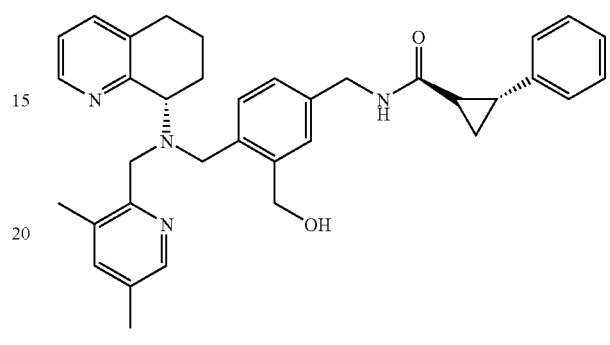

COMPOUND 434: trans-2-Phenyl-cyclopropanecarboxylic acid 4-{[(3,5-dimethyl-pyridin-2-ylmethyl)-(5,6,7,8-tetrahydro-quinolin-8-yl)-amino]-methyl}-3-hydroxymethyl-benzylamide Using General Procedure G: COMPOUND 436 (50 mg, 0.12 mmol) was reacted with trans-2-phenyl-cyclopropanecarboxylic acid (24 mg, 0.15 mmol) to give COMPOUND 434 (46 mg, 69%) as a white solid. ¹H NMR (CDCl₃) δ 1.19-1.26 (m, 2H), 1.58-1.66 (m, 2H), 1.96-2.05 (m, 1H), 2.09-2.15 (m, 2H), 2.21 (s, 3H), 2.25 (s, 3H), 2.49-2.55 (m, 1H), 2.58-2.68 (m, 1H), 2.74-2.85 (m, 1H), 3.60-3.75 (m, 3H), 3.87 (s br, 1H), 4.15 (d, 2H, J=12.0 Hz), 4.33-4.44 (m, 3H), 5.83 (s br, 1H), 6.99-7.11 (m, 5H), 7.16-7.32 (m, 6H), 8.17 (s, 1H), 8.37 (d, 1H, J=4.5 Hz); ES-MS m/z 561 (M+H).

Example 435

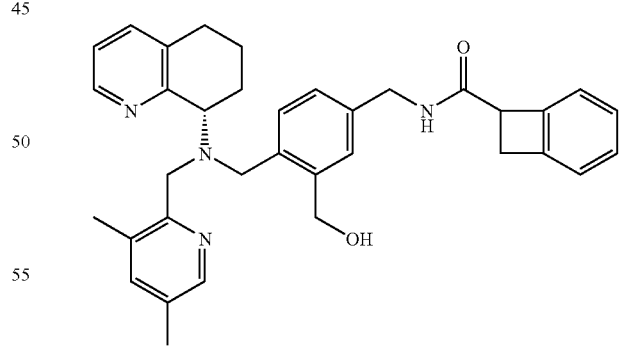

COMPOUND 435: Bicyclo[4.2.0]octa-1(6),2,4-triene-7-carboxylic acid 4-{[(3,5-dimethyl-pyridin-2-ylmethyl)-(5,6,7,8-tetrahydro-quinolin-8-yl)-amino]-methyl}-3-hydroxymethyl-benzylamide Using General Procedure G: COMPOUND 436 (50 mg, 0.12 mmol) was reacted with bicyclo[4.2.0]octa-1(6),2,4- triene-7-carboxylic acid (22 mg, 0.15 mmol) to give COMPOUND 435 (34 mg, 52%) as a white solid. $^1$H NMR (CDCl$_3$) δ 1.54-1.62 (m, 1H), 1.95-2.05 (m, 1H), 2.09-2.16 (m, 2H), 2.21 (s, 3H), 2.25 (s, 3H), 2.57-2.67 (m, 1H), 2.73-2.85 (m, 1H), 3.32 (dd, 1H, J=15.0, 3.0 Hz), 3.53-3.75 (m, 4H), 3.87 (t, 1H, J=7.5 Hz), 4.08-4.17 (m, 2H), 4.21-4.26 (m, 1H), 4.31-4.50 (m, 3H), 5.93 (s br, 1H), 6.99-7.15 (m, 4H), 7.18-7.27 (m, 5H), 7.31 (d, 1H, J=8.7 Hz), 8.16 (s, 1H), 8.37 (d, 1H, J=4.5 Hz); ES-MS m/z 547 (M+H).

Example 436

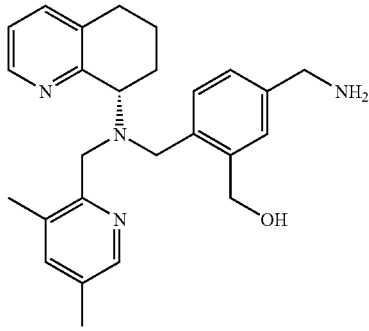

COMPOUND 436: (5-aminomethyl-2-{[(3,5-dimethyl-pyridin-2-ylmethyl)-(5,6,7,8-tetrahydro-quinolin-8-yl)-amino]-methyl}-phenyl)-methanol Using General Procedure A: Reaction of (S)-(3,5-dimethyl-pyridin-2-ylmethyl)-(5,6,7,8-tetrahydro-quinolin-8-yl)-amine in CH$_3$CN with 2-Bromomethyl-5-cyano-benzoic acid methyl ester, DIPEA and KI gave 5-cyano-2-{[(3,5-dimethyl-pyridin-2-ylmethyl)-(5,6,7,8-tetrahydro-quinolin-8yl)-amino]-methyl}-benzoic acid methyl ester as a red oil. $^1$H NMR (CDCl$_3$) δ 1.76 (m, 1H), 2.06 (m, 2H), 2.16 (s, 3H), 2.27 (s, 3H), 2.28 (m, 1H), 2.75 (m, 2H), 3.86 (m, 2H), 3.90 (s, 3H), 4.15 (m, 1H), 4.29 (m, 2H), 6.99 (d, 2H, J=15.8 Hz), 7.35 (d, 1H, J=6.6 Hz), 7.46 (d, 1H, J=7.9 Hz), 7.88 (s, 1H), 8.01 (s, 2H), 8.51 (s, 1H).

To a solution of 5-cyano-2-{[(3,5-dimethyl-pyridin-2-ylmethyl)-(5,6,7,8-tetrahydro-quinolin-8yl)-amino]-methyl}-benzoic acid methyl ester (6.29 g, 14.3 mmol) dissolved in MeOH (72 mL) was added LiBH$_4$ (3.1 g, 0.14 mmol). The mixture was stirred for 18 hours under a positive pressure of N$_2$. The mixture was concentrated in vacuo and redissolved in CH$_2$Cl$_2$ (75 mL). A saturated solution of NaHCO$_3$ (75 mL) was added. Extract with CH$_2$Cl$_2$ (2×50 mL). The combined organic extracts were dried (Na$_2$SO$_4$), filtered, and concentrated in vacuo to afford 4-{[(3,5-dimethyl-pyridin-2-ylmethyl)-(5,6,7,8-tetrahydro-quinolin-8-yl)-amino]-methyl}-3-hydroxymethyl-benzonitrile as an off white foam (5.82 g, 99%). $^1$H NMR (CDCl$_3$) δ 1.62 (m, 1H), 2.02 (m, 1H), 2.13 (m, 1H), 2.18 (s, 3H), 2.26 (s, 3H), 2.68 (m, 1H), 2.81 (m, 1H), 3.82 (m, 4H), 4.23 (m, 3H), 7.06 (dd, 1H, J=7.0, 5.7 Hz), 7.36 (d, 2H, J=7.5 Hz), 7.44 (m, 2H), 7.65 (s, 1H), 8.17 (s, 1H), 8.37 (d, 1H, J=3.9 Hz).

To a solution of (5-aminomethyl-2-{[(3,5-dimethyl-pyridin-2-ylmethyl)-(5,6,7,8-tetrahydro-quinolin-8-yl)-amino]-methyl}-phenyl)-methanol (5.82 g, 14.1 mmol) dissolved in MeOH (50 mL) bubble through NH$_3$ gas for 18 min. Add a prewashed mixture of Raney Nickel (4 g) to the nitrile and place onto the hydrogenator at 30 psi for 16 hours. Filter the mixture through a sintered glass funnel containing celite and concentrate. Purification via column chromatography on silica gel (CH$_2$Cl$_2$:MeOH:NH$_4$OH, 94:5:1, v/v/v) afforded the product as a off white solid (4.45 g, 76%). $^1$H NMR (CDCl$_3$) δ 1.56 (m, 1H), 1.96 (m, 2H), 2.16 (m, 1H), 2.19 (s, 3H), 2.24 (s, 3H), 2.60 (m, 1H), 2.77 (m, 1H), 3.64 (m, 3H), 3.74 (m, 3H), 4.09 (s, 1H), 4.13 (d, 1H, J=12.3 Hz), 4.34 (d, 1H, J=10.5 Hz), 6.97 (dd, 1H, J=7.5, 4.4 Hz), 7.12 (d, 1H, J=8.3 Hz), 7.14 (d, 2H, J=8.8 Hz), 7.22 (d, 2H, J=12.7 Hz), 8.15 (s, 1H), 8.33 (d, 1H, J=3.5 Hz). $^{13}$C NMR (CDCl$_3$) δ 18.30, 18.58, 20.97, 22.09, 29.78, 45.88, 54.27, 54.64, 57.76, 62.86, 121.99, 126.80, 130.99, 131.51, 132.28, 133.78, 134.99, 136.28, 137.06, 139.38, 141.60, 142.55, 146.53, 146.94, 153.67, 157.23. Anal. Calcd. For (C$_{26}$H$_{32}$N$_4$O) 0.3 (CH$_2$Cl$_2$): C, 71.46; H, 7.43; N, 12.67. Found: C, 71.47; H, 7.52; N, 12.60.

Example 437

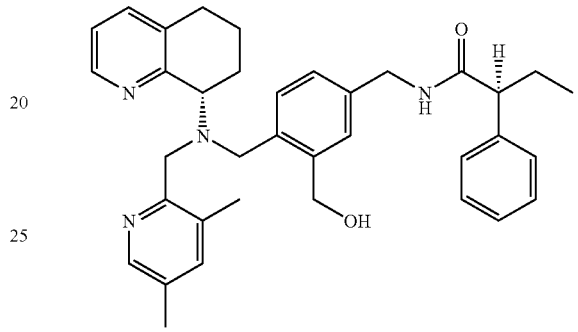

COMPOUND 437: N-(4-{[(3,5-dimethyl-pyridin-2-ylmethyl)-(5,6,7,8-tetrahydro-quinolin-8-yl)-amino]-methyl}-3-hydroxymethyl-benzyl)-2-phenyl-butyramide Using General Procedure G: To a solution of (5-aminomethyl-2-{[(3,5-dimethyl-pyridin-2-ylmethyl)-(5,6,7,8-tetrahydro-quinolin-8-yl)-amino]-methyl}-phenyl)-methanol (0.12 g, 0.26 mmol) dissolved in CH$_2$Cl$_2$ (10 mL) was added (S)-2-phenylbutyric acid (60 µl, 0.39 mmol), EDCI (0.08 g, 0.39 mmol), HOBT (0.05 g, 0.39 mmol), and DIPEA (67 µl, 0.39 mmol). Purification via column chromatography on silica gel (CH$_2$Cl$_2$:MeOH, 97:3, v/v) afforded the product as a colorless oil (0.08 g, 53%). $^1$H NMR (CDCl$_3$) δ 0.88 (m, 3H), 1.51 (m, 1H), 1.86 (m, 1H), 2.05 (m, 1H), 2.11 (m, 3H), 2.14 (s, 3H), 2.24 (s, 3H), 2.79 (m, 2H), 3.20 (m, 1H), 3.70 (m, 4H), 4.09 (m, 2H), 4.33 (m, 3H), 5.69 (s, 1H), 6.95 (m, 2H), 7.13 (m, 2H), 7.22 (m, 7H), 8.15 (s, 1H), 8.35 (s, 1H); ES-MS m/z 564 (M+H).

Example 438

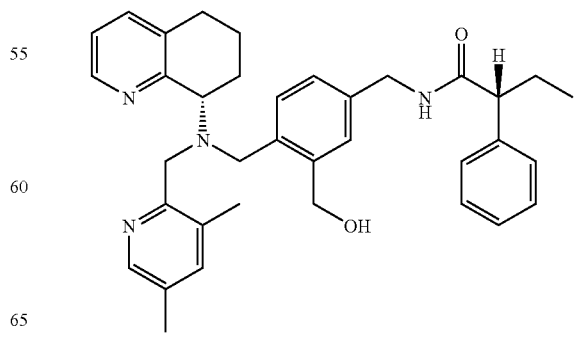

361

COMPOUND 438: N-(4-{[(3,5-dimethyl-pyridin-2-ylmethyl)-(5,6,7,8-tetrahydro-quinolin-8-yl)-amino]-methyl}-3-hydroxymethyl-benzyl)-2-phenyl-butyramide Using General Procedure G: To a solution of (5-aminomethyl-2-{[(3,5-dimethyl-pyridin-2-ylmethyl)-(5,6,7,8-tetrahydro-quinolin-8-yl)-amino]-methyl}-phenyl)-methanol (0.12 g, 0.26 mmol) dissolved in $CH_2Cl_2$ (10 mL) was added (R)-2-phenylbutyric acid (60 µl, 0.39 mmol), EDCI (0.08 g, 0.39 mmol), HOBT (0.05 g, 0.39 mmol), and DIPEA (67 µl, 0.39 mmol). Purification via column chromatography on silica gel ($CH_2Cl_2$:MeOH, 97:3, v/v) afforded the product as a colorless oil (0.06 g, 36%). $^1$H NMR ($CDCl_3$) δ 0.88 (m, 3H), 1.51 (m, 1H), 1.86 (m, 1H), 2.05 (m, 1H), 2.11 (m, 3H), 2.14 (s, 3H), 2.24 (s, 3H), 2.79 (m, 2H), 3.20 (m, 1H), 3.70 (m, 4H), 4.09 (m, 2H), 4.33 (m, 3H), 5.69 (s, 1H), 6.95 (m, 2H), 7.13 (m, 2H), 7.22 (m, 7H), 8.15 (s, 1H), 8.35 (s, 1H); ES-MS m/z 564 (M+H).

Example 439

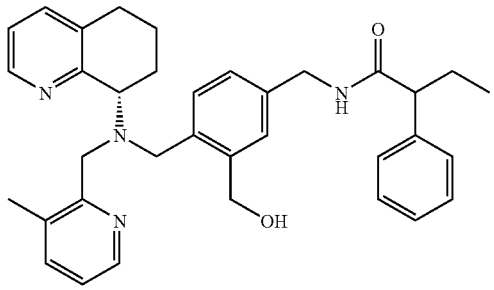

COMPOUND 439: N-(-3-hydroxymethyl-4-{[(3-methyl-pyridin-2-ylmethyl)-(5,6,7,8-tetrahydro-quinolin-8-yl)-amino]-methyl}-benzyl)-2-phenyl-butyramide Using General Procedure G: To a solution (S)-(5-aminomethyl-2-{[(3-methyl-pyridin-2-ylmethyl)-(1,2,3,4-tetrahydro-naphthalen-1-yl)amino]-methyl}-phenyl)-methanol (128 mg, 0.32 mmol) dissolved in $CH_2Cl_2$ (10 mL) was added (S)-2-phenylbutyric acid (74 µl, 0.48 mmol), EDCI (92 mg, 0.48 mmol), HOBT (65 mg, 0.48 mmol), and DIPEA (83 µl, 0.48 mmol). Purification via column chromatography on silica gel ($CH_2Cl_2$:MeOH, 97:3, v/v) afforded COMPOUND 439 as a colorless oil (37 mg, 22%). $^1$H NMR ($CDCl_3$) δ 0.86 (m, 3H), 1.44 (m, 2H), 1.81 (m, 1H), 2.18 (m, 1H), 2.23 (s, 6H), 2.64 (m, 2H), 3.22 (m, 1H), 3.85 (m, 4H), 4.14 (m, 2H), 4.31 (m, 2H), 5.73 (m, 1H), 7.14 (m, 12H), 8.36 (m, 2H); ES-MS m/z 572 (M+H).

Example 440

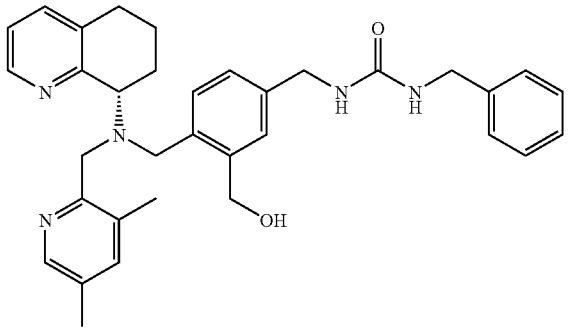

362

COMPOUND 440: 1-benzyl-3-(4-{[(3,5-dimethyl-pyridin-2-ylmethyl)-(5,6,7,8-tetrahydro-quinolin-8-yl)-amino]-methyl}-3-hydroxymethyl-benzyl)-urea A solution (5-aminomethyl-2-{[(3,5-dimethyl-pyridin-2-ylmethyl)-(5,6,7,8-tetrahydro-quinolin-8-yl)-amino]-methyl}-phenyl)-methanol (0.12 g, 0.26 mmol) dissolved in $CH_2Cl_2$ (10 mL) was cooled down to a temperature of 0° C. Benzyl isocyanate (0.03 g, 0.26 mmol) was added and the solution was stirred at 0° C. for 16 hours under a positive pressure of $N_2$. The reaction was quenched using a saturated $NaHCO_3$ solution (25 mL). Extract with $CH_2Cl_2$ (2×25 mL). The combined organic extracts were dried ($Na_2SO_4$), filtered, and concentrated in vacuo to afford a light yellow oil. Purification via column chromatography on silica gel ($CH_2Cl_2$:MeOH, 99:1, v/v) afforded the product as a white solid (0.13 g, 91%). $^1$H NMR ($CDCl_3$) δ 1.38 (m, 1H), 1.89 (m, 2H), 2.04 (m, 1H), 2.09 (s, 3H), 2.19 (s, 3H), 2.47 (m, 1H), 2.67 (m, 1H), 3.49 (d, 2H, J=11.8 Hz), 3.65 (d, 2H, J=12.7 Hz), 4.06 (m, 7H), 5.94 (m, 2H), 7.04 (m, 11H), 8.10 (s, 1H), 8.17 (d, 1H, J=3.9 Hz); $^{13}$C NMR ($CDCl_3$) δ 18.28, 18.48, 21.06, 21.90, 29.63, 44.07, 44.23, 53.89, 54.05, 54.33, 57.51, 62.87, 122.05, 127.01, 127.57, 128.60, 130.86, 131.33, 132.27, 133.57, 134.94, 136.03, 137.01, 139.35, 140.11, 140.30, 142.03, 146.55, 146.87, 153.54, 156.99, 159.26; HPLC (98.05%); ES-MS m/z 550 (M+H). Anal. Calcd. for ($C_{34}H_{39}N_5O_2$) 0.1 ($CH_2Cl_2$): C, 73.37; H, 7.08; N, 12.55. Found: C, 72.95; H, 7.07; N, 12.43.

Example 441

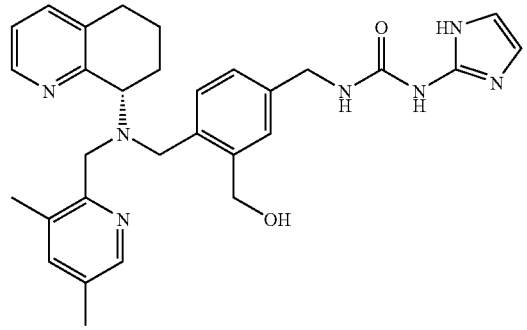

COMPOUND 441: 1-(4-{[(3,5-dimethyl-pyridin-2-ylmethyl)-(1,2,3,4-tetrahydro-naphthalen-1-yl)-amino]-methyl}-3-hydroxymethyl-benzyl)-3-(1H-imidazol-2-yl)-urea To a solution of 1,1-carbonyldiimidazole (117 mg, 0.72 mmol) dissolved in $CH_2Cl_2$ (10 mL) add 2-aminoimidazole sulfate (95 mg, 0.72 mmol). The solution was stirred for 16 hours under a positive pressure of $N_2$. The reaction mixture was concentrated in vacuo and redissolved in DMF (10 mL). Addition of DIPEA (250 ul, 1.44 mmol) and (5-aminoethyl-2-{[(3,5-dimethyl-pyridin-2-ylmethyl)-(1,2,3,4-tetrahydro-naphthalen-1-yl)-amino]-methyl}-phenyl)-methanol (100 mg, 0.24 mmol) was made to the solution. The solution was stirred at 75° C. for 16 hours under a positive pressure of $N_2$. The solution was concentrated in vacuo and redissolved in $CH_2Cl_2$ (20 mL). The reaction mixture was quenched with a solution of saturated $NaHCO_3$ (20 mL). Extract with $CH_2Cl_2$ (3×25 mL). The combined organic extracts were dried ($Na_2SO_4$), filtered, and concentrated in vacuo to afford a light yellow oil. Purification via column chromatography on silica gel ($CH_2Cl_2$:MeOH, 97:3, v/v) afforded the product as a colorless oil (20 mg, 16%). $^1H$ NMR ($CDCl_3$) δ 1.55 (m, 1H), 2.05 (m, 3H), 2.18 (s, 3H), 2.24 (s, 3H), 2.77 (m, 2H), 3.61 (m, 1H), 3.67 (d, 1H, J=11.4 Hz), 3.72 (d, 1H, J=12.7 Hz), 3.83 (m, 1H), 4.11 (m, 2H), 4.35 (m, 3H), 6.59 (s, 2H), 7.23 (m, 5H), 7.66 (s, 1H), 8.16 (s, 1H), 8.31 (m, 1H). ES-MS m/z 526 (M+H).

Example 442

Assay for Inhibition of HIV-1 (NL4.3) Replication in PBMC's

Inhibition of HIV-1 NL4.3 replication assays in PBMC's (peripheral blood mononuclear cells) are performed as previously described (De Clercq et al. *Proc. Natl. Acad. Sci*, 1992, 89, 5286-5290; De Clercq et al. *Antimicrob. Agents Chemother.* 1994, 38, 668-674; Schols, D. et al. *J. Exp. Med.* 1997, 186, 1383-1388). Briefly, PBMC's from healthy donors are isolated by density gradient centrifugation and stimulated with PHA at 1 μg/ml (Sigma Chemical Co., Bornem, Belgium) for 3 days at 37° C. The activated cells (PHA-stimulated blasts) are washed three times with PBS, and viral infections are performed as described by Cocchi et al. (Science 1995, 270, 1811-1815). HIV-infected or mock-infected PHA-stimulated blasts are cultured in the presence of 25 U/mL of IL-2 and varying concentrations of test compounds. Supernatant is collected at days 6 and 10, and HIV-1 core antigen in the culture supernatant is analyzed by the p24 ELISA kit (DuPont-Merck Pharmaceutical Co, Wilmington, Del.). The 50% inhibitory concentration ($IC_{50}$) is defined as the concentration of test compound required to inhibit p24 antigen production by 50%.

When tested in the assay described above, many compounds of the invention exhibit $IC_{50}$'s in the range 0.5 nM-5 μM.

Example 443

Assay for Inhibition of SDF-1α Induced Ca Flux in CEM Cells

Inhibition of SDF-1 induced calcium flux is assayed using CCRF-CEM cells, a T-lymphoblastoid cell line which expresses CXCR4. CCRF-CEM cells (5×10$^6$ cells/mL in RPMI 1640 medium containing 2% foetal bovine serum) is pre-loaded with 1 μM Fluo-4 fluorescent calcium indicator dye and incubated at 37° C. for 40 minutes. The loaded cells are washed and resuspended in buffer containing 20 mM HEPES pH 7.4, 1× Hanks Balanced Salt Solution (HBSS), 0.2% bovine serum albumin, 2.5 mM probenecid and plated out in 96 well tissue culture plates at 3.5×10$^5$ cells per well. The cells are incubated with test compound, or buffer control, for 15 minutes at 37° C. Calcium flux is stimulated by addition of 25 nM SDF-1 and fluorescence measured using a FLEXstation fluorescence plate reader (Molecular Devices). Ionomycin is added 80 seconds after addition of SDF-1 in order to measure total calcium loading. Compounds are tested at a concentration range of 2000-0.128 nM. Fluorescence measurements are normalised with respect to untreated controls. The 50% inhibitory concentration ($IC_{50}$ value) is defined as the concentration of test compound required to inhibit SDF-1-induced calcium flux by 50% relative to untested controls.

When tested in the assay described above, the compounds of the invention exhibit $IC_{50}$s in the range 0.5 nM-5 μM.

Example 444

Elevation of Mouse Progenitor Cell Levels

The effects of subcutaneous (s.c.) administration of 1,1'-[1,4-phenylene-bis(methylene)]-bis-1,4,8,11-tetraazacyclotetradecane (AMD3100) to C3H/H3 J mice on numbers of granulocyte macrophage (CFU-GM), erythroid (BFU-E), and multipotential (CFU-GEMM) progenitor cells per mL of blood were measured. Progenitors were stimulated to form colonies in vitro with the combination of 1 U/ml rhu Epo, 50 ng/ml rhu SLF, 5% $^{vol}/_{vol}$ pokeweed mitogen mouse spleen cell conditioned medium (PWMSCM), and 0.1 mM hemin. Plates were scored 7 days after incubation.

The time dependent effects on the number of progenitors mobilized with AMD3100 are for a single s.c. injection of 5 mg/Kg and are shown in Table 11.

TABLE 11

| | Absolute Progenitors Per ML Blood Methylcellulose Culture | | |
|---|---|---|---|
| | CFU-GM | BFU-E | CFU-GEMM |
| Control | 289.8 | 49.4 | 25.8 |
| AMD3100: 15" | 791.6 | 134.5 | 90.4 |
| AMD3100: 30" | 1805.5 | 209.3 | 113.5 |
| AMD3100: 120" | 828.7 | 102.3 | 47.6 |

To measure the dose-dependent effects, AMD3100 was administered at 1, 2.5, 5 and 10 mg/Kg via a single s.c. injection and the number of progenitors per mL of blood was measured at 1 hour post administration, and the results are shown in Table 12.

TABLE 12

| | Absolute Number Progenitors Per ML Blood Methylcellulose Culture | | |
|---|---|---|---|
| | CFU-GM | BFU-E | CFU-GEMM |
| Saline | 188.1 | 16 | 19 |
| AMD3100: 10 mg/kg | 825.6 | 120.5 | 79.8 |
| AMD3100: 5 mg/kg | 608.4 | 92.8 | 69.5 |
| AMD3100: 2.5 mg/kg | 687.6 | 98.9 | 70.6 |
| AMD3100: 1 mg/kg | 424 | 62 | 27.1 |

| Fold Change Compared to Time 0 | | | |
|---|---|---|---|
| | Progenitors Methylcellulose Culture | | |
| Time | GM | BFU-E | CFU-GEMM |
| 15" | 2.73 | 2.72 | 3.51 |
| 30" | 6.23 | 4.24 | 4.41 |
| 2' | 2.86 | 2.07 | 1.85 |

Maximum mobilization of mouse progenitors is achieved at a dose of 2.5 to 10 mg/kg AMD3100, approximately 0.5 to 1 hour after injection, as shown in Table 13. The compounds of the invention behave in a manner similar to AMD3100.

Example 445

Mobilization of Mouse Progenitor Cells in Combination with MIP-1α and G-CSF

The progenitor cell mobilization capacity of AMD3100 in combination with mouse (mu) macrophage inflammatory protein (MIP-1α) was tested with or without prior administration of rhu G-CSF. MIP-1α has been previously shown to mobilize progenitor cells in mice and humans (Broxmeyer, H. E., et al., *Blood Cells, Molecules, and Diseases* (1998) 24(2): 14-30).

Groups of mice were randomized to receive control diluent (saline) or G-CSF at a dose of 2.5 µg per mouse, twice a day, for two days via s.c. injection. Eleven hours after the final injection of saline or G-CSF, the mice were divided into groups to receive MIP-1α administered I.V. at a total dose of 5 µg, AMD3100 administered s.c. at a dose of 5 mg/Kg, or a combination of both MIP-1α and AMD3100 at the same doses. One hour later, the mice were sacrificed and the number of progenitor cells per mL of blood were measured.

AMD3100 acts in an additive to greater than additive manner for mobilization of progenitor cells when used in combination with mouse (mu) macrophage inflammatory protein (MIP)-1α, each given 11 hours after the addition of rhu G-CSF or control diluent (saline) and 1 hour prior to assessing the blood. The compounds of the invention behave in a manner similar to AMD3100.

Example 446

Clinical Elevation of Progenitor Cell Levels

Five healthy human volunteers having initial white blood cell counts of 4,500-7,500 cells/mm$^3$ were used in the study. Each patient was given a single subcutaneous (s.c.) injection of 80 µg/kg AMD3100 (i.e., 1,1'-[1,4-phenylene-bis(methylene)]-bis-1,4,8,11-tetraazacyclotetradecane) in 0.9% saline, from a stock solution of 10 mg/mL AMD3100 in saline, under sterile conditions. Blood samples were obtained via catheter prior to the dose, and at various times up to 24 hours after dosing.

The blood samples were evaluated for total white blood cells, CD34 positive progenitor cells (via FACS analysis) as a percentage of total white blood cells, as well as the absolute numbers per mL and cycling status of granulocyte macrophage (CFU-GM), erythroid (BFU-E), and multipotential (CFU-GEMM) progenitor cells.

As shown in Tables 13 and 14, administration of AMD3100 caused an elevation of the white blood cell count and of CD34 positive progenitor cells in human volunteers which maximized at 6 hours post-administration.

TABLE 13

AMD3100 induced mobilization of white blood cells in individual volunteers (×10$^3$ WBC's).

| | | | | TREATMENT | | | | | | |
|---|---|---|---|---|---|---|---|---|---|---|
| ID | Screen | Base-line | 30 Min | 1 Hr | 2 Hr | 4 Hr | 6 Hr | 9 Hr | Day 2 |
| P1 | 7.4 | 6.41 | 8.02 | 14.8 | 21.4 | 23.2 | 26.2 | 22.3 | 7.07 |
| P2 | 6.04 | 5.45 | 6.53 | 8.93 | 13.5 | 18.00 | 19.2 | 19.6 | 8.03 |
| P3 | 4.38 | 5.8 | 7.14 | 9.28 | ND | 18.10 | 17.9 | 18.4 | 4.98 |
| P4 | 5.08 | 5.31 | 4.37 | 7.38 | 12.4 | 14.6 | 15.8 | 13.9 | 4.98 |
| P5 | 4.53 | 5.02 | 6.08 | 8.43 | ND | 16.90 | 19.3 | 19.00 | 4.57 |

TABLE 14

AMD3100 induced mobilization of CD34 positive cells, expressed as the percentage of the total WBC's in individual volunteers.

| | | TREATMENT | | | | |
|---|---|---|---|---|---|---|
| ID | Baseline | 1 Hr | 3 Hr | 6 Hr | 9 Hr | Day 2 |
| P1 | .07 | .04 | .07 | .11 | .11 | .08 |
| P2 | .08 | .06 | .08 | .13 | .11 | .12 |
| P3 | .07 | .16 | .06 | ND | .11 | .07 |
| P4 | .05 | .07 | .09 | .09 | .1 | .1 |
| P5 | .12 | .12 | .13 | .2 | .2 | .16 |

The blood was also analyzed for AMD3100 mobilized these progenitors.

Absolute numbers of unseparated and low density (Fico-hypaque separated) nucleated cells per ml of blood, as well as the absolute numbers per ml and cycling status of granulocyte macrophage (CFU-GM), erythroid (BFU-E), and multipotential (CFU-GEMM) progenitor cells were measured in normal donors injected s.c. with AMD3100. The above parameters were assessed prior to injection and at 1, 3, 6, 9 and 24 hours after injection of AMD3100. All progenitor cell results are based on the scoring of 3 culture plates per assay per point.

For the progenitor cell numbers and cycling status, the numbers of CFU-GM, BFU-E and CFU-GEMM in methylcellulose cultures by stimulation of the cells with 1 Unit (U)/ml recombinant human (rhu) erythropoietin, 100 U/ml rhu granulocyte-macrophage colony stimulating factor (GM-CSF), 100 U/ml rhu interleukin-3 (IL-3) and 50 ng/ml rhu steel factor (SLF=stem cell factor (SCF)). The CFU-GM were also evaluated in agar cultures stimulated with 100 U/ml rhu GM-CSF and 50 ng/ml rhu SLF. For both types of assays, colonies were scored after 14 day incubation in a humidified atmosphere with 5% $CO_2$ and lowered (5%) $O_2$ tension. Cell cycling status of progenitors was measured using a high specific activity tritiated thymidine kill technique as previously described (Broxmeyer, H. E., et al., *Exp. Hematol.* (1989) 17:455-459).

The results are given first, as the mean fold change in absolute numbers of nucleated cells and progenitors at 1, 3, 6, 9 and 24 hours compared to the preinjection (=Time (T) 0) counts for all five donors, as seen in Tables 15-17.

In the tables below,

TABLE 15

Fold Change Compared to TIME = 0 (Average of 5 donors)

NUCLEATED CELLULARITY

| | PBL-US | | | | | PBL-LD | | | | |
|---|---|---|---|---|---|---|---|---|---|---|
| | MEAN | STD | STE | % CHG | P | MEAN | STD | STE | % CHG | P |
| T = 0 | 1.00 | 0.00 | 0.00 | 0.0% | | 1.00 | 0.00 | 0.00 | 0.0% | |
| T = 1 | 1.69 | 0.00 | 0.00 | 68.6% | 0.017 | 1.86 | 0.00 | 0.00 | 86.2% | 0.000 |
| T = 3 | 2.80 | 0.51 | 0.23 | 180.2% | 0.000 | 2.86 | 0.28 | 0.12 | 185.6% | 0.000 |
| T = 6 | 3.26 | 0.61 | 0.27 | 225.8% | 0.000 | 3.66 | 0.43 | 0.19 | 266.3% | 0.001 |
| T = 9 | 3.09 | 0.69 | 0.31 | 209.4% | 0.000 | 3.64 | 1.18 | 0.53 | 264.3% | 0.001 |
| T = 24 | 1.07 | 0.65 | 0.29 | 7.0% | 0.553 | 1.05 | 1.19 | 0.53 | 4.6% | 0.815 |

STD - Standard deviation
STE - Standard error
PBL-US - peripheral blood-useparated
PBL-LD - peripheral blood-low density (Ficoll Separated)
P - Significance using a 2 tailed t test

TABLE 16

METHYLCELLULOSE CULTURE

| | CFU-GM | | | | | BFU-E | | | | | CFU-GEMM | | | | |
|---|---|---|---|---|---|---|---|---|---|---|---|---|---|---|---|
| | MEAN | STD | STE | % CHG | P | MEAN | STD | STE | % CHG | P | MEAN | STD | STE | % CHG | P |
| T = 0 | 1.00 | 0.00 | 0.00 | 0.0% | | 1.00 | 0.00 | 0.00 | 0.0% | | 1.00 | 0.00 | 0.00 | 0.0% | |
| T = 1 | 4.77 | 0.00 | 0.00 | 376.7% | 0.001 | 1.99 | 0.00 | 0.00 | 98.9% | 0.002 | 2.32 | 0.00 | 0.00 | 131.8% | 0.000 |
| T = 3 | 13.66 | 1.56 | 0.70 | 1266.5% | 0.001 | 3.21 | 0.50 | 0.22 | 221.3% | 0.004 | 4.33 | 0.44 | 0.20 | 332.5% | 0.000 |
| T = 6 | 21.71 | 5.78 | 2.58 | 2070.6% | 0.000 | 6.01 | 1.25 | 0.56 | 500.5% | 0.006 | 10.07 | 0.59 | 0.27 | 907.2% | 0.002 |
| T = 9 | 10.47 | 5.09 | 2.28 | 947.3% | 0.000 | 4.34 | 2.99 | 1.34 | 334.4% | 0.000 | 5.25 | 4.54 | 2.03 | 425.4% | 0.014 |
| T = 24 | 1.56 | 3.01 | 1.34 | 55.5% | 0.005 | 1.26 | 1.02 | 0.45 | 26.3% | 0.194 | 1.53 | 3.04 | 1.36 | 53.2% | 0.199 |

TABLE 17

AGAR CULTURE
CFU-GM

| | MEAN | STD | STE | % CHG | P |
|---|---|---|---|---|---|
| T = 0 | 1.00 | 0.00 | 0.00 | 0.0% | |
| T = 1 | 2.81 | 0.00 | 0.00 | 180.8% | 0.001 |
| T = 3 | 8.54 | 0.75 | 0.34 | 754.1% | 0.000 |
| T = 6 | 17.93 | 1.62 | 0.72 | 1692.8% | 0.000 |
| T = 9 | 10.25 | 4.57 | 2.04 | 924.9% | 0.000 |
| T = 24 | 2.08 | 2.06 | 1.03 | 108.3% | 0.073 |

The results are then shown as a fold change from T=0 levels for each individual donor, as shown in Tables 18-20.

TABLE 18

FOLD CHANGE COMPARED TO TIME = 0 for each individual patient (P)

NUCLEATED CELLULARITY

| | PBL-US | | | | | PBL-LD | | | | |
|---|---|---|---|---|---|---|---|---|---|---|
| | P1 | P2 | P3 | P4 | P5 | P1 | P2 | P3 | P4 | P5 |
| T = 0 | 1.00 | 1.00 | 1.00 | 1.00 | 1.00 | 1.00 | 1.00 | 1.00 | 1.00 | 1.00 |
| T = 1 | 2.54 | 1.38 | 1.38 | 1.36 | 1.76 | 2.07 | 1.99 | 1.48 | 1.66 | 2.10 |
| T = 3 | 3.55 | 2.74 | 2.02 | 2.46 | 3.23 | 2.83 | 3.25 | 2.17 | 2.82 | 3.20 |
| T = 6 | 3.97 | 2.94 | 2.74 | 2.60 | 4.04 | 4.07 | 3.90 | 2.27 | 2.78 | 5.30 |
| T = 9 | 3.27 | 3.30 | 2.69 | 2.24 | 3.96 | 3.65 | 4.43 | 2.47 | 2.48 | 5.17 |
| T = 24 | 1.21 | 1.43 | 0.96 | 0.77 | 0.99 | 1.01 | 1.71 | 0.79 | 0.60 | 1.12 |

TABLE 19

PROGENITORS

METHYLCELLULOSE CULTURE

| | CFU-GM | | | | | BFU-E | | | | | CFU-GEMM | | | | |
|---|---|---|---|---|---|---|---|---|---|---|---|---|---|---|---|
| | P1 | P2 | P3 | P4 | P5 | P1 | P2 | P3 | P4 | P5 | P1 | P2 | P3 | P4 | P5 |
| T = 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| T = 1 | 5.09 | 5.33 | 3.70 | 6.87 | 2.84 | 2.58 | 1.43 | 2.30 | 1.46 | 2.13 | 2.07 | 2.26 | 2.22 | 1.96 | 3.07 |
| T = 3 | 7.12 | 17.02 | 15.07 | 20.72 | 8.40 | 5.13 | 1.98 | 2.61 | 2.60 | 3.75 | 4.25 | 3.47 | 4.34 | 5.14 | 4.43 |
| T = 6 | 14.66 | 23.96 | 20.99 | 28.54 | 20.39 | 9.14 | 3.67 | 4.54 | 3.34 | 9.35 | 7.47 | 9.35 | 6.52 | 9.10 | 17.92 |
| T = 9 | 6.26 | 12.51 | 9.42 | 14.08 | 10.09 | 5.43 | 4.61 | 3.71 | 2.93 | 5.05 | 2.64 | 7.09 | 2.47 | 4.52 | 9.55 |
| T = 24 | 1.10 | 1.91 | 1.43 | 1.51 | 1.83 | 1.06 | 1.88 | 1.14 | 0.79 | 1.44 | 1.12 | 2.62 | 0.69 | 0.98 | 2.25 |

TABLE 20

AGAR CULTURE
CFU-GM

| | P1 | P2 | P3 | P4 | P5 |
|---|---|---|---|---|---|
| T = 0 | 1.00 | 1.00 | 1.00 | 1.00 | 1.00 |
| T = 1 | 3.05 | 3.74 | 1.67 | 2.71 | 2.87 |
| T = 3 | 8.88 | 9.49 | 7.47 | 10.46 | 6.40 |
| T = 6 | 17.77 | 24.01 | 14.04 | 13.07 | 20.75 |
| T = 9 | | 10.28 | 7.72 | 10.22 | 12.78 |
| T = 24 | | 3.69 | 1.13 | 1.30 | 2.20 |

The actual nucleated cell and progenitor cell numbers per ml of blood and the cycling status (=% progenitors in DNA synthesis (S) phase of the cell cycle) of progenitors for each of the five donors (#'s P1, P2, P3, P4, and P5) is shown in Tables 21 and 22.

TABLE 21

| | P1 | | | | | | P2 | | | | | |
|---|---|---|---|---|---|---|---|---|---|---|---|---|
| | CFU-GM | | BFU-E | | CFU-GEMM | | CFU-GM | | BFU-E | | CFU-GEMM | |
| | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 247 | 6% | 261 | 0% | 127 | 6% | 273 | 0% | 410 | 2% | 120 | 0% |
| T = 1 | 1259 | 1% | 674 | 0% | 264 | 0% | 1455 | 0% | 608 | 3% | 272 | 6% |
| T = 3 | 1760 | 1% | 1340 | 13% | 540 | 7% | 4646 | 2% | 809 | 0% | 418 | 0% |
| T = 6 | 3624 | 0% | 2388 | 0% | 949 | 0% | 6540 | 0% | 1502 | 0% | 1126 | 0% |
| T = 9 | 1547 | 2% | 1418 | 11% | 335 | 0% | 3416 | 0% | 1886 | 0% | 854 | 4% |
| T = 24 | 271 | 0% | 278 | 0% | 142 | 0% | 521 | 3% | 768 | 2% | 316 | 0% |

| | P3 | | | | | | P4 | | | | | |
|---|---|---|---|---|---|---|---|---|---|---|---|---|
| | CFU-GM | | BFU-E | | CFU-GEMM | | CFU-GM | | BFU-E | | CFU-GEMM | |
| | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 281 | 0% | 351 | 0% | 140 | 0% | 138 | 0% | 460 | 0% | 101 | 0% |
| T = 1 | 1040 | 0% | 806 | 0% | 312 | 0% | 947 | 0% | 672 | 0% | 199 | 0% |
| T = 3 | 4233 | 1% | 915 | 0% | 610 | 0% | 2857 | 5% | 1195 | 9% | 519 | 0% |
| T = 6 | 5895 | 0% | 1593 | 0% | 916 | 0% | 3936 | 0% | 1533 | 0% | 920 | 8% |
| T = 9 | 2647 | 0% | 1302 | 0% | 347 | 0% | 1942 | 0% | 1343 | 0% | 457 | 0% |
| T = 24 | 402 | 0% | 402 | 0% | 97 | 0% | 208 | 5% | 362 | 3% | 99 | 0% |

TABLE 21-continued

|  | CFU-GM | | BFU-E P5 | | CFU-GEMM | |
| --- | --- | --- | --- | --- | --- | --- |
|  | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 169 | 0% | 343 | 1% | 55 | 0% |
| T = 1 | 481 | 0% | 730 | 0% | 169 | 0% |
| T = 3 | 1423 | 5% | 1288 | 3% | 244 | 0% |
| T = 6 | 3454 | 0% | 3208 | 1% | 987 | 0% |
| T = 9 | 1710 | 0% | 1731 | 0% | 526 | 0% |
| T = 24 | 310 | 0% | 495 | 0% | 124 | 0% |

TABLE 22

|  | AGAR Culture CFU-GM P1 | | AGAR Culture CFU-GM P2 | | AGAR Culture CFU-GM P3 | | AGAR Culture CFU-GM P4 | | AGAR Culture CFU-GM P5 | |
| --- | --- | --- | --- | --- | --- | --- | --- | --- | --- | --- |
|  | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 233 | 6% | 100 | 0% | 140 | 0% | 124 | 0% | 104 | 0% |
| T = 1 | 710 | 0% | 376 | 0% | 234 | 0% | 336 | 0% | 298 | 3% |
| T = 3 | 2070 | 0% | 953 | 1% | 1049 | 0% | 1299 | 0% | 664 | 0% |
| T = 6 | 4142 | 0% | 2409 | 3% | 1972 | 3% | 1623 | 0% | 2153 | 1% |
| T = 9 |  |  | 1032 | 0% | 1085 | 0% | 1268 | 0% | 1326 | 0% |
| T = 24 |  |  | 371 | 0% | 159 | 0% | 162 | 0% | 229 | 0% |

The results for all five donors were very consistent with maximal fold increases in circulating levels of progenitor cells seen 6 hours after injection of AMD3100 into the human donor subjects. Progenitors were in a slow or non-cycling state prior to and 1, 3, 6, 9 and 24 hours after injection of AMD3100. The compounds of the invention behave in a manner similar to AMD3100.

Example 447

Mobilized Bone Marrow Stem Cells for Myocardial Repair

Adult rats are anesthetized and a thoracotomy is performed. The descending branch of the left coronary artery is ligated and not reperfused. Within 4 to 6 hours after ligation the animals are injected with limit dilution AMD-3100 or AMD-3100 plus rhG-CSF. Control rats are not treated with the reagents. The animals are monitored at one-week intervals by echocardiography and MRI. The experiment is terminated at 2, 6 to 12 weeks post-surgery. On the day of sacrifice, the hemodynamic functions are analyzed for left ventricle-end diastolic pressure, left ventricle-developed pressure and the rate of rise and fall of left ventricle pressure. The heart is then arrested in diastole and perfused via the abdominal aorta to flush residual blood from the vascular network of the myocardium. This is followed by perfusion of the heart with 10% formalin. Several slices are made through the fixed heart and these are embedded in paraffin and sections. The sections are stained and analyzed by light microscopy to determine the size of the infarct in the treated and control animals. Tissue sections from hearts taken at 2 weeks after surgery are stained with antibodies specific for immature, developing myocyte and blood vessel proteins and analyzed by confocal microscopy. The immunohistochemical analysis involves the identification of transcription factors and surface markers expressed in early stages of myocyte development. The results of this experiment will show that when the reagent AMD-3100 is administered within hours after induction of cardiac ischemia, together with or without rhG-CSF, this reagent mobilizes bone marrow stem cells rapidly, and will result in a block to cardiac remodeling and scar formation and will lead to regeneration of the dead myocardium. The compounds of the invention behave in a manner similar to AMD3100.

Example 448

Clinical Elevation of WBC Levels—Healthy Volunteers

Eleven human patients having initial white blood cell counts of 4,000-6,500 cells/mm$^3$ were used in the study. An intravenous dosing solution of AMD3100 (i.e., 1,1'-[1,4-phenylene-bis(methylene)]-bis-1,4,8,11-tetraazacyclotetradecane) were prepared from a stock solution which is a 1 mg/ml 1:10 dilution of a concentrate in 0.9% saline (normal saline) under sterile conditions. Aliquots from this stock solution were added to 50-ml bags of 0.9% saline for intravenous injection in amounts to achieve the desired dosage levels (10 µg/kg-80 µg/kg).

The subjects described in this example already contained an indwelling peripheral intravenous catheter. The prescribed amount of AMD3100 was administered over 15 minutes by intravenous fusion in a single dose. Blood samples were obtained prior to the dose, and at various times up to 24 hours after dose administration.

Eleven human subjects received intravenous administration of AMD-3100 at doses 10, 20, 40, and 80 µg/kg. Five subjects also received a single subcutaneous injection of AMD-3100 at doses of 40 and 80 μg/kg. The effect of AMD3100 given intravenously in these 11 human subject is shown in FIG. 1. Three patients were administered dosages of 10 μg/kg (open circles); 3 patients were administered dosages of 20 μg/kg (solid circles); 3 patients were administered 40 μg/kg (open triangles); and 2 patients were administered 80 μg/kg (closed triangles).

As shown in FIG. 1, all of the patients at all levels of administration showed a marked increase in white blood cell count over the succeeding 5-10 hours after administration which WBC count tapered off after about 24 hours, although not, in any case, returning to the original level. Generally, the levels of WBC correlate with the concentration levels of the compound in the bloodstream. For example, one patient who received 80 μg/kg experienced an enhancement of white blood cell count from 6,000 cells/mm³ to a peak value of 19,000 cells/mm³. Even the patient showing the least response, who was given 20 μg/kg, experienced an increase from about 6,300 cells/mm³ to about 9,000 cells/mm³. Thus, it appears that AMD3100 is consistently able to enhance WBC count in human patients. The compounds of the invention behave in a manner similar to AMD3100.

While not intending to be bound by any theory, the ability to enhance WBC count across various species and the use of various compounds of formula (1) is believed due to the similarity of action of this compound in its antiviral applications and a possible mechanism for enhancing WBC count. The compounds of the invention are believed to exert their antiviral effects by inhibiting the binding of the second receptor for the HIV virus, CXCR4, and thus to inhibit entry of the virus into the cell. These particular receptors appear homologous throughout a wide range of species, including mouse, rat, cat and man. The compounds of the invention behave in a manner similar to AMD3100.

Example 449

Clinical Elevation of WBC Levels—HIV-Infected Patients

Figure 2:
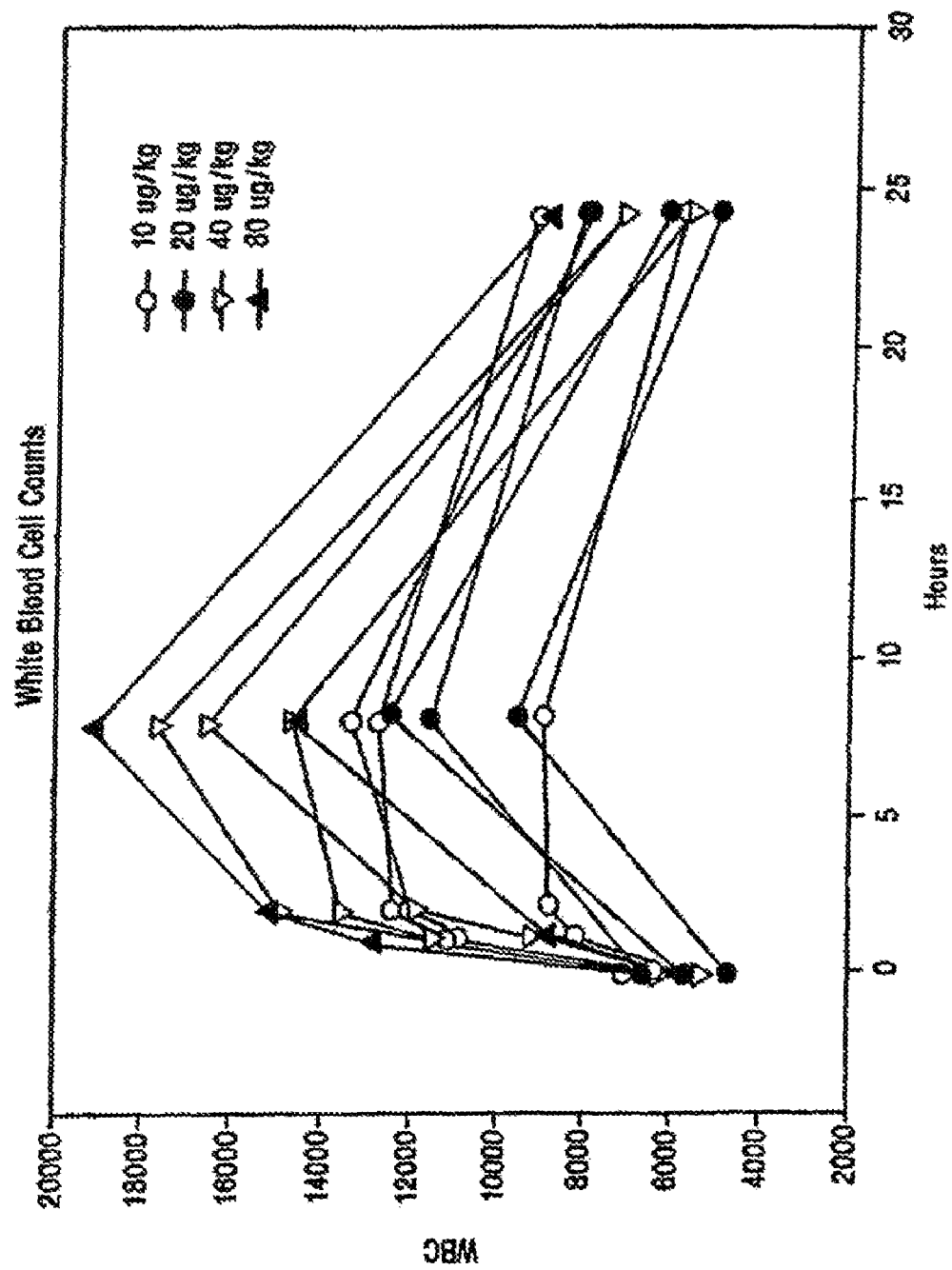
FIG. 2 is a graph showing the response in elevation of WBC counts observed in HIV-infected patients who received AMD-3100 by continuous infusion for up to 10 consecutive days.

Elevations in WBC counts have also been observed in HIV-infected patients who received AMD-3100 by continuous infusion for up to 10 consecutive days (FIG. 2). Eight patients received AMD-3100 at infusion dose rates of 2.5 μg/kg/hr (patients 1-4) and 5.0 μg/kg/hr (patients 5-8). Elevations relative to the baseline were noted in samples taken on days 2, 6, and 11 (immediately prior to end of infusion) of the infusion period. Elevations in WBC count ratios (Day 11 samples) ranged from 1.4 to 2.8 times the baseline. WBC counts returned to baseline 7 days after discontinuation of the infusion. Thus, it appears that AMD3100 is consistently able to enhance WBC count following single dose or with continuous infusion in human patients. The compounds of the invention behave in a manner similar to AMD3100.

While not intending to be bound by any theory, the ability to enhance WBC count across various species and the use of various compounds of formula (1) is believed due to the similarity of action of this compound in its antiviral applications and a possible mechanism for enhancing WBC count. The compounds of the invention are believed to exert their antiviral effects by inhibiting the binding of the second receptor for the HIV virus, CXCR4, and thus to inhibit entry of the virus into the cell. These particular receptors appear homologous throughout a wide range of species, including mouse, rat, cat and man. The compounds of the invention behave in a manner similar to AMD3100.

The invention claimed is:
1. A compound of the formula

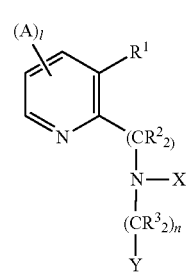

(1)

or a pharmaceutically acceptable salt, or stereoisomeric form thereof,
wherein X is $(CR^3{}_2)_o$—$(CR^3{=}CR^3)_p$—$(CR^3{}_2)_q$—$NR^5{}_2$; $(CR^3{}_2)_r$—$R^4$; a monocyclic or bicyclic ring optionally containing N, O or S; or a benzyl, each of which is optionally substituted; provided said benzyl is not substituted with a 5-6 membered aryl or heteroaryl via an L-NH-L linker, where each L is a bond, CO, SO₂ or CH₂;
Y is an optionally substituted nitrogen-containing monocyclic or bicyclic aromatic or partially aromatic moiety;
A and $R^1$ are each a non-interfering substituent wherein said non-interfering substituent is independently H, alkyl ($C_{1-10}$), alkenyl ($C_{2-10}$), alkynyl ($C_{2-10}$), aryl (5-12 members), arylalkyl, arylalkenyl, or arylalkynyl, each of which may optionally contain one or more heteroatoms selected from O, S, and N and each of which may further be substituted; or optionally substituted acyl, arylacyl, alkyl-, alkenyl-, alkynyl- or arylsulfonyl and forms thereof which contain heteroatoms in the alkyl, alkenyl, alkynyl or aryl moieties; or halo, CN, CF₃, NO₂, OR, SR, NR₂, COOR, CONR₂, OOCR or NROCR, where R is H or alkyl, alkenyl, alkynyl or aryl; and provided that two As do not form an additional ring;
$R^2$ and $R^3$ are independently H or an optionally substituted alkyl;
$R^4$ is an optionally substituted heterocyclic ring; or a hetero compound containing at least one =O, SO, C=N, cyano, NROR, or halo, wherein said hetero compound is optionally substituted with a heterocyclic ring;
$R^5$ is H or alkyl;
wherein at least one of $R^1$ and $R^2$ is not H;
l and n are independently 0-4;
p is 0-1;
o and q are independently 1-4;
r is 1-6;
provided that if X is $(CR^3{}_2)_r$—$R^4$, r is at least two if $R^4$ is 2-pyridinyl, quinolinyl, imidazolyl or furan; and
further provided that said compound is not (1-pyridin-2-ethyl)-(2-pyridin-2-yl-ethyl)-pyridin-2-ylmethyl-amine; and
wherein X is a disubstituted benzyl; or
wherein X is $(CR^3{}_2)_r$—$R^4$, wherein $R^4$ is an acyclic nitrogen-containing hetero compound; or
wherein X is $(CR^3{}_2)_p$—$R^4$ and $R^4$ is a nitrogen-containing heterocyclic ring, or a heteroaryl; or
wherein X is a monocyclic or bicyclic ring optionally containing N, O or S.
2. The compound of claim 1, wherein said noninterfering substituents are selected from optionally substituted alkyl ($C_{1-10}$), optionally substituted alkenyl ($C_{2-10}$), optionally substituted alkynyl ($C_{2-10}$), optionally substituted aryl (5-12 members), optionally substituted arylalkyl, optionally substituted arylalkenyl, and optionally substituted arylalkynyl, each of which may optionally contain one or more heteroatoms selected from O, S, and N.

3. The compound of claim 1, wherein said noninterfering substituents are selected from halo, CN, $CF_3$, $NO_2$, OR, SR, $NR_2$, COOR, and $CONR_2$, where R is H or alkyl, alkenyl, alkynyl or aryl.

4. The compound of claim 1, wherein each optionally substituted moiety is substituted with one or more inorganic substituents, halo; OR; $C_{1-6}$ alkyl or $C_{2-6}$ alkenyl optionally containing one or more N, O, or S, and optionally substituted with halo; cyano; optionally substituted carbonyl; $NR_2$; $C=NR_2$; an optionally substituted carbocyclic or heterocyclic ring; or an optionally substituted aryl or heteroaryl.

5. The compound of claim 1, wherein p is 0.

6. The compound of claim 5, wherein o and q together are 2-6.

7. The compound of claim 1, wherein X is $(CR^3{}_2)_r$—$R^4$, wherein $R^4$ is an acyclic nitrogen-containing hetero compound and wherein $R^4$ comprises a urea, hydroxyurea, sulfamide, acetamide, guanidine, cyanamide, hydroxylamine, cyanamide, imidazolidine-2-one, or a nicotinamide moiety.

8. The compound of claim 1, wherein X is $(CR^3{}_2)_p$—$R^4$ and $R^4$ is a nitrogen-containing heterocyclic ring, or a heteroaryl and wherein $R^4$ is azetidine, pyrrolidinyl, pyridinyl, thiophenyl, imidazolyl, or benzimidazolyl.

9. The compound of claim 1, wherein X is cyclohexyl, piperidine, 8-aza-bicyclo[3.2.1]octane or 3-aza-bicyclo[3.2.1]octane.

10. The compound of claim 1, wherein Y is a nitrogen-containing monocyclic or bicyclic aromatic or partially aromatic moiety.

11. The compound of claim 10, wherein Y is a 5-6 membered ring containing nitrogen, and wherein said nitrogen is in said ring at a position adjacent the position attached to the remainder of the molecule.

12. The compound of claim 1, wherein Y is a fused ring system.

13. The compound of claim 10, wherein Y is pyridine, pyrimidine, pyrazine, indole, benzimidazole, benzthiazole, imidazole, isoquinoline, tetrahydroquinoline, pyridazine, or thiazole.

14. The compound of claim 13, wherein Y is a tetrahydroquinoline system attached at position 8 to the remainder of the molecule.

15. The compound of claim 1, wherein A and $R^1$ are independently halo, optionally substituted aryl, arylalkyl; alkyl, alkoxy, or $CF_3$.

16. A compound selected from the group of compounds consisting of
N-(1H-benzimidazol-2-ylmethyl)-N-(3-methylpyridin-2-ylmethyl)-butane-1,4-diamine;
$N^1$-(1H-Benzoimidazol-2-ylmethyl)-$N^1$-(3-isopropylpyridin-2-ylmethyl)-butane-1,4-diamine;
$N^1$-(3-Methyl-pyridin-2-ylmethyl)-$N^1$-(1-phenyl-1H-imidazol-2-ylmethyl)-butane-1,4-diamine;
$N^1$-(3-Methyl-pyridin-2-ylmethyl)-$N^1$-(2-phenyl-3H-imidazol-4-ylmethyl)-butane-1,4-diamine;
$N^1$-(2-Methyl-3H-imidazol-4-ylmethyl)-$N^1$-(3-methyl-pyridin-2-ylmethyl)-butane-1,4-diamine;
$N^1$-(5-Methyl-3H-imidazol-4-ylmethyl)-$N^1$-(3-methyl-pyridin-2-ylmethyl)-butane-1,4-diamine;
$N^1$-(3-Benzyloxy-pyrazin-2-ylmethyl)-$N^1$-(3-methyl-pyridin-2-ylmethyl)-butane-1,4-diamine;
$N^1$-(3-allyloxy-pyridin-2-ylmethyl)-$N^1$-(3-methyl-pyridin-2-ylmethyl)-butane-1,4-diamine;
$N^1$-[3-(2-Methoxy-phenyl)-pyridin-2-ylmethyl]-$N^1$-(3-methyl-pyridin-2-ylmethyl)-butane-1,4-diamine;
$N^1$-(3-Methyl-pyridin-2-ylmethyl)-$N^1$-(3-thiophen-2-yl-pyridin-2-ylmethyl)-butane-1,4-diamine;
$N^1$-[2,3']Bipyridinyl-6'-ylmethyl-$N^1$-(3-methyl-pyridin-2-ylmethyl)-butane-1,4-diamine;
N-(3-Methylpyridin-2-ylmethyl)-N-pyridin-2-ylmethyl-butane-1,4-diamine;
$N^1$,$N^1$-bis-(3-methyl-pyridin-2-ylmethyl)-butane-1,4-diamine;
2-{[(4-aminobutyl)-(3-methyl-pyridin-2-ylmethyl)-amino]-methyl}-pyridin-3-ol;
$N^1$-(3-Chloro-pyridin-2-ylmethyl)-$N^1$-(3-methyl-pyridin-2-ylmethyl)-butane-1,4-diamine;
$N^1$-(3-Fluoro-pyridin-2-ylmethyl)-$N^1$-(3-methyl-pyridin-2-ylmethyl)-butane-1,4-diamine;
$N^1$-(3-Bromo-pyridin-2-ylmethyl)-$N^1$-(3-methyl-pyridin-2-ylmethyl)-butane-1,4-diamine;
$N^1$-(3-Methyl-pyridin-2-ylmethyl)-$N^1$-[3-(2,2,2-trifluoro-ethoxy)-pyridin-2-ylmethyl]-butane-1,4-diamine;
N-(2-{[(4-amino-butyl)-(3-methyl-pyridin-2-ylmethyl)-amino]-methyl}-pyridin-3-yl)-methanesulfonamide;
$N^1$-(3-benzyloxy-pyridin-2-ylmethyl)-$N^1$-(3-methyl-pyridin-2-ylmethyl)-butane-1,4-diamine;
$N^1$-(3-methyl-5-trifluoromethyl-pyridin-2-ylmethyl)-$N^1$-(3-methyl-pyridin-2-ylmethyl)-butane-1,4-diamine;
$N^1$-(3-methyl-pyridine-2-ylmethyl)-$N^1$-(5-phenyl-pyridine-2-ylmethyl)-butane-1,4-diamine;
N-(1-Allyl-1H-benzimidazol-2-ylmethyl)-N-(3-methyl-pyridin-2-yl-methyl)-butane-1,4-diamine;
$N^1$-(1-Allyl-1H-imidazol-2-ylmethyl)-$N^1$-(3-methyl-pyridin-2-ylmethyl)-butane-1,4-diamine;
$N^1$-(3H-imidazol-4-ylmethyl)-$N^1$-(3-methyl-pyridin-2-ylmethyl)-butane-1,4-diamine;
$N^1$-(3-Benzyl-3H-imidazol-4-ylmethyl)-$N^1$-(3-methyl-pyridin-2-ylmethyl)-butane-1,4-diamine;
$N^1$-(2-Ethyl-5-methyl-3H-imidazol-4-ylmethyl)-$N^1$-(3-methyl-pyridin-2-ylmethyl)-butane-1,4-diamine;
$N^1$-(3-Methyl-pyridin-2-ylmethyl)-$N^1$-(3-p-tolyl-pyridin-2-ylmethyl)-butane-1,4-diamine;
N-(3-Methoxypyridin-2-ylmethyl)-N-(3-methylpyridin-2-ylmethyl)-butane-1,4-diamine;
$N^1$-(3-Methyl-pyridin-2-ylmethyl)-$N^1$-(3-trifluoromethyl-pyridin-2-ylmethyl)-butane-1,4-diamine;
$N^1$-(3-isobutyl-pyridin-2-ylmethyl)-$N^1$-(3-methyl-pyridin-2-ylmethyl)-butane-1,4-diamine;
$N^1$-(3-Methyl-pyridin-2-ylmethyl)-$N^1$-(1-phenyl-1H-benzoimidazol-2-ylmethyl)-butane-1,4-diamine;
$N^1$-(1-Benzyl-1H-benzoimidazol-2-ylmethyl)-$N^1$-(3-methyl-pyridin-2-ylmethyl)-butane-1,4-diamine;
$N^1$-(3-Methyl-pyridin-2-ylmethyl)-$N^1$-[3-(3-nitro-phenyl)-pyridin-2-ylmethyl]-butane-1,4-diamine;
$N^1$-Isoquinolin-3-ylmethyl-$N^1$-(3-methyl-pyridin-2-ylmethyl)-butane-1,4-diamine;
3-(2-{[(4-Amino-butyl)-(3-methyl-pyridin-2-ylmethyl)-amino]-methyl}-pyridin-3-yl)-benzoic acid methyl ester;
N-(3,5-Dimethyl-pyridin-2-ylmethyl)-N-(3-methyl-pyridin-2-ylmethyl)-butane-1,4-diamine;
N-(3-Methyl-pyridin-2-ylmethyl)-N-[1-(2-pyridin-2-yl-ethyl)-1H-benzoimidazol-2-ylmethyl]-butane-1,4-diamine;
N-(3,5-Dimethylpyridin-2-ylmethyl)-N-(3-isopropylpyridin-2-ylmethyl)-butane-1,4-diamine;

Acetic acid 1-(2-{[(4-amino-butyl)-(3,5-dimethyl-pyridin-2-ylmethyl)-amino]-methyl}-pyridin-3-yl)-1-methyl-ethyl ester;
$N^1$-(3-cyclopentyloxy-pyridin-2-ylmethyl)-$N^1$-(3,5-dimethyl-pyridin-2-ylmethyl)-butane-1,4-diamine;
$N^1$-(3,5-dimethyl-pyridin-2-ylmethyl)-$N^1$-[1-(3-methyl-but-2-enyl)-1H-benzoimidazol-2-ylmethyl]-butane-1,4-diamine;
$N^1$-{3-[1-(4-chloro-phenyl)-1-methyl-ethyl]-pyridin-2-ylmethyl}-$N^1$-(3,5-dimethyl-pyridin-2-ylmethyl)-butane-1,4-diamine;
$N^1$-(3,5-dimethyl-pyridin-2-ylmethyl)-$N^1$-{3-[1-(4-fluoro-phenyl)-cyclopentyl]-pyridin-2-$N^1$-(3,5-dimethyl-pyridin-2-ylmethyl)-$N^1$-[3-(1-methoxy-cyclobutyl)-pyridin-2-ylmethyl]-butane-1,4-diamine;
$N^1$-(3,5-dimethyl-pyridin-2-ylmethyl)-$N^1$-{3-[1-(2-fluoro-phenyl)-1-methyl-ethyl]-pyridin-2-ylmethyl}-butane-1,4-diamine;
$N^1$-(3,5-dimethyl-pyridin-2-ylmethyl)-$N^1$-[3-(1-methoxy-cyclohexyl)-pyridin-2-ylmethyl]-butane-1,4-diamine;
N'-(3,5-Dimethyl-pyridin-2-ylmethyl)-N'-(4-methyl-pyridin-2-ylmethyl)-butane-1,4-diamine;
N'-(4-tert-Butyl-pyridin-2-ylmethyl)-N'-(3,5-dimethyl-pyridin-2-ylmethyl)-butane-1,4-diamine;
N'-(3,5-Dimethyl-pyridin-2-ylmethyl)-N'-(3-methyl-pyrazin-2-ylmethyl)-butane-1,4-diamine;
$N^1$-(3,5-Dimethyl-pyridin-2-ylmethyl)-$N^1$-[3-(1-phenyl-cyclopentyl)-pyridin-2-ylmethyl]-butane-1,4-diamine;
2-{[(4-Amino-butyl)-(3,5-dimethyl-pyridin-2-ylmethyl)-amino]-methyl}-nicotinic acid ethyl ester;
$N^1$-(3,5-Dimethyl-pyridin-2-ylmethyl)-$N^1$-(3-vinyl-pyridin-2-ylmethyl)-butane-1,4-diamine;
$N^1$-(3,5-Dimethyl-pyridin-2-ylmethyl)-$N^1$-[3-(4-methanesulfonyl-phenyl)-pyridin-2-ylmethyl]-butane-1,4-diamine;
$N^1$-(3,5-Dimethyl-pyridin-2-ylmethyl)-$N^1$-(3-thiazol-2-yl-pyridin-2-ylmethyl)-butane-1,4-diamine;
$N^1$-(3,5-Dimethyl-pyridin-2-ylmethyl)-$N^1$-(3,4-dimethyl-pyridin-2-ylmethyl)-butane-1,4-diamine;
$N^1$-(3,5-Dimethyl-pyridin-2-ylmethyl)-$N^1$-(5,6,7,8-tetrahydro-isoquinolin-1-ylmethyl)-butane-1,4-diamine;
$N^1$-(3,5-Dimethyl-pyridin-2-ylmethyl)-$N^1$-(3-phenoxy-pyridin-2-ylmethyl)-butane-1,4-diamine;
$N^1$-(3,5-Dimethyl-pyridin-2-ylmethyl)-$N^1$-isoquinolin-1-ylmethyl-butane-1,4-diamine;
$N^1$-(5,6-Dihydro-4H-imidazo[4,5,1-ij]quinolin-2-ylmethyl)-$N^1$-(3,5-dimethyl-pyridin-2-ylmethyl)-butane-1,4-diamine;
$N^1$-(3-Benzenesulfinyl-pyridin-2-ylmethyl)-$N^1$-(3,5-dimethyl-pyridin-2-ylmethyl)-butane-1,4-diamine;
$N^1$-(3,5-Dimethyl-pyridin-2-ylmethyl)-$N^1$-(3-phenylsulfanyl-pyridin-2-ylmethyl)-butane-1,4-diamine;
$N^1$-[3,3']Bipyridinyl-2-ylmethyl-$N^1$-(3,5-dimethyl-pyridin-2-ylmethyl)-butane-1,4-diamine;
$N^1$-[3-(2,2-Dimethyl-propyl)-pyridin-2-ylmethyl]-$N^1$-(3,5-dimethyl-pyridin-2-ylmethyl)-butane-1,4-diamine;
N-(3-Cyclohexyl-pyridin-2-ylmethyl)-N-(3,5-dimethyl-pyridin-2-ylmethyl)-butane-1,4-diamine;
N-(3,5-dimethyl-pyridin-2-ylmethyl)-N-(4-phenyl-pyridin-2-ylmethyl)-butane-1,4-diamine;
$N^1$-[3-(3,5-Difluoro-phenyl)-pyridin-2-ylmethyl]-$N^1$-(3,5-dimethyl-pyridin-2-ylmethyl)-butane-1,4-diamine;
$N^1$-(3,5-Dimethyl-pyridin-2-ylmethyl)-$N^1$-[3-(1-methyl-1-phenyl-ethyl)-pyridin-2-ylmethyl]-butane-1,4-diamine;
N-(2-{[(4-amino-butyl)-(3,5-dimethyl-pyridin-2-ylmethyl)-amino]-methyl}-pyridin-3-yl)-benzamide;
$N^1$-(3,5-dimethyl-pyridin-2-ylmethyl)-$N^1$-pyridin-2-ylmethyl-butane-1,4-diamine;
$N^1$-(3,5-dimethyl-pyridin-2-ylmethyl)-$N^1$-(5-methyl-pyridin-2-ylmethyl)-butane-1,4-diamine;
$N^1$-(3,5-dimethyl-pyridin-2-ylmethyl)-$N^1$-(6-methyl-pyridin-2-ylmethyl)-butane-1,4-diamine;
$N^1$-(3,5-dimethyl-pyridin-2-ylmethyl)-$N^1$-(4-nitro-pyridin-2-ylmethyl)-butane-1,4-diamine;
$N^1$-(4-chloro-pyridin-2-ylmethyl)-$N^1$-(3,5-dimethyl-pyridin-2-ylmethyl)-butane-1,4-diamine;
($N^1$-(3-amino-pyridin-2-ylmethyl)-$N^1$-(3-isopropyl-pyridin-2-ylmethyl)-butane-1,4-diamine;
$N^1$-(3,5-dimethyl-pyridin-2-ylmethyl)-$N^1$-(3-isopropoxy-pyridin-2-ylmethyl)-butane-1,4-diamine;
$N^1$-(3,5-dimethyl-pyridin-2-ylmethyl)-$N^1$-[3-(1-ethyl-1-methoxy-propyl)-pyridin-2-ylmethyl]-butane-1,4-diamine;
$N^1$-(3,5-dimethyl-pyridin-2-ylmethyl)-$N^1$-(4-trifluoromethyl-pyridin-2-ylmethyl)-butane-1,4-diamine;
$N^1$-(3,5-dichloro-pyridin-2-ylmethyl)-$N^1$-(3-isopropyl-pyridin-2-ylmethyl)-butane-1,4-diamine;
$N^1$-(5-chloro-3-methyl-pyridin-2-ylmethyl)-$N^1$-(3-isopropyl-pyridin-2-ylmethyl)-butane-1,4-diamine;
$N^1$-(3-chloro-5-methyl-pyridin-2-ylmethyl)-$N^1$-(3-isopropyl-pyridin-2-ylmethyl)-butane-1,4-diamine;
$N^1$-(5-fluoro-3-methyl-pyridin-2-ylmethyl)-$N^1$-(3-isopropyl-pyridin-2-ylmethyl)-butane-1,4-diamine;
$N^1$-(3,5-difluoro-pyridin-2-ylmethyl)-$N^1$-(3-isopropyl-pyridin-2-ylmethyl)-butane-1,4-diamine;
N-(3,5-Dimethyl-pyridin-2-ylmethyl)-N-isoquinolin-1-ylmethyl-N'-methyl-butane-1,4-diamine;
N-(3,5-Dimethyl-pyridin-2-ylmethyl)-N-(3-isopropyl-pyridin-2-ylmethyl)-N'-methyl-butane-1,4-diamine;
N-{3-[1-(4-Chloro-phenyl)-1-methyl-ethyl]-pyridin-2-ylmethyl}-N-(3,5-dimethyl-pyridin-2-ylmethyl)-N'-methyl-butane-1,4-diamine;
N-(3,5-Dimethyl-pyridin-2-ylmethyl)-N-{3-[1-(4-fluoro-phenyl)-1-methyl-ethyl]-pyridin-2-ylmethyl}-$N^1$-methyl-butane-1,4-diamine;
N-(3,5-dimethyl-pyridin-2-ylmethyl)-N'-methyl-N-[3-(1-methyl-1-phenyl-ethyl)-pyridin-2-ylmethyl]-butane-1,4-diamine;
N-(5-Chloro-3-methyl-pyridin-2-ylmethyl)-N-(3-isopropyl-pyridin-2-ylmethyl)-N'-methyl-butane-1,4-diamine;
N-(5-Chloro-3-methyl-pyridin-2-ylmethyl)-N {3-[1-(4-fluoro-phenyl)-1-methyl-ethyl]-pyridin-2-ylmethyl}-N'-methyl-butane-1,4-diamine;
$N^1$-(1-methyl-1H-benzoimidazol-2-ylmethyl)-$N^1$-(5,6,7,8-tetrahydro-quinolin-8-yl)-butane-1,4-diamine;
N-(1-Allyl-1H-imidazol-2-ylmethyl)-N-(1-pyridin-2-yl-ethyl)-butane-1,4-diamine;
$N^1$-(3-Isobutyl-pyridin-2-ylmethyl)-$N^1$-(1-pyridin-2-yl-ethyl)-butane-1,4-diamine;
$N^1$-(1-Pyridin-2-yl-ethyl)-$N^1$-(3-trifluoromethyl-pyridin-2-ylmethyl)-butane-1,4-diamine;
$N^1$-(3-amino-pyridin-2-ylmethyl)-$N^1$-(1-pyridin-2-yl-ethyl)-butane-1,4-diamine;
N-(3,5-dimethylpyridin-2-ylmethyl)-N-(1-pyridin-2-yl-ethyl)-butane-1,4-diamine;
$N^1$-(6-Methyl-pyridin-2-ylmethyl)-$N^1$-(1-pyridin-2-yl-ethyl)-butane-1,4-diamine;
$N^1$-(5-Methyl-pyridin-2-ylmethyl)-$N^1$-(1-pyridin-2-yl-ethyl)-butane-1,4-diamine;

$N^1$-(3-Methyl-pyridin-2-ylmethyl)-$N^1$-(1-pyridin-2-yl-ethyl)-butane-1,4-diamine;
$N^1$-(3-chloro-pyridin-2-ylmethyl)-$N^1$-(5,6,7,8-tetrahydro-quinolin-8-yl)-butane-1,4-diamine;
$N^1$-(3,5-Dimethyl-pyridin-2-ylmethyl)-$N^1$-(5,6,7,8-tetrahydro-quinolin-8-yl)-butane-1,4-diamine;
N-(3-methylpyridin-2-ylmethyl)-N-(5,6,7,8-tetrahydro-quinolin-8-yl)-butane-1,4-diamine;
2-{[(4-aminobutyl)-(5,6,7,8-tetrahydroquinolin-8-yl)-amino]-methyl}-pyridin-3-ol;
($N^1$-(3-isopropyl-pyridin-2-ylmethyl)-$N^1$-(5,6,7,8-tetrahydro-quinolin-8-yl)-butane-1,4-diamine;
$N^1$-(3-Amino-pyridin-2-ylmethyl)-$N^1$-(5,6,7,8-tetrahydro-quinolin-8-yl)-butane-1,4-diamine;
N-(2-{[(4-amino-butyl)-(5,6,7,8-tetrahydro-quinolin-8-yl)-amino]-methyl}-pyridin-3-yl)-methanesulfonamide;
$N^1$-(1-Benzenesulfonyl-1H-benzoimidazol-2-ylmethyl)-$N^1$-(3-methyl-pyridin-2-ylmethyl)-butane-1,4-diamine;
$N^1$-(3-Methyl-pyridin-2-ylmethyl)-N'-(1-thiazol-2-yl-ethyl)-butane-1,4-diamine;
$N^1$-(3-Methyl-pyridin-2-ylmethyl)-N'-(1-pyrazin-2-yl-ethyl)-butane-1,4-diamine;
N'-(3,5-Dimethyl-1-oxy-pyridin-2-ylmethyl)-N'-(3-isopropyl-pyridin-2-ylmethyl)-butane-1,4-diamine;
N'-(3,4-Dimethoxy-pyridin-2-ylmethyl)-N'-(3,5-dimethyl-pyridin-2-ylmethyl)-butane-1,4-diamine;
N'-Methyl-N,N-bis-(3-methyl-pyridin-2-ylmethyl)-butane-1,4-diamine;
N-{3-[1-(4-Chloro-phenyl)-1-methyl-ethyl]-pyridin-2-ylmethyl}-N'-cyclopropyl-N-(3,5-dimethyl-pyridin-2-ylmethyl)-butane-1,4-diamine;
2-{[(4-Amino-butyl)-(3,5-dimethyl-pyridin-2-ylmethyl)-amino]-methyl}-nicotinic acid;
Benzenesulfonic acid 2-{[(4-amino-butyl)-(3,5-dimethyl-pyridin-2-ylmethyl)-amino]-methyl}-pyridin-3-yl ester;
$N^1$-(3,5-Dimethyl-pyridin-2-ylmethyl)-$N^1$-(3-indol-1-yl-pyridin-2-ylmethyl)-butane-1,4-diamine;
Dimethyl-sulfamic acid 2-{[(4-amino-butyl)-(3,5-dimethyl-pyridin-2-ylmethyl)-amino]-methyl}-pyridin-3-yl ester;
$N^1$-[3-(3,4-Dihydro-2H-quinolin-1-yl)-pyridin-2-ylmethyl]-$N^1$-(3,5-dimethyl-pyridin-2-ylmethyl)-butane-1,4-diamine;
$N^1$-(3,5-Dimethyl-pyridin-2-ylmethyl)-$N^1$-(1-methyl-1-pyridin-2-yl-ethyl)-butane-1,4-diamine;
N-(5-chloro-3-methyl-pyridin-2-ylmethyl)-N-{3-[1-(4-fluoro-phenyl)-1-methyl-ethyl]-pyridin-2-ylmethyl}-butane-1,4-diamine;
(2-{[(4-amino-butyl)-(3,5-dimethyl-pyridin-2-ylmethyl)-amino]-methyl}-pyridin-3-yl)-urea;
$N^1$-(1H-benzoimidazol-4-ylmethyl)-$N^1$-(3,5-dimethyl-pyridin-2-ylmethyl)-butane-1,4-diamine;
$N^1$-(3,5-dimethyl-pyridin-2-ylmethyl)-$N^1$-(3-morpholin-4-yl-pyridin-2-ylmethyl)-butane-1,4-diamine;
$N^1$-(3,5-dimethyl-pyridin-2-ylmethyl)-$N^1$-(3,4,5,6-tetrahydro-2H-[1,3']bipyridinyl-2'-ylmethyl)-butane-1,4-diamine;
$N^1$-(3-isopropyl-pyridin-2-ylmethyl)-$N^1$-(5-methyl-trifluoromethyl-pyridin-2-ylmethyl)-butane-1,4-diamine;
N-(3,5-dimethyl-pyridin-2-ylmethyl)-N',N'-dimethyl-N-[3-(1-methyl-1-phenyl-ethyl)-pyridin-2-ylmethyl]-butane-1,4-diamine;
N-(3,5-dimethyl-pyridin-2-ylmethyl)-N'-ethyl-N-{3-[1-(4-fluoro-phenyl)-1-methyl-ethyl]-pyridin-2-ylmethyl}-butane-1,4-diamine;
N-cyclopropyl-N'-(3,5-dimethyl-pyridin-2-ylmethyl)-N'-{3-[1-(4-fluoro-phenyl)-1-methyl-ethyl]-pyridin-2-ylmethyl}-butane-1,4-diamine;
N-{3-[1-(4-chloro-phenyl)-1-methyl-ethyl]-pyridin-2-ylmethyl}-N-(3,5-dimethyl-pyridin-2-ylmethyl)-N'-ethyl-butane-1,4-diamine;
N-(5-chloro-3-methyl-pyridin-2-ylmethyl)-N-{3-[1-(4-chloro-phenyl)-1-methyl-ethyl]-pyridin-2-ylmethyl}-N'-(2-fluoro-ethyl)-butane-1,4-diamine;
N-{3-[1-(4-chloro-phenyl)-1-methyl-ethyl]-pyridin-2-ylmethyl}-N-(3-chloro-pyridin-2-ylmethyl)-N'-methyl-butane-1,4-diamine;
N-{3-[1-(4-chloro-phenyl)-1-methyl-ethyl]-pyridin-2-ylmethyl}-N'-methyl-N-(3-trifluoromethyl-pyridin-2-ylmethyl)-butane-1,4-diamine;
N-{3-[1-(4-chloro-phenyl)-1-methyl-ethyl]-pyridin-2-ylmethyl}-N-(3,5-dichloro-pyridin-2-ylmethyl)-N'-methyl-butane-1,4-diamine;
N-(1H-benzimidazol-2-ylmethyl)-N-(1-pyridin-2-yl-ethyl)-butane-1,4-diamine;
$N^1$-(1H-benzoimidazol-2-ylmethyl)-$N^1$-(3,5-dimethyl-pyridine-2-ylmethyl)-butane-1,4-diamine;
N-(1H-benzimidazol-2-ylmethyl)-N-[1-(3-methylpyridin-2-yl)-ethyl]-butane-1,4-diamine;
$N^1$-(1H-Benzimidazol-2-ylmethyl)-$N^1$-(1-methyl-1-pyridin-2-yl-ethyl)-butane-1,4-diamine;
$N^1$-(1H-benzimidazol-2-ylmethyl)-$N_1$-(1-pyridin-2-yl-propyl)-butane-1,4-diamine;
$N^1$-[1-(1H-Benzimidazol-2-yl)-ethyl]-$N^1$-(3-methyl-pyridin-2-ylmethyl)-butane-1,4-diamine;
$N^1$-(1-methyl-1H-benzoimidazol-2-ylmethyl)-$N^1$-(3-methyl-pyridin-2-ylmethyl)-butane-1,4-diamine;
2-[(4-amino-butyl)-(1H-benzimidazol-2-ylmethyl)-amino]-2-pyridin-2-yl-ethanol;
$N^1$-(1H-Benzimidazol-2-ylmethyl)-$N^1$-[1-(4-methyl-pyridin-2-yl)-ethyl]-butane-1,4-diamine;
$N^1$-(1H-Benzimidazol-2-ylmethyl)-$N^1$-[1-(5-methyl-pyridin-2-yl)-ethyl]-butane-1,4-diamine;
$N^1$-(1-methyl-1H-imidazol-2-ylmethyl)-$N^1$-(3-methyl-pyridin-2-ylmethyl)-butane-1,4-diamine;
N-[1-(1-Methyl-1H-Imidazol-2-yl)-ethyl]-N-(3-methylpyridin-2-ylmethyl)-butane-1,4-diamine;
$N^1$-(3,5-Dimethyl-pyridin-2-ylmethyl)-$N^1$-(3-phenyl-pyridin-2-ylmethyl)-butane-1,4-diamine;
N,N-Bis-(3-Methyl-pyridin-2-ylmethyl)-cis-but-2-ene-1,4-diamine;
$N^1$,$N^1$-Bis-(3-chloro-pyridin-2-ylmethyl)-butane-1,4-diamine;
2-(2-{[(4-Amino-butyl)-(3,5-dimethyl-pyridin-2-ylmethyl)-amino]-methyl}-pyridin-3-yl)-propan-2-ol;
$N^1$-(3,5-dimethyl-pyridin-2-ylmethyl)-$N^1$-(3-hydroxymethyl-pyridin-2-ylmethyl)-cis-but-2-ene-1,4-diamine;
$N^4$,$N^4$-bis-(3-methyl-pyridin-2-ylmethyl)-pentane-1,4-diamine;
$N^1$-(3-methyl-pyridin-2-ylmethyl)-$N^1$-(1-pyridin-2-yl-ethyl)-butane-1,4-diamine;
$N^1$,$N^1$-bis-(1-pyridin-2-yl-ethyl)-butane-1,4-diamine;
N-(3-Methyl-pyridin-2-ylmethyl)-N-(1-pyridin-2-yl-ethyl)-cis-but-2-ene-1,4-diamine;
(R)—$N^1$-(3-methyl-pyridin-2-ylmethyl)-$N^1$-(1-pyridin-2-yl-ethyl)-butane-1,4-diamine;
N-[1-(4-Methylpyridin-2-yl)-ethyl]-N-(3-methylpyridin-2-ylmethyl)-butane-1,4-diamine;

N⁴-(3-methyl-pyridin-2-ylmethyl)-N⁴-(1-pyridin-2-yl-ethyl)-pentane-1,4-diamine;
(2-{[1-Allyl-1H-benzoimidazol-2-ylmethyl)-(4-amino-butyl)-amino]-methyl}-pyridin-3-yl)-methanol;
N-[1-(1H-Imidazol-2-yl)-ethyl]-N¹-(3-methylpyridin-2-ylmethyl)-butane-1,4-diamine;
N¹-(3-Aminopyridin-2-ylmethyl)-N'-(3-chloropyridin-2-ylmethyl)-butane-1,4-diamine;
N¹-(1-methyl-1-pyridin-2-yl-ethyl)-(5,6,7,8-tetrahydro-quinolin-8-yl)-butane-1,4-diamine;
(2-{[(4-Aminobutyl)-(5,6,7,8-tetrahydroquinolin-8-yl)-amino]-methyl}-pyridin-3-yl)-methanol;
N¹-[1-(3-methyl-pyridin-2-yl)-ethyl]-N¹-(5,6,7,8-tetrahydro-quinolin-8-yl)-butane-1,4-diamine;
N-(3,5-Dimethyl-pyridin-2-ylmethyl)-N'-methyl-N-(5,6,7,8-tetrahydro-quinolin-8-yl)-butane-1,4-diamine;
(R)—N-(3,5-dimethyl-pyridin-2-ylmethyl)-N-(5,6,7,8-tetrahydro-quinolin-8-yl)-butane-1,4-diamine;
N¹-(3-Amino-pyridin-2-ylmethyl)-N¹-(5,6,7,8-tetrahydro-quinolin-8-yl)-butane-1,4-diamine;
N¹-(5,6,7,8-tetrahydro-quinolin-8-yl)-N¹-thiazol-4-ylmethyl-butane-1,4-diamine;
(S)-(N¹-(3,5-dimethyl-pyridin-2-ylmethyl)-N¹-(5,6,7,8-tetrahydro-quinolin-8-yl)-butane-1,4-diamine;
N¹-pyridine-2-ylmethyl-N¹-(5,6,7,8-tetrahydro-quinolin-8-yl)-butane-1,4-diamine;
N-(4,6-dimethylpyridin-2-ylmethyl)-N-(5,6,7,8-tetrahydroquinolin-8-yl)-butane-1,4-diamine;
N¹-(6-Methyl-pyridin-2-ylmethyl)-N¹-(5,6,7,8-tetrahydro-quinolin-8-yl)-butane-1,4-diamine;
N¹-(4-Methyl-pyridin-2-ylmethyl)-N¹-(5,6,7,8-tetrahydro-quinolin-8-yl)-butane-1,4-diamine;
N¹-(5-Methyl-pyridin-2-ylmethyl)-N¹-(5,6,7,8-tetrahydro-quinolin-8-yl)-butane-1,4-diamine;
N¹-quinolin-2-ylmethyl-N¹-(5,6,7,8-tetrahydro-quinolin-8-yl)-butane-1,4-diamine;
N¹-pyridazin-3-ylmethyl-N¹-(5,6,7,8-tetrahydro-quinolin-8-yl)-butane-1,4-diamine;
N¹-(5,6,7,8-tetrahydro-quinolin-8-yl)-N¹-thiazol-2-ylmethyl-butane-1,4-diamine;
N¹-benzothiazol-2-ylmethyl-N¹-(5,6,7,8-tetrahydro-quinolin-8-yl)-butane-1,4-diamine;
N¹-pyrazin-2-ylmethyl-N¹-(5,6,7,8-tetrahydro-quinolin-8-yl)-butane-1,4-diamine;
N-(3-Isopropyl-pyridin-2-ylmethyl)-N-(3-methyl-pyridin-2-ylmethyl)-cyclohexane-1,4-diamine;
N-(1-allyl-1H-benzimidazol-2-ylmethyl)-N-(3-methyl-pyridin-2-ylmethyl)-cyclohexane-1,4-diamine;
N-(3-Chloropyridin-2-ylmethyl)-N-(3-methylpyridin-2-ylmethyl)-cyclohexane-1,4-diamine;
{4-[bis-(3-methyl-pyridin-2-ylmethyl)-amino]-piperidin-1-yl}-(6-hydroxy-pyridin-3-yl)-methanone;
{4-[Bis-(3-methyl-pyridin-2-ylmethyl)-amino]-piperidin-1-yl}-isoquinolin-1-yl-methanone;
{4-[Bis-(3-methyl-pyridin-2-ylmethyl)-amino]-piperidin-1-yl}-isoquinolin-3-yl-methanone;
1-{4-[Bis-(3-methyl-pyridin-2-ylmethyl)-amino]-piperidin-1-yl}-2-dimethylamino-ethanone;
1-{4-[Bis-(3-methyl-pyridin-2-ylmethyl)-amino]-piperidin-1-yl}-2-dimethylamino-3-phenyl-propan-1-one;
1-{4-[Bis-(3-methyl-pyridin-2-ylmethyl)-amino]-piperidin-1-yl}-2-pyridin-2-yl-ethanone;
{4-[Bis-(3-methyl-pyridin-2-ylmethyl)-amino]-piperidin-1-yl}-(1H-indol-2-yl)-methanone;
1-{4-[Bis-(3-methyl-pyridin-2-ylmethyl)-amino]-piperidin-1-yl}-2-(1H-imidazol-4-yl)-ethanone;
1-{4-[Bis-(3-methyl-pyridin-2-ylmethyl)-amino]-piperidin-1-yl}-3-morpholin-4-yl-propan-1-one;
1-(2-{4-[Bis-(3-methyl-pyridin-2-ylmethyl)-amino]-piperidin-1-yl}-2-oxo-ethyl)-pyrrolidin-2-one;
1-{4-[Bis-(3-methyl-pyridin-2-ylmethyl)-amino]-piperidin-1-yl}-2-(1H-indol-3-yl)-ethane-1,2-dione;
{4-[Bis-(3-methyl-pyridin-2-ylmethyl)-amino]-piperidin-1-yl}-phenyl-methanone;
1-{4-[Bis-(3-methyl-pyridin-2-ylmethyl)-amino]-piperidin-1-yl}-2-phenyl-ethanone;
{4-[Bis-(3-methyl-pyridin-2-ylmethyl)-amino]-piperidin-1-yl}-(2-methylamino-phenyl)-methanone;
(2-Amino-pyridin-3-yl)-{4-[Bis-(3-methyl-pyridin-2-ylmethyl)-amino]-piperidin-1-yl}-methanone;
1-{4-[Bis-(3-methyl-pyridin-2-ylmethyl)-amino]-piperidin-1-yl}-2-phenylamino-ethanone;
{4-[Bis-(3-methyl-pyridin-2-ylmethyl)-amino]-piperidin-1-yl}-(2,3-dihydro-1H-indol-2-yl)-methanone;
{4-[Bis-(3-methyl-pyridin-2-ylmethyl)-amino]-piperidin-1-yl}-(1H-indazol-3-yl)-methanone;
1-{4-[Bis-(3-methyl-pyridin-2-ylmethyl)-amino]-piperidin-1-yl}-2-morpholin-4-yl-ethanone;
{4-[Bis-(3-methyl-pyridin-2-ylmethyl)-amino]-piperidin-1-yl}-(1H-indol-7-yl)-methanone;
(1H-Benzoimidazol-2-yl)-{4-[bis-(3-methyl-pyridin-2-ylmethyl)-amino]-piperidin-1-yl}-methanone;
{4-[bis-(3-methyl-pyridin-2-ylmethyl)-amino]-piperidin-1-yl}-pyridin-2-yl-methanone;
{4-[bis-(3-methyl-pyridin-2-ylmethyl)-amino]-piperidin-1-yl}-(2,4-dimethyl-1-oxy-pyridin-3-yl)-methanone;
{4-[(3,5-dimethyl-pyridin-2-ylmethyl)-(3-methyl-pyridin-2-ylmethyl)-amino]-piperidin-1-yl}-(1H-imidazol-2-yl)-methanone;
N-{3-[Bis-(3-methyl-pyridin-2-ylmethyl)-amino]-1-propoxy}-guanidine;
{3-[(3,5-Dimethyl-pyridin-2-ylmethyl)-(1-pyridin-2-yl-ethyl)-amino]-propyl}-urea;
(S)-N-{4-[(3,5-Dimethyl-pyridin-2-ylmethyl)-(1-pyridin-2-yl-ethyl)-amino]-butyl}-6-hydroxy-nicotinamide;
(S)-{4-[(3,5-Dimethyl-pyridin-2-ylmethyl)-(1-pyridin-2-yl-ethyl)-amino]-butyl}-urea;
1-{4-[(3,5-Dimethyl-pyridin-2-ylmethyl)-[3-(1-methyl-1-(4-fluoro-phenyl)-ethyl)-pyridin-2-ylmethyl]-amino]-butyl}-3-(hydroxy)-urea;
{4-[(3,5-Dimethyl-pyridin-2-ylmethyl)-(3-isopropyl-pyridin-2-ylmethyl)-amino]-butyl}-urea;
1-{4-[(3,5-Dimethyl-pyridin-2-ylmethyl)-(3-isopropyl-pyridin-2-ylmethyl)-amino]-butyl}-imidazolidin-2-one;
{4-[(3,5-Dimethyl-pyridin-2-ylmethyl)-(3-isopropyl-pyridin-2-ylmethyl)-amino]-butyl}-sulfamide;
1-{4-[(3,5-Dimethyl-pyridin-2-ylmethyl)-(3-isopropyl-pyridin-2-ylmethyl)-amino]-butyl}-3-hydroxy-imidazolidin-2-one;
1-{4-[(3,5-Dimethyl-pyridin-2-ylmethyl-isoquinolin-1-ylmethyl-amino]-butyl}-3-(1H-imidazol-2-yl)-urea;
1-{4-[(3,5-Dimethyl-pyridin-2-ylmethyl-isoquinolin-1-ylmethyl-amino]-butyl}-3-hydroxy-1-methyl-urea;
1-{4-[(3,5-Dimethyl-pyridin-2-ylmethyl-isoquinolin-1-ylmethyl-amino]-butyl}-3-(1H-imidazol-2-yl)-1-methyl-urea;
(3,5-Dimethyl-pyridin-2-ylmethyl)-[2-(1H-imidazol-4-yl)-ethyl]-isoquinolin-1-ylmethyl-amine;
(5-Chloro-3-methyl-pyridin-2-ylmethyl)-{3-[1-(4-fluoro-phenyl)-1-methyl-ethyl]-pyridin-2-ylmethyl}-[2-(1H-imidazol-4-yl)-ethyl]-amine;

(3,5-Dimethyl-pyridin-2-ylmethyl)-isoquinolin-1-ylmethyl-(2-pyridin-2-yl-ethyl)-amine;
1-(1H-Benzimidazol-2-yl)-5-[bis-(3-methyl-pyridin-2-ylmethyl)-amino]-pentan-1-one;
(5-Chloro-3-methyl-pyridin-2-ylmethyl)-{3-[1-(4-chloro-phenyl)-1-methyl-ethyl]-pyridin-2-ylmethyl}-[2-(1H-imidazol-4-yl)-ethyl]-amine;
(5-Chloro-3-methyl-pyridin-2-ylmethyl)-{3-[1-(4-fluoro-phenyl)-1-methyl-ethyl]-pyridin-2-ylmethyl}-(2-pyridin-2-yl-ethyl)-amine;
5-[Bis-(3-methyl-pyridin-2-ylmethyl)-amino]-pentanoic acid hydroxyamide;
(5-Chloro-3-methyl-pyridin-2-ylmethyl)-[2-(1H-imidazol-4-yl)-ethyl]-isoquinolin-1-ylmethyl-amine;
(3,5-dimethyl-pyridin-2-ylmethyl)-{3-[1-(4-fluoro-phenyl)-1-methyl-ethyl]-pyridin-2-ylmethyl}-[2-(1H-imidazol-4-yl)-ethyl]-amine;
(3,5-dimethyl-pyridin-2-ylmethyl)-[2-(1H-imidazol-4-yl)-ethyl]-(3-isopropyl-pyridin-2-ylmethyl)-amine;
[4-(1H-Benzoimidazole-2-sulfonyl)-butyl]-(3,5-dimethyl-pyridin-2-ylmethyl)-isoquinolin-1-ylmethyl-amine;
{3-[Bis-(3-methyl-pyridin-2-ylmethyl)-amino]-propyl}-urea;
N-(4-{(3,5-Dimethyl-pyridin-2-ylmethyl)-[3-(1-hydroxy-1-methyl-ethyl)-pyridin-2-ylmethyl]-amino}-butyl)-6-hydroxy-nicotinamide;
(4-{(3,5-Dimethyl-pyridin-2-ylmethyl)-[3-(1-hydroxy-1-methyl-ethyl)-pyridin-2-ylmethyl]-amino}-butyl)-urea;
N-(3-{(3,5-dimethyl-pyridin-2-ylmethyl)-[3-(1-hydroxy-1-methyl-ethyl)-pyridin-2-ylmethyl]-amino}-propyl)-acetamide;
{3-[Bis-(3-methyl-pyridin-2-ylmethyl)-amino]-propyl}-hydroxyurea;
[4-((3,5-Dimethyl-pyridin-2-ylmethyl)-{3-[1-(4-fluoro-phenyl)-1-methyl-ethyl]-pyridin-2-ylmethyl}-amino)-butyl]-urea;
{4-[(3,5-Dimethyl-pyridin-2-ylmethyl)-(3-isopropyl-pyridin-2-ylmethyl)-amino]-butyl}-hydroxyurea;
{4-[(3,5-Dimethyl-pyridin-2-ylmethyl)-(3-phenyl-pyridin-2-ylmethyl)-amino]-butyl}-hydroxyurea;
1-{4-[(3,5-Dimethyl-pyridin-2-ylmethyl)-(3-isopropyl-pyridin-2-ylmethyl)-amino]-butyl}-1-methyl-urea;
1-{4-[(3,5-Dimethyl-pyridin-2-ylmethyl)-(3-isopropyl-pyridin-2-ylmethyl)-amino]-butyl}-1-methyl-hydroxyurea;
1-{4-[(5-Chloro-3-methyl-pyridin-2-ylmethyl)-isoquinolin-1-ylmethyl-amino]-butyl}-1-methyl-hydroxyurea;
1-{4-[(5-Chloro-3-methyl-pyridin-2-ylmethyl)-{3-[1-(4-fluoro-phenyl)-1-methyl-ethyl]-pyridin-2-ylmethyl}-amino]-butyl}-1-methyl-hydroxyurea;
(3,5-dimethyl-pyridin-2-ylmethyl)-isoquinolin-1-ylmethyl-[2-(1-methyl-1H-imidazol-4-yl)-ethyl]-amine;
1H-benzoimidazole-2-carboxylic acid-{4-[(3,5-dimethyl-pyridin-2-ylmethyl)-isoquinolin-1-ylmethyl-amino]-butyl}-amide;
1H-benzimidazole-4-carboxylic acid-{4-[(3,5-dimethyl-pyridin-2-ylmethyl)-isoquinolin-1-ylmethyl-amino]-butyl}-amide;
N-{4-[bis-(3-methyl-pyridin-2-ylmethyl)-amino]-butyl}-guanidine;
N-(4-{(3,5-Dimethyl-pyridin-2-ylmethyl)-[3-(1-hydroxy-1-methyl-ethyl)-pyridin-2-ylmethyl]-amino}-butyl)-guanidine;
4-[Bis-(3-methyl-pyridin-2-ylmethyl)-amino-]butyl-cyanamide;
hydroxylaminecarboxylic acid 4-[(3,5-dimethyl-pyridin-2-ylmethyl)-(3-isopropyl-pyridin-2-ylmethyl)-amino]-butyl ester;
4-[{3-[1-(4-chloro-phenyl)-1-methyl-ethyl]-pyridin-2-ylmethyl}-(3,5-dimethyl-pyridin-2-ylmethyl)-amino]-butyl-cyanamide;
{4-[{3-[1-(4-chloro-phenyl)-1-methyl-ethyl]-pyridin-2-ylmethyl}-(3,5-dimethyl-pyridin-2-ylmethyl)-amino]-butylamino}-acetonitrile;
{3-[1-(4-chloro-phenyl)-1-methyl-ethyl]-pyridin-2-ylmethyl}-(3,5-dimethyl-pyridin-2-ylmethyl)-(4-pyrrolidin-1-yl-butyl)-amine;
4-[N-(1H-benzimidazol-2-ylmethyl)-N'-methyl-N'-pyridin-2-yl-hydrazino]-butylamine;
N-{3-[Bis-(3-methyl-pyridin-2-ylmethyl)-amino]-propyl}-6-hydroxy-nicotinamide;
6-Hydroxy-N-{3-[(3-methyl-pyridin-2-ylmethyl)-(1-pyridin-2-yl-ethyl)-amino]-propyl}-nicotinamide;
Bis-(3-methyl-pyridin-2-ylmethyl)-piperidin-4-yl-amine;
4-[bis-(3-methyl-pyridin-2-yl)-amino]-piperidine-1-carboxylic acid amide;
1-{4-[bis-(3-methyl-pyridin-2-ylmethyl)-amino]-piperidin-1-yl}-ethanone;
bis-(3-methyl-pyridin-2-ylmethyl)-(1-pyridin-2-ylmethyl-piperidin-4-yl)-amine;
4-[Bis-(3-methyl-pyridin-2-ylmethyl)-amino]-piperidine-1-carboxamidine;
N,N-Bis-(3-methyl-pyridin-2-ylmethyl)-cyclohexane-1,4-diamine;
3-{[Bis-(3-methyl-pyridin-2-ylmethyl)-amino]-methyl}-piperidine-1-carboxylic acid amide;
Bis-(3-methyl-pyridin-2-ylmethyl)-piperidin-3-ylmethyl-amine;
N-(3,5-Dimethyl-pyridin-2-ylmethyl)-N-(3-hydroxymethyl-pyridin-2-ylmethyl)-trans-cyclohexane-1,4-diamine;
N-(3,5-Dimethyl-pyridin-2-ylmethyl)-N-(3-isopropyl-pyridin-2-ylmethyl)-trans-cyclohexane-1,4-diamine;
N-(3-methyl-pyridine-2-ylmethyl)-N-(3-phenyl-pyridine-2-ylmethyl)-cyclohexane-1,4-diamine;
N-(3-methyl-pyridin-2-ylmethyl)-N-(1-pyridin-2-yl-ethyl)-cyclohexane-1,4-diamine;
4-[(3,5-Dimethyl-pyridin-2-ylmethyl)-(1-pyridin-2-yl-ethyl)-amino]-piperidine-1-carboxylic acid hydroxyamide;
4-[(3,5-Dimethyl-pyridin-2-ylmethyl)-(1-pyridin-2-yl-ethyl)-amino]-piperidine-1-carboxylic acid amide;
4-{(3,5-Dimethyl-pyridin-2-ylmethyl)-[3-(1-methoxy-1-methyl-ethyl)-pyridin-2-ylmethyl]-amino}-piperidine-1-carboxylic acid hydroxyamide;
4-[(5-Chloro-3-methyl-pyridin-2-ylmethyl)-(3-isopropyl-pyridin-2-ylmethyl)-amino]-piperidine-1-carboxylic acid hydroxyamide;
{4-[Bis-(3-methyl-pyridin-2-ylmethyl)-amino]-piperidin-1-yl}-pyridin-3-yl-methanone;
{4-[Bis-(3-methyl-pyridin-2-ylmethyl)-amino]-piperidin-1-yl}-pyridin-4-yl-methanone;
{4-[Bis-(3-methyl-pyridin-2-ylmethyl)-amino]-piperidin-1-yl}-quinolin-2-yl-methanone;
{4-[Bis-(3-methyl-pyridin-2-ylmethyl)-amino]-piperidin-1-yl}-quinolin-6-yl-methanone;
{4-[Bis-(3-methyl-pyridin-2-ylmethyl)-amino]-piperidin-1-yl}-quinolin-8-yl-methanone;
4-[Bis-(3-methyl-pyridin-2-ylmethyl)-amino]-piperidine-1-carboxylic acid phenylamide;
4-[Bis-(3-methyl-pyridin-2-ylmethyl)-amino]-piperidine-1-carboxylic acid benzylamide;

4-[Bis-(3-methyl-pyridin-2-ylmethyl)-amino]-piperidine-1-carboxylic acid benzyl-hydroxy-amide;
{4-[Bis-(3-methyl-pyridin-2-ylmethyl)-amino]-piperidin-1-yl}-(1H-imidazol-4-yl)-methanone;
4-[(3,5-Dimethyl-pyridin-2-ylmethyl)-isoquinolin-1-ylmethyl-amino]-piperidine-1-carboxylic acid (1H-imidazol-2-yl)-amide;
4-[{3-[1-(4-Chloro-phenyl)-1-methyl-ethyl]-pyridin-2-ylmethyl}-(3,5-dimethyl-pyridin-2-ylmethyl)-amino]-piperidine-1-carboxylic acid (1H-imidazol-2-yl)-amide;
4-{(3,5-Dimethyl-pyridin-2-ylmethyl)-[3-(1-methyl-1-phenyl-ethyl)-pyridin-2-ylmethyl]-amino}-piperidine-1-carboxylic acid (1H-imidazol-2-yl)-amide;
4-[(3,5-Dimethyl-pyridin-2-ylmethyl)-isoquinolin-1-ylmethyl-amino]-piperidine-1-carboxylic acid hydroxyamide;
N-{4-trans-[(3,5-Dimethyl-pyridin-2-ylmethyl)-(3-phenyl-pyridin-2-ylmethyl)-amino]-cyclohexyl}-guanidine;
4-[Bis-(3-methyl-pyridin-2-ylmethyl)-amino]-4-methyl-piperidine-1-carboxylic acid hydroxyamide;
4-[(3,5-Dimethyl-pyridin-2-ylmethyl)-(3-methyl-pyridin-2-ylmethyl)-amino]-piperidine-1-carboxylic acid hydroxyamide;
4-[Bis-(3-methyl-pyridin-2-ylmethyl)-amino]-piperidine-1-carboxylic acid isoxazol-3-ylamide;
1H-Benzoimidazole-2-carboxylic acid {4-trans-[(3-isopropyl-pyridin-2-ylmethyl)-(3-methyl-pyridin-2-ylmethyl)-amino]-cyclohexyl}-amide;
1-(1H-Imidazol-2-yl)-3-{4-trans-[(3-isopropyl-pyridin-2-ylmethyl)-(3-methyl-pyridin-2-ylmethyl)-amino]-cyclohexyl}-urea;
4-[(3,5-Dimethyl-pyridin-2-ylmethyl)-(3-isopropyl-pyridin-2-ylmethyl)-amino]-piperidine-1-carboxylic acid pyridin-2-ylamide;
4-[(3,5-Dimethyl-pyridin-2-ylmethyl)-(3-isopropyl-pyridin-2-ylmethyl)-amino]-piperidine-1-carboxylic acid (1H-benzoimidazol-2-yl)-amide;
4-[bis-(3-methyl-pyridin-2-ylmethyl)-amino]-N-hydroxy-piperidine-1-carboxamidine;
4-[(3,5-Dimethyl-pyridin-2-ylmethyl)-(3-isopropyl-pyridin-2-ylmethyl)-amino]-piperidine-1-carboxylic acid hydroxyamide;
4-[(1H-Benzoimidazol-4-ylmethyl)-(3-methyl-pyridin-2-ylmethyl)-amino]-piperidine-1-carboxylic acid hydroxyamide;
4-[Bis-(3-methyl-pyridin-2-ylmethyl)-amino]-piperidine-1-carboxylic acid thiazol-2-ylamide;
4-[Bis-(3-methyl-pyridin-2-ylmethyl)-amino]-piperidine-1-carboxylic acid (1-methyl-1H-benzoimidazol-2-yl)-amide;
4-[Bis-(3-methyl-pyridin-2-ylmethyl)-amino]-piperidine-1-carboxylic acid benzothiazol-2-ylamide;
[1-(4,5-Dihydro-1H-imidazol-2-yl)-piperidin-4-yl]-bis-(3-methyl-pyridin-2-ylmethyl)-amine;
4-[(3,5-Dimethyl-pyridin-2-ylmethyl)-(3-hydroxymethyl-pyridin-2-ylmethyl)-amino]-piperidine-1-carboxamidine;
4-[(3,5-Dimethyl-pyridin-2-ylmethyl)-(3-isopropyl-pyridin-2-ylmethyl)-piperidine]-1-carboxamidine;
4-[(3,5-Dimethyl-pyridin-2-ylmethyl)-(3-isopropyl-pyridin-2-ylmethyl)-amino]-N-hydroxypiperidine-1-carboxamidine;
4-[(3,5-Dimethyl-pyridin-2-ylmethyl)-(3-phenyl-pyridin-2-ylmethyl)-piperidine]-1-carboxamidine;
4-[(3,5-Dimethyl-pyridin-2-ylmethyl)-(3-phenyl-pyridin-2-ylmethyl)-amino]-N-hydroxypiperidine-1-carboxamidine;
(3,5-Dimethyl-pyridin-2-ylmethyl)-(3-isopropyl-pyridin-2-ylmethyl)-piperidin-4-yl-amine;
4-((3,5-Dimethyl-pyridin-2-ylmethyl)-{3-[1-(4-fluoro-phenyl)-1-methyl-ethyl]-pyridin-2-ylmethyl}-amino)-piperidine-1-carboxylic acid hydroxyamide;
4-[(3,5-Dimethyl-pyridin-2-ylmethyl)-(3-isopropyl-pyridin-2-ylmethyl)-amino]-piperidine-1-carboxylic acid methoxy-amide;
4-[(3,5-Dimethyl-pyridin-2-ylmethyl)-(3-isopropyl-pyridin-2-ylmethyl)-amino]-piperidine-1-carboxylic acid amide;
{4-[Bis-(3-methyl-pyridin-2-ylmethyl)-amino]-piperidin-1-yl}-(1-oxy-pyridin-3-yl)-methanone;
{4-[Bis-(3-methyl-pyridin-2-ylmethyl)-amino]-piperidin-1-yl}-(1-oxy-pyridin-4-yl)-methanone;
4-((3,5-Dimethyl-pyridin-2-ylmethyl)-{3-[1-(4-fluoro-phenyl)-1-methyl-ethyl]-pyridin-2-ylmethyl}-amino)-piperidine-1-carboxylic acid (1H-imidazol-2-yl)-amide;
4-[(5-Chloro-3-methyl-pyridin-2-ylmethyl)-isoquinolin-1-ylmethyl-amino]-piperidine-1-carboxylic acid (1H-imidazol-2-yl)-amide;
4-[(5-Chloro-3-methyl-pyridin-2-ylmethyl)-(3-isopropyl-pyridin-2-ylmethyl)-amino]-piperidine-1-carboxylic acid (1H-imidazol-2-yl)-amide;
4-((5-Chloro-3-methyl-pyridin-2-ylmethyl)-{3-[1-(4-fluoro-phenyl)-1-methyl-ethyl]-pyridin-2-ylmethyl}-amino)-piperidine-1-carboxylic acid (1H-imidazol-2-yl)-amide;
4-[(5-Chloro-3-methyl-pyridin-2-ylmethyl)-isoquinolin-1-ylmethyl-amino]-piperidine-1-carboxylic acid hydroxyamide;
4-{(5-Chloro-3-methyl-pyridin-2-ylmethyl)-[3-(1-methyl-1-phenyl-ethyl)-pyridin-2-ylmethyl]-amino}-piperidine-1-carboxylic acid (1H-imidazol-2-yl)-amide;
4-[(1-allyl-1H-benzomidazol-2-ylmethyl)-(3,5-dimethyl-pyridin-2-ylmethyl)-amino]-piperidine-1-carboxamidine;
(1H-benzoimidazol-2-yl)-{4-[(3,5-dimethyl-pyridin-2-ylmethyl)-(3-isopropyl-pyridin-2-ylmethyl)-amino]-piperidin-1-yl}-methanone;
4-[(3,5-dimethyl-pyridin-2-ylmethyl)-(3-isopropyl-pyridin-2-ylmethyl)-amino]-piperidine-1-carboxylic acid thiazol-2-ylamide;
4-[(3,5-dimethyl-pyridin-2-ylmethyl)-(3-isopropyl-pyridin-2-ylmethyl)-amino]-piperidine-1-carboxylic acid benzothiazol-2-ylamide;
(1H-benzoimidazol-2-yl)-{4-[(3,5-dimethyl-pyridin-2-ylmethyl)-(3-isopropyl-pyridin-2-ylmethyl)-amino]-piperidin-1-yl}-methanone;
4-[(3,5-dimethyl-pyridin-2-ylmethyl)-(3-isopropyl-pyridin-2-ylmethyl)-amino]-piperidine-1-carboxylic acid pyridazin-3-ylamide;
4-[(3,5-dimethyl-pyridin-2-ylmethyl)-(3-isopropyl-pyridin-2-ylmethyl)-amino]-piperidine-1-carboxylic acid triazol-3-ylamide;
(3,5-dimethyl-pyridin-2-ylmethyl)-{3-[1-(4-fluoro-phenyl)-1-methyl-ethyl]-pyridin-2-ylmethyl}-piperidin-4-yl-amine;
[4-((3,5-dimethyl-pyridin-2-ylmethyl)-{3-[1-(4-fluoro-phenyl)-1-methyl-ethyl]-pyridin-2-ylmethyl}-amino)-piperidin-1-yl]-imidazol-1-yl-methanone;

4-((5-chloro-3-methyl-pyridin-2-ylmethyl)-{3-[1-(4-fluoro-phenyl)-1-methyl-ethyl]-pyridin-2-ylmethyl}-amino)-piperidine-1-carboxylic acid hydroxyamide;
4-{[Bis-(3-methyl-pyridin-2-ylmethyl)-amino]-methyl}-piperidine-1-carboxamidine;
4-[Bis-3-methyl-pyridin-2-ylmethyl)-amino]-N-nitro-piperidine-1-carboxamidine;
[1-(1-Amino-2-nitro-vinyl)-piperidin-4-yl]-bis-(3-methyl-pyrin-2-ylmethyl)-amine;
N-({4-[Bis-(3-methyl-pyridin-2-ylmethyl)-amino]-piperidin-1-yl}-imino-methyl)-acetamide;
4-[Bis-(3-methyl-pyridin-2-ylmethyl)-amino]-piperidine-1-carboxylic acid hydroxyamide;
4-[Bis-(3-methyl-pyridin-2-ylmethyl)-amino]-piperidine-1-carboxylic acid hydroxy-methyl-amide;
4-[Bis-(3-methyl-pyridin-2-ylmethyl)-amino]-piperidine-1-carboxylic acid hydrazide;
4-[Bis-(3-methyl-pyridin-2-ylmethyl)-amino]-piperidine-1-carboxylic acid methoxy-amide;
[4-((3,5-dimethyl-pyridin-2-ylmethyl)-{3-[1-(4-fluoro-phenyl)-1-methyl-ethyl]-pyridin-2-ylmethyl}-amino)-piperidin-1-yl]-imidazol-1-yl-methanone;
4-((5-chloro-3-methyl-pyridin-2-ylmethyl)-{3-[1-(4-fluoro-phenyl)-1-methyl-ethyl]-pyridin-2-ylmethyl}-amino)-piperidine-1-carboxylic acid hydroxyamide;
3-{[Bis-(3-methyl-pyridin-2-ylmethyl)-amino]-methyl}-azetidine-1-carboxylic acid hydroxyamide;
trans-4-[Bis-(3-methyl-pyridin-2-ylmethyl)-amino]-cyclohexanecarboxylic acid hydroxyamide;
2-{4-[Bis-(3-methyl-pyridin-2-ylmethyl)-amino]-piperidin-1-yl}-N-hydroxyacetamide;
cis-4-[Bis-(3-methyl-pyridin-2-ylmethyl)-amino]-cyclohexanecarboxylic acid hydroxyamide;
trans-4-[(3,5-dimethyl-pyridin-2-ylmethyl)-(3-isopropyl-pyridin-2-ylmethyl)-amino]-cyclohexanecarboxylic acid hydroxyamide;
Bis-(3-methyl-pyridin-2-ylmethyl)-(1-[1,2,4]oxadiazol-3-yl-piperidine-4-yl)-amine;
[1-(1H-imidazol-2-ylmethyl)-piperidin-4-yl]-bis-(3-methyl-pyridin-2-ylmethyl)-amine;
4-[bis-(3-methyl-pyridin-2-ylmethyl)-amino]-N-cyano-piperidine-1-carboxamidine;
[1-(1-imino-ethyl)-piperidin-4-yl]-bis-(3-methyl-pyridin-2-ylmethyl)-amine;
2-{4-[bis-(3-methyl-pyridin-2-ylmethyl)-amino]-piperidin-1-yl}-ethanol;
1-{4-[bis-(3-methyl-pyridin-2-ylmethyl)-amino]-piperidin-1-yl}-2-hydroxy-ethanone;
4-[bis-(3-methyl-pyridin-2-ylmethyl)-amino]-piperidine-1-carboxylic acid (2-hydroxy-ethyl)-amide;
4-[bis-(3-methyl-pyridin-2-ylmethyl)-amino]-piperidine-1-sulfonic acid amide;
4-[bis-(3-methyl-pyridin-2-ylmethyl)-amino]-piperidine-1-carboxylic acid (2-hydroxy-phenyl)-amide;
4-[bis-(3-methyl-pyridin-2-ylmethyl)-amino]-piperidine-1-carboxylic acid pyridin-2-ylamide;
4-[bis-(3-methyl-pyridin-2-ylmethyl)-amino]-piperidine-1-carboxylic acid (1H-imidazol-2-yl)-amide;
2-(3-{[bis-(3-methyl-pyridin-2-ylmethyl)-amino]-methyl}-azetidin-1-yl)-N-hydroxy-acetamide;
4-[bis-(3-methyl-pyridin-2-ylmethyl)-amino]-piperidine-1-carboxylic acid (1H-benzoimidazol-2-yl)-amide;
4-[(3,5-dimethyl-pyridin-2-ylmethyl)-(3-isopropyl-pyridin-2-ylmethyl)-amino]-piperidine-1-carboxylic acid (1H-imidazol-2-yl)-amide;
L-2-amino-1-{4-[bis-(3-methyl-pyridin-2-ylmethyl)-amino]-piperidin-1-yl}-3-mercapto-propan-1-one;
4-{(3,5-Dimethyl-pyridin-2-ylmethyl)-[3-(1-methyl-1-phenyl-ethyl)-pyridin-2-ylmethyl]-amino}-piperidine-1-carboxylic acid hydroxyamide;
1-{trans-4-[(3-Isopropyl-pyridin-2-ylmethyl)-(3-methyl-pyridin-2-ylmethyl)-amino]-cyclohexyl}-3-hydroxy-urea;
3-[Bis-(3-methyl-pyridin-2-ylmethyl)-amino]-8-aza-bicyclo[3.2.1]octane-8-carboxylic acid hydroxyamide;
8-[bis-(3-methyl-pyridin-2-ylmethyl)-amino]-3-aza-bicyclo[3.2.1]octane-3-carboxylic acid hydroxyamide;
(3H-benzoimidazol-4-yl)-{4-[bis-(3-methyl-pyridin-2-ylmethyl)-amino]-piperidin-1-yl}-methanone;
$N^1$-(6-amino-pyridin-2-ylmethyl)-$N^1$-(5,6,7,8-tetrahydro-quinolin-8-yl)-butane-1,4-diamine;
$N^1$-(6-methoxymethyl-pyridin-2-ylmethyl)-$N^1$-(5,6,7,8-tetrahydro-quinolin-8-yl)-butane-1,4-diamine;
$N^1$-(5,6,7,8-tetrahydroquinolin-8-yl)-$N^1$-(5,6,7,8-tetrahydroquinolin-3-ylmethyl)-butane-1,4-diamine;
$N^1$-[2,2']Bipyridinyl-6-ylmethyl-$N^1$-(5,6,7,8-tetrahydro-quinolin-8-yl)-butane-1,4-diamine;
N-{3-[(3,5-Dimethyl-pyridin-2-ylmethyl)-(5,6,7,8-tetrahydro-quinolin-8-yl)-amino]-propyl}-acetamide;
{3-[(3,5-Dimethyl-pyridin-2-ylmethyl)-(5,6,7,8-tetrahydro-quinolin-8-yl)-amino]-propyl}-urea;
N-{3-[(3,5-Dimethyl-pyridin-2-ylmethyl)-(5,6,7,8-tetrahydro-quinolin-8-yl)-amino]-propyl}-6-hydroxy-nicotinamide;
(S)-N-{4-[(3,5-Dimethyl-pyridin-2-ylmethyl)-(5,6,7,8-tetrahydro-quinolin-8-yl)-amino]-butyl}-acetamide;
N-{4-[(3,5-Dimethyl-pyridin-2-ylmethyl)-(5,6,7,8-tetrahydro-quinolin-8-yl)-amino]-butyl}-6-hydroxy-nicotinamide;
(S)-{4-[(3,5-Dimethyl-pyridin-2-ylmethyl)-(5,6,7,8-tetrahydro-quinolin-8-yl)-amino]-butyl}-urea;
4-[(3,5-Dimethyl-pyridin-2-ylmethyl)-(5,6,7,8-tetrahydro-quinolin-8-yl)-amino]-piperidine-1-carboxylic acid (1H-imidazol-2-yl)-amide;
4-[(3,5-Dimethyl-pyridin-2-ylmethyl)-(5,6,7,8-tetrahydro-quinolin-8-yl)-amino]-piperidine-1-carboxylic acid hydroxyamide;
$N^1$-(5-Methyl-3H-imidazol-4-ylmethyl)-$N^1$-(5,6,7,8-tetrahydro-quinolin-8-yl)-butane-1,4-diamine;
{3-[(3-methyl-pyridin-2-yl)-(5,6,7,8-tetrahydro-quinolin-8-yl)-amino]-propyl}-urea;
{3-[(3-methyl-pyridin-2-yl)-(5,6,7,8-tetrahydro-quinolin-8-yl)-amino]-propyl}-guanidine;
N-{3-[(3,5-dimethyl-pyridin-2-yl)-(5,6,7,8-tetrahydro-quinolin-8-yl)-amino]-propyl}-N-hydroxyurea;
N-{4-[(3,5-dimethyl-pyridin-2-yl)-(5,6,7,8-tetrahydro-quinolin-8-yl)-amino]-butyl}-N-hydroxyurea;
N-{3-[(3,5-Dimethyl-pyridin-2-yl)-(5,6,7,8-tetrahydro-quinolin-8-yl)-amino]-propyl}-hydroxylamine;
N-{3-[(3,5-Dimethyl-pyridin-2-yl)-(5,6,7,8-tetrahydro-quinolin-8-yl)-amino]-propyl}-N-hydroxyurea;
N-{4-[(3,5-Dimethyl-pyridin-2-yl)-(5,6,7,8-tetrahydro-quinolin-8-yl)-amino]-butyl}-hydroxylamine;
N-{4-[(3,5-Dimethyl-pyridin-2-yl)-(5,6,7,8-tetrahydro-quinolin-8-yl)-amino]-butyl}-N-hydroxyurea;
(3,5-dimethyl-pyridin-2-ylmethyl)-(5,6,7,8-tetrahydro-quinolin-8-yl)-amine;
$N^1$-(5,6,7,8-tetrahydro-quinolin-8-yl)-$N^1$-thiazol-4-ylmethyl-butane-1,4-diamine;
(5-Aminomethyl-2-{[bis-(3-methyl-pyridin-2-ylmethyl)-amino]-methyl}-phenyl)-methanol;
(5-aminomethyl-2-{[(3-methyl-pyridin-2-ylmethyl)-(3-isopropyl-pyridin-2-ylmethyl)-amino]-methyl}-phenyl)-methanol;

(5-Aminomethyl-2-{[(3-amino-pyridin-2-ylmethyl)-(3-methyl-pyridin-2-ylmethyl)-amino]-methyl}-phenyl)-methanol;

(5-Aminomethyl-2-{[(3-chloro-pyridin-2-ylmethyl)-(3-methyl-pyridin-2-ylmethyl)-amino]-methyl}-phenyl)-methanol;

N-(4-{[Bis-(3-methyl-pyridin-2-ylmethyl)-amino]-methyl}-3-hydroxymethyl-benzyl)-acetamide;

(4-aminomethyl-2-methoxymethyl-benzyl)-bis-(3-methyl-pyridin-2-ylmethyl)-amine;

(4-aminomethyl-2-hydroxymethyl-benzyl)-(3,5-dimethyl-pyridin-2-ylmethyl)-(3-hydroxymethyl-pyridin-2-ylmethyl)-amine;

N-(4-{[bis-(3-methyl-pyridin-2-ylmethyl)-amino]-methyl}-3-hydroxymethyl-benzyl)-methanesulfonamide;

(2-aminomethyl-4-methoxy-benzyl)-(3-methyl-pyridin-2-ylmethyl)-(1-pyridin-2-yl-ethyl)-amine;

(5-aminomethyl-2-{[(3-methyl-pyridin-2-ylmethyl)-(1-pyridin-2-yl-ethyl)-amino]-methyl}-phenyl)-methanol;

(2-Aminoethyl-pyridin-3-ylmethyl)-bis-(3-methyl-pyridin-2-ylmethyl)-amine;

(4-Aminomethyl-thiophen-3-ylmethyl)-bis-(3-methyl-pyridin-2-ylmethyl)-amine;

(4-aminomethyl-thiophen-3-ylmethyl)-(3-methyl-pyridin-2-yl-ethyl)-amine;

(5-aminomethyl-2-{[(1H-benzoimidazol-2-ylmethyl)-(1-pyridin-2-yl-ethyl)-amino]-methyl}-phenyl)-methanol;

(4-aminomethyl-thiophen-3-ylmethyl)-(1H-benzimidazol-2-ylmethyl)-(1-pyridin-2-yl-ethyl)-amine;

4-[((3,5-dimethyl-pyridin-2-ylmethyl)-{3-[1-(4-fluoro-phenyl)-1-methyl-ethyl]-pyridin-2-ylmethyl}-amino)-methyl]-3-hydroxymethyl-benzamide;

N-(3-Hydroxymethyl-4-{[(3-methyl-pyridin-2-ylmethyl)-(1-pyridin-2-yl-ethyl)-amino]-methyl}-benzyl)-acetamide;

(5-aminomethyl-2-{[(5-chloro-3-methyl-pyridin-2-ylmethyl)-(1-methyl-1-pyridin-2-yl-ethyl)-amino]-methyl}-phenyl)-methanol;

N-(4-{[(5-chloro-3-methyl-pyridin-2-ylmethyl)-(1-methyl-1-pyridin-2-yl-ethyl)-amino]-methyl}-3-hydroxymethyl-benzyl)-acetamide;

4-{[(5-chloro-3-methyl-pyridin-2-ylmethyl)-(1-methyl-1-pyridin-2-yl-ethyl)-amino]-methyl}-3-hydroxymethyl-benzonitrile;

(5-aminomethyl-2-{[(3-methyl-pyridin-2-ylmethyl)-(5,6,7,8-tetrahydro-quinolin-8-yl)-amino]-methyl}-phenyl)-methanol;

(5-aminomethyl-2-{[(3-amino-pyridin-2-ylmethyl)-(5,6,7,8-tetrahydro-quinolin-8-yl)-amino]-methyl}-phenyl)-methanol;

N-(2-{[(S)-(4-aminomethyl-2-hydroxymethyl-benzyl)-5,6,7,8-tetrahydro-quinolin-8-yl-amino]-methyl}-pyridin-3-yl)-3,5-dichloro-isonicotinamide;

(S)-4-{[(3,5-dimethyl-pyridin-2-ylmethyl)-(5,6,7,8-tetrahydro-quinolin-8-yl)-amino]-methyl}-isophthalic acid dimethyl ester;

4-{[(3,5-dimethyl-pyridin-2-ylmethyl)-(5,6,7,8-tetrahydro-quinolin-8-yl)-amino]-methyl}-3-hydroxymethyl-benzoic acid methyl ester;

(2-{[(3,5-Dimethyl-pyridin-2-ylmethyl)-(5,6,7,8-tetrahydro-quinolin-8-yl)-amino]-methyl}-5-hydroxymethyl-phenyl)-methanol;

4-{[(3,5-dimethyl-pyridin-2-ylmethyl)-(5,6,7,8-tetrahydro-quinolin-8-yl)-amino]-methyl}-3-hydroxymethyl-benzoic acid;

(4-{[(3,5-Dimethyl-pyridin-2-ylmethyl)-(5,6,7,8-tetrahydro-quinolin-8-yl)-amino]-methyl}-3-hydroxymethyl-benzylamino)-acetic acid methyl ester;

(4-{[(3,5-Dimethyl-pyridin-2-ylmethyl)-(5,6,7,8-tetrahydro-quinolin-8-yl)-amino]-methyl}-3-hydroxymethyl-benzylamino)-acetic acid;

2-(4-{[(3,5-dimethyl-pyridin-2-ylmethyl)-(5,6,7,8-tetrahydro-quinolin-8-yl)-amino]-methyl}-3-hydroxymethyl-benzylamino)-ethanol;

N-(4-{[(5-chloro-3-methyl-pyridin-2-ylmethyl)-(5,6,7,8-tetrahydro-quinolin-8-yl)-amino]-methyl}-3-hydroxymethyl-benzyl)-acetamide;

N-(4-{[{3-[1-(4-fluoro-phenyl)-1-methyl-ethyl]-pyridin-2-ylmethyl}-(5,6,7,8-tetrahydro-quinolin-8-yl)-amino]-methyl}-3-hydroxymethyl-benzyl)-acetamide;

N-(4-{[(5-chloro-3-methyl-pyridin-2-ylmethyl)-(5,6,7,8-tetrahydro-quinolin-8-yl)-(S)-amino]-methyl}-3-hydroxymethyl-benzyl)-(S)-2-phenyl-butyramide;

N-(3-hydroxymethyl-4-{[(4-phenyl-pyridin-2-ylmethyl)-(5,6,7,8-tetrahydro-quinolin-8-yl)-(S)-amino]-methyl}-benzyl)-(S)-2-phenyl-butyramide;

N-(4-{[(3,5-dimethyl-pyridin-2-ylmethyl)-(5,6,7,8-tetrahydro-quinolin-8-yl)-(R)-amino]-methyl}-3-hydroxymethyl-benzyl)-(S)-2-phenyl-butyramide;

N-(4-{[(3,5-dimethyl-pyridin-2-ylmethyl)-(5,6,7,8-tetrahydro-quinolin-8-yl)-(R)-amino]-methyl}-3-hydroxymethyl-benzyl)-(R)-2-phenyl-butyramide;

N-(4-{[(4-tert-butyl-pyridin-2-ylmethyl)-(5,6,7,8-tetrahydro-quinolin-8-yl)-(S)-amino]-methyl}-3-hydroxymethyl-benzyl)-(S)-2-phenyl-butyramide;

1,2,3,4-tetrahydro-isoquinoline-3-carboxylic acid 4-{[(4-tert-butyl-pyridin-2-ylmethyl)-(5,6,7,8-tetrahydro-quinolin-8-yl)-amino]-methyl}-3-hydroxymethyl-benzylamide;

N-(3-hydroxymethyl-4-{[(3-methyl-pyridin-2-ylmethyl)-(5,6,7,8-tetrahydro-quinolin-8-yl)-amino]-methyl}-benzyl)-acetamide;

N-(4-{[(3-Methyl-pyridin-2-ylmethyl)-(5,6,7,8-tetrahydro-quinolin-8-yl)-amino]-methyl}-3-hydroxymethyl-benzyl amine;

N-(4-{[(3,5-Dimethyl-pyridin-2-ylmethyl)-(5,6,7,8-tetrahydro-quinolin-8-yl)-amino]-methyl}-3-hydroxymethyl-benzyl)-2-phenyl-propionamide;

N-(4-{[(3,5-Dimethyl-pyridin-2-ylmethyl)-(5,6,7,8-tetrahydro-quinolin-8-yl)-amino]-methyl}-3-hydroxymethyl-benzyl)-3-phenyl-propionamide;

N-(4-{[(3,5-Dimethyl-pyridin-2-ylmethyl)-(5,6,7,8-tetrahydro-quinolin-8-yl)-amino]-methyl}-3-hydroxymethyl-benzyl)-butyramide;

N-(4-{[(3,5-Dimethyl-pyridin-2-ylmethyl)-(5,6,7,8-tetrahydro-quinolin-8-yl)-amino]-methyl}-3-hydroxymethyl-benzyl)-2-phenyl-acetamide;

1,2,3,4-Tetrahydro-isoquinoline-3-carboxylic acid 4-{[(3,5-dimethyl-pyridin-2-ylmethyl)-(5,6,7,8-tetrahydro-quinolin-8-yl)-amino]-methyl}-3-hydroxymethyl-benzylamide;

N-(4-{[(3,5-Dimethyl-pyridin-2-ylmethyl)-(5,6,7,8-tetrahydro-quinolin-8-yl)-amino]-methyl}-3-hydroxymethyl-benzyl)-3-methyl-2-phenyl-butyramide;

N-(4-{[(3,5-Dimethyl-pyridin-2-ylmethyl)-(5,6,7,8-tetrahydro-quinolin-8-yl)-amino]-methyl}-3-hydroxymethyl-benzyl)-2-phenyl-isobutyramide;

N-(4-{[(3,5-Dimethyl-pyridin-2-ylmethyl)-(5,6,7,8-tetrahydro-quinolin-8-yl)-amino]-methyl}-3-hydroxymethyl-benzyl)-2-(4-isobutyl-phenyl)-propionamide;

1-p-Tolyl-cyclopentanecarboxylic acid 4-{[(3,5-Dimethyl-pyridin-2-ylmethyl)-(5,6,7,8-tetrahydro-quinolin-8-yl)-amino]-methyl}-3-hydroxymethyl-benzylamide;

1,2,3,4-Tetrahydro-naphthalene-2-carboxylic acid 4-{[(3,5-dimethyl-pyridin-2-ylmethyl)-(5,6,7,8-tetrahydro-quinolin-8-yl)-amino]-methyl}-3-hydroxymethyl-benzylamide;

trans-2-Phenyl-cyclopropanecarboxylic acid 4-{[(3,5-dimethyl-pyridin-2-ylmethyl)-(5,6,7,8-tetrahydro-quinolin-8-yl)-amino]-methyl}-3-hydroxymethyl-benzylamide;

bicyclo[4.2.0]octa-1(6),2,4-triene-7-carboxylic acid 4-{[(3,5-dimethyl-pyridin-2-ylmethyl)-(5,6,7,8-tetrahydro-quinolin-8-yl)-amino]-methyl}-3-hydroxymethyl-benzylamide;

(5-aminomethyl-2-{[(3,5-dimethyl-pyridin-2-ylmethyl)-(5,6,7,8-tetrahydro-quinolin-8-yl)-amino]-methyl}-phenyl)-methanol;

N-(4-{[(3,5-dimethyl-pyridin-2-ylmethyl)-(5,6,7,8-tetrahydro-quinolin-8-yl)-amino]-methyl}-3-hydroxymethyl-benzyl)-2-phenyl-butyramide;

N-(4-{[(3,5-dimethyl-pyridin-2-ylmethyl)-(5,6,7,8-tetrahydro-quinolin-8-yl)-amino]-methyl}-3-hydroxymethyl-benzyl)-2-phenyl-butyramide;

N-(-3-hydroxymethyl-4-{[(3-methyl-pyridin-2-ylmethyl)-(5,6,7,8-tetrahydro-quinolin-8-yl)-amino]-methyl}-benzyl)-2-phenyl-butyramide;

1-benzyl-3-(4-{[(3,5-dimethyl-pyridin-2-ylmethyl)-(5,6,7,8-tetrahydro-quinolin-8-yl)-amino]-methyl}-3-hydroxymethyl-benzyl)-urea;

1-(4-{[(3,5-dimethyl-pyridin-2-ylmethyl)-(1,2,3,4-tetrahydro-naphthalen-1-yl)-amino]-methyl}-3-hydroxymethyl-benzyl)-3-(1H-imidazol-2-yl)-urea; and 3-(4-{[(3,5-dimethyl-pyridin-2-ylmethyl)-(5,6,7,8-tetrahydro-quinolin-8-yl)-amino]-methyl}-3-hydroxymethyl-benzyl)-1-ethyl-1-phenyl-urea;

or a pharmaceutically acceptable salt thereof.

17. A pharmaceutical composition which comprises as active ingredient the compound of claim 16 along with at least one excipient.

18. The pharmaceutical composition of claim 17, which further comprises one or more of G-CSF, granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin, and/or growth related oncogene.

* * * * *